(12) United States Patent
Turkson et al.

(10) Patent No.: US 11,299,480 B2
(45) Date of Patent: Apr. 12, 2022

(54) 2-ARYLSULFONAMIDO-N-ARYLACETAMIDE DERIVATIZED STAT3 INHIBITORS

(71) Applicant: University of Hawaii, Honolulu, HI (US)

(72) Inventors: James Turkson, Honolulu, HI (US); Peibin Yue, Honolulu, HI (US); Marcus Tius, Honolulu, HI (US); Christine Brotherton-Pleiss, Honolulu, HI (US); Francisco Javier Lopez Tapia, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 16/480,090

(22) PCT Filed: Jan. 23, 2018

(86) PCT No.: PCT/US2018/014855
§ 371 (c)(1),
(2) Date: Jul. 23, 2019

(87) PCT Pub. No.: WO2018/136935
PCT Pub. Date: Jul. 26, 2018

(65) Prior Publication Data
US 2019/0389844 A1 Dec. 26, 2019

Related U.S. Application Data

(60) Provisional application No. 62/449,515, filed on Jan. 23, 2017.

(51) Int. Cl.
| | | |
|---|---|---|
| *C07D 403/14* | (2006.01) |
| *C07D 403/12* | (2006.01) |
| *A61P 35/00* | (2006.01) |
| *A61K 9/00* | (2006.01) |
| *C07D 401/12* | (2006.01) |
| *C07D 401/14* | (2006.01) |
| *C07D 207/48* | (2006.01) |
| *C07D 205/04* | (2006.01) |

(52) U.S. Cl.
CPC .......... *C07D 403/14* (2013.01); *A61K 9/0019* (2013.01); *A61K 9/0053* (2013.01); *A61P 35/00* (2018.01); *C07D 401/12* (2013.01); *C07D 401/14* (2013.01); *C07D 403/12* (2013.01)

(58) Field of Classification Search
CPC .. C07D 205/04; C07D 403/12; C07D 403/14; C07D 207/48; C07D 405/14; C07D 405/12; C07D 401/14; C07D 401/12; A61K 9/0053; A61K 9/0019; A61K 9/00; A61P 35/00
See application file for complete search history.

(56) References Cited

U.S. PATENT DOCUMENTS

| 10,772,859 B2 * | 9/2020 | Kelley ................. A61K 31/63 |
| 2010/0093811 A1 | 4/2010 | Colburn et al. |
| 2015/0335022 A1 | 11/2015 | Buysse et al. |

FOREIGN PATENT DOCUMENTS

| WO | WO 1998/053818 A1 | 12/1998 |
| WO | WO-2012/018868 A1 | 2/2012 |
| WO | WO-2013/177534 A2 | 11/2013 |
| WO | WO-2014/153495 A2 | 9/2014 |

OTHER PUBLICATIONS

Kelley et al., 2016, caplus an 2016:1912096.*
Haftchenary, Sina, et al. "Potent targeting of the STAT3 protein in brain cancer stem cells: a promising route for treating glioblastoma." ACS Medicinal Chemistry Letters 4.11 (2013): 1102-1107.
Page, Brent DG, et al. "Identification of a non-phosphorylated, cell permeable, small molecule ligand for the Stat3 SH2 domain." Bioorganic & Medicinal Chemistry Letters 21.18 (2011): 5605-5609.
Zhang, Xiaolei, et al. "A novel small-molecule disrupts Stat3 SH2 domain-phosphotyrosine interactions and Stat3-dependent tumor processes." Biochemical Pharmacology 79.10 (2010): 1398-1409.
Fletcher, Steven, et al. "Disruption of Transcriptionally Active Stat3 Dimers with Non-phosphorylated, Salicylic Acid-Based Small Molecules: Potent in vitro and Tumor Cell Activities." ChemBioChem 10.12 (2009): 1959-1964.
Cumaraswamy, Abbarna A., et al. "Nanomolar-potency small molecule inhibitor of STAT5 protein." ACS Medicinal Chemistry Letters 5.11 (2014): 1202-1206.
Extended European Search Report in EP Application No. 18742226.6, dated Jul. 22, 2020, in 3 pages.
PubChem-CID-86781981, Create Date: 07 Feb. 7, 2015.
International Search Report dated May 18, 2018 in connection with PCT International Application No. PCT/US2018/014855.
Written Opinion of the International Searching Authority dated May 18, 2018 in connection with PCT International Application No. PCT/US2018/014855.
Arpin, Carolyn C., et al. "Applying small molecule signal transducer and activator of transcription-3 (STAT3) protein inhibitors as pancreatic cancer therapeutics." Molecular Cancer Therapeutics 15.5 (2016): 794-805.

* cited by examiner

*Primary Examiner* — Sun Jae Yoo
(74) *Attorney, Agent, or Firm* — Duane Morris LLP

(57) ABSTRACT

The present disclosure provides pharmaceutical compositions comprising 2-arylsulfonamido-N-arylacetamide derivatized Stat3 inhibitors and certain pharmaceutically acceptable salts thereof, and methods of their use.

29 Claims, 12 Drawing Sheets
Specification includes a Sequence Listing.

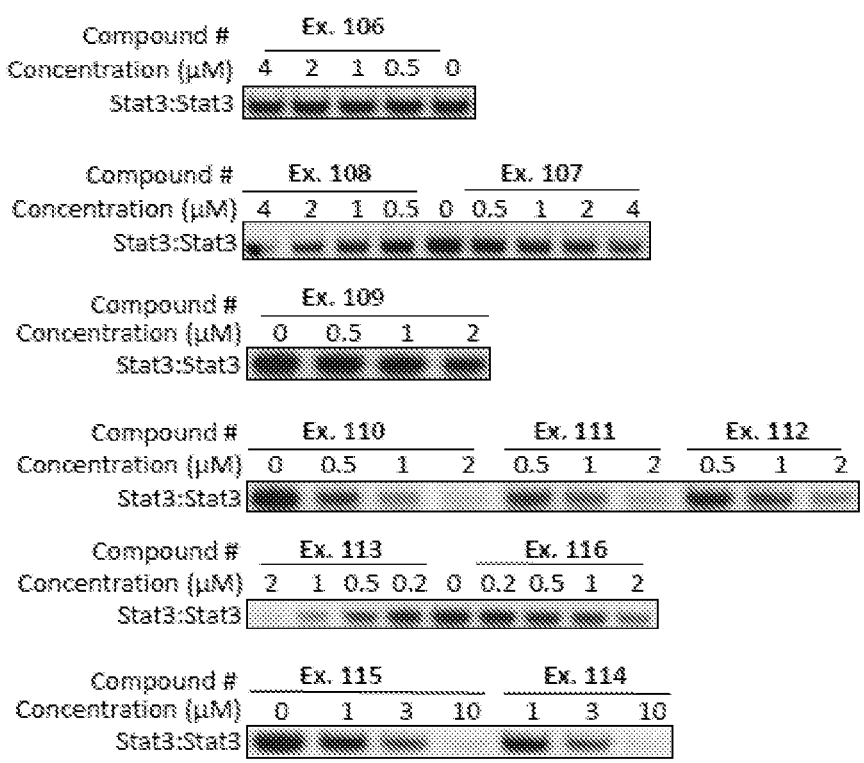

FIG. 1H)

| Compound # | Ex. 147 | | | Ex. 148 | | | | Ex. 149 | | | |
|---|---|---|---|---|---|---|---|---|---|---|---|
| Concentration (μM) | 30 | 10 | 3 | 4 | 2 | 1 | 0.5 | C | 0.5 | 1 | 2 | 4 |
| Stat3:Stat3 | | | | | | | | | | | | |

| Compound # | Ex. 150 | | | | Ex. 154 | | | Ex. 155 | |
|---|---|---|---|---|---|---|---|---|---|
| Concentration (μM) | 30 | 10 | 3 | C | 30 | 10 | 3 | 3 | 10 |
| Stat3:Stat3 | | | | | | | | | |

| Compound # | Ex. 153 | | | | | Ex. 151 | | |
|---|---|---|---|---|---|---|---|---|
| Concentration (μM) | 0 | 0.5 | 1 | 2 | 4 | 0.5 | 1 | 2 |
| Stat3:Stat3 | | | | | | | | |

| Compound # | Ex. 152 | | | |
|---|---|---|---|---|
| Concentration (μM) | 0 | 0.5 | 1 | 2 |
| Stat3:Stat3 | | | | |

| Compound # | Ex. 156 | | | |
|---|---|---|---|---|
| Concentration (μM) | 30 | 10 | 3 | 0 |
| Stat3:Stat3 | | | | |

| Compound # | Ex. 157 | | | | |
|---|---|---|---|---|---|
| Concentration (μM) | 0 | 1 | 3 | 10 | 30 |
| Stat3:Stat3 | | | | | |

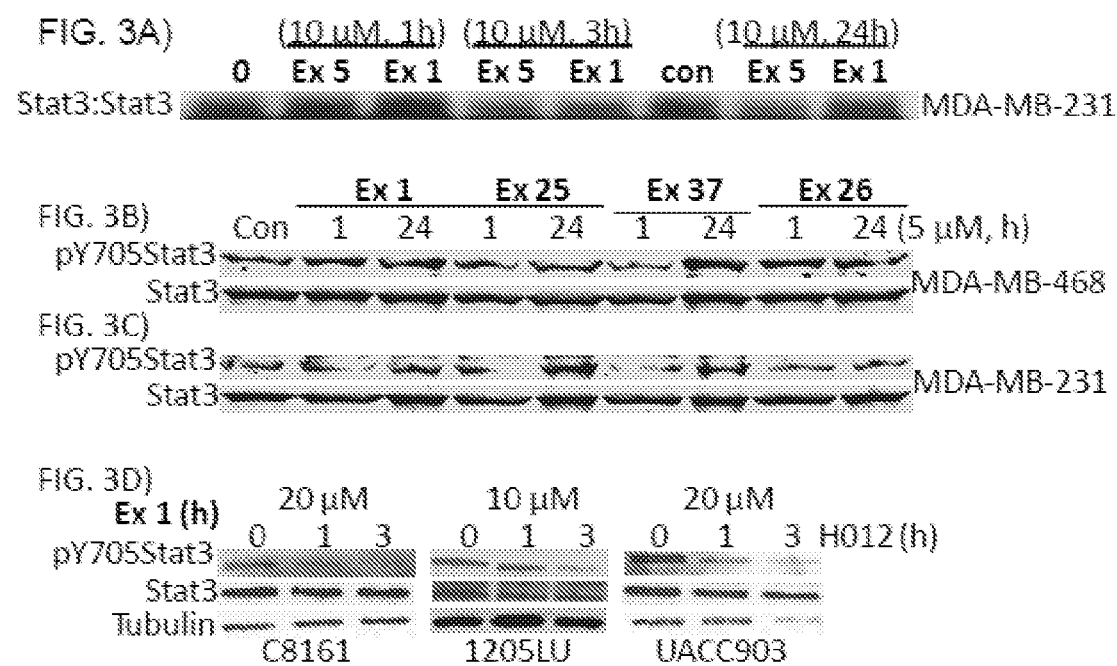

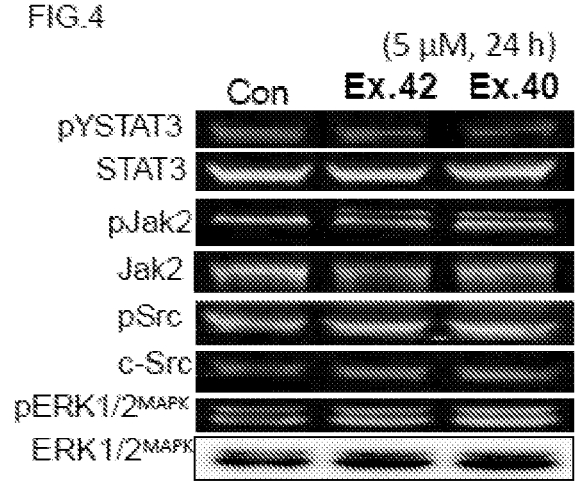

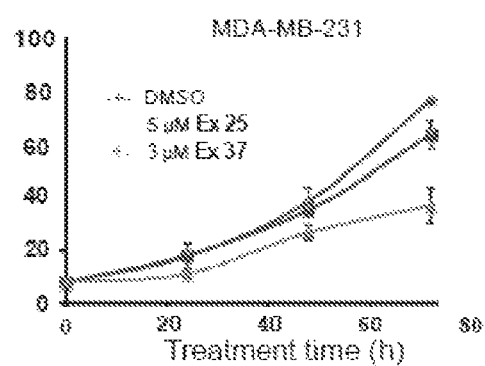
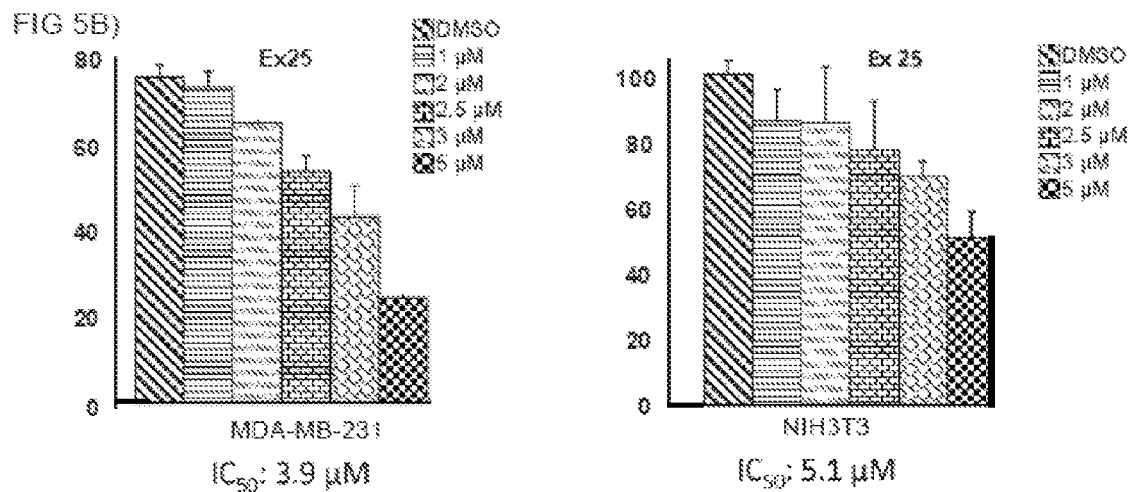

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 1
agcttcattt cccgtaaatc ccta                                           24

<210> SEQ ID NO 2
<211> LENGTH: 18
<212> TYPE: DNA

```
<213> ORGANISM: Artificial Sequence
<220> FEATURE:
<223> OTHER INFORMATION: synthetic oligonucleotide

<400> SEQUENCE: 2
agatttctag gaattcaa                                                      18
```

2-ARYLSULFONAMIDO-N-ARYLACETAMIDE DERIVATIZED STAT3 INHIBITORS

CROSS-REFERENCE TO RELATED APPLICATIONS

This application is a § 371 national stage of PCT International Application No. PCT/US2018/014855, filed Jan. 23, 2018, claiming the benefit of U.S. Provisional Application No. 62/449,515, filed Jan. 23, 2017, the contents of each of which are hereby incorporated by reference into the application.

GOVERNMENT RIGHTS

This invention was made with government support under grant number R01 CA161931 awarded by the National Institutes of Health. The government has certain rights in the invention.

REFERENCE TO A SEQUENCE LISTING

This application incorporates-by-reference nucleotide and/or amino acid sequences which are present in the file named "190723_91046 Sequence_Listing_CAS.txt", which is 701 bytes in size, and which was created Jan. 23, 2019 in the IBM-PC machine format, having an operating system compatibility with MS-Windows, which is contained in the text file filed Jan. 23, 2019 as part of this application.

FIELD

The present disclosure is generally related to novel, potent and selective 2-arylsulfonamido-N-arylacetamide derivatized Stat3 inhibitors of Formulae I-VIII, and pharmaceutically acceptable salts thereof. The present disclosure also relates to pharmaceutical compositions containing the inhibitors and their use in the treatment or prevention of cancer, and other pathogenic conditions in which Stat3 activation is implicated. As an example, the disclosure provides methods and compositions for the treatment of cancer by modulating Stat3.

BACKGROUND

The following includes information that may be useful in understanding various aspects and embodiments of the present disclosure. It is not an admission that any of the information provided herein is prior art, or relevant, to the presently described or claimed inventions, or that any publication or document that is specifically or implicitly referenced is prior art.

The signal transducer and activator of transcription (Stat) family of cytoplasmic transcription factors have important roles in many cellular processes, including cell growth and differentiation, inflammation and immune responses. (Bromberg, et al., *Breast Cancer Res.* 2:86-90 (2000); Darnell, J., et al., *Nat. Rev. Cancer* 2:740-749 (2002)). STAT proteins are classically activated by tyrosine (Tyr) kinases, such as Janus kinases (JAKs) and Src family kinases, in response to the binding of cytokine and growth factors to their cognate receptors. The Tyr phosphorylation (pTyr) promotes dimerization between two activated STAT:STAT monomers through a reciprocal pTyr-Src homology SH2 domain interactions. Active STAT:STAT dimers translocate to the nucleus to induce gene transcription by binding to specific DNA-response elements in the promoters of target genes to regulate gene expression. By contrast, aberrantly-active Stat3, one of the Stat family members, has been implicated in many human tumors and represents an attractive target for drug discovery. The aberrant activation of Stat3 occurs in glioma, breast, prostate, ovarian, and many other human cancers, whereby it promotes malignant progression (Yu & Jove, *Nat. Rev. Cancer* 4:97-105 (2004)). Mechanisms by which constitutively-active Stat3 mediates tumorigenesis include dysregulation of gene expression that leads to uncontrolled growth and survival of tumor cells, enhanced tumor angiogenesis, and metastasis and the suppression of tumor immune surveillance (Yu & Jove (2004); Bromberg & Darnell, *Oncogene* 19:2468-2473 (2000); Bowman et al., *Oncogene* 19:2474-2488 (2000); Turkson J & Jove, *Oncogene* 19:6613-6626 (2000); Turkson, *Expert Opin Ther Targets* 8:409-422 (2004); Wang et al., *Nat Med* 10:48-54 (2004)).

Stat3 modulates mitochondrial functions and Stat3 crosstalk with other proteins, such as NF-κB, that promotes the malignant phenotype. Many human tumors harbor aberrantly-active signal transducer and activator of transcription Stat3 signaling.

SUMMARY OF THE INVENTION

In one aspect, this invention relates to novel, selective and potent 2-arylsulfonamido-N-arylacetamide derivatized Stat3 inhibitors, useful as cancer therapeutics. In some aspects, the compounds of this invention are useful for inhibiting malignant transformation, tumor development and progression.

In one aspect, this invention relates to compounds of Formula I, which selectively inhibit Stat3.

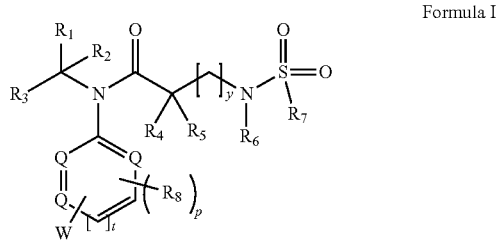

Formula I wherein $R^1$ can include or exclude aryl or a 5 or 6-membered heteroaryl, where the heteroatoms are one or more of O, N, and $S(A)_2$, where S is sulfur and A can include or exclude oxygen or an electron pair, the aryl or the 5 or 6-membered heteroaryl are optionally substituted with halo, $CF_3$, $C_1$-$C_6$ alkyl, $C_1$-$C_6$ branched alkyl, aryl, heteroaryl, $C_3$-$C_7$ cycloalkyl, $C_3$-$C_7$ cycloalkenyl, three- to six-membered heterocycle, three- to seven-membered saturated heterocycle, fused $C_2$-$C_5$ alkylene, where one or more $CH_2$ groups can be replaced with O, $NR^9$, and $S(A)_2$, where S is sulfur and A can include or exclude oxygen or an electron pair, the aryl or the 5 or 6-membered heteroaryl are optionally substituted naphthalene, optionally substituted indole, benzofuran, benzothiophene; $R^2$ and $R^3$ are independently selected from H or $C_1$-$C_6$ alkyl; where $R^2$ and $R^3$ can form a $C_3$-$C_6$ cycloalkane ring, where this $C_3$-$C_6$ cycloalkane ring can be substituted with 1 or more of $C_1$-$C_6$ alkyl, hydroxyl, $NR^9R^{10}$, or $C_1$-$C_6$ alkoxy; $R^4$ can include or exclude H, $C_1$-$C_6$ alkyl, $(CH_2)_f NR^9R^{10}$, $(CH_2)_f OR^9$, $(CH_2)_f CO_2R^9$, $(CH_2)_f CO_2NR^9R^{10}$; $R^5$ can include or exclude $C_1$-$C_6$ alkyl, $(CH_2)_f NR^9R^{10}$, $(CH_2)_f OR^9$, $(CH_2)_f CO_2R^9$, $(CH_2)_f CO_2NR^9R^{10}$, where $R^4$ and $R^5$ can form a $C_3$-$C_6$ cycloalkane ring, where this $C_3$-$C_6$ cycloalkane ring can be substituted with 1 or more of $C_1$-$C_6$ alkyl, hydroxyl, $NR^9R^{10}$, or $C_1$-$C_6$ alkoxy, where one or more $CH_2$ groups can be replaced with O, $NR^9$, and $S(A)_2$, where S is sulfur and A can include or exclude oxygen or an electron pair; $R^6$ can include or exclude $C_1$-$C_6$ alkyl; where $R^4$ and $R^6$ can form a $C_3$-$C_6$ cycloalkane ring, where this $C_3$-$C_6$ cycloalkane ring can be substituted with 1 or more of $C_1$-$C_6$ alkyl, hydroxyl, $NR^9R^{10}$ and where one or more $CH_2$ groups can be replaced with O, $NR^9$, and $S(A)_2$, where S is sulfur and A can include or exclude oxygen or an electron pair; wherein $R^4$ and $R^6$ can form an optionally substituted pyrrole ring, wherein one or more CH groups of said pyrrole ring can be replaced with O, N, and $S(A)_2$, where S is sulfur and A can include or exclude oxygen or an electron pair; $R^7$ can include or exclude $CF_3$, aryl or heteroaryl group where the aryl or heteroaryl group is substituted with 1-5 substituents selected from $C_1$-$C_6$ alkyl, halo, hydroxyl, CN, or $CF_3$; $R^8$ is substitution selected from one or more of H, $C_1$-$C_6$ alkyl, $C_1$-$C_6$ alkoxy, hydroxyl, halogen, $OC(O)CH_3$, $NR^9R^{10}$, CN, $CF_3$, $CO_2R^9$, $CO_2NR^9R^{10}$, $(CH_2)_f NR^9R^{10}$, $(CH_2)_f OR^9$, or $(CH_2)_f CO_2R^9$; $R^9$ can include or exclude H or $C_1$-$C_6$ alkyl; $R^{10}$ can include or exclude H, $C_1$-$C_6$ alkyl; W can include or exclude $CO_2H$, tetrazole, benzyl, $C(O)NHOR^{10}$ and $CF_2OH$; Q is C, CH, N, O, S; where Q and $R^8$ can form a heterocyclic ring; p is selected from 0 or 1; y is selected from 0 or 1, f is selected from 0 to 4; t is selected from 0 or 1;

and solvates, hydrates, or pharmaceutically acceptable salts thereof.

In one aspects, this invention relates to pharmaceutical compositions comprising a therapeutically effective amount of a compound of Formula I and a pharmaceutically acceptable excipient.

In one aspect, this invention relates to compounds of Formula II, which selectively inhibit Stat3.

Formula II

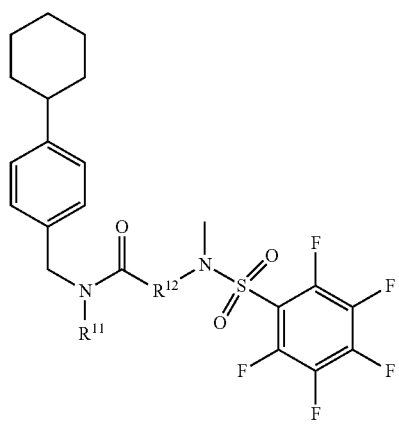

wherein $R^{11}$ can include or exclude optionally substituted aryl or optionally substituted heteroaryl, wherein the aryl or heteroaryl can be substituted with one or more of hydroxyl, carboxylic acid, carboxylate, benzohydroxamic acid, hydroxyl-substituted alkyl;

wherein $R^{12}$ can include or exclude (R)—CH($CH_3$), (S)—CHCH$_3$, (S)—CH($CH_2CH_3$), (R)—CH($CH_2CH_3$), bridging cylcopropyl

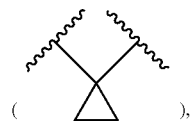 [SMILES: *C1(*)CC1]

$C(CH_3)_2$, (S)—CH($CH_2OH$), (R)—CH($CH_2OH$), (R)—CH($CH_2CH_2OH$), (S)—CH($CH_2CH_2OH$), (S)—CH[(R)—CH($CH_3$)OH], (R)—CH[(S)—CH($CH_3$)OH], (S)—CH($CH_2NH_2$), (R)—CH($CH_2NH_2$), (S)—CH($CH_2CO_2H$), and (R)—CH($CH_2CO_2H$);

and solvates, hydrates, or pharmaceutically acceptable salts thereof.

In one aspect, this invention relates to compounds of Formula III, which selectively inhibit Stat3.

Formula III

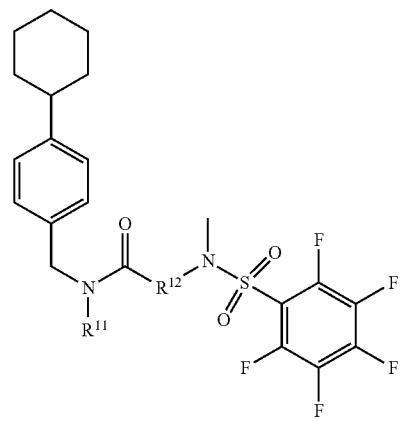

wherein $R^{11}$ can include or exclude aryl or heteroaryl, wherein the aryl or heteroaryl can be substituted with one or more of hydroxyl, carboxylic acid, carboxylate, benzohydroxamic acid, nitroso, alkyl carboxylic acid, $C_1$-$C_6$ alkyl, and halo;

wherein $R^{12}$ is (R)—CH($CH_3$);

and solvates, hydrates, or pharmaceutically acceptable salts thereof.

In some aspects, $R^{11}$ can include or exclude:

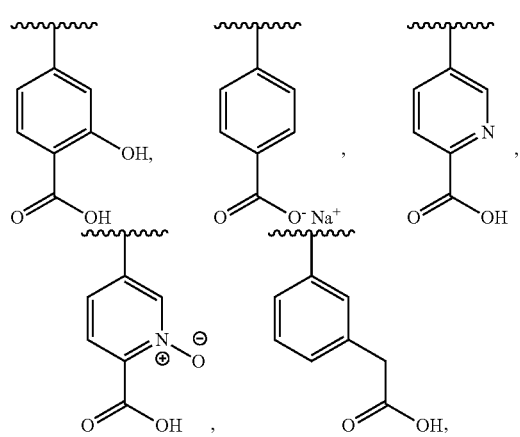

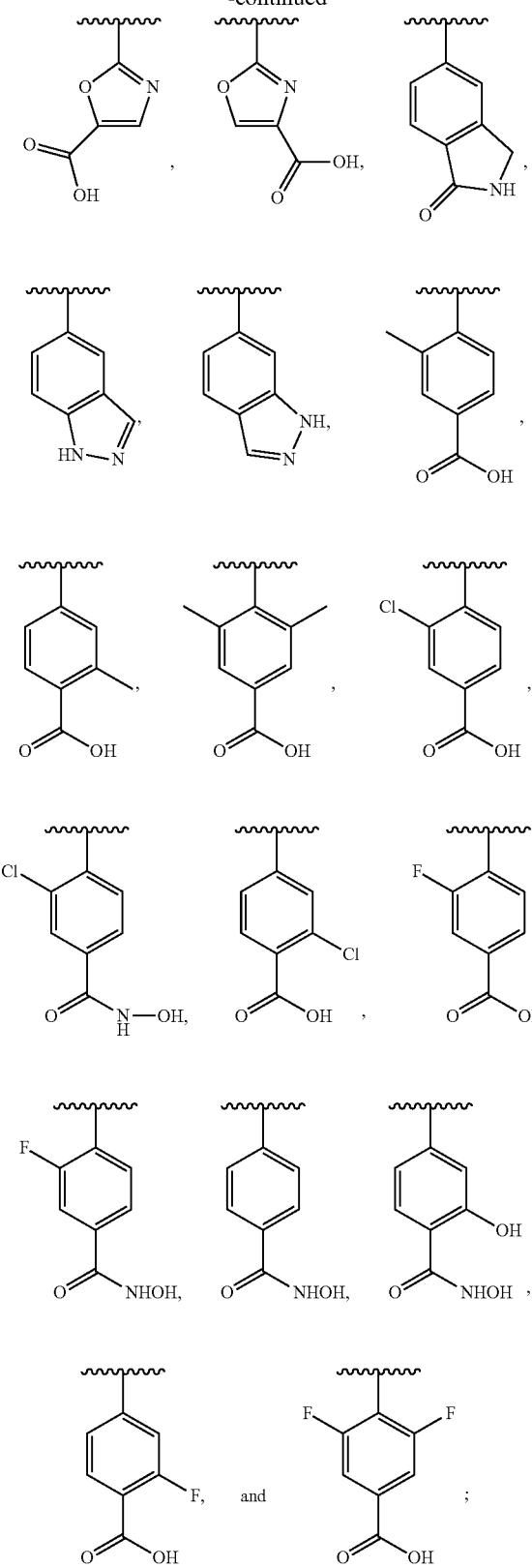

and salts thereof.

In one aspect, this invention relates to compounds of Formula IV, which selectively inhibit Stat3.

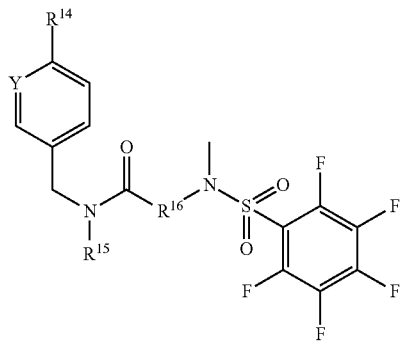

wherein $R^{14}$ can include or exclude a five- to seven-membered cycloalkyl or heteroxycloalkyl group, wherein the cycloalkyl group can be substituted with one or more of halo;

wherein $R^{15}$ can include or exclude substituted aryl, wherein the substitution is one or more of hydroxy, caroboxylic acid, and benzohydroxamic acid;

wherein $R^{16}$ is (R)—CH(CH$_3$);

wherein Y can include or exclude CH and N, and solvates, hydrates, or pharmaceutically acceptable salts thereof.

In some aspects, $R^{14}$ can include or exclude:

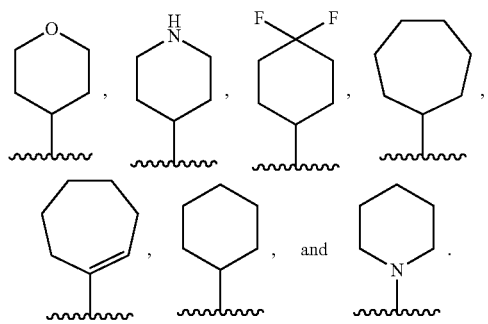

In some aspects, $R^{15}$ can include or exclude:

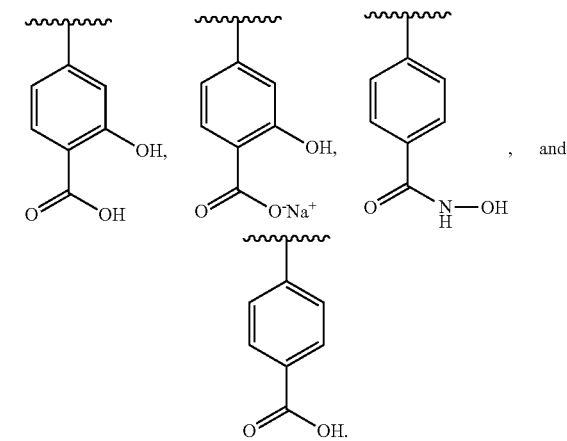

In one aspect, this invention relates a compound selected from:

(compound of Example 26)
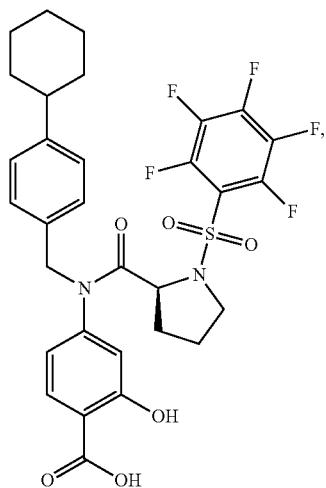
(compound of Example 31)
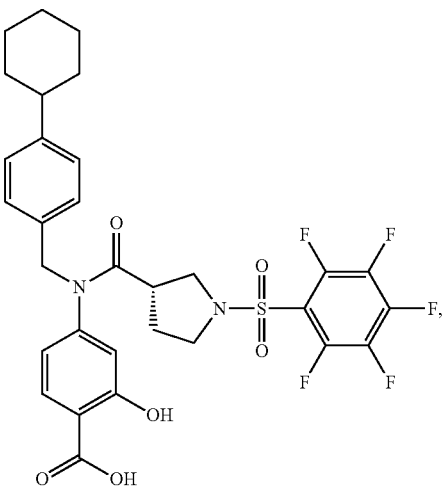
(compound of Example 25)
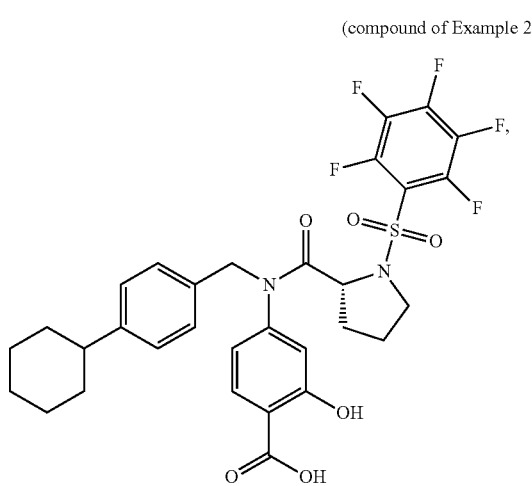
(compound of Example 39)
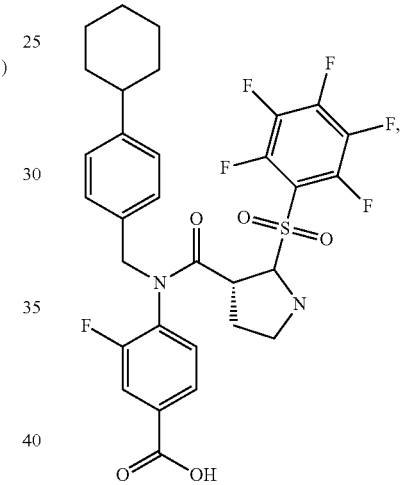
(compound of Example 30)
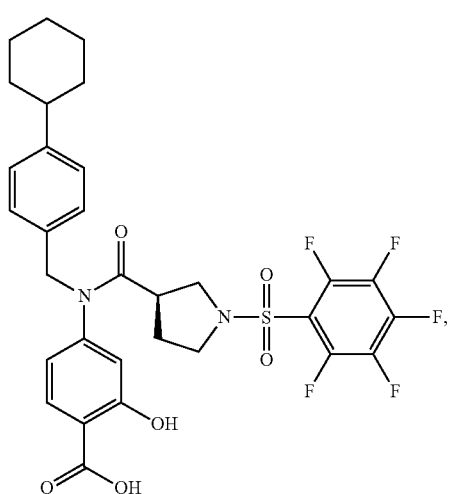
(compound of Example 60)
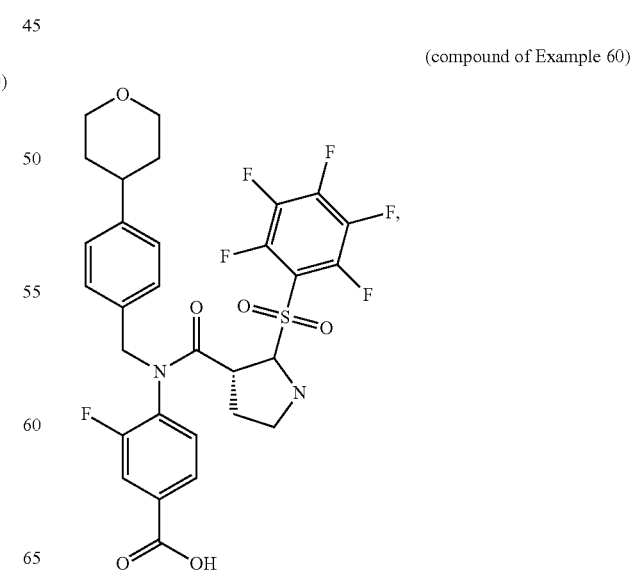

(compound of Example 27)

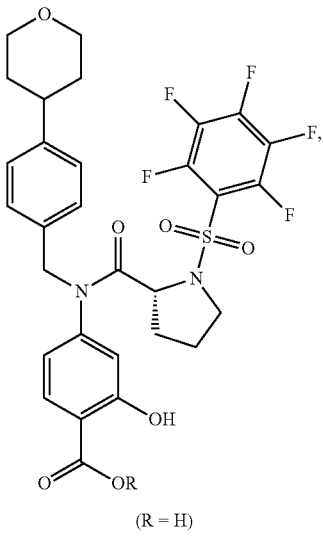

(R = H)

(compound of Example 28)

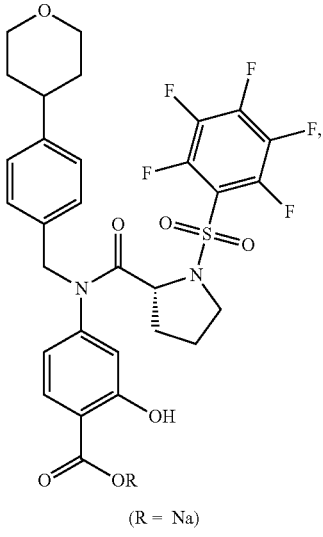

(R = Na)

(compound of Example 79)

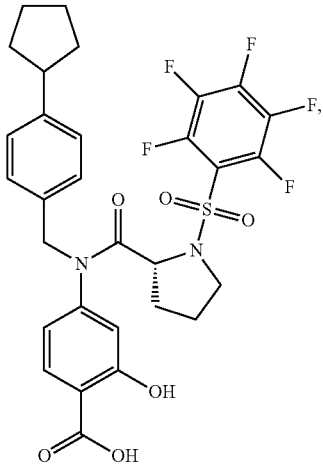

(compound of Example 29)

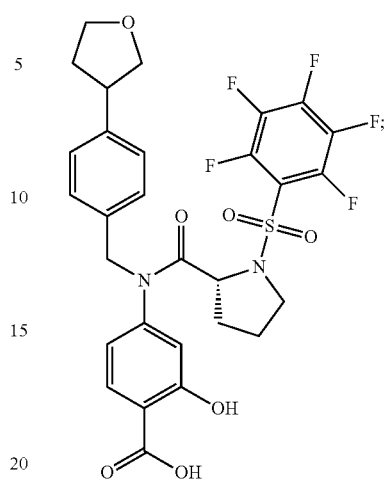

and solvates, hydrates, or pharmaceutically acceptable salts thereof.

In one aspect, this invention relates to compounds of Formula VI, which selectively inhibit Stat3.

Formula VI

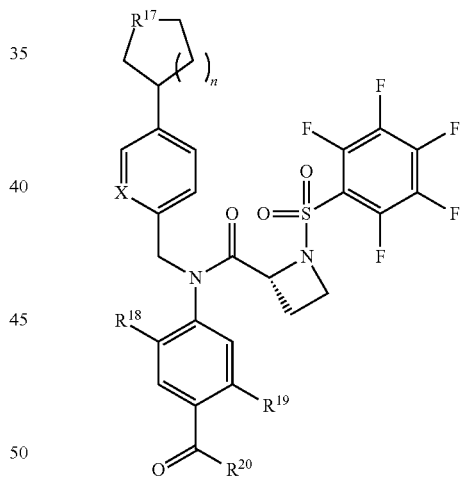

wherein n is selected from 1 to 3
wherein X can include or exclude CH and N;
wherein $R^{17}$ can include or exclude $CH_2$ and O;
wherein $R^{18}$ can include or exclude hydrogen and halo;
wherein $R^{19}$ can include or exclude hydrogen and hydroxyl;
wherein $R^{20}$ can include or exclude —OH, NHOH, and —($O^-$, $Na^+$),
and solvates, hydrates, or pharmaceutically acceptable salts thereof.

In one aspect, this invention relates a compound selected from:

(compound of Example 34)

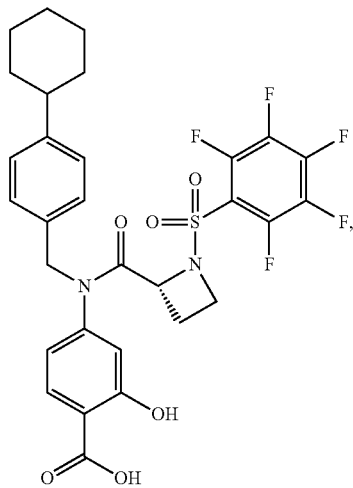

(compound of Example 85)

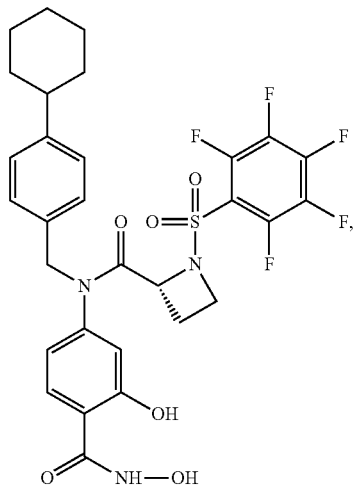

(compound of Example 52)

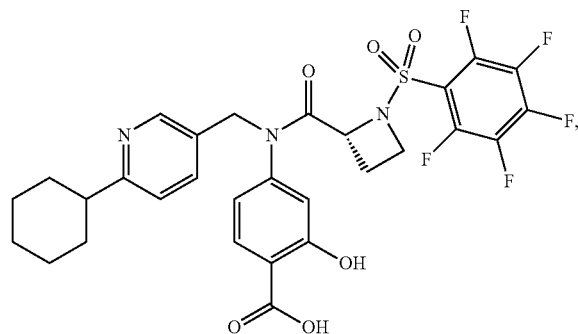

-continued (compound of Example 53)

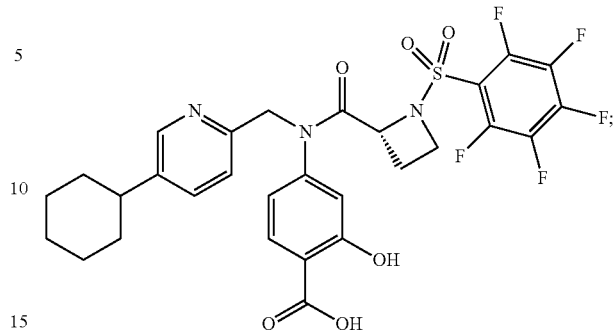

and solvates, hydrates, or pharmaceutically acceptable salts thereof.

In some aspects, this invention relates to compounds of Formula VII, which selectively inhibit Stat3.

Formula VII

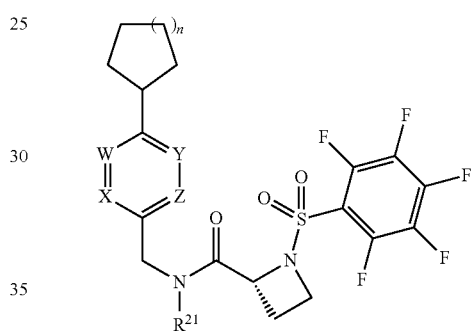

wherein W, X, Y, and Z each independently can include or exclude CH or N, wherein $R^{21}$ can include or exclude optionally substituted aryl, optionally substituted heteroaryl, or an optionally substituted aryl fused with a heterocyclic ring, wherein the substituted aryl or substituted heteroaryl or the substituted aryl fused with a heterocyclic ring can be substituted with one or more of hydroxyl, carboxylic acid, carboxylate, hydroxamic acid, amide, alkyl amide, dialkylamide, alkoxyamino, alkyl carboxylic acid, C1-C6 alkyl, and halo, wherein n is selected from 1 to 3;

and solvates, hydrates, or pharmaceutically acceptable salts thereof.

In some aspects, $R^{21}$ can include or exclude any of the following moieties:

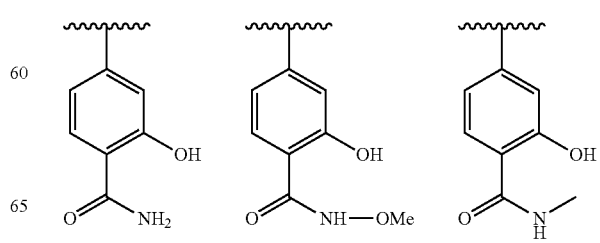

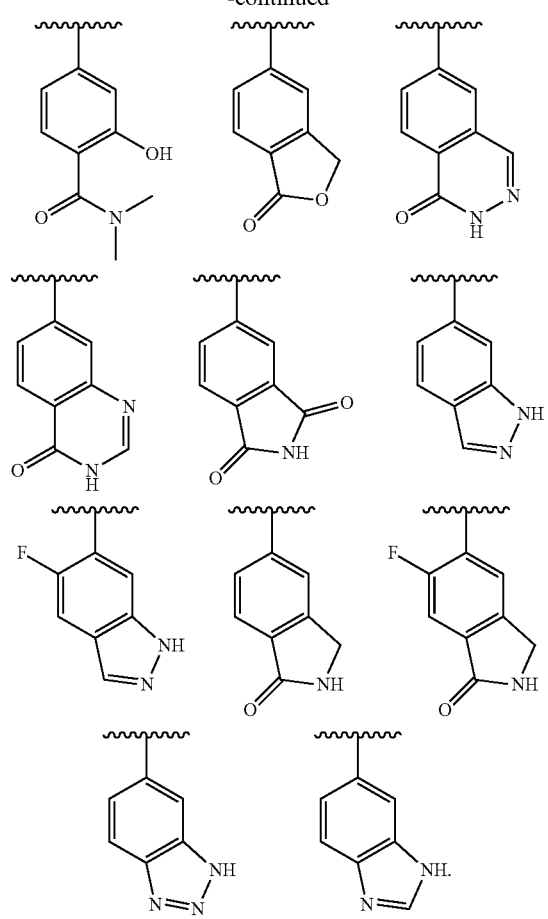
In some aspects, the compounds of this disclosure can include or exclude:
(compound of Example 102)
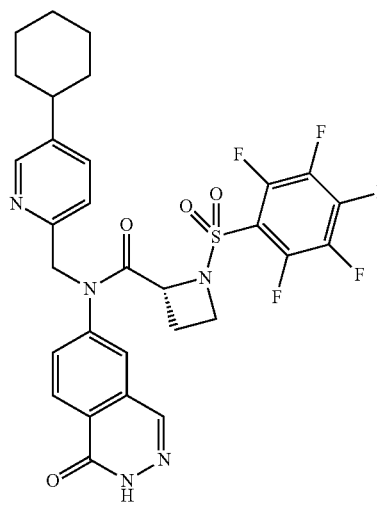
(compound of Example 104)
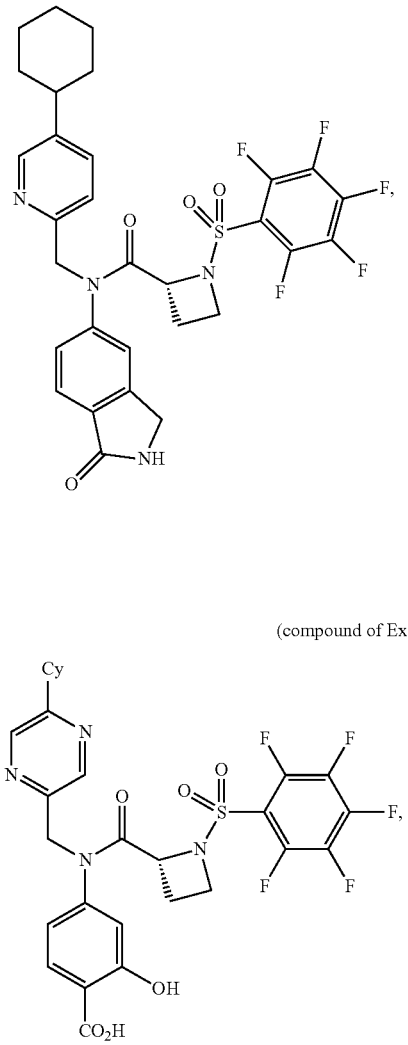
(compound of Example 110)
(compound of Example 113)
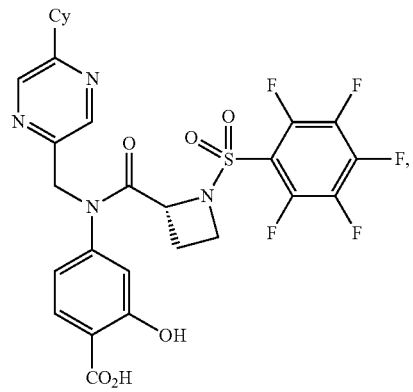

(compound of Example 119)
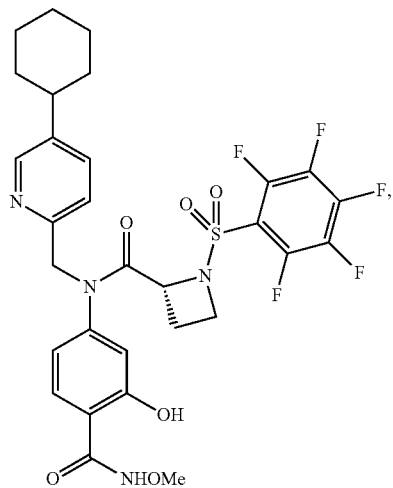
(compound of Example 122)
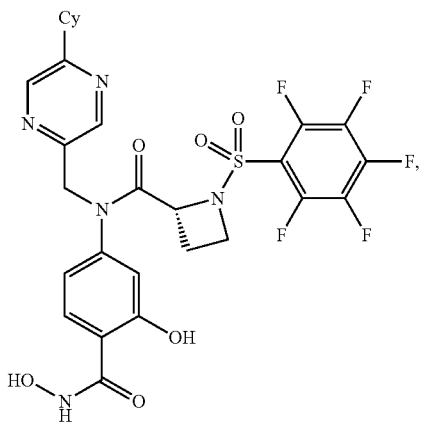
(compound of Example 125)
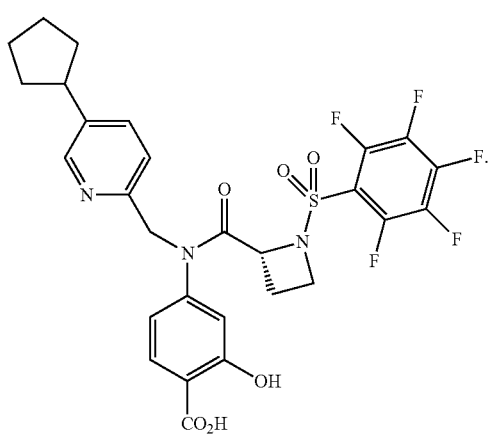
(compound of Example 134)
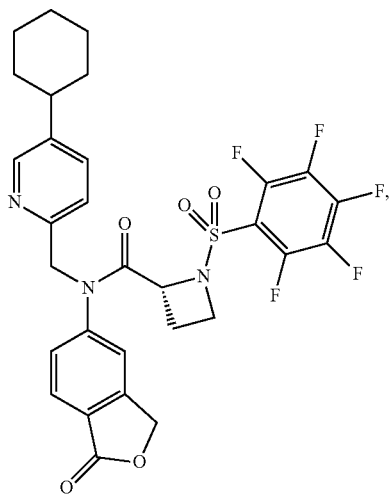
(compound of Example 135)
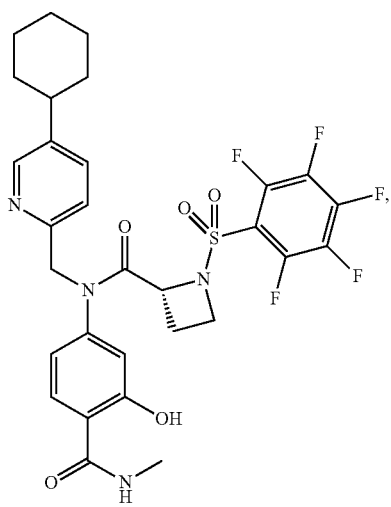
(compound of Example 136)
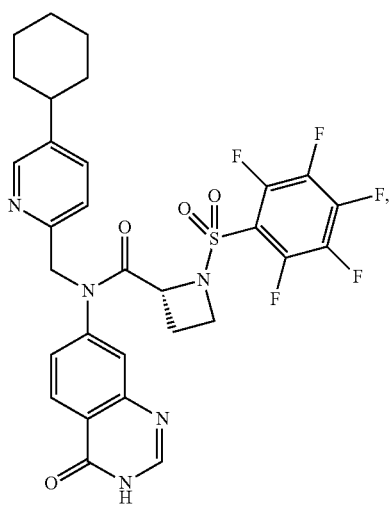

(compound of Example 137)

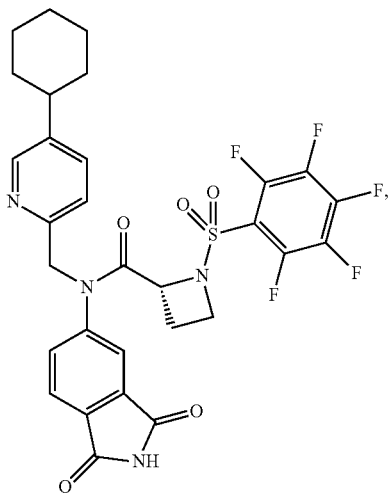

(compound of Example 143)

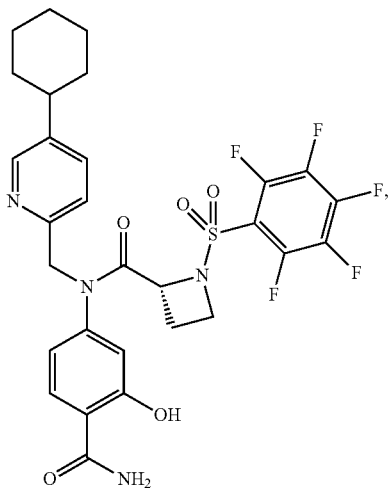

(compound of Example 148)

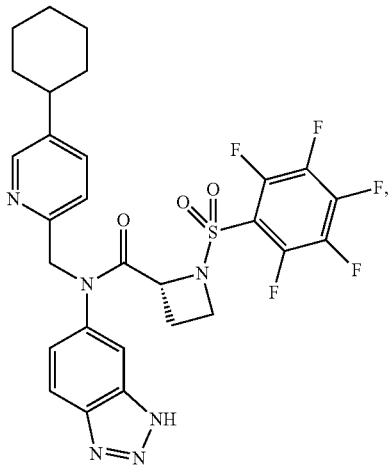

(compound of Example 149)

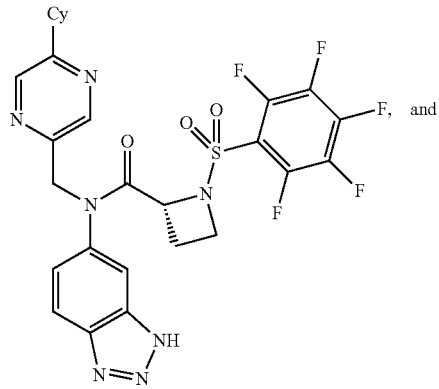

and (compound of Example 151)

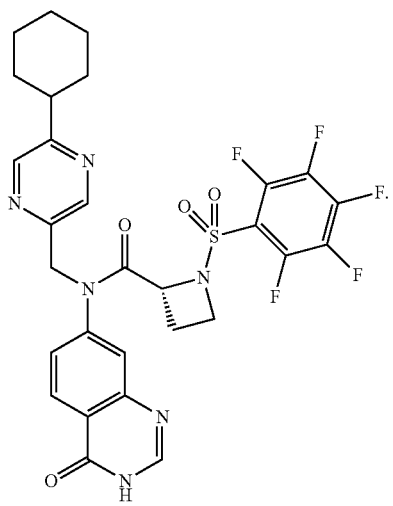

In some aspects, this inventions relates to compounds of Formula VIII.

Formula VIII

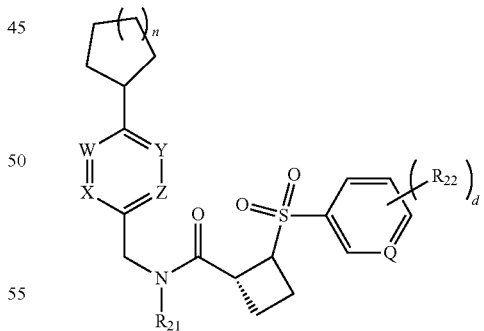

wherein W, X, Y, Z, and Q each independently can include or exclude CH or N,
wherein d is selected from 0, 1, 2, 3, or 4,
wherein $R^{21}$ is as described herein, and
wherein $R^{22}$ is halogen.

In some aspects, any R group described herein can include or exclude the recited options.

In one aspect, the compounds of this invention inhibit Stat3 while exhibiting little or no inhibition of Stat1 at concentrations of at least twice the $IC_{50}$ for Stat3 inhibition. The compounds of this invention uniquely interact with three sub-pockets on the stat3:stat3 dimer interface, in contrast to other previously described Stat3 inhibitors, which interacts with only two sub-pockets. As a result of the unique and specific mechanism by which the 2-arylsulfonamido-N-arylacetamide derivatized Stat3 inhibitors of this invention exert their effects, the compounds are more potent and less toxic. The compounds of this invention also suprisingly selectively bind inhibit the activated form of Stat3, consequently attenuating Stat3 functions in cancer cells. The compounds of this invention are useful, for example, for inhibiting cancer cell growth, survival, migration and/or metastasis.

In one aspect, this invention relates to compounds which preferentially inhibit Stat3 DNA-binding activity with $IC_{50}$'s of 10 µM or less, but exhibit little or no disruption of Stat5 DNA-binding activity. In one aspect, this invention relates to compositions and formulations useful for inhibiting cancer growth. In some aspects, the anti-cancer activity of the compounds is determined by the ability to inhibit growth of mouse xenografts of human breast and non-small cell lung cancers.

Dimerization of Stat3 occurs through SH2-phosphotyrosyl peptide interactions. See Shuai et al., Interferon activation of the transcription factor Stat91 involves dimerization through SH2-phosphotyrosyl peptide interactions (*Cell*, 76:821-828 (1994); Miklossy et al. *Nat Rev Drug Discov* 12:611-629 (2013); Turkson et al., *Mol Cancer Ther* 3:261-269 (2004); Turkson et al., *J. Biol. Chem.* 276:45443-45455 (2001); Siddiquee et al., *Proc Natl Acad Sci USA*. 104:7391-7396 (2007); Coleman et al., *J Med Chem.* 48(6661-70) (2005)).

In one aspect, the invention relates to the inventors' design of 2-arylsulfonamido-N-arylacetamide derivatized Stat3 inhibitors which interfere with the dimerization between two monomers, and the inventors' recognition that this represents an attractive strategy to develop drugs that inhibit Stat3 activation and functions.

The inventors have appreciated that glycine-based compounds such as BP-1-102 inhibit Stat3 activity (Zhang et al., *Proc Natl Acad Sci USA* 109:9623-8 (2012)). In the present invention, the inventors have developed analogues of glycine based compounds with increased potency, reduced lipophilicity, and lower molecular weight compared to the glycine based compounds such as BP-1-102.

The compounds of this invention surprisingly show improved Stat3-inhibitory activity. For example, the compounds of this invention have $IC_{50}$'s or activities that are two to ten times lower than (and therefore more potent than) the compound BP-1-102.

The present disclosure provides novel, selective 2-arylsulfonamido-N-arylacetamide derivatized Stat3 inhibitors, and pharmaceutical formulations and kits comprising the inhibitors. The compounds and pharmaceutical formulations are useful as therapeutics for cancer and other conditions mediated by aberrantly active Stat3, a substrate for growth factor receptor tyrosine kinases, or cytoplasmic tyrosine kinases, including Janus kinases or the Src family kinases. In some aspects, the processes inhibited by the compounds and compositions of this invention include proliferation, survival, angiogenesis, migration/metastasis/invasion, and immunity.

The compounds of this invention are useful for inhibiting activities resulting from constitutive Stat3 activation, which include: a) stimulating proliferation by increasing the expression of c-Myc and/or cyclin D1/D2, and/or decreasing expression of p53; b) increasing survival by increasing the expression of survivin, Bcl-x/Bcl-2, Mcl-1 and/or Akt-2; stimulating angiogenesis by increasing expression of VEGF; and/or increasing migration/metastasis or invasion by increasing the expression MMP-2 or MMP-9.

In some aspects, the compounds of Formulae I-VIII including compounds of Examples 25-31, 50, 52, 53, 60-64, 79, 85, 102, 104, 110, 113, 119, 122, 125, 134-137, 143, 148, 149, 151 and 152 are used in the compositions and methods of this invention as described herein.

In one aspect, the present disclosure provides the use of a compound of any of Formulae I-VIII including compounds of Examples 25-31, 50, 52, 53, 60-64, 79, 85, 102, 104, 110, 113, 119, 122, 125, 134-137, 143, 148, 149, 151 and 152 for the preparation of a medicament for the treatment of a condition selected from the group consisting of cancer, hyperplasia, autoimmune indications, and neoplasia. In one aspect, the tumor progression, including metastasis and/or growth is thereby inhibited and/or reduced. In one aspect, multi-drug resistance is thereby inhibited and/or reduced.

In another aspect the present disclosure provides a method of treating cancer comprising administering to a subject in need thereof a therapeutically effective amount of a pharmaceutical composition comprising a compound of any of Formulae I-VIII including compounds of Examples 25-31, 50, 52, 53, 60-64, 79, 85, 102, 104, 110, 113, 119, 122, 125, 134-137, 143, 148, 149, 151 and 152 whereby the cancer is treated, cancer progression is stopped or slowed, and/or Stat3 is inhibited.

In one aspect, the level of Stat3 activity is reduced in cancer cells. In one aspect, the effective dose of the 2-arylsulfonamido-N-arylacetamide derivatized Stat3 inhibitor compound is administered at a dose ranging from 0.05 mg/kg to 4 mg/kg. In some aspects, the therapeutically effective dose is about 0.05, 0.06, 0.07, 0.08, 0.09, 0.1, 0.2, 0.3, 0.4, 0.5, 0.6, 0.7, 0.8. 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.9, 3.0, 3.1, 3.2, 3.3, 3.4, 3.5, 3.6, 3.7, 3.8, 3.9, or about 4.0 mg/kg, or any range in between any two of the recited doses. In some aspects, the dose will be 0.08 mg/kg to about 0.5 mg/kg, from about 0.08 to about 0.24 mg/kg, or from about 0.24 to about 0.5 mg/kg. In another aspect, the effective dose of the Stat3 inhibitor is given in one or more doses. In some aspects, the therapeutically effective amount of the Stat3 inhibitor dose is selected from: 0.08, 0.24, and 0.5 mg/kg for each dose. In one aspect, the dose is administered by a delivery route selected from the group consisting of intraperitoneal, intradermal, intramuscular, intraperitoneal, intravenous, topical, subcutaneous, intranasal, or epidural routes. In one aspect, the one or more effective doses of the 2-arylsulfonamido-N-arylacetamide derivatized Stat3 inhibitor are administered orally, intravenously, intramuscularly, or subcutaneously. In one aspect, the one or more effective doses of the Stat3 inhibitor are administered orally. In one aspect, the one or more effective doses of the Stat3 inhibitor are administered intravenously. In some aspects, the one or more effective doses of the Stat3 inhibitor are administered subcutaneously. In one aspect, the one or more effective doses of the Stat3 inhibitor are administered intramuscularly.

In one aspect, this disclosure provides a method of treatment comprising administering to a subject in need thereof an effective amount of a pharmaceutical composition comprising a 2-arylsulfonamido-N-arylacetamide derivatized Stat3 inhibitor of this invention. In one aspect, the subject has a glioma, breast cancer, or pancreatic cancer. In some aspects, the subject has a solid tumor cancer. In one aspect, the solid tumor comprises sarcomas, carcinomas or lymphomas. In one aspect, the cancer can include or exclude: brain tumors, such as gliomas, medulloblastomas, cerebral menangiomas, breast, prostate, pancreatic, ovarian, bladder, head and neck, malignant melanoma, multiple myeloma, lymphomas, including anaplastic large T cell lymphoma, sezary syndrome, EBV-related Burkitt's Lymphoma, HSV Saimiri-dependent (T Cell), cutaneous T cell lymphoma, mycosis fungoides, leukemia, including HTLV-I dependent leukemia, erythroleukemia, acute lymphocytic leukemia (ALL), chronic lymphocytic leukemia (CLL), acute myelogenous leukemia (AML), chronic myelogenous lekemia (CML), megakaryocytic leukemia, and large granula lymphocyte (LGL) leukemia, or thyroid, skin, lung, or kidney cancer. In some aspects the cancer can include or exclude: renal cell carcinoma, pancreatic adenocarcinoma, ovarian carcinoma, suamous cell carcinoma of the head and neck, or Hodgkin's Lymphoma.

According to one aspect of the present invention, there are provided novel compositions comprising compounds represented by Formulae I-VIII including compounds of Examples 25-31, 50, 52, 53, 60-64, 79, 85, 102, 104, 110, 113, 119, 122, 125, 134-137, 143, 148, 149, 151 and 152 their pharmaceutically acceptable salts, and pharmaceutical compositions containing them, or mixture thereof.

The inventions described and claimed herein have many attributes and embodiments, including, but not limited to, those set forth, or described, or referenced, in this Brief Summary. It is not intended to be all-inclusive and the inventions described and claimed herein are not limited to, or by the features or embodiments identified in, this Brief Summary, which is included for purposes of illustration only and not restriction. Additional embodiments may be disclosed in the Detailed Description below.

BRIEF DESCRIPTION OF THE FIGURES

FIG. 1. Effect of select compounds of the present invention on Stat3 DNA-binding activity in vitro. FIG. 1E shows the EMSA analysis for the compounds of Examples 106-116. FIG. 1H shows the EMSA analysis for the compounds of Examples 147-157. Positions of Stat3:DNA complexes in gel are labeled; control lanes (0) represent nuclear extracts pre-treated with 10% DMSO. Data are representative of 1-3 independent determinations.

FIG. 3. Effects of select compounds of the present invention on Stat3 DNA-binding activity and Stat3 tyrosine phosphorylation in cells. (FIG. 3A) EMSA analysis of Stat3 DNA-binding activity in nuclear extracts of equal total protein prepared from cells treated with DMSO (0 as control, Con), 5 or 10 µM of compounds for 1-34 h. Positions of Stat3:DNA complexes in gel are labeled. FIG. 3B shows immunoblotting analysis of whole-cell lysates of equal total protein prepared from the designated tumor cells treated with DMSO (Control, "Con") or 5 or 10 µM of the indicated compounds for 1-24 h. FIG. 3C shows immunoblotting analysis of or with 0-30 µM of the compound of Example 1 for 1-3 h and probing for pY705Stat3, Stat3 or tubulin. Positions of Stat3:DNA complexes or proteins in gel are shown; control (0 or Con) lane represents whole-cell lysates or nuclear extracts prepared from 0.05% DMSO-treated cells. FIG. 3D shows immunoblotting analyses of whole-cell lysates of equal total protein prepared from the designated tumor cells treated with DMSO (Control, "Con") or 5 or 10 µM of the indicated compounds for 1-24 h of Example 1 at 20, or 10 micromolar against the cell types C8161, 1205LU, or UACC903. Data are representative of 2-3 independent determinations.

FIG. 4. Effects of select compounds of the present invention on Stat3-independent signal transduction events. Immunoblots of pY705Stat3, Stat3, pJak2, Jak2, pSrc, Src, pERK1/2MAPK, and ERK1/2MAPK from whole-cell lysates prepared from MDA-MB-231 cells treated with 5 µM of the indicated compounds for 34 h. Positions of proteins in gel are labeled; control lane (Con) represents whole-cell lysate prepared from 0.05% DMSO-treated cells.

FIG. 5. Effects of select compounds of the present invention on cell viability, growth, colony survival and migration in vitro. FIG. 5A shows that cells in 6-well plates were treated once with 0.05% DMSO, or 3 µM of compound of Example 37 or 5 µM of compound 25 for 0-96 h. Cell numbers were counted by trypan blue exclusion/phase-contrast microscopy every 34 h, and cell growth curve was plotted. FIG. 5B shows that cells in 6-well plates were treated once with 0.05% DMSO or 1-5 µM of compound of Example 37 for 72 h, and cell number was counted by trypan blue exclusion/phase-contrast microscopy and plotted against concentration from which $IC_{50}$ values were derived.

FIG. 6. Effects of select compounds of the present invention on cell viability.

DETAILED DESCRIPTION

Figure 1A:
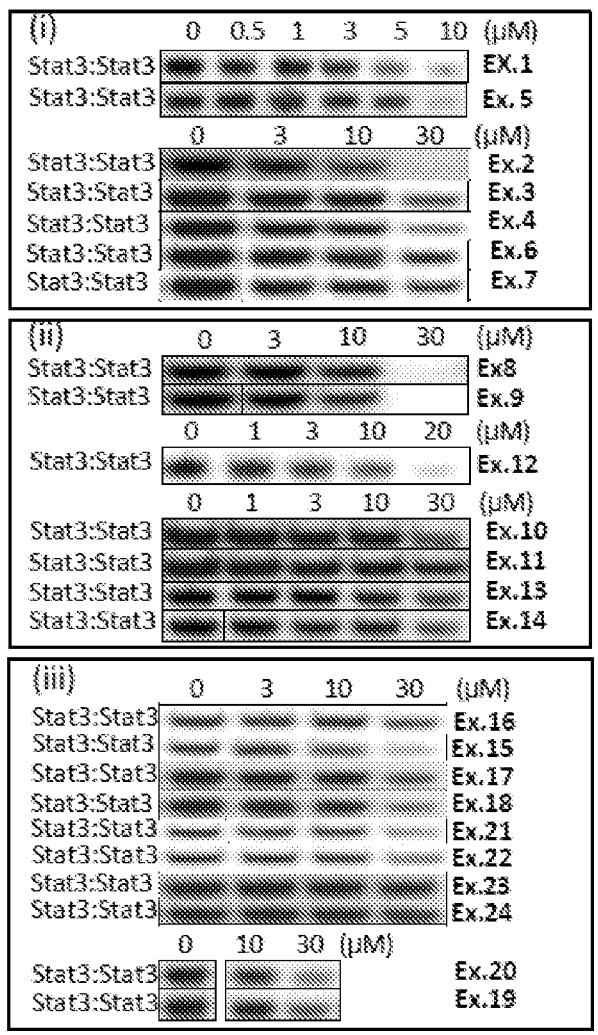
FIG. 1A shows the Electrophoretic mobility shift assay (EMSA) analysis for the compounds of Examples 1-24 of Stat3 DNA-binding activity in nuclear extracts of equal total protein containing activated Stat3 pre-incubated with 0-100 µM of the indicated compounds for 30 min at room temperature prior to incubation with the radiolabeled hSIE probe that binds Stat3.
Figure 1B:
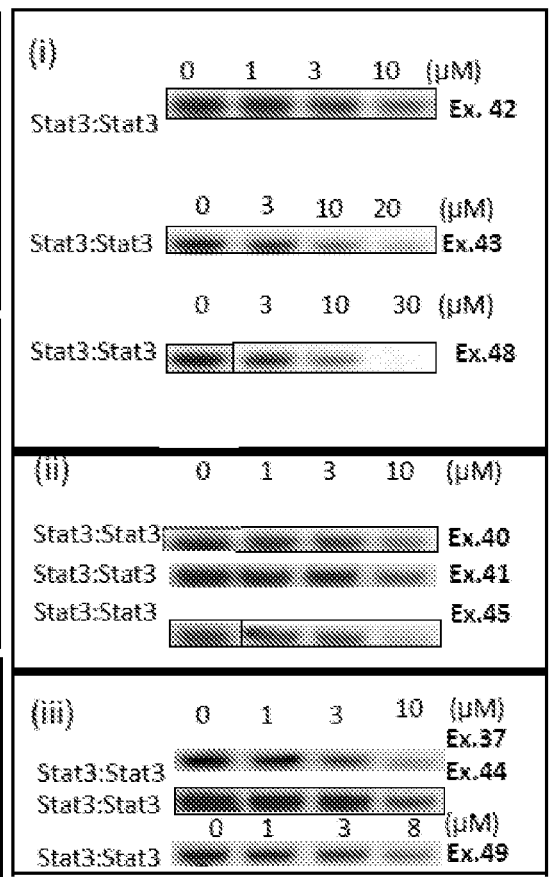
FIG. 1B shows the EMSA analysis for the compounds of Examples 37-49.
Figure 1C:
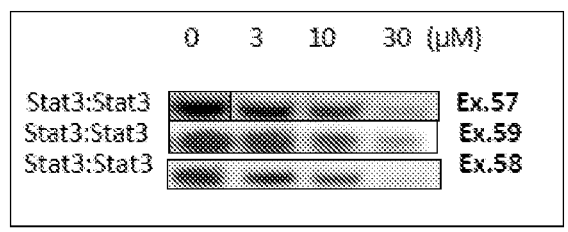
FIG. 1C shows the EMSA analysis for the compounds of Examples 57-59.
Figure 1D:
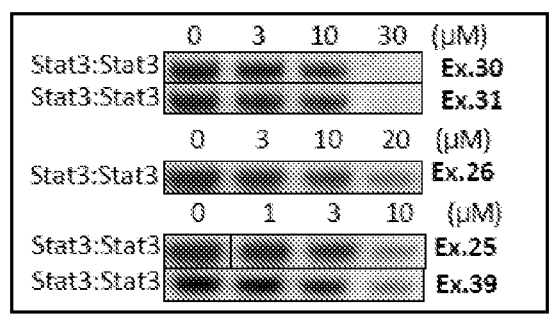
FIG. 1D shows the EMSA analysis of compounds of Examples 25-39.
Figure 1F:
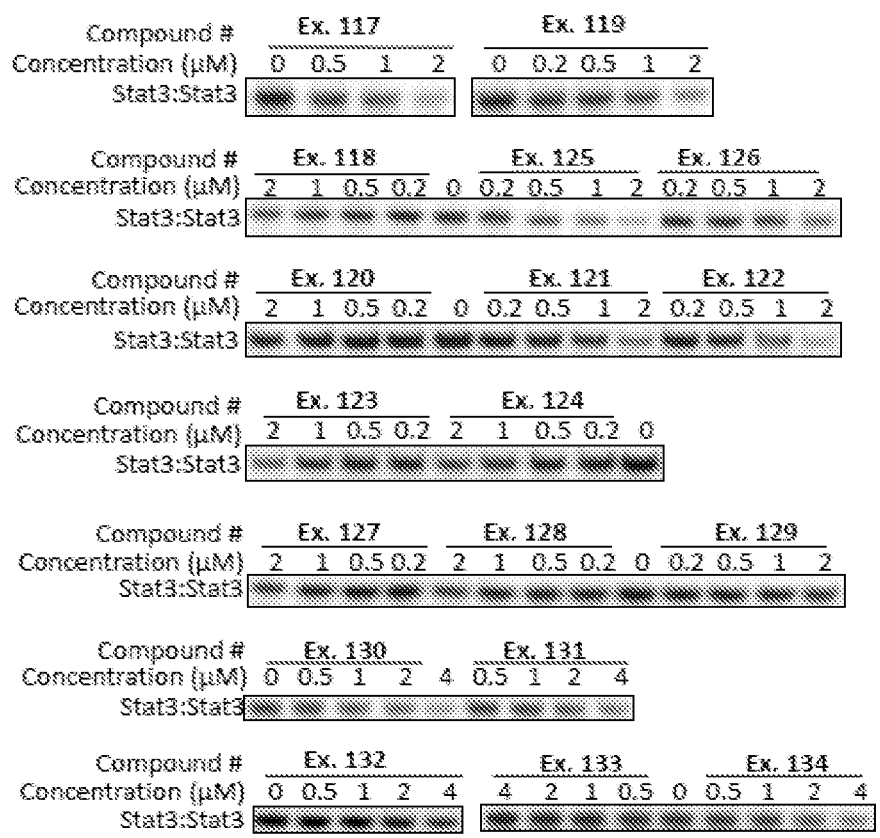
FIG. 1F shows the EMSA analysis for the compounds of Examples 117-134.
Figure 1G:
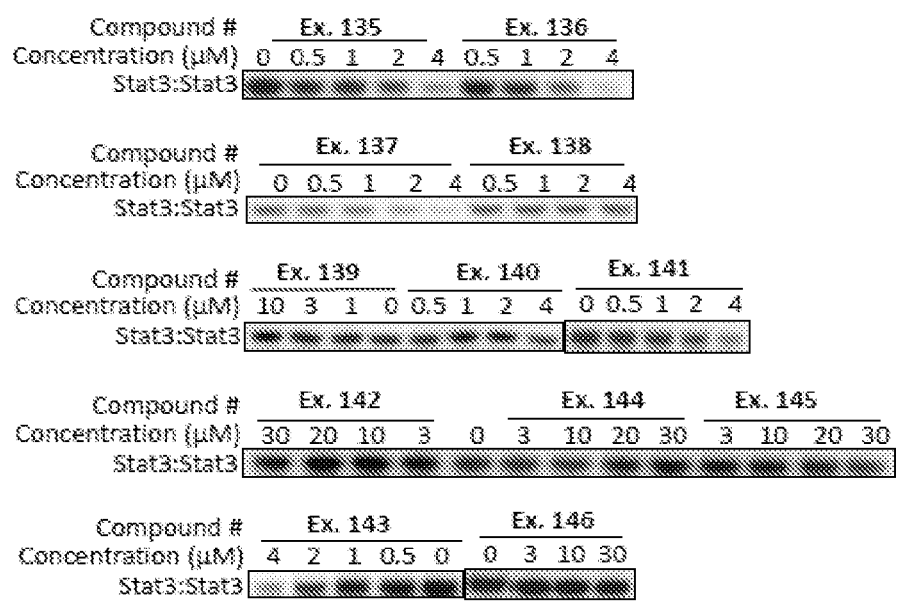
FIG. 1G shows the EMSA analysis for the compounds of Examples 135-146.

The present disclosure relates generally to novel, potent and selective 2-arylsulfonamido-N-arylacetamide derivatized Stat3 inhibitors. Constituitively activated Stat3 has been found to play a role in cancerous cells and the substantially faster proliferation, invasiveness and rate of cancerous cells compared to cells of the non-cancerous origin. In some embodiments, the selective Stat3 inhibitors of this invention can suppress cancer cell growth, proliferation, survival, angiogenesis, migration/invasion and/or immunity. The inhibition of Stat3 can be achieved by inhibiting dimerization of Stat3.

Stat3:Stat3 protein complexes are mediated through reciprocal pTyr705-SH2 domain interactions. Most drugs targeting Stat3 include a phosphoryl group to mimic pTyr705. While the phosphate functionality is regarded as being essential to targeting the SH2 domain, it is unsuitable for drug discovery as it suffers from poor cell permeability and metabolic degradation. As described herein, it was suprisingly found that the compounds of Formulae I-VIII including compounds of Examples 25-31, 50, 52, 53, 60-64, 79, 85, 102, 104, 110, 113, 119, 122, 125, 134-137, 143, 148, 149, 151 and 152 are highly potent 2-arylsulfonamido-N-arylacetamide derivatized Stat3 inhibitors with micromolar and sub-micromolar potency against some of the most aggressive brain cancer cells identified to this date.

The prevalence of constitutively-active Stat3 in human tumors places an increasing importance on the discovery of suitable Stat3-inhibitors as novel anticancer drugs; however, although many Stat3 inhibiting modalities have been reported, no Stat3 small-molecule inhibitor drug has yet reached to the clinic (Miklossy et al., *Nat Rev Drug Discov* 12:611-629 (2013)). As described herein, compounds of Formulae I-VIII including compounds of Examples 25-31, 50, 52, 53, 60-64, 79, 85, 102, 104, 110, 113, 119, 122, 125, 134-137, 143, 148, 149, 151 and 152, exhibit Stat3-inhibitory potency in vitro. As described herein, the compounds also show antitumor cell responses to breast cancer cells at low micromolar concentrations.

Substantive evidence demonstrates that aberrant Stat3 activity promotes cancer cell growth and survival, and induces tumor angiogenesis and metastasis. Inhibitors of Stat3 activation promote antitumor cell effects, although many of these have low potencies (See Turkson et al., *Mol Cancer Ther* 3:261-269 (2004); Turkson et al., *J. Biol. Chem.* 276:45443-45455 (2001); Garcia et al., *Oncogene* 20:2499-2513 (2001); Catlett-Falcone et al., *Immunity* 10:105-115 (1999); Mora et al., *Cancer Res* 62:6659-66 (2002); Niu et al., *Oncogene* 21:2000-2008 (2002); Wei et al., *Oncogene* 22:319-29 (2003); Xie et al., *Oncogene* 23:3550-60 (2004)).

The present disclosure is based on the surprising discovery that certain structurally distinct analogs of previously reported Stat3 inhibitors had unexpected and potentiated therapeutic activity. Mechanistic insight into the biological effects of select compounds of the invention as a Stat3 inhibitor is provided by the evidence disclosed herein of suppression of the constitutive expression of genes regulated by Stat3 genes, including Bcl-2, Bcl-xL, Cyclin D1, c-Myc, and Survivin, which control cell growth and survival (Song et al., *Proc Natl Acad Sci USA.* 102:4700-5 (2005); Zhang et al., *Proc Natl Acad Sci USA* 109:9623-8 (2012); Catlett-Falcone et al., *Immunity* 10:105-115 (1999); Gritsko et al., *Clin Cancer Res.* 12:11-9 (2006)). The inventors have developed potent and physicochemically acceptable compounds with proper selectivity by utilizing a rational, computer-aided molecule optimization and chemical synthesis approach to furnish potent and drug-like compounds. The inventors surprisingly discovered that the compounds of Examples 1, 31, 37, 110, 113, 119, 122, 125, 143, 148, 149, and 152 strongly inhibited Stat3 DNA-binding activity in vitro, with an $IC_{50}$ of 3.0±0.9, 2.4±0.2, 1.80±0.94, 0.46±0.054 µM, 0.337±0.017, 0.511±0.021, 0.534±0.047, 0.628±0.074, 0.664±0.167, 0.612±0.037, 0.628±0.006, and 0.433±0.052 micromolar, respectively. Altogether the present study provides evidence for the inhibition of constitutively-active Stat3 in malignant cells that lead to antitumor cell effects against human breast cancer cells in vitro.

DEFINITIONS

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which comprise oxygen, nitrogen, sulfur, or phosphorous, atoms replacing one or more carbons of the hydrocarbon backbone. The term "aromatic-alkyl" includes alkyl groups substituted with one or more aryl groups. The term "lower alkyl" as used herein refers to 4 or fewer carbons.

The term "aryl" includes groups with aromaticity, including 5- and 6-membered single-ring aromatic groups that may include from zero to four heteroatoms, as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused, or bridged, with alicyclic or heterocyclic rings which are not aromatic, so as to form a multicyclic system (e.g., tetralin, methylenedioxyphenyl).

As used herein, the term "alkylene" refers to divalent saturated aliphatic groups and includes both straight chain and branched chain groups.

As used herein, the term "alkenylene" refers to divalent aliphatic groups having a double bond and includes both straight chain and branched chain groups.

As used herein, the designation "Cy" represents a cyclohexyl moiety. The designation "Cp" represents a cyclopentyl moiety.

As used herein, "cycloalkyl" or "carbocyclic" refers to a radical of a non-aromatic cyclic hydrocarbon group having from 3 to 10 ring carbon atoms ("$C_{3-10}$ cycloalkyl") and zero heteroatoms in the non-aromatic ring system. In some embodiments, a cycloalkyl group has 3 to 8 ring carbon atoms ("$C_{3-8}$ cycloalkyl"). In some embodiments, a cycloalkyl group has 3 to 7 ring carbon atoms ("$C_{3-7}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Exemplary $C_{3-6}$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ cycloalkyl groups include, without limitation, the aforementioned $C_{3-6}$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$) heptanyl ($C_7$), octanyl ($C_8$), and the like. Exemplary $C_{3-10}$ cycloalkyl groups include, without limitation, the aforementioned $C_{3-8}$ cycloalkyl groups as well as cyclononyl ($C_9$), cyclononenyl ($C_9$), cyclodecyl ($C_{10}$), cyclodecenyl ($C_{10}$), and the like. As the foregoing examples illustrate, in certain embodiments, the cycloalkyl group is either monocyclic ("monocyclic cycloalkyl") or polycyclic (e.g., containing a fused or ring system such as a bicyclic system ("bicyclic cycloalkyl") or tricyclic system ("tricyclic cycloalkyl")) and can be saturated or can contain one or more carbon-carbon double or triple bonds. "Cycloalkyl" also includes ring systems wherein the cycloalkyl ring, as defined above, is fused with one or more aryl or heteroaryl groups wherein the point of attachment is on the cycloalkyl ring, and in such instances, the number of carbons continue to designate the number of carbons in the carbocyclic ring system. Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heteroaryl" refers to a radical of a 5-14 membered monocyclic or polycyclic (e.g., bicyclic, tricyclic) 4n+2 aromatic ring system (e.g., having 6, 10, or 14 electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom or the ring that does not contain a heteroatom.

As understood from the above, alkyl, alkenyl, alkylenyl, cycloalkyl, cycloalkenyl, heterocyclyl, aryl, and heteroaryl groups, as defined herein, are, in certain embodiments, optionally substituted. Optionally substituted refers to a group which may be substituted or unsubstituted. In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this present disclosure, heteroatoms such as nitrogen may have hydrogen substituents and/or any suitable substituent as described herein which satisfy the valencies of the heteroatoms and results in the formation of a stable moiety.

As used herein, the term "halo" or "halogen" refers to fluorine (fluoro, —F), chlorine (chloro, —Cl), bromine (bromo, —Br), or iodine (iodo, —I).

As used herein, a "subject" refers to an animal that is the object of treatment, observation or experiment. "Animal" includes cold- and warm-blooded vertebrates and invertebrates, such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, apes, and prenatal, pediatric, and adult humans.

As used herein, "preventing" or "protecting" means preventing in whole or in part, or ameliorating, or controlling.

As used herein, the term "treating" refers to both therapeutic treatment and prophylactic, or preventative, measures, or administering an agent suspected of having therapeutic potential. The term includes preventative (e.g., prophylactic) and palliative treatment.

The term "a pharmaceutically effective amount," as used herein, means an amount of active compound, or pharmaceutical agent, that elicits the biological, or medicinal, response in a tissue, system, animal, or human that is being sought, which includes alleviation or palliation of the symptoms of the disease being treated and/or an amount sufficient to have utility and provide desired therapeutic endpoint. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. In some embodiments, the drug is cytostatic and/or cytotoxic to prevent growth and/or kill existing cancer cells. For cancer therapy, efficacy can be measured, e.g., by assessing the time to disease progression and/or determining the response rate.

The term "pharmaceutically acceptable," as used herein, means that the substance or composition must be compatible chemically and/or toxicologically, with the other ingredients comprising a formulation, and/or the mammal being treated therewith.

The term "cancer" refers to, or describes, the physiological condition in mammals that is characterized by unregulated cell growth and/or hyperproliferative activities. A "tumor" comprises one or more cancerous cells. Examples of cancer include, but are not limited to, carcinoma, lymphoma, blastoma, sarcoma, and leukemia or lymphoid malignancies. In one embodiment, the cancer is a solid tumor. More particular examples of such cancers include breast cancer, cervical cancer, ovarian cancer, bladder cancer, endometrial or uterine carcinoma, prostate cancer, glioma and other brain or spinal cord cancers, squamous cell cancer (e.g., epithelial squamous cell cancer), lung cancer, including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, liver cancer, hepatoma, colon cancer, rectal cancer, colorectal cancer, salivary gland carcinoma, kidney or renal cancer, vulval cancer, thyroid cancer, hepatic carcinoma, anal carcinoma, penile carcinoma, as well as head and neck cancer. In one embodiment, the treatment comprises treatment of solid tumors. In one embodiment, the tumors comprises sarcomas, carcinomas or lymphomas.

In some embodiments, the cancer can include or exclude: brain tumors, such as gliomas, medulloblastomas, cerebral menangiomas, pancreatic cancer, malignant melanoma, multiple myeloma, lymphomas, including anaplastic large T cell lymphoma, sezary syndrome, EBV-related Burkitt's Lymphoma, HSV Saimiri-dependent (T Cell), cutaneous T cell lymphoma, mycosis fungoides, leukemia, including HTLV-I dependent leukemia, erythroleukemia, acute lymphocytic leukemia (ALL), chronic lymphocytic leukemia (CLL), acute myelogenous leukemia (AML), chronic myelogenous lekemia (CML), megakaryocytic leukemia, and large granula lymphocyte (LGL) leukemia, thyroid cancer, brain cancer, skin cancer, lung cancer, and kidney cancer. In some embodiments the cancer can include or exclude renal cell carcinoma, pancreatic adenocarcinoa, ovarian carcinoa or Hodgkin Lymphoma.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: trastuzumab (HERCEPTIN®, Genentech), erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine,dichloroplatinum(II), CAS No. 15663-27-1), carboplatin (CAS No. 41575-94-4), paclitaxel (TAXOL®, Bristol-Myers Squibb Oncology, Princeton, N.J.), pemetrexed (ALIMTA®, Eli Lilly), temozolomide (4-methyl-5-oxo-2,3,4,6,8-pentazabicyclo[4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L- norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate, or inhibit, hormone action on tumors, such as anti-estrogens and selective estrogen receptor modulators (SERMs), including, e.g., tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, e.g., 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, e.g., PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, e.g., ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents, in combination with the compounds of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound, or salt thereof. Metabolites of a compound may be identified using tests such as those described herein. Such products may result e.g., from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The phrase "pharmaceutically acceptable salt" as used herein, refers to pharmaceutically acceptable organic, or inorganic, salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule, such as an acetate ion, a succinate ion, or other counter ion. In some embodiments, the counter ion is any organic, or inorganic, moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

In some embodiments, when the compound of the invention is a base, the desired pharmaceutically acceptable salt is prepared by any suitable method available in the art, e.g., treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

In some embodiments, when the compound of the invention is an acid, the desired pharmaceutically acceptable salt is prepared by any suitable method, e.g., treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association, or complex, of one or more solvent molecules and a compound of the invention. Examples of solvents that form solvates include, but are not limited to, water, isopropanol, ethanol, methanol, DMSO, ethylacetate, acetic acid, and ethanolamine.

Administration of Formulae I-VIII Compounds

In some embodiments, the Formulae I-VIII compounds of the invention, including compounds of Examples 25-31, 50, 52, 53, 60-64, 79, 85, 102, 104, 110, 113, 119, 122, 125, 134-137, 143, 148, 149, 151 and 152 are administered by any route appropriate to the condition to be treated. Suitable routes can include or exclude oral, parenteral (including subcutaneous, intramuscular, intravenous, intraarterial, intradermal, intrathecal and epidural), intraperitoneal (IP), transdermal, rectal, nasal, topical (including buccal and sublingual), vaginal, intrapulmonary and intranasal. In some embodiments, for local treatment, the compounds are administered by intratumor administration, including perfusing or otherwise contacting the tumor with the inhibitor. It will be appreciated that the preferred route may vary with, e.g., the condition of the recipient. In some embodiments, where the compound is administered orally, it is formulated as a pill, capsule, tablet, etc., with a pharmaceutically acceptable carrier or excipient. In some embodiments, where the compound is administered parenterally, it is formulated with a pharmaceutically acceptable parenteral vehicle, and in a unit dosage injectable form, as described herein.

In some embodiments, a dose to treat human patients is from about 1 mg to about 1000 mg of compound of Formulae I-VIII, including compounds of Examples 25-31, 50, 52, 53, 60-64, 79, 85, 102, 104, 110, 113, 119, 122, 125, 134-137, 143, 148, 149, 151 and 152. The dose is from about 1 mg, 2 mg, 2.5 mg, 4 mg, 5 mg, 7.5 mg, 10 mg, 12.5 mg, 15 mg, 17.5 mg, 20 mg, 25 mg, 30 mg, 40 mg, 50 mg, 60 mg, 70 mg, 75 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg of a compound of Formulae I-VIII (including compounds of Examples 25-31, 50, 52, 53, 60-64, 79, 85, 102, 104, 110, 113, 119, 122, 125, 134-137, 143, 148, 149, 151 and 152), or any dose ranging between any two of those doses.

In some embodiments, a dose is administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. In some embodiments, for orally administered doses, the pill, capsule, or tablet is ingested daily or less frequently for a specified period of time. In some embodiments, the regimen is repeated for a number of cycles of therapy.

Methods of Treatment With Formulae I-VIII Compounds

Compounds of Formulae I-VIII, including compounds of Examples 25-31, 50, 52, 53, 60-64, 79, 85, 102, 104, 110, 113, 119, 122, 125, 134-137, 143, 148, 149, 151 and 152, are useful for treating hyperproliferative diseases, conditions and/or disorders including, but not limited to, cancer. Accordingly, an embodiment of this invention includes methods of treating, or preventing, diseases or conditions that can be treated or prevented by inhibiting Stat3. In one embodiment, the method comprises administering to a subject, in need thereof, a therapeutically effective amount of a compound of Formula I, or pharmaceutically acceptable salt thereof. In one embodiment, a human patient is treated with a compound of Formulae I-VIII, including compounds of Examples 25-31, 50, 52, 53, 60-64, 79, 85, 102, 104, 110, 113, 119, 122, 125, 134-137, 143, 148, 149, 151 and 152 and a pharmaceutically acceptable carrier, adjuvant, or vehicle, wherein said compound of Formulae I-VIII, including compounds of Examples 25-31, 50, 52, 53, 60-64, 79, 85, 102, 104, 110, 113, 119, 122, 125, 134-137, 143, 148, 149, 151 and 152, is present in an amount to treat cancer and/or detectably inhibit Stat3 activity.

In some embodiments, the methods of this inventions can treat Cancers which can include or exclude: glioma, glioblastoma, neuroblastoma, breast, ovary, cervix, prostate, testis, genitourinary tract, esophagus, larynx, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

In some embodiments, compounds of Formulae I-VIII, including compounds of Examples 25-31, 50, 52, 53, 60-64, 79, 85, 102, 104, 110, 113, 119, 122, 125, 134-137, 143, 148, 149, 151 and 152, are useful for in vitro, in situ, and in vivo diagnosis or treatment of mammalian cells, organisms, or associated pathological conditions, such as hyperproliferative disease and/or cancer.

In some embodiments, compounds of Formulae I-VIII, including compounds of Examples 25-31, 50, 52, 53, 60-64, 79, 85, 102, 104, 110, 113, 119, 122, 125, 134-137, 143, 148, 149, 151 and 152, are useful for treating conditions of the brain and central nervous system which require transport across the blood-brain barrier. Certain compounds of Formulae I-VIII, including compounds of Examples 25-31, 50, 52, 53, 60-64, 79, 85, 102, 104, 110, 113, 119, 122, 125, 134-137, 143, 148, 149, 151 and 152, have favorable penetrant properties for delivery to the brain. In some embodiments, compounds of Formulae I-VIII, including compounds of Examples 25-31, 50, 52, 53, 60-64, 79, 85, 102, 104, 110, 113, 119, 122, 125, 134-137, 143, 148, 149, 151 and 152 are used to treat disorders of the brain which can include or exclude metastatic and primary brain tumors, such as glioblastoma and melanoma.

In some embodiments, compounds of Formulae I-VIII, including compounds of Examples 25-31, 50, 52, 53, 60-64, 79, 85, 102, 104, 110, 113, 119, 122, 125, 134-137, 143, 148, 149, 151 and 152 are useful for treating eye cancers by localized delivery to the eye. Certain compounds of Formulae I-VIII, including compounds of Examples 25-31, 50, 52, 53, 60-64, 79, 85, 102, 104, 110, 113, 119, 122, 125, 134-137, 143, 148, 149, 151 and 152 have favorable properties for delivery to, and uptake into, the eye. In some embodiments, selected compounds of Formulae I-VIII, including compounds of Examples 25-31, 50, 52, 53, 60-64, 79, 85, 102, 104, 110, 113, 119, 122, 125, 134-137, 143, 148, 149, 151 and 152 enhance efficacy and extend duration of response for treatment of wet AMD in combination with ranibizumab (LUCENTIS®, Genentech, Inc.) and bevacizumab (AVASTIN®, Genentech, Inc.).

Another embodiment of this invention includes a compound of this invention for use in the treatment of the diseases or conditions described herein in a subject, e.g., a human, suffering from such disease or condition. Also provided is the use of a compound of this invention in the preparation of a medicament for the treatment of the diseases and conditions described herein in a warm-blooded animal, such as a mammal, e.g. a human, suffering from such disorder.

Pharmaceutical Formulation/Compositions and Uses

In order to use a compound of Formulae I-VIII, including compounds of Examples 25-31, 50, 52, 53, 60-64, 79, 85, 102, 104, 110, 113, 119, 122, 125, 134-137, 143, 148, 149, 151 and 152 for the therapeutic treatment (including prophylactic treatment) of mammals including humans, in some embodiments the compound is formulated in accordance with standard pharmaceutical practice as a pharmaceutical composition. According to this embodiment of the invention, there is provided a pharmaceutical composition comprising a compound of this invention in association with a pharmaceutically acceptable diluent or carrier.

In some embodiments, a formulation of the present invention is prepared by mixing a compound of Formulae I-VIII, and a carrier, diluent or excipient. Suitable carriers, diluents and excipients include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

In some embodiments, formulations of the present invention are prepared using dissolution and mixing procedures. For example, the bulk drug substance (i.e., compound of the present invention or stabilized form of the compound of Formulae I-VIII, including compounds of Examples 25-31, 50, 52, 53, 60-64, 79, 85, 102, 104, 110, 113, 119, 122, 125, 134-137, 143, 148, 149, 151 and 152 (e.g., complex with a cyclodextrin derivative or other complexation agent) is dissolved in a suitable solvent in the presence of one or more of the excipients described above. In some embodiments, the compound of the present invention is formulated into pharmaceutical dosage forms to provide an easily controllable dosage of the drug and to enable patient compliance with the prescribed regimen.

In some embodiments, the pharmaceutical composition (or formulation) for application is packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

In some embodiments, pharmaceutical formulations of the compounds of the present invention are prepared for various routes and types of administration. In some embodiments, a compound of Formulae I-VIII, including compounds of Examples 25-31, 50, 52, 53, 60-64, 79, 85, 102, 104, 110, 113, 119, 122, 125, 134-137, 143, 148, 149, 151 and 152 having the desired degree of purity is mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. In some embodiments, formulation is conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

In some embodiments, the compound is stored as a solid composition, a lyophilized formulation or as an aqueous solution (e.g. in saline).

In some embodiments, the pharmaceutical compositions of the invention comprising a compound of Formulae I-VIII, including compounds of Examples 25-31, 50, 52, 53, 60-64, 79, 85, 102, 104, 110, 113, 119, 122, 125, 134-137, 143, 148, 149, 151 and 152 is formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In addition to the compounds and salt forms provided herein, the invention includes pharmaceutical compositions, including tablets, capsules, solutions, and suspensions for parenteral and oral delivery forms and formulations, comprising a pharmaceutically acceptable carrier and therapeutically effective amounts of one or more of the 2-arylsulfonamido-N-arylacetamide derivatized Stat3 inhibitors herein provided. Stat3 inhibitor pharmaceutical compositions can include salts and hydrates.

In human and animal therapy for the treatment of cancer, for example in the treatment of cancer and other related disorders, diseases and conditions noted herein, the compounds and their crystal forms described and provided herein, their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice. Preferably, they are administered orally in the form of tablets comprising pharmaceutically acceptable excipients, such as starch or lactose, or in capsules or ovules either alone or in admixture with excipients, or in the form of elixirs, solutions or suspensions comprising flavouring or colouring agents. They can also be injected parenterally, for example, intravenously, intramuscularly or subcutaneously. For parenteral administration, they are best used in the form of a sterile aqueous solution which may contain other substances, for example enough salts or monosaccharides to make the solution isotonic with blood. For buccal or sublingual administration they may be administered in the form of tablets or lozenges which can be formulated in a conventional manner.

In some embodiments, the initial pharmaceutically effective amount of the compound of Formulae I-VIII, including compounds of Examples 25-31, 50, 52, 53, 60-64, 79, 85, 102, 104, 110, 113, 119, 122, 125, 134-137, 143, 148, 149, 151 and 152 administered parenterally per dose will be in the range of about 0.001-10 mg/kg, 0.001-0.01, or 0.01-1.0, or 1.0 to 10.0 or 10.0 to 100.0 mg/kg. In some embodiments, the amount of the compound of Formulae I-VIII, including compounds of Examples 25-31, 50, 52, 53, 60-64, 79, 85, 102, 104, 110, 113, 119, 122, 125, 134-137, 143, 148, 149, 151 and 152 administered parenterally per dose is about 0.05 to 5 mg/kg of patient body weight per day, with the initial range of compound used being 0.05 to 10 mg/kg/day. In some embodiments, a dose is about 1 mg to about 30.0 mg once, twice or four times a day of the compound. In some embodiments, the dose is about 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8. 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.9, 3.0, 3.1, 3.2, 3.3, 3.4, 3.5, 3.6, 3.7, 3.8, 3.9, or about 4.0 mg/kg, or any range in between any two of the recited doses. In some embodiments the dose will be 0.08 mg/kg to about 0.5 mg/kg, from about 0.08 to about 0.24 mg/kg, or from about 0.24 to 0.5 mg/kg. In some embodiments, the effective dose of the Stat3 inhibitor is given in one or more doses. In some embodiments, a therapeutically effective amount is selected from: 0.08, 0.24, or 0.5 mg/kg for each dose.

Acceptable diluents, carriers, excipients and stabilizers are nontoxic to recipients at the dosages and concentrations employed, and include saline and/or buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, e.g., by coacervation techniques or by interfacial polymerization, e.g., hydroxymethylcellulose or gelatin-microcapsules and poly-(methylmethacylate) microcapsules, respectively, in colloidal drug delivery systems (e.g., liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, sustained-release formulations of compounds of Formulae I-VIII, including compounds of Examples 25-31, 50, 52, 53, 60-64, 79, 85, 102, 104, 110, 113, 119, 122, 125, 134-137, 143, 148, 149, 151 and 152 are prepared. In some embodiments, sustained-release formulations can include or exclude semipermeable matrices of solid hydrophobic polymers comprising a compound of Formulae I-VIII, including compounds of Examples 25-31, 50, 52, 53, 60-64, 79, 85, 102, 104, 110, 113, 119, 122, 125, 134-137, 143, 148, 149, 151 and 152 which matrices are in the form of shaped articles, e.g., films, or microcapsules. In some embodiments, examples of sustained-release matrices can include or exclude polyesters, hydrogels (e.g., poly(2-hydroxyethyl-methacrylate), or poly(vinyl alcohol)), polylactides (U.S. Pat. No. 3,773,919 herein incorporated by reference), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations of this disclosure include those suitable for the administration routes detailed herein. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

In some embodiments, formulations of a compound of Formulae I-VIII, including compounds of Examples 25-31, 50, 52, 53, 60-64, 79, 85, 102, 104, 110, 113, 119, 122, 125, 134-137, 143, 148, 149, 151 and 152 suitable for oral administration are prepared as discrete units such as pills, capsules, cachets or tablets each comprising a predetermined amount of a compound of Formulae I-VIII, including compounds of Examples 25-31, 50, 52, 53, 60-64, 79, and 85.

In some embodiments, compressed tablets are prepared by compressing in a suitable machine the active ingredient in a free-flowing form such as a powder or granules, optionally mixed with a binder, lubricant, inert diluent, preservative, surface active or dispersing agent. In some embodiments, molded tablets are made by molding in a suitable machine a mixture of the powdered active ingredient moistened with an inert liquid diluent. In some embodiments, the tablets are coated or scored and are formulated so as to provide slow or controlled release of the active ingredient therefrom.

In some embodiments, the formulations are prepared for oral use in the format which can include or exclude: tablets, troches, lozenges, aqueous or oil suspensions, dispersible powders or granules, emulsions, hard or soft capsules, e.g., gelatin capsules, syrups or elixirs. In some embodiments, formulations of compounds of Formulae I-VIII, including compounds of Examples 25-31, 50, 52, 53, 60-64, 79, 85, 102, 104, 110, 113, 119, 122, 125, 134-137, 143, 148, 149, 151 and 152 intended for oral use are prepared for the manufacture of pharmaceutical compositions and such compositions may contain one or more agents including sweetening agents, flavoring agents, coloring agents and preserving agents, in order to provide a palatable preparation. Tablets comprising the active ingredient in admixture with non-toxic pharmaceutically acceptable excipient which are suitable for manufacture of tablets are acceptable. These excipients can include or exclude inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. In some embodiments, tablets are uncoated or coated by techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In some embodiments, for treatment of the eye or other external tissues, e.g., mouth and skin, the formulations are applied as a topical ointment or cream comprising the active ingredient(s) in an amount of, e.g., 0.075 to 20% w/w. When formulated in an ointment, the active ingredients are employed with either a paraffinic or a water-miscible ointment base. In some embodiments, the active ingredients are formulated in a cream with an oil-in-water cream base.

In some embodiments, the aqueous phase of the cream base can include or exclude a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. In some embodiments, the topical formulations include a compound which enhances absorption or penetration of the active ingredient through the skin or other affected areas. Examples of such dermal penetration enhancers include dimethyl sulfoxide and related analogs.

In some embodiments, the oily phase of the emulsions of this invention is constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formulae I-VIII compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

In some embodiments, the pharmaceutical compositions of compounds of Formulae I-VIII, including compounds of Examples 25-31, 50, 52, 53, 60-64, 79, 85, 102, 104, 110, 113, 119, 122, 125, 134-137, 143, 148, 149, 151 and 152 are in the form of a sterile injectable preparation, such as a sterile injectable aqueous or oleaginous suspension. In some embodiments, the suspension is formulated according to methods using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol prepared as a lyophilized powder. In some embodiments, the acceptable vehicles and solvents that are employed can include or exclude: water, Ringer's solution (including Ringer's lactate solution), Hartmann's solution, Tyrode's solution, and isotonic sodium chloride solution. In some embodiments, sterile fixed oils are employed as a solvent or suspending medium. For this purpose any bland fixed oil is employed including synthetic mono- or diglycerides. In some embodiments, fatty acids such as oleic acid is used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). In some embodiments, the pharmaceutical composition is prepared to provide easily measurable amounts for administration. For example, an aqueous solution intended for intravenous infusion may contain from about 10 to 10,000 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, about 0.5 to 10% w/w, or about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

In some embodiments, formulations for rectal administration are presented as a suppository with a suitable base comprising, e.g. cocoa butter or a salicylate.

Formulations suitable for intrapulmonary or nasal administration have a particle size, e.g. in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. In some embodiments, formulations suitable for aerosol or dry powder administration are prepared and delivered with other therapeutic agents such as compounds heretofore used in the treatment or prophylaxis disorders as described herein.

In some embodiments, formulations suitable for vaginal administration are presented as pessaries, tampons, creams, gels, pastes, foams or spray formulations comprising the active ingredient and pharmaceutically acceptable carriers.

In some embodiments, the formulations are packaged in unit-dose or multi-dose containers, e.g. sealed ampoules and vials, and are stored in a freeze-dried (lyophilized) condition requiring only the addition of the sterile liquid carrier, e.g., water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

In some embodiments, the compounds of Formulae I-VIII, including compounds of Examples 25-31, 50, 52, 53, 60-64, 79, 85, 102, 104, 110, 113, 119, 122, 125, 134-137, 143, 148, 149, 151 and 152 are employed alone, or in combination with other therapeutic agents, for the treatment of a disease or disorder described herein, such as a hyperproliferative disorder (e.g., cancer). In certain embodiments, a compound of Formulae I-VIII, including compounds of Examples 25-31, 50, 52, 53, 60-64, 79, 85, 102, 104, 110, 113, 119, 122, 125, 134-137, 143, 148, 149, 151 and 152 is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formulae I-VIII, including compounds of Examples 25-31, 50, 52, 53, 60-64, 79, 85, 102, 104, 110, 113, 119, 122, 125, 134-137, 143, 148, 149, 151 and 152 such that they do not adversely affect each other. Such compounds are suitably present in combination in amounts that are effective for the purpose intended. In one embodiment, a composition of this invention comprises a compound of Formulae I-VIII, including compounds of Examples 25-31, 50, 52, 53, 60-64, 79, 85, 102, 104, 110, 113, 119, 122, 125, 134-137, 143, 148, 149, 151 and 152 in combination with a chemotherapeutic agent such as described herein.

In some embodiments, the combination therapy is administered as a simultaneous or sequential regimen. In some embodiments, when administered sequentially, the combination is administered in two or more administrations. The combined administration includes coadministration, using separate formulations or a single pharmaceutical formulation, and consecutive administration in either order, wherein preferably there is a time period while both (or all) active agents simultaneously exert their biological activities.

In some embodiments, suitable dosages for any of the above coadministered agents are those presently used and can be lowered due to the combined action (synergy) of the newly identified agent and other chemotherapeutic agents or treatments.

The combination therapy may provide "synergy" and prove "synergistic," i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formulae I-VIII, including compounds of Examples 25-31, 50, 52, 53, 60-64, 79, 85, 102, 104, 110, 113, 119, 122, 125, 134-137, 143, 148, 149, 151 and 152 or a stereoisomer, geometric isomer, tautomer, solvate, metabolite, or pharmaceutically acceptable salt or prodrug thereof, is combined with other chemotherapeutic, hormonal or antibody agents such as those described herein, as well as combined with surgical therapy and radiotherapy. Combination therapies according to the present invention thus comprise the administration of at least one compound of Formulae I-VIII, including compounds of Examples 25-31, 50, 52, 53, 60-64, 79, 85, 102, 104, 110, 113, 119, 122, 125, 134-137, 143, 148, 149, 151 and 152 or a solvate, metabolite, or pharmaceutically acceptable salt or prodrug thereof, and the use of at least one other cancer treatment method. The amounts of the compound(s) of Formulae I-VIII, including compounds of Examples 25-31, 50, 52, 53, 60-64, 79, 85, 102, 104, 110, 113, 119, 122, 125, 134-137, 143, 148, 149, 151 and 152 and the other pharmaceutically active chemotherapeutic agent(s) and the relative timings of administration will be selected in order to achieve the desired combined therapeutic effect.

Metabolites of Formulae I-VIII Compounds

Also falling within the scope of this invention are the in vivo metabolic products of Formulae I-VIII, including compounds of Examples 25-31, 50, 52, 53, 60-64, 79, 85, 102, 104, 110, 113, 119, 122, 125, 134-137, 143, 148, 149, 151 and 152 described herein. Such products may result, e.g., from the condensation, oxidation, reduction, hydrolysis, amidation, deamidation, esterification, deesterification, enzymatic cleavage, and the like, of the administered compound. Accordingly, the invention includes metabolites of compounds of Formulae I-VIII, including compounds of Examples 25-31, 50, 52, 53, 60-64, 79, 85, 102, 104, 110, 113, 119, 122, 125, 134-137, 143, 148, 149, 151 and 152 including compounds produced by a process comprising contacting a compound of this invention with a mammal for a period of time sufficient to yield a metabolic product thereof.

In some embodiments, metabolite products are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined by an analytical chemistry method, e.g., by MS, LC/MS or NMR analysis. The metabolite products, so long as they are not otherwise found in vivo, may be useful in diagnostic assays for therapeutic dosing of the compounds of the invention.

Articles of Manufacture/Kits

In another embodiment of the invention, an article of manufacture, or "kit," containing materials useful for the treatment of the diseases and disorders described above is provided. The kit contains a composition comprising a compound of Formulae I-VIII, including compounds of Examples 25-31, 50, 52, 53, 60-64, 79, and 85. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, e.g., bottles, vials, syringes, blister pack, etc. The container may be formed from a variety of materials such as glass or plastic. The container may hold a compound of Formulae I-VIII, including compounds of Examples 25-31, 50, 52, 53, 60-64, 79, 85, 102, 104, 110, 113, 119, 122, 125, 134-137, 143, 148, 149, 151 and 152, or a composition thereof which is effective for treating the condition and may have a sterile access port (e.g., the container is an intravenous solution bag or a vial having a stopper pierceable by a hypodermic injection needle). At least one active agent in the composition is a compound of Formulae I-VIII, including compounds of Examples 25-31, 50, 52, 53, 60-64, 79, 85, 102, 104, 110, 113, 119, 122, 125, 134-137, 143, 148, 149, 151 and 152. The label or package insert indicates that the composition is used for treating the condition of choice, such as cancer. In addition, the label or package insert may indicate that the patient to be treated is one having a disorder such as a hyperproliferative disorder. In one embodiment, the label or package inserts indicates that the composition comprising a compound of Formulae I-VIII, including compounds of Examples 25-31, 50, 52, 53, 60-64, 79, 85, 110, 113, 119, 122, 125, 143, 148, 149, and 152 is used to treat a disorder resulting from abnormal cell growth. The label or package insert also indicates that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution (including Ringer's lactate solution), Tyrode's solution, Hellmann's solution, and dextrose solution. In some embodiments, the article of manufacture includes or excludes other buffers, diluents, filters, needles, and syringes.

The kit may further comprise directions for the administration of the compound of Formulae I-VIII, including compounds of Examples 25-31, 50, 52, 53, 60-64, 79, 85, 102, 104, 110, 113, 119, 122, 125, 134-137, 143, 148, 149, 151 and 152 and, if present, the second pharmaceutical formulation. For example, if the kit comprises a first composition comprising a compound of Formulae I-VIII, including compounds of Examples 25-31, 50, 52, 53, 60-64, 79, 85, 102, 104, 110, 113, 119, 122, 125, 134-137, 143, 148, 149, 151 and 152, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formulae I-VIII, including compounds of Examples 25-31, 50, 52, 53, 60-64, 79, 85, 102, 104, 110, 113, 119, 122, 125, 134-137, 143, 148, 149, 151 and 152, such as tablets or capsules. Such a kit preferably includes a number of unit dosages. Such kits can include a card having the dosages oriented in the order of their intended use. An example of such a kit is a "blister pack." Blister packs are well known in the packaging industry and are widely used for packaging pharmaceutical unit dosage forms. If desired, a memory aid can be provided, e.g. in the form of numbers, letters, or other markings or with a calendar insert, designating the days in the treatment schedule in which the dosages can be administered.

According to one embodiment, a kit may comprise (a) a first container with a compound of Formulae I-VIII, including compounds of Examples 25-31, 50, 52, 53, 60-64, 79, 85, 102, 104, 110, 113, 119, 122, 125, 134-137, 143, 148, 149, 151 and 152 contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution (including Ringer's lactate solution), Hellmann's solution, Tyrode's solution, and dextrose solution. It may further include other materials desirable from a commercial and user standpoint, including other buffers, diluents, filters, needles, and syringes.

In certain other embodiments wherein the kit comprises a composition of Formulae I-VIII, including compounds of Examples 25-31, 50, 52, 53, 60-64, 79, 85, 102, 104, 110, 113, 119, 122, 125, 134-137, 143, 148, 149, 151 and 152 and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

The invention includes an article of manufacture comprising packaging material containing one or more dosage forms containing a Stat3 inhibitor provided herein, wherein the packaging material has a label that indicates that the dosage form can be used for a subject having or suspected of having or predisposed to any of the diseases, disorders and/or conditions described or referenced herein. Such dosage forms include, for example, tablets, capsules, solutions and suspensions for parenteral and oral delivery forms and formulations.

In yet another aspect of this invention is a kit comprising (a) at least one Stat3 inhibitor described herein, or salt or crystal thereof, and a pharmaceutically acceptable carrier, excipient and/or additive in a unit dosage form, and (b) means for containing the unit form. Since the present invention has an aspect that relates to the treatment of the disease/conditions described herein with a combination of active ingredients, the invention also relates to combining separate pharmaceutical compositions in kit form. A kit may contain a pharmaceutical composition comprising a Stat3 inhibitor, or salt or crystal thereof, as provided herein, either alone or together with a second compound as described herein.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Synthesis of Stat3 Inhibitors

The reaction schemes 1-4 show exemplary reaction schemes for the preparation of selected Stat3 inhibitor compounds of this invention, which may include a Stat3 inhibitor salt.

The preparation of the 4-(N-benzyl-(N-methylpentafluorophenylsulfonamido)acylamino)benzoic acids is illustrated in Scheme 1 with the preparation of the alanine-based benzoic acid derivatives of Examples 1-4. Sulfonamide 7 was prepared from D-alanine t-butyl ester using pentafluorobenzenesulfonyl chloride to provide intermediate sulfonamide 6, which was readily N-methylated in good overall yield. Deprotection of the t-butyl ester using TFA provided the acid, which was cleanly converted to the acid chloride 8 using oxalyl chloride and catalytic DMF. Acylation of aniline 9 with acid chloride 8 could be effected using the standard DMAP conditions or through the metallated anilide by pre-treating the aniline with methyl magnesium bromide or trimethylaluminum before introduction of acid chloride. The best yield was obtained using the latter method provided amide 10 in 83% yield. Both O-benzyl-protecting groups could be cleanly removed by catalytic hydrogenolysis to afford the salycilate 1b that could be converted to the corresponding sodium salt 1b using sub-stoichiometric quantities of sodium bicarbonate. Benzoic acid analog 1c was prepared starting from aniline 10 using the standard DMAP coupling procedure. Further elaboration to the corresponding benzohydroxamic acid 1d (the compound of Example 4) was accomplished by coupling the corresponding acid chloride with O-benzylhydroxylamine followed by catalytic hydrogenolysis of the benzyl protecting group. In parallel, the corresponding enantiomeric analogs of Examples 5-7 were prepared starting from L-alanine t-butyl ester. Other amino acid-based benzoic acid derivatives were prepared analogously starting from the appropriate orthogonally-protected amino acid starting material. In each case, before the final hydrogenolysis step, normal-phase chiral HPLC was used to determine the enantiomeric purity.

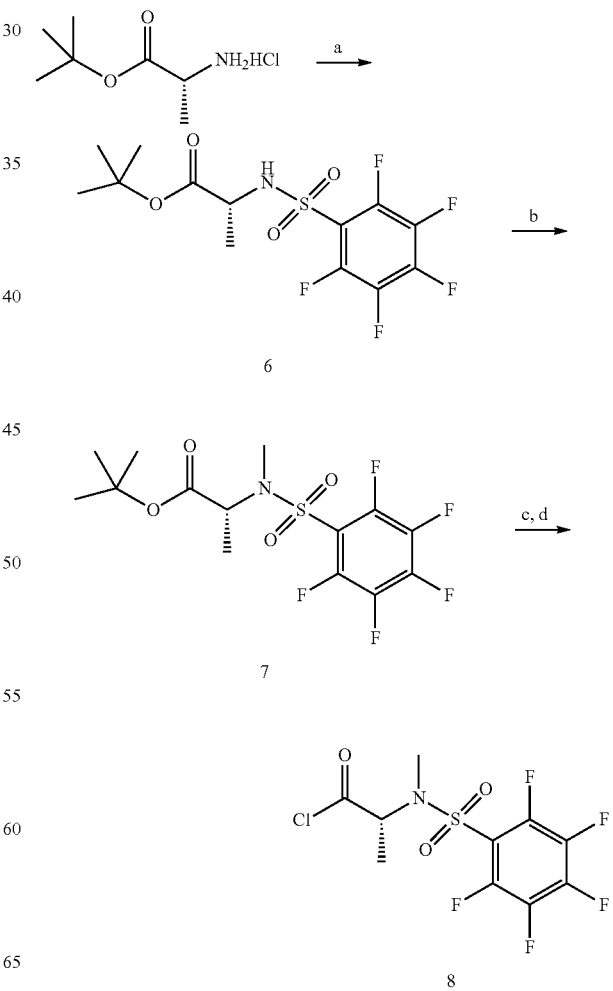

Scheme 1.

45
-continued
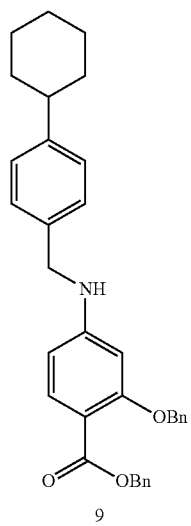
9
e, f →
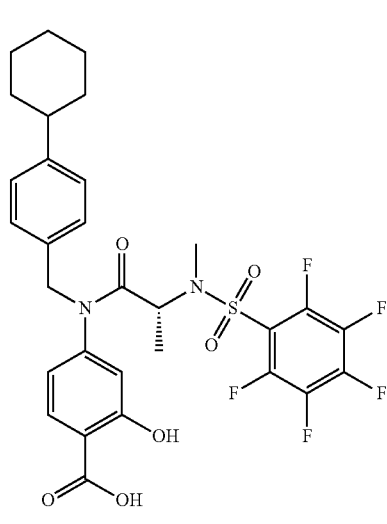
1a
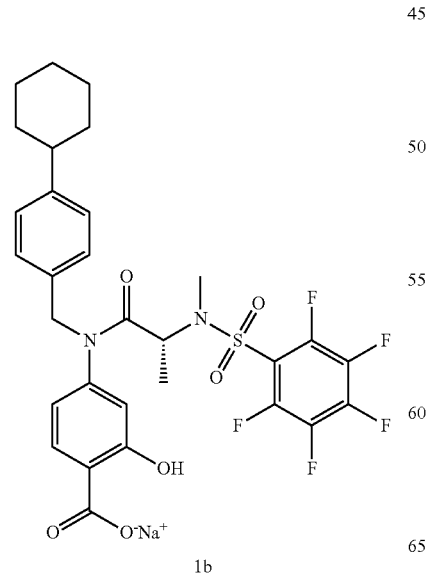
1b
46
-continued
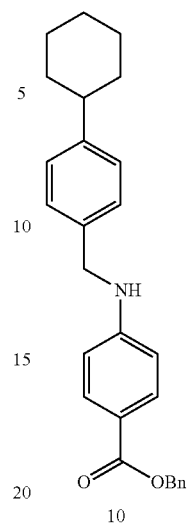
10
h, i →
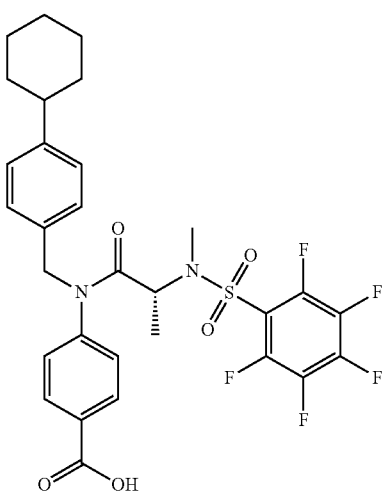
1c
j →
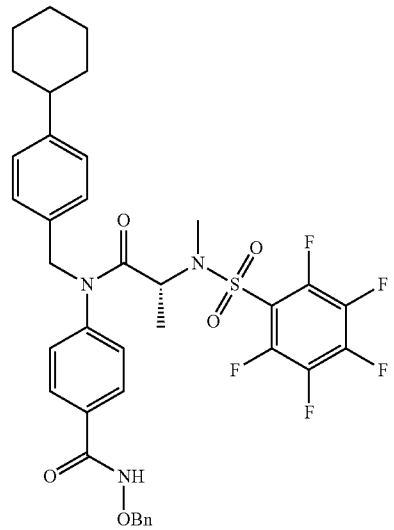
11
k →

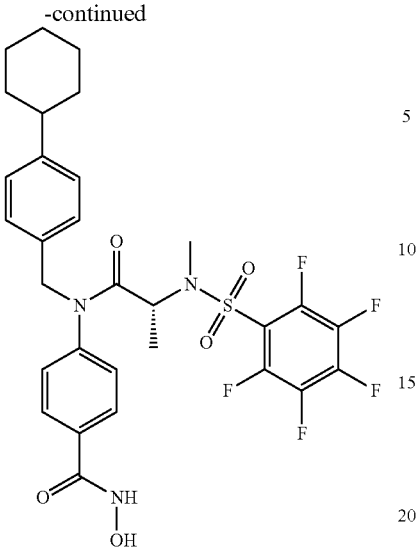

1d

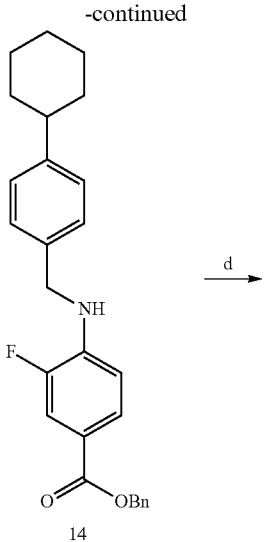

14

Reagents and conditions: a) DIPEA (2.3 eq), pentafluorobenzenesulfonyl chloride (1.1 eq), DCM, 0° C. then rt, 14 h, 80%; b) $K_2CO_3$, DMF, rt 10 min, then $CH_3I$, 1 h, 96%; c) 1:1 TFA: DCM, 12 h, 98%; d) oxalyl chloride DMF, DCM, 95%; e) i. $Me_3Al$ (2M in toluene, 2.5 eq), THF, 0° C. then rt, 15 min, ii. 8, reflux 3 h, 83%; f) $H_2$, 10% Pd/C, 1:1 MeOH: THF, rt, 2 h, 100%; g) $NaHCO_3$ (0.9 eq), THF, MeOH, $H_2O$ (1:1:1); h) 8 (1.5 eq), DMAP (1.2 eq), DCM, rt, 20 h, 44%; i) $H_2$, 10% Pd/C, 1:1 MeOH: THF, rt, 12 h, 100%; j) i. oxalyl chloride (1.2 eq), DMF (1 drop), DCM, 2 h, ii. HNOBn·HCL (1.4 eq in DMF), TEA (2.6 eq), THF, 0° C. then rt, 1.5 h, 64%; k) $H_2$, 10% Pd/C, 1:1 MeOH: THF, rt, 1 h, 81%.

An example of variation of the benzoic acid portion of the molecule is illustrated in Scheme 2 with the preparation of analogs 2v (the compound of Example 37) and 2w (the compound of Example 38). Starting with protection of 3-fluoro-4-nitrobenzoic acid as the benzyl ester using benzyl bromide and potassium carbonate, followed by reduction of the nitro group with stannous chloride, aniline 13 was prepared in 88% overall yield. Reductive alkylation with 4-cyclohexylbenzaldehyde using sodium cyanoborohydride in TFA (WO 2013056070, herein incorporated by reference) provided the desired secondary aniline 14 which was acylated through the corresponding aluminum anilide with acid chloride 8 to give the benzyl-protected intermediate 15. Catalytic hydrogenolysis afforded benzoic acid derivative compound 2v, which was further elaborated to the benzohydroxamic acid 2w using the method described above for compound 1d.

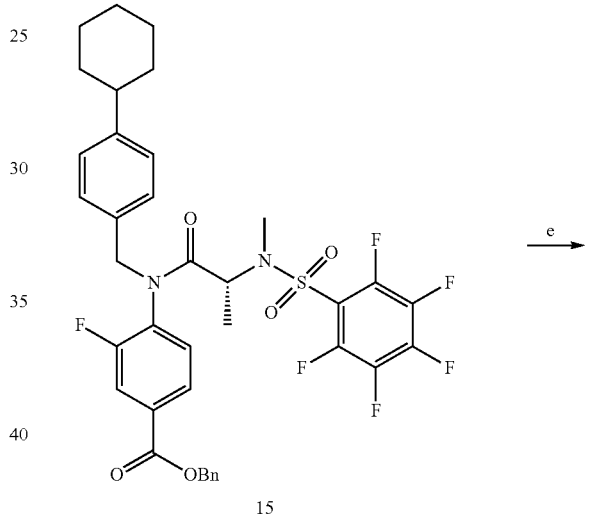

15

Scheme 2.

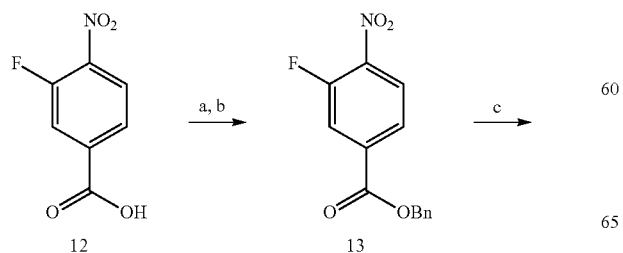

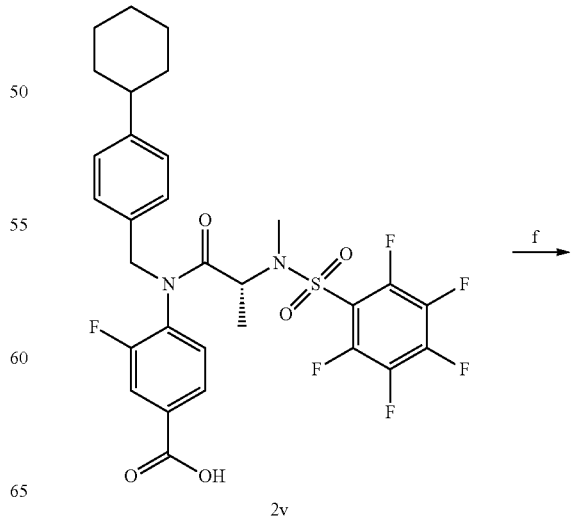

2v

Scheme 3.

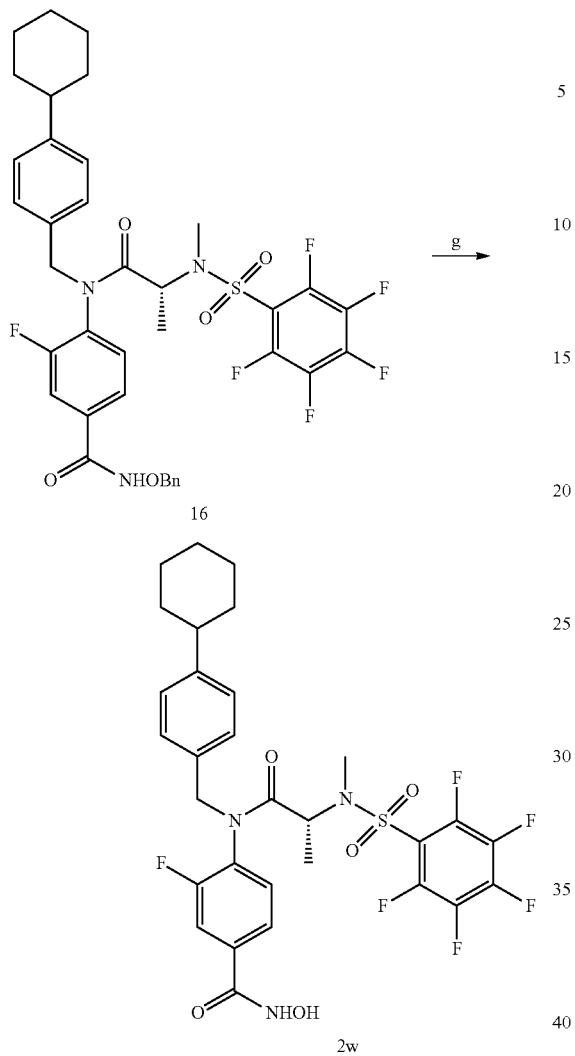

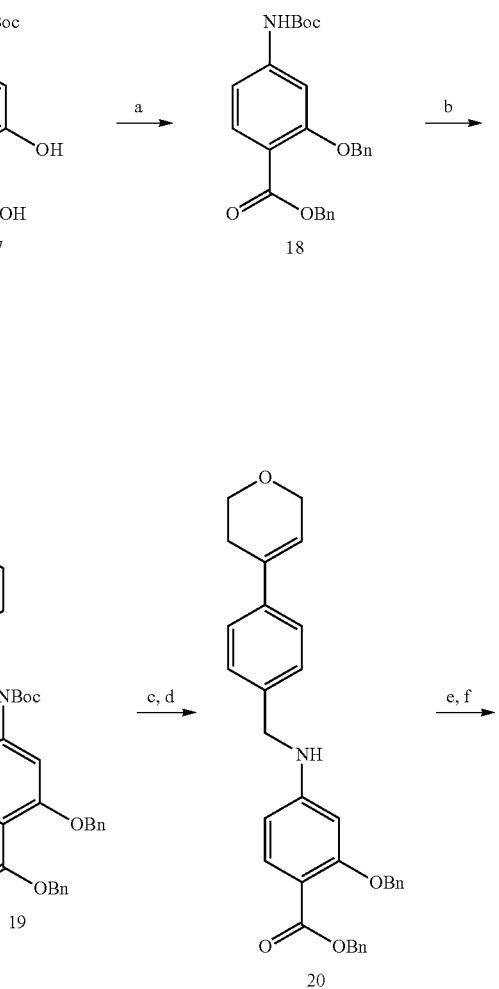

Reagents and conditions: a) K₂CO₃ (1.1 eq), benzyl bromide (0.95 eq), DMF, rt, 4 h; b) SnCl₂•2H₂O (5.0 eq), EtOAc, 80° C., 16 h, 90% for 2 steps; c) NaBH(OAc)₃, TFA, 0° C., 10 min, then 4-cyclohexylbenzaldehyde, rt, 4 h, 74%; d) i. Me₃Al (2M in toluene, 2.5 eq), THF, 0° C. then rt, 15 mn, ii. 8, 80° C., 4.5 h, 48%; e) H₂, 10% Pd/C, 1:1 MeOH: THF, rt, 97%; f) i. oxalyl chloride (1.2 eq), DMF (1 drop), DCM, 2 h, ii. HNOBn•HCl (1.4 eq in DMF), TEA (2.8 eq), THF, 0° C. then rt, 1 h 31%; g) H₂, 10% Pd/C, 1:1 MeOH: THF, rt 53%.

Scheme 3 demonstrates preparation of analogs with variation of the cyclohexylbenzyl group as represented by the synthesis of tetrahydropyranylbenzyl analogs 4b (the compound of Example 57) and 4c (the compound of Example 59). Deprotonation of anilide 18 with KHMDS and alkylation with 4-bromobenzylbromide gave intermediate arylbromide 19. Suzuki-Miyaura cross coupling reaction of 19 with 3,6-dihydro-2H-pyran-4-boronic acid pinacol ester to obtain the dihydropyanyl intermediate followed by thermal removal of the t-butoxycarbonyl protecting group using hexafluoroisopropanol (as described in WO 2013056070, herein incorporated by reference) afforded the desired aniline 20. Coupling with acid chloride 8 using trimethylaluminum and subsequent hydrogenolysis of the salicylate protecting groups yielded the tetrahydropyran (THP) analog 4b, which was subsequently converted to the sodium salt, compound 4c.

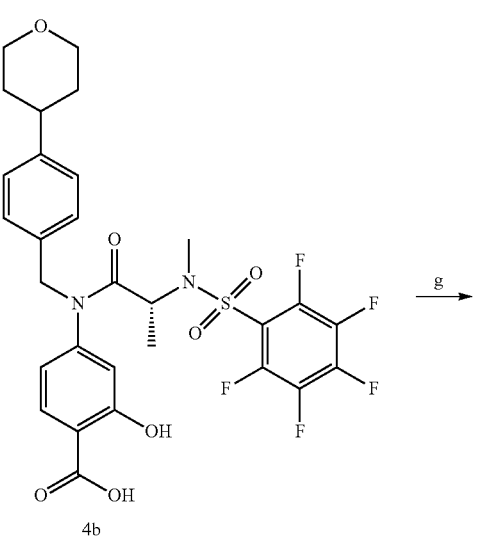

-continued

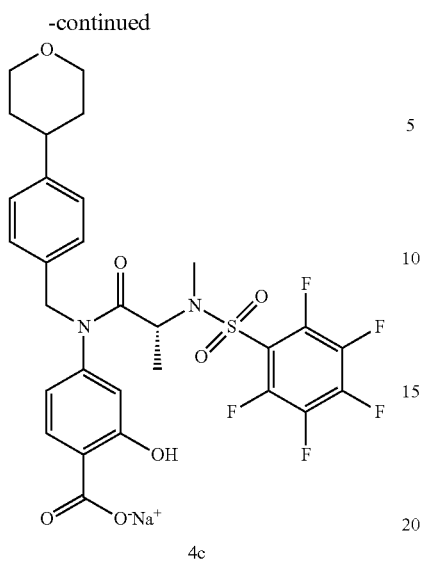

4c

Reagents and conditions: a) K₂CO₃ (2.2 eq), benzyl bromide (2.1 eq), DMF, rt, 14 h, 92%; b) i. KHMDS (1.2 eq), DMF, 0° C., 10 min, ii. 4-bromobenzyl bromide (1.4 eq), 0° C. then rt, 14 h, 84%; c) 3,6-dihydro-2H-pyran-4-boronic acid pinacol ester (1 eq), K₃PO₄ (2 eq), SPhos (0.1 eq), Pd(OAc)₂ (0.05 eq), H₂O (2 eq), THF, 40° C., 14 h, 30%; d) HFIP (0.06 M), sealed tube, 120° C., 15 h, 73%; e) i. Me₃Al (2M in toluene, 2.5 eq), THF, 0° C. then rt, 15 min, ii. 8 (1.4 eq), reflux 2 h, 42%; f) H₂, 10% Pd/C, 1:1 MeOH: THF, rt, 2 h, 100%; g) NaHCO₃ (0.9 eq), THF, MeOH, H2O (1:1:1).

The synthesis of proline analog 5d (the compound of Example 31) (Scheme 4) was similar to that described for the alanine analog. The starting D-proline acid chloride 24 was prepared from D-proline t-butyl ester in 3 steps in 93% overall yield as a stable white solid. After pre-treatment of aniline 9 with trimethylaluminum, coupling with acid chloride 24 and final hydrogenolysis of the resultant intermediate 24, the desired product 5d was obtained in 48% overall yield. THP analog 5g (the compound of Example 27) was prepared using a modified route (Scheme 4). Deprotonation of anilide 18 with KHMDS and alkylation with (4-(bromomethyl)phenyl)boronic acid gave intermediate boronic acid compound 25 in 54% yield.

The boronic acid 25 was coupled to the sulfonylhydrazide 26 in the presence of cesium carbonate in dioxane at 110° C. following Allwood's procedure (Allwood, D., et al., (2014) J. Org. Chem. 79:328-338) providing the protected aniline 27 in 66% yield. Treatment with TFA gave the aniline 28 which was converted to product 5g in 89% yield by acylation with acid chloride 23 in the presence of DMAP, followed by catalytic hydrogenolysis of the purified intermediate. Treatment of 5g with a sub-stoichiometric amount of sodium bicarbonate afforded the sodium salt, compound 5h (the compound of Example 28).

Scheme 4.

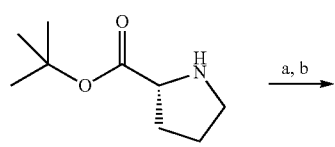

-continued

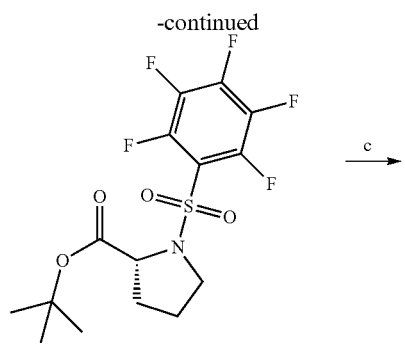

23

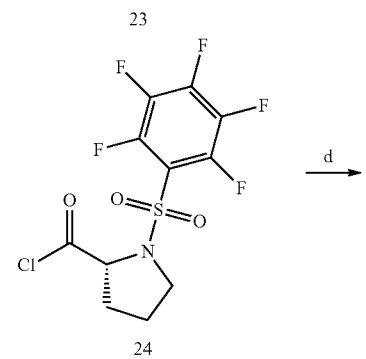

24

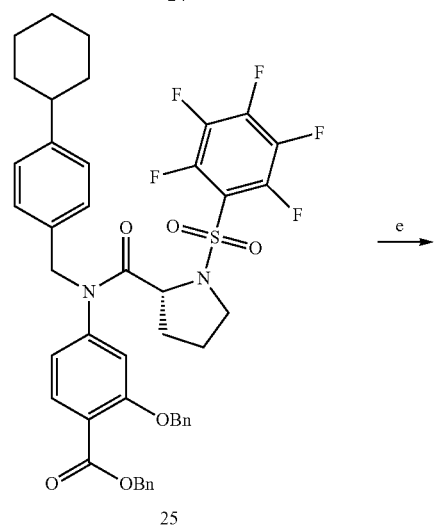

25

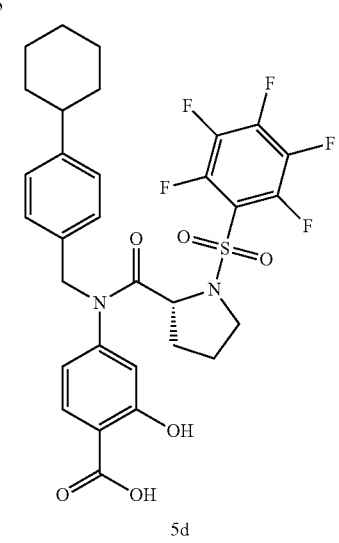

5d

53

-continued

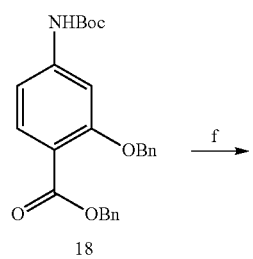
18 f→

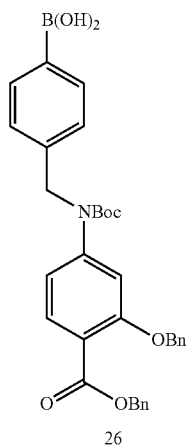
26

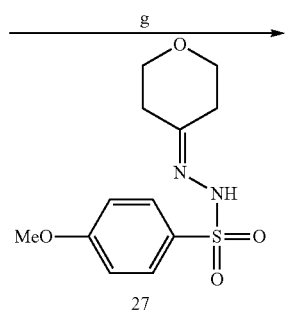
27 g→

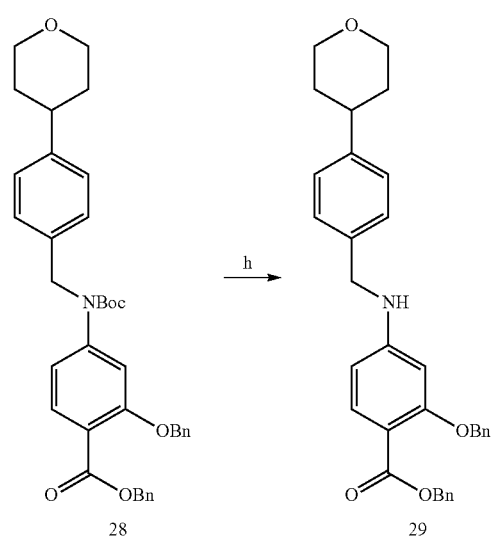
28 → h → 29 → i, e →

54

-continued

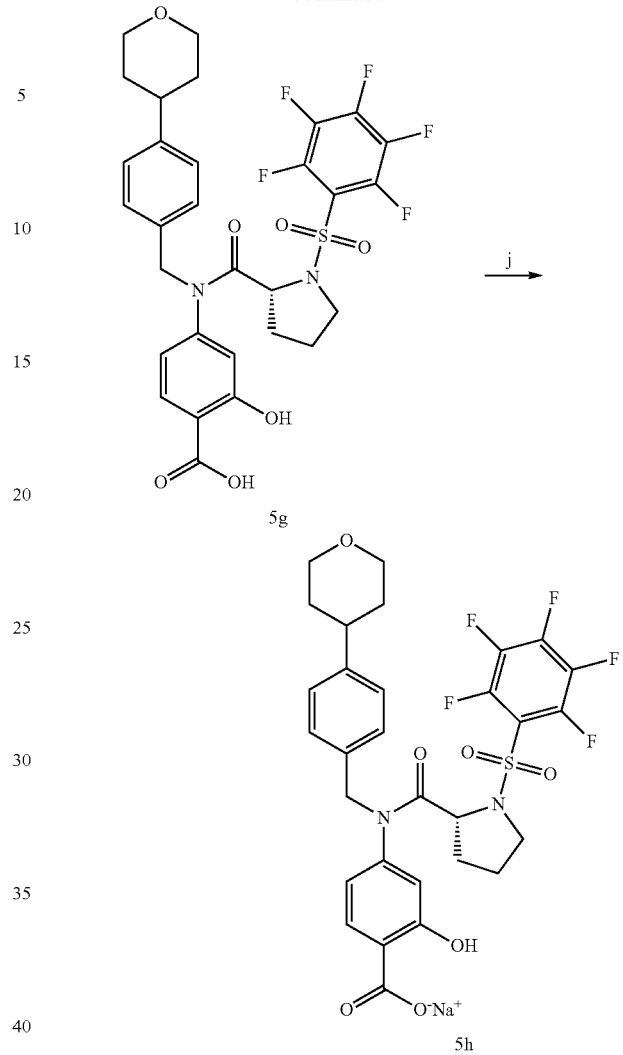

Reagents and conditions: a) DIPEA (1.4 eq), pentafluorobenzenesulfonyl chloride (1.2 eq), DCM, 0° C. then rt, 14 h; b) 1:1 TFA: DCM, 12 h, 98%; c) oxalyl chloride, DMF, DCM, 95%; d) i. Me$_3$Al (2M in toluene, 2.5 eq), THF, 0° C. then rt, 15 min, ii. 9, reflux, 4 h, 48%; e) H$_2$, 10% Pd/C, 1:1 MeOH: THF, rt, 2 h, 100%; f) i. KHMDS (2 eq), DMF, 0° C., 10 min, ii. (4-(bromomethyl)phenyl)boronic acid (1.4 eq) 0° C. then rt, 14 h, 54%; g) 27[37] (0.7 eq), Cs$_2$CO$_3$ (1 eq), dioxane, 110° C., 24 h, 55-66%; h) TFA/DCM (5:1), 0° C., 1.4 h, 64%; i) 24 (1.5 eq), DMAP (1.2 eq) DCM, rt, 23 h, 89%; j) NaHCO$_3$ (0.9 eq), THF, MeOH, H$_2$O (1:1:1).

Organic acids include both aliphatic and aromatic carboxylic acids and include, for example, aliphatic monocarboxylic acids, aliphatic dicarboxylic acids, aliphatic tricarboxylic acids, aromatic monocarboxylic acids, aromatic dicarboxylic acids, and aromatic tricarboxylic acids.

Aliphatic carboxylic acids may be saturated or unsaturated. Suitable aliphatic carboxylic acids include those having from 2 to about 10 carbon atoms.

Aliphatic monocarboxylic acids include saturated aliphatic monocarboxylic acids and unsaturated aliphatic monocarboxylic acids. Examples of saturated monocarboxylic acids include acetic acid, propronic acid, butyric acid, valeric acid, caproic acid, enanthic acid, caprylic acid, pelargonic acid, and caprynic acid. Examples of unsaturated aliphatic monocarboxylic acids include acrylic acid, propiolic acid, methacrylic acid, crotonic acid and isocrotonic acid.

Aliphatic dicarboxylic acids include saturated aliphatic dicarboxylic acids and unsaturated aliphatic dicarboxylic acids. Examples of saturated aliphatic dicarboxylic acids include oxalic acid, malonic acid, succinic acid, glutaric acid, adipic acid, pimelic acid, suberic acid, azelaic acid, and sebacic acid. Examples of unsaturated aliphatic dicarboxylic acids include maleic acid, fumaric acid, citraconic acid, mesaconic acid, itaconic acid and the like.

In certain aspects, crystalline 2-arylsulfonamido-N-arylacetamide derivatized Stat3 inhibitors and salts thereof are described. These include crystalline Stat3 inhibitor maleate, Stat3 inhibitor fumarate, and Stat3 inhibitor succinate. Different Stat3 inhibitor crystals include those comprising the geometric structures, unit cell structures, and structural coordinates.

Also described are Stat3 inhibitor salts of high purity, methods for their preparation, and dosage forms including Stat3 inhibitor salts.

The pharmaceutical compositions may include, for example, one or more pharmaceutically acceptable excipients, carriers, and/or additives suitable for oral or parenteral administration.

The product formed by the described processes is substantially pure, that is, substantially free from any other compounds. Preferably, it contains less than 10% impurities, and more preferably, less than about 5% impurities, and even more preferably, less than about 1% impurities. The product thus formed is also preferably substantially pure, i.e., contains less than 10% impurity, more preferably less than 5% impurity, and still more preferably less than 1% impurity. The present invention also includes a substantially pure anhydrous crystalline form of Stat3 inhibitor disuccinate. The term "substantially pure" means that a sample of the relevant anhydrous crystalline form of Stat3 inhibitor disuccinate contains more than 90% of a single polymorphic form, preferably more than 95% of a single polymorphic form, and still more preferably more than 99% of a single polymorphic form.

Doses

In some embodiments, a therapeutically effective amount of the compounds herein and their pharmaceutically acceptable salts and solvates, is from about 1 mg to about 1000 mg of Formulae I-VIII compounds including compounds of Examples 25-31, 50, 52, 53, 60-64, 79, and 85. The dose is from about 1 mg, 2 mg, 2.5 mg, 4 mg, 5 mg, 7.5 mg, 10 mg, 12.5 mg, 15 mg, 17, 5 mg, 20 mg, 25 mg, 30 mg, 40 mg, 50 mg, 60 mg, 70 mg, 75 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg of a compound of Formulae I-VIII including compounds of Examples 25-31, 50, 52, 53, 60-64, 79, 85, 102, 104, 110, 113, 119, 122, 125, 134-137, 143, 148, 149, 151 and 152 or any dose ranging between any two of those doses.

In some embodiments, a dose is about 1 mg to about 30.0 mg once, twice or four times a day of the compound. In some embodiments, the dose is about 0.05, 0.06, 0.07, 0.08, 0.09, 0.1, 0.2, 0.3, 0.4, 0.5, 0.6, 0.7, 0.8. 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.9, 3.0, 3.1, 3.2, 3.3, 3.4, 3.5, 3.6, 3.7, 3.8, 3.9, 4.0, 5.0, 6.0, 7.0, 8.0, 9.0, 10.0, 11.0, 12.0, 13.0, 14.0, 15.0, 16.0, 17.0, 18.0, 19.0, 20.0, 22.5, 25.0, 27.5, 30.0, 32.5, 35.0, 37.5, or about 40.0 mg/kg, or any range in between any two of the recited doses. In some embodiments the dose will be 0.08 mg/kg to about 0.5 mg/kg, from about 0.08 to about 0.24 mg/kg, or from about 0.24 to about 0.5 mg/kg. In some embodiments, the effective dose of the 2-arylsulfonamido-N-arylacetamide derivatized Stat3 inhibitor is given in one or more doses. In some embodiments, the therapeutically is selected from: 0.08, 0.24, and 0.5 mg/kg for each dose.

In some embodiments, a daily dosage level of the compounds herein, and their pharmaceutically acceptable salts and solvates, is from about 1 mg to about 5 g per day, or up to about 50 g per day (in single or divided doses). Other therapeutically effective dose ranges include, for example, from about 5 mg to about 25 mg, from about 5 mg to about 15 mg, from about 4 mg to about 35 mg, from about 35 mg to about 50 mg, from about 50 mg to about 100 mg, from about 100 mg to about 200 mg, from about 200 mg to about 500 mg, or from about 500 mg to about 1000 mg per day. In some embodiments, the total dose is selected from: 1 mg BID, 2 mg BID, 3 mg BID, 4 mg BID, 5 mg BID, 6 mg BID, 7 mg BID, 8 mg BID, 9 mg BID, 10 mg BID, 20 mg BID, 30 mg BID, 40 mg BID, 50 mg BID, 60 mg BID, 70 mg BID, 80 mg BID, 90 mg BID, 100 mg BID, 110 mg BID, 120 mg BID, 130 mg BID, 140 mg BID, 150 mg BID, 160 mg BID, 170 mg BID, 180 mg BID, 190 mg BID, 200 mg BID, 250 mg BID, 300 mg BID, or any total dose range between any of the aforementioned dose values.

Compounds described herein, and their pharmaceutically acceptable salts and solvates, will also be effective at doses in the order of $\frac{1}{10}$, $\frac{1}{50}$, $\frac{1}{100}$, $\frac{1}{200}$, $\frac{1}{300}$, $\frac{1}{400}$, $\frac{1}{500}$ and even $\frac{1}{1000}$ of those described herein.

In some embodiments of the invention, a therapeutically effective amount is the amount effective to elicit a plasma concentration of the compounds provided herein, and their pharmaceutically acceptable salts and solvates, from about 0.01 mg/L to about 20 mg/L, about 0.01 mg/L to about 15 mg/L, about 0.1 mg/L to about 10 mg/L, about 0.5 mg/L to about 9 mg/L, about 1 mg/L to about 8 mg/L, about 2 mg/L to about 7 mg/L or about 3 mg/L to about 6 mg/L.

In some embodiments, the doses described herein are administered in a single dose or multiple doses. In some embodiments, the doses are administered once, twice, three, four or more times a day, or one, two, three, four, five, or six times per week.

The physician will determine the actual dosage which will be most suitable for an individual patient, and it will vary with the age, weight and response of the particular patient. The above dosages are exemplary of the average case; there can, of course, be individual instances where higher or lower dosage ranges are merited, and such are within the scope of this invention.

Generally, in humans, IP administration of the compounds of the invention is the preferred route. A preferred oral dosing regimen in cancer treatment for a typical man is from about 1 mg to about 1000 mg per day of compound when required. Preventative doses are lower, from about 0.3-100 mg to about 1-50 mg per day.

For veterinary use, a compound provided herein, or a veterinarily acceptable salt thereof, or a veterinarily acceptable solvate of either entity, is administered as a suitably acceptable formulation.

Thus the invention provides a pharmaceutical composition comprising a 2-arylsulfonamido-N-arylacetamide derivatized Stat3 inhibitor, which may include a Stat3 inhibitor salt compound provided herein, or a pharmaceutically acceptable salt thereof, or a pharmaceutically acceptable solvate of either entity, together with a pharmaceutically acceptable diluent or carrier.

It further provides a veterinary formulation comprising a 2-arylsulfonamido-N-arylacetamide derivatized Stat3 inhibitor provided herein, or a veterinarily acceptable salt thereof, or a veterinarily acceptable solvate of either entity, together with a veterinarily acceptable diluent or carrier.

The invention also provides a 2-arylsulfonamido-N-arylacetamide derivatized Stat3 inhibitor provided herein, or a pharmaceutically acceptable salt thereof, or a pharmaceutically acceptable solvate of either entity, or a pharmaceutical composition containing any of the foregoing, for use as a human medicament.

In addition, it provides a 2-arylsulfonamido-N-arylacetamide derivatized Stat3 inhibitor compound provided herein, or a veterinarily acceptable salt thereof, or a veterinarily acceptable solvate of either entity, or a veterinary formulation containing any of the foregoing, for use as an animal medicament.

In yet another aspect, the invention provides the use of a 2-arylsulfonamido-N-arylacetamide derivatized Stat3 inhibitor compound provided herein, or a pharmaceutically acceptable salt thereof, or a pharmaceutically acceptable solvate of either entity, for the manufacture of a human medicament for the curative or prophylactic treatment of a medical condition for which a Stat3 inhibitor is indicated.

It also provides the use of a 2-arylsulfonamido-N-arylacetamide derivatized Stat3 inhibitor compound provided herein, or a veterinarily acceptable salt thereof, or a veterinarily acceptable solvate of either entity, for the manufacture of an animal medicament for the curative or prophylactic treatment of a medical condition for which a Stat3 inhibitor is indicated.

Moreover, the invention includes use of the compounds and compositions provided herein for methods for treating and/or preventing, in whole or in part, various diseases, disorders and conditions, including but not limited to hyperproliferative disease such as cancer.

The invention also includes pharmaceutical compositions, including tablets and capsules and other oral delivery forms and formulations, comprising a pharmaceutically acceptable carrier and therapeutically effective amounts of a 2-arylsulfonamido-N-arylacetamide derivatized Stat3 inhibitor as provided herein.

The invention includes methods for the use of therapeutically effective amounts of a Stat3 inhibitor provided herein in the manufacture of a medicament. Such medicaments include, for example, tablets, capsules, solutions and suspensions for parenteral and oral delivery forms and formulations. Such medicaments include those for the treatment of a subject as disclosed herein.

The compounds of the invention, particularly 2-arylsulfonamido-N-arylacetamide derivatized Stat3 inhibitor salts, and hydrates, for example, in the disclosed crystal form, may also be prepared with another anti-cancer agent.

Doses for such 2-arylsulfonamido-N-arylacetamide derivatized Stat3 inhibitors, salts and/or solvates as provided herein are envisaged to be administered in a therapeutically effective amount, for example, to inhibit cancer, delay tumor progression, and/or to reduce multidrug resistance in a subject.

The invention includes a formulation comprising a 2-arylsulfonamido-N-arylacetamide derivatized Stat3 inhibitor provided herein in amounts effective to reduce glutathione transport in the body of a subject. Such formulations include, for example, tablets, capsules, solutions and suspensions for parenteral and oral delivery forms and formulations.

Methods of Administration of Stat3 Inhibitors

The present invention is based a surprising, and unexpected, discovery that the 2-arylsulfonamido-N-arylacetamide derivatized Stat3 inhibitors of this invention are potent, selective inhibitors of Stat3 with anti-tumor activity. In addition, aspects of the present invention are based on the surprising discovery that the potent and selective Stat3 inhibitors of this invention have the ability to treat cancer, for example, to suppress, and/or prevent metastasis of cancer cells.

For the purpose of the current disclosure, the following definitions shall, in their entireties, be used to define technical terms, and to define the scope of the composition of matter for which protection is sought in the claims.

The instant disclosure provides methods of treatment by administration to a subject of one or more effective dose(s) of 2-arylsulfonamido-N-arylacetamide derivatized Stat3 inhibitors for a duration to achieve the desired therapeutic effect. The subject is preferably a mammal, including, but not limited to, animals such as cows, pigs, horses, chickens, cats, dogs, etc., and is most preferably human.

In some embodiments, compositions comprising 2-arylsulfonamido-N-arylacetamide derivatized Stat3 inhibitor compounds of the present invention are delivered in accordance with the methods of the invention, e.g., encapsulation in liposomes, microparticles or microcapsules. Methods of introduction include, but are not limited to, topical, subcutaneous, intradermal, intramuscular, intraperitoneal, intravenous, subcutaneous, intranasal, epidural, and oral routes. For treatment of certain cancers, topical, subcutaneous, intradermal, and systemic deliveries can be particularly efficacious.

In some embodiments, 2-arylsulfonamido-N-arylacetamide derivatized Stat3 inhibitors are administered by any convenient route, for example by infusion or bolus injection, by absorption through epithelial or mucocutaneous linings (e.g., oral mucosa, rectal and intestinal mucosa). In some embodiments, the Stat3 inhibitors are administered together with other biologically active agents. In some embodiments, administration is systemic or local. In some embodiments, pharmaceutical compositions comprising a Stat3 inhibitor are introduced into the central nervous system by any suitable route, including intraventricular and intrathecal injection; intraventricular injection may be facilitated by an intraventricular catheter, for example, attached to a reservoir, such as an Ommaya reservoir. In some embodiments, pulmonary administration is employed, e.g., by use of an inhaler or nebulizer, and formulation with an aerosolizing agent. In some embodiments, pharmaceutical compositions comprising Stat3 inhibitor are administered locally to the area in need of treatment by topical application, by injection, by means of a catheter, by means of a suppository, or by means of an implant, said implant being of a porous, non-porous, or gelatinous material, including membranes, such as Silastic™ membranes, or fibers.

Still other modes of administration of 2-arylsulfonamido-N-arylacetamide derivatized Stat3 inhibitors involve delivery in a controlled release system. In some embodiments, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In some embodiments, polymeric materials can be used, or a controlled release system is placed in proximity of the therapeutic target, i.e., the brain, thus requiring only a fraction of the systemic dose (see, e.g., Goodson, in *Medical Applications of Controlled Release, supra*, vol. 2, pp. 115-138 (1984)).

Forms and Dosages of Compositions Comprising Stat3 Inhibitors

As used herein, for cancer treatment, lyophilized formulation and liquid formulation suitable for injection are particularly efficacious. Suitable dosage forms of Stat3 inhibitors for use in embodiments of the present invention encompass physiologically/pharmaceutically acceptable carriers that are inherently non-toxic and non-therapeutic. Examples of such carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, P6N (Neumedicines, Pasadena, Calif.) and PEG. Carriers for topical or gel-based forms of Stat3 inhibitors include polysaccharides, such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations.

Suitable examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919, herein incorporated by reference), copolymers of L-glutamic acid and gamma-ethyl-L-glutamate (Sidman et al, supra), non-degradable ethylene-vinyl acetate (Langer et al., supra), degradable lactic acid-glycolic acid copolymers such as the Lupron Depot™ (injectable microspheres composed of lactic acid-glycolicacid copolymer and leuprolide acetate), and poly-D-(–)-3-hydroxybutyric acid. While polymers, such as ethylene-vinyl acetate and lactic acid-glycolic acid, enable release of molecules for over 100 days, certain hydrogels release proteins for shorter time periods. When encapsulated Stat3 inhibitors remain in the body for a long time, they may denature, or aggregate, as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In the case of administrations over several days or longer, depending on the condition, the treatment is sustained until a desired suppression of disease symptoms occurs. The progress of this therapy is monitored by conventional techniques and assays.

Therapeutic formulations comprising 2-arylsulfonamido-N-arylacetamide derivatized Stat3 inhibitors are prepared for storage by mixing Stat3 inhibitors, having the desired degree of purity, with optional physiologically acceptable carriers, excipients, or stabilizers (*Remington's Pharmaceutical Sciences*, 16th edition, Osol, A., Ed., (1980)), in the form of lyophilized cake, or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween®, Pluronics™ or polyethylene glycol (PEG).

The term "buffer," as used herein, denotes a pharmaceutically acceptable excipient, which stabilizes the pH of a pharmaceutical preparation. Pharmaceutically acceptable buffers include, but are not limited to, histidine-buffers, citrate-buffers, succinate-buffers, acetate-buffers, phosphate-buffers, arginine-buffers, or mixtures thereof. The abovementioned buffers are generally used in an amount of about 1 mM to about 100 mM, of about 5 mM to about 50 mM and of about 10-20 mM. In some embodiments, the pH of the buffered solution is at least 4.0, at least 4.5, at least 5.0, at least 5.5 or at least 6.0. In some embodiments, the pH of the buffered solution is less than 7.5, less than 7.0, or less than 6.5. In some embodiments, the pH of the buffered solution is about 4.0 to about 7.5, about 5.5 to about 7.5, about 5.0 to about 6.5, and about 5.5 to about 6.5 with an acid or a base described herein, e.g. hydrochloric acid, acetic acid, phosphoric acid, sulfuric acid and citric acid, sodium hydroxide and potassium hydroxide. As used herein when describing pH, "about" means plus or minus 0.2 pH units.

As used herein, the term "surfactant" can include a pharmaceutically acceptable excipient which is used to protect protein formulations against mechanical stresses, like agitation and shearing. Examples of pharmaceutically acceptable surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulphate (SDS). Suitable surfactants include polyoxyethylenesorbitan-fatty acid esters such as polysorbate 20, (sold under the trademark Tween 20®) and polysorbate 80 (sold under the trademark Tween 80®). Suitable polyethylene-polypropylene copolymers are those sold under the names Pluronic® F68 or Poloxamer 188®. Suitable Polyoxyethylene alkyl ethers are those sold under the trademark Brij®. Suitable alkylphenolpolyoxyethylene esthers are sold under the tradename Triton-X. When polysorbate 20 (Tween 20®) and polysorbate 80 (Tween 80®) are used, they are generally used in a concentration range of about 0.001 to about 1%, of about 0.005 to about 0.2% and of about 0.01% to about 0.1% w/v (weight/volume).

As used herein, the term "stabilizer" can include a pharmaceutically acceptable excipient, which protects the active pharmaceutical ingredient and/or the formulation from chemical and/or physical degradation during manufacturing, storage and application. Stabilizers include, but are not limited to, sugars, amino acids, polyols, cyclodextrins (e.g. hydroxypropyl-beta-cyclodextrine, sulfobutylethyl-beta-cyclodextrin, beta-cyclodextrin), polyethylenglycols (e.g. PEG 3000, PEG 3350, PEG 4000, PEG 6000), albumin, human serum albumin (HSA), bovine serum albumin (BSA), salts (e.g., sodium chloride, magnesium chloride, calcium chloride), chelators (e.g., EDTA) as hereafter defined. In some embodiments, stabilizers are present in the formulation in an amount of about 10 to about 500 mM, an amount of about 10 to about 300 mM, or in an amount of about 100 mM to about 300 mM. In some embodiments, exemplary Stat3 inhibitors are dissolved in an appropriate pharmaceutical formulation, wherein it is stable.

In some embodiments, 2-arylsulfonamido-N-arylacetamide derivatized Stat3 inhibitors are entrapped in microcapsules prepared by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in Remington's Pharmaceutical Sciences, supra.

2-arylsulfonamido-N-arylacetamide derivatized Stat3 inhibitors to be used for in vivo administration must be sterile. This is readily accomplished by filtration through sterile filtration membranes, prior to, or following, lyophilization and reconstitution. Stat3 inhibitors ordinarily will be stored in lyophilized form, or in solution. Therapeutic Stat3 inhibitors compositions generally are placed into a container having a sterile access port, for example, an intravenous solution bag, or vial, having a stopper pierceable by a hypodermic injection needle.

When applied topically, 2-arylsulfonamido-N-arylacetamide derivatized Stat3 inhibitors is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with, or without, purified collagen. In some embodiments, the compositions are impregnated into articles which can include or exclude transdermal patches, plasters, and bandages, preferably in liquid or semi-liquid form.

In some embodiments, a gel formulation of 2-arylsulfonamido-N-arylacetamide derivatized Stat3 inhibitor compound is formulated in a liquid composition by mixing the compound with an effective amount of a water-soluble polysaccharide, or synthetic polymer, such as PEG, to form a gel of the proper viscosity to be applied topically. In some embodiments, the polysaccharide can include or exclude cellulose derivatives, such as etherified cellulose derivatives, including alkyl celluloses, hydroxyalkyl celluloses, and alkylhydroxyalkyl celluloses (e.g., methylcellulose, hydroxyethyl cellulose, carboxymethyl cellulose, hydroxypropyl methylcellulose, and hydroxypropyl cellulose); starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the Stat3 inhibitor molecule held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

In some embodiments, the polyethylene glycol useful for gelling is a mixture of low and high molecular weight PEGs to obtain the proper viscosity. For example, a mixture of a PEG of molecular weight 400-600 with one of molecular weight 1500 would be effective for this purpose, when mixed in the proper ratio to obtain a paste.

The term "water soluble," as applied to the polysaccharides and PEGs, is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. In some embodiments, the cellulose derivatives are in the form of alkali metal salts, for example, the Li, Na, K, or Cs salts.

If methylcellulose is employed in the gel, preferably it comprises about 2-5%, more preferably about 3%, of the gel and the Stat3 inhibitor is present in an amount of about 5-100 mg per ml of gel or up to about 0.5 mM in 0.5% DMSO (in PBS or H20) based on the limit of solubility.

An effective amount of 2-arylsulfonamido-N-arylacetamide derivatized Stat3 inhibitors to be employed therapeutically will depend, for example, upon the therapeutic objectives, the route of administration, and the condition of the patient. Accordingly, it will be necessary for the therapist to titer the dosage and modify the route of administration, as required to obtain the optimal therapeutic effect. Typically, the clinician will administer Stat3 inhibitors until a dosage is reached that achieves the desired effect. In certain embodiments, the appropriate dosing is determined based on an amount of Stat3 inhibitors administered per surface area of the affected region.

"Near the time of administration of the treatment" refers to the administration of Stat3 inhibitors at any reasonable time period, either before, and/or after the administration of the treatment, such as about one month, about three weeks, about two weeks, about one week, several days, about 120 hours, about 96 hours, about 72 hours, about 48 hours, about 24 hours, about 20 hours, several hours, about one hour or minutes. Near the time of administration of the treatment may also refer to either the simultaneous, or near simultaneous, administration of the treatment and 2-arylsulfonamido-N-arylacetamide derivatized Stat3 inhibitors, i.e., within minutes to one day.

"Chemotherapy" refers to any therapy that includes natural or synthetic agents now known, or to be developed in the medical arts. Examples of chemotherapy include the numerous cancer drugs that are currently available. However, chemotherapy also includes any drug, natural or synthetic, that is intended to treat a disease state. In certain embodiments of the invention, chemotherapy may include the administration of several state of the art drugs intended to treat the disease state. Examples include combined chemotherapy with docetaxel, cisplatin, and 5-fluorouracil, for patients with locally advanced squamous cell carcinoma of the head (Tsukuda, M. et al., *Int J Clin Oncol.* 2004 June; 9 (3): 161-6), and fludarabine and bendamustine in refractory and relapsed indolent lymphoma (Konigsmann M, et al., *Leuk Lymphoma.* 2004; 45 (9): 1821-1827).

As used herein, exemplary sources of therapeutic or accidental ionizing radiation can include, for example, alpha, beta, gamma, x-ray, and neutron sources.

"Radiation therapy" refers to any therapy where any form of radiation is used to treat the disease state. The instruments that produce the radiation for the radiation therapy are either those instruments currently available, or to be available in the future.

"Chemoprotection or radioprotection" refers to protection from, or an apparent decrease in, the associated hematopoietic toxicity of a treatment intended to target the disease state.

"Solid tumors" generally refers to the presence of cancer of body tissues other than blood, bone marrow, or the lymphatic system.

EXAMPLES

The invention is now described with reference to the following Examples. These Examples are provided for the purpose of illustration only, and the invention is not limited to these Examples, but rather encompasses all variations that are evident as a result of the teaching provided herein.

The Examples described herein demonstrate that the potent and selective 2-arylsulfonamido-N-arylacetamide derivatized Stat3 inhibitors of Formulae I-VIII, including compounds of Examples 25-31, 50, 52, 53, 60-64, 79, 85, 102, 104, 110, 113, 119, 122, 125, 134-137, 143, 148, 149, 151 and 152 have efficacy for treating cancer and other proliferative diseases. Aspects and embodiments of the instant disclosure stem from the unexpected discovery that certain Stat3 inhibitor formulations have surprising, and unexpected, utility and efficacy when administered to a subject.

The therapeutically effective 2-arylsulfonamido-N-arylacetamide derivatized Stat3 inhibitors of this invention are prepared according to the synthetic scheme outlined above. However, the invention is not limited to those method. The compositions may also be prepared as described herein for structurally related compounds.

Synthesis of Selected Compounds of the Present Invention.
General Methods for Chemistry.

All reagents and solvents were purchased from commercial sources and used without further purification. All moisture sensitive reactions were performed under a static atmosphere of nitrogen or argon in oven dried glassware. Tetrahydrofuran (THF), dichloromethane (DCM), diethyl ether (Et$_2$O), toluene, dimethylformamide (DMF) used in the reactions were dried by being passed through a SPS system. Other anhydrous solvents were purchased from commercial sources. Thin layer chromatography (TLC) was performed on glass plates, 250-1000 μm. Flash column chromatography was performed on silica gel, 200-400 mesh. $^1$H NMR spectra were obtained as CDCl$_3$, CD$_3$OD, or (CD$_3$)$_2$SO, solutions using an Agilent 300 MHz NMR spectrometer with a Agilent DD2 console, and chemical shifts were expressed in δ (ppm) using residual solvent (CDCl$_3$, 7.26 ppm; CD$_3$OD, 3.31 ppm; and (CD$_3$)$_2$SO, 2.50 ppm) as the reference standard. When peak multiplicities are reported, the following abbreviations are used: s (singlet), d (doublet), t (triplet), q (quartet), m (multiplet), br-s (broadened singlet), dd (doublet of doublets), dt (doublet of triplets). Coupling constants, when reported, are reported in hertz (Hz). All compounds were analyzed by LC/MS (liquid chromatography/mass spectrometry) using an Agilent Triple Quad 640 LC/MS. Ionization was generally achieved via electron spray (ESI) unless otherwise indicated. The LC fraction detection consisted of a variable wavelength detector and all tested compounds had purity greater than 95%. High resolution mass spectral (HRMS) data was obtained for all tested compounds using either and Agilent 6200 LC/MSD TOF or an Agilent 6545 Q-TOF LC/MS and reported exact masses were calculated based on an algorithm using MS (ESI) m/z for [M+H]$^+$ and [M+Na]$^+$ adducts and were within 5 ppm of the expected target mass. Chiral molecules were analyzed by chiral HPLC using Chiralpak AD-H or OD-H columns (4.6 mm×250 mm, UV detection at 254 or 261 nm), eluents used were hexane and i-PrOH.

Commonly Used Abbreviations.

Commonly used abbreviations include: acetic acid (AcOH), acetonitrile (MeCN, CH$_3$CN), azobisisobutyronitrile (AIBN), 2,2'-bis(diphenylphosphino)-1,1'-binaphthyl (BINAP), 4,5-Bis(diphenylphosphino)-9,9-dimethylxanthene (Xantphos), tert-butoxycarbonyl (Boc), benzyl (Bn), butyl (Bu), benzyloxycarbonyl (CBZ or Z), ceric ammonium nitrate (CAN), cyclohexyl (Cy), cyclopentyl (Cp), dibenzylideneacetone (dba), dichloroethane (DCE), dichloromethane (DCM), N-[(Dimethylamino)-1H-1,2,3-triazolo-[4,5-b]pyridin-1-ylmethylene]-N-methylmethanaminium hexafluorophosphate N-oxide (HATU), 2-Dicyclohexylphosphino-2',6'-dimethoxybiphenyl (SPhos), diphenylphosphoryl azide (DPPA), di-iso-propylethylamine (DIPEA), methanesulfonyl chloride (MsCl), 4-N,N-dimethylaminopyridine (DMAP), N,N-dimethylformamide (DMF), dimethyl sulfoxide (DMSO), electrospray ionization (ESI), ethyl (Et), ethyl acetate (EtOAc, EA), 1-Ethyl-3-(3-dimethylaminopropyl)carbodiimide (EDCI), ethanol (EtOH), diethyl ether (Et$_2$O, ether), 9H-fluoren-9-yl)methoxy)carbonyl (Fmoc), high resolution mass spectrometry (HRMS), high pressure liquid chromatography (HPLC), lithium hexamethyldisilazane (LiHMDS), liquid chromatography-mass spectrometry (LCMS), methanol (MeOH), melting point (mp or MP), methyl (Me), mass spectrum (ms or MS), methylmagnesium bromide (MeMgBr), N-bromosuccinumide (NBS), N-methylmorpholine (NMM), N-methylpyrrolidone (NMP), palladium on carbon (Pd/C), phenyl (Ph), potassium hexamethyldisilazane (KHMDS), propyl (Pr), iso-propyl (i-Pr), room temperature (rt or RT), sodium hexamethyldisilazane (NaHMDS), triethylamine (TEA, or Et$_3$N), 2-(trimethylsilyl)ethoxymethyl (SEM), trifluoroacetic acid (TFA), trifluoroacetic anhydride (TFAA), thin layer chromatography (TLC), and tetrahydrofuran (THF), 2-methyltetrahydrofuan (MeTHF), (STAT) signal transducer and activator of transcription; (EMSA) electrophoretic mobility shift assay; (MAPK) mitogen-activated protein kinase; (ERK) extracellular signal-regulated kinases.

Example 1

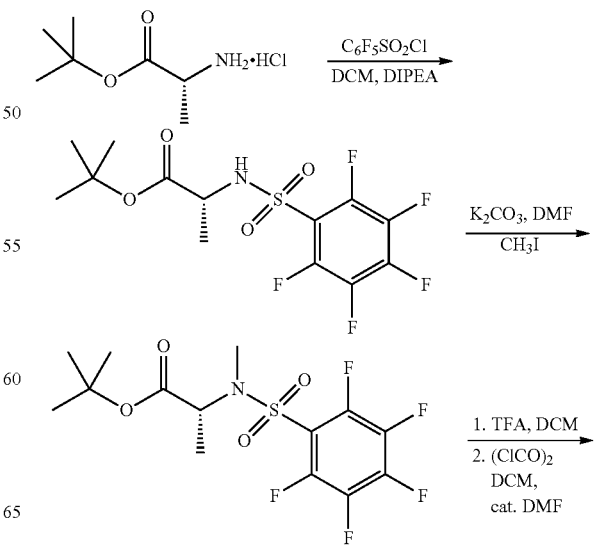

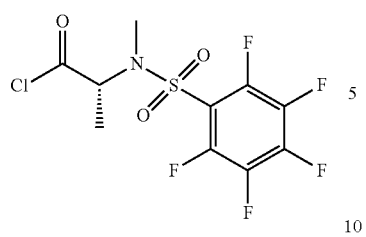
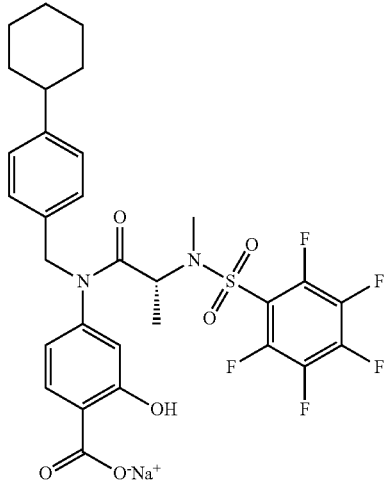
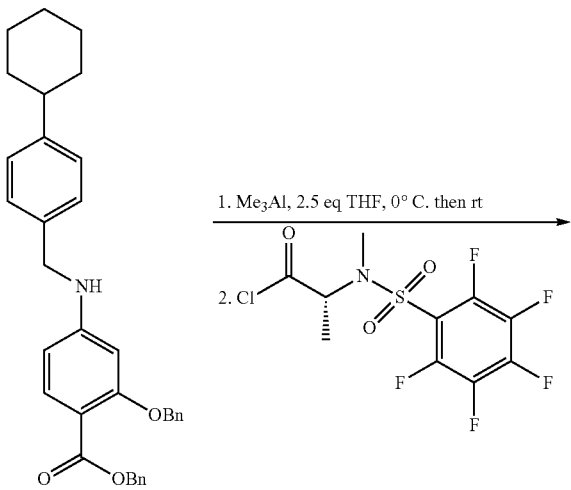
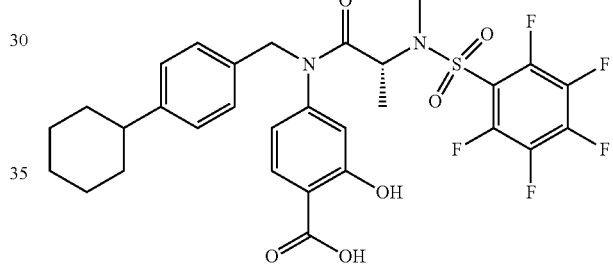

(R)-4-(N-(4-Cyclohexylbenzyl)-2-((2,3,4,5,6-pentafluoro-N-methylphenyl)sulfonamido)propanamido)-2-hydroxybenzoic acid

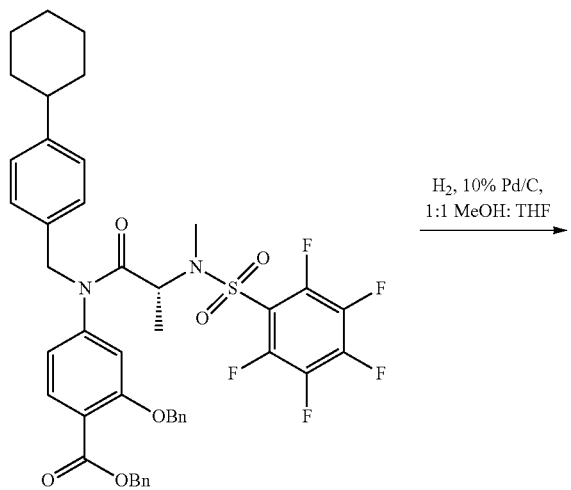
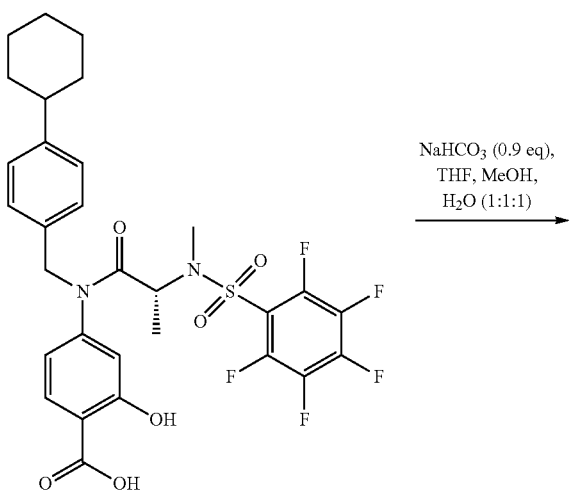

Step 1: To a solution of D-alanine tert-butyl ester hydrochloride (5 g, 27.5 mmol) and DIPEA (11 mL, 63.3 mmol) in 100 mL of anhydrous DCM at 0° C. was added pentafluorobenzenesulfonyl chloride (4.5 mL, 30.25 mmol) dropwise. The reaction mixture was allowed to warm to room temperature and stirred overnight. The mixture was poured onto water and extracted with DCM (3×). The combined organic layers were dried over anhydrous sodium sulfate, concentrated under reduced pressure, and the resulting residue was purified by flash chromatography (15% EtOAc/hexanes) to afford tert-butyl ((pentafluorophenyl)sulfonyl)-D-alaninate as a cream colored solid (8.21 g, 80% yield). 1H NMR (300 MHz, Chloroform-d) δ 5.70 (d, J=8.4 Hz, 1H), 4.18 (p, J=7.2 Hz, 1H), 1.47 (d, J=7.2 Hz, 3H), 1.40 (s, 9H).

Step 2: To a stirred solution of tert-butyl ((pentafluorophenyl)sulfonyl)-D-alaninate (8.21 g, 21.9 mmol) in 130 mL of anhydrous DMF was added $K_2CO_3$ (3.63 g, 26.3 mmol) and the resultant mixture was stirred for 10 min before dropwise addition methyl iodide (1.77 mL, 28.5 mmol). The reaction mixture was stirred for 1 h, then poured onto ice water (500 mL) and extracted with ether (3×250 mL). The combined organic extracts were washed with brine, dried over anhydrous sodium sulfate and concentrated under reduced pressure. The resulting residue was purified by flash chromatography (0-8% EtOAc/hexanes step-wise gradient) to afford tert-butyl N-methyl-N-((pentafluorophenyl)sulfonyl)-D-alaninate as a white solid (8.16 g, 96% yield). 1H NMR (300 MHz, Chloroform-d) δ 4.80 (q, J=7.3 Hz, 1H), 2.99 (s, 3H), 1.50 (d, J=7.3 Hz, 3H), 1.40 (s, 9H).

Step 3: To a stirred solution of combined batches of tert-butyl N-methyl-N-((pentafluorophenyl)sulfonyl)-D-alaninate (11.4 g, 29.3 mmol) in 100 mL of DCM was added TFA (100 mL) and the resultant mixture was stirred at room temperature overnight. The resultant mixture was concentrated under reduced pressure, re-dissolved in toluene and concentrated in vacuo to give a cream-colored solid (9.6 g, 98% yield). The solid was triturated with a cold solution of 10% ether in hexanes (25 mL), washed twice and dried to provide N-methyl-N-((pentafluorophenyl)sulfonyl)-D-alanine as a white solid (8.1 g). 1H NMR (300 MHz, Chloroform-d) δ 4.97 (q, J=7.3 Hz, 1H), 3.00 (s, 3H), 1.57 (d, J=7.3 Hz, 3H).

Step 4: To a stirred solution of N-methyl-N-((pentafluorophenyl)sulfonyl)-D-alanine (4.44 g, 13.33 mmol) in 100 mL of DCM under nitrogen was added DMF (3 drops) followed by oxalyl chloride (1.72 mL, 20 mmol) and the resultant mixture was stirred at room temperature for 2.5 h. The solution was concentrated under reduced pressure to give a cream colored solid that was triturated with hexanes and dried on the pump to afford pure N-methyl-N-((pentafluorophenyl)sulfonyl)-D-alaninoyl chloride (4.46 g, 95% yield). 1H NMR (300 MHz, Chloroform-d) δ 5.25-5.09 (m, 1H), 3.02 (s, 3H), 1.69 (d, J=7.4 Hz, 3H).

Step 5: To a stirred solution of benzyl 2-(benzyloxy)-4-((4-cyclohexylbenzyl)amino)benzoate (see US2012018868) (303 mg, 0.6 mmol) in THF (7 mL) under nitrogen at 0° C. was added a solution of trimethylaluminum (0.75 mL of 2M in toluene, 1.5 mmol) and the mixture was warmed to room temperature over 15 min. To the resulting solution was added a solution of N-methyl-N-((pentafluorophenyl)sulfonyl)-D-alaninoyl chloride (263 mg, 0.75 mmol) in THF (7 mL). The reaction mixture was stirred at reflux temperature for 3 h, poured onto 10% aqueous KHSO$_4$/Na$_2$SO$_4$ buffer and ice and then extracted 3 times with EtOAc. The combined organic layers were dried over anhydrous sodium sulfate, concentrated under reduced pressure, and the resulting residue was purified by flash chromatography (0-5-10% EtOAc/(8:1 hexanes:DCM mixture)) as a stepwise gradient to afford benzyl (R)-2-(benzyloxy)-4-(N-(4-cyclohexylbenzyl)-2-((2,3,4,5,6-pentafluoro-N-methylphenyl)sulfonamido)propanamido)benzoate (407 mg, 83% yield) as a white foam. MS (ESI) m/z 821 [M+H]$^+$.

Step 6: To a stirred solution of benzyl (R)-2-(benzyloxy)-4-(N-(4-cyclohexylbenzyl)-2-((2,3,4,5,6-pentafluoro-N-methylphenyl)sulfonamido)propanamido)benzoate (375 mg, 0.46 mmol) in methanol (10 mL) and THF (10 mL) was added 10% Pd/C (32 mg) and the resulting suspension was stirred at room temperature under a hydrogen atmosphere until the reaction was complete as determined by LCMS (2 h). The reaction mixture was filtered through Celite® and washed with methanol (2×). The combined filtrate and washes were concentrated to provide (R)-4-(N-(4-cyclohexylbenzyl)-2-((2,3,4,5,6-pentafluoro-N-methylphenyl)sulfonamido)propanamido)-2-hydroxybenzoic acid (298 mg, 100% yield) as a pale pink foam. MS (ESI) m/z 641.1743 [M+H]+.

Example 2

Sodium (R)-4-(N-(4-cyclohexylbenzyl)-2-((2,3,4,5,6-pentafluoro-N-methylphenyl)sulfonamido)-propanamido)-2-hydroxybenzoate

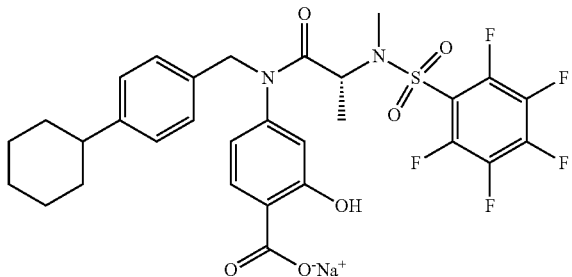

To a solution of (R)-4-(N-(4-cyclohexylbenzyl)-2-((2,3,4,5,6-pentafluoro-N-methylphenyl)sulfonamido)-propanamido)-2-hydroxybenzoic acid (298 mg, 0.46 mmol) in 12 mL of 1:1:1 THF:MeOH:H$_2$O was added sodium bicarbonate (34.5 mg, 0.41 mmol) and the resultant mixture was stirred at room temperature for 5 h and then concentrated in vacuo to give a foam. Trituration with 1:1 ether:hexanes provided sodium (R)-4-(N-(4-cyclohexylbenzyl)-2-((2,3,4,5,6-pentafluoro-N-methylphenyl)-sulfonamido)propanamido)-2-hydroxybenzoate as a yellow solid. MS (ESI) m/z 663.1562 [M+Na]+.

Example 3

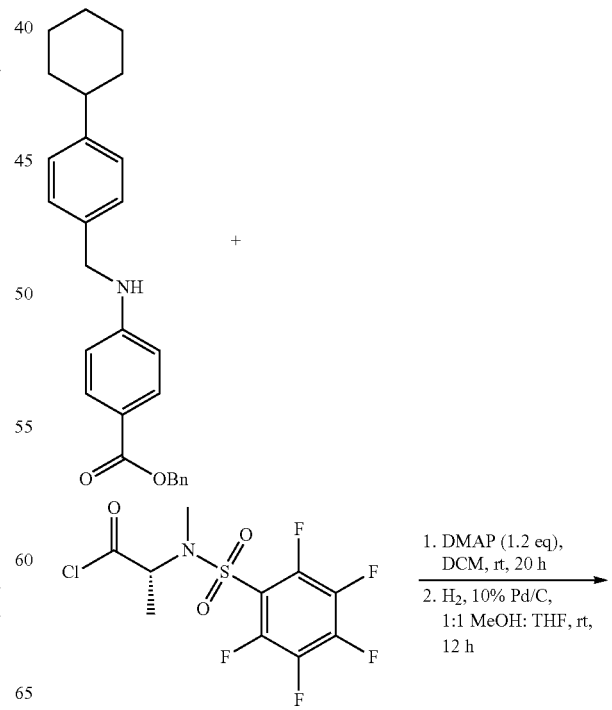

69

-continued

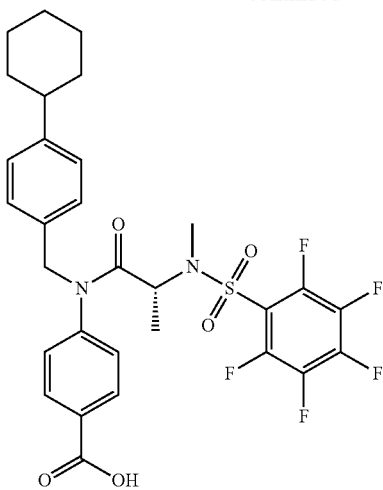

1. oxalyl chloride, DMF (cat.), DCM, 2 h
2. H₂NOBn·HCl, DMF, TEA, THF, 0° C. then rt, 1.5 h

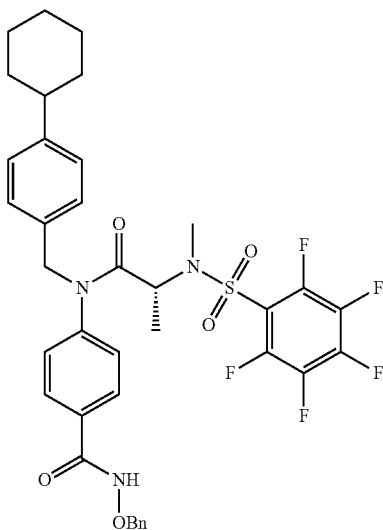 [SMILES: C[C@H](C(=O)N(Cc1ccc(C2CCCCC2)cc1)c1ccc(C(=O)NO)cc1)N(C)S(=O)(=O)c1c(F)c(F)c(F)c(F)c1F]

H₂, 10% Pd/C, 1:1 MeOH: THF, rt, 1 h

70

(R)-4-(N-(4-cyclohexylbenzyl)-2-((2,3,4,5,6-pentafluoro-N-methylphenyl)sulfonamido)propanamido)-benzoic acid

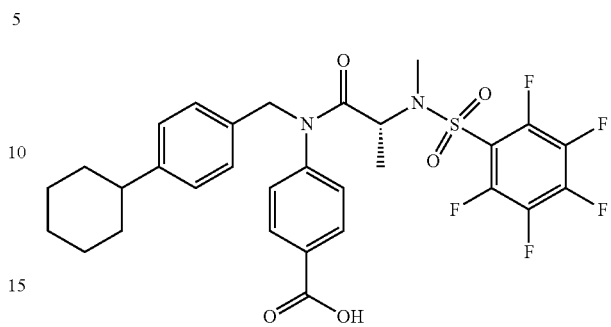

Step 1: To a solution of benzyl 4-((4-cyclohexylbenzyl)amino)benzoate (see Haftchenary, Sina et al. ACS Medicinal Chemistry Letters, 4(11), 1102-1107; 2013) (450 mg, 1.12 mmol) and N-methyl-N-((pentafluorophenyl)sulfonyl)-D-alaninoyl chloride (590 mg, 1.68 mmol) in DCM (15 mL) under nitrogen was added DMAP (164 mg, 1.34 mmol) and the resultant solution was stirred at room temperature overnight. The reaction mixture was poured onto water and extracted with DCM (3×). The combined organic layers were dried over anhydrous sodium sulfate, concentrated under reduced pressure, and the resulting residue purified by flash chromatography (10-25% EtOAc/hexanes) to afford benzyl (R)-4-(N-(4-cyclohexylbenzyl)-2-((2,3,4,5,6-pentafluoro-N-methylphenyl)sulfonamido)propanamido)-benzoate (350 mg, 44% yield). MS (ESI) m/z 715.2265 [M+H]+.

Step 2: To a stirred solution of benzyl (R)-4-(N-(4-cyclohexylbenzyl)-2-((2,3,4,5,6-pentafluoro-N-methylphenyl)sulfonamido)propanamido)benzoate (330 mg, 0.43 mmol) in methanol (10 mL) and THF (10 mL) was added 10% Pd/C (50 mg) and the resulting suspension was stirred at room temperature under a hydrogen atmosphere overnight. The reaction mixture was filtered through Celite® and washed with methanol (2×). The combined filtrate and washes were concentrated to provide (R)-4-(N-(4-cyclohexylbenzyl)-2-((2,3,4,5,6-pentafluoro-N-methylphenyl)sulfonamido)propanamido)-benzoic acid (286 mg, 100% yield) as a white foam. MS (APCI) m/z 625.1900 [M+H]+.

Example 4

(R)-4-(N-(4-Cyclohexylbenzyl)-2-((2,3,4,5,6-pentafluoro-N-methylphenyl)sulfonamido)propanamido)-N-hydroxybenzamide

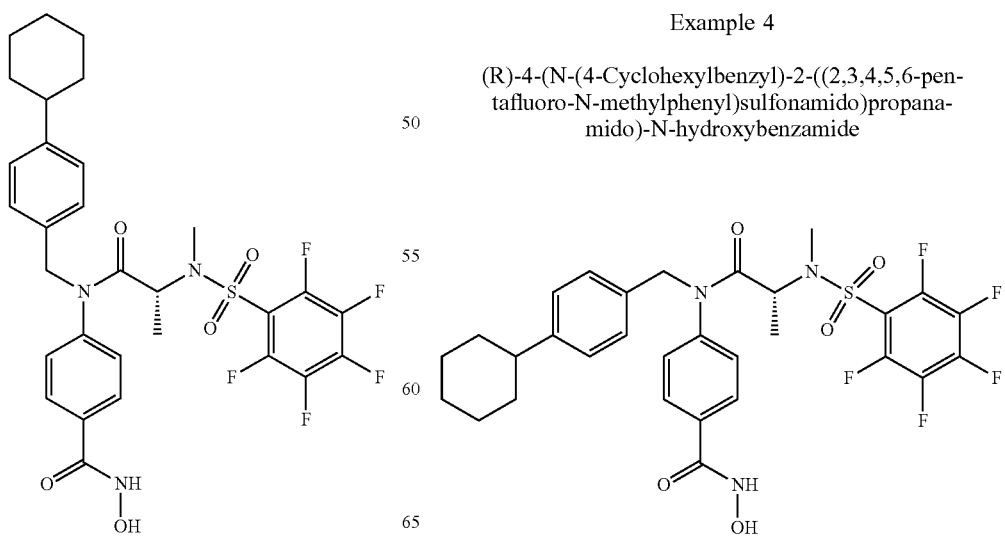

Step 1: To a stirred solution of (R)-4-(N-(4-cyclohexylbenzyl)-2-((2,3,4,5,6-pentafluoro-N-methylphenyl)sulfonamido)propanamido)benzoic acid (211 mg, 0.34 mmol) in DCM (10 mL) was added 1 drop of DMF followed by oxalyl chloride (0.035 mL, 0.41 mmol). The resulting reaction solution was stirred at room temperature under nitrogen for 2 h and then concentrated under reduced pressure to afford (R)-4-(N-(4-cyclohexylbenzyl)-2-((2,3,4,5,6-pentafluoro-N-methylphenyl)sulfonamido)-propanamido)benzoyl chloride, which was used as is. 1H NMR (300 MHz, Chloroform-d) δ 8.17 (d, J=8.4 Hz, 2H), 7.30 (d, J=8.4 Hz, 2H), 7.13 (d, J=8.1 Hz, 2H), 7.00 (d, J=8.1 Hz, 2H), 4.93-4.73 (m, 3H), 3.17 (s, 3H), 2.60-2.44 (m, 1H), 2.04-1.66 (m, 6H), 1.54-1.31 (m, 4H), 1.25 (d, J=7.2 Hz, 3H).

Step 2: To a stirred solution of (R)-4-(N-(4-cyclohexylbenzyl)-2-((2,3,4,5,6-pentafluoro-N-methylphenyl)-sulfonamido)propanamido)benzoyl chloride (0.34 mmol) in THF (5 mL) under nitrogen at 0° C. was added a solution of O-benzylhydroxylamine hydrochloride (76 mg, 0.473 mmol) and TEA (0.12 mL, 0.879 mmol) in DMF (4 mL). The resultant reaction mixture was stirred at room temperature for 1.5 h and then quenched with 10% potassium bisulfate, poured onto water and extracted with ether (2×). The combined organic extracts were washed with water, then washed with brine, dried over anhydrous sodium sulfate and concentrated under reduced pressure. The resulting residue was purified by flash chromatography (40% EtOAc/hexanes) to provide (R)—N-(benzyloxy)-4-(N-(4-cyclohexylbenzyl)-2-((2,3,4,5,6-pentafluoro-N-methylphenyl)sulfonamido)propanamido)benzamide (159 mg, 64% yield). 1H NMR (300 MHz, Chloroform-d) δ 7.70 (d, J=8.1 Hz, 2H), 7.56-7.33 (m, 5H), 7.21-7.14 (m, 2H), 7.14-7.06 (m, 2H), 6.97 (d, J=7.8 Hz, 2H), 5.06 (s, 2H), 4.88-4.64 (m, 3H), 3.18 (s, 3H), 2.55-2.41 (m, 1H), 1.94-1.69 (m, 6H), 1.50-1.32 (m, 4H), 1.22 (d, J=7.2 Hz, 3H).

Step 3: To a stirred solution of (R)—N-(benzyloxy)-4-(N-(4-cyclohexylbenzyl)-2-((2,3,4,5,6-pentafluoro-N-methylphenyl)sulfonamido)-propanamido)benzamide in methanol (8 mL) and THF (8 mL) was added 10% Pd/C (40 mg) and the resulting suspension was stirred at room temperature under a hydrogen atmosphere for 1 h. The reaction mixture was filtered through Celite® and washed with methanol (2×). The combined filtrate and washes were concentrated and the resulting residue was purified by flash chromatography (3% MeOH in DCM eluent) to provide (R)-4-(N-(4-cyclohexylbenzyl)-2-((2,3,4,5,6-pentafluoro-N-methylphenyl)sulfonamido)propanamido)-N-hydroxybenzamide (109 mg, 81% yield). MS (APCI+) m/z 640.1877 [M+H]+.

Example 5

(S)-4-(N-(4-Cyclohexylbenzyl)-2-((2,3,4,5,6-pentafluoro-N-methylphenyl)sulfonamido)propanamido)-2-hydroxybenzoic acid

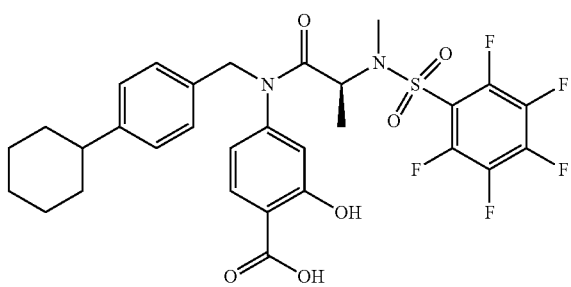 [SMILES: C[C@@H](C(=O)N(Cc1ccc(C2CCCCC2)cc1)c1ccc(C(=O)O)c(O)c1)N(C)S(=O)(=O)c1c(F)c(F)c(F)c(F)c1F]

Preparation by a similar procedure to example 1, except substituting L-alanine tert-butyl ester hydrochloride for D-alanine tert-butyl ester hydrochloride in step 1 afforded (S)-4-(N-(4-cyclohexylbenzyl)-2-((2,3,4,5,6-pentafluoro-N-methylphenyl)sulfonamido)propanamido)-2-hydroxybenzoic acid. MS (ESI) m/z 641.1751 [M+H]+.

Example 6

(S)-4-(N-(4-Cyclohexylbenzyl)-2-((2,3,4,5,6-pentafluoro-N-methylphenyl)sulfonamido)propanamido)benzoic acid

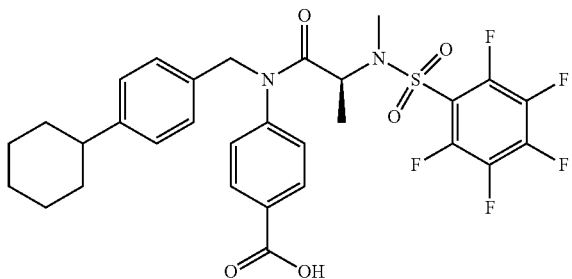 [SMILES: C[C@@H](C(=O)N(Cc1ccc(C2CCCCC2)cc1)c1ccc(C(=O)O)cc1)N(C)S(=O)(=O)c1c(F)c(F)c(F)c(F)c1F]

Preparation by a similar procedure to example 3, except substituting L-alanine tert-butyl ester hydrochloride for D-alanine tert-butyl ester hydrochloride in step 1 afforded (S)-4-(N-(4-cyclohexylbenzyl)-2-((2,3,4,5,6-pentafluoro-N-methylphenyl)sulfonamido)propan-amido)benzoic acid. MS (APCI) m/z 625.18 [M+H]+.

Example 7

(S)-4-(N-(4-cyclohexylbenzyl)-2-((2,3,4,5,6-pentafluoro-N-methylphenyl)sulfonamido)propanamido)-N-hydroxybenzamide

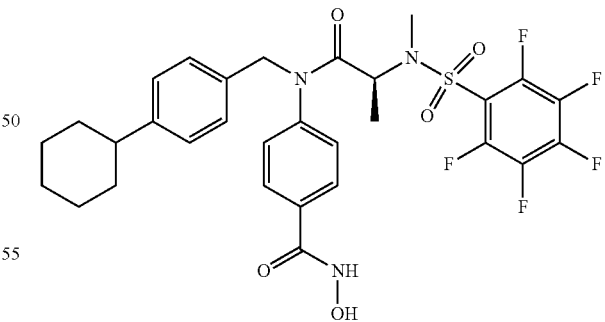

Preparation by a similar procedure to example 4, except substituting L-alanine tert-butyl ester hydrochloride for D-alanine tert-butyl ester hydrochloride in step 1 afforded (S)-4-(N-(4-cyclohexylbenzyl)-2-((2,3,4,5,6-pentafluoro-N-methylphenyl)sulfonamido)propan-amido)-N-hydroxybenzamide. MS (ESI) m/z 640.20 [M+H]+. HRMS (ESI+) calculated for C30H30F5N3O5S: 639.1826, found 639.1823.

Example 8

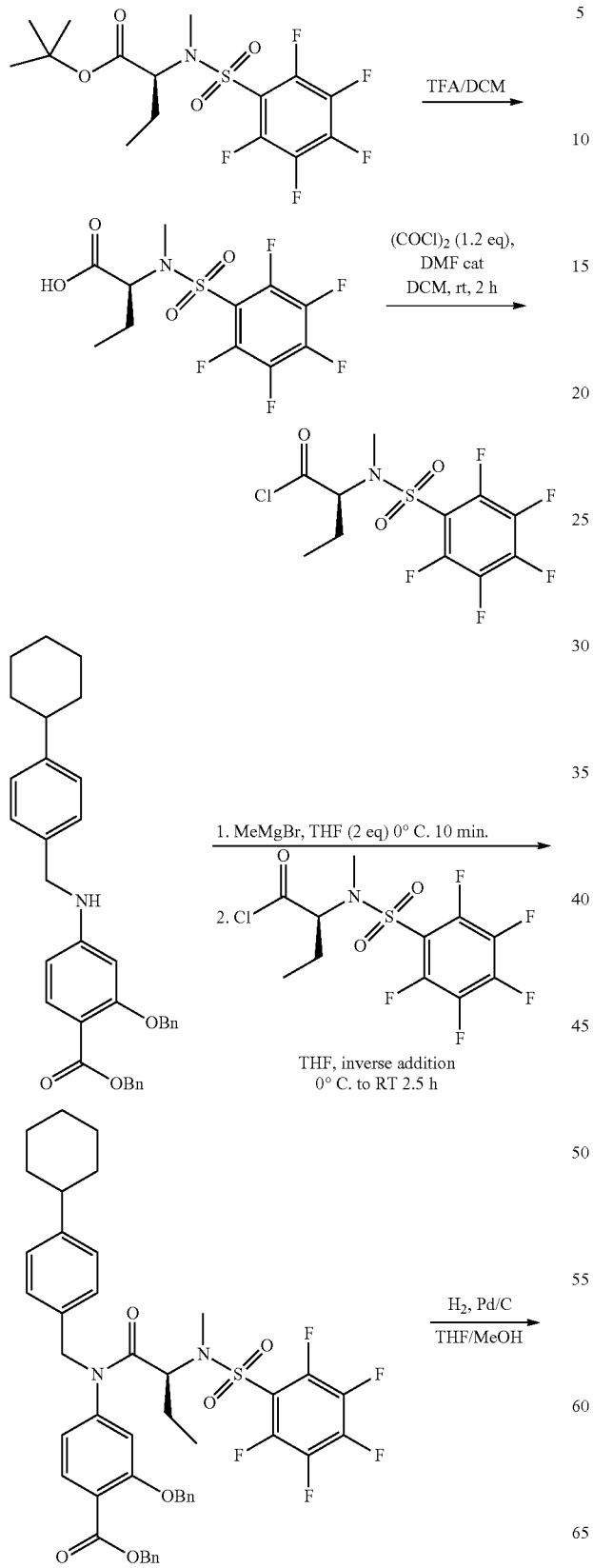

(S)-4-(N-(4-Cyclohexylbenzyl)-2-((2,3,4,5,6-pentafluoro-N-methylphenyl)sulfonamido)butanamido)-2-hydroxybenzoic acid Step 1: tert-Butyl (S)-2-((2,3,4,5,6-pentafluoro-N-methylphenyl)sulfonamido)butanoate, was prepared as described for tert-butyl N-methyl-N-((perfluorophenyl)sulfonyl)-D-alaninate in example 1 (steps 1-2) except starting with L-2-aminobutyric acid tert-butyl ester hydrochloride instead of D-alanine tert-butyl ester hydrochloride in step 1. 1H NMR (300 MHz, Chloroform-d) δ 4.55 (dd, J=11.0, 4.8 Hz, 1H), 2.97 (s, 3H), 2.05 (dqd, J=14.8, 7.5, 4.8 Hz, 1H), 1.70 (ddq, J=14.5, 11.0, 7.2 Hz, 1H), 1.39 (s, 9H), 1.05 (t, J=7.4 Hz, 3H).

Step 2: To a stirred solution of tert-butyl (S)-2-((2,3,4,5,6-pentafluoro-N-methylphenyl)sulfonamido)-butanoate (782 mg, 1.94 mmol) in DCM (10 mL) was added TFA (10 mL) and the resulting reaction solution was stirred overnight at room temperature and then concentrated in vacuo to provide (S)-2-((2,3,4,5,6-pentafluoro-N-methylphenyl)sulfonamido)butanoic acid (718 mg, 100%). 1H NMR (300 MHz, Chloroform-d) δ 7.61 (br. s, 1H), 4.71 (dd, J=11.0, 4.8 Hz, 1H), 2.95 (s, 3H), 2.10 (dtd, J=14.5, 7.4, 4.8 Hz, 1H), 1.77 (ddq, J=14.5, 11.0, 7.4 Hz, 1H), 1.06 (t, J=7.4 Hz, 3H).

Step 3: To a stirred solution of (S)-2-((2,3,4,5,6-pentafluoro-N-methylphenyl)sulfonamido)butanoic acid (76 mg, 0.22 mmol) in 2 mL of DCM under nitrogen was added DMF (2 drops) followed by oxalyl chloride (0.024 mL, 0.28 mmol) and the resultant mixture was stirred at room temperature for 2.5 h. The solution was concentrated under reduced pressure to provide acid chloride, (S)-2-((2,3,4,5,6- pentafluoro-N-methylphenyl)sulfonamido)butanoyl chloride, which was used as is. To a stirred solution of aniline, benzyl 2-(benzyloxy)-4-((4-cyclohexylbenzyl)amino)benzoate, (88 mg, 0.175 mmol) in THF (2 mL) under nitrogen at 0° C. was added methylmagnesium bromide (0.25 mL of 1.4 M in 1:3 THF:toluene, 0.35 mmol, 2 equiv). Stirring was continued at 0-5° C. for 10 min. The resultant solution was added drop-wise to a stirred solution of freshly prepared (S)-2-((2,3,4,5,6-pentafluoro-N-methylphenyl)sulfonamido)butanoyl chloride (0.21 mmol) in THF (2 mL) under nitrogen at 0° C. The resulting reaction mixture was allowed to warm to room temperature and stirred at this temperature for 2.5 h, quenched with aqueous saturated ammonium chloride, poured onto water and extracted with EtOAc (3×). The combined organic extracts were dried over anhydrous sodium sulfate, concentrated under reduced pressure and resulting residue purified by flash chromatography (20% EtOAc/hexane eluent) to afford benzyl (S)-2-(benzyloxy)-4-(N-(4-cyclohexylbenzyl)-2-((2,3,4,5,6-pentafluoro-N-methylphenyl)-sulfonamido)butanamido)benzoate (88 mg, 48% yield). MS (ESI) m/z 857.2 [M+Na]+.

Step 4: To a stirred solution of benzyl (S)-2-(benzyloxy)-4-(N-(4-cyclohexylbenzyl)-2-((2,3,4,5,6-pentafluoro-N-methylphenyl)-sulfonamido)butanamido)benzoate (88 mg, 0.105 mmol) in methanol (8 mL) and THF (8 mL) was added 10% Pd/C (20 mg) and the resulting suspension was stirred at room temperature under a hydrogen atmosphere overnight. The reaction mixture was filtered through Celite® and washed with methanol (2×). The combined filtrate and washes were concentrated, purified by flash chromatography (3-7% MeOH/DCM gradient) to provide (S)-4-(N-(4-cyclohexylbenzyl)-2-((2,3,4,5,6-pentafluoro-N-methylphenyl) sulfonamido)butanamido)-2-hydroxybenzoic acid (54 mg, 79% yield) as an off-white solid. MS (ESI) m/z 653.1752 [M−H]−.

Example 9

(R)-4-(N-(4-Cyclohexylbenzyl)-2-((2,3,4,5,6-pentafluoro-N-methylphenyl)sulfonamido)butanamido)-2-hydroxybenzoic acid

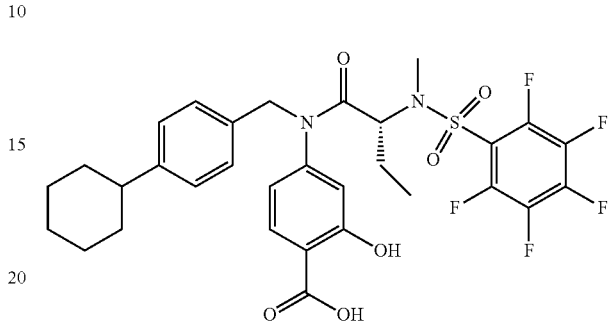

Preparation by a similar procedure to example 8, except substituting tert-butyl (R)-2-((2,3,4,5,6-pentafluoro-N-methylphenyl)sulfonamido)butanoate for tert-butyl (S)-2-((2,3,4,5,6-pentafluoro-N-methylphenyl)sulfonamido)butanoate in step 1 afforded (R)-4-(N-(4-cyclohexylbenzyl)-2-((2,3,4,5,6-pentafluoro-N-methylphenyl)sulfonamido) butanamido)-2-hydroxybenzoic acid. MS (ESI) m/z 653.1737 [M−H]−. HRMS (ESI−) calculated for C31H31F5N2O6S: 654.1823, found 654.1811.

Example 10

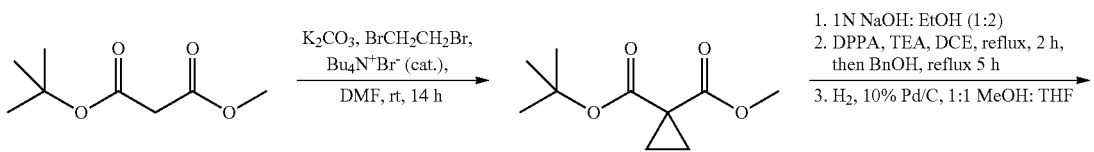

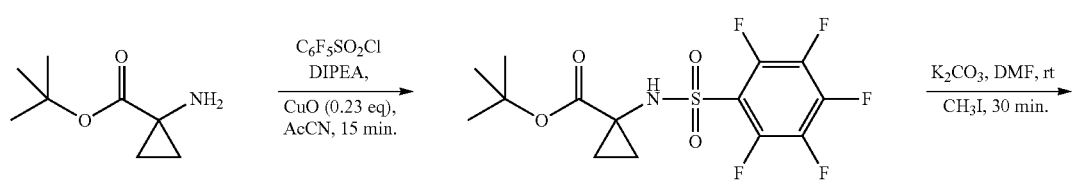

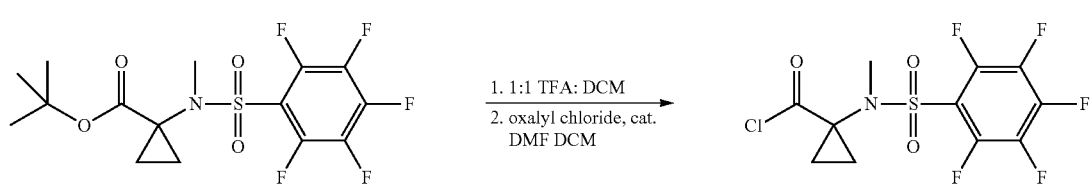

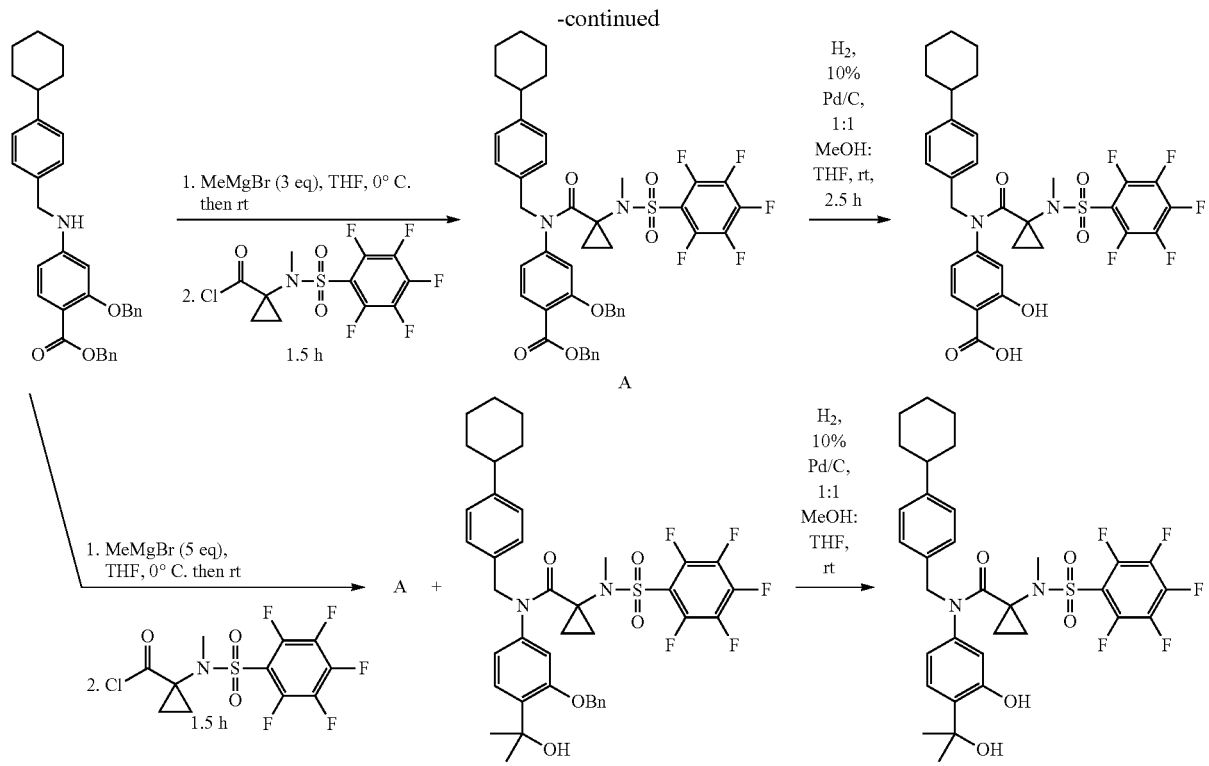

4-(N-(4-Cyclohexylbenzyl)-1-((2,3,4,5,6-pentafluoro-N-methylphenyl)sulfonamido)cyclopropane-1-carboxamido)-2-hydroxybenzoic acid

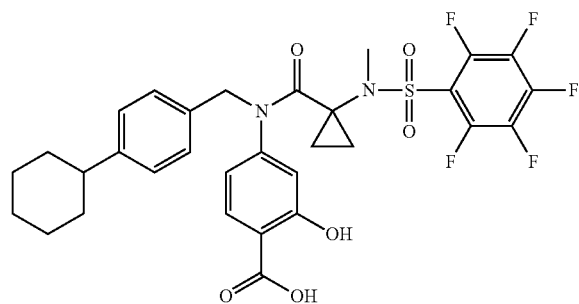 [SMILES: CN(C1(C(=O)N(Cc2ccc(C3CCCCC3)cc2)c2ccc(C(=O)O)c(O)c2)CC1)S(=O)(=O)c1c(F)c(F)c(F)c(F)c1F]

Step 1: tert-Butyl methyl malonate (3.9 mL, 23 mmol), potassium carbonate (7.9 g, 57.5 mmol) and dibromoethane (2.57 mL, 29.9 mmol) were combined in DMF (75 mL) and the resulting reaction mixture was stirred at room temperature overnight. The mixture was poured onto water (500 mL) and extracted with ether (3×). The combined ethereal layers were washed with water, then washed with brine, dried over anhydrous sodium sulfate and concentrated under reduced pressure. Purification by flash chromatography (0-5% EtOAc/hexane) provided 1-(tert-butyl) 1-methyl cyclopropane-1,1-dicarboxylate (2.35 g, 51% yield). Combined with another batch afforded the desired product (4.28 g). 1H NMR (300 MHz, Chloroform-d) δ 3.75 (s, 3H), 1.47 (s, 9H), 1.38 (s, 4H).

Step 2: To a stirred solution of 1-(tert-butyl) 1-methyl cyclopropane-1,1-dicarboxylate (4.28 g, 21.4 mmol) in ethanol (30 mL) was added 1N aqueous sodium hydroxide (30 mL, 30 mmol) and the resulting reaction mixture was stirred overnight. The crude reaction mixture was diluted with water and washed with ether (1×). The aqueous phase was acidified with aqueous 1N HCl and the resulting mixture was extracted with DCM (3×). The combined DCM extracts were dried over anhydrous sodium sulfate and concentrated in vacuo to provide 1-(tert-butoxycarbonyl)cyclopropane-1-carboxylic acid (3.7 g, 93%) as a colorless oil. 1H NMR (300 MHz, Chloroform-d) δ 1.84-1.76 (m, 2H), 1.70-1.63 (m, 2H), 1.49 (s, 9H).

Step 3: To a stirred solution of 1-(tert-butoxycarbonyl)cyclopropane-1-carboxylic acid (3.7 g, 19.8 mmol) in DCM (40 mL) was added under nitrogen TEA (2.75 mL, 19.8 mmol) followed by diphenylphosphoryl azide (4.27 mL, 19.8 mmol). The resultant reaction solution was warmed at reflux temperature for 2 h and removed from the oil bath. Benzyl alcohol (3.1 mL, 29.8 mmol) was added and the resulting reaction solution was warmed at reflux temperature for 5 h. The reaction mixture was allowed to cool to room temperature, poured onto 10% aqueous citric acid and extracted with DCM (2×). The combined organic extracts were washed with 5% sodium bicarbonate, dried over sodium sulfate and concentrated under reduced pressure. Flash chromatography (10-20% stepwise gradient) afforded intermediate product, tert-butyl 1-(((benzyloxy)carbonyl)amino)cyclopropane-1-carboxylate (4 g, 67% yield). To a stirred solution of tert-butyl 1-(((benzyloxy)carbonyl)amino)cyclopropane-1-carboxylate (2.4 g, 8.2 mmol) in methanol (40 mL) and THF (40 mL) was added 10% Pd/C (150 mg) and the resulting suspension was stirred at room temperature under a hydrogen atmosphere (6 h). The reaction mixture was filtered through Celite® and washed with methanol (2×). The combined filtrate and washes were concentrated and the resultant residue purified by flash chromatography (2-5% MeOH in DCM gradient) to provide tert-butyl 1-aminocyclopropane-1-carboxylate (0.86 g, 67% yield). 1H NMR (300 MHz, Chloroform-d) δ 1.96 (br. s, 2H), 1.44 (s, 9H), 1.25-1.17 (m, 2H), 0.97-0.89 (m, 2H).

Step 4: To a stirred solution of tert-butyl 1-aminocyclopropane-1-carboxylate (505 mg, 3.2 mmol) in dry acetonitrile (18 mL) was added copper (II) oxide (60 mg, 0.74 mmol) and DIPEA (0.612 mL, 3.52 mmol). To this vigorously stirred mixture was added pentafluorobenzenesulfonyl chloride (0.52 mL, 3.52 mmol). The reaction was exothermic and complete within 15 min. The mixture was poured onto water and extracted with EtOAc (3×). The combined organic extracts were washed with brine, dried over anhydrous magnesium sulfate and concentrated under reduced pressure. Flash chromatography (10-20% EtOAc/hexanes) provided intermediate, tert-butyl 1-((perfluorophenyl)sulfonamido)cyclopropane-1-carboxylate (867 mg, 50% yield). 1H NMR (300 MHz, Chloroform-d) δ 1.61-1.45 (m, 4H), 1.32 (s, 9H).

Step 5: To a stirred solution of tert-butyl 1-((perfluorophenyl)sulfonamido)cyclopropane-1-carboxylate (863 mg, 2.23 mmol) in DMF (20 mL) was added potassium carbonate (370 mg, 2.68 mmol) and following stirring at room temperature for 10 min by addition of methyl iodide (0.17 mL, 2.68 mmol). The resultant reaction mixture was stirred at room temperature for 30 min, then poured onto water and extracted with ether (3×). The combined ethereal layers were washed with brine, dried over anhydrous sodium sulfate and concentrated under reduced pressure. Flash chromatography (7% EtOAc/hexanes eluent) provided tert-butyl 1-((2,3,4,5,6-pentafluoro-N-methylphenyl)sulfonamido)cyclopropane-1-carboxylate (871 mg, 97% yield) as a white solid. 1H NMR (300 MHz, Chloroform-d) δ 3.15 (s, 3H), 1.87 (br. s, 4H), 1.37 (s, 9H).

Step 6: To a stirred solution of tert-butyl 1-((2,3,4,5,6-pentafluoro-N-methylphenyl)sulfonamido)-cyclopropane-1-carboxylate (868 mg, 2.16 mmol) in DCM (20 mL) was added TFA (20 mL) and the resultant reaction solution was stirred at room temperature overnight. Concentration in vacuo afforded 1-((2,3,4,5,6-pentafluoro-N-methylphenyl)sulfonamido)cyclopropane-1-carboxylic acid (750 mg, 99% yield) as a white solid. 1H NMR (300 MHz, Chloroform-d) δ 3.15 (s, 3H), 1.98 (br. s, 2H), 1.59 (br. s, 1H), 1.41-1.10 (m, 1H).

Step 7: To a stirred solution of 1-((2,3,4,5,6-pentafluoro-N-methylphenyl)sulfonamido)cyclopropane-1-carboxylic acid (376 mg, 1.09 mmol) in DCM (20 mL) under nitrogen was added DMF (2 drops) followed by oxalyl chloride (0.13 mL, 1.5 mmol). The resulting reaction mixture was stirred at room temperature for 1.5 h and then concentrated in vacuo to afford 1-((2,3,4,5,6-pentafluoro-N-methylphenyl)sulfonamido)cyclopropane-1-carbonyl chloride (373 mg, 100% yield) as an off-white solid. 1H NMR (300 MHz, Chloroform-d) δ 3.16 (s, 3H), 2.30 (br. s, 2H), 1.91 (br. s, 1H), 1.45 (br. s, 1H).

Step 8: To a stirred solution of benzyl 2-(benzyloxy)-4-((4-cyclohexylbenzyl)amino)benzoate (253 mg, 0.5 mmol) in THF (8 mL) under nitrogen at 0° C. was added methylmagnesium bromide (1.07 mL of 1.4 M in 1:3 THF:toluene, 1.5 mmol, 3 equiv). Stirring was continued at 0-5° C. for 5 min and then room temperature for 5 min. The resultant solution was added drop-wise to a stirred solution of 1-((2,3,4,5,6-pentafluoro-N-methylphenyl)sulfonamido)cyclopropane-1-carbonyl chloride (254 mg, 0.7 mmol) in THF (8 mL) under nitrogen. The resulting reaction mixture was stirred at room temperature for 1.5 h, quenched with aqueous saturated ammonium chloride, poured onto water and extracted with EtOAc (3×). The combined organic extracts were dried over anhydrous sodium sulfate, concentrated under reduced pressure and resulting residue purified by flash chromatography (15-25% EtOAc/hexane) to afford benzyl 2-(benzyloxy)-4-(N-(4-cyclohexylbenzyl)-1-((2,3,4,5,6-pentafluoro-N-methylphenyl)sulfon-amido)cyclopropane-1-carboxamido)benzoate (205 mg, 49% yield). MS (ESI) m/z 833.2 [M+H]+, m/z 855.2 [M+Na]+.

Step 9: To a stirred solution of benzyl 2-(benzyloxy)-4-(N-(4-cyclohexylbenzyl)-1-((2,3,4,5,6-pentafluoro-N-methylphenyl)sulfonamido)cyclopropane-1-carboxamido)benzoate (193 mg, 0.23 mmol) in methanol (3 mL) and THF (3 mL) was added 10% Pd/C (30 mg) and the resulting suspension was stirred at room temperature under a hydrogen atmosphere for 2.5 h. The reaction mixture was filtered through Celite® and washed with methanol (2×). The combined filtrate and washes were concentrated, purified by flash chromatography (5-7% MeOH/DCM gradient) to provide 4-(N-(4-cyclohexylbenzyl)-1-((2,3,4,5,6-pentafluoro-N-methylphenyl)sulfonamido)cyclopropane-1-carboxamido)-2-hydroxybenzoic acid (107 mg, 71% yield) as a tan solid. MS (ESI) m/z 653.1751 [M+H]+.

Example 11

N-(4-cyclohexylbenzyl)-N-(3-hydroxy-4-(2-hydroxypropan-2-yl)phenyl)-1-((2,3,4,5,6-pentafluoro-N-methylphenyl)sulfonamido)cyclopropane-1-carboxamide

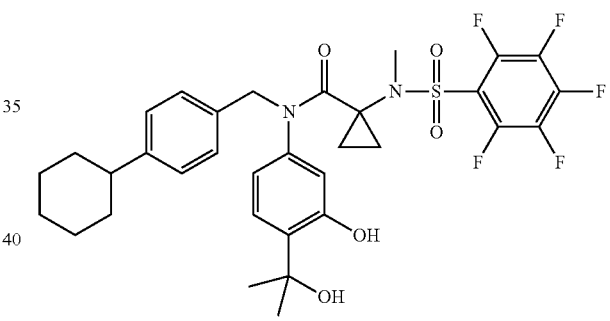

Step 1: To a stirred solution of benzyl 2-(benzyloxy)-4-((4-cyclohexylbenzyl)amino)benzoate (253 mg, 0.5 mmol) in THF (8 mL) under nitrogen at 0° C. was added methylmagnesium bromide (1.8 mL of 1.4 M in 1:3 THF:toluene, 2.5 mmol, 5 equiv). Stirring was continued at 0-5° C. for 10 min. The resultant solution was added drop-wise to a stirred solution of 1-((2,3,4,5,6-pentafluoro-N-methylphenyl)sulfonamido)cyclopropane-1-carbonyl chloride (254 mg, 0.7 mmol) in THF (8 mL) under nitrogen. The resulting reaction mixture was stirred at room temperature for 40 min, quenched with saturated aqueous ammonium chloride, poured onto water and extracted with EtOAc (3×). The combined organic extracts were dried over anhydrous sodium sulfate, concentrated under reduced pressure and resulting residue purified by flash chromatography (25% EtOAc/hexane eluent) to afford impure benzyl 2-(benzyloxy)-4-(N-(4-cyclohexylbenzyl)-1-((2,3,4,5,6-pentafluoro-N-methylphenyl)sulfonamido)-cyclopropane-1-carboxamido)benzoate (115 mg) and major side product, N-(3-(benzyloxy)-4-(2-hydroxypropan-2-yl)phenyl)-N-(4-cyclohexylbenzyl)-1-((2,3,4,5,6-pentafluoro-N-methylphenyl)sulfonamido)cyclopropane-1-carboxamide (127 mg). MS (ESI) m/z 757 [M+H]+, m/z 779 [M+Na]+.

Step 2: To a stirred solution of N-(3-(benzyloxy)-4-(2-hydroxypropan-2-yl)phenyl)-N-(4-cyclohexylbenzyl)-1-((2,3,4,5,6-pentafluoro-N-methylphenyl)sulfonamido)cyclopropane-1-carboxamide (121 mg, 0.16 mmol) in methanol (3 mL) and THF (3 mL) was added 10% Pd/C (40 mg) and the resulting suspension was stirred at room temperature under a hydrogen atmosphere for 2.5 h. The reaction mixture was filtered through Celite® and washed with methanol (2×). The combined filtrate and washes were concentrated, purified by flash chromatography (25-35% EtOAc/hexane) to provide N-(4-cyclohexylbenzyl)-N-(3-hydroxy-4-(2-hydroxypropan-2-yl)phenyl)-1-((2,3,4,5,6-pentafluoro-N-methylphenyl)sulfonamido)cyclopropane-1-carboxamide (76 mg, 71% yield) as a white foam. MS (ESI) m/z 667.2241 [M+H]+.

Example 12

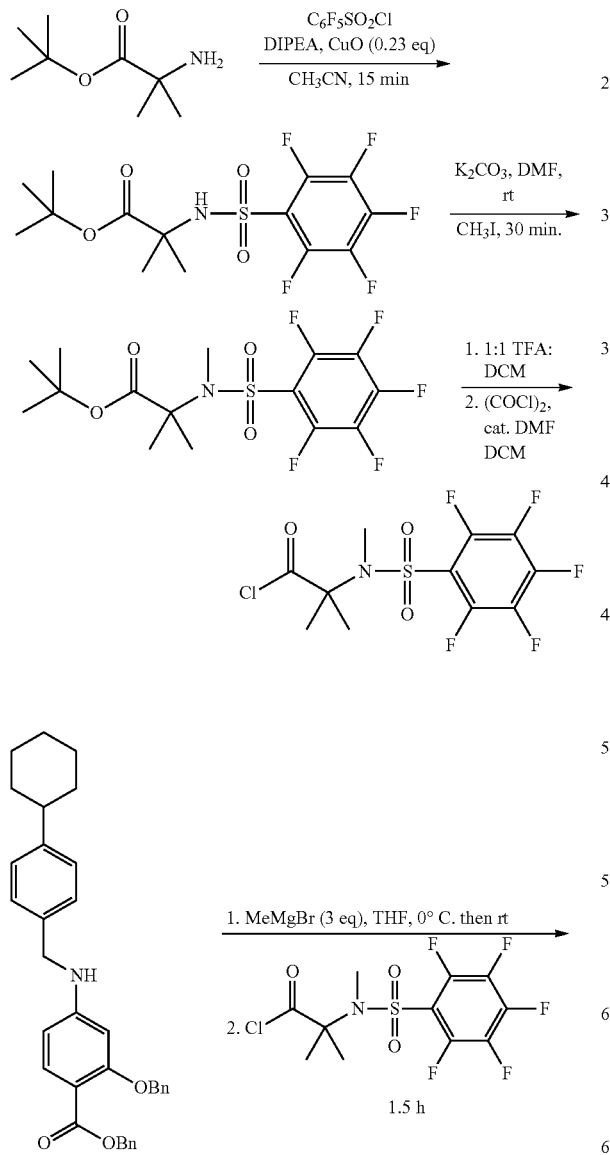

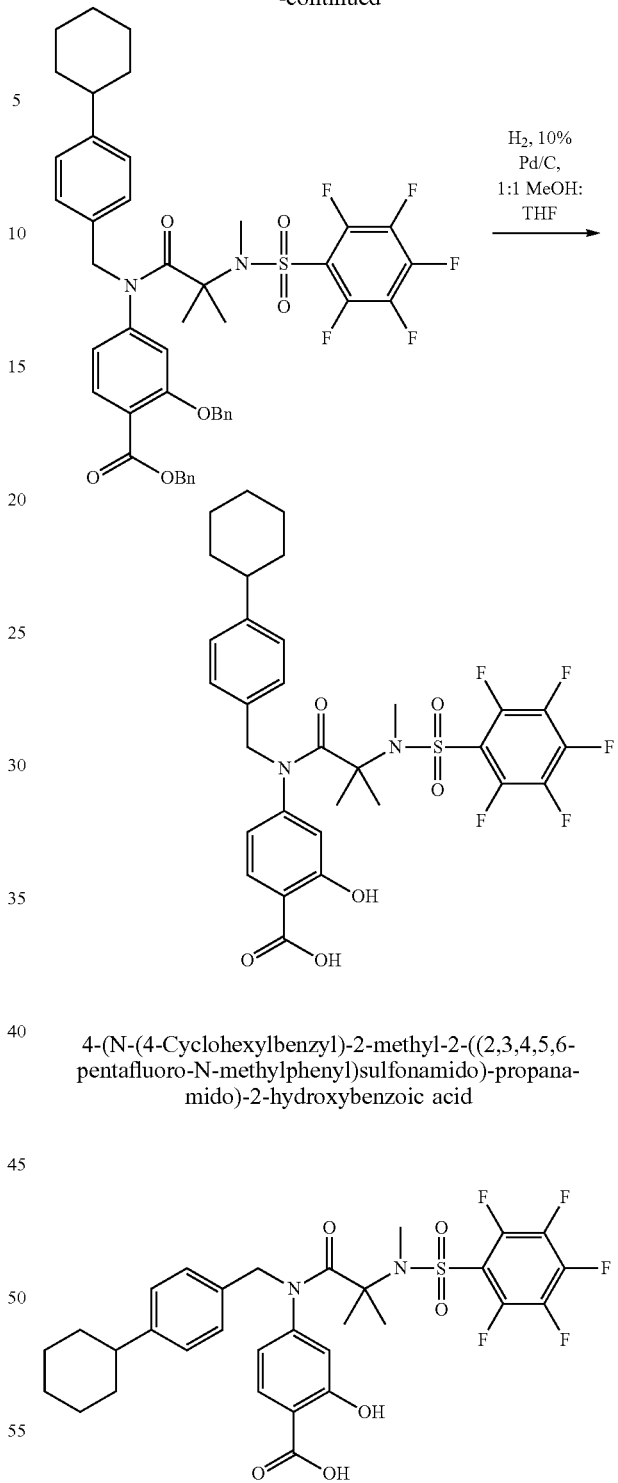

4-(N-(4-Cyclohexylbenzyl)-2-methyl-2-((2,3,4,5,6-pentafluoro-N-methylphenyl)sulfonamido)-propanamido)-2-hydroxybenzoic acid Step 1: To a stirred solution of tert-butyl 2-amino-2-methylpropanoate (803 mg, 5.05 mmol) in dry acetonitrile (10 mL) under nitrogen was added copper (II) oxide (20 mg, 0.25 mmol) and DIPEA (0.97 mL, 5.55 mmol). To this vigorously stirred mixture was added pentafluorobenzenesulfonyl chloride (0.75 mL, 5.05 mmol). The reaction was exothermic and complete within 10 min. The mixture was poured onto water and extracted with EtOAc (3×). The combined organic extracts were dried over anhydrous sodium sulfate and concentrated under reduced pressure. Flash chromatography (10-20% EtOAc/hexanes) provided tert-butyl 2-methyl-2-((perfluorophenyl)sulfonamido)propanoate (1.33 g, 74% yield) as a white solid. Combined with previous batch to provide 1.7 g of product. 1H NMR (300 MHz, Chloroform-d) δ 6.07 (s, 1H), 1.54 (s, 6H), 1.48 (s, 9H).

Step 2: To a stirred solution of tert-butyl 2-methyl-2-((perfluorophenyl)sulfonamido)propanoate (1.676 g, 4.31 mmol) in DMF (40 mL) under nitrogen was added potassium carbonate (0.72 g, 5.17 mmol) and following stirring at room temperature for 10 min by addition of methyl iodide (0.33 mL, 5.17 mmol). The resultant reaction mixture was stirred at room temperature for 1 h, then poured onto water and extracted with ether (3×). The combined ethereal layers were washed with brine, dried over anhydrous sodium sulfate and concentrated under reduced pressure. Flash chromatography (5% EtOAc/hexanes eluent provided tert-butyl 2-methyl-2-((2,3,4,5,6-pentafluoro-N-methylphenyl)sulfonamido)propanoate (1.77 g, 100% yield). 1H NMR (300 MHz, Chloroform-d) δ 3.13 (t, J=1.6 Hz, 3H), 1.57 (s, 6H), 1.45 (s, 9H).

Step 3: To a stirred solution of tert-butyl 2-methyl-2-((2,3,4,5,6-pentafluoro-N-methylphenyl)sulfonamido)propanoate (1.768 g, 5.17 mmol) in DCM (35 mL) was added TFA (35 mL) and the resultant reaction solution was stirred at room temperature overnight. Concentration in vacuo afforded 2-methyl-2-((2,3,4,5,6-pentafluoro-N-methylphenyl)sulfonamido)propanoic acid (1.476 g, 97% yield) as a white solid. 1H NMR (300 MHz, Chloroform-d) δ 3.17 (td, J=1.7, 0.5 Hz, 3H), 1.65 (s, 6H).

Step 4: To a stirred solution of 2-methyl-2-((2,3,4,5,6-pentafluoro-N-methylphenyl)sulfonamido)propanoic acid (821 mg, 2.37 mmol) in DCM (30 mL) under nitrogen was added DMF (2 drops) followed by oxalyl chloride (0.264 mL, 3.0 mmol). The resulting reaction mixture was stirred at room temperature for 0.5 h and then concentrated in vacuo to afford 2-methyl-2-((2,3,4,5,6-pentafluoro-N-methylphenyl)sulfonamido)propanoyl chloride (820 mg, 100% yield) as an off-white solid. 1H NMR (300 MHz, Chloroform-d) δ 3.23 (t, J=1.6 Hz, 3H), 1.72 (s, 6H).

Step 5: To a stirred solution of benzyl 2-(benzyloxy)-4-((4-cyclohexylbenzyl)amino)benzoate (260 mg, 0.51 mmol) in THF (8 mL) under nitrogen at 0° C. was added methylmagnesium bromide (0.8 mL of 1.4 M in 1:3 THF:toluene, 1.12 mmol, 2.2 equiv). Stirring was continued at 0-5° C. for 5 min and then room temperature for 5 min. The resultant solution was added drop-wise to a stirred solution of 2-methyl-2-((2,3,4,5,6-pentafluoro-N-methylphenyl)sulfonamido)propanoyl chloride (226 mg, 0.62 mmol) in THF (8 mL) under nitrogen. The resulting reaction mixture was stirred at 40° C. for 1.5 h, quenched with aqueous saturated ammonium chloride, poured onto water and extracted with EtOAc (3×). The combined organic extracts were dried over anhydrous sodium sulfate, concentrated under reduced pressure and resulting residue purified by flash chromatography (15-25% EtOAc/hexane) to afford benzyl 2-(benzyloxy)-4-(N-(4-cyclohexylbenzyl)-2-methyl-2-((2,3,4,5,6-pentafluoro-N-methylphenyl)sulfonamido)propanamido)-benzoate (120.6 mg, 28% yield). MS (ESI) m/z 835.25 [M+H]+.

Step 6: To a stirred solution of benzyl 2-(benzyloxy)-4-(N-(4-cyclohexylbenzyl)-2-methyl-2-((2,3,4,5,6-pentafluoro-N-methylphenyl)sulfonamido)propanamido)-benzoate (114 mg, 0.137 mmol) in methanol (10 mL) and THF (10 mL) was added 10% Pd/C (25 mg) and the resulting suspension was stirred at room temperature under a hydrogen atmosphere for 4 h. The reaction mixture was filtered through Celite® and washed with methanol (2×). The combined filtrate and washes were concentrated, purified by flash chromatography (5% MeOH/DCM gradient) and triturated with 10% ether in hexanes to provide 4-(N-(4-cyclohexylbenzyl)-2-methyl-2-((2,3,4,5,6-pentafluoro-N-methylphenyl)sulfonamido)-propanamido)-2-hydroxybenzoic acid (54 mg, 60% yield) as a white solid. MS (ESI) m/z 655.1911 [M+H]+.

Example 13

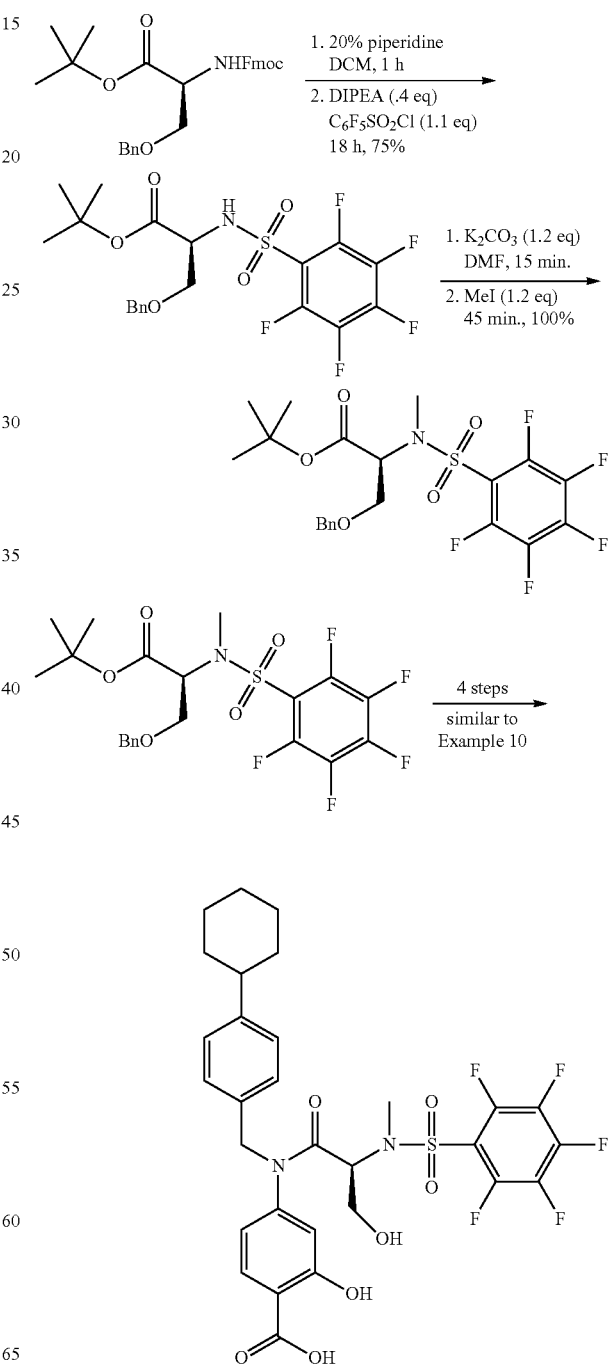

(S)-4-(N-(4-Cyclohexylbenzyl)-3-hydroxy-2-((2,3,4,5,6-pentafluoro-N-methylphenyl)sulfonamido)-propanamido)-2-hydroxybenzoic acid

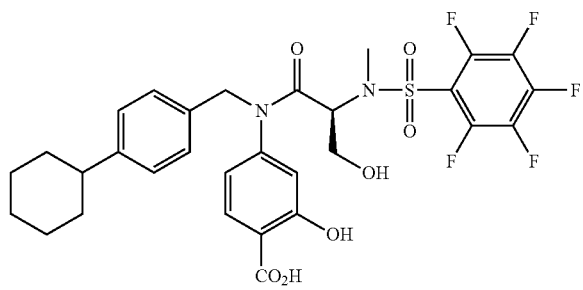 [SMILES: CN([C@@H](CO)C(=O)N(Cc1ccc(C2CCCCC2)cc1)c1ccc(C(=O)O)c(O)c1)S(=O)(=O)c1c(F)c(F)c(F)c(F)c1F]

Step 1: tert-Butyl N-(((9H-fluoren-9-yl)methoxy)carbonyl)-O-benzyl-L-serinate was prepared as previously described (Foley, David et al., Organic & Biomolecular Chemistry, 7(18), 3652-3656; 2009) from commercially-available Fmoc-O-benzyl-L-serine. To a stirred solution of tert-butyl N-(((9H-fluoren-9-yl)methoxy)carbonyl)-O-benzyl-L-serinate (885 mg, 1.87 mmol) in DCM (10 mL) was added 3.9 mL of tris(2-aminoethyl)amine and the resultant mixture was stirred for 4 h at room temperature under nitrogen, then diluted with phosphate buffer (pH=5-6) and extracted with DCM (2×). The combined organic extracts were washed with phosphate buffer (1×), saturated aqueous KHCO₃ (1×), dried over sodium sulfate and concentrated under reduced pressure. The resulting crude product, tert-butyl O-benzyl-L-serinate (500 mg), was used as for the next step. 1H NMR (300 MHz, Chloroform-d) δ 7.48-7.22 (m, 5H), 4.70-4.41 (m, 2H), 3.80-3.62 (m, 2H), 3.54 (dd, J=5.1, 3.9 Hz, 1H), 1.71 (br. s, 2H), 1.47 (s, 9H).

Step 2: To a stirred solution of tert-butyl O-benzyl-L-serinate (500 mg, 1.87 mmol) in DCM (10 mL) under nitrogen at 0° C. was added DIPEA (0.43 mL, 2.43 mmol) followed by pentafluorobenzenesulfonyl chloride (0.31 mL, 2.06 mmol) and the resulting mixture was allowed to warm to room temperature and stirred at this temperature for 5 h. The reaction mixture was poured onto water and extracted with DCM (3×). The combined extracts were dried over anhydrous sodium sulfate, concentrated under reduced pressure and the resulting residue purified by flash chromatography (10% EtOAc/hexane) to provide tert-butyl O-benzyl-N-((perfluorophenyl)sulfonyl)-L-serinate (672 mg, 75% yield). MS (ESI) m/z 504 [M+Na]+.

Step 3: To a stirred solution of tert-butyl O-benzyl-N-((perfluorophenyl)sulfonyl)-L-serinate (660 mg, 1.37 mmol) in DMF (12 mL) under nitrogen was added potassium carbonate (227 mg, 1.65 mmol) and the resulting mixture was stirred at room temperature for 15 min before addition of methyl iodide (0.103 mL, 1.65 mmol). The resulting mixture was stirred at room temperature for an additional 45 min, poured onto water and extracted with ether (3×). The combined ether extracts were washed with water and then brine, dried over sodium sulfate and concentrated under reduced pressure. Purification by flash chromatography (8% EtOAc/hexane) afforded tert-butyl O-benzyl-N-methyl-N-((perfluorophenyl)sulfonyl)-L-serinate (650 mg, 96% yield). 1H NMR (300 MHz, Chloroform-d) δ 7.38-7.31 (m, 3H), 7.27-7.19 (m, 2H), 4.92 (dd, J=7.0, 4.3 Hz, 1H), 4.53 (d, J=11.5 Hz, 1H), 4.42 (d, J=11.5 Hz, 1H), 3.97-3.78 (m, 2H), 3.12 (s, 3H), 1.43 (s, 9H).

Step 4: To a stirred solution of tert-butyl O-benzyl-N-methyl-N-((perfluorophenyl)sulfonyl)-L-serinate (632 mg, 1.28 mmol) in DCM (9 mL) under nitrogen was added TFA (9 mL) and the resultant reaction solution was stirred at room temperature for 9 h. Concentration in vacuo afforded O-benzyl-N-methyl-N-((perfluorophenyl)sulfonyl)-L-serine (663 mg, 100% yield) as a pale yellow solid. MS (ESI) m/z 462 [M+Na]+.

Step 5: To a stirred solution of O-benzyl-N-methyl-N-((perfluorophenyl)sulfonyl)-L-serine (663 mg, 1.28 mmol) in DCM (16 mL) under nitrogen was added DMF (2 drops) followed by oxalyl chloride (0.15 mL, 1.8 mmol). The resulting reaction mixture was stirred at room temperature for 1.5 h and then concentrated in vacuo to afford O-benzyl-N-methyl-N-((perfluorophenyl)sulfonyl)-L-serinoyl chloride as a pale yellow solid. 1H NMR (300 MHz, Chloroform-d) δ 7.44-7.33 (m, 3H), 7.26-7.11 (m, 2H), 5.28 (dd, J=7.5, 3.4 Hz, 1H), 4.60-4.39 (m, 2H), 4.19-3.91 (m, 2H), 3.13 (s, 3H).

Step 6: To a stirred solution of benzyl 2-(benzyloxy)-4-((4-cyclohexylbenzyl)amino)benzoate (194 mg, 0.38 mmol) in THF (6 mL) under nitrogen at 0° C. was added methylmagnesium bromide (0.81 mL of 1.4 M in 1:3 THF:toluene, 1.14 mmol, 3 equiv). Stirring was continued at 0-5° C. for 5 min and then room temperature for 5 min. The resultant solution was added drop-wise to a stirred solution of O-benzyl-N-methyl-N-((perfluorophenyl)sulfonyl)-L-serinoyl chloride (257 mg, 0.5 mmol) in THF (6 mL) under nitrogen. The resulting reaction mixture was stirred at room temperature for 1 h, quenched with aqueous saturated ammonium chloride, poured onto water and extracted with EtOAc (3×). The combined organic extracts were washed with brine, dried over anhydrous sodium sulfate and concentrated under reduced pressure. The resulting residue purified by flash chromatography (0-10% EtOAc in (25% DCM/hexane) gradient) to afford benzyl (S)-2-(benzyloxy)-4-(3-(benzyloxy)-N-(4-cyclohexylbenzyl)-2-((2,3,4,5,6-pentafluoro-N-methylphenyl)sulfonamido)propanamido)benzoate (130 mg, 36% yield) as a white foam. MS (ESI) m/z 949.2 [M+Na]+.

Step 7: To a stirred solution of benzyl (S)-2-(benzyloxy)-4-(3-(benzyloxy)-N-(4-cyclohexylbenzyl)-2-((2,3,4,5,6-pentafluoro-N-methylphenyl)sulfonamido)propanamido)benzoate (120 mg, 0.13 mmol) in methanol (5 mL) and THF (5 mL) was added 10% Pd/C (20 mg) and the resulting suspension was stirred at room temperature under a hydrogen atmosphere overnight. The reaction mixture was filtered through Celite® and washed with methanol (2×). The combined filtrate and washes were concentrated and triturated with DCM in hexanes to provide (S)-4-(N-(4-cyclohexylbenzyl)-3-hydroxy-2-((2,3,4,5,6-pentafluoro-N-methylphenyl)sulfonamido)propanamido)-2-hydroxybenzoic acid (85.2 mg, 98% yield) as a pale yellow solid. HRMS (ESI) m/z 657.1697 [M+H]+.

Example 14

(R)-4-(N-(4-Cyclohexylbenzyl)-3-hydroxy-2-((2,3,4,5,6-pentafluoro-N-methylphenyl)sulfonamido)-propanamido)-2-hydroxybenzoic acid

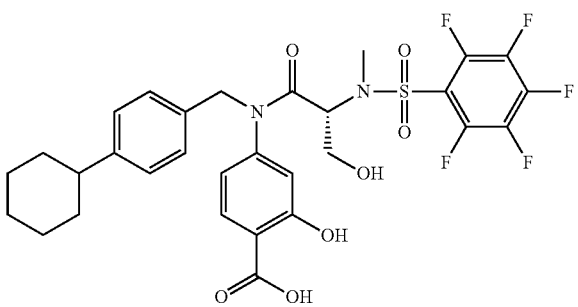

Preparation by a similar sequence to example 13, except substituting Fmoc-O-benzyl-D-serine for Fmoc-O-benzyl-L-serine in step 1 afforded (R)-4-(N-(4-cyclohexylbenzyl)-3-hydroxy-2-((2,3,4,5,6-pentafluoro-N-methylphenyl)sulfonamido)-propanamido)-2-hydroxybenzoic acid as a foam. MS (ESI) m/z 657.1695 [M+H]+.
Example 15
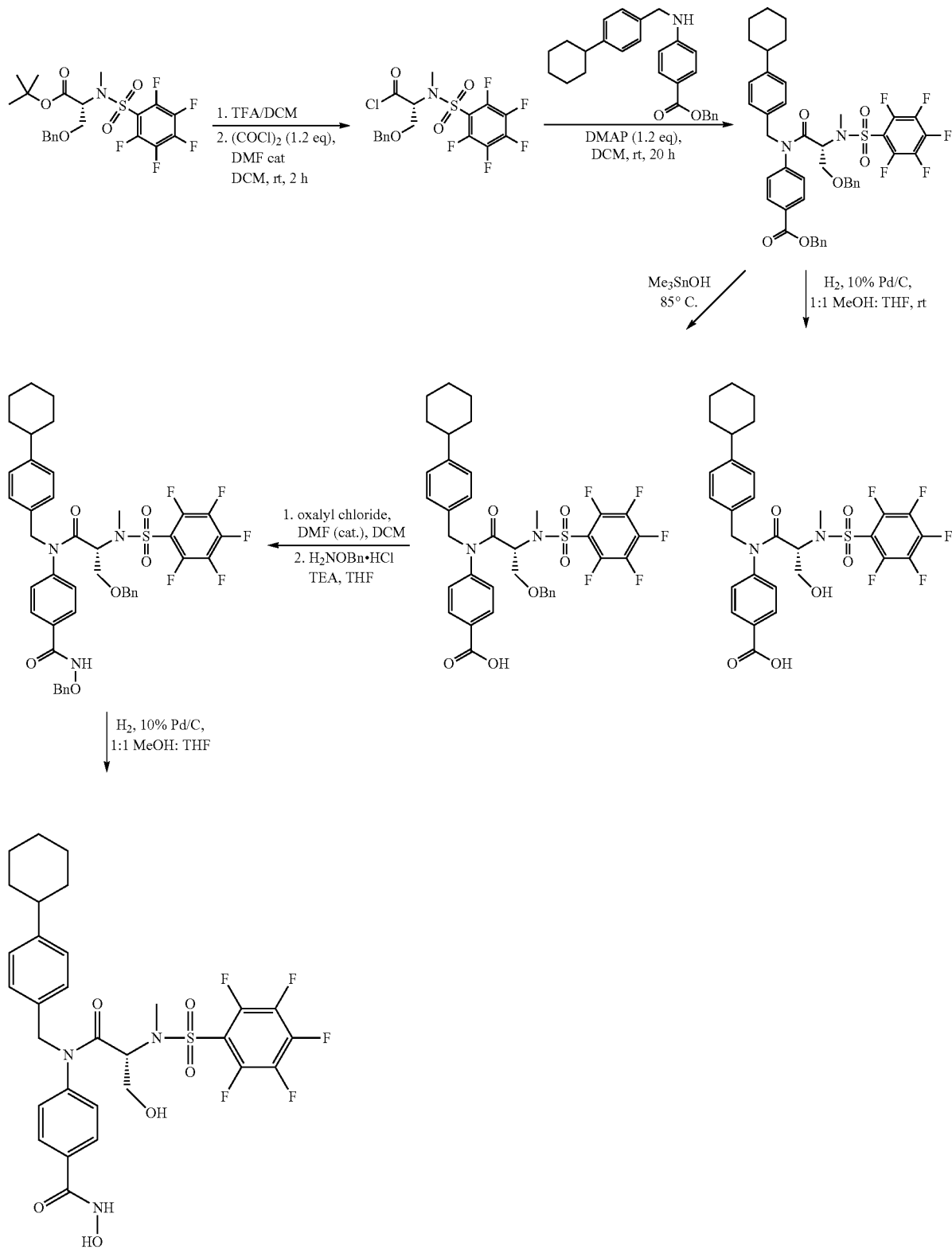

(R)-4-(N-(4-Cyclohexylbenzyl)-3-hydroxy-2-((2,3,4,5,6-pentafluoro-N-methylphenyl)sulfonamido)-propanamido)-N-hydroxybenzamide

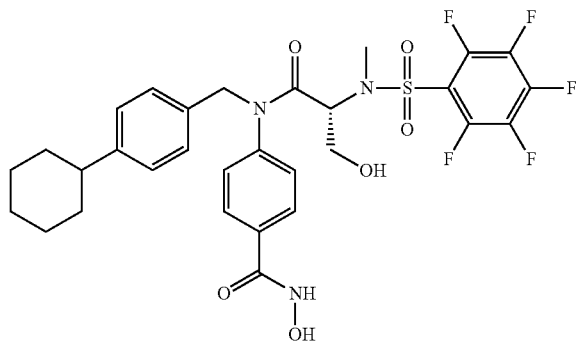 [SMILES: CN([C@H](CO)C(=O)N(Cc1ccc(C2CCCCC2)cc1)c1ccc(C(=O)NO)cc1)S(=O)(=O)c1c(F)c(F)c(F)c(F)c1F]

Starting tert-butyl O-benzyl-N-methyl-N-((perfluorophenyl)sulfonyl)-D-serinate was prepared as described in example 13 (Steps 1-3) except substituting Fmoc-O-benzyl-D-serine for Fmoc-O-benzyl-L-serine in step 1.

Step 1: To a stirred solution of tert-butyl O-benzyl-N-methyl-N-((perfluorophenyl)sulfonyl)-D-serinate (836 mg, 1.69 mmol) in DCM (12 mL) under nitrogen was added TFA (12 mL) and the resulting reaction solution was stirred at room temperature overnight. The crude reaction mixture was concentrated in vacuo to give O-benzyl-N-methyl-N-((pentafluorophenyl)sulfonyl)-D-serine (763 mg, 100% yield) as a cream colored solid. 1H NMR (300 MHz, Chloroform-d) δ 7.41-7.31 (m, 3H), 7.23-7.13 (m, 2H), 5.02 (dd, J=6.9, 3.6 Hz, 1H), 4.44 (q, J=11.2 Hz, 2H), 4.07-3.79 (m, 2H), 3.09 (s, 3H).

Step 2: To a stirred solution of O-benzyl-N-methyl-N-((pentafluorophenyl)sulfonyl)-D-serine (440 mg, 1 mmol) in DCM (18 mL) under nitrogen was added DMF (2 drops) followed by oxalyl chloride (0.12 mL, 1.4 mmol) and the resulting reaction solution was stirred at room temperature before concentration under reduced pressure. The residue was dissolved in toluene and concentrated in vacuo to afford O-benzyl-N-methyl-N-((pentafluorophenyl)sulfonyl)-D-serinoyl chloride which was used as is. 1H NMR (300 MHz, Chloroform-d) δ 7.40-7.31 (m, 3H), 7.23-7.14 (m, 2H), 5.26 (dd, J=7.4, 3.4 Hz, 1H), 4.54-4.39 (m, 2H), 4.15-3.92 (m, 2H), 3.11 (s, 3H).

Step 3: To a solution of the above, O-benzyl-N-methyl-N-((pentafluorophenyl)sulfonyl)-D-serinoyl chloride (1 mmol) and benzyl 4-((4-cyclohexylbenzyl)amino)benzoate (332 mg, 0.83 mmol) in DCM (15 mL) was added DMAP (122 mg, 1 mmol) and the resulting reaction solution was stirred under nitrogen overnight. The crude reaction mixture was then poured onto water and extracted with DCM (3×). The combined organic extracts were dried over sodium sulfate, concentrated under reduced pressure and the resulting residue purified by flash chromatography (20-30% EtOAc/hexanes) afforded benzyl (R)-4-(3-(benzyloxy)-N-(4-cyclohexylbenzyl)-2-((2,3,4,5,6-pentafluoro-N-methylphenyl)-sulfonamido)prop-anamido)benzoate (152 mg, 22% yield). Product was combined with earlier batch to provide 225 mg. MS (ESI) m/z 821.20 [M+H]+.

Step 4: To a stirred solution of benzyl (R)-4-(3-(benzyloxy)-N-(4-cyclohexylbenzyl)-2-((2,3,4,5,6-pentafluoro-N-methylphenyl)-sulfonamido)propanamido)benzoate (222 mg, 0.27 mmol) in DCE (25 mL) under nitrogen was added trimethyltin hydroxide (390 mg, 2.16 mmol) and the resulting mixture was stirred at 85° C. for 24 h. The crude reaction was acidified with 10% aqueous HCl, poured onto water and extracted with EtOAc (3×). The combined organic extracts were washed with brine, dried over sodium sulfate and concentrated under reduced pressure. Purification by flash chromatography (1-6% EtOAc/hexanes eluent) afforded recovered benzyl (R)-4-(3-(benzyloxy)-N-(4-cyclohexylbenzyl)-2-((2,3,4,5,6-pentafluoro-N-methylphenyl)sulfonamido)propanamido)benzoate (32 mg) and then continued elution with 5% methanol in DCM provided product (R)-4-(3-(benzyloxy)-N-(4-cyclohexylbenzyl)-2-((2,3,4,5,6-pentafluoro-N-methylphenyl)sulfon-amido)propanamido)benzoic acid (153 mg, 63% yield). MS (ESI) m/z 731.25 [M+H]+.

Step 5: To a stirred solution of (R)-4-(3-(benzyloxy)-N-(4-cyclohexylbenzyl)-2-((2,3,4,5,6-pentafluoro-N-methylphenyl)sulfon-amido)propanamido)benzoic acid (153 mg, 0.21 mmol) in DCM (11 mL) was added 1 drop of DMF followed by oxalyl chloride (0.039 mL, 0.46 mmol). The resulting reaction solution was stirred at room temperature under nitrogen for 2 h and then concentrated under reduced pressure to afforded (R)-4-(3-(benzyloxy)-N-(4-cyclohexylbenzyl)-2-((2,3,4,5,6-pentafluoro-N-methylphenyl)sulfonamido)propanamido)benzoyl chloride, which was used as is.

Step 6: To a stirred solution of (R)-4-(3-(benzyloxy)-N-(4-cyclohexylbenzyl)-2-((2,3,4,5,6-pentafluoro-N-methylphenyl)sulfonamido)propanamido)benzoyl chloride (0.21 mmol) in THF (5 mL) under nitrogen at 0° C. was added a solution of O-benzylhydroxylamine hydrochloride (67 mg, 0.42 mmol) and TEA (0.088 mL, 0.63 mmol) in DMF (5 mL). The resultant reaction mixture was stirred at room temperature for 40 min and then quenched with 10% aqueous potassium bisulfate, poured onto water and extracted with ether (3×). The combined organic extracts were washed with water, then washed with brine, dried over sodium sulfate and concentrated under reduced pressure. The resulting residue was purified by flash chromatography (30% EtOAc/hexanes) to provide (R)—N-(benzyloxy)-4-(3-(benzyloxy)-N-(4-cyclohexylbenzyl)-2-((2,3,4,5,6-pentafluoro-N-methyl-phenyl)sulfonamido)propanamido)benzamide (125 mg, 71% yield) as a white foam. MS (ESI) m/z 836.3 [M+H]+.

Step 7: To a stirred solution of (R)—N-(benzyloxy)-4-(3-(benzyloxy)-N-(4-cyclohexylbenzyl)-2-((2,3,4,5,6-pentafluoro-N-methyl-phenyl)sulfonamido)propanamido)benzamide (120 mg, 0.14 mmol) in methanol (5 mL) and THF (5 mL) was added 10% Pd/C (15 mg) and the resulting suspension was stirred at room temperature under a hydrogen atmosphere for 7 h. The reaction mixture was filtered through Celite® and washed with methanol (2×). The combined filtrate and washes were concentrated and the resulting residue was purified by trituration with ether:hexane to provide (R)-4-(N-(4-cyclohexylbenzyl)-3-hydroxy-2-((2,3,4,5,6-pentafluoro-N-methylphenyl)sulfonamido)-propanamido)-N-hydroxybenzamide (50 mg, 55% yield). HRMS (ESI) m/z 656.1847 [M+H]+.

Example 16

(R)-4-(N-(4-Cyclohexylbenzyl)-3-hydroxy-2-((2,3,4,5,6-pentafluoro-N-methylphenyl)sulfonamido)-propanamido)benzoic acid

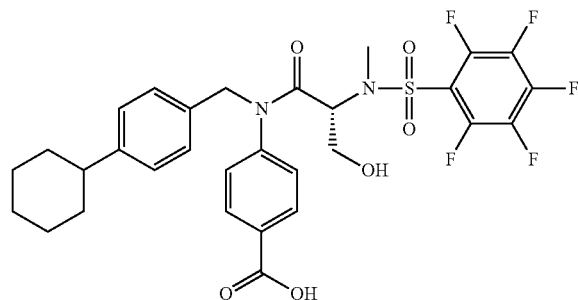 [SMILES: CN([C@H](CO)C(=O)N(Cc1ccc(C2CCCCC2)cc1)c1ccc(C(=O)O)cc1)S(=O)(=O)c1c(F)c(F)c(F)c(F)c1F]

To a stirred solution of benzyl (R)-4-(3-(benzyloxy)-N-(4-cyclohexylbenzyl)-2-((2,3,4,5,6-pentafluoro-N-methylphenyl)-sulfonamido)propanamido)benzoate (30 mg, 0.037 mmol) in methanol (4 mL) and THF (4 mL) was added 10% Pd/C (5 mg) and the resulting suspension was stirred at room temperature under a hydrogen atmosphere 24 h. The reaction mixture was filtered through Celite® and washed with methanol (2×). The combined filtrate and washes were concentrated and purified by preparative TLC to provide (R)-4-(N-(4-Cyclohexylbenzyl)-3-hydroxy-2-((2,3,4,5,6-pentafluoro-N-methylphenyl)sulfonamido)-propanamido) benzoic acid as a foam. HRMS (ESI) m/z 639.1597 [M−H]−.

Example 17

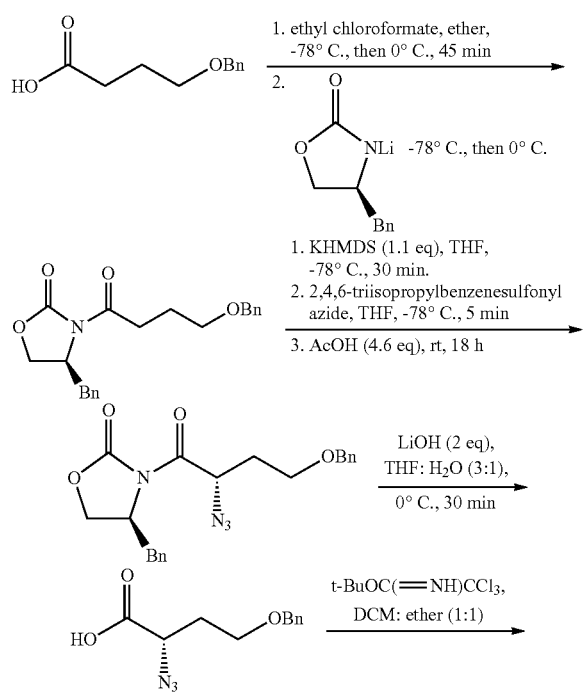

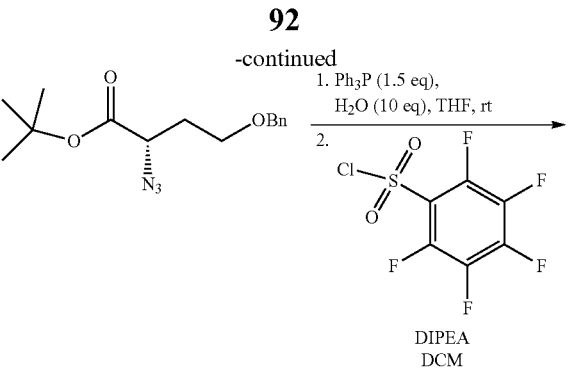

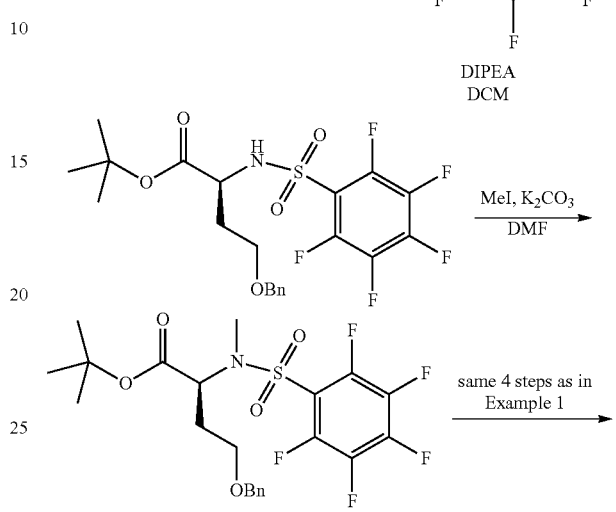

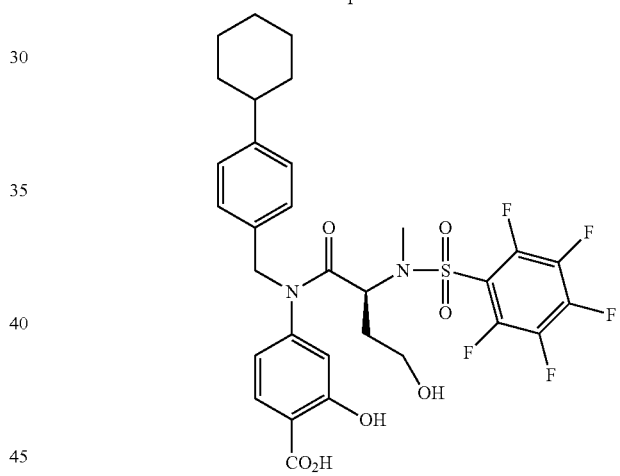

(S)-4-(N-(4-Cyclohexylbenzyl)-4-hydroxy-2-((2,3,4,5,6-pentafluoro-N-methylphenyl)-sulfonamido)-butanamido)-2-hydroxybenzoic acid

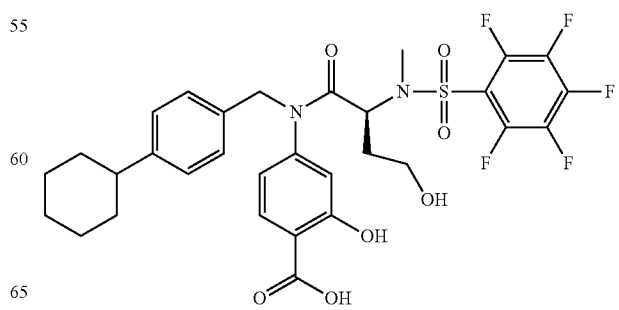

Step 1: To a stirred solution of 4-benzyloxybutyric acid (2.05 mL, 11.6 mmol) in dry ether (115 mL) under nitrogen was added TEA (1.62 mL, 11.6 mmol) and the resulting solution was cooled to −78° C. Ethyl chloroformate (1.10 mL, 11.6 mmol) was added dropwise to the solution and the resulting thick white suspension was stirred at 0° C. for 45 min and then cooled to −78° C. In the meantime in a separate flask, to a solution of (S)-4-benzyloxazolidin-2-one (2.06 g, 11.6 mmol) in dry THF under nitrogen at −78° C. was added a solution of n-butyl lithium (5.8 mL of 2M in hexanes, 11.6 mmol) and the resulting solution was stirred at −78° C. for 45 min before being added dropwise via cannula to the mixed anhydride of 4-benzyloxybutyric acid, prepared above at −78° C. The resulting reaction was stirred for 1 h at −78° C., then quenched with saturated ammonium chloride, warmed to room temperature, poured onto water and extracted with EtOAc (3×). The combined organic extracts were washed with brine, dried over sodium sulfate and concentrated under reduced pressure. Purification by flash chromatography afforded (S)-4-benzyl-3-(4-(benzyloxy)butanoyl)oxazolidin-2-one (2.00 g, 53% yield). 1H NMR (300 MHz, Chloroform-d) δ 7.43-7.14 (m, 10H), 4.63 (tdd, J=7.2, 5.4, 3.5 Hz, 1H), 4.53 (s, 2H), 4.25-3.99 (m, 2H), 3.60 (t, J=6.2 Hz, 2H), 3.29 (dd, J=13.4, 3.5 Hz, 1H), 3.09 (t, J=7.2 Hz, 2H), 2.72 (dd, J=13.4, 9.7 Hz, 1H), 2.17-1.92 (m, 2H).

Step 2: A mixture of (S)-4-benzyl-3-(4-(benzyloxy)butanoyl)oxazolidin-2-one (1.907 g, 5.4 mmol) in dry THF (18 mL) was added at −78° C. under nitrogen to a solution of KHDMS (5.9 mL of 1.0 M solution in THF, 5.94 mmol) in dry THF (18 mL) at −78° C. under nitrogen by cannula. After stirring at −78° C. for 30 minutes, a −78° C. solution of 2,4,6-triisopropylbenzenesulfonyl azide (2.0 g, 6.48 mmol) in THF (13 mL) was added to the mixture by cannula. After five minutes of stirring, glacial acetic acid (1.4 mL, 24.84 mmol) was added. The solution was stirred at room temperature for 20 hours. The resulting solution was then diluted with EtOAc, poured onto saturated aqueous sodium bicarbonate and water and extracted with EtOAc (3×). The combined organic layers were washed with brine, dried over anhydrous sodium sulfate and evaporated under reduced pressure. The crude residue was taken up in DCM and filtered through Celite® and washed with DCM (2×). Concentration under reduced pressure and purification by flash column chromatography (hexane:DCM:EtOAc (80:12:8) eluent) gave (S)-3-((S)-2-azido-4-(benzyloxy)butanoyl)-4-benzyloxazolidin-2-one (0.92 g, 43% yield) as a clear oil. 1H NMR (300 MHz, Chloroform-d) δ 7.40-7.13 (m, 10H), 5.28 (t, J=6.4 Hz, 1H), 4.46 (d, J=2.3 Hz, 2H), 4.33 (ddt, J=9.5, 8.0, 3.2 Hz, 1H), 4.01 (dd, J=9.0, 2.9 Hz, 1H), 3.80-3.64 (m, 3H), 3.27 (dd, J=13.5, 3.4 Hz, 1H), 2.77 (dd, J=13.5, 9.5 Hz, 1H), 2.42-2.11 (m, 2H).

Step 3: To a mixture of compound (S)-3-((S)-2-azido-4-(benzyloxy)butanoyl)-4-benzyloxazolidin-2-one (0.889 g, 2.3 mmol) in 3:1 THF/H$_2$O mix (24 mL/8 mL) was added lithium hydroxide (0.108 g, 4.5 mmol) at 0° C. under argon. After stirring for 30 minutes, saturated aqueous sodium bicarbonate was added to solution and the THF was removed by evaporation under reduced pressure. The resulting mixture was extracted with DCM (3×) and the organic layers were collected and discarded. The aqueous phase was acidified with HCl (1N) to pH 2 and extracted with DCM (3×). The combined extracts from the second organic layer was collected, dried over sodium sulfate, and evaporated under reduced pressure to afford (S)-2-azido-4-(benzyloxy)butanoic acid (515 mg, 95% yield). 1H NMR (300 MHz, Chloroform-d) δ 7.44-7.25 (m, 5H), 4.55 (d, J=1.3 Hz, 2H), 4.22 (dd, J=8.5, 5.0 Hz, 1H), 3.66 (t, J=5.6 Hz, 2H), 2.31-1.94 (m, 2H).

Step 4: To a stirred solution of (S)-2-azido-4-(benzyloxy)butanoic acid (506 mg, 2.15 mmol) in dry ether (10 mL) and dry DCM (10 mL) under nitrogen was added tert-butyl-2,2,2-trichloroacetimidate (1.16 mL, 6.46 mmol) and the resulting reaction mixture was stirred at room temperature for 5 days. Additional tert-butyl-2,2,2-trichloroacetimidate (0.6 mL, 3.22 mmol) was added and the reaction mixture was stirred at room temperature for 2 days. The reaction was poured onto saturated aqueous sodium bicarbonate and water (1:1) and extracted with DCM (3×). The combined organic extract was dried over sodium sulfate, concentrated under reduced pressure and the resulting residue was purified by flash chromatography (hexanes eluent for one column volume and then 20% EtOAc/hexanes eluent) to give tert-butyl (S)-2-azido-4-(benzyloxy)butanoate (440 mg, 70% yield). 1H NMR (300 MHz, Chloroform-d) δ 7.44-7.30 (m, 5H), 4.54 (s, 2H), 4.06-3.94 (m, 1H), 3.66-3.55 (m, 2H), 2.26-2.09 (m, 1H), 1.93 (ddtd, J=14.2, 9.1, 5.1, 0.8 Hz, 1H), 1.50 (s, 9H).

Step 5: To a stirred solution of tert-butyl (S)-2-azido-4-(benzyloxy)butanoate (436 mg, 1.5 mmol) in THF (12 mL) under nitrogen was added triphenylphosphine (589 mg, 2.25 mmol) followed by water (0.270 mL, 15 mmol) and the resulting mixture was stirred at room temperature for 48 h, then poured onto 1:1 water:brine and extracted with EtOAc (3×). The combined organic extracts were washed with brine, dried over sodium sulfate and concentrated in vacuo to give crude tert-butyl O-benzyl-L-homoserinate. To a stirred solution of the crude tert-butyl O-benzyl-L-homoserinate (approx. 1.5 mmol) in DCM (15 mL) at 0° C. under nitrogen was added pyridine (0.253 mL, 3.15 mmol) followed by pentafluorobenzenesulfonyl chloride (0.45 mL, 3.0 mmol) and the resulting mixture was stirred at room temperature for 24 h. The reaction mixture was poured onto water and extracted with DCM (3×). The combined organic extracts were dried over sodium sulfate, concentrated under reduced pressure and the resulting residue purified by flash chromatography (10-20% EtOAc/hexanes eluent) to provide tert-butyl O-benzyl-N-((perfluorophenyl)sulfonyl)-L-homoserinate (260 mg, 35% yield over the 2 steps). 1H NMR (300 MHz, Chloroform-d) δ 7.45-7.28 (m, 5H), 6.30 (d, J=8.9 Hz, 1H), 4.52 (d, J=14.1 Hz, 1H), 4.48 (d, J=14.1 Hz, 1H), 4.35 (ddd, J=8.9, 6.5, 4.2 Hz, 1H), 3.71-3.45 (m, 2H), 2.30-2.12 (m, 1H), 2.04 (dddd, J=14.8, 6.5, 5.0, 3.9 Hz, 1H), 1.35 (s, 9H).

Steps 6-9: Preparation by a similar procedure to example 1 (steps 3-6), except substituting tert-butyl O-benzyl-N-((perfluorophenyl)sulfonyl)-L-homoserinate for tert-butyl ((pentafluorophenyl)sulfonyl)-D-alaninate in step 3 afforded (S)-4-(N-(4-cyclohexylbenzyl)-4-hydroxy-2-((2,3,4,5,6-pentafluoro-N-methylphenyl)-sulfonamido)-butanamido)-2-hydroxybenzoic acid. HRMS (ESI) m/z 693.1651 [M+Na]+.

Example 18

(R)-4-(N-(4-Cyclohexylbenzyl)-4-hydroxy-2-((2,3,4,5,6-pentafluoro-N-methylphenyl)-sulfonamido)-butanamido)-2-hydroxybenzoic acid

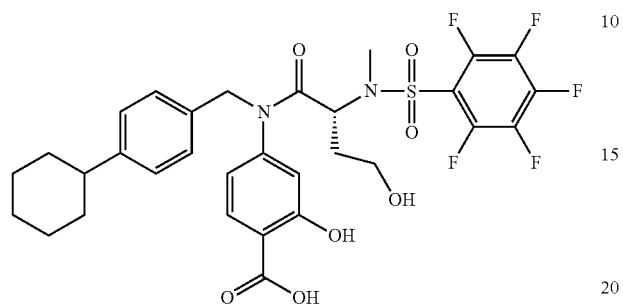

Preparation by a similar procedure to example 17, except substituting (R)-4-benzyloxazolidin-2-one for (S)-4-benzyloxazolidin-2-one in step 1 afforded (R)-4-(N-(4-cyclohexylbenzyl)-4-hydroxy-2-((2,3,4,5,6-pentafluoro-N-methylphenyl)-sulfonamido)-butanamido)-2-hydroxybenzoic acid as a peach-colored solid. HRMS (ESI) m/z 671.1846 [M+H]+.

Example 19

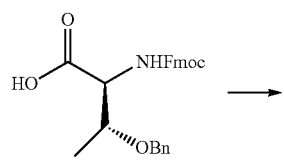

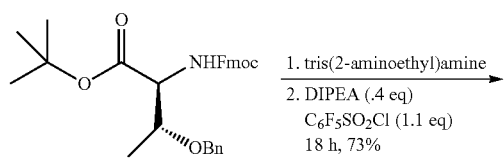

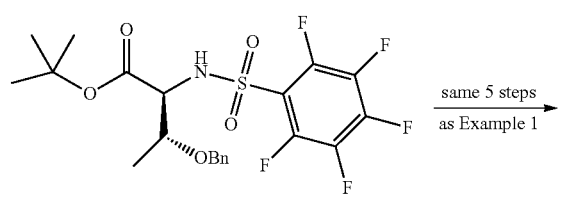

4-((2S,3R)—N-(4-Cyclohexylbenzyl)-3-hydroxy-2-((2,3,4,5,6-pentafluoro-N-methylphenyl)sulfonamido)butanamido)-2-hydroxybenzoic acid

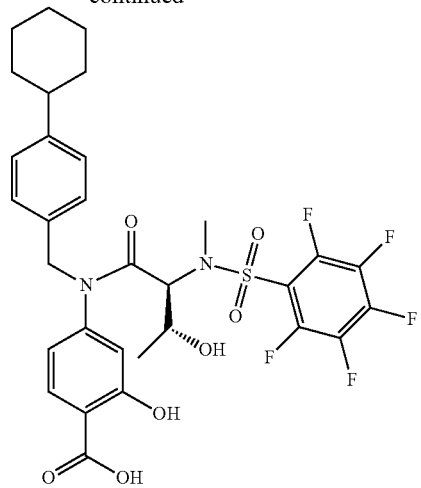

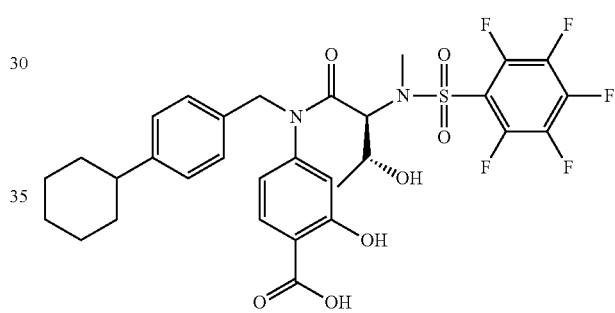

Step 1: To a stirred solution of commercially-available Fmoc-O-benzyl-L-threonine (1.5 g, 3.48 mmol) in dry ether (3 mL) and dry DCM (3 mL) under nitrogen was added tert-butyl-2,2,2-trichloroacetimidate (1.9 mL, 10.4 mmol) and the resulting reaction mixture was stirred at room temperature for 7 days. The suspension was filtered and rinsed once with a small volume of 1:1 ether:DCM and the combined filtrate and washes were applied directly to the flash column packed with silica in 80:20 hexanes DCM. The column was eluted with 80:20 hexanes:DCM eluent, then 80:20:7 hexanes:DCM:EtOAc eluent to afford tert-butyl N-(((9H-fluoren-9-yl)methoxy)carbonyl)-O-benzyl-L-threoninate (1.63 g, 96% yield). 1H NMR (300 MHz, Chloroform-d) δ 7.86-7.74 (m, 2H), 7.65 (dd, J=7.5, 3.6 Hz, 2H), 7.47-7.27 (m, 9H), 5.56 (d, J=9.7 Hz, 1H), 4.62 (d, J=11.5 Hz, 1H), 4.55-4.13 (m, 7H), 1.48 (s, 9H), 1.29 (d, J=11.5 Hz, 2H). MS (ESI) m/z 510.2319 [M+Na]+.

Step 2: To a stirred solution of tert-butyl N-(((9H-fluoren-9-yl)methoxy)carbonyl)-O-benzyl-L-threoninate (1.6 g, 3.28 mmol) in DCM (25 mL) was added 3.0 mL of tris(2-aminoethyl)amine and the resultant mixture was stirred overnight under nitrogen at room temperature. The crude reaction mixture was diluted with phosphate buffer (pH=5-6), adjusted to pH=7 with 5% aqueous HCl and extracted with DCM (2×). The combined organic extracts were washed with phosphate buffer (1×), saturated aqueous sodium bicarbonate (1×), dried over sodium sulfate and concentrated under reduced pressure. The resulting crude product, tert-butyl O-benzyl-L-threoninate was used as for the next step. 1H NMR (300 MHz, Chloroform-d) δ 7.40-7.29 (m, 5H), 4.61 (d, J=11.6 Hz, 1H), 4.47 (d, J=11.6 Hz, 1H), 3.97 (qd, J=6.3, 3.7 Hz, 1H), 3.30 (d, J=3.7 Hz, 1H), 1.61 (br. s, 2H), 1.48 (s, 9H), 1.32 (d, J=6.3 Hz, 3H).

Step 3: To a stirred solution of tert-butyl O-benzyl-L-threoninate (approx. 3.28 mmol) in DCM (28 mL) under nitrogen at 0° C. was added DIPEA (0.80 mL, 4.59 mmol) followed by pentafluorobenzenesulfonyl chloride (0.58 mL, 3.94 mmol) and the resulting mixture was allowed to warm to room temperature and stirred at this temperature for overnight. The reaction mixture was poured onto water and extracted with DCM (3×). The combined extracts were dried over anhydrous sodium sulfate, concentrated under reduced pressure and the resulting residue purified by flash chromatography (0-15% EtOAc/hexane) to provide tert-butyl O-benzyl-N-((pentafluorophenyl)sulfonyl)-L-threoninate (1.26 g, 78% yield). 1H NMR (300 MHz, Chloroform-d) δ 7.39-7.29 (m, 3H), 7.27-7.21 (m, 2H), 5.81 (d, J=10.1 Hz, 1H), 4.58 (d, J=11.5 Hz, 1H), 4.38 (d, J=11.5 Hz, 1H), 4.20-4.06 (m, 2H), 1.38 (d, J=6.2 Hz, 3H), 1.35 (s, 9H).

Steps 4-8: Preparation by a similar procedure to example 1 (steps 2-6), except substituting tert-butyl O-benzyl-N-((pentafluorophenyl)sulfonyl)-L-threoninate for tert-butyl ((pentafluorophenyl)sulfonyl)-D-alaninate in step 2 afforded 4-((2S,3R)—N-(4-cyclohexylbenzyl)-3-hydroxy-2-((2,3,4,5,6-pentafluoro-N-methylphenyl)sulfonamido)butanamido)-2-hydroxybenzoic acid as a pink foam. HRMS (ESI) m/z 671.1851 [M+H]+.

Example 20

4-((2R,3S)—N-(4-Cyclohexylbenzyl)-3-hydroxy-2-((2,3,4,5,6-pentafluoro-N-methylphenyl)sulfonamido)butanamido)-2-hydroxybenzoic acid

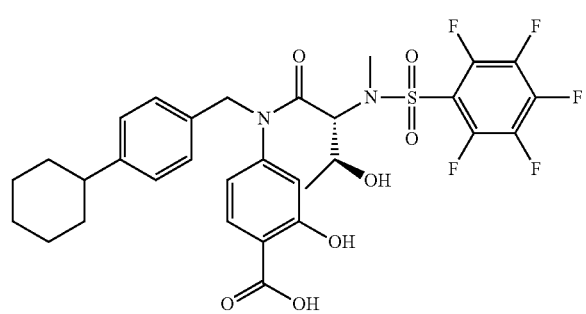 [SMILES: C[C@H](O)[C@H](C(=O)N(Cc1ccc(C2CCCCC2)cc1)c1ccc(C(=O)O)c(O)c1)N(C)S(=O)(=O)c1c(F)c(F)c(F)c(F)c1F]

Preparation by a similar procedure to example 19, except substituting Fmoc-O-benzyl-D-threonine for Fmoc-O-benzyl-L-threonine in step 1 afforded 4-((2R,3S)—N-(4-cyclohexylbenzyl)-3-hydroxy-2-((2,3,4,5,6-pentafluoro-N-methylphenyl)sulfon-amido)butanamido)-2-hydroxybenzoic acid as a pink foam. MS (ESI+) m/z 671.1831 [M+H]+.

Example 21

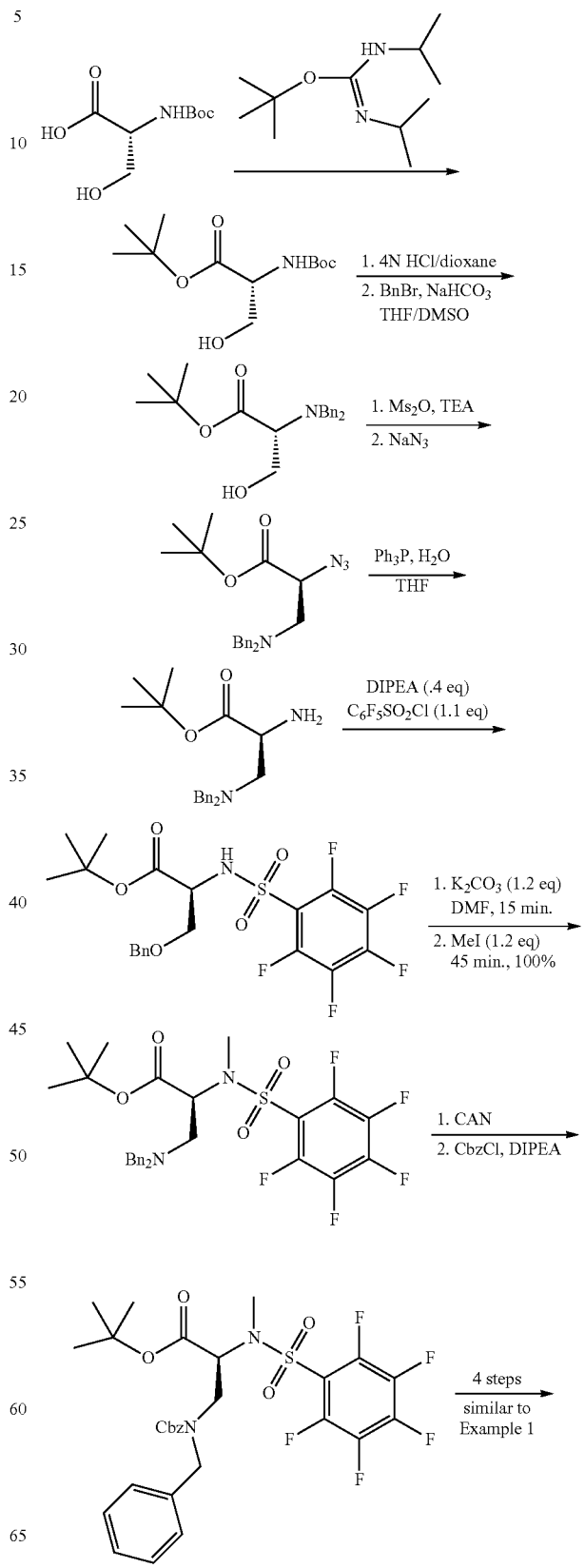

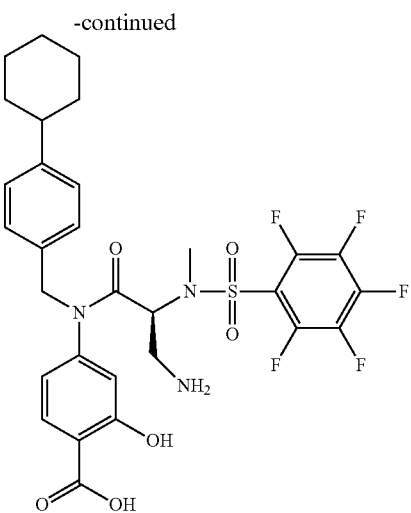

(S)-4-(3-Amino-N-(4-cyclohexylbenzyl)-2-((2,3,4,5,6-pentafluoro-N-methylphenyl)sulfonamido)-propanamido)-2-hydroxybenzoic acid

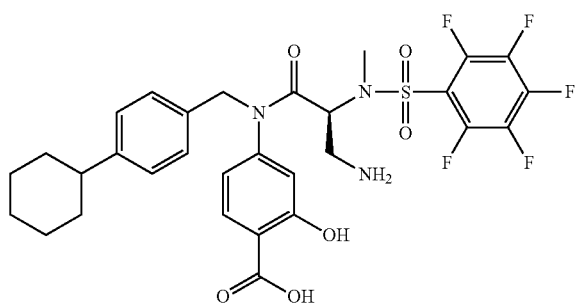 [SMILES: CN([C@@H](CN)C(=O)N(Cc1ccc(C2CCCCC2)cc1)c1ccc(C(=O)O)c(O)c1)S(=O)(=O)c1c(F)c(F)c(F)c(F)c1F]

Step 1: A solution of Boc-D-serine (2 g, 9.75 mmol) in dry DCM (20 mL) was treated with 2-tert-butyl-1,3-diisopropylisourea (3.5 mL, 15.5 mmol) under nitrogen and the reaction was stirred at reflux overnight. The reaction was not complete. An additional portion of 2-tert-butyl-1,3-diisopropylisourea (3.5 mL, 15.5 mmol) was added and the reaction was stirred at reflux for 36 h. The reaction was cooled to room temperature, and the resulting suspension diluted with 40% ether/hexane, filtered and the solid washed with 40% ether/hexane. The combined filtrate and washes were concentrated under reduced pressure and the resulting residue purified by flash chromatography (0-30% EtOAc in hexanes gradient) to provide tert-butyl (tert-butoxycarbonyl)-D-serinate (1.69 g, 66% yield). 1H NMR (300 MHz, Chloroform-d) δ 5.43 (br. s, 1H), 4.27 (br. s, 1H), 3.91 (dd, J=6.1, 3.9 Hz, 2H), 2.41 (br. s, 1H), 1.50 (s, 9H), 1.47 (s, 9H).

Step 2: To a stirred solution of 4N HCl in anhydrous dioxane (70 mL) at 0° C. under nitrogen was added tert-butyl (tert-butoxycarbonyl)-D-serinate (1.5 g, 5.75 mmol) in one portion. The resulting reaction mixture was stirred at 0-20° C. for 2 h and then concentrated in vacuo to afford tert-butyl D-serinate hydrochloride (1.17 g, 100% yield) as a white solid which was used as is. To a stirred solution of tert-butyl D-serinate hydrochloride (1.16 g, 5.7 mmol) in dry THF (28 mL) and dry DMSO (7 mL) was added sodium bicarbonate (2.4 g, 28.5 mmol) and benzyl bromide (2.0 mL, 17.1 mmol) and the resulting mixture was heated at reflux for 18 h under argon. The suspension was added to EtOAc and water and extracted with EtOAc (3×). The combine organic extract was washed with brine, dried over sodium sulfate and concentrated under reduced pressure. Purification by flash chromatography (0-20% EtOAc/hexanes eluent) gave tert-butyl dibenzyl-D-serinate (1.42 g, 73% yield). 1H NMR (300 MHz, Chloroform-d) δ 7.39-7.25 (m, 10H), 3.95 (d, J=13.4 Hz, 2H), 3.72 (d and overlapping m, J=13.4 Hz, 3H), 3.46 (t, J=7.6 Hz, 1H), 2.55 (t, J=5.7 Hz, 1H), 1.59 (s, 9H).

Step 3: Following the procedure of Couturier (Couturier et al., Organic Letters (2006), 8(10), 2183-2186), to a stirred solution of tert-butyl dibenzyl-D-serinate (1.41 g, 4.13 mmol) in dry acetonitrile (28 mL) under nitrogen was added TEA (0.8 mL, 5.7 mmol) followed by methanesulfonic anhydride (0.93 g, 5.37 mmole) and the resulting reaction solution was stirred at room temperature until complete by TLC (2 h). To this reaction mixture was added sodium azide (0.81 g, 12.39 mmol) followed by dry DMF (7 mL) and the resulting mixture was warmed at 60-70° C. for 4 h, then cooled in an ice bath. The reaction mixture was poured onto water and ether and extracted with ether (3×). The combined ethereal layers were washed with brine, dried over anhydrous sodium sulfate and concentrated under reduced pressure. Flash chromatography (0-15% EtOAc/hexanes gradient) provided tert-butyl (S)-2-azido-3-(dibenzylamino)propanoate (1.32 g, 87% yield) as a colorless oil. 1H NMR (300 MHz, Chloroform-d) δ 7.45-7.28 (m, 10H), 3.81 (dd, J=8.0, 5.1 Hz, 1H), 3.70 (q, J=13.6 Hz, 4H), 3.07-2.82 (m, 2H), 1.48 (s, 9H).

Step 4: To a stirred solution of tert-butyl (S)-2-azido-3-(dibenzylamino)propanoate (1.3 g, 3.55 mmol) in dry THF (24 mL) under nitrogen was added triphenylphosphine (1.4 g, 5.32 mmol) followed by water (0.64 mL, 35.5 mmol) and the resulting mixture was stirred at room temperature for 4 h, then poured onto water and EtOAc and extracted with EtOAc (3×). The combined organic extracts were washed with brine, dried over anhydrous sodium sulfate and concentrated under reduced pressure. Flash chromatography (30-60% EtOAc/hexanes gradient) provided tert-butyl (S)-2-amino-3-(dibenzylamino)propanoate (0.989 g, 82% yield) as a colorless oil. 1H NMR (300 MHz, Chloroform-d) δ 7.40-7.22 (m, 10H), 3.72 (d, J=13.5 Hz, 2H), 3.56 (d and overlapping m, J=13.5 Hz, 3H), 2.80 (dd, J=12.7, 4.9 Hz, 1H), 2.57 (dd, J=12.7, 8.4 Hz, 1H), 1.47 (s, 9H).

Step 5: To a stirred solution of tert-butyl (S)-2-amino-3-(dibenzylamino)propanoate (0.98 g, 2.88 mmol) in dry DCM (17 mL) under nitrogen at 0° C. was added DIPEA (0.65 mL, 3.74 mmol) followed by pentafluorobenzenesulfonyl chloride (0.47 mL, 3.17 mmol) and the resulting solution was allowed to warm to room temperature and stirred at this temperature for 18 h. The crude reaction mixture was poured onto water and extracted with DCM (3×). The combined organic extracts were dried over anhydrous sodium sulfate, concentrated under reduced pressure and the resulting residue purified by chromatography (8-15% EtOAc/hexanes gradient) to give tert-butyl (S)-3-(dibenzylamino)-2-((pentafluorophenyl)sulfonamido)propanoate (1.34 g, 82% yield) as a film. 1H NMR (300 MHz, Chloroform-d) δ 7.59-7.12 (m, 10H), 5.71 (br. s, 1H), 4.23 (t, J=5.9 Hz, 1H), 3.74-3.52 (m, 4H), 2.88 (qd, J=13.5, 5.9 Hz, 2H), 1.36 (s, 9H).

Step 6: To a stirred solution of tert-butyl (S)-3-(dibenzylamino)-2-((pentafluorophenyl)-sulfonamido)propanoate (1.28 g, 2.24 mmol) in dry DMF (18 mL) under nitrogen was added potassium carbonate (0.43 g, 3.14 mmol) and the resulting suspension was stirred at room temperature for 5 min before addition of methyl iodide (0.2 mL, 3.14 mmol). After stirring continued for an additional 50 min, the reaction mixture was poured onto water and extracted with ether (3×). The combined organic layers were washed with brine, dried over sodium sulfate, concentrated under reduced pressure and the resulting residue purified by flash chromatography (0-10% EtOAc/hexanes gradient) to afford tert-butyl (S)-3-(dibenzylamino)-2-((2,3,4,5,6-pentafluoro-N-methylphenyl)sulfonamido)-propanoate (1.15 g, 88% yield) as a foam. 1H NMR (300 MHz, Chloroform-d) δ 7.47-7.23 (m, 10H), 5.03 (t, J=7.4 Hz, 1H), 3.99 (d, J=13.3 Hz, 2H), 3.38 (d, J=13.3 Hz, 2H), 2.84 (d, J=7.4 Hz, 2H), 2.59 (s, 3H), 1.36 (s, 9H).

Step 7: To a stirred solution of tert-butyl (S)-3-(dibenzylamino)-2-((2,3,4,5,6-pentafluoro-N-methylphenyl)sulfonamido)propanoate (1.13 g, 1.93 mmol) in acetonitrile (25 mL) and water (5 mL) under nitrogen was added ceric ammonium nitrate (2.65 g, 4.8 mmol) in one portion and the resulting orange mixture was stirred at room temperature for 2 h. The crude reaction mixture was poured onto water/saturated aqueous sodium bicarbonate (1:1) and extracted into EtOAc (2×) and DCM (1×). The combined organic extracts were washed with brine, dried over anhydrous sodium sulfate and concentrated in vacuo to afford tert-butyl (S)-3-(benzylamino)-2-((2,3,4,5,6-pentafluoro-N-methylphenyl)-sulfonamido)propanoate (1.09 g) which was used as is.

Step 8: To tert-butyl (S)-3-(benzylamino)-2-((2,3,4,5,6-pentafluoro-N-methylphenyl)sulfonamido)-propanoate (1.09 g, 1.9 mmol) in dry THF (18 mL) under nitrogen was added DIPEA (0.4 mL, 2.3 mmol) followed by benzyl chloroformate (0.33 mL, 2.3 mmol) and the resulting solution was stirred at room temperature for 24 h. The crude reaction mixture was poured onto water and extracted with DCM (3×). The combined organic extracts were dried over anhydrous sodium sulfate, concentrated under reduced pressure and the resulting residue purified by flash chromatography (18% EtOAc/hexanes eluent) to provide tert-butyl (S)-3-(benzyl((benzyloxy)carbonyl)amino)-2-((2,3,4,5,6-pentafluoro-N-methylphenyl)-sulfonamido)propanoate (1.16 g, 95% yield). 1H NMR (300 MHz, Chloroform-d) Rotomer 1:Rotomer 2 (1.8:1 ratio) δ 7.48-7.30 (m, 9H), 7.27-7.18 (m, 1H), 5.34-5.14 (m, 2H), 5.09-4.96 (m, 1H), 4.85 (rotomer 1: d, J=16.1 Hz, 1H), 4.75 (rotomer 2: d, J=15.5 Hz, 1H), 4.54 (rotomer 2: d, J=15.5 Hz, 1H), 4.41 (rotomer 1: d, J=16.1 Hz, 1H), 3.93 (dd, J=14.8, 10.8 Hz, 1H), 3.64-3.43 (m, 2H), 3.03 (rotomer 1: s, 3H), 2.84 (rotomer 2: s, 3H), 1.35 (rotomer 1: s, 9H), 1.29 (rotomer 2: s, 9H).

Steps 9-12: Preparation by a similar procedure to example 1 (steps 3-6), except substituting tert-butyl (S)-3-(benzyl((benzyloxy)carbonyl)amino)-2-((2,3,4,5,6-pentafluoro-N-methylphenyl)sulfonamido)propanoate for tert-butyl ((pentafluorophenyl)sulfonyl)-D-alaninate in step 3 afforded (S)-4-(3-amino-N-(4-cyclohexylbenzyl)-2-((2,3,4,5,6-pentafluoro-N-methylphenyl)-sulfonamido)propanamido)-2-hydroxybenzoic acid as a tan solid. HRMS (ESI+) m/z 656.1848 [M+H]+.

Example 22

(R)-4-(3-Amino-N-(4-cyclohexylbenzyl)-2-((2,3,4,5,6-pentafluoro-N-methylphenyl)sulfonamido)-propanamido)-2-hydroxybenzoic acid

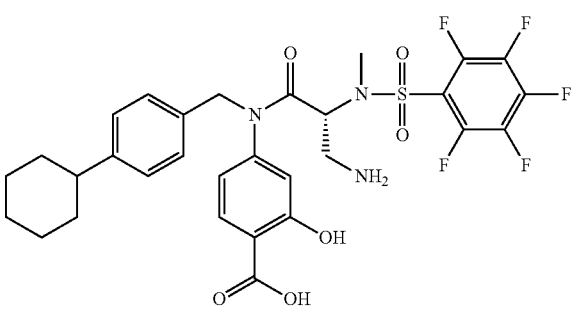 [SMILES: CN([C@H](CN)C(=O)N(Cc1ccc(C2CCCCC2)cc1)c1ccc(C(=O)O)c(O)c1)S(=O)(=O)c1c(F)c(F)c(F)c(F)c1F]

Preparation by a similar procedure to example 21, except substituting Boc-L-serine for Boc-D-serine in step 1 afforded (R)-4-(3-amino-N-(4-cyclohexylbenzyl)-2-((2,3,4,5,6-pentafluoro-N-methylphenyl)-sulfonamido)propanamido)-2-hydroxybenzoic acid as a pale grey solid. HRMS (ESI+) m/z 656.1849 [M+H]+.

Example 23

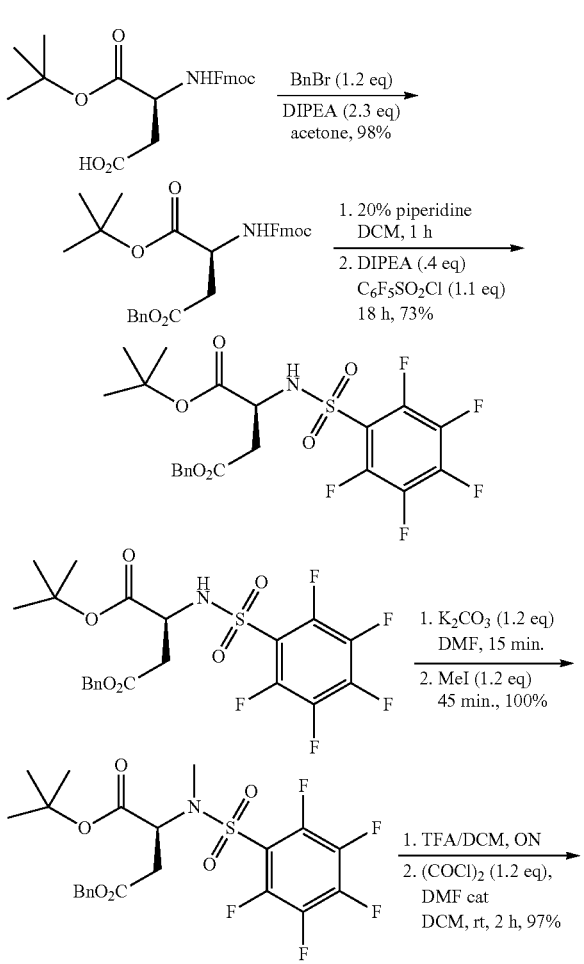

(S)-4-(3-Carboxy-N-(4-cyclohexylbenzyl)-2-((2,3,4,5,6-pentafluoro-N-methylphenyl)sulfonamido)-propanamido)-2-hydroxybenzoic acid

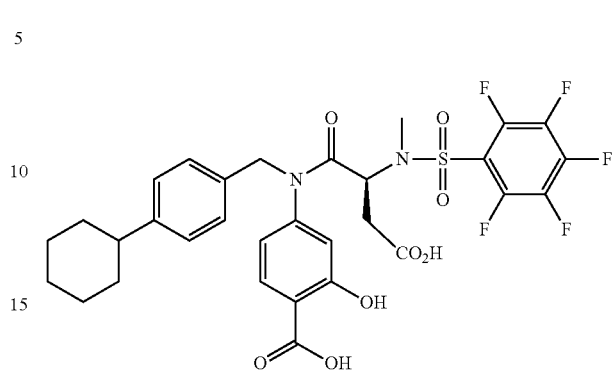

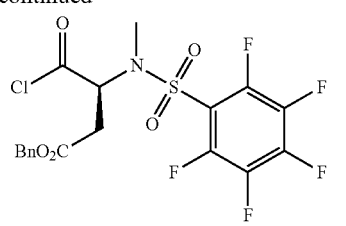

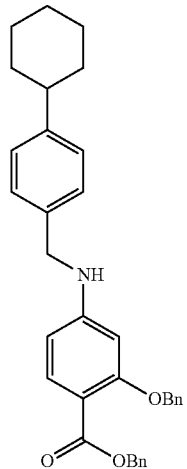

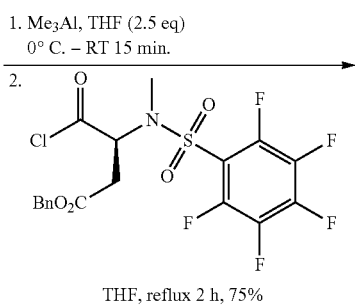

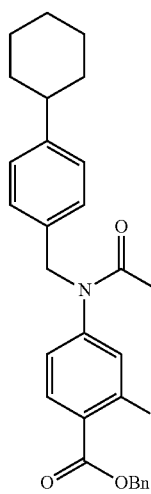

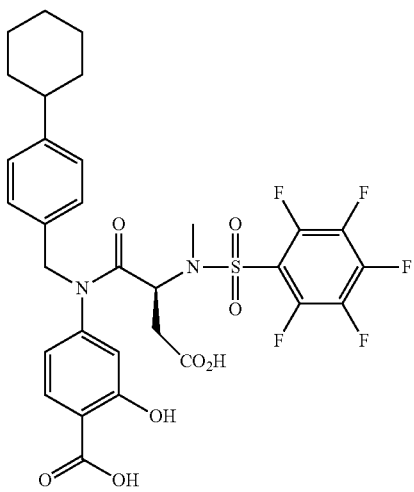

Step 1: To a stirred solution of N-Fmoc-L-aspartic acid tert-butyl ester (1.02 g, 2.48 mmol) in acetone (12 mL) under nitrogen at 0° C. was added DIPEA (0.52 mL, 2.98 mmol) followed by benzyl bromide (0.35 mL, 2.98 mmol). The reaction mixture was allowed to warm to room temperature and stirring was continued for 3 days. The resultant mixture was concentrated under reduced pressure, dissolved in EtOAc/water, poured onto saturated aqueous sodium bicarbonate and extracted with EtOAc (3×). The combined organic extracts were washed with brine, dried over anhydrous sodium sulfate, concentrated under reduced pressure and the resulting residue purified by flash chromatography (0-20% EtOAc/hexanes gradient) to provide 4-benzyl 1-(tert-butyl) (((9H-fluoren-9-yl)methoxy)carbonyl)-L-aspartate (1.23 g, 98% yield) as a colorless film. 1H NMR (300 MHz, Chloroform-d) δ 7.78 (d, J=7.5 Hz, 2H), 7.61 (d, J=7.5 Hz, 2H), 7.47-7.25 (m, 9H), 5.79 (d, J=8.2 Hz, 1H), 5.16 (q, J=12.2 Hz, 2H), 4.55 (dd, J=8.2, 4.5 Hz, 1H), 4.48-4.29 (m, 2H), 4.24 (t, J=7.1 Hz, 1H), 3.14-2.79 (m, 2H), 1.44 (s, 9H).

Step 2: To a stirred solution of 4-benzyl 1-(tert-butyl) (((9H-fluoren-9-yl)methoxy)carbonyl)-L-aspartate (1.2 g, 2.4 mmol) in dry DCM (15 mL) under nitrogen at 0° C. was added piperidine (3.75 mL) and the reaction was stirred for 1 h at 0° C. and concentrated under reduced pressure. Toluene was added and the mixture was concentrated in vacuo to afford crude 4-benzyl 1-(tert-butyl) L-aspartate, which was used as is. To a stirred solution of crude 4-benzyl 1-(tert-butyl) L-aspartate (2.4 mmol) and DIPEA (0.17 mL, 0.96 mmol) in DCM (18 mL) under nitrogen at 0° C. was added pentafluorobenzenesulfonyl chloride (0.39 mL, 2.64 mmol). The reaction was allowed to warm to room temperature and stirred at this temperature overnight. The crude reaction mixture was poured onto 5% aqueous HCl and extracted with DCM (3×). The combined extracts were washed with water, then brine and dried over anhydrous sodium sulfate and concentrated under reduced pressure. Purification of the resulting residue by flash chromatography (75:15:5 to 75:15:10 hexanes:DCM:EtOAc eluent) provided 4-benzyl 1-(tert-butyl) ((pentafluorophenyl)sulfonyl)-L-aspartate (0.89 g, 73% yield). MS (ESI+) m/z 532 [M+Na]+. 1H NMR (300 MHz, Chloroform-d) δ 7.44-7.30 (m, 5H), 5.14 (q, J=12.1 Hz, 2H), 4.38 (dt, J=8.9, 4.4 Hz, 1H), 3.19-2.82 (m, 2H), 1.33 (s, 9H).

Steps 3-7: Preparation by a similar procedure to example 1 (steps 2-6), except substituting 4-benzyl 1-(tert-butyl) ((pentafluorophenyl)sulfonyl)-L-aspartate for tert-butyl ((pentafluorophenyl)sulfonyl)-D-alaninate in step 2 afforded (S)-4-(3-carboxy-N-(4-cyclohexylbenzyl)-2-((2,3,4,5,6- pentafluoro-N-methylphenyl)sulfonamido)-propanamido)-2-hydroxybenzoic acid as a pink solid. MS (ESI) m/z 683.1497 [M−H]−.

Example 24

(R)-4-(3-Carboxy-N-(4-cyclohexylbenzyl)-2-((2,3,4,5,6-pentafluoro-N-methylphenyl)sulfonamido)-propanamido)-2-hydroxybenzoic acid

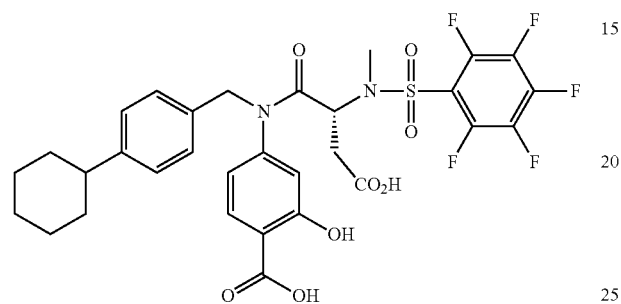

Preparation by a similar procedure to example 23, except substituting N-Fmoc-D-aspartic acid tert-butyl ester for N-Fmoc-L-aspartic acid tert-butyl ester in step 1 afforded (R)-4-(3-carboxy-N-(4-cyclohexylbenzyl)-2-((2,3,4,5,6-pentafluoro-N-methylphenyl)sulfonamido)-propanamido)-2-hydroxybenzoic acid as a pink solid. MS (ESI) m/z 707.1468 [M+Na]+.

Example 25

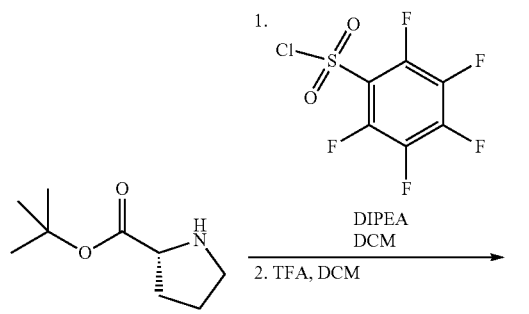

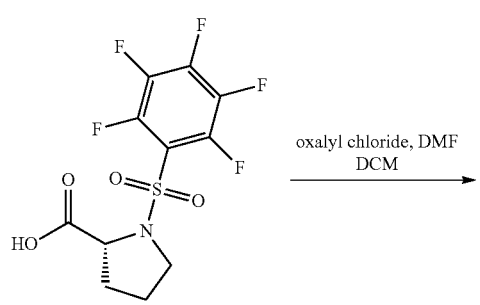

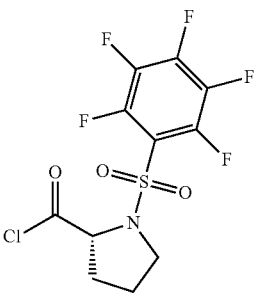

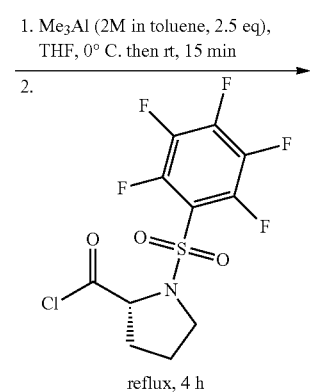

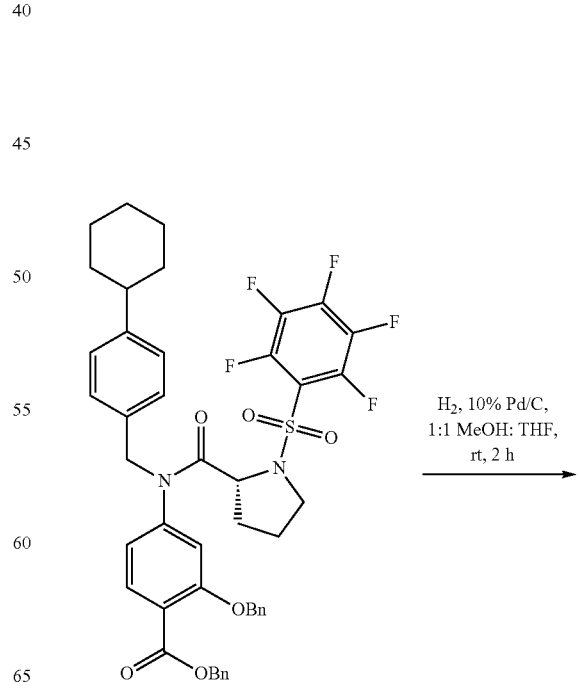

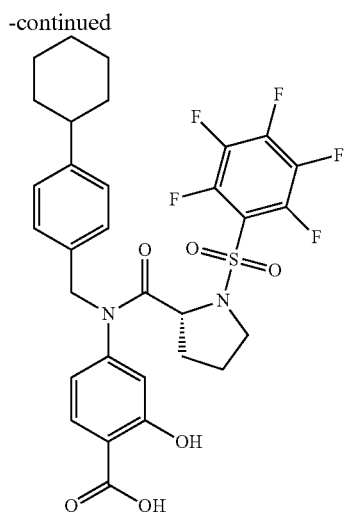

(R)-4-(N-(4-Cyclohexylbenzyl)-1-((pentafluorophenyl)sulfonyl)pyrrolidine-2-carboxamido)-2-hydroxybenzoic acid

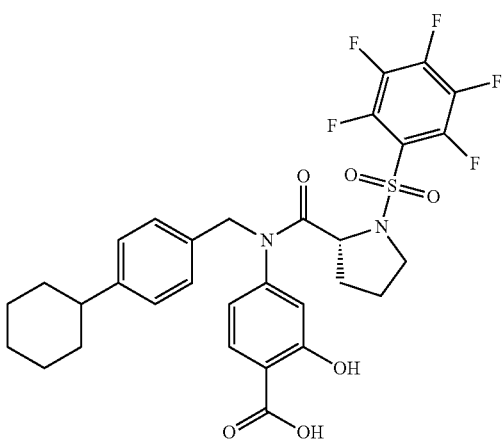 [SMILES: O=C(O)c1ccc(N(Cc2ccc(C3CCCCC3)cc2)C(=O)[C@H]2CCCN2S(=O)(=O)c2c(F)c(F)c(F)c(F)c2F)cc1O]

Step 1: To as stirred solution of tert-butyl D-prolinate (1.5 g, 8.7 mmol) and DIPEA (2.1 mL, 12.2 mmol) in DCM (100 mL) under nitrogen at 0° C. was added pentafluorobenzenesulfonyl chloride (1.55 mL, 10.4 mmol). The reaction mixture was allowed to warm to room temperature, stirred overnight, then poured onto water and extracted with DCM (3×). The combined organic layers were dried over anhydrous sodium sulfate, concentrated under reduced pressure, and the resulting residue purified by flash chromatography (2% EtOAc and 2% DCM in hexanes) to afford tert-butyl ((perfluorophenyl)sulfonyl)-D-prolinate (3.65 g). 1H NMR (300 MHz, Chloroform-d) δ 4.51 (dd, J=8.5, 3.2 Hz, 1H), 3.78-3.56 (m, 2H), 2.42-2.19 (m, 1H), 2.14-1.87 (m, 3H), 1.43 (s, 9H).

Step 2: To a stirred solution of tert-butyl ((pentafluorophenyl)sulfonyl)-D-prolinate (3.64 g, 9 mmol) in DCM (40 mL) was added TFA (40 mL) and the resulting reaction was stirred at room temperature overnight before concentration in vacuo. The residue was triturated with 10% ether in hexanes and washed with this mixture (2×) to give ((pentafluorophenyl)sulfonyl)-D-proline (2.96 g, 98% yield) as a white powder. LCMS: >98% purity, MS (ESI) m/z 368 [M+Na]+. 1H NMR (300 MHz, Chloroform-d) δ 4.64 (dd, J=8.7, 3.6 Hz, 1H), 3.67 (q, J=7.0, 6.5 Hz, 2H), 2.38 (dq, J=12.7, 8.7 Hz, 1H), 2.28-1.98 (m, 3H).

Step 3: To a stirred solution of ((pentafluorophenyl)sulfonyl)-D-proline (2.89 g, 8.38 mmol) in DCM (70 mL) was added DMF (2 drops) followed by oxalyl chloride (1.08 mL, 12.6 mmol) under nitrogen. The resultant reaction mixture was stirred for 1.7 h and then concentrated in vacuo. A small volume of EtOAc was added and the suspension was concentrated again to afford a white solid. The solid was triturated with a small volume of cold 5% ether in hexanes and washed with cold 5% ether in hexanes to provide ((pentafluorophenyl)sulfonyl)-D-prolinoyl chloride (2.91 g, 96% yield) as a white solid. 1H NMR (300 MHz, Chloroform-d) δ 4.94 (dd, J=8.8, 3.8 Hz, 1H), 3.71 (ddd, J=7.3, 6.5, 0.7 Hz, 2H), 2.58-2.28 (m, 2H), 2.19-2.00 (m, 2H).

Step 4: To a stirred solution of benzyl 2-(benzyloxy)-4-((4-cyclohexylbenzyl)amino)benzoate (314 mg, 0.62 mmol) in THF (10 mL) under nitrogen at 0° C. was added trimethylaluminum (0.93 mL of a 2M solution in toluene, 1.86 mmol) and the resultant reaction solution was allowed to stir at room temperature for 10 min. To the reaction mixture was added a solution of ((pentafluorophenyl)sulfonyl)-D-prolinoyl chloride (316 mg, 0.87 mmol) in THF (6 mL). The resultant reaction mixture was warmed at reflux with stirring for 4 h, cooled to room temperature, poured onto 10% potassium bisulfate/sodium sulfate buffer and extracted with EtOAc (3×). The combined organic layers were washed with saturated aqueous sodium bicarbonate, then with brine, dried over anhydrous sodium sulfate and concentrated under reduced pressure. The resulting residue was purified by flash chromatography (10-20% EtOAc/hexanes) to provide benzyl (R)-2-(benzyloxy)-4-(N-(4-cyclohexylbenzyl)-1-((pentafluorophenyl)sulfonyl)pyrrolidine-2-carboxamido)benzoate (250 mg, 48% yield) as a white foam. 1H NMR (300 MHz, Chloroform-d) δ 7.83 (d, J=8.2 Hz, 1H), 7.48-7.29 (m, 10H), 7.11 (d, J=8.0 Hz, 2H), 6.95 (d, J=8.0 Hz, 2H), 6.72 (d, J=8.2 Hz, 1H), 6.60 (s, 1H), 5.36 (s, 2H), 5.11 (d, J=14.3 Hz, 1H), 4.95-4.74 (m, 2H), 4.53 (d, J=14.3 Hz, 1H), 4.45 (t, J=6.7 Hz, 1H), 3.83-3.55 (m, 2H), 2.57-2.38 (m, 1H), 2.17-1.64 (m, 9H), 1.52-1.11 (m, 5H). LCMS: 98% purity, MS (ESI) m/z 833 [M+H]+.

Step 5: To a stirred solution of benzyl (R)-2-(benzyloxy)-4-(N-(4-cyclohexylbenzyl)-1-((pentafluorophenyl)sulfonyl)pyrrolidine-2-carboxamido)benzoate (218 mg, 0.26 mmol) in methanol (9 mL) and THF (9 mL) was added 10% Pd/C (30 mg) and the resulting suspension was stirred at room temperature under a hydrogen atmosphere 2.5 h. The reaction mixture was filtered through Celite® and washed with methanol (2×). The combined filtrate and washes were concentrated, then taken up in ether and concentrated again to provide (R)-4-(N-(4-cyclohexylbenzyl)-1-((pentafluorophenyl)sulfonyl)-pyrrolidine-2-carboxamido)-2-hydroxybenzoic acid (194 mg, 100% yield) as a white foam. HRMS (ESI) m/z 653.1750 [M+H]+.

Example 26

(S)-4-(N-(4-Cyclohexylbenzyl)-1-((pentafluorophenyl)sulfonyl)pyrrolidine-2-carboxamido)-2-hydroxybenzoic acid

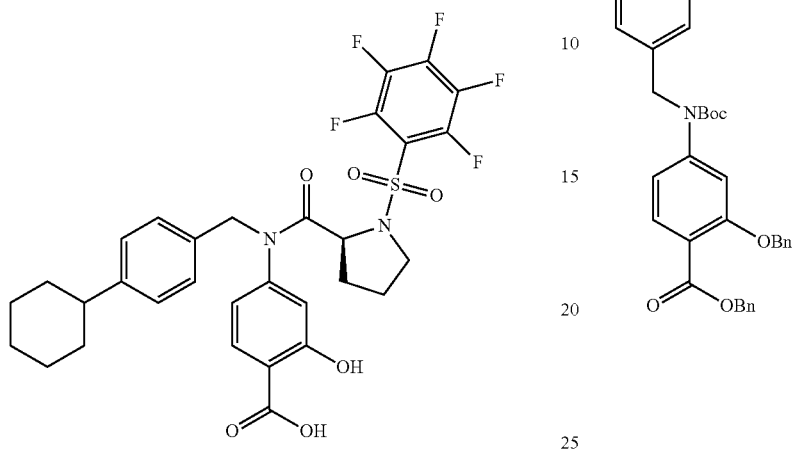

Preparation by a similar procedure to example 25, except substituting tert-butyl L-prolinate for tert-butyl D-prolinate in step 1 afforded (S)-4-(N-(4-cyclohexyl benzyl)-1-((pentafluorophenyl)sulfonyl)pyrrolidine-2-carboxamido)-2-hydroxybenzoic acid as a peach-colored foam. HRMS (ESI) m/z 653.1761 [M+H]+.

Example 27

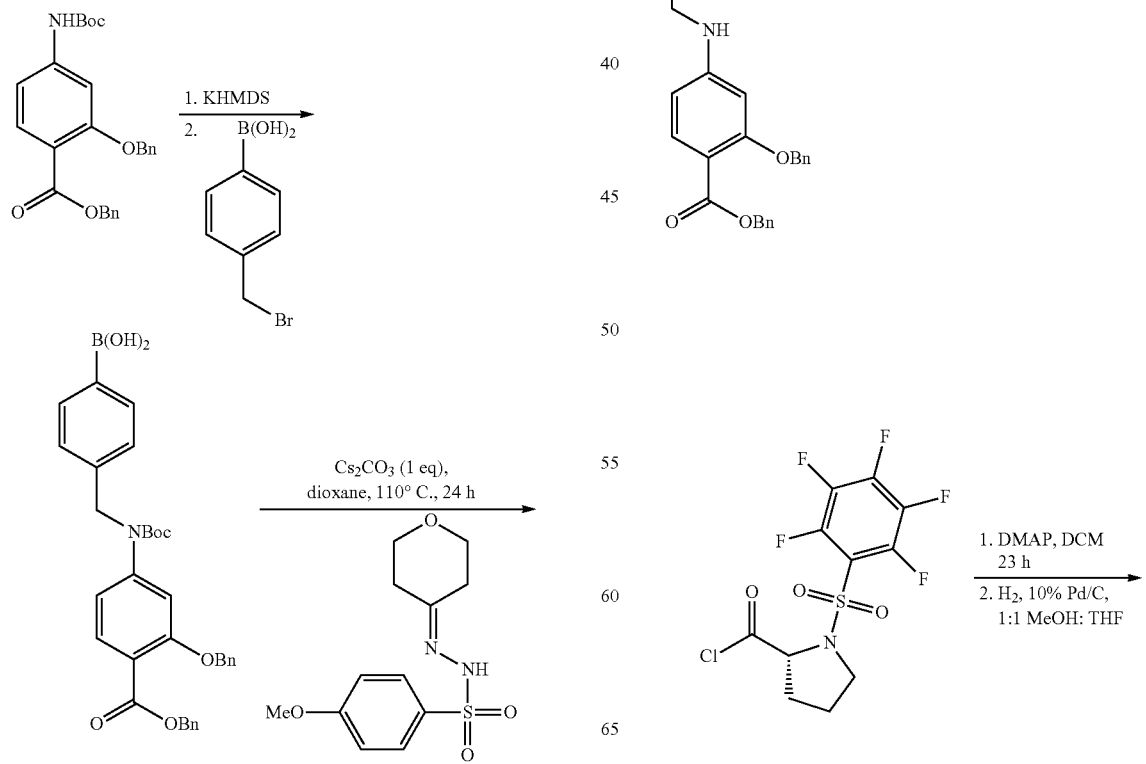

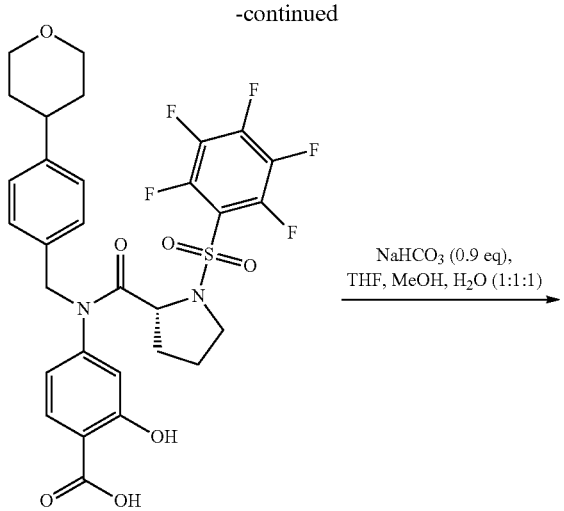

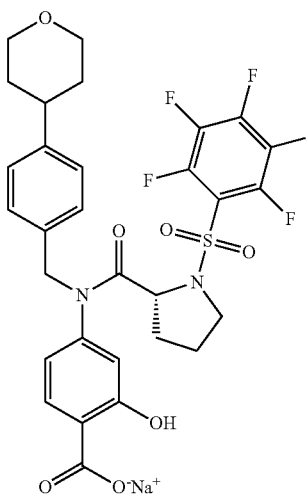

(R)-2-Hydroxy-4-(1-((pentafluorophenyl)sulfonyl)-N-(4-(tetrahydro-2H-pyran-4-yl)benzyl)pyrrolidine-2-carboxamido)benzoic acid

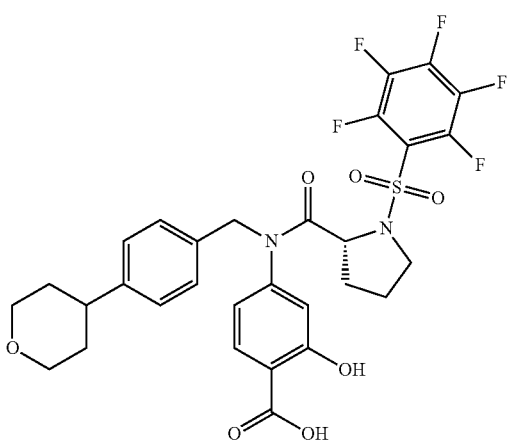 [SMILES: O=C(O)c1ccc(N(Cc2ccc(C3CCOCC3)cc2)C(=O)[C@H]2CCCN2S(=O)(=O)c2c(F)c(F)c(F)c(F)c2F)cc1O]

Step 1: To a stirred solution of benzyl 2-(benzyloxy)-4-((tert-butoxycarbonyl)amino)benzoate (Fletcher, et al., Tetrahedron Letters (2008), 49(33), 4817-4819) (4.1 g, 9.5 mmol) in 40 mL DMF at 0° C. under nitrogen was added KHDMS (23 mL of 1M in THF, 23 mmol, 2.4 equiv.). Stirring was continued for 10 min. After 10 min, a solution of 4-bromomethylphenylboronic acid (2.9 g, 13.3 mmol, 1.4 equiv.) in 20 mL DMF was added. The flask was rinsed with an additional 4 mL of DMF and that was added to reaction mixture. The reaction was allowed to warm to room temperature and stirring continued at room temperature overnight. The reaction mixture was poured onto dilute aqueous HCl and extracted with ether (3×). The combined ether layers were washed with brine, dried over anhydrous sodium sulfate and evaporated under reduced pressure. Purification by flash column chromatography on silica with EtOAc/hexane (25-40%) eluent gave (4-4(3-(benzyloxy)-4-((benzyloxy)carbonyl)phenyl)(tert-butoxycarbonyl)amino) methyl)phenyl)boronic acid (3.02 g, 54% yield) as a white solid. MS (ESI): [M+Na]+=590, [2M+Na]+=1157.

Step 2: A stirred solution of (4-(43-(benzyloxy)-4-((benzyloxy)carbonyl)phenyl)(tert-butoxycarbonyl)amino) methyl)phenyl)-boronic acid (0.5 g, 1.75 mmol, 1 equiv.), 4-methoxy-N'-(tetrahydro-4H-pyran-4-ylidene)benzenesulfonohydrazide (Allwood, Daniel M. et al. Journal of Organic Chemistry, 79(1), 328-338; 2014) (1.5 g, 2.6 mmol, 1.5 equiv.), and cesium carbonate (0.86 g, 2.6 mmol, 1.5 equiv.) in 1.4 dioxane (13 mL) was degassed and backfilled with argon. The flask was heated to 110° C. for 23 hours. The reaction mixture was poured onto aqueous sodium bicarbonate and extracted with DCM (3×). The combined organic layers were dried over anhydrous sodium sulfate and evaporated under reduced pressure. Purification by flash column chromatography with EtOAc/hexane (10-15%) eluent provided benzyl 2-(benzyloxy)-4-((tert-butoxycarbonyl)(4-(tetrahydro-2H-pyran-4-yl)benzyl)amino)benzoate (0.58 g, 55% yield) as a white solid. MS (ESI): [M+Na]+=630, [2M+Na]+=1237.

Step 3: To a stirred solution of benzyl 2-(benzyloxy)-4-((tert-butoxycarbonyl)(4-(tetrahydro-2H-pyran-4-yl)benzyl) amino)benzoate (0.57 g, 0.95 mmol) in DCM (12 mL) under nitrogen at 0° C. was added TFA (2.4 mL). Stirring was continued at 0° C. for 1.4 hours. The reaction mixture was poured onto cold aqueous saturated NaHCO3 and extracted with DCM (3×). The combined organic layers were dried over anhydrous sodium sulfate and evaporated under reduced pressure. Purification by flash column chromatography with hexane/DCM/EtOAc (7:2:1) eluent yielded benzyl 2-(benzyloxy)-4-((4-(tetrahydro-2H-pyran-4-yl)benzyl) amino)benzoate (0.44 g, 66% yield) as a white solid. 1H NMR (300 MHz, Chloroform-d) δ 7.85 (d, J=8.6 Hz, 1H), 7.52-7.14 (m, 14H), 6.23 (dd, J=8.6, 2.2 Hz, 1H), 6.18 (d, J=2.2 Hz, 1H), 5.32 (s, 2H), 5.10 (s, 2H), 4.46 (t, J=5.4 Hz, 1H), 4.33 (d, J=5.4 Hz, 2H), 4.11 (dt, J=10.5, 3.3 Hz, 2H), 3.55 (td, J=11.3, 3.3 Hz, 2H), 2.78 (tt, J=10.5, 4.9 Hz, 1H), 1.97-1.69 (m, 4H). MS (ESI): [M+H]+=508.2, [2M+Na]+=1037.4.

Step 4: To a stirred solution of benzyl 2-(benzyloxy)-4-((4-(tetrahydro-2H-pyran-4-yl)benzyl)amino)-benzoate (0.20 g, 0.39 mmol) and ((pentafluorophenyl)sulfonyl)-D-prolinoyl chloride (0.214 g, 0.59 mmol) in dry DCM (8 mL) under nitrogen was added DMAP (0.06 g, 0.47 mmol). Stirring was continued for 23 hours. Methanol (2-3 drops) was added to consume any excess acid chloride. The mixture was poured onto water and extracted with DCM (3×). The combined organic layers were dried over anhydrous sodium sulfate and evaporated under reduced pressure. Purification by flash column chromatography (25% EtOAc/hexane eluent and then eluting with a mix of 25% EtOAc/(4:1 hexane: DCM mixture) afforded benzyl (R)-2-(benzyloxy)-4-(1-

((pentafluorophenyl)sulfonyl)-N-(4-(tetrahydro-2H-pyran-4-yl)benzyl)-pyrrolidine-2-carboxamido)benzoate (289 mg, 89% yield) as a white solid. MS (ESI): [M+H]+=835.2, [M+Na]+=857.2, [2M+Na]+=1691.45.

Step 5: To a stirred solution of benzyl (R)-2-(benzyloxy)-4-(1-((pentafluorophenyl)sulfonyl)-N-(4-(tetrahydro-2H-pyran-4-yl)benzyl)pyrrolidine-2-carboxamido)benzoate (266 mg, 0.32 mmol) in THF (6 mL) and methanol (6 mL) under nitrogen was added 20% Pd(OH)$_2$ on carbon (0.025 g). The solution was placed under a hydrogen balloon and stirred for 1 hour. The solution was filtered through Celite®, washed with methanol and evaporated under reduced pressure to afford (R)-2-hydroxy-4-(1-((pentafluorophenyl)sulfonyl)-N-(4-(tetrahydro-2H-pyran-4-yl)benzyl)pyrrolidine-2-carboxamido)benzoic acid (214 mg, 100% yield) as a white foam. HRMS (ESI) m/z 655.1516 [M+H]+.

Example 28

Sodium (R)-2-hydroxy-4-(1-((pentafluorophenyl)sulfonyl)-N-(4-(tetrahydro-2H-pyran-4-yl)benzyl)pyrrolidine-2-carboxamido)benzoate

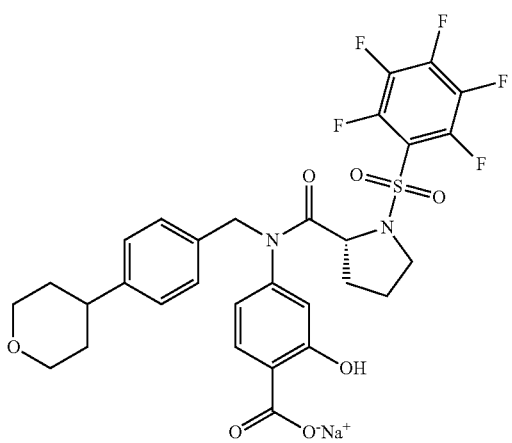

To (R)-2-hydroxy-4-(1-((pentafluorophenyl)sulfonyl)-N-(4-(tetrahydro-2H-pyran-4-yl)benzyl)pyrrolidine-2-carboxamido)benzoic acid (134 mg, 0.20 mmol) in 9 mL 1:1:1 THF:methanol:water was added sodium bicarbonate (15.5 mg, 0.18 mmol). The reaction was stirred at room temperature for 5 hours, then concentrated under reduced pressure. Ethanol was added and resulting solution was concentrated in vacuo to yield sodium (R)-2-hydroxy-4-(1-((pentafluorophenyl)sulfonyl)-N-(4-(tetrahydro-2H-pyran-4-yl)benzyl)pyrrolidine-2-carboxamido)benzoate (128 mg) as a salmon colored solid. HRMS (ESI) m/z 655.1537 [M+H]+.

Example 29

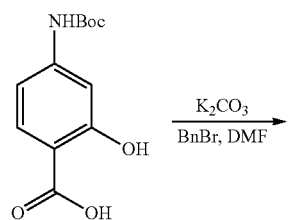

-continued

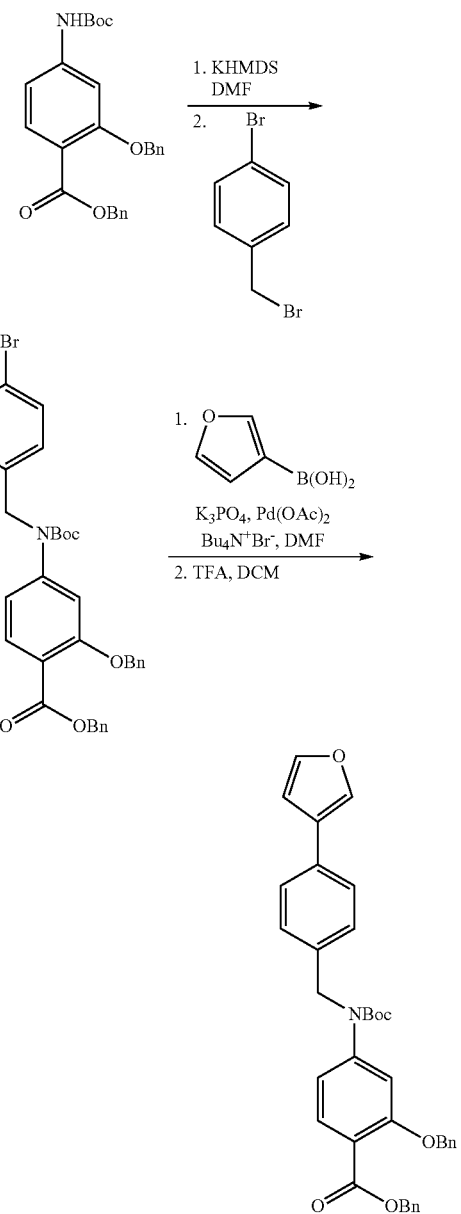

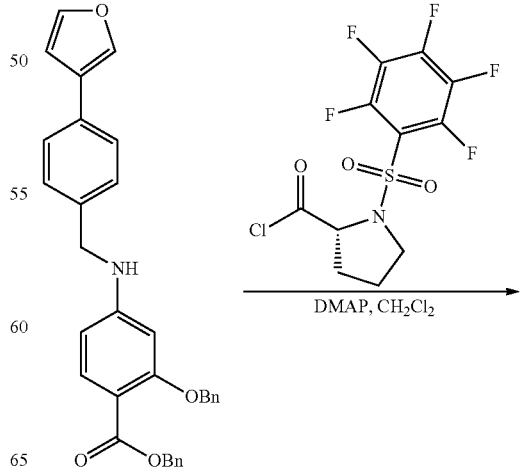

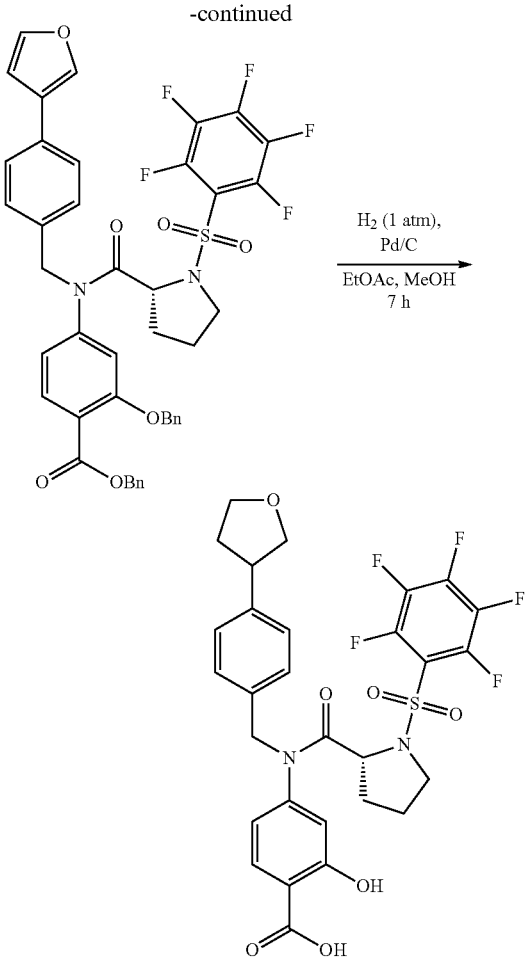

2-Hydroxy-4-((2R)-1-((pentafluorophenyl)sulfonyl)-
N-(4-(tetrahydrofuran-3-yl)benzyl)pyrrolidine-2-
carboxamido)benzoic acid

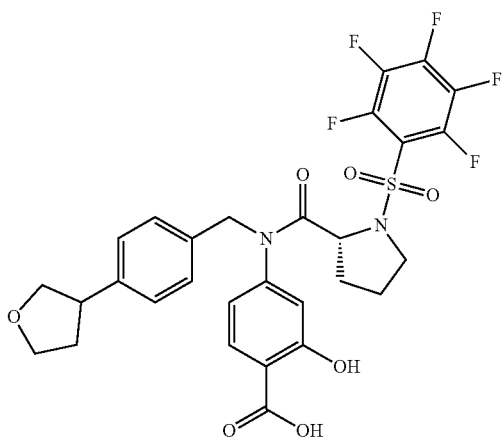 [SMILES: O=C(O)c1ccc(N(Cc2ccc(C3CCOC3)cc2)C(=O)[C@H]2CCCN2S(=O)(=O)c2c(F)c(F)c(F)c(F)c2F)cc1O]

Step 1: To a stirred solution of 4-((tert-butoxycarbonyl) amino)-2-hydroxybenzoic acid (4.68 g, 18.48 mmol) in DMF (90 mL) under nitrogen was added potassium carbonate (6 g, 43 mmol) followed by benzyl bromide (4.95 mL, 41.7 mmol). The resultant mixture was stirred at room temperature overnight, then poured onto water and extracted with ether (3×). The combined organic extracts were washed with brine, dried over anhydrous sodium sulfate and concentrated under reduced pressure. Purification by flash chromatography (0-8% EtOAc/hexanes gradient) provided benzyl 2-(benzyloxy)-4-((tert-butoxycarbonyl)amino)benzoate (7.34 g, 92% yield). 1H NMR (300 MHz, Chloroform-d) δ 7.88 (d, J=8.5 Hz, 1H), 7.57-7.29 (m, 11H), 6.75 (dd, J=8.5, 2.0 Hz, 1H), 6.66 (br. s, 1H), 5.34 (s, 2H), 5.19 (s, 2H), 1.55 (s, 9H).

Step 2: To a stirred solution of benzyl 2-(benzyloxy)-4-((tert-butoxycarbonyl)amino)benzoate (3.97 g, 9.17 mmol) in DMF (45 mL) at 0° C. under nitrogen was added KHMDS (11 mL of 1M in THF, 11 mmol). After stirring at 0° C. for 10 min, a solution of 4-bromobenzyl bromide (3.2 g, 12.8 mmol) in DMF (5 mL) was added. The reaction was allowed to warm to room temperature and stirring was continued at this temperature overnight. The reaction mixture was quenched with saturated aqueous ammonium chloride, poured onto water and extracted with ether (3×). The combined organic extracts were washed with brine, dried over anhydrous sodium sulfate and concentrated under reduced pressure. Purification by flash chromatography (8-26% gradient) provided benzyl 2-(benzyloxy)-4-((4-bromobenzyl) (tert-butoxycarbonyl)amino)benzoate (4.63 g, 84% yield) as a cream colored solid. 1H NMR (300 MHz, Chloroform-d) δ 7.81 (d, J=8.4 Hz, 1H), 7.46-7.30 (m, 12H), 7.03 (d, J=8.3 Hz, 2H), 6.85-6.76 (m, 2H), 5.35 (s, 2H), 5.07 (s, 2H), 4.75 (s, 2H), 1.43 (s, 9H). MS (ESI): 624, 626 [M+Na]+.

Step 3: A mixture of benzyl 2-(benzyloxy)-4-((4-bromobenzyl)(tert-butoxycarbonyl)amino)benzoate (904 mg, 1.5 mmol), furan-3-boronic acid (252 mg, 2.25 mmol, 1.5 equiv), potassium phosphate tribasic (1.6 g, 6 mmol, 4 equiv), and tetrabutylammonium bromide (60 mg) in DMF (20 mL) was degassed and backfilled with argon. Palladium (II) acetate (27 mg, 0.12 mmol, 0.08 equiv) was added and the reaction mixture was stirred at 80° C. for 48 h. The reaction mixture was poured onto water and extracted with ether (3×). The combined organic layers were washed with brine, dried over anhydrous sodium sulfate and concentrated under reduced pressure. LCMS showed a mixture of product, starting material, mono-de-benzylated starting material and mono-de-benzylated product. This crude mixture was resubmitted to a benzylation reaction.

To a stirred solution of the crude mixture containing approx. 0.7 mmol of debenzylated product (0.714 mg, 0.7 mmol) and potassium carbonate (116.1 mg, 0.84 mmol, 1.2 equiv) in DMF (5 mL) under nitrogen was added benzyl bromide (0.9 mL, 0.77 mmol, 1.1 equiv). The reaction was stirred at room temperature overnight, then poured onto water and extracted with ether (3×). The combined organic layers were washed with brine, dried over sodium sulfate and concentrated under reduced pressure.

The procedure was repeated on the same scale except using 30 mg of tetrabutylammonium bromide and heating at 90° C. for 24 h. The combined crude reaction mixtures were purified by flash chromatography (8% acetone/hexanes eluent) to provide recovered benzyl 2-(benzyloxy)-4-((4-bromobenzyl)(tert-butoxycarbonyl)amino)benzoate (635 mg) and benzyl 2-(benzyloxy)-4-((tert-butoxycarbonyl)(4-(furan-3-yl)benzyl)amino)benzoate (579 mg, 27% yield). 1H NMR (300 MHz, Chloroform-d) δ 7.81 (d, J=8.4 Hz, 1H), 7.77-7.70 (m, 1H), 7.50 (t, J=1.7 Hz, 1H), 7.46-7.28 (m, 12H), 7.18 (d, J=8.0 Hz, 2H), 6.92-6.80 (m, 2H), 6.71 (dd, J=1.9, 0.9 Hz, 1H), 5.34 (s, 2H), 5.06 (s, 2H), 4.82 (s, 2H), 1.45 (d, J=1.1 Hz, 9H).

Step 4: To a stirred solution of benzyl 2-(benzyloxy)-4-((tert-butoxycarbonyl)(4-(furan-3-yl)benzyl)amino)benzoate (575 mg, 0.97 mmol) in DCM under nitrogen at 0° C. was added dropwise TFA (2.4 mL). Stirring was continued for 1 h at room temperature. The solution was poured onto saturated sodium bicarbonate (aqueous phase kept at pH=8-9) and extracted with DCM (3×). The combined organic layers were dried over anhydrous sodium sulfate, concentrated under reduced pressure and the resulting residue purified by flash chromatography (13:1:2 hexane/ethyl acetate/DCM eluent) to yield benzyl 2-(benzyloxy)-4-((4-(furan-3-yl)benzyl)amino)benzoate (247 mg, 52% yield). 1H NMR (300 MHz, Chloroform-d) δ 7.85 (d, J=8.6 Hz, 1H), 7.75 (dd, J=1.5, 0.9 Hz, 1H), 7.56-7.23 (m, 12H), 6.71 (dd, J=1.9, 0.9 Hz, 1H), 6.24 (dd, J=8.6, 2.2 Hz, 1H), 6.19 (d, J=2.2 Hz, 1H), 5.32 (s, 2H), 5.10 (s, 2H), 4.36 (s, 2H). MS (ESI+) m/z 490.2 [M+H]+.

Step 5: To a stirred solution of benzyl 2-(benzyloxy)-4-((4-(furan-3-yl)benzyl)amino)benzoate (152 mg, 0.31 mmol) in dry DCM (8 mL) under nitrogen was added ((pentafluorophenyl)sulfonyl)-D-prolinoyl chloride (171 mg, 0.47 mmol, 1.5 equiv.) and DMAP (45 mg, 0.37 mmol, 1.2 equiv.) and the reaction mixture was stirred at room temperature overnight. The solution was poured onto water and extracted with DCM (3×). The combined organic layers were dried over sodium sulfate. A few drops of methanol were added and then the resulting mixture was concentrated under reduced pressure. Purification by flash column chromatography (20% EtOAc/hexane to 31% EtOAc/hexane gradient) provided benzyl (R)-2-(benzyloxy)-4-(N-(4-(furan-3-yl)benzyl)-1-((pentafluorophenyl)sulfonyl)pyrrolidine-2-carboxamido)benzoate (181 mg, 71% yield) as a white foam. MS (ESI+) m/z 817.1 [M+H]+.

Step 6: To a stirred solution of benzyl (R)-2-(benzyloxy)-4-(N-(4-(furan-3-yl)benzyl)-1-((pentafluorophenyl)sulfonyl)pyrrolidine-2-carboxamido)benzoate (155 mg, 0.19 mmol) in methanol (6 mL) and EtOAc (6 mL) under nitrogen was added 20% Pd(OH)₂ on C (15 mg). The reaction mixture was stirred under a hydrogen atmosphere for 7 h, then filtered through Celite® and washed with EtOAc (2×). The combined filtrate and washes were concentrated in vacuo to yield 2-hydroxy-4-((2R)-1-((pentafluorophenyl)sulfonyl)-N-(4-(tetrahydrofuran-3-yl)benzyl)pyrrolidine-2-carboxamido)benzoic acid (114.6 mg, 94% yield) as a pale pink white foam. HRMS (ESI+) m/z 641.1386 [M+H]+.

Example 30

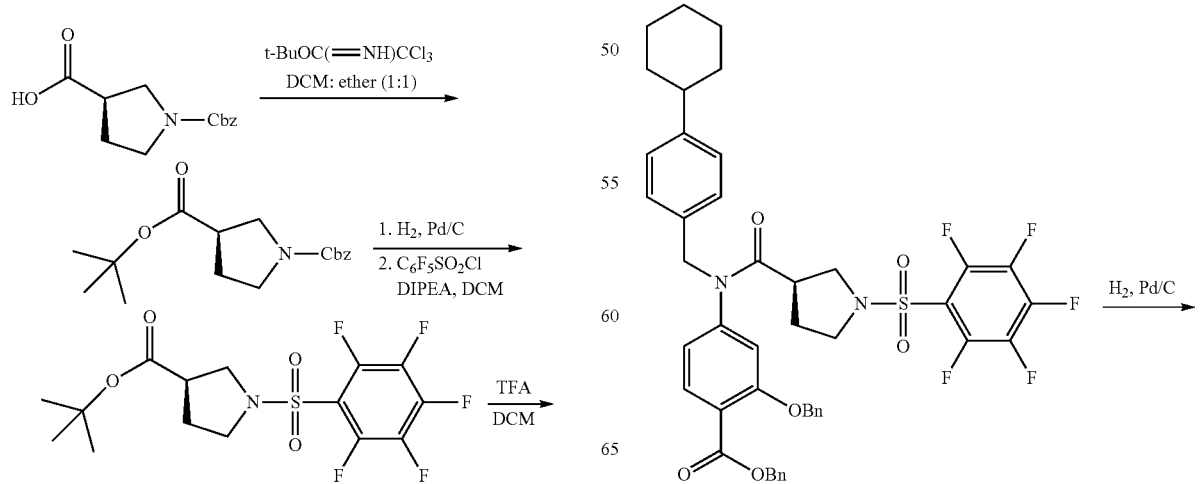

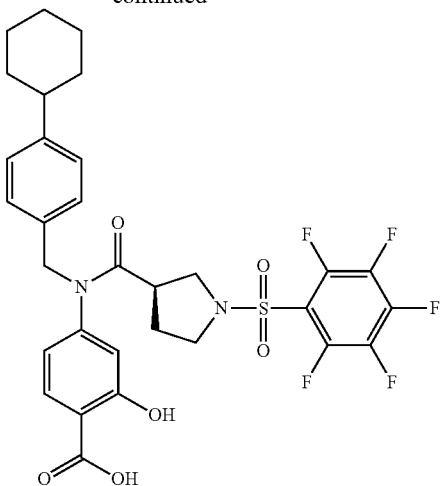

(R)-4-(N-(4-cyclohexylbenzyl)-1-((perfluorophenyl)sulfonyl)pyrrolidine-3-carboxamido)-2-hydroxybenzoic acid

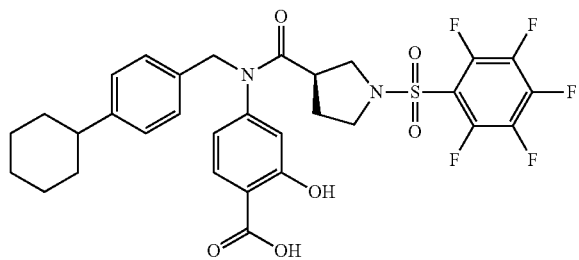 [SMILES: O=C(O)c1ccc(N(Cc2ccc(C3CCCCC3)cc2)C(=O)[C@@H]2CCN(S(=O)(=O)c3c(F)c(F)c(F)c(F)c3F)C2)cc1O]

Step 1: To a stirred solution of commercially-available (R)-1-((benzyloxy)carbonyl)pyrrolidine-3-carboxylic acid (500 mg, 2 mmol) in 1:1 ether:DCM (4 mL) was added tert-butyl-2,2,2-trichloroacetimidate (0.716 mL, 4 mmol) and the resulting reaction for 36 h. Additional tert-butyl-2,2,2-trichloroacetimidate (0.4 mL, 2.2 mmol) was added and the mixture was stirred for 3 days. The resulting suspension was filtered and washed several times with 1:1 ether:DCM. The combined filtrate and washes were concentrated under reduced pressure, taken up in DCM with a drop of methanol, mixed with a small amount of silica and concentrated. The resulting silica mixture was dry-loaded onto a flash column and eluted with 14:5:1 hexane:DCM:EtOAc solvent mix to provide 1-benzyl 3-(tert-butyl) (R)-pyrrolidine-1,3-dicarboxylate (516 mg, 84% yield). 1H NMR (300 MHz, Chloroform-d) δ 7.43-7.29 (m, 5H), 5.15 (s, 2H), 3.84-3.21 (m, 4H), 3.17-2.78 (m, 1H), 2.20-2.02 (m, 2H), 1.45 (s, 9H).

Step 2: To a stirred solution of 1-benzyl 3-(tert-butyl) (R)-pyrrolidine-1,3-dicarboxylate (510 mg, 1.6 mmol) in THF (5 mL) and methanol (10 mL) was added 10% Pd/C (30 mg) and the resulting mixture was placed under a hydrogen atmosphere and stirred for 2 h. The reaction was then flushed with nitrogen, filtered through Celite® and washed with methanol (2×). The combined filtrate and washes were concentrated under reduced pressure to provide tert-butyl (R)-pyrrolidine-3-carboxylate (310 mg) as a colorless oil. 1H NMR (300 MHz, Chloroform-d) δ 3.19-2.74 (m and overlapping br. s, 7H), 2.16-1.81 (m, 2H), 1.45 (s, 9H).

Step 3: To a stirred solution of tert-butyl (R)-pyrrolidine-3-carboxylate (1.6 mmol) in dry DCM (8 mL) under nitrogen at 0° C. was added DIPEA (0.4 mL, 2.24 mmol) followed by pentafluorobenzenesulfonyl chloride (0.28 mL, 1.9 mmol). The reaction was allowed to warm to room temperature, stirred at this temperature overnight, then poured onto water and extracted with DCM (3×). The combined organic extracts were dried over anhydrous sodium sulfate, concentrated under reduced pressure and the resulting residue purified by flash chromatography (0-18% EtOAc/hexanes eluent) to provide tert-butyl (R)-1-((pentafluorophenyl)sulfonyl)pyrrolidine-3-carboxylate (474 mg, 74% yield). 1H NMR (300 MHz, Chloroform-d) δ 3.74-3.61 (m, 2H), 3.60-3.44 (m, 2H), 3.04 (p, J=6.7 Hz, 1H), 2.20 (q, J=6.9 Hz, 2H), 1.43 (s, 9H). MS (ESI) m/z 424 [M+Na]+.

Step 4: To a stirred solution of tert-butyl (R)-1-((pentafluorophenyl)sulfonyl)pyrrolidine-3-carboxylate (465 mg, 1.16 mmol) in DCM (8 mL) under nitrogen was added TFA (8 mL) and the resulting reaction solution was stirred at room temperature overnight. Concentration in vacuo afforded (R)-1-((pentafluorophenyl)sulfonyl)pyrrolidine-3-carboxylic acid (405 mg, 100% yield) as a white solid. MS (ESI) m/z 368 [M+Na]+.

Step 5: To a stirred solution of (R)-1-((pentafluorophenyl)sulfonyl)pyrrolidine-3-carboxylic acid (398 mg, 1.15 mmol) in 16 mL of DCM under nitrogen was added DMF (2 drops) followed by oxalyl chloride (0.138 mL, 1.6 mmol) and the resultant mixture was stirred at room temperature for 3 h. The solution was concentrated in vacuo to provide acid chloride, (R)-1-((pentafluorophenyl)sulfonyl)pyrrolidine-3-carbonyl chloride which was used as is.

Step 6: To a stirred solution of benzyl 2-(benzyloxy)-4-((4-cyclohexylbenzyl)amino)benzoate (157 mg, 0.31 mmol) in THF (5 mL) under nitrogen at 0° C. was added methylmagnesium bromide (0.66 mL of 1.4 M in 1:3 THF:toluene, 0.93 mmol, 3 equiv). Stirring was continued at room temperature for 5 min. The resultant solution was added dropwise to a stirred solution of (R)-1-((pentafluorophenyl)sulfonyl)pyrrolidine-3-carbonyl chloride (173 mg, 0.47 mmol) in THF (5 mL) under nitrogen at room temperature. The resulting reaction mixture was stirred at room temperature for 2 h, quenched with saturated aqueous ammonium chloride, poured onto water and extracted with EtOAc (3×). The combined organic extracts were dried over anhydrous sodium sulfate, concentrated under reduced pressure and resulting residue purified by flash chromatography (30% DCM/hexane, then 5% EtOAc in (30% DCM/hexanes mixture) eluent) to afford benzyl (R)-2-(benzyloxy)-4-(N-(4-cyclohexylbenzyl)-1-((pentafluorophenyl)sulfonyl)pyrrolidine-3-carboxamido)benzoate (64 mg, 25% yield). 1H NMR (300 MHz, Chloroform-d) δ 7.81 (d, J=8.1 Hz, 1H), 7.49-7.23 (m, 10H), 7.12 (d, J=8.1 Hz, 2H), 6.96 (d, J=8.1 Hz, 2H), 6.59 (dd, J=8.1, 1.8 Hz, 1H), 6.30 (d, J=1.8 Hz, 1H), 5.36 (s, 2H), 4.97 (d, J=12.5 Hz, 1H), 4.86 (d, J=12.5 Hz, 1H), 4.75 (d, J=14.1 Hz, 1H), 4.62 (d, J=14.1 Hz, 1H), 3.64-3.19 (m, 4H), 2.73 (p, J=7.2 Hz, 1H), 2.58-2.38 (m, 1H), 2.02-1.59 (m, 8H), 1.49-1.08 (m, 4H). MS (ESI) m/z 833 [M+H]+.

Step 7: To a stirred solution of benzyl (R)-2-(benzyloxy)-4-(N-(4-cyclohexylbenzyl)-1-((pentafluorophenyl)sulfonyl)pyrrolidine-3-carboxamido)benzoate (60 mg, 0.072 mmol) in methanol (2.5 mL) and THF (2.5 mL) was added 10% Pd/C (25 mg) and the resulting suspension was stirred at room temperature under a hydrogen atmosphere for 6 h. The reaction mixture was filtered through Celite® and washed with methanol (2×). The combined filtrate and washes were concentrated, foamed with EtOAc/hexanes to provide (R)-

4-(N-(4-cyclohexylbenzyl)-1-((pentafluorophenyl)sulfonyl)pyrrolidine-3-carboxamido)-2-hydroxybenzoic acid (55 mg, 100% yield) as an off-white foam. HRMS (ESI) m/z 653.1741 [M+H]+.

Example 31

(S)-4-(N-(4-cyclohexylbenzyl)-1-((perfluorophenyl)sulfonyl)pyrrolidine-3-carboxamido)-2-hydroxybenzoic acid

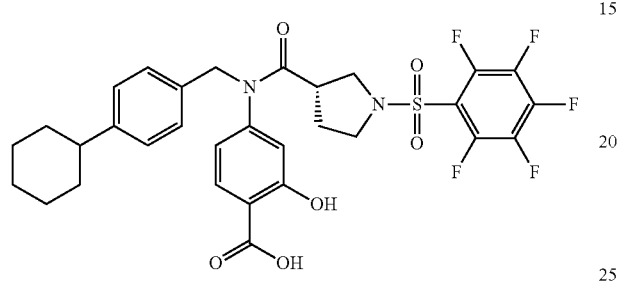

Preparation by a similar procedure to example 30, except substituting (S)-1-((benzyloxy)carbonyl)pyrrolidine-3-carboxylic acid for (R)-1-((benzyloxy)carbonyl)pyrrolidine-3-carboxylic acid in step 1 afforded (S)-4-(N-(4-cyclohexylbenzyl)-1-((perfluorophenyl)sulfonyl)pyrrolidine-3-carboxamido)-2-hydroxybenzoic acid as an off-white solid. HRMS (ESI) m/z 653.1737 [M+H]+.

Example 32

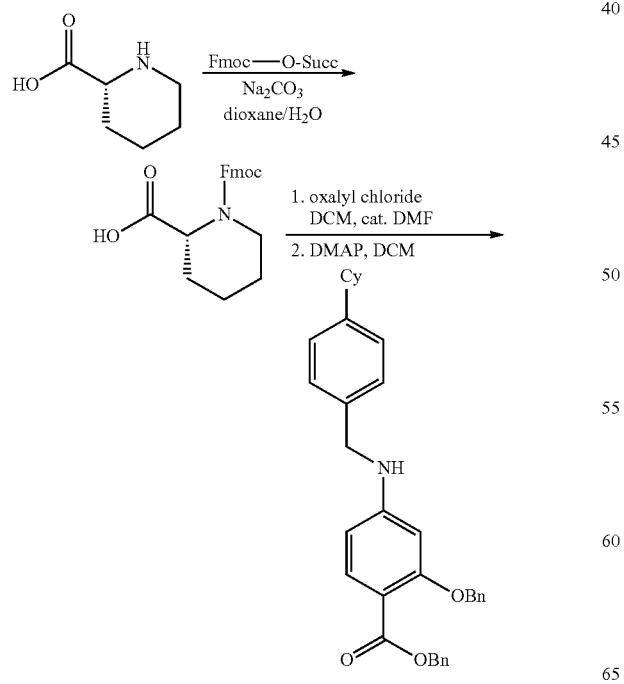

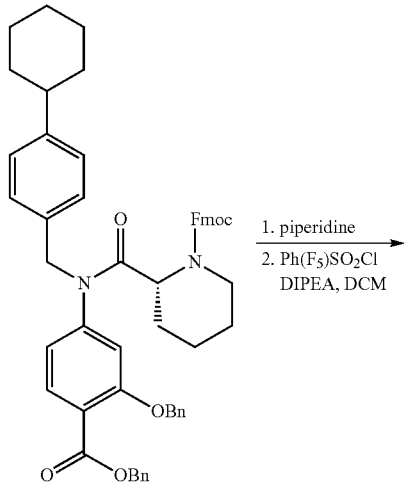

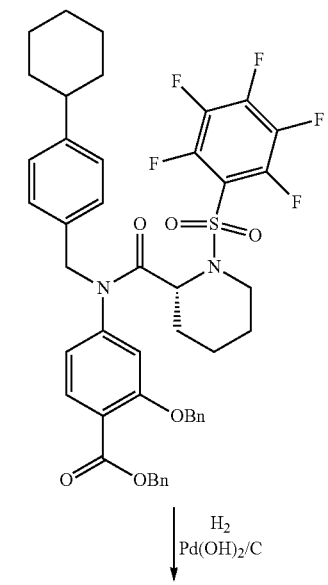

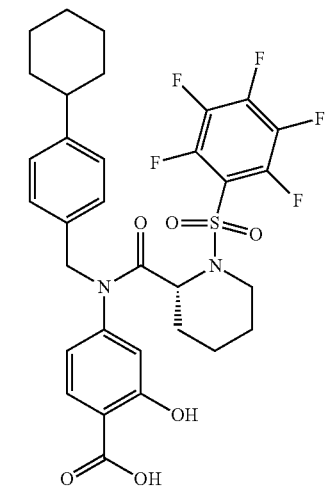 [SMILES: O=C(O)c1ccc(N(Cc2ccc(C3CCCCC3)cc2)C(=O)[C@H]2CCCCN2S(=O)(=O)c2c(F)c(F)c(F)c(F)c2F)cc1O]

123

(R)-4-(N-(4-cyclohexylbenzyl)-1-((pentafluorophenyl)sulfonyl)piperidine-2-carboxamido)-2-hydroxybenzoic acid

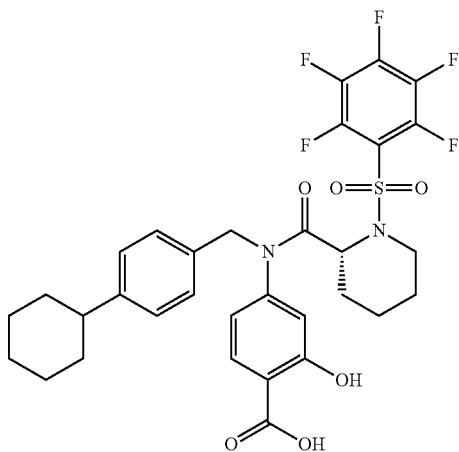 [SMILES: O=C(O)c1ccc(N(Cc2ccc(C3CCCCC3)cc2)C(=O)[C@H]2CCCCN2S(=O)(=O)c2c(F)c(F)c(F)c(F)c2F)cc1O]

Step 1: To a stirred solution of D-pipecolic acid (500 mg, 3.87 mmol) in 10% aqueous sodium carbonate (5 mL) was added N-(9-fluorenylmethoxycarbonyloxy)succinimide (1.3 g, 3.87 mmol) in dioxane (5 mL) and the resulting milky-white suspension was stirred at room temperature overnight. The crude reaction mixture was poured onto water, the pH was adjusted to pH=9 with saturated sodium bicarbonate, and the resulting mixture was washed into EtOAc (3×). The combined EtOAc washes were discarded. The aqueous phase was acidified to pH=4 with 10% aqueous HCl and the resultant mixture was extracted with EtOAc (3×). The combined EtOAc extracts were dried over sodium sulfate and concentrated in vacuo to afford (R)-1-(((9H-fluoren-9-yl)methoxy)carbonyl)piperidine-2-carboxylic acid (1.21 g, 90% yield) as a white powder. MS (ESI) m/z 374.1 [M+Na]+.

Step 2: To a stirred solution of (R)-1-(((9H-fluoren-9-yl)methoxy)carbonyl)piperidine-2-carboxylic acid (526 mg, 1.50 mmol) in 15 mL of DCM under nitrogen was added DMF (2 drops) followed by oxalyl chloride (0.19 mL, 2.25 mmol) and the resultant mixture was stirred at room temperature for 90 min. The solution was concentrated in vacuo to provide acid chloride, (9H-fluoren-9-yl)methyl (R)-2-(chlorocarbonyl)piperidine-1-carboxylate, which was used as is.

Step 3: To a stirred solution of (9H-fluoren-9-yl)methyl (R)-2-(chlorocarbonyl)piperidine-1-carboxylate (1.5 mmol) and benzyl 2-(benzyloxy)-4-((4-cyclohexylbenzyl)amino)benzoate (505 mg, 1 mmol) in DCM (15 mL) under nitrogen was added DMAP (146 mg, 1.2 mmol) and the resultant solution was stirred at room temperature overnight. The reaction mixture was then poured onto water and extracted with DCM (3×). The combined organic extracts were dried over anhydrous sodium sulfate, concentrated under reduced pressure and the resultant residue purified by flash chromatography (10-20% EtOAc/hexanes eluent) to provide (9H-fluoren-9-yl)methyl (R)-2-((3-(benzyloxy)-4-((benzyloxy)carbonyl)phenyl)(4-cyclohexylbenzyl)carbamoyl)piperidine-1-carboxylate (559 mg, 77% yield) as a white foam. MS (ESI) m/z 861.35 [M+Na]+.

Step 4: To a stirred solution of (9H-fluoren-9-yl)methyl (R)-2-((3-(benzyloxy)-4-((benzyloxy)carbonyl)phenyl)(4-cyclohexylbenzyl)carbamoyl)piperidine-1-carboxylate (214 mg, 0.255 mmol) in DCM (4 mL) at 0° C. under nitrogen was added piperidine (1 mL) and the resulting mixture was stirred at this temperature for 1 h and then concentrated in vacuo to provide crude benzyl (R)-2-(benzyloxy)-4-(N-(4-cyclohexylbenzyl)piperidine-2-carboxamido)benzoate, which was used as is in the next step. MS (ESI) m/z 617.3 [M+H]+.

Step 5: To a stirred solution of crude benzyl (R)-2-(benzyloxy)-4-(N-(4-cyclohexylbenzyl)piperidine-2-carboxamido)benzoate (0.255 mmol) in DCM (5 mL) at 0° C. under nitrogen was added DIPEA (0.075 mL, 0.43 mmol) followed by pentafluorobenzene sulfonyl chloride (0.057 mL, 0.38 mmol). The resulting reaction mixture was allowed to warm to room temperature and stirred at this temperature overnight. Reaction was not complete so reaction was cooled to 0° C. and additional DIPEA (0.075 mL, 0.43 mmol) was added followed by pentafluorobenzene sulfonyl chloride (0.057 mL, 0.38 mmol). The reaction was allowed to warm to room temperature and stirred at this temperature overnight. The crude reaction mixture was poured onto water and extracted with DCM (3×). The combined organic extracts were dried over sodium sulfate, concentrated under reduced pressure and the resulting residue purified by flash chromatography (0-10% EtOAc/hexanes gradient) to provide benzyl (R)-2-(benzyloxy)-4-(N-(4-cyclohexylbenzyl)-1-((pentafluorophenyl)sulfonyl)piperidine-2-carboxamido)benzoate (191 mg, 88% yield). 1H NMR (300 MHz, Chloroform-d) δ 7.87 (d, J=8.2 Hz, 1H), 7.48-7.28 (m, 10H), 7.12 (d, J=8.0 Hz, 2H), 6.94 (d, J=8.0 Hz, 2H), 6.78 (dd, J=8.2, 1.7 Hz, 1H), 6.67 (s, 1H), 5.37 (s, 2H), 5.15 (d, J=12.2 Hz, 1H), 5.05-4.76 (m, 3H), 4.50 (d, J=14.4 Hz, 1H), 3.99-3.62 (m, 2H), 2.58-2.38 (m, 1H), 1.98-1.11 (m, 14H). MS (ESI) m/z 847.3 [M+H]+.

Step 6: To a stirred solution of benzyl (R)-2-(benzyloxy)-4-(N-(4-cyclohexylbenzyl)-1-((pentafluorophenyl)sulfonyl)piperidine-2-carboxamido)benzoate (171 mg, 0.20 mmol) in methanol (5 mL) and EtOAc (5 mL) under nitrogen was added 20% Pd(OH)$_2$ on C (20 mg). The reaction mixture was stirred under a hydrogen atmosphere for 1.5 h, then filtered through Celite® and washed with EtOAc (2×). The combined filtrate and washes were concentrated in vacuo to yield (R)-4-(N-(4-cyclohexylbenzyl)-1-((perfluorophenyl)sulfonyl)piperidine-2-carboxamido)-2-hydroxybenzoic acid (125 mg, 94% yield) as a white powder. HRMS (ESI) m/z 667.1902 [M+H]+.

Example 33

(S)-4-(N-(4-cyclohexylbenzyl)-1-((pentafluorophenyl)sulfonyl)piperidine-2-carboxamido)-2-hydroxybenzoic acid

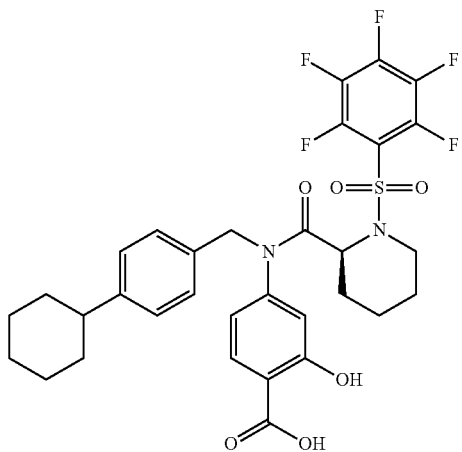 [SMILES: O=C(O)c1ccc(N(Cc2ccc(C3CCCCC3)cc2)C(=O)[C@@H]2CCCCN2S(=O)(=O)c2c(F)c(F)c(F)c(F)c2F)cc1O]

Preparation by a similar procedure to example 32, except substituting L-pipecolic acid for D-pipecolic acid in step 1 afforded (S)-4-(N-(4-cyclohexylbenzyl)-1-((pentafluorophenyl)sulfonyl)piperidine-2-carboxamido)-2-hydroxybenzoic acid as an off-white solid. HRMS (ESI) m/z 667.1903 [M+H]+.
Example 34
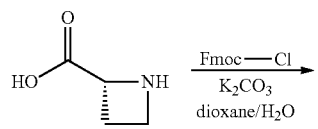
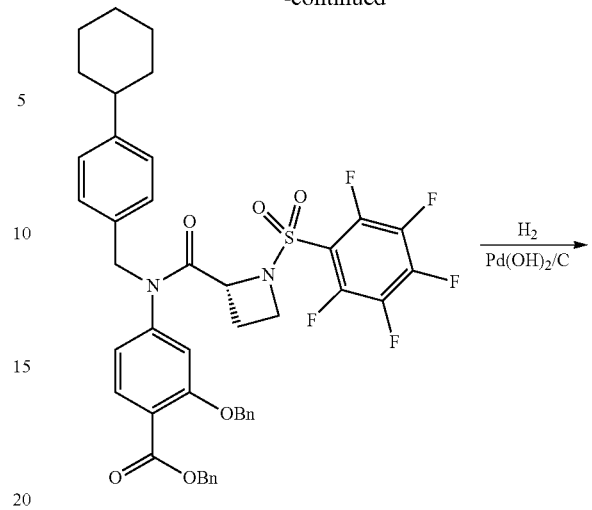
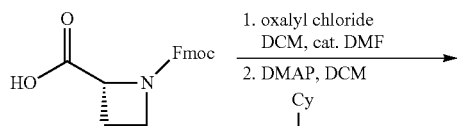
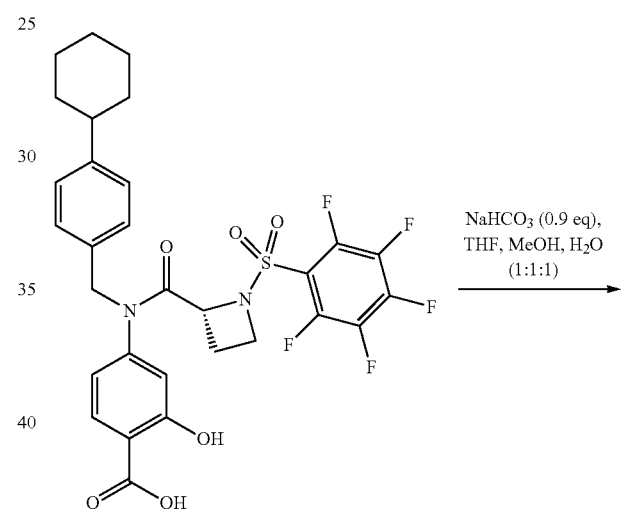
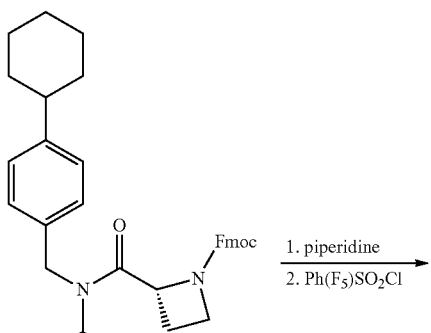
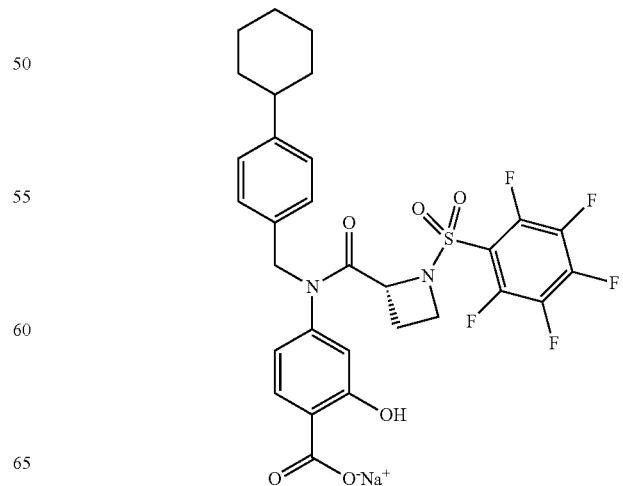

(R)-4-(N-(4-Cyclohexylbenzyl)-1-((perfluorophenyl)sulfonyl)azetidine-2-carboxamido)-2-hydroxybenzoic acid

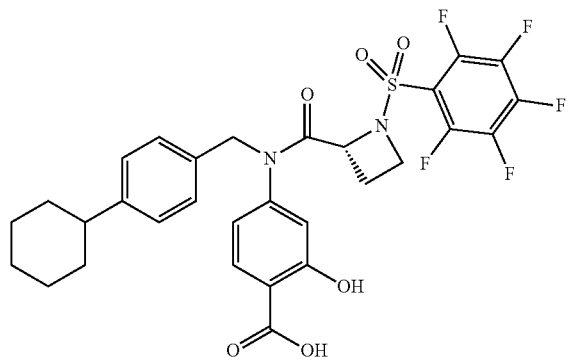 [SMILES: O=C(O)c1ccc(N(Cc2ccc(C3CCCCC3)cc2)C(=O)[C@H]2CCN2S(=O)(=O)c2c(F)c(F)c(F)c(F)c2F)cc1O]

Step 1: To a solution of (R)-azetidine-2-carboxylic acid (200 mg, 2 mmol) and potassium carbonate (138 mg, 1 mmol) in 1:1 dioxane (1 mL) under nitrogen was added 9-fluorenylmethyl chloroformate (435 mg, 1.68 mmole) in dioxane (3 mL) and the resulting mixture was stirred at room temperature overnight. The resultant reaction mixture was poured onto 10% aqueous sodium bicarbonate and washed with ether (3×). The ether washes were discarded. The aqueous phase was acidified to pH=2 with 10% aqueous potassium sulfate/10% sodium sulfate buffer and extracted with DCM (3×). The combined DCM extracts were dried over sodium sulfate and concentrated in vacuo to afford (R)-1-(((9H-fluoren-9-yl)methoxy)carbonyl)azetidine-2-carboxylic acid (488 mg, 90% yield) as a white foam. MS (ESI) m/z 346.1 [M+Na]+.

Step 2: To a stirred solution of (R)-1-(((9H-fluoren-9-yl)methoxy)carbonyl)azetidine-2-carboxylic acid (261 mg, 0.80 mmol) in 8 mL of DCM under nitrogen was added DMF (1 drops) followed by oxalyl chloride (0.15 mL, 1.80 mmol) and the resultant mixture was stirred at room temperature for 90 min. The solution was concentrated in vacuo to provide acid chloride, (9H-fluoren-9-yl)methyl (R)-2-(chlorocarbonyl)azetidine-1-carboxylate, which was used as is.

Step 3: To a stirred solution of (9H-fluoren-9-yl)methyl (R)-2-(chlorocarbonyl)azetidine-1-carboxylate (0.8 mmol) and benzyl 2-(benzyloxy)-4-((4-cyclohexylbenzyl)amino)benzoate (269 mg, 0.53 mmol) in DCM (8 mL) under nitrogen was added DMAP (78 mg, 0.64 mmol) and the resultant solution was stirred at room temperature overnight. The reaction mixture was then poured onto water and extracted with DCM (3×). The combined organic extracts were dried over sodium sulfate, concentrated under reduced pressure and the resultant residue purified by flash chromatography (30-50% EtOAc/hexanes eluent) to provide (9H-fluoren-9-yl)methyl (R)-2-((3-(benzyloxy)-4-((benzyloxy)carbonyl)phenyl)(4-cyclohexylbenzyl)carbamoyl)azetidine-1-carboxylate (341 mg, 79% yield) as a white foam. MS (ESI) m/z 811.35 [M+H]+.

Step 4: To a stirred solution of (9H-fluoren-9-yl)methyl (R)-2-((3-(benzyloxy)-4-((benzyloxy)carbonyl)phenyl)(4-cyclohexylbenzyl)carbamoyl)azetidine-1-carboxylate (305 mg, 0.37 mmol) in DCM (6 mL) at 0° C. under nitrogen was added piperidine (1.5 mL) and the resulting mixture was stirred at this temperature for 1 h and then concentrated under reduced pressure. Re-dissolved in toluene and concentrated in vacuo to provide crude benzyl (R)-2-(benzyloxy)-4-(N-(4-cyclohexylbenzyl)azetidine-2-carboxamido)benzoate, which was used as is in the next step. MS (ESI) m/z 589.3 [M+H]+.

Step 5: To a stirred solution of crude benzyl (R)-2-(benzyloxy)-4-(N-(4-cyclohexylbenzyl)azetidine-2-carboxamido)benzoate (0.37 mmol) in DCM (10 mL) at 0° C. under nitrogen was added DIPEA (0.11 mL, 0.63 mmol) followed by pentafluorobenzene sulfonyl chloride (0.080 mL, 0.55 mmol). The resulting reaction mixture was allowed to warm to room temperature and stirred at this temperature for 2 h. The crude reaction mixture was poured onto water and extracted with DCM (3×). The combined organic extracts were dried over anhydrous sodium sulfate, concentrated under reduced pressure and the resulting residue purified by flash chromatography (30% EtOAc/hexanes eluent) to provide benzyl (R)-2-(benzyloxy)-4-(N-(4-cyclohexylbenzyl)-1-((perfluorophenyl)sulfonyl)azetidine-2-carboxamido)benzoate (206 mg, 68% yield over steps 4-5). 1H NMR (300 MHz, Chloroform-d) δ 7.81 (d, J=8.2 Hz, 1H), 7.47-7.29 (m, 10H), 7.13 (d, J=8.1 Hz, 2H), 6.99 (d, J=8.1 Hz, 2H), 6.62 (dd, J=8.2, 1.8 Hz, 1H), 6.43 (s, 1H), 5.37 (s, 2H), 5.05 (d, J=12.4 Hz, 1H), 4.90-4.76 (m, 2H), 4.72 (s, 2H), 4.15-3.88 (m, 2H), 2.59-2.38 (m, 1H), 1.97 (q, J=8.4, 7.9 Hz, 1H), 1.91-1.70 (m, 5H), 1.50-1.15 (m, 6H). MS (ESI) m/z 819.2 [M+H]+.

Step 6: To a stirred solution of benzyl (R)-2-(benzyloxy)-4-(N-(4-cyclohexylbenzyl)-1-((perfluorophenyl)sulfonyl)azetidine-2-carboxamido)benzoate (196 mg, 0.24 mmol) in methanol (6 mL) and EtOAc (6 mL) under nitrogen was added 20% Pd(OH)$_2$ on C (18 mg). The reaction mixture was stirred under a hydrogen atmosphere for 1 h, then filtered through Celite® and washed with EtOAc (2×). The combined filtrate and washes were concentrated in vacuo to yield (R)-4-(N-(4-cyclohexylbenzyl)-1-((perfluorophenyl)sulfonyl)azetidine-2-carboxamido)-2-hydroxybenzoic acid (147 mg, 99% yield) as a pale pink foam. HRMS (ESI) m/z 639.1581 [M+H]+.

Example 35

Sodium (R)-4-(N-(4-cyclohexylbenzyl)-1-((perfluorophenyl)sulfonyl)azetidine-2-carboxamido)-2-hydroxybenzoate

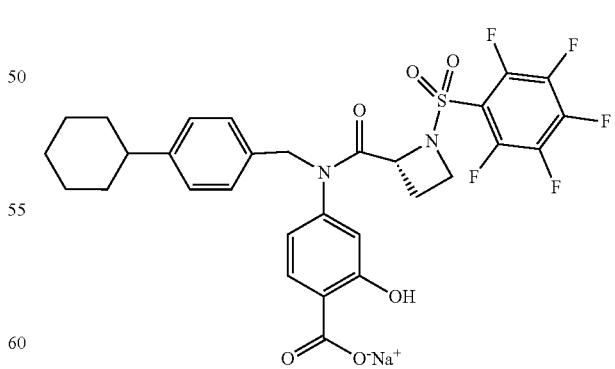

To a stirred solution of (R)-4-(N-(4-cyclohexylbenzyl)-1-((perfluorophenyl)sulfonyl)azetidine-2-carboxamido)-2-hydroxybenzoic acid (64.3 mg, 0.101 mg) in THF (5 mL), methanol (5 mL) and water (5 mL) was added sodium bicarbonate (7.6 mg, 0.091 mmol) and the resulting solution was stirred at room temperature for 4 h. The reaction mixture was concentrated under reduced pressure. The resulting residue was dissolved in ethanol and the mixture was concentrated in vacuo to provide sodium (R)-4-(N-(4-cyclohexylbenzyl)-1-((perfluorophenyl)sulfonyl)azetidine-2-carboxamido)-2-hydroxybenzoate (40 mg) as a pale pink powder. HRMS (ESI) m/z 639.1597 [M+H]+.

Example 36

(S)-4-(N-(4-Cyclohexylbenzyl)-1-((perfluorophenyl) sulfonyl)azetidine-2-carboxamido)-2-hydroxybenzoic acid Preparation by a similar procedure to example 34, except substituting (S)-1-(((9H-fluoren-9-yl)methoxy)carbonyl) azetidine-2-carboxylic acid for (S)-1-(((9H-fluoren-9-yl) methoxy)carbonyl)-azetidine-2-carboxylic acid in step 2 afforded (S)-4-(N-(4-cyclohexylbenzyl)-1-((perfluorophenyl)-sulfonyl)azetidine-2-carboxamido)-2-hydroxybenzoic acid as a white foam. HRMS (ESI) m/z 639.1583 [M+H]+.

Example 37

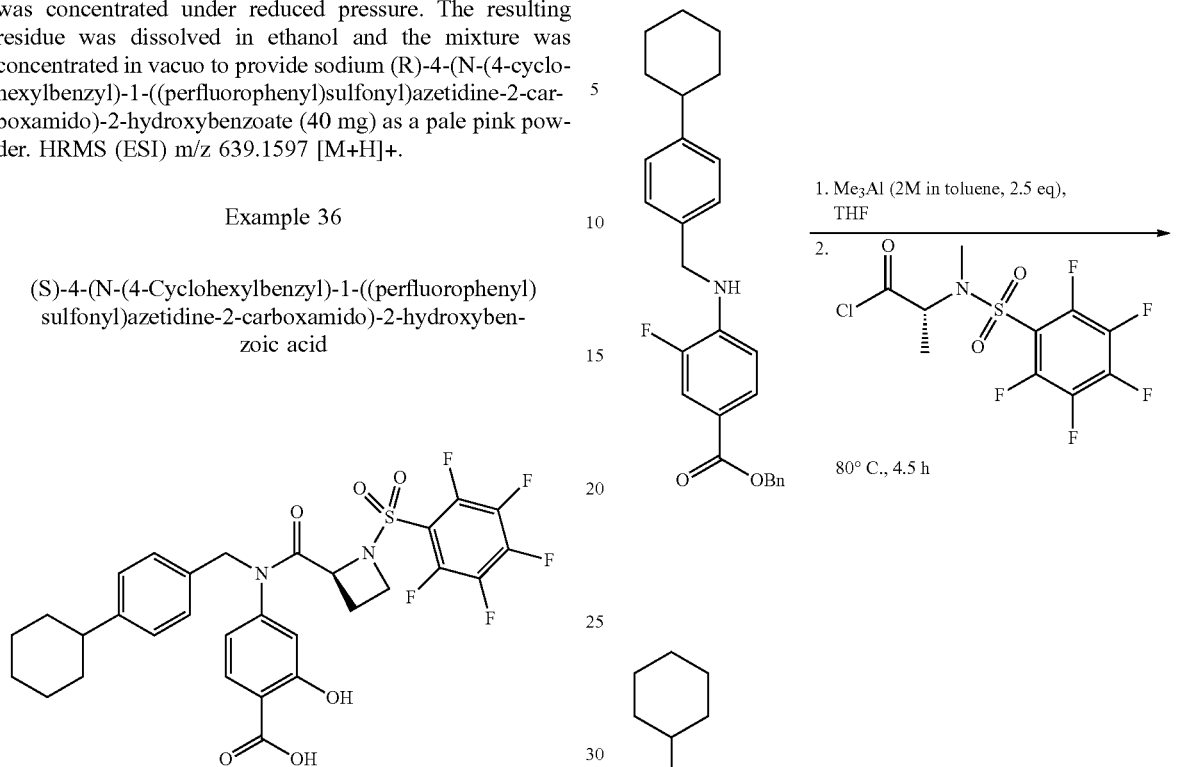

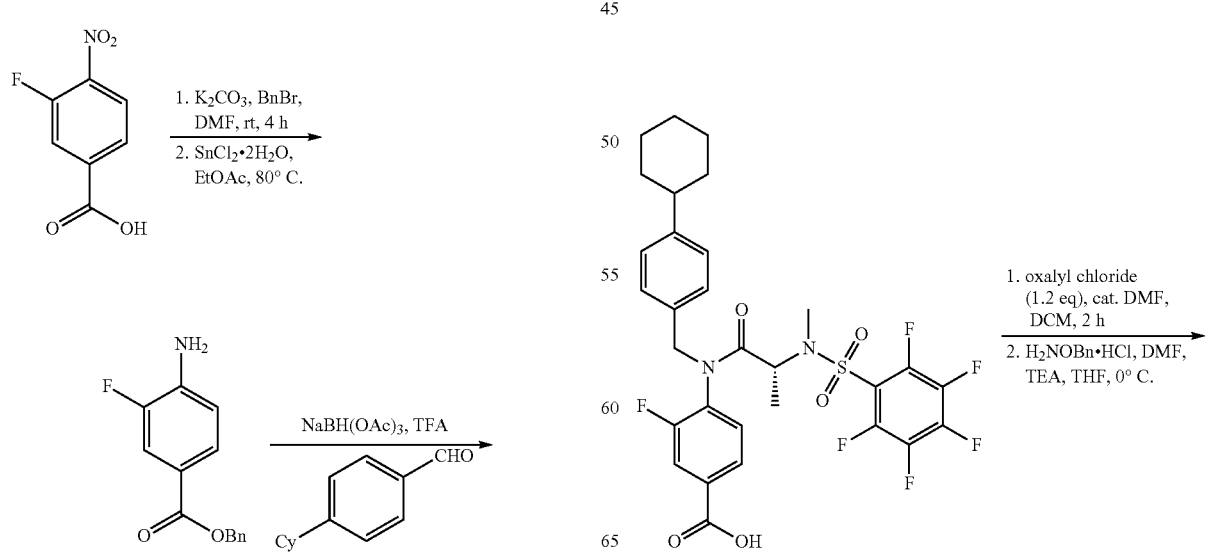

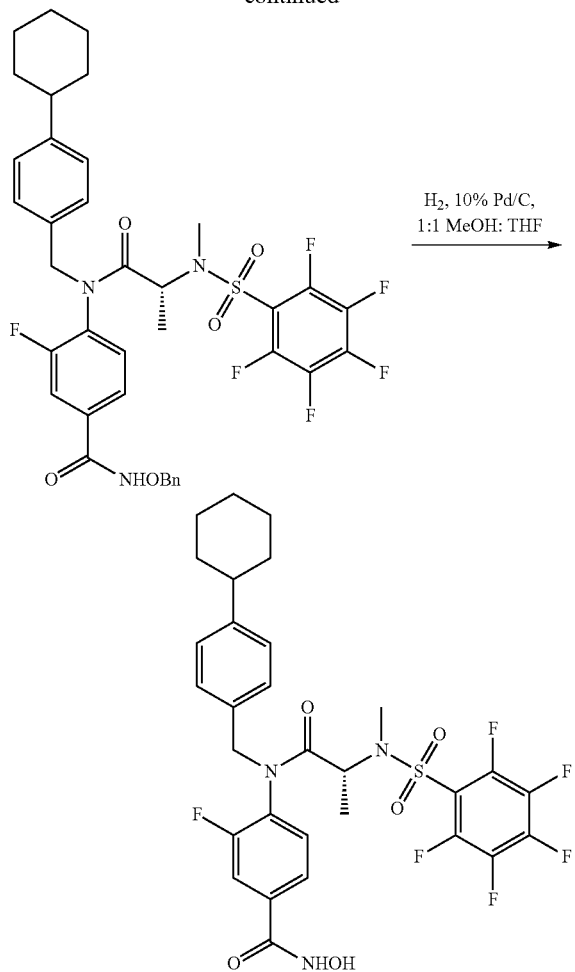

(R)-4-(N-(4-cyclohexylbenzyl)-2-((2,3,4,5,6-pentafluoro-N-methylphenyl)sulfonamido)propanamido)-3-fluorobenzoic acid

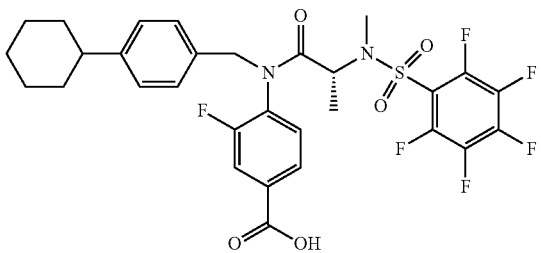 [SMILES: C[C@H](C(=O)N(Cc1ccc(C2CCCCC2)cc1)c1ccc(C(=O)O)cc1F)N(C)S(=O)(=O)c1c(F)c(F)c(F)c(F)c1F]

Step 1: To a stirred solution of 3-fluoro-4-nitrobenzoic acid (4.05 g, 21.9 mmol) in DMF (109 mL) was added potassium carbonate (3.32 g, 24.1 mmol). Stirring continued at room temperature for 10 min before addition of benzyl bromide (2.51 mL, 20.8 mmol). The resulting reaction mixture was stirred at room temperature for 3.75 h, then poured onto cold water and extracted with EtOAc (2×). The combined organic extracts were washed with water (3×), then brine, dried over anhydrous sodium sulfate and concentrated in vacuo to afford benzyl 3-fluoro-4-nitrobenzoate (6.19 g) as a yellow oil. 1H NMR (300 MHz, Chloroform-d) δ 8.12 (dd, J=8.8, 7.0 Hz, 1H), 8.04-8.00 (m, 1H), 8.00-7.96 (m, 1H), 7.54-7.37 (m, 5H), 5.43 (s, 2H).

Step 2: To a stirred solution of crude 3-fluoro-4-nitrobenzoate (6.19 g, 22 mmol) in EtOAc (238 mL) under nitrogen was added SnCl$_2$.2H$_2$O (25.4 g, 112.6 mmol). The resulting reaction mixture was stirred over night at 80° C., cooled, then poured onto cold water. The pH was adjusted to pH=8 using aq. 10% sodium bicarbonate and the resulting mixture was stirred at room temperature for 45 min and then extracted with EtOAc (3×). The combined organic extracts were washed with water and then brine, dried over anhydrous sodium sulfate and concentrated under reduced pressure. Purification by flash chromatography (2:8 EtOAc/hexanes) provided benzyl 4-amino-3-fluorobenzoate (4.83 g, 90% yield) as a pale yellow solid. 1H NMR (300 MHz, Chloroform-d) δ 7.75-7.72 (m, 1H), 7.72-7.68 (m, 1H), 7.48-7.32 (m, 5H), 6.77 (t, J=8.6 Hz, 1H), 5.33 (s, 2H).

Step 3: To a solution of benzyl 4-amino-3-fluorobenzoate (356 mg, 1.45 mmol) in TFA (3.3 mL) under nitrogen at 0° C. was added sodium triacetoxyborohydride (617 mg, 2.91 mmol) portion wise. The mixture was stirred at 0° C. for 10 min. before addition of 4-cyclohexylbenzaldehyde (290 mg, 1.54 mmol). The resulting reaction mixture was stirred at room temperature for 4 h, poured onto cold water and extracted with EtOAc (2×). The combined organic extracts were washed with water (3×), then with 10% aqueous sodium bicarbonate (2×), dried over anhydrous sodium sulfate and concentrated under reduced pressure. The pH after the last wash was 7-8. Purification by flash chromatography (12:88 EtOAc/hexanes) provided benzyl 4-((4-cyclohexylbenzyl)amino)-3-fluorobenzoate (446 mg, 74% yield) as a white solid. 1H NMR (300 MHz, Chloroform-d) δ 7.77 (ddd, J=8.5, 1.9, 0.8 Hz, 1H), 7.70 (dd, J=12.3, 1.9 Hz, 1H), 7.50-7.34 (m, 5H), 7.32-7.16 (m, 4H), 6.68 (t, J=8.5 Hz, 1H), 5.33 (s, 2H), 4.40 (s, 2H), 2.64-2.36 (m, 1H), 2.03-1.68 (m, 5H), 1.59-1.15 (m, 5H).

Step 4: To a stirred solution of benzyl 4-((4-cyclohexylbenzyl)amino)-3-fluorobenzoate (596 mg, 1.42 mmol) in THF (11 mL) under nitrogen at 0° C. was added a solution of trimethylaluminum (1.78 mL of 2M in toluene, 3.57 mmol) and the mixture was warmed to room temperature and stirred at this temperature for 15 min. To the resulting solution was added a solution of N-methyl-N-((pentafluorophenyl)sulfonyl)-D-alaninoyl chloride (652 mg, 1.85 mmol) in THF (7.7 mL). The reaction mixture was stirred at 80° C. for 4.5 h, poured onto 10% KHSO$_4$/Na$_2$SO$_4$ buffer and ice and then extracted with EtOAc (2×). The combined organic layers were washed with water and then brine, dried over anhydrous sodium sulfate, and concentrated under reduced pressure. Purification by flash chromatography (10-14% EtOAc/hexane) provided benzyl (R)-4-(N-(4-cyclohexylbenzyl)-2-((2,3,4,5,6-pentafluoro-N-methylphenyl) sulfonamido) propanamido)-3-fluorobenzoate (497 mg, 48% yield) as a colorless oil. 1H NMR (300 MHz, Chloroform-d) δ 7.85 (dd, J=12.0, 9.8 Hz, 2H), 7.51-7.33 (m, 5H), 7.20-6.87 (m, 5H), 5.38 (s, 2H), 5.32 (d, J=14.3 Hz, 1H), 4.75 (q, J=7.1 Hz, 1H), 4.20 (d, J=14.3 Hz, 1H), 3.16 (s, 3H), 2.46 (s, 1H), 1.93-1.69 (m, 6H), 1.47-1.30 (m, 4H), 1.23 (d, J=7.1 Hz, 3H).

Step 5: To a stirred solution of benzyl (R)-4-(N-(4-cyclohexylbenzyl)-2-((2,3,4,5,6-pentafluoro-N-methylphenyl)sulfonamido) propanamido)-3-fluorobenzoate (487 mg, 0.665 mmol) in methanol (8 mL) and THF (8 mL) was added 10% Pd/C (60.3 mg) and the resulting suspension was stirred at room temperature under a hydrogen atmosphere for 6.5 h. The reaction mixture was filtered through Celite® and washed with EtOAc. The combined filtrate and washes were concentrated to afford (R)-4-(N-(4-cyclohexylbenzyl)-2-((2,3,4,5,6-pentafluoro-N-methylphenyl)sulfonamido)-propanamido)-3-fluorobenzoic acid (443 mg, 100% yield). A portion of the product (100 mg) was purified by preparative TLC (1:1 hexane:EtOAc with 0.1% AcOH) and the resulting oil was recrystallized from 1:1 ether hexanes to give pure (R)-4-(N-(4-cyclohexylbenzyl)-2-((2,3,4,5,6-pentafluoro-N-methylphenyl)sulfonamido)-propanamido)-3-fluorobenzoic acid. MS (ESI) m/z 643 [M+H]+. HRMS (ESI+) calculated for C30H28F6N2O5S: 642.1623, found 642.1613.

Example 38

(R)-4-(N-(4-Cyclohexylbenzyl)-2-((2,3,4,5,6-pentafluoro-N-methylphenyl)sulfonamido)propanamido)-3-fluoro-N-hydroxybenzamide

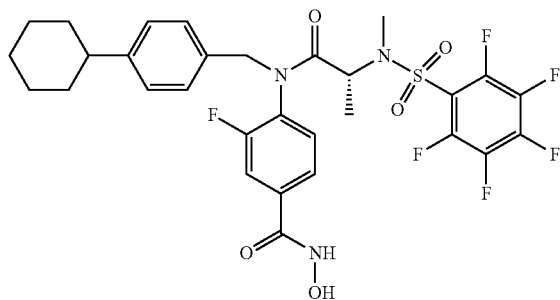 [SMILES: C[C@H](C(=O)N(Cc1ccc(C2CCCCC2)cc1)c1ccc(C(=O)NO)cc1F)N(C)S(=O)(=O)c1c(F)c(F)c(F)c(F)c1F]

Step 1: To a stirred solution of (R)-4-(N-(4-cyclohexylbenzyl)-2-((2,3,4,5,6-pentafluoro-N-methylphenyl)sulfonamido)-propanamido)-3-fluorobenzoic acid (111 mg, 0.17 mmol) in DCM (3.1 mL) was added oxalyl chloride (0.018 mL, 0.208 mmol) and DMF (1 drop). The resulting reaction solution was stirred at room temperature under nitrogen for 2 h and then concentrated under reduced pressure. The resulting residue was re-dissolved in DCE (3 mL) and concentrated in vacuo to afford (R)-4-(N-(4-cyclohexylbenzyl)-2-((2,3,4,5,6-pentafluoro-N-methylphenyl)sulfonamido)propanamido)-3-fluorobenzoyl chloride, which was used as is.

Step 2: To a solution of O-benzylhydroxylamine hydrochloride (38.6 mg, 0.242 mmol) in DMF (3.1 mL) was added TEA (0.068 mL, 0.49 mmol). The mixture was stirred for 15 min, then added to a solution of (R)-4-(N-(4-cyclohexylbenzyl)-2-((2,3,4,5,6-pentafluoro-N-methylphenyl)sulfonamido)propanamido)-3-fluorobenzoyl chloride (0.173 mmol) in THF (3.1 mL) at 0° C. under nitrogen. The resultant reaction mixture was warmed to room temperature and stirred for 1 h. The reaction was quenched with 10% aqueous potassium bisulfate, poured onto water and extracted with EtOAc (2×). The combined organic extracts were washed with water, then washed with brine, dried over anhydrous sodium sulfate and concentrated under reduced pressure. The resulting residue was purified by flash chromatography (25% EtOAc/hexanes) to provide (R)—N-(benzyloxy)-4-(N-(4-cyclohexylbenzyl)-2-((2,3,4,5,6-pentafluoro-N-methylphenyl)sulfonamido)propanamido)-3-fluorobenzamide (40.4 mg, 31% yield). 1H NMR (300 MHz, Chloroform-d) δ 7.62 (d, J=10.3 Hz, 1H), 7.51-7.37 (m, 5H), 7.14-6.89 (m, 6H), 5.30 (d, J=13.8 Hz, 1H), 5.06 (br. s, 1H), 4.79-4.60 (m, 1H), 4.20 (d, J=13.8 Hz, 1H), 3.16 (s, 3H), 2.53-2.39 (m, 1H), 1.93-1.69 (m, 6H), 1.47-1.33 (m, 4H), 1.23 (d, J=7.1 Hz, 3H).

Step 3: To a stirred solution of (R)—N-(benzyloxy)-4-(N-(4-cyclohexylbenzyl)-2-((2,3,4,5,6-pentafluoro-N-methylphenyl)-sulfonamido)propanamido)-3-fluorobenzamide (36.2 mg, 0.0484 mmol) in methanol (1.6 mL) and THF (1.6 mL) was added 10% Pd/C (4.2 mg) and the resulting suspension was stirred at room temperature under a hydrogen atmosphere for 2.5 h. The reaction mixture was filtered through Celite® and washed with EtOAc. The combined filtrate and washes were concentrated under reduced pressure and residue purified by preparative TLC (65:35 hexane/acetone eluent) to provide (R)-4-(N-(4-cyclohexylbenzyl)-2-((2,3,4,5,6-pentafluoro-N-methylphenyl)sulfonamido)propanamido)-3-fluoro-N-hydroxybenzamide (17 mg, 53% yield) as a foam. MS (ESI) m/z 658 [M+H]+. HRMS (ESI+) calculated for C30H29F6N3O5S: 657.1732, found 657.1716.

Example 39

(R)-4-(N-(4-cyclohexylbenzyl)-1-((perfluorophenyl)sulfonyl)pyrrolidine-2-carboxamido)-3-fluorobenzoic acid

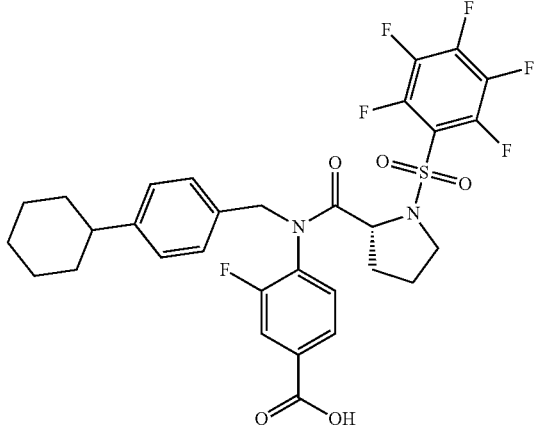 [SMILES: O=C(O)c1ccc(N(Cc2ccc(C3CCCCC3)cc2)C(=O)[C@H]2CCCN2S(=O)(=O)c2c(F)c(F)c(F)c(F)c2F)c(F)c1]

Preparation by a similar procedure to example 37, except substituting ((perfluorophenyl)sulfonyl)-D-prolinoyl chloride for N-methyl-N-((perfluorophenyl)sulfonyl)-D-alaninoyl chloride in step 4 afforded (R)-4-(N-(4-cyclohexylbenzyl)-1-((perfluorophenyl)sulfonyl)pyrrolidine-2-carboxamido)-3-fluorobenzoic acid. HRMS (ESI+) m/z 655.1692 [M+H]+.

Example 40

(R)-3-chloro-4-(N-(4-cyclohexylbenzyl)-2-((2,3,4,5,6-pentafluoro-N-methylphenyl)sulfonamido)propanamido)benzoic acid

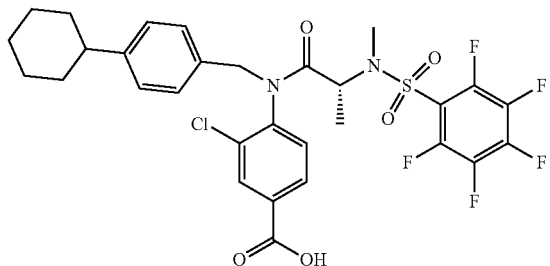 [SMILES: C[C@H](C(=O)N(Cc1ccc(C2CCCCC2)cc1)c1ccc(C(=O)O)cc1Cl)N(C)S(=O)(=O)c1c(F)c(F)c(F)c(F)c1F]

Step 1: To a solution of 3-chloro-4-nitrobenzoic acid (1.0 g, 4.96 mmol) in DMF (25 mL) under nitrogen was added potassium carbonate (0.75 g, 5.46 mmol). After 10 min benzyl bromide (0.57 mL, 4.71 mmol) was added and the resultant solution was stirred at room temperature for 3.5 h. The mixture was poured onto cold water and extracted with EtOAc (2×). The combined organic extract was washed with water (2×), and then washed with brine, dried over anhydrous sodium sulfate and concentrated in vacuo to provide crude product, benzyl 3-chloro-4-nitrobenzoate (1.49 g) as a yellow oil, which was used as is. 1H NMR (300 MHz, Chloroform-d) δ 8.25 (d, J=1.7 Hz, 1H), 8.10 (dd, J=8.4 Hz, J=1.7 Hz, 1H), 7.90 (d, J=8.4 Hz, 1H), 7.53-7.34 (m, 5H), 5.42 (s, 2H).

Step 2: To a stirred solution of benzyl 3-chloro-4-nitrobenzoate (1.485 g) in EtOAc (60 mL) under nitrogen was added SnCl$_2$.2H$_2$O (28.4 mmol) and the mixture was stirred at 80° C. overnight. After cooling to room temperature, the mixture was poured onto cold water, the pH was adjusted to pH=8 by addition of 10% aqueous sodium bicarbonate and mixture was extracted with EtOAc (2×). The combined organic phase was washed with brine, dried over anhydrous sodium sulfate and concentrated under reduced pressure. Purification by flash chromatography (10-20% EtOAc/hexanes eluent) provided benzyl 4-amino-3-chlorobenzoate (1.12 g, 86% yield over the 2 steps) as a white solid.

Step 3: To a solution of benzyl 4-amino-3-chlorobenzoate (310 mg, 1.18 mmol) in TFA (2.7 mL) under nitrogen at 0° C. was added sodium triacetoxyborohydride (503 mg, 2.37 mmol) portion wise. The mixture was stirred at 0° C. for 10 min before addition of 4-cyclohexylbenzaldehyde (237 mg, 1.26 mmol). The resulting reaction mixture was stirred at room temperature for 4 h, poured onto cold water and extracted with EtOAc (2×). The combined organic extracts were washed with water (3×), then with 10% aqueous sodium bicarbonate (2×), dried over anhydrous sodium sulfate and concentrated under reduced pressure. Purification by flash chromatography (3% EtOAc/hexanes eluent) provided benzyl 4-((4-cyclohexylbenzyl)amino)-3-chlorobenzoate (370 mg, 72% yield). The reaction was repeated using 424 mg of starting benzyl 4-amino-3-chlorobenzoate to provide additional benzyl 4-((4-cyclohexylbenzyl)amino)-3-chlorobenzoate (462 mg, 66% yield). 1H NMR (300 MHz, Chloroform-d) δ 8.01 (d, 2.0 Hz, 1H), 7.86 (dd, J=8.6, 2.0 Hz, 1H), 7.50-7.32 (m, 5H), 7.28 (d, J=8.3 Hz, 2H), 7.22 (d, J=8.3 Hz, 2H), 6.65 (d, J=8.6 Hz, 1H), 5.33 (s, 2H), 5.16 (t, J=5.5 Hz, 1H), 4.43 (d, J=5.5 Hz, 2H), 2.61-2.42 (m, 1H), 1.99-1.70 (m, 6H), 1.52-1.32 (m, 4H).

Step 4: To a stirred solution of benzyl 4-((4-cyclohexylbenzyl)amino)-3-chlorobenzoate (509 mg, 1.17 mmol) in THF (9 mL) under nitrogen at 0° C. was added trimethylaluminum (1.47 mL of 2M in toluene, 2.94 mmol) and the resulting mixture was allowed to warm to room temperature and stirred at this temperature for 15 min before addition of N-methyl-N-((perfluorophenyl)sulfonyl)-D-alaninoyl chloride (516 mg, 1.47 mmol) in THF (6.3 mL). The resulting mixture was heated at reflux for 4.5 h. After cooling to 5° C. the resultant mixture was poured onto cold 10% aqueous potassium bisulfate/sodium sulfate buffer and extracted with EtOAc (2×). The combined organic extracts were washed with brine, dried over anhydrous sodium sulfate and concentrated under reduced pressure. Purification by flash chromatography (10% EtOAc/hexanes eluent) provided benzyl (R)-3-chloro-4-(N-(4-cyclohexylbenzyl)-2-((2,3,4,5,6-pentafluoro-N-methylphenyl)sulfonamido)propanamido)benzoate (170.4 mg, 19% yield) as a colorless oil.

Step 5: To a stirred solution of benzyl (R)-3-chloro-4-(N-(4-cyclohexylbenzyl)-2-((2,3,4,5,6-pentafluoro-N-methylphenyl)sulfonamido)propanamido)benzoate (34.3 mg, 0.047 mmol) in DCE (2.5 mL) under nitrogen was added trimethyltin hydroxide (84.8 mg, 0.47 mmol) and the resulting mixture was heated at 85° C. overnight. The mixture was concentrated under reduced pressure and the residue was taken up in EtOAc. The organic solution was washed with 10% aqueous potassium bisulfate/sodium sulfate buffer, washed with brine, dried over anhydrous sodium sulfate and concentrated under reduced pressure. The resulting residue was purified by preparative TLC (run up with 40% EtOAc/hexane with 0.1-0.2% HOAc) and the product band eluted off the silica with 20% methanol in DCM to provide 23 mg of an oil. Hexanes was added and mixture re-concentrated to provide pure (R)-3-chloro-4-(N-(4-cyclohexylbenzyl)-2-((2,3,4,5,6-pentafluoro-N-methylphenyl)sulfonamido)propanamido)benzoic acid (20 mg) as a foam. HRMS (ESI) m/z 659.1455 [M+H]+.

Example 41

(R)-3-chloro-4-(N-(4-cyclohexylbenzyl)-2-((2,3,4,5,6-pentafluoro-N-methylphenyl)sulfonamido)propanamido)-N-hydroxybenzamide

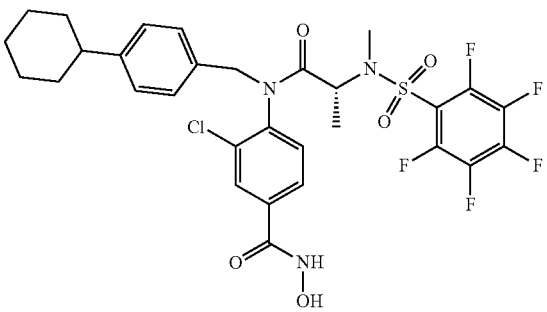 [SMILES: C[C@H](C(=O)N(Cc1ccc(C2CCCCC2)cc1)c1ccc(C(=O)NO)cc1Cl)N(C)S(=O)(=O)c1c(F)c(F)c(F)c(F)c1F]

Step 1: To a stirred solution of (R)-3-chloro-4-(N-(4-cyclohexylbenzyl)-2-((2,3,4,5,6-pentafluoro-N-methylphenyl)sulfonamido)propanamido)benzoic acid (85 mg, 0.129 mmol) in DCM (2.3 mL) was added 1 drop of DMF followed by oxalyl chloride (0.013 mL, 0.15 mmol). The resulting reaction solution was stirred at room temperature under nitrogen for 2 h and then concentrated under reduced pressure to afforded (R)-3-chloro-4-(N-(4-cyclohexylbenzyl)-2-((2,3,4,5,6-pentafluoro-N-methylphenyl)-sulfonamido)propanamido)benzoyl chloride, which was used as is.

Step 2: To a stirred solution of (R)-3-chloro-4-(N-(4-cyclohexylbenzyl)-2-((2,3,4,5,6-pentafluoro-N-methylphenyl)-sulfonamido)propanamido)benzoyl chloride (0.129 mmol) in THF (2.3 mL) under nitrogen at 0° C. was added a solution of O-benzylhydroxylamine hydrochloride (28.8 mg, 0.18 mmol) and TEA (0.05 mL, 0.365 mmol) in DMF (2.3 mL). The resultant reaction mixture was stirred at room temperature for 1.5 h and then quenched with 10% aqueous potassium bisulfate, poured onto water and extracted with ether (2×). The combined organic extracts were washed with water, then washed with brine, dried over anhydrous sodium sulfate and concentrated under reduced pressure. The resulting residue was purified by flash chromatography (20% EtOAc/hexanes) to provide (R)—N-(benzyloxy)-3-chloro-4-(N-(4-cyclohexylbenzyl)-2-((2,3,4,5,6-pentafluoro-N-methylphenyl)sulfonamido)propanamido)benzamide (49 mg, 50% yield). 1H NMR (300 MHz, Chloroform-d) δ 7.93 (s, 1H), 7.55-7.33 (m, 6H), 7.08 (d, J=8.0 Hz, 2H), 7.04-6.88 (m, 3H), 5.49 (d, J=14.3 Hz, 1H), 5.04 (s, 2H), 4.74-4.49 (m, 1H), 4.06 (d, J=14.3 Hz, 1H), 3.13 (s, 3H), 2.58-2.39 (m, 1H), 1.95-1.68 (m, 6H), 1.49-1.26 (m, 4H), 1.22 (d, J=7.1 Hz, 3H).

Step 3: To a stirred solution of (R)—N-(benzyloxy)-3-chloro-4-(N-(4-cyclohexylbenzyl)-2-((2,3,4,5,6-pentafluoro-N-methylphenyl)sulfonamido)propanamido)benzamide (45.8 mg, 0.06 mmol) in DCM (1.5 mL) under nitrogen at −15° C. was added boron tribromide (0.014 mL). The mixture was allowed to reach 0° C. and was stirred at this temperature for 3 h. Ice and saturated aqueous sodium bicarbonate were added and the resulting mixture was extracted with EtOAc (1×). The organic extract was washed with brine, dried over anhydrous sodium sulfate and concentrated under reduced pressure. Purification by preparative TLC (50% EtOAc/hexanes eluent) provided (R)-3-chloro-4-(N-(4-cyclohexylbenzyl)-2-((2,3,4,5,6-pentafluoro-N-methylphenyl)sulfonamido)propanamido)-N-hydroxybenzamide (17 mg, 42% yield) as a foam. HRMS (ESI) m/z 674.1532 [M+H]+.

Examples 42

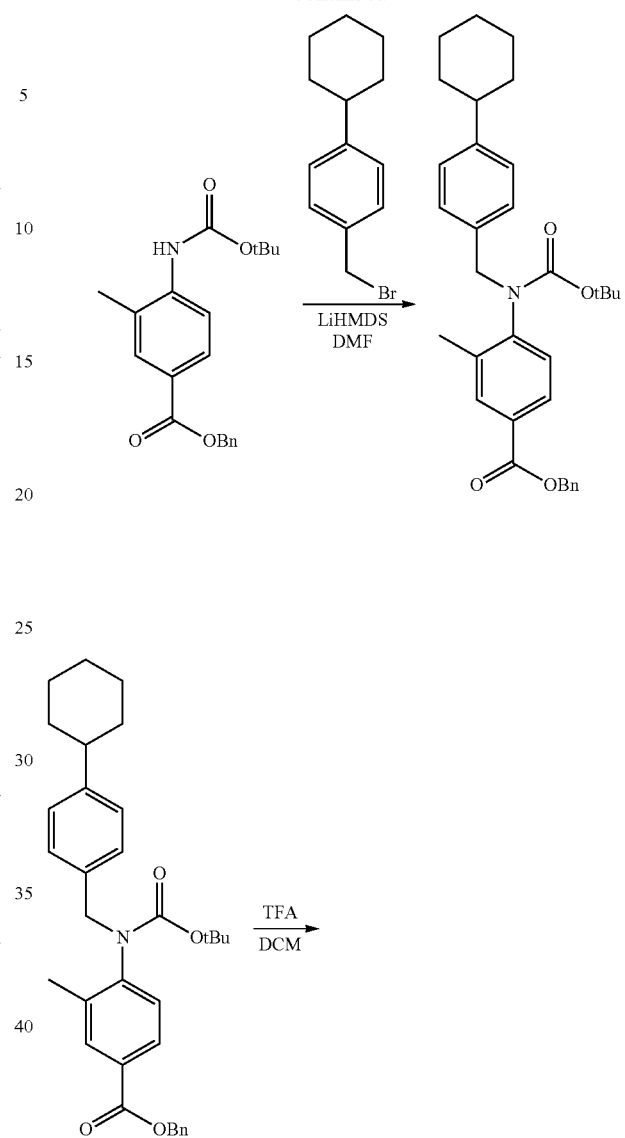

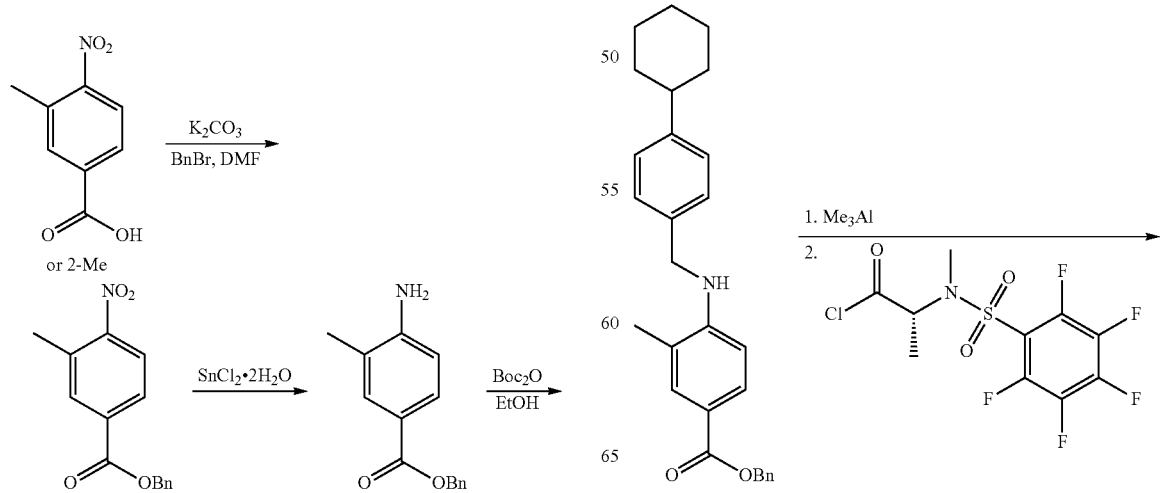

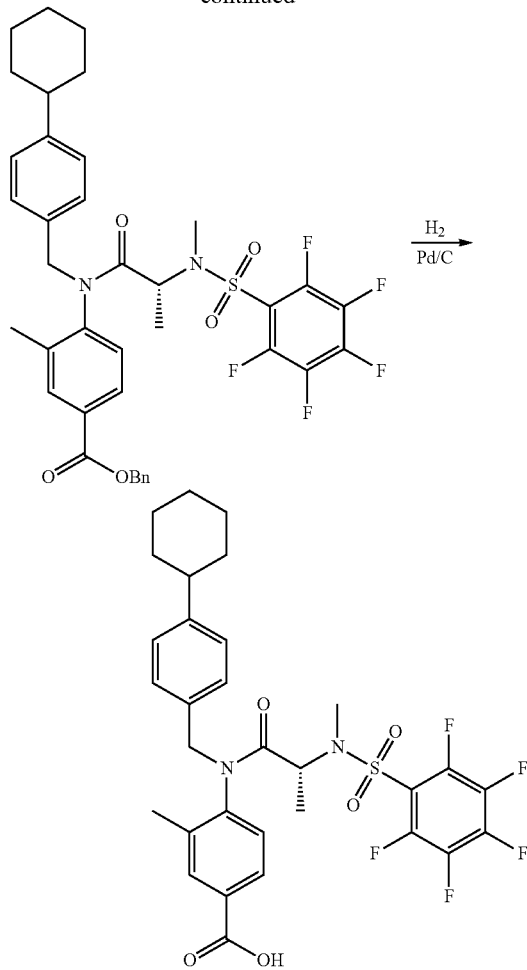

(R)-4-(N-(4-cyclohexylbenzyl)-2-((2,3,4,5,6-pentafluoro-N-methylphenyl)sulfonamido)propanamido)-3-methylbenzoic acid

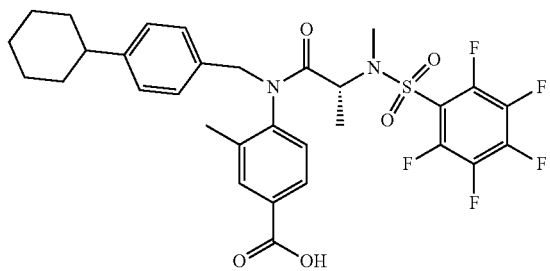 [SMILES: Cc1cc(C(=O)O)ccc1N(Cc1ccc(C2CCCCC2)cc1)C(=O)[C@@H](C)N(C)S(=O)(=O)c1c(F)c(F)c(F)c(F)c1F]

Step 1: To a solution of 3-methyl-4-nitrobenzoic acid (1.0 g, 5.52 mmol) in DMF (25 mL) under nitrogen was added potassium carbonate (0.836 g, 6.08 mmol). After 10 min benzyl bromide (0.63 mL, 5.24 mmol) was added and the resultant solution was stirred at room temperature for 3.5 h. The mixture was poured onto cold water and extracted with EtOAc (2×). The combined organic extract was washed with water (2×), and then washed with brine, dried over anhydrous sodium sulfate and concentrated in vacuo to provide crude product, benzyl 3-methyl-4-nitrobenzoate (1.64 g) as a yellow oil, which was used as is.

Step 2: To a stirred solution of benzyl 3-methyl-4-nitrobenzoate (1.64 g) in EtOAc (60 mL) under nitrogen was added $SnCl_2 \cdot 2H_2O$ (6.82 g) and the mixture was stirred at 80° C. overnight. After cooling to room temperature, the mixture was poured onto cold water, the pH was adjusted to pH=8 by addition of 10% aqueous sodium bicarbonate and mixture was extracted with EtOAc (2×). The combined organic phase was washed with brine, dried over anhydrous sodium sulfate and concentrated under reduced pressure to provide benzyl 4-amino-3-methylbenzoate (1.36 g, 100% yield over the 2 steps) as an oil. 1H NMR (300 MHz, Chloroform-d) δ 7.86-7.76 (m, 2H), 7.52-7.32 (m, 5H), 6.65 (d, J=9.0 Hz, 1H), 5.34 (s, 2H), 4.02 (br. s, 2H), 2.20 (s, 3H).

Step 3: To a stirred solution of benzyl 4-amino-3-methylbenzoate (419 mg, 1.74 mmol) in ethanol (4 mL) under nitrogen was added di-tert-butyl dicarbonate (1 mL, 4.35 mmol). The reaction mixture was heated at 50° C. for 3 days and then concentrated under reduced pressure. Hexanes was added and the resultant solid was filtered off and washed with hexanes to provide benzyl 4-((tert-butoxycarbonyl)amino)-3-methylbenzoate (483 mg, 82% yield) as a white solid. 1H NMR (300 MHz, Chloroform-d) δ 8.09 (d, J=8.6 Hz, 1H), 7.94 (dd, J=8.6, 2.1 Hz, 1H), 7.88 (d, J=2.1 Hz, 1H), 7.53-7.33 (m, 5H), 6.48 (s, 1H), 5.36 (s, 2H), 2.29 (s, 3H), 1.56 (s, 9H).

Step 4: To a stirred solution of benzyl 4-((tert-butoxycarbonyl)amino)-3-methylbenzoate (462 mg, 1.35 mmol) in DMF (4.6 mL) at 0° C. under nitrogen was added LiHMDS (1.63 mL of 1M in THF, 1.63 mmol). After stirring at 0° C. for 10 min, a solution of 1-(bromomethyl)-4-cyclohexylbenzene (514 mg, 1.98 mmol) was added in DMF (2.5 mL). The reaction was stirred at 0° C. for 1 h and then at room temperature for 1 h. The reaction mixture was quenched with saturated aqueous ammonium chloride, poured onto water and extracted with EtOAc (2×). The combined organic extracts were washed with water and then brine, dried over anhydrous sodium sulfate and concentrated under reduced pressure. Purification by flash chromatography (5-7.5% EtOAc/hexanes gradient) provided benzyl 4-((tert-butoxycarbonyl)(4-cyclohexylbenzyl)amino)-3-methylbenzoate (628.5 mg, 91% yield). 1H NMR (300 MHz, Chloroform-d) δ 7.89 (s, 1H), 7.81 (d, J=8.2 Hz, 1H), 7.56-7.33 (m, 5H), 7.10 (s, 4H), 6.99-6.85 (m, 1H), 5.36 (s, 2H), 4.82 (d, J=14.7 Hz, 1H), 4.53 (d, J=14.7 Hz, 1H), 2.58-2.39 (m, 1H), 2.04 (s, 3H), 1.93-1.69 (m, 5H), 1.52-1.07 (m, 5H).

Step 5: To a stirred solution of benzyl 4-((tert-butoxycarbonyl)(4-cyclohexylbenzyl)amino)-3-methylbenzoate (621.7 mg, 1.21 mmol) under nitrogen in DCM (7.7 mL) was added TFA (2.5 mL) and the resultant mixture was stirred at room temperature for 1 h. The mixture was concentrated under reduced pressure and the resulting residue was dissolved in EtOAc, poured onto aqueous sodium bicarbonate and extracted with EtOAc (2×). The combined organic extracts were washed with brine, dried over anhydrous sodium sulfate and concentrated in vacuo to provide benzyl 4-((4-cyclohexylbenzyl)amino)-3-methylbenzoate (534 mg) as a pale yellow oil. 1H NMR (300 MHz, Chloroform-d) δ 7.88 (dd, J=8.5, 2.1 Hz, 1H), 7.82 (d, J=2.1 Hz, 1H), 7.52-7.33 (m, 5H), 7.30 (d, J=8.2 Hz, 2H), 7.22 (d, J=8.2 Hz, 2H), 6.62 (d, J=8.5 Hz, 1H), 5.33 (s, 2H), 4.40 (s, 2H), 4.30 (br. s, 1H), 2.63-2.43 (m, 1H), 2.19 (s, 3H), 1.97-1.70 (m, 6H), 1.53-1.31 (m, 4H).

Step 6: To a stirred solution of benzyl 4-((4-cyclohexylbenzyl)amino)-3-methylbenzoate (257 mg, 0.622 mmol) in THF (5.03 mL) under nitrogen at 0° C. was added trimethylaluminum (0.776 mL of 2M in toluene, 1.55 mmol) and the resulting mixture was allowed to warm to room temperature and stirred at this temperature for 15 min before addition of N-methyl-N-((perfluorophenyl)sulfonyl)-D-alaninoyl chloride (263 mg, 0.75 mmol) in THF (3.5 mL). The resulting mixture was heated at reflux for 4 h. After cooling to 5° C. the resultant mixture was poured onto cold 10% aqueous potassium bisulfate/sodium sulfate buffer and extracted with EtOAc (2×). The combined organic extracts were washed with brine, dried over anhydrous sodium sulfate and concentrated under reduced pressure. Purification by flash chromatography (10% EtOAc/hexanes then 20% EtOAc/hexanes eluent) provided benzyl (R)-4-(N-(4-cyclohexylbenzyl)-2-((2,3,4,5,6-pentafluoro-N-methylphenyl)sulfonamido)propanamido)-3-methylbenzoate (310 mg, 68% yield).

Step 7: To a stirred solution of benzyl (R)-4-(N-(4-cyclohexylbenzyl)-2-((2,3,4,5,6-pentafluoro-N-methylphenyl)sulfonamido)propanamido)-3-methylbenzoate (307 mg, 0.422 mmol) in methanol (5 mL) and THF (5 mL) was added 10% Pd/C (38.3 mg) and the resulting suspension was stirred at room temperature under a hydrogen atmosphere for 5 h. The reaction mixture was filtered through Celite® and washed with EtOAc. The combined filtrate and washes were concentrated under reduced pressure to provide crude product as an oil (281 mg). Purification of a 50 mg sample by preparative TLC (6:4 hexanes:EtOAc with 0.1% HOAc) provided (R)-4-(N-(4-cyclohexylbenzyl)-2-((2,3,4,5,6-pentafluoro-N-methylphenyl)sulfonamido)propanamido)-3-methylbenzoic acid as a foam (45 mg). HRMS (ESI+) m/z 639.2027 [M+H]+.

Example 43

(R)-4-(N-(4-cyclohexylbenzyl)-2-((2,3,4,5,6-pentafluoro-N-methylphenyl)sulfonamido)propanamido)-2-methylbenzoic acid

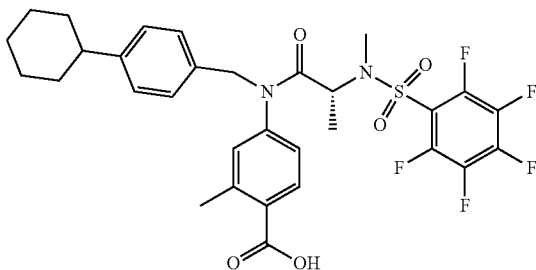 [SMILES: Cc1cc(N(Cc2ccc(C3CCCCC3)cc2)C(=O)[C@@H](C)N(C)S(=O)(=O)c2c(F)c(F)c(F)c(F)c2F)ccc1C(=O)O]

Preparation by a similar procedure to example 37, except substituting 2-methyl-4-nitrobenzoic acid for 3-fluoro-4-nitrobenzoic acid in step 1 afforded (R)-4-(N-(4-cyclohexylbenzyl)-2-((2,3,4,5,6-pentafluoro-N-methylphenyl)sulfonamido)propanamido)-2-methylbenzoic acid. HRMS (ESI+) m/z 639.1980 [M+H]+.

Example 44

(R)-4-(N-(4-cyclohexylbenzyl)-2-((2,3,4,5,6-pentafluoro-N-methylphenyl)sulfonamido)propanamido)-2-fluorobenzoic acid

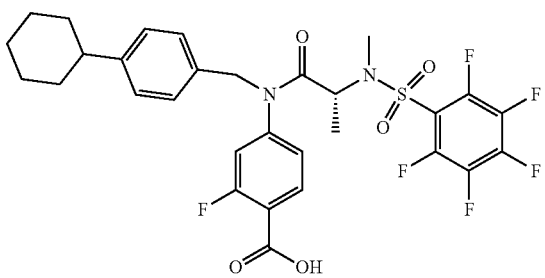

Preparation by a similar procedure to example 37, except substituting 2-fluoro-4-nitrobenzoic acid for 3-fluoro-4-nitrobenzoic acid in step 1 afforded (R)-4-(N-(4-cyclohexylbenzyl)-2-((2,3,4,5,6-pentafluoro-N-methylphenyl)sulfonamido)propanamido)-2-fluorobenzoic acid. MS (ESI+) m/z 643.1 [M+H]+.

Example 45

(R)-2-chloro-4-(N-(4-cyclohexylbenzyl)-2-((2,3,4,5,6-pentafluoro-N-methylphenyl)sulfonamido)propanamido)benzoic acid

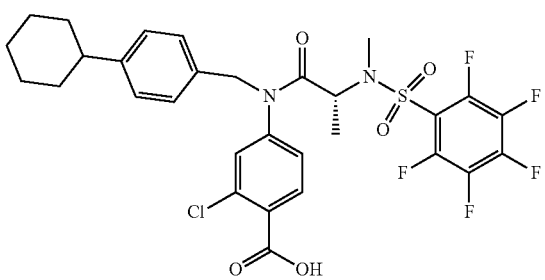 [SMILES: C[C@H](C(=O)N(Cc1ccc(C2CCCCC2)cc1)c1ccc(C(=O)O)c(Cl)c1)N(C)S(=O)(=O)c1c(F)c(F)c(F)c(F)c1F]

Preparation by a similar procedure to example 40, except substituting except substituting 2-chloro-4-nitrobenzoic acid for 3-chloro-4-nitrobenzoic acid in step 1 afforded (R)-2-chloro-4-(N-(4-cyclohexylbenzyl)-2-((2,3,4,5,6-pentafluoro-N-methylphenyl)sulfonamido)propanamido)benzoic acid. HRMS (ESI+) m/z 659.1408 [M+H]+.

Example 46

(R)-2-chloro-4-(N-(4-cyclohexylbenzyl)-1-((perfluorophenyl)sulfonyl)pyrrolidine-2-carboxamido)benzoic acid

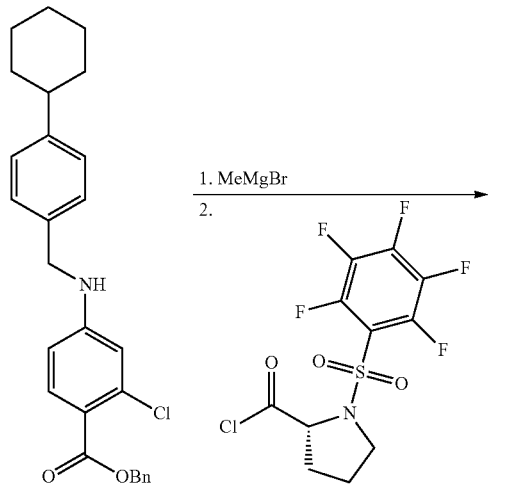

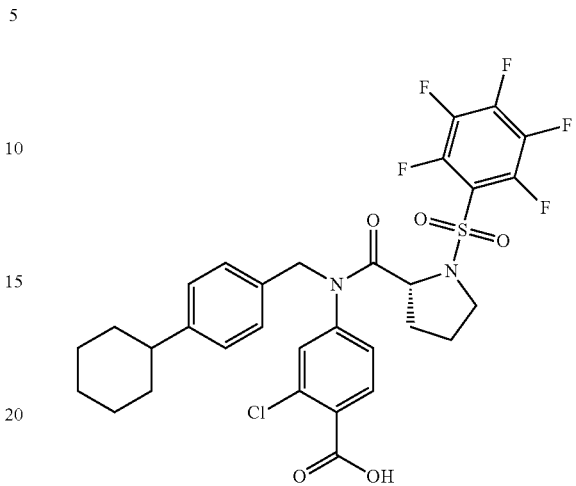

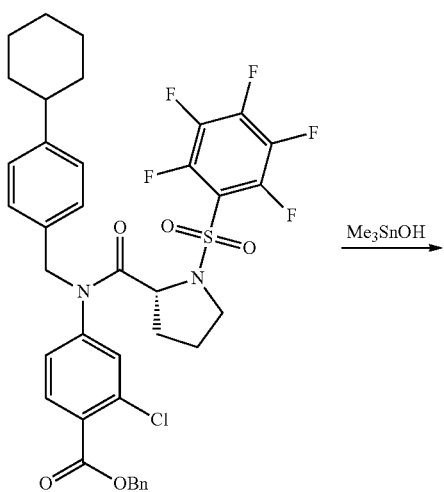

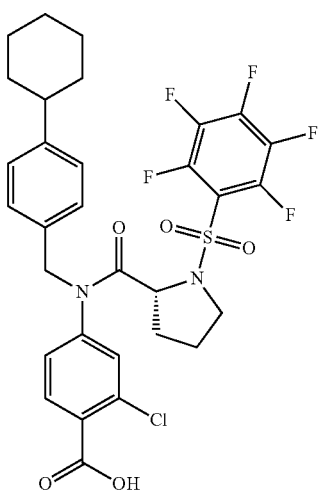

Step 1: To a stirred solution of benzyl 2-chloro-4-((4-cyclohexylbenzyl)amino)benzoate (164 mg, 0.378 mmol) in THF (3 mL) at 0° C. under nitrogen was added a solution of methylmagnesium bromide (0.67 mL of 1.4M in THF, 0.945 mmol) and the mixture was stirred a 0° C. for 10 min before addition of ((perfluorophenyl)sulfonyl)-D-prolinoyl chloride (206 mg, 0.567 mmol). The reaction mixture was allowed to warm to room temperature and stirred at this temperature for 7.5 h. To the reaction mixture was added a cold solution of saturated aqueous ammonium chloride followed by water and the resultant mixture was extracted with EtOAc (2×). The combined organic extracts were washed with brine, dried over anhydrous sodium sulfate and concentrated under reduced pressure. Purification by flash chromatography (20% EtOAc/hexanes eluent) provided benzyl (R)-2-chloro-4-(N-(4-cyclohexylbenzyl)-1-((perfluorophenyl)sulfonyl)pyrrolidine-2-carboxamido)benzoate (238 mg, 83% yield). 1H NMR (300 MHz, Chloroform-d) δ 7.85 (d, J=8.2 Hz, 1H), 7.51-7.35 (m, 5H), 7.17 (s, 1H), 7.12 (d, J=7.8 Hz, 2H), 7.05 (d, J=8.2 Hz, 1H), 6.98 (d, J=7.8 Hz, 2H), 5.40 (s, 2H), 4.84 (d, J=14.3 Hz, 1H), 4.66 (d, J=14.3 Hz, 1H), 4.43 (t, J=6.1 Hz, 1H), 3.85-3.59 (m, 2H), 2.58-2.40 (m, 1H), 2.00-1.65 (m, 8H), 1.48-1.32 (m, 6H).

Step 2: To a stirred solution of benzyl (R)-2-chloro-4-(N-(4-cyclohexylbenzyl)-1-((perfluorophenyl)sulfonyl)pyrrolidine-2-carboxamido)benzoate (227.7 mg, 0.299 mmol) in DCE (8 mL) under nitrogen was added trimethyltin hydroxide (540 mg, 2.99 mmol) and the resulting mixture was heated at 85° C. for 6.5 h. The mixture was concentrated under reduced pressure and the residue was taken up in EtOAc. The organic solution was washed with 10% aqueous potassium bisulfate/sodium sulfate buffer, washed with brine, dried over anhydrous sodium sulfate and concentrated under reduced pressure. A small portion was purified by preparative TLC (run up with 50% EtOAc/hexane with 0.1% HOAc) to provide pure (R)-2-chloro-4-(N-(4-cyclohexylbenzyl)-1-((perfluorophenyl)sulfonyl)-pyrrolidine-2-carboxamido)benzoic acid. HR MS (ESI) m/z 671.1404 [M+H]+.

Example 47

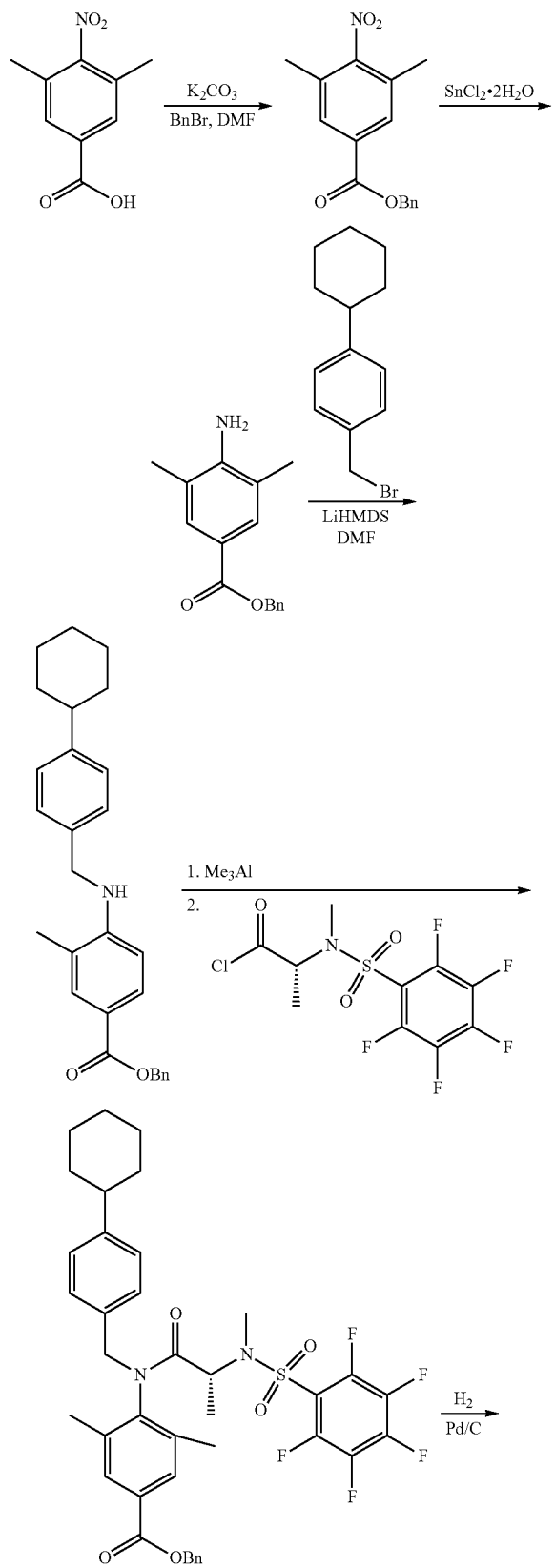

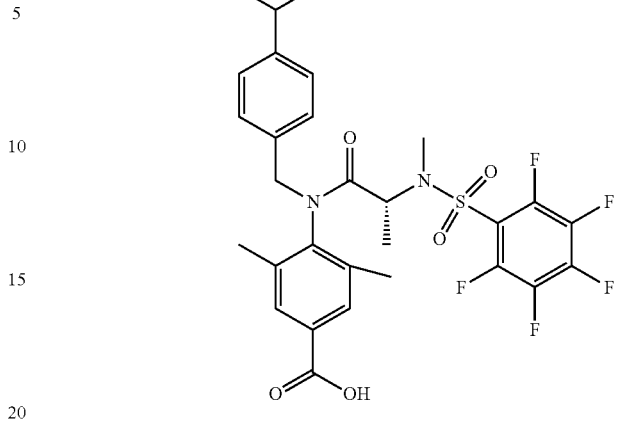

(R)-4-(N-(4-cyclohexylbenzyl)-2-((2,3,4,5,6-pentafluoro-N-methylphenyl)sulfonamido)propanamido)-3,5-dimethylbenzoic acid

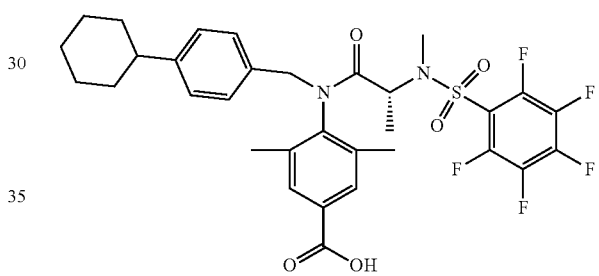

Step 1: To a solution of 3,5-dimethyl-4-nitrobenzoic acid (500 mg, 2.56 mmol) in DMF (12.5 mL) under nitrogen was added potassium carbonate (0.388 g, 2.82 mmol). After 10 min benzyl bromide (0.29 mL, 2.43 mmol) was added and the resultant solution was stirred at room temperature for 3.5 h. The mixture was poured onto cold water and extracted with EtOAc (2×). The combined organic extract was washed with water (2×), and then washed with brine, dried over anhydrous sodium sulfate and concentrated in vacuo to provide crude product, benzyl 3,5-dimethyl-4-nitrobenzoate (679 mg, 93% yield) as an oil, which was used as is. 1H NMR (300 MHz, Chloroform-d) δ 7.86 (s, 2H), 7.56-7.33 (m, 5H), 5.39 (s, 2H), 2.36 (s, 6H).

Step 2: To a stirred solution of benzyl 3,5-dimethyl-4-nitrobenzoate (679 mg, 2.38 mmol) in EtOAc (25.2 mL) under nitrogen was added SnCl$_2$·2H$_2$O (2.68 g) and the mixture was stirred at 80° C. overnight. After cooling to room temperature, the mixture was poured onto cold water, the pH was adjusted to pH=8 by addition of 10% aqueous sodium bicarbonate and mixture was extracted with EtOAc (2×). The combined organic phase was washed with brine, dried over anhydrous sodium sulfate and concentrated under reduced pressure to provide benzyl 4-amino-3,5-dimethylbenzoate (579 mg, 88% yield over the 2 steps). 1H NMR (300 MHz, Chloroform-d) δ 7.72 (s, 2H), 7.53-7.31 (m, 5H), 5.34 (s, 2H), 2.25 (s, 6H).

Step 3: To a stirred solution of benzyl 4-amino-3,5-dimethylbenzoate (212.5 mg, 0.83 mmol) in THF (6 mL)

was added at 0° C. under nitrogen, a solution of LiHMDS (1.0 mL of 1M in THF, 1.0 mmol) and the resulting solution was stirred at 0° C. for 15 min before addition of 1-(bromomethyl)-4-cyclohexylbenzene (210.8 mg, 0.83 mmol) in THF (4 mL). The reaction mixture was allowed to warm to room temperature and stirred at this temperature overnight. The reaction mixture was poured onto saturated aqueous ammonium chloride and extracted with EtOAc (2×). The combined organic extracts were washed with brine, dried over anhydrous sodium sulfate and concentrated under reduced pressure. Purification by flash chromatography (5-10% EtOAc/hexanes eluent) provided benzyl 4-((4-cyclohexylbenzyl)amino)-3,5-dimethylbenzoate (212 mg, 60% yield) as a colorless oil. 1H NMR (300 MHz, Chloroform-d) δ 7.72 (s, 2H), 7.51-7.33 (m, 5H), 7.24 (d, J=8.0 Hz, 2H), 7.16 (d, J=8.0 Hz, 2H), 5.35 (s, 2H), 4.34 (s, 2H), 2.59-2.42 (m, 1H), 2.32 (s, 6H), 2.00-1.65 (m, 6H), 1.49-1.25 (m, 4H).

Step 4: To a stirred solution of benzyl 4-((4-cyclohexylbenzyl)amino)-3,5-dimethylbenzoate (197 mg, 0.46 mmol) in THF (3.7 mL) under nitrogen at 0° C. was added trimethylaluminum (0.586 mL of 2M in toluene, 1.15 mmol) and the resulting mixture was allowed to warm to room temperature and stirred at this temperature for 15 min before addition of N-methyl-N-((perfluorophenyl)sulfonyl)-D-alaninoyl chloride (202.6 mg, 0.576 mmol) in THF (2.5 mL). The resulting mixture was heated at 80° C. for 3 h. After cooling to 5° C. the resultant mixture was poured onto cold 10% aqueous potassium bisulfate/sodium sulfate buffer and extracted with EtOAc (2×). The combined organic extracts were washed with brine, dried over anhydrous sodium sulfate and concentrated under reduced pressure. Purification by flash chromatography (10% EtOAc/hexanes then 20% EtOAc/hexanes eluent) provided benzyl (R)-4-(N-(4-cyclohexylbenzyl)-2-((2,3,4,5,6-pentafluoro-N-methylphenyl)sulfonamido)propanamido)-3,5-dimethylbenzoate (226 mg, 66% yield) as a white foam. $^1$H NMR (300 MHz, Chloroform-d) δ 7.81 (s, 2H), 7.55-7.37 (m, 5H), 7.06 (d, J=8.1 Hz, 2H), 6.96 (d, J=8.1 Hz, 2H), 5.38 (s, 2H), 4.80 (d, J=13.5 Hz, 1H), 4.53 (d, J=13.5 Hz, 1H), 4.46 (q, J=7.0 Hz, 1H), 3.09 (s, 3H), 2.55-2.37 (m, 1H), 1.96 (s, 3H), 1.91 (s, 3H), 1.88-1.69 (m, 5H), 1.48-1.21 (m, 5H), 1.09 (d, J=7.0 Hz, 3H).

Step 5: To a stirred solution of benzyl (R)-4-(N-(4-cyclohexylbenzyl)-2-((2,3,4,5,6-pentafluoro-N-methylphenyl)sulfonamido)propanamido)-3,5-dimethylbenzoate (216 mg, 0.29 mmol) in methanol (4 mL) and THF (4 mL) was added 10% Pd/C (26.4 mg) and the resulting suspension was stirred at room temperature under a hydrogen atmosphere for 5 h. The reaction mixture was filtered through Celite® and washed with EtOAc. The combined filtrate and washes were concentrated under reduced pressure to provide crude product as an oil (281 mg). Purification of a 50 mg sample by preparative TLC (6:4 hexanes:EtOAc with 0.1% HOAc) provided (R)-4-(N-(4-cyclohexylbenzyl)-2-((2,3,4,5,6-pentafluoro-N-methylphenyl)sulfonamido)propanamido)-3,5-dimethylbenzoic acid. HRMS (ESI+) m/z 653.2095 [M+H]+.

Example 48

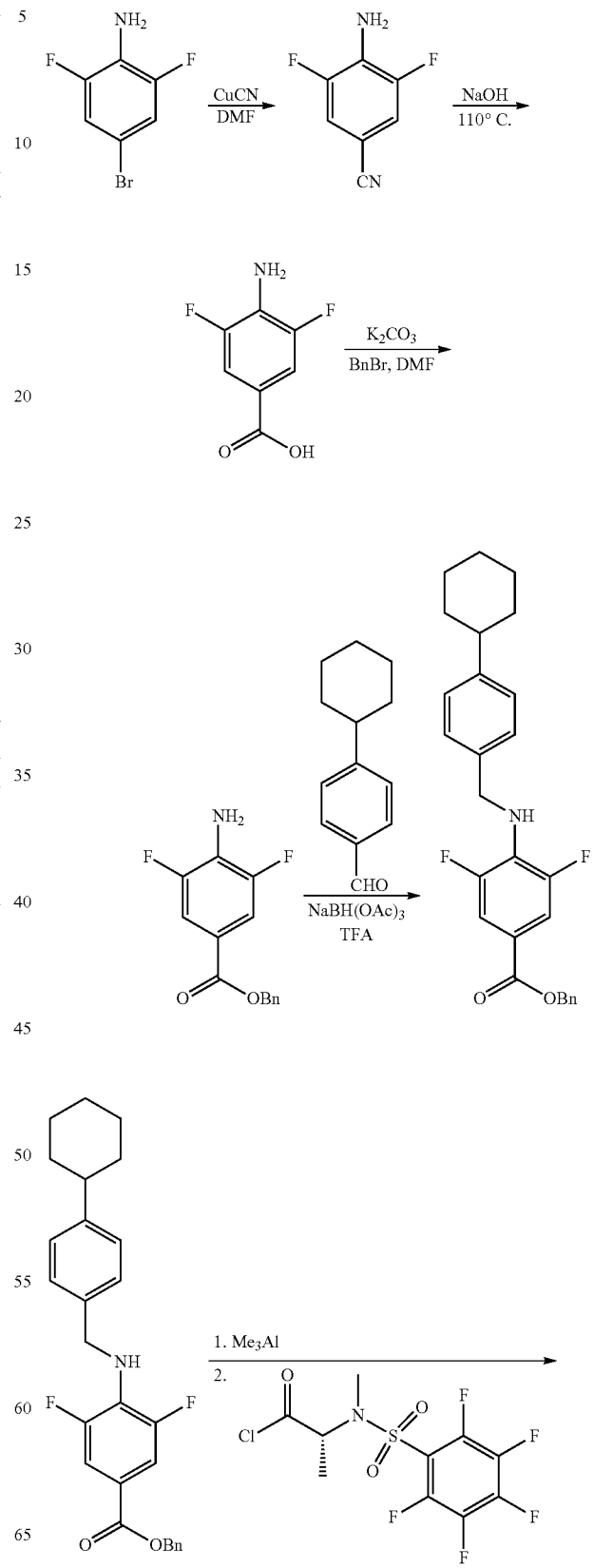

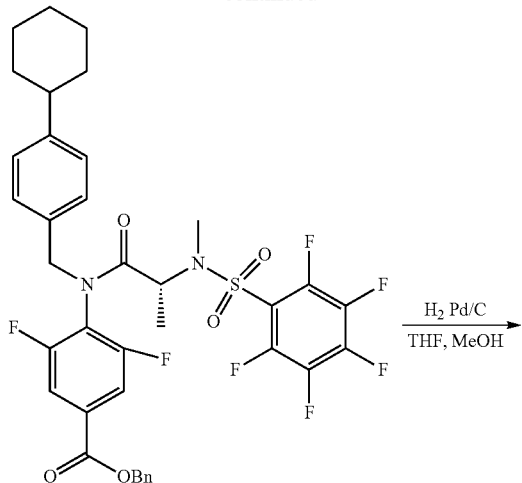

(R)-4-(N-(4-cyclohexylbenzyl)-2-((2,3,4,5,6-pentafluoro-N-methylphenyl)sulfonamido)propanamido)-3,5-difluorobenzoic acid

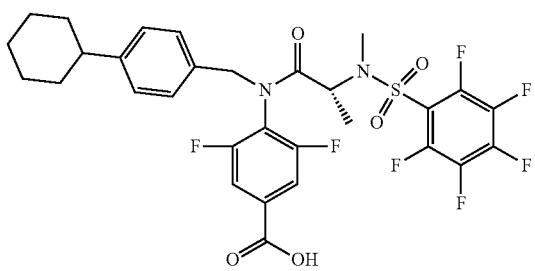 [SMILES: C[C@H](C(=O)N(Cc1ccc(C2CCCCC2)cc1)c1c(F)cc(C(=O)O)cc1F)N(C)S(=O)(=O)c1c(F)c(F)c(F)c(F)c1F]

Step 1: To 4-bromo-2,6-difluoroaniline (1.0 g, 4.81 mmol) and copper (I) cyanide (1.28 g, 14.3 mmol) was added DMF (10 mL) under nitrogen and the resulting mixture was heated at 160° C. for 18 h. After 18 h, the mixture was cooled, poured onto a 12% aqueous ammonia solution and extracted with EtOAc (2×). The combined organic extract was washed with water. The organic phase was combined with a little water and was filtered through celite to remove suspended solids. The organic phase was then separated from the water, then washed with brine, dried over anhydrous sodium sulfate and concentrated under reduced pressure. Purification by flash chromatography (12% EtOAc/hexanes eluent) provided 4-amino-3,5-difluorobenzonitrile as a white solid. 1H NMR (300 MHz, Chloroform-d) δ 7.19-7.14 (m, 2H), 4.29 (br. s, 2H).

Step 2: 4-amino-3,5-difluorobenzonitrile (354.3 mg, 2.3 mmol) was suspended in 1M aqueous sodium hydroxide (12 mL) and the resulting suspension was heated at 110° C. for 16 h. After cooling, the mixture was washed with ether. The aqueous phase was acidified to pH=2 with 10% KHSO₄/Na₂SO₄ buffer and extracted with EtOAc (2×). The combined EtOAc extracts were washed with water, and then brine, dried over anhydrous sodium sulfate and concentrated in vacuo to provide 4-amino-3,5-difluorobenzoic acid (335 mg, 84% yield) as a yellow solid. 1H NMR (300 MHz, Chloroform-d) δ 7.66-7.58 (m, 2H).

Step 3: To a stirred solution of 4-amino-3,5-difluorobenzoic acid (332.2 mg, 1.92 mmol) in DMF (9.7 mL) was added potassium carbonate (0.29 g, 2.11 mmol) under nitrogen. Stirring continued at room temperature for 10 min before addition of benzyl bromide (0.22 mL, 1.82 mmol). The resulting reaction mixture was stirred at room temperature for 3 h, then poured onto cold water and extracted with EtOAc (2×). The combined organic extracts were washed with water (2×), then brine, dried over anhydrous sodium sulfate and concentrated in vacuo to afford benzyl 4-amino-3,5-difluorobenzoate (423 mg, 84% yield) as a pink solid. 1H NMR (300 MHz, Chloroform-d) δ 7.62-7.55 (m, 2H), 7.49-7.32 (m, 5H), 5.34 (s, 2H), 4.16 (br. s, 2H).

Step 4: To a solution of benzyl 4-amino-3,5-difluorobenzoate (199 mg, 0.756 mmol) in TFA (1.72 mL) under nitrogen at 0° C. was added sodium triacetoxyborohydride (321 mg, 1.51 mmol) portion wise. The mixture was stirred at 0° C. for 10 min. before addition of 4-cyclohexylbenzaldehyde (151 mg, 0.803 mmol). The resulting reaction mixture was stirred at room temperature for 4 h, poured onto cold water and extracted with EtOAc (2×). The combined organic extracts were washed with water (3×), then with 10% aqueous sodium bicarbonate (2×), dried over anhydrous sodium sulfate and concentrated under reduced pressure. Purification by flash chromatography (3-6% EtOAc/hexanes) provided benzyl 4-((4-cyclohexylbenzyl)amino)-3,5-difluorobenzoate (251 mg, 92% yield) as a pale yellow oil. 1H NMR (300 MHz, Chloroform-d) δ 7.59-7.50 (m, 2H), 7.48-7.31 (m, 5H), 7.27 (d, J=8.1 Hz, 2H), 7.20 (d, J=8.1 Hz, 2H), 5.33 (s, 2H), 4.59 (s, 2H), 2.65-2.41 (m, 1H), 2.00-1.59 (m, 6H), 1.54-1.12 (m, 6H).

Step 5: To a stirred solution of benzyl 4-((4-cyclohexylbenzyl)amino)-3,5-difluorobenzoate (245 mg, 0.682 mmol) in THF (5.25 mL) under nitrogen at 0° C. was added a solution of trimethylaluminum (0.854 mL of 2M in toluene, 1.71 mmol) and the mixture was warmed to room temperature and stirred at this temperature for 15 min. To the resulting solution was added a solution of N-methyl-N-((pentafluorophenyl)sulfonyl)-D-alaninoyl chloride (311.9 mg, 0.885 mmol) in THF (3.7 mL). The reaction mixture was stirred at 80° C. for 5 h, cooled and then poured onto 10% KHSO₄/Na₂SO₄ buffer and ice and then extracted with EtOAc (2×). The combined organic layers were washed with water and then brine, dried over anhydrous sodium sulfate, and concentrated under reduced pressure. Purification by flash chromatography (4-6% EtOAc/hexane) provided benzyl (R)-4-(N-(4-cyclohexylbenzyl)-2-((2,3,4,5,6-pentafluoro-N-methylphenyl)sulfonamido)propanamido)-3,5-difluorobenzoate (125 mg, 24% yield). HRMS (ESI+) m/z 751.2072 [M+H]+.

Step 6: To a stirred solution of benzyl (R)-4-(N-(4-cyclohexylbenzyl)-2-((2,3,4,5,6-pentafluoro-N-methylphenyl)sulfonamido)propanamido)-3,5-difluorobenzoate (119 mg, 0.159 mmol) in methanol (2 mL) and THF (2 mL) was added 10% Pd/C (14.4 mg) and the resulting suspension was stirred at room temperature under a hydrogen atmosphere for 5 h. The reaction mixture was filtered through Celite® and washed with EtOAc. The combined filtrate and washes were concentrated and the resulting residue was purified by preparative TLC (1:1 hexane:EtOAc with 1% AcOH) to provide (R)-4-(N-(4-cyclohexylbenzyl)-2-((2,3,4,5,6-pentafluoro-N-methylphenyl)sulfonamido)propanamido)-3,5-difluorobenzoic acid as a light green foam (92.5 mg). HRMS (ESI+) m/z 661.1610 [M+H]+.

Example 49

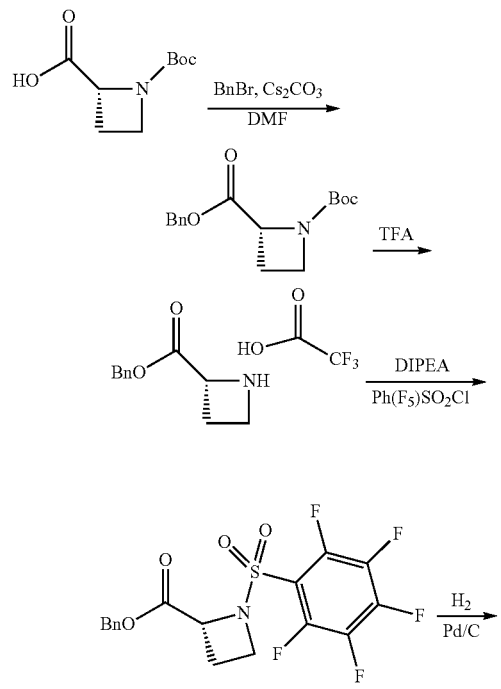

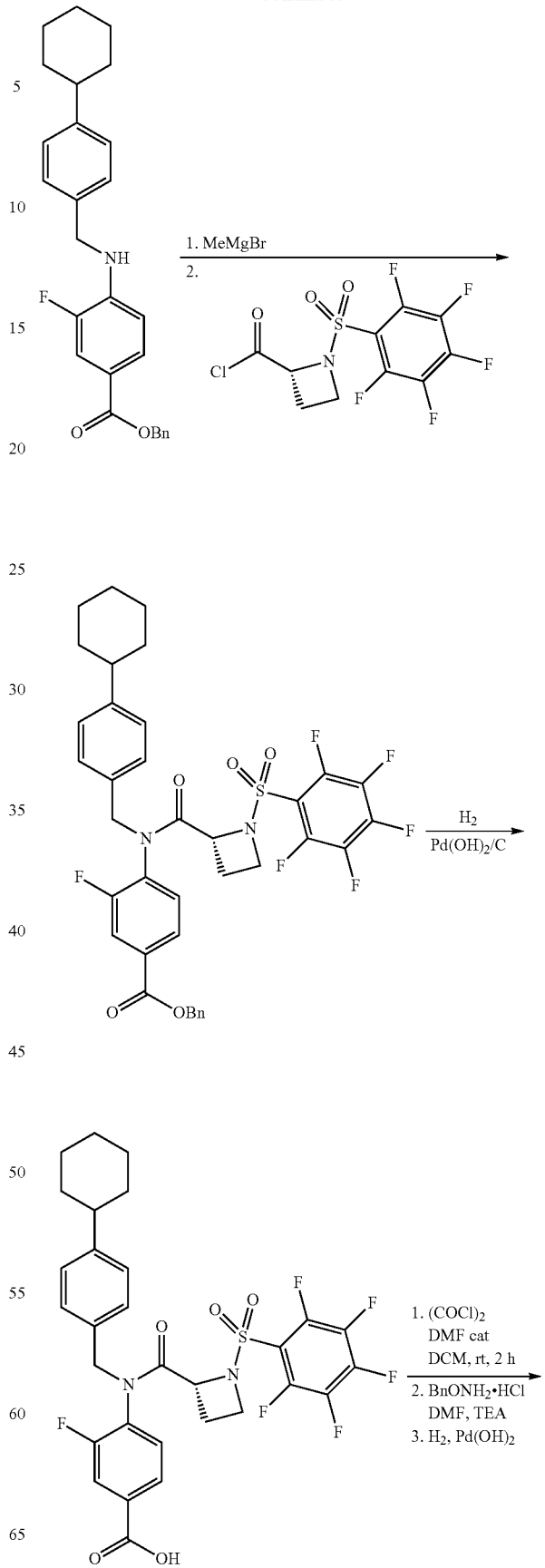

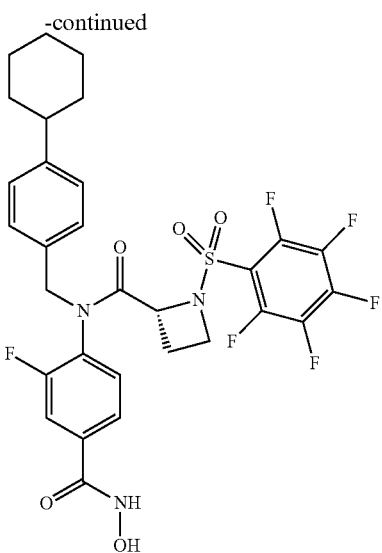

(R)-4-(N-(4-Cyclohexylbenzyl)-1-((perfluorophenyl)sulfonyl)azetidine-2-carboxamido)-3-fluorobenzoic acid

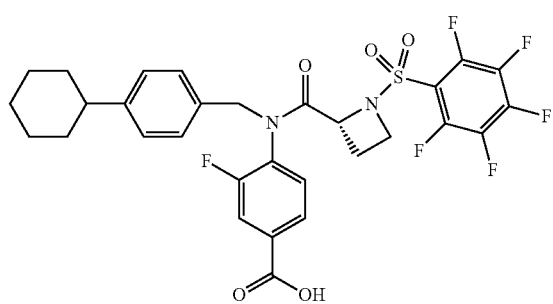 [SMILES: O=C(O)c1ccc(N(Cc2ccc(C3CCCCC3)cc2)C(=O)[C@H]2CCN2S(=O)(=O)c2c(F)c(F)c(F)c(F)c2F)c(F)c1]

Step 1: To a stirred solution of (R)-1-(tert-butoxycarbonyl)azetidine-2-carboxylic acid (900 mg, 4.45 mmol) in DMF (10 mL) under nitrogen was added cesium carbonate (2.2 g, 6.7 mmol) and stirring was continued at room temperature for 30 min. To the reaction mixture was added benzyl bromide (0.8 mL, 6.7 mmol) and the resulting milky-white mixture was allowed to stir at room temperature overnight. The mixture was poured onto water and extracted with ether (3×). The combined ethereal extracts were washed with water, then washed with brine, dried over anhydrous sodium sulfate and concentrated under reduced pressure. Flash chromatography (hexanes, then 30% EtOAc/hexanes eluent) provided 2-benzyl 1-(tert-butyl) (R)-azetidine-1,2-dicarboxylate (1.26 g, 97% yield) as a colorless liquid. 1H NMR (300 MHz, Chloroform-d) δ 7.44-7.32 (m, 5H), 5.23 (s, 2H), 4.67 (dd, J=9.2, 5.5 Hz, 1H), 4.06 (ddd, J=8.9, 8.0, 6.2 Hz, 1H), 3.91 (ddd, J=8.9, 8.0, 5.5 Hz, 1H), 2.52 (dtd, J=11.2, 9.2, 6.2 Hz, 1H), 2.18 (ddt, J=11.2, 8.9, 5.5 Hz, 1H), 1.40 (s, 9H).

Step 2: To a stirred solution of 2-benzyl 1-(tert-butyl) (R)-azetidine-1,2-dicarboxylate (1.25 g, 4.30 mmol) in DCM (10 mL) at 0° C. under nitrogen was added TFA (2 mL) and the resultant solution was stirred at 0° C. for 30 min and allowed to warm to room temperature and was stirred at this temperature for 3 h before concentration under reduced pressure. The resulting residue was dissolved in toluene and concentrated in vacuo to provide benzyl (R)-azetidine-2-carboxylate 2,2,2-trifluoroacetate (1.86 g) which was used as is for step 3. 1H NMR (300 MHz, Chloroform-d) δ 10.48 (br. s, 1H), 7.46-7.31 (m, 5H), 5.83 (br.s, 3H), 5.35-5.19 (m, 2H), 5.13 (dd, J=10.2, 7.7 Hz, 1H), 4.26 (td, J=9.8, 7.7 Hz, 1H), 4.10 (td, J=10.2, 665 Hz, 1H), 2.95 (dtd, J=12.4, 9.7, 6.6 Hz, 1H), 2.65 (ddt, J=12.4, 9.8, 7.6 Hz, 1H).

Step 3: To a stirred solution of benzyl (R)-azetidine-2-carboxylate 2,2,2-trifluoroacetate (4.3 mmol) in DCM (50 mL) at 0° C. under nitrogen was added DIPEA (2.2 mL, 12.9 mmol) followed by pentafluorobenzenesulfonyl chloride (0.83 mL, 5.6 mmol) and the resulting solution was allowed to warm to room temperature and was stirred at this temperature for 3 h. The crude reaction mixture was poured onto water and extracted with DCM (3×). The combined organic layers were dried over anhydrous sodium sulfate, concentrated under reduced pressure and the resultant residue purified by flash chromatography (10-15% EtOAc/hexanes eluent) to provide benzyl (R)-1-((perfluorophenyl)sulfonyl)azetidine-2-carboxylate (1.44 g, 80% yield) as a white solid. MS (ESI) m/z 444.0 [M+Na]+. 1H NMR (300 MHz, Chloroform-d) δ 7.42-7.31 (m, 3H), 7.27-7.18 (m, 2H), 5.21-5.00 (m, 3H), 4.36 (dt, J=9.4, 7.4 Hz, 1H), 4.05 (td, J=8.0, 4.9 Hz, 1H), 2.65 (dtd, J=11.4, 9.4, 4.9 Hz, 1H), 2.46 (ddt, J=11.5, 9.1, 7.4 Hz, 1H).

Step 4: To a stirred solution of benzyl (R)-1-((perfluorophenyl)sulfonyl)azetidine-2-carboxylate (1.43 g, 3.4 mmol) in EtOAc (15 mL) and methanol (15 mL) under nitrogen was added 20% Pd(OH)$_2$ on carbon (160 mg) and the resultant mixture was placed under a hydrogen atmosphere and stirred at room temperature for 1.5 h. The reaction mixture was filtered through Celite® and washed with EtOAc. The combined filtrate and washes were concentrated to afford (R)-1-((perfluorophenyl)sulfonyl)azetidine-2-carboxylic acid (1.18 g, 100% yield) as a white solid. 1H NMR (300 MHz, Chloroform-d) δ 5.05 (dd, J=9.8, 7.1 Hz, 1H), 4.50-3.92 (m, 2H), 2.66 (dtd, J=11.5, 9.4, 4.9 Hz, 1H), 2.49 (ddt, J=11.5, 9.0, 7.3 Hz, 1H).

Step 5a: To a stirred suspension of (R)-1-((perfluorophenyl)sulfonyl)azetidine-2-carboxylic acid (831 mg, 2.5 mmol) in DCM (25 mL) under nitrogen was added DMF (6 uL) followed by oxalyl chloride (0.32 mL, 3.75 mmol) and the resulting suspension was stirred for 15 min at room temperature until it became a solution and then stirring of the resultant solution was continued for 1.5 h. The reaction mixture was concentrated in vacuo to yield (R)-1-((perfluorophenyl)sulfonyl)azetidine-2-carbonyl chloride (848 mg, 100% yield) as an off-white solid. 1H NMR (300 MHz, Chloroform-d) δ 5.26 (dd, J=10.0, 7.1 Hz, 1H), 4.33 (dt, J=9.2, 7.3 Hz, 1H), 4.02 (ddd, J=9.1, 7.4, 4.9 Hz, 1H), 2.79 (dddd, J=11.7, 10.0, 9.0, 4.9 Hz, 1H), 2.56 (ddt, J=11.6, 9.1, 7.1 Hz, 1H).

Step 5b: To a solution of benzyl 4-amino-3-fluorobenzoate (712 mg, 1.9 mmol) in TFA (7 mL) under nitrogen at 0° C. was added sodium triacetoxyborohydride (1.23 g, 5.8 mmol) portion wise. The mixture was stirred at 0° C. for 15 min before addition of 4-cyclohexylbenzaldehyde (581 mg, 3.1 mmol). The resulting reaction mixture was stirred at room temperature for 4.5 h, poured onto cold saturated aqueous sodium bircarbonate and extracted with EtOAc (2×). The combined organic extracts were dried over sodium sulfate and concentrated under reduced pressure to give a solid. The solid was triturated with 10% ether/hexane and washed with 10% ether/hexanes to provide benzyl 4-((4-cyclohexylbenzyl)amino)-3-fluorobenzoate (575 mg, 72% yield) as a white solid. 1H NMR (300 MHz, Chloroform-d)

δ 7.77 (ddd, J=8.5, 1.9, 0.8 Hz, 1H), 7.70 (dd, J=12.3, 1.9 Hz, 1H), 7.50-7.33 (m, 5H), 7.31-7.16 (m, 4H), 6.68 (t, J=8.5 Hz, 1H), 5.33 (s, 2H), 4.40 (s, 2H), 2.63-2.40 (m, 1H), 2.04-1.69 (m, 5H), 1.60-1.13 (m, 5H).

Step 6: To a stirred solution of benzyl 4-((4-cyclohexylbenzyl)amino)-3-fluorobenzoate (572 mg, 1.37 mmol) in THF (20 mL) under nitrogen at 0° C. was added methylmagnesium bromide (2.93 mL of 1.4M solution in 1:3 THF:toluene, 4.11 mmol), and the resulting solution was stirred for 5 min at 0° C. and then 10 min at room temperature. The resulting solution was added to a stirred solution of (R)-1-((perfluorophenyl)sulfonyl)azetidine-2-carbonyl chloride (670 mg, 1.92 mmol) in THF (20 mL) by dropwise addition over 20 min. The reaction mixture was stirred at room temperature for an additional 2 h, then poured onto saturated aqueous ammonium chloride and extracted with EtOAc (3×). The combined organic extracts were dried over sodium sulfate and concentrated under reduced pressure and the resulting residue purified by flash chromatography (20% EtOAc/hexanes) to afford benzyl (R)-4-(N-(4-cyclohexylbenzyl)-1-((perfluorophenyl)sulfonyl)azetidine-2-carboxamido)-3-fluorobenzoate (454 mg, 45% yield) as a foam. MS (ESI) m/z 731.2032 [M+H]+.

Step 6: To a stirred solution of (R)-4-(N-(4-cyclohexylbenzyl)-1-((perfluorophenyl)sulfonyl)azetidine-2-carboxamido)-3-fluorobenzoate (422 mg, 0.57 mmol) in methanol (8 mL) and EtOAc (8 mL) under nitrogen was added 20% Pd(OH)$_2$ on C (40 mg). The reaction mixture was stirred under a hydrogen atmosphere for 1.5 h, then filtered through Celite® and washed with EtOAc (2×). The combined filtrate and washes were concentrated in vacuo to yield (R)-4-(N-(4-cyclohexylbenzyl)-1-((perfluorophenyl)sulfonyl)azetidine-2-carboxamido)-3-fluorobenzoic acid (384 mg, 100% yield) as a white foam. MS (ESI) m/z 641.1550 [M+H]+.

Example 50

(R)—N-(4-cyclohexylbenzyl)-N-(2-fluoro-4-(hydroxycarbamoyl)phenyl)-1-((perfluorophenyl)sulfonyl)azetidine-2-carboxamide

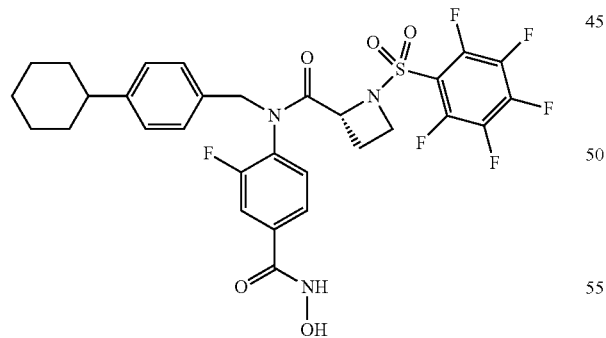

Preparation by a similar procedure to example 38, except substituting (R)-4-(N-(4-cyclohexylbenzyl)-1-((perfluorophenyl)sulfonyl)azetidine-2-carboxamido)-3-fluorobenzoic acid for (R)-4-(N-(4-cyclohexylbenzyl)-2-((2,3,4,5,6-pentafluoro-N-methylphenyl)sulfonamido) propanamido)-3-fluorobenzoic acid in step 1 afforded (R)—N-(4-cyclohexylbenzyl)-N-(2-fluoro-4-(hydroxycarbamoyl)phenyl)-1-((perfluorophenyl) sulfonyl)azetidine-2-carboxamide as a pink foam. MS (ESI) m/z 656.1655 [M+H]+.

Example 51

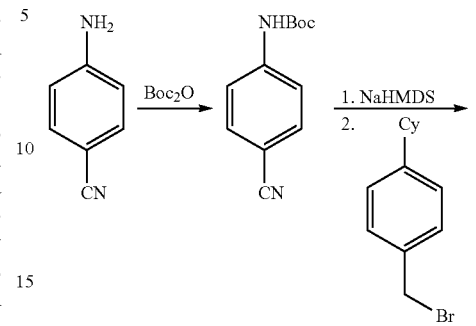

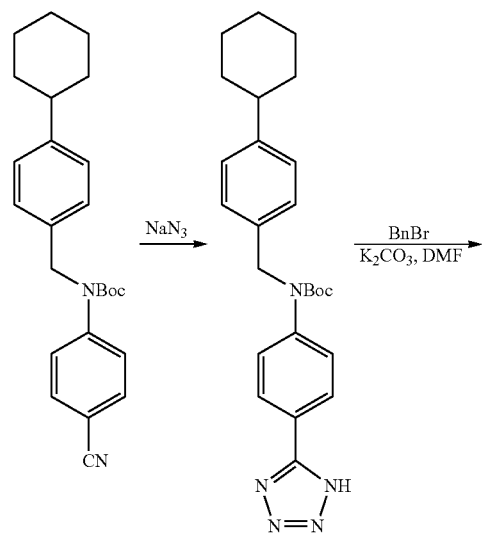

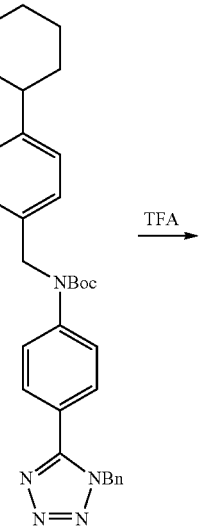

158

(R)—N-(4-(1H-tetrazol-5-yl)phenyl)-N-(4-cyclohexylbenzyl)-1-((perfluorophenyl)sulfonyl)azetidine-2-carboxamide

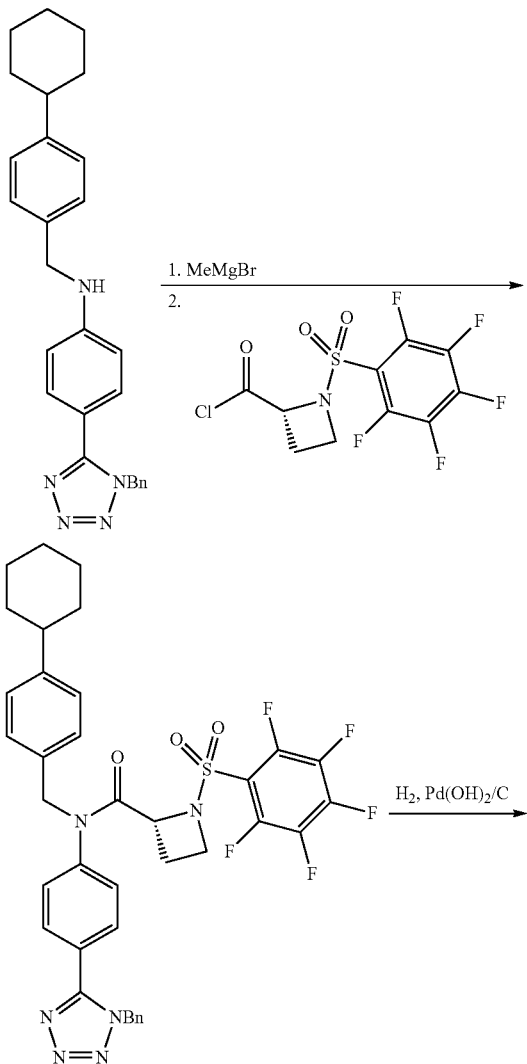

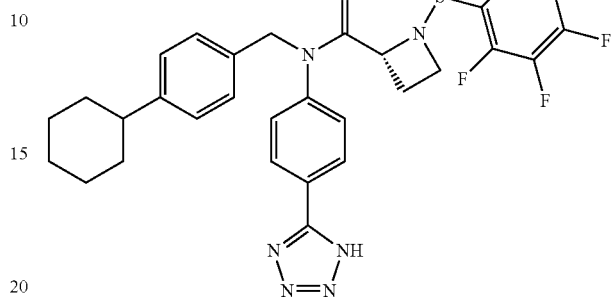

Step 1: To a solution of 4-aminobenzonitrile (1.0 g, 8.47 mmol) in ethanol (16 mL) under nitrogen was added di-tert-butyl dicarbonate (4.86 mL, 21.15 mmol). The reaction mixture was heated at 50° C. for 20 h and then 55° C. for 14 h. The crude reaction mixture was concentrated under reduced pressure. Purification by flash chromatography (15-20% EtOAc/hexanes eluent) provided tert-butyl (4-cyanophenyl)carbamate (1.49 g, 81% yield) as a white solid. $^1$H NMR (300 MHz, Chloroform-d) δ 7.59 (d, J=8.8 Hz, 2H), 7.50 (d, J=8.8 Hz, 2H), 6.71 (br s, 1H), 1.55 (s, 9H).

Step 2: To a solution of tert-butyl (4-cyanophenyl)carbamate (1.48 g, 6.78 mmol) in DMF (31 mL) under nitrogen at 0° C. was added NaHMDS (4.06 mL of a 2M solution in THF, 8.15 mmol). The mixture was stirred for 10 min at 0° C., then 1-(bromomethyl)-4-cyclohexylbenzene (2.06 g, 8.15 mmol) was added. Stirring was continued for 1 h at 0° C. and then for 19 h at room temperature. The reaction mixture was poured onto cold aqueous ammonium chloride and extracted with ether (2×). The combined organic extracts were washed with water and then with brine, dried over sodium sulfate and concentrated under reduced pressure. Purification by flash chromatography (7-10% EtOAc/hexanes eluent) provided tert-butyl (4-cyanophenyl)(4-cyclohexylbenzyl)carbamate (2.6 g, 98% yield) as a colorless oil.

Step 3: To a stirred solution of tert-butyl (4-cyanophenyl)(4-cyclohexylbenzyl)carbamate (810 mg, 2.07 mmol) in DMF (6 mL) were added sodium azide (339 mg, 5.21 mmol) and ammonium chloride (279 mg, 5.21 mmol) under nitrogen. The mixture was heated at 140° C. with vigorous stirring for 7 h. After cooling to room temperature, a 10% aqueous solution of KHSO$_4$ and Na$_2$SO$_4$ was added, followed by water. The mixture was extracted with EtOAc (2×). The combined organic extract was washed with water (2×) and then brine (1×), dried over sodium sulfate and concentrated under reduced pressure. Purification by flash chromatography (25% EtOAc/hexanes followed by 40% EtOAc/hexanes with 1% AcOH eluent) provided tert-butyl (4-(1H-tetrazol-5-yl)phenyl)(4-cyclohexylbenzyl)carbamate (827.5 mg, 92% yield) as a colorless oil. $^1$H NMR (300 MHz, Chloroform-d) δ 7.67 (d, J=8.1 Hz, 2H), 7.41 (s, 1H), 7.25-7.04 (m, 6H), 4.82 (s, 2H), 2.59-2.42 (m, 1H), 1.97-1.70 (m, 6H), 1.59 (s, 9H), 1.51-1.30 (m, 4H).

Step 4: To a stirred solution of tert-butyl (4-(1H-tetrazol-5-yl)phenyl)(4-cyclohexylbenzyl)carbamate (823 mg, 1.90

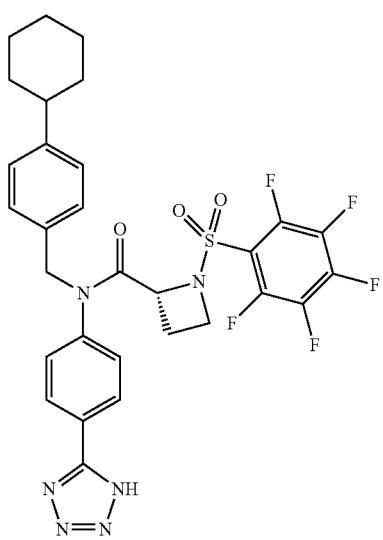

mmol) in DMF (6 mL) under nitrogen was added potassium carbonate (0.28 g, 2.09 mmol). After 10 min, benzyl bromide (0.22 mL, 1.8 mL) was added. The reaction mixture was stirred at room temperature for 4 h. The mixture was poured onto cold water and extracted with EtOAc (2×). The combined organic extracts were washed with water (2×) and then with brine (1×), dried over sodium sulfate and concentrated under reduced pressure. Purification by flash chromatography (15-20% EtOAc/hexanes eluent) provided tert-butyl (4-(1-benzyl-1H-tetrazol-5-yl)phenyl)(4-cyclohexylbenzyl)carbamate (770 mg, 77% yield). $^1$H NMR (300 MHz, Chloroform-d) δ 8.05 (d, J=8.7 Hz, 2H), 7.50-7.34 (m, 5H), 7.28 (d, J=8.7 Hz, 2H), 7.15 (m, 4H), 5.81 (s, 2H), 4.85 (s, 2H), 2.56-2.41 (m, 1H), 1.96-1.69 (m, 6H), 1.45 (s and overlapping m, 13H).

Step 5: To a stirred solution of tert-butyl (4-(1-benzyl-1H-tetrazol-5-yl)phenyl)(4-cyclohexylbenzyl)carbamate (761 mg, 1.45 mmol) under nitrogen in DCM (9.2 mL) was added TFA (3.0 mL) and the resultant mixture was stirred at room temperature for 1 h. The mixture was poured onto ice and aqueous sodium bicarbonate and checked to confirm that the pH was 6-8. The mixture was extracted with DCM (3×). The combined organic phase was washed with aqueous sodium bicarbonate, dried over sodium sulfate and concentrated under reduced pressure to provide 4-(1-benzyl-1H-tetrazol-5-yl)-N-(4-cyclohexylbenzyl)aniline (616 mg, 100% yield) as a cream-colored solid. $^1$H NMR (300 MHz, Chloroform-d) δ 7.96 (d, J=8.8 Hz, 2H), 7.39 (m, 5H), 7.31 (d, J=8.0 Hz, 2H), 7.21 (d, J=8.0 Hz, 2H), 6.71 (d, J=8.8 Hz, 2H), 5.78 (s, 2H), 4.36 (s, 2H), 2.63-2.42 (m, 1H), 2.02-1.66 (m, 6H), 1.58-1.16 (m, 4H).

Step 6: To a stirred solution of 4-(1-benzyl-1H-tetrazol-5-yl)-N-(4-cyclohexylbenzyl)aniline (308 mg, 0.73 mmol) in dry THF (7.3 mL) under nitrogen at 0° C. was added methylmagnesium bromide (1.65 mL of 1.4 M in THF, 2.31 mmol) and the resulting solution was stirred at 0° C. for 10 min before addition of solid (R)-1-((perfluorophenyl)sulfonyl)-azetidine-2-carbonyl chloride (484.3 mg, 1.30 mmol). The resulting mixture was allowed to warm to room temperature and stirred at room temperature for 5 h. To the crude reaction mixture was added cold saturated aqueous ammonium chloride followed by water and the resulting mixture was extracted with EtOAc (2×). The combined organic extract was washed with brine, dried over sodium sulfate and concentrated under reduced pressure. The crude residue was purified by flash chromatography (20% EtOAc/hexanes eluent) to provide (R)—N-(4-(1-benzyl-1H-tetrazol-5-yl)phenyl)-N-(4-cyclohexylbenzyl)-1-((perfluorophenyl)sulfonyl)azetidine-2-carboxamide (514 mg, 96% yield) as a colorless oil. $^1$H NMR (300 MHz, Chloroform-d) δ 8.12 (d, J=8.6 Hz, 2H), 7.49-7.35 (m, 5H), 7.16-6.96 (m, 6H), 5.83 (s, 2H), 5.01-4.91 (m, 1H), 4.87 (d, J=14.3 Hz, 1H), 4.72 (d, J=14.3 Hz, 1H), 4.26 (t, J=8.2 Hz, 1H), 4.09-3.85 (m, 1H), 2.56-2.40 (m, 1H), 2.33-2.15 (m, 1H), 1.98-1.69 (m, 6H), 1.39 (t, J=10.1 Hz, 4H).

Step 7: To a stirred solution of (R)—N-(4-(1-benzyl-1H-tetrazol-5-yl)phenyl)-N-(4-cyclohexylbenzyl)-1-((perfluorophenyl)sulfonyl)azetidine-2-carboxamide (230 mg, 0.31 mmol) in methanol (3 mL) and THF (1.0 mL) was added 20% Pd(OH)$_2$/C (23 mg) and the resulting suspension was stirred at room temperature under a hydrogen atmosphere for 15 h. The reaction mixture was filtered through Celite® and washed with EtOAc. Reaction was not complete by LCMS. To the resulting crude reaction residue in methanol (3 mL) and EtOAc (1.0 mL) was added 20% Pd(OH)$_2$/C (23 mg) and the resulting suspension was stirred at room temperature under a hydrogen atmosphere for 48 h. The reaction mixture was filtered through Celite® and washed with EtOAc. The combined filtrate and washes were concentrated under reduced pressure. Purification by flash chromatography (30% EtOAc/hexanes and subsequent 40% EtOAc/hexanes with 1% AcOH eluent) and further purification by preparative TLC (7% MeOH in DCM) provided pure (R)—N-(4-(1H-tetrazol-5-yl)phenyl)-N-(4-cyclohexylbenzyl)-1-((perfluorophenyl)sulfonyl-azetidine-2-carboxamide (34 mg) as an off-white solid. HRMS (ESI+) m/z 647.1866 [M+H]$^+$.

Example 52

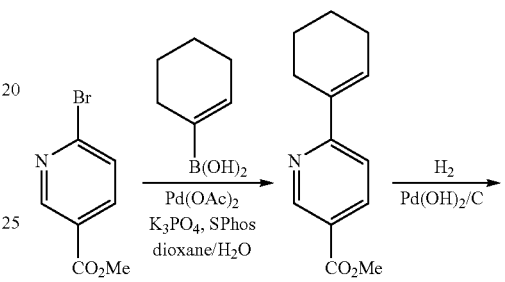

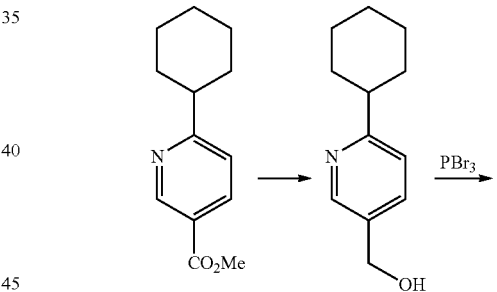

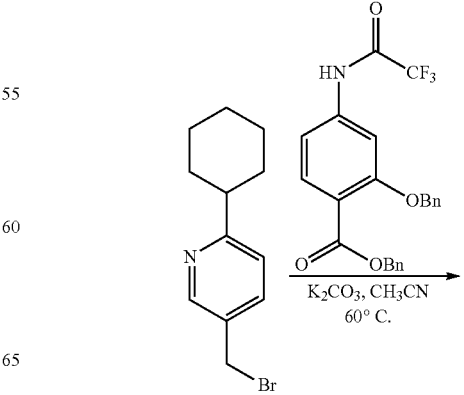

161
-continued

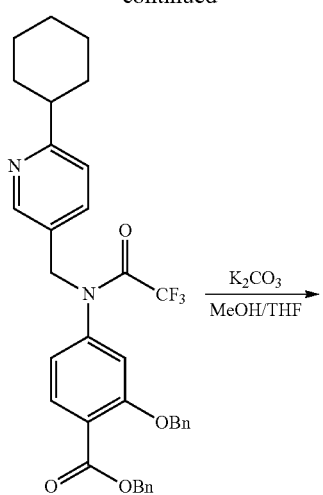

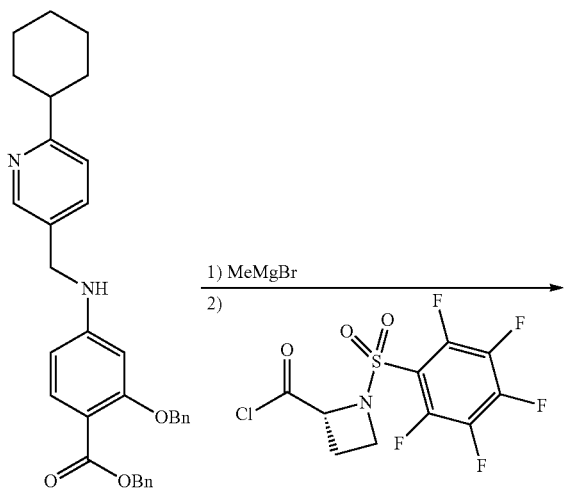

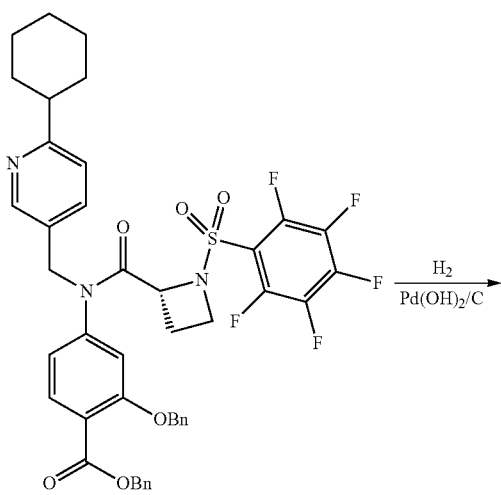

162
-continued

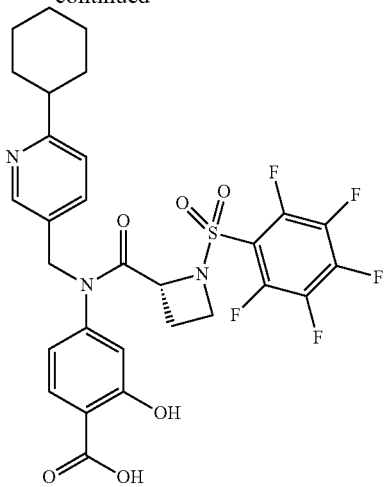

(R)-4-(N-((6-cyclohexylpyridin-3-yl)methyl)-1-((perfluorophenyl)sulfonyl)azetidine-2-carbox-amido)-2-hydroxybenzoic acid Step 1: Methyl 6-bromonicotinate (842 mg, 3.9 mmol), cyclohexenylboronic acid (540 mg, 4.29 mmol), potassium phosphate tribasic (2.48 g, 11.7 mmol), and SPhos (160 mg, 0.39 mmol) were placed in a flask that had been back-flushed with nitrogen. To the flask was added 12 mL of dioxane and 1.6 mL of deionized water. The mixture was degassed (3×) with nitrogen. Palladium (II) acetate (45 mg, 0.2 mmol) was added and the resulting biphasic mixture was heated at 80° C. with stirring overnight and then allowed to cool to room temperature. The reaction mixture was poured onto water and extracted with EtOAc (3×). The combined organic extracts were dried over sodium sulfate and concentrated under reduced pressure. Purification by flash chromatography (50% DCM/hexanes and subsequently 25% EtOAc/hexanes) provided methyl 6-(cyclohex-1-en-1-yl) nicotinate (431 mg, 51% yield). $^1$H NMR (300 MHz, Chloroform-d) δ 9.20 (d, J=2.2 Hz, 1H), 8.32 (d, J=8.2 Hz, 1H), 7.51 (d, J=8.2 Hz, 1H), 7.03 (br s, 1H), 3.97 (s, 3H), 2.62-2.48 (m, 2H), 2.42-2.27 (m, 2H), 1.92-1.78 (m, 2H), 1.77-1.66 (m, 2H).

Step 2: To a stirred solution of methyl 6-(cyclohex-1-en-1-yl) nicotinate (431 mg, 1.99 mmol) in EtOAc (7 mL) and methanol (3 mL) was added Pd(OH)$_2$ (43 mg). The reaction was stirred under a hydrogen atmosphere overnight. The reaction mixture was filtered through Celite® and washed with EtOAc. The combined filtrate and washes were concentrated under reduced pressure to provide methyl 6-cyclohexylnicotinate (439 mg, 100% yield) as a white solid. $^1$H NMR (300 MHz, Chloroform-d) δ 9.15 (d, J=2.2, 1H), 8.25 (dd, J=8.2, 2.2 Hz, 1H), 7.28 (d, J=8.2, 1H), 3.96 (s, 3H), 2.83 (tt, J=11.7, 3.4 Hz, 1H), 2.10-1.70 (m, 5H), 1.68-1.18 (m, 5H).

Step 3: A solution of methyl 6-cyclohexylnicotinate (439 mg, 2 mmol) in THF (6 mL) was added dropwise to a stirred suspension of lithium aluminum hydride (122 mg, 3.2 mmol) in THF (6 mL) under nitrogen at 0° C. Stirring was continued at 0° C. for 3.5 h before addition of saturated aqueous sodium sulfate. The mixture was filtered, poured onto water/EtOAc and extracted with EtOAc (3×). The combined extracts were dried over MgSO$_4$ and concentrated under reduced pressure to provide (6-cyclohexylpyridin-3-yl)methanol (417 mg, 100% yield). $^1$H NMR (300 MHz, Chloroform-d) δ 8.56-8.49 (m, 1H), 7.67 (dd, J=8.0, 2.3 Hz, 1H), 7.18 (d, J=8.0 Hz, 1H), 4.71 (s, 2H), 2.73 (tt, J=11.7, 3.4 Hz, 1H), 2.04-1.15 (m, 10H).

Step 4a: To a stirred solution of (6-cyclohexylpyridin-3-yl)methanol (417 mg, 2 mmol) in DCM (7 mL) under nitrogen at 0° C. was added PBr$_3$ (0.3 mL, 3.2 mmol) and the resulting mixture was stirred at room temperature for 2 h. The mixture was poured onto saturated aqueous sodium bicarbonate and extracted with DCM (2×). The combined organic layer was washed with saturated aqueous sodium bicarbonate, dried over sodium sulfate and concentrated under reduced pressure to provide 5-(bromomethyl)-2-cyclohexylpyridine (443 mg, 87% yield) as a colorless liquid. $^1$H NMR (300 MHz, Chloroform-d) δ 8.55 (d, J=2.4 Hz, 1H), 7.67 (dd, J=8.1, 2.4 Hz, 1H), 7.17 (d, J=8.1 Hz, 1H), 4.49 (s, 2H), 2.72 (tt, J=11.6, 3.4 Hz, 1H), 2.08-1.71 (m, 5H), 1.58-1.21 (m, 5H).

Step 4b: To a stirred solution of benzyl 4-amino-2-(benzyloxy)benzoate (3.03 g, 9.1 mmol) in DCM (50 mL) under nitrogen at 0° C. was added pyridine (0.88 mL, 10.9 mmol) followed by TFFA (1.41 mL, 10 mmol). The reaction mixture was allowed to warm to room temperature and stirred at this temperature for 1.5 h. The mixture was diluted with DCM, poured onto 10% aqueous KHSO$_4$/Na$_2$SO$_4$ buffer and extracted DCM (2×). The combined organic extract was washed with saturated aqueous sodium bicarbonate, dried over anhydrous sodium sulfate and concentrated under reduced pressure. Purification by trituration with hexanes provided benzyl 2-(benzyloxy)-4-(2,2,2-trifluoroacetamido)benzoate (3.75 g, 96% yield) as a tan solid.

Step 5: To a stirred solution of benzyl 2-(benzyloxy)-4-(2,2,2-trifluoroacetamido)benzoate (623 mg, 1.45 mmol) and 5-(bromomethyl)-2-cyclohexylpyridine (443 mg, 1.7 mmol) in acetonitrile (14 mL) was added potassium carbonate (303 mg, 2.2 mmol). The resulting reaction mixture under nitrogen was stirred at 60° C. for 4 h. After cooling to room temperature the reaction mixture was poured onto water and extracted with EtOAc (3×). The combined organic extract was washed with brine, dried over anhydrous sodium sulfate and concentrated under reduced pressure. The resulting residue was purified by flash chromatography (10% EtOAc/hexanes eluent) to provide benzyl 2-(benzyloxy)-4-(N-((6-cyclohexylpyridin-3-yl)methyl)-2,2,2-trifluoroacetamido)benzoate (661.8 mg, 76% yield) as a colorless oil. $^1$H NMR (300 MHz, Chloroform-d) δ 8.26 (d, J=2.3 Hz, 1H), 7.85 (d, J=8.3 Hz, 1H), 7.52-7.44 (m, 1H), 7.43-7.32 (m, 10H), 7.12 (d, J=8.0 Hz, 1H), 6.74-6.64 (m, 1H), 6.57 (s, 1H), 5.36 (s, 2H), 4.98 (s, 2H), 4.84 (s, 2H), 2.77-2.61 (m, 1H), 2.02-1.69 (m, 6H), 1.54-1.32 (m, 4H).

Step 6: To a stirred solution of benzyl 2-(benzyloxy)-4-(N-((6-cyclohexylpyridin-3-yl)methyl)-2,2,2-trifluoroacetamido)benzoate (661 mg, 1.1 mmol) in THF (8.6 mL) and methanol (8.6 mL) was added potassium carbonate (258 mg, 1.87 mmol) under nitrogen and the mixture was stirred at room temperature for 2.5 h. To the crude reaction mixture was added cold saturated aqueous ammonium chloride followed by water and the resulting mixture was extracted with EtOAc (3×). The combined organic extract was washed with brine, dried over anhydrous sodium sulfate and concentrated under reduced pressure to provide crude product as a white solid. Trituration with 3:1 hexanes/ethyl ether provided benzyl 2-(benzyloxy)-4-(((6-cyclohexylpyridin-3-yl)methyl)amino)benzoate (516 mg, 93% yield) as a white solid. $^1$H NMR (300 MHz, Chloroform-d) δ 8.53 (d, J=2.1 Hz, 1H), 7.85 (d, J=8.6 Hz, 1H), 7.58 (dd, J=8.1, 2.4 Hz, 1H), 7.15 (d, J=8.1 Hz, 1H), 6.23 (dd, J=8.6, 2.2 Hz, 1H), 6.18 (d, J=2.2 Hz, 1H), 5.32 (s, 2H), 5.11 (s, 2H), 4.43 (br s, 1H), 4.33 (s, 2H), 2.86-2.62 (m, 1H), 2.08-1.69 (m, 6H), 1.66-1.18 (m, 4H).

Step 7: To a stirred solution of benzyl 2-(benzyloxy)-4-(((6-cyclohexylpyridin-3-yl)methyl)amino)benzoate (201 mg, 0.40 mmol) in dry THF (8 mL) under nitrogen at 0° C. was added methylmagnesium bromide (0.85 mL of 1.4 M in THF, 1.19 mmol) and the resulting solution was stirred at 0° C. for 5 min and room temperature for 10 min before addition of solid (R)-1-((perfluorophenyl)sulfonyl)-azetidine-2-carbonyl chloride (194 mg, 0.56 mmol). The resulting mixture was allowed to warm to room temperature and stirred at room temperature for 23 h. A few drops of methanol were added and then the crude reaction mixture was poured onto water and extracted with EtOAc (3×). The combined organic extract was washed with brine, dried over sodium sulfate and concentrated under reduced pressure. The crude residue was purified by flash chromatography (1:1:3 EtOAc:DCM:hexanes eluent) to provide benzyl (R)-2-(benzyloxy)-4-(N-((6-cyclohexylpyridin-3-yl)methyl)-1-((perfluorophenyl)sulfonyl)azetidine-2-carboxamido)benzoate (378 mg). MS (ESI+) m/z 820.3 [M+H]$^+$.

Step 8: To a stirred solution of benzyl (R)-2-(benzyloxy)-4-(N-((6-cyclohexylpyridin-3-yl)methyl)-1-((perfluorophenyl)sulfonyl)azetidine-2-carboxamido)benzoate (118 mg, 0.14 mmol) in methanol (4 mL) and EtOAc (4 mL) was added 20% Pd(OH)$_2$/C (11 mg) and the resulting suspension was stirred at room temperature under a hydrogen atmosphere for 2.5 h. The reaction mixture was filtered through Celite® and washed with EtOAc. The combined filtrate and washes were concentrated in vacuo to provide (R)-4-(N-((6-cyclohexylpyridin-3-yl)methyl)-1-((perfluorophenyl)sulfonyl)azetidine-2-carboxamido)-2-hydroxybenzoic acid (90.5 mg, 98% yield) as a white solid. MS (ESI+) m/z 640.2 [M+H]$^+$.

Example 53

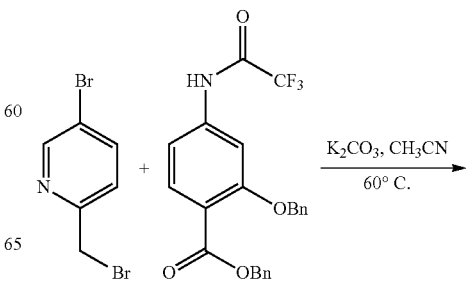

165
-continued

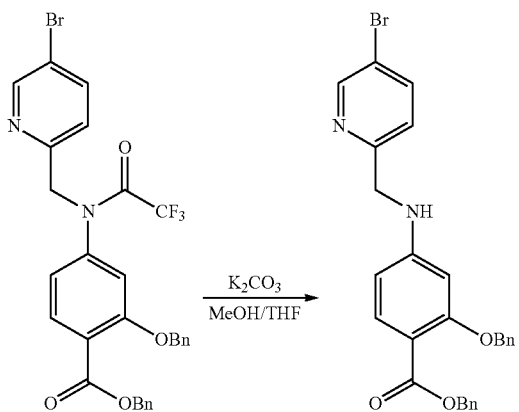

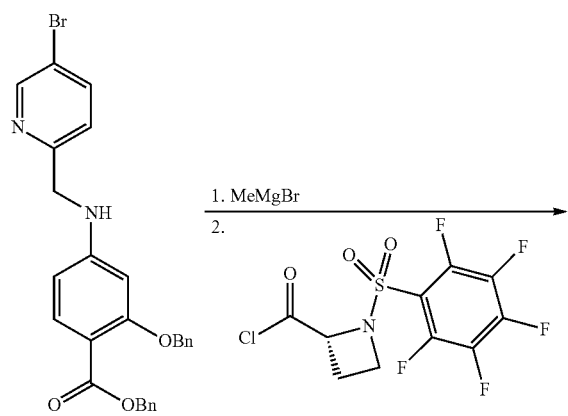

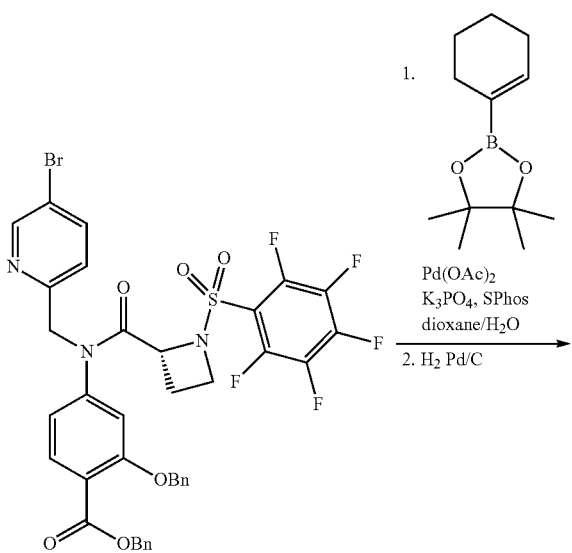

166
-continued

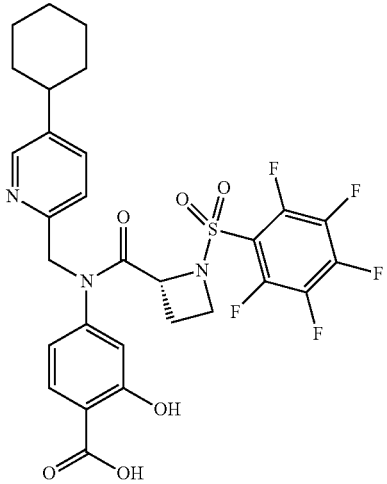 [SMILES: O=C(O)c1ccc(N(Cc2ccc(C3CCCCC3)cn2)C(=O)[C@H]2CCN2S(=O)(=O)c2c(F)c(F)c(F)c(F)c2F)cc1O]

(R)-4-(N-((5-cyclohexylpyridin-2-yl)methyl)-1-((perfluorophenyl)sulfonyl)azetidine-2-carboxamido)-2-hydroxybenzoic acid

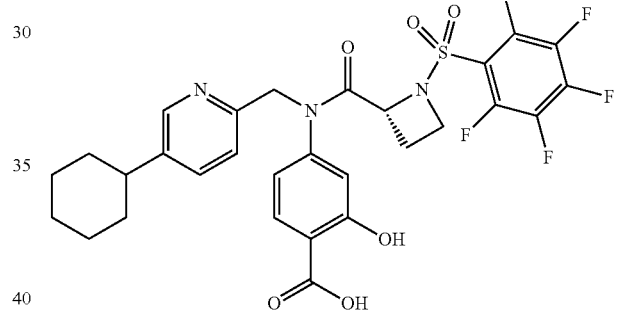

Step 1: To a stirred solution of benzyl 2-(benzyloxy)-4-(2,2,2-trifluoroacetamido)benzoate (339.6 mg, 0.791 mmol) and 5-bromo-2-(bromomethyl)pyridine (277.8 mg, 1.107 mmol) in acetonitrile (13.2 mL) was added potassium carbonate (142 mg, 1.028 mmol). The resulting reaction mixture under nitrogen was stirred at 60° C. for 3 h. After cooling to room temperature the reaction mixture was poured onto cold aqueous 10% KHSO$_4$/Na$_2$SO$_4$ buffer and extracted with EtOAc (2×). The combined organic extract was washed with brine, dried over anhydrous sodium sulfate and concentrated under reduced pressure. The resulting residue was purified by flash chromatography (15-30% EtOAc/hexanes eluent) to provide benzyl 2-(benzyloxy)-4-(N-((5-bromopyridin-2-yl)methyl)-2,2,2-trifluoroacetamido)benzoate (370 mg, 78% yield) as a colorless oil. $^1$H NMR (300 MHz, Chloroform-d) δ 8.56 (d, J=2.5 Hz, 1H), 7.85 (dd, J=8.2, 1.0 Hz, 1H), 7.78 (dd, J=8.3, 2.4 Hz, 1H), 7.52-7.31 (m, 10H), 7.17 (d, J=8.6 Hz, 1H), 6.96 (d, J=1.7 Hz, 1H), 6.88 (d, J=8.4 Hz, 1H), 5.35 (s, 2H), 5.10 (s, 2H), 4.93 (s, 2H).

Step 2: To a stirred solution of benzyl 2-(benzyloxy)-4-(N-((5-bromopyridin-2-yl)methyl)-2,2,2-trifluoroacetamido)benzoate (363 mg, 0.606 mmol) in THF (3 mL) and methanol (3.7 mL) was added potassium carbonate (377 mg, 2.73 mmol) under nitrogen and the mixture was stirred at room temperature for 2 h. To the crude reaction mixture was added cold saturated aqueous ammonium chloride followed by water and the resulting mixture was extracted with EtOAc (2×). The combined organic extract was washed with brine, dried over anhydrous sodium sulfate and concentrated under reduced pressure. Purification by flash chromatography (25-30% EtOAc/hexanes eluent) provided benzyl 2-(benzyloxy)-4-(((5-bromopyridin-2-yl)methyl)amino) benzoate (290 mg, 95% yield) as a white solid. $^1$H NMR (300 MHz, Chloroform-d) δ 8.65 (d, J=2.3 Hz, 1H), 7.93-7.81 (m, 1H), 7.77 (dd, J=8.3, 2.3 Hz, 1H), 7.53-7.29 (m, 10H), 7.21-7.13 (m, 1H), 6.25 (dd, J=8.5, 2.2 Hz, 1H), 6.20 (d, J=2.2 Hz, 1H), 5.32 (s, 2H), 5.26-5.17 (m, 1H), 5.13 (s, 2H), 4.44 (d, J=4.9 Hz, 2H).

Step 3: To a stirred solution of benzyl 2-(benzyloxy)-4-(((5-bromopyridin-2-yl)methyl)amino)benzoate (287 mg, 0.57 mmol) in dry THF (4.5 mL) under nitrogen at 0° C. was added methylmagnesium bromide (1.02 mL of 1.4 M in THF, 1.422 mmol) and the resulting solution was stirred at 0° C. for 5 min before addition of solid (R)-1-((perfluorophenyl)sulfonyl)-azetidine-2-carbonyl chloride (298.8 mg, 0.858 mmol). The resulting mixture was allowed to warm to room temperature and stirred at room temperature for 24 h. To the crude reaction mixture was added cold saturated ammonium chloride followed by water and the mixture was extracted with EtOAc (2×). The combined organic extract was washed with brine, dried over sodium sulfate and concentrated under reduced pressure. The crude residue was purified by flash chromatography (25-30% EtOAc in hexanes eluent) to provide benzyl (R)-2-(benzyloxy)-4-(N-((5-bromopyridin-2-yl)methyl)-1-((perfluorophenyl)sulfonyl)azetidine-2-carboxamido)benzoate (260 mg, 55% yield) as a colorless oil. $^1$H NMR (300 MHz, Chloroform-d) δ 8.54 (s, 1H), 7.83 (d, J=8.2 Hz, 1H), 7.76 (d, J=8.5 Hz, 1H), 7.51-7.32 (m, 10H), 7.13 (d, J=8.3 Hz, 1H), 6.88 (s, 1H), 6.79 (d, J=8.2 Hz, 1H), 5.38 (s, 2H), 5.26-5.06 (m, 2H), 5.00-4.89 (m, 1H), 4.83 (s, 2H), 4.10-3.86 (m, 2H), 2.18-1.97 (m, 1H), 1.85-1.67 (m, 1H).

Step 4: In a dry flask under nitrogen was added benzyl (R)-2-(benzyloxy)-4-(N-((5-bromopyridin-2-yl)methyl)-1-((perfluorophenyl)sulfonyl)azetidine-2-carboxamido)benzoate (142 mg, 0.174 mmol), Pd(OAc)$_2$ (1.95 mg, 0.0086 mmol), SPhos (7.17 mg, 0.0173 mmol), 2-(cyclohex-1-en-1-yl)-4,4,5,5-tetramethyl-1,3,2-dioxaborolane (68 mg, 0.32 mmol), potassium phosphate tribasic (74 mg) and HPLC-grade water (6.2 mg). Reaction mixture was thoroughly flushed with nitrogen. THF (2.2 mL) was added. The mixture was stirred at 40° C. for 23.5 h. Water was added and the mixture was extracted with EtOAc (2×). The combined organic extract was washed with brine, dried over sodium sulfate and concentrated under reduced pressure. Purification by flash column (10-15% EtOAc in hexanes eluent) provided benzyl (R)-2-(benzyloxy)-4-(N-((5-(cyclohex-1-en-1-yl)pyridin-2-yl)methyl)-1-((perfluorophenyl)sulfonyl)-azetidine-2-carboxamido)benzoate (87.1 mg, 88%) as a white solid. MS (ESI+) m/z 818.2 [M+H]$^+$.

Step 5: To a stirred solution of benzyl (R)-2-(benzyloxy)-4-(N-((5-(cyclohex-1-en-1-yl)pyridin-2-yl)methyl)-1-((perfluorophenyl)sulfonyl)-azetidine-2-carboxamido)benzoate (76 mg, 0.093 mmol) in methanol (3.1 mL) and EtOAc (3.1 mL) was added 10% Pd/C (8.02 mg) and the resulting suspension was stirred at room temperature under a hydrogen atmosphere for 6 h. The reaction was incomplete. The reaction mixture was filtered through Celite® and washed with EtOAc. The combined filtrate and washes were concentrated. The crude mixture was resubjected to the above hydrogenation conditions for 21.5 h. The reaction mixture was filtered through Celite® and washed with EtOAc. The combined filtrate and washes were concentrated in vacuo to provide (R)-4-(N-((5-cyclohexylpyridin-2-yl)methyl)-1-((perfluorophenyl)sulfonyl)azetidine-2-carboxamido)-2-hydroxybenzoic acid (52 mg) as a brown solid. HRMS (ESI) m/z 640.1538 [M+H]$^+$.

Example 54

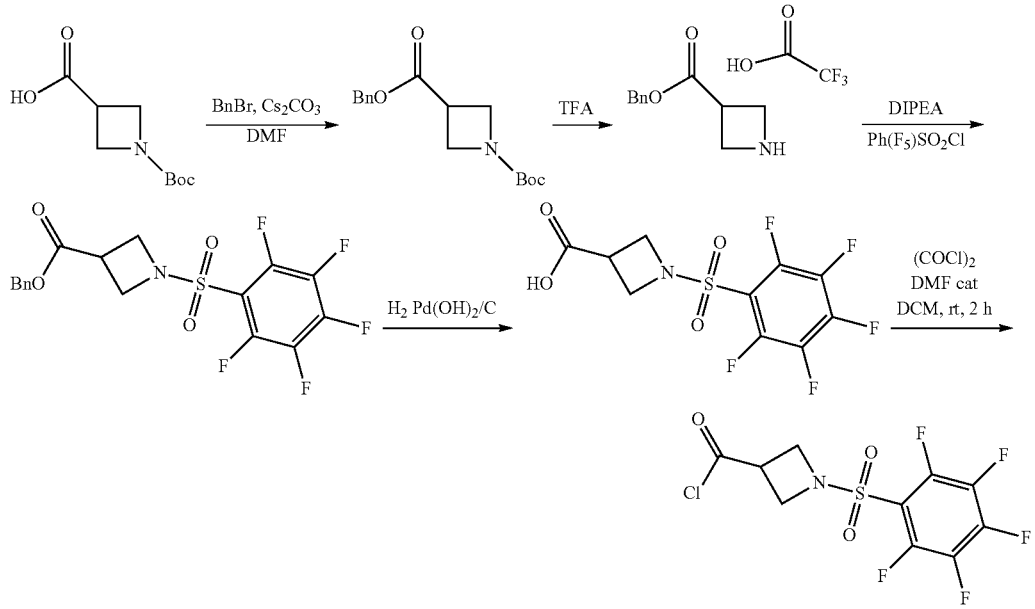

-continued
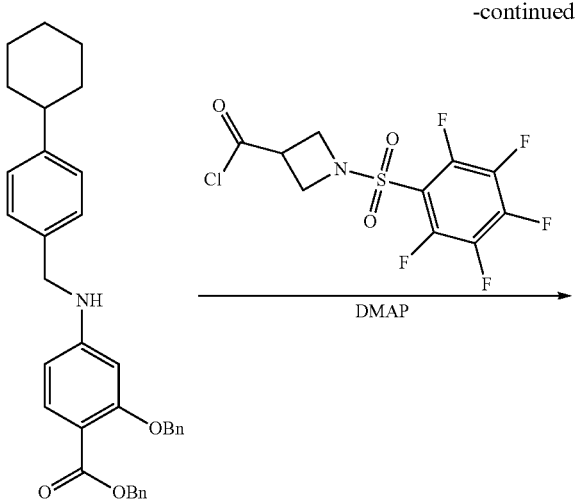
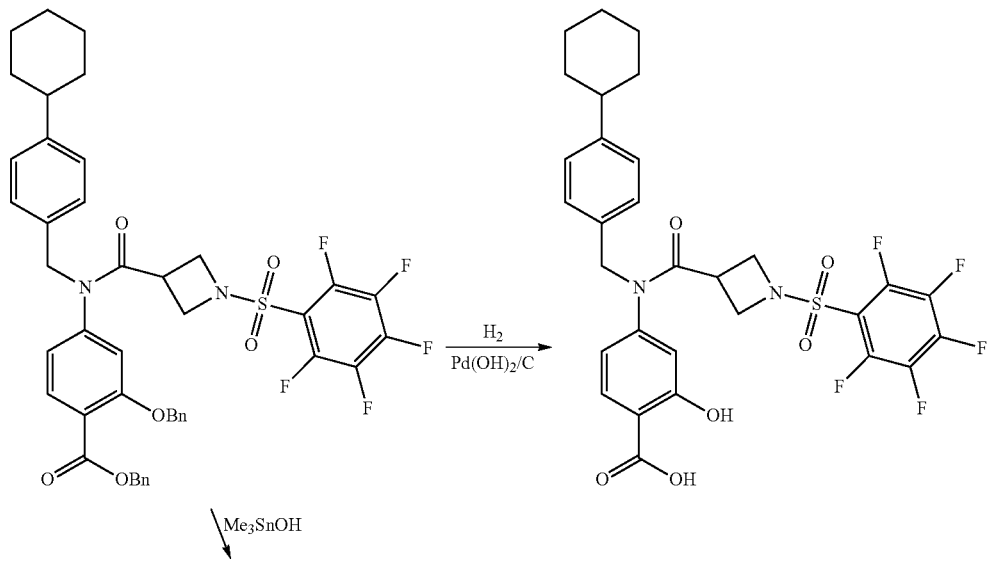
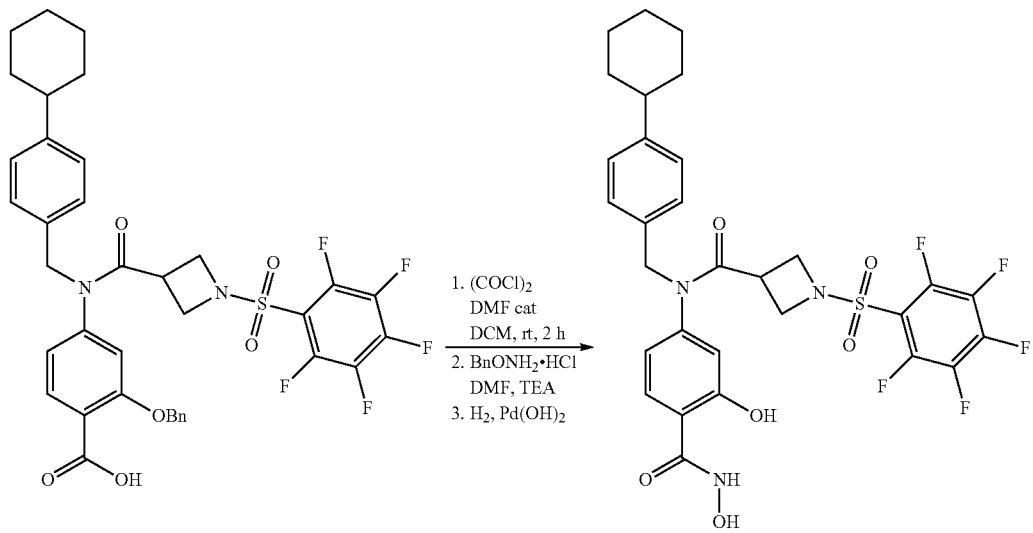

4-(N-(4-cyclohexylbenzyl)-1-((perfluorophenyl)sulfonyl)azetidine-3-carboxamido)-2-hydroxybenzoic acid

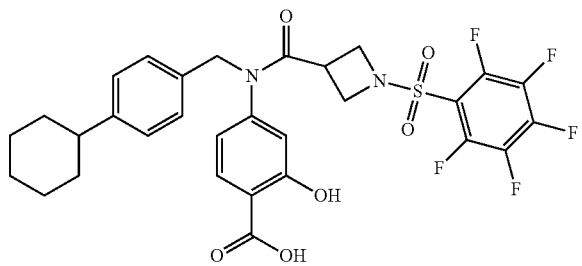 [SMILES: O=C(O)c1ccc(N(Cc2ccc(C3CCCCC3)cc2)C(=O)C2CN(S(=O)(=O)c3c(F)c(F)c(F)c(F)c3F)C2)cc1O]

Step 1: To a stirred solution of 1-(tert-butoxycarbonyl)azetidine-3-carboxylic acid (1 g, 4.97 mmol) in DMF (12 mL) under nitrogen was added cesium carbonate (2.43 g, 7.45 mmol) and stirring was continued at room temperature for 30 min. To the reaction mixture was added benzyl bromide (0.9 mL, 7.45 mmol) and the resulting milky-white mixture was allowed to stir at room temperature for 22 h. The mixture was poured onto water and extracted with ether (3×). The combined ethereal extracts were washed with brine, dried over anhydrous sodium sulfate and concentrated under reduced pressure. Flash chromatography (hexanes, then 15% EtOAc/hexanes eluent) provided 3-benzyl 1-(tert-butyl) azetidine-1,3-dicarboxylate (1.35 g, 93% yield). $^1$H NMR (300 MHz, Chloroform-d) δ 7.48-7.32 (m, 5H), 5.19 (s, 2H), 4.21-4.00 (m, 4H), 3.50-3.30 (m, 1H), 1.45 (s, 9H).

Step 2: To a stirred solution of 3-benzyl 1-(tert-butyl) azetidine-1,3-dicarboxylate (1.35 g 4.63 mmol) in DCM (11 mL) at 0° C. under nitrogen was added TFA (2.1 mL) and the resultant solution was stirred at 0° C. for 30 min and allowed to warm to room temperature and was stirred at this temperature for 1 h before concentrated in vacuo to provide benzyl azetidine-3-carboxylate 2,2,2-trifluoroacetate which was used as is for step 3. $^1$H NMR (300 MHz, Chloroform-d) δ 7.44-7.31 (m, 5H), 5.22 (s, 2H), 4.47-4.18 (m, 4H), 3.81 (td, J=8.9, 7.5 Hz, 1H).

Step 3: To a stirred solution of benzyl azetidine-3-carboxylate 2,2,2-trifluoroacetate (4.63 mmol) in DCM (30 mL) at 0° C. under nitrogen was added DIPEA (2.5 mL, 13.9 mmol) followed by pentafluorobenzenesulfonyl chloride (0.9 mL, 6.0 mmol) and the resulting solution was allowed to warm to room temperature and was stirred at this temperature for 24 h. The crude reaction mixture was poured onto water and extracted with DCM (3×). The combined organic layers were dried over anhydrous sodium sulfate, concentrated under reduced pressure and the resultant residue purified by flash chromatography (80:20:2 hexanes:DCM:EtOAc followed by 75:25:2 hexanes:DCM:EtOAc eluent) to provide benzyl 1-((perfluorophenyl)sulfonyl)azetidine-3-carboxylate (1.55 g, 86% yield). $^1$H NMR (300 MHz, Chloroform-d) δ 7.44-7.30 (m, 5H), 5.15 (s, 2H), 4.43-4.11 (m, 4H), 3.47 (tt, J=9.0, 6.4 Hz, 1H).

Step 4: To a stirred solution of benzyl 1-((perfluorophenyl)sulfonyl)azetidine-3-carboxylate (1.55 g, 3.95 mmol) in EtOAc (18 mL) and methanol (18 mL) under nitrogen was added 20% Pd(OH)$_2$ on carbon (180 mg) and the resultant mixture was placed under a hydrogen atmosphere and stirred at room temperature for 19 h. The reaction mixture was filtered through Celite® and washed with EtOAc. The combined filtrate and washes were concentrated under reduced pressure. Purification by flash chromatography (0-3% MeOH in DCM step-wise gradient) provided 1-((perfluorophenyl)sulfonyl)azetidine-3-carboxylic acid (668 mg, 56% yield). $^1$H NMR (300 MHz, Chloroform-d) δ 4.32 (dt, J=24.9, 8.2 Hz, 4H), 3.64-3.39 (m, 1H).

Step 5: To a stirred suspension of 1-((perfluorophenyl)sulfonyl)azetidine-3-carboxylic acid (334 mg, 1.04 mmol) in DCM (9 mL) under nitrogen was added DMF (1 drop) followed by oxalyl chloride (0.13 mL, 1.56 mmol) and the resulting suspension was stirred for 5 min at room temperature until it became a solution and then stirring of the resultant solution was continued for 2 h. The reaction mixture was concentrated in vacuo to yield 1-((perfluorophenyl)sulfonyl)azetidine-3-carbonyl chloride (366 mg, 100% yield). $^1$H NMR (300 MHz, Chloroform-d) δ 4.37 (h, J=8.0, 7.3 Hz, 4H), 3.88 (tt, J=9.1, 6.4 Hz, 1H).

Step 6: To a stirred solution of benzyl 2-(benzyloxy)-4-((4-cyclohexylbenzyl)amino)benzoate (338 mg, 0.67 mmol) and 1-((perfluorophenyl)sulfonyl)azetidine-3-carbonyl chloride (360 mg, 1.0 mmol) in dry DCM (3 mL) under nitrogen was added DMAP (97 mg, 0.80 mmol). Stirring was continued for 7 hours. Methanol (2-3 drops) was added to consume any excess acid chloride. The mixture was poured onto water and extracted with DCM (3×). The combined organic layers were dried over anhydrous sodium sulfate and evaporated under reduced pressure. Purification by flash column chromatography (20% EtOAc in hexanes eluent) afforded benzyl 2-(benzyloxy)-4-(N-(4-cyclohexylbenzyl)-1-((perfluorophenyl)sulfonyl)azetidine-3-carboxamido)benzoate (511 mg, 93% yield). $^1$H NMR (300 MHz, Chloroform-d) δ 7.82 (d, J=8.1 Hz, 1H), 7.53-7.32 (m, 10H), 7.15 (d, J=7.8 Hz, 2H), 6.98 (d, J=7.8 Hz, 2H), 6.60-6.45 (m, 1H), 6.23 (s, 1H), 5.38 (s, 2H), 4.93 (s, 2H), 4.72 (s, 2H), 4.03 (t, J=7.5 Hz, 2H), 3.63 (t, J=8.4 Hz, 2H), 3.05 (q, J=7.5 Hz, 1H), 2.60-2.41 (m, 1H), 1.97-1.70 (m, 5H), 1.52-1.14 (m, 5H).

Step 7: To a stirred solution of benzyl 2-(benzyloxy)-4-(N-(4-cyclohexylbenzyl)-1-((perfluorophenyl)sulfonyl)azetidine-3-carboxamido)benzoate (238 mg, 0.29 mmol) in EtOAc (8 mL) and methanol (8 mL) under nitrogen was added 20% Pd(OH)$_2$ on carbon (22 mg). The solution was placed under a hydrogen balloon and stirred for 3.5 hour. The solution was filtered through Celite®, washed with EtOAc and evaporated under reduced pressure to afford 4-(N-(4-cyclohexylbenzyl)-1-((perfluorophenyl)sulfonyl) azetidine-3-carboxamido)-2-hydroxybenzoic acid (181 mg, 98% yield). HRMS (ESI) m/z 639.1591 [M+H]$^+$.

Example 55

N-(4-cyclohexylbenzyl)-N-(3-hydroxy-4-(hydroxycarbamoyl)phenyl)-1-((perfluorophenyl)sulfonyl) azetidine-3-carboxamide

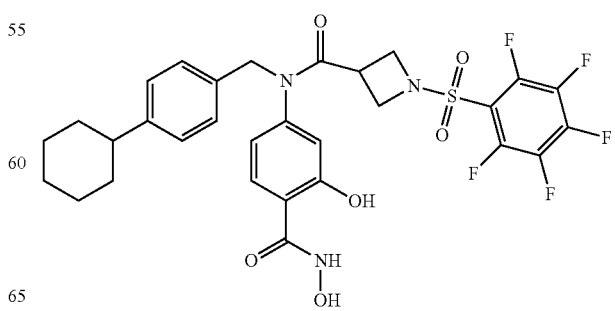

Step 1: To a stirred solution of benzyl 2-(benzyloxy)-4-(N-(4-cyclohexylbenzyl)-1-((perfluorophenyl)sulfonyl)azetidine-3-carboxamido)benzoate (220 mg, 0.27 mmol) in DCE (28 mL) under nitrogen was added trimethyltin hydroxide (387 mg, 2.14 mmol). The reaction was warmed at 85° C. for 3 days. After cooling to room temperature, the reaction mixture was poured onto saturated aqueous ammonium chloride and extracted with DCM (2×). To the aqueous phase was added sodium bicarbonate solution and the aqueous phase was extracted with DCM (2×). The combined organic layers were washed with brine, dried over sodium sulfate and concentrated under reduced pressure. Purification by flash chromatography (30% EtOAc/hexanes eluent) provided 2-(benzyloxy)-4-(N-(4-cyclohexylbenzyl)-1-((perfluorophenyl)sulfonyl)azetidine-3-carboxamido)benzoic acid (136 mg, 70% yield). LCMS (ESI+) m/z 729.10 [M+H]⁺.

Step 2: To a stirred solution of 2-(benzyloxy)-4-(N-(4-cyclohexylbenzyl)-1-((perfluorophenyl)sulfonyl)azetidine-3-carboxamido)benzoic acid (136 mg, 0.19 mmol) in DCM (3 mL) under nitrogen was added oxalyl chloride (0.05 mL, 0.42 mmol) and DMF (small drop). The resulting reaction solution was stirred at room temperature under nitrogen for 2 h and then concentrated in vacuo to provide 2-(benzyloxy)-4-(N-(4-cyclohexylbenzyl)-1-((perfluorophenyl)sulfonyl)azetidine-3-carboxamido)benzoyl chloride, which was used as is.

Step 3: To a solution of O-benzylhydroxylamine hydrochloride (61 mg, 0.38 mmol) in DMF (2 mL) was added TEA (0.08 mL, 0.57 mmol). The mixture was stirred for 5 min, then added to a solution of the crude acid chloride, 2-(benzyloxy)-4-(N-(4-cyclohexylbenzyl)-1-((perfluorophenyl)sulfonyl)azetidine-3-carboxamido)benzoyl chloride (0.19 mmol), in THF (6 mL) at 0° C. under nitrogen. The resultant reaction mixture was warmed to 0° C. for 1 h. The reaction was quenched with 10% aqueous potassium bisulfate/sodium sulfate buffer, poured onto water and extracted with EtOAc (3×). The combined organic extracts were washed with brine, dried over anhydrous sodium sulfate and concentrated under reduced pressure. The resulting residue was purified by flash chromatography to provide N-(3-(benzyloxy)-4-((benzyloxy)carbamoyl)phenyl)-N-(4-cyclohexylbenzyl)-1-((perfluorophenyl)sulfonyl)-azetidine-3-carboxamide (85 mg, 53% yield). MS (ESI) m/z 834.20 [M+H]⁺.

Step 4: To a stirred solution of N-(3-(benzyloxy)-4-((benzyloxy)carbamoyl)phenyl)-N-(4-cyclohexylbenzyl)-1-((perfluorophenyl)sulfonyl)azetidine-3-carboxamide (85 mg, 0.1 mmol) in methanol (2.5 mL) and EtOAc (2.5 mL) was added 20% Pd(OH)₂/C (6 mg) and the resulting suspension was stirred at room temperature under a hydrogen atmosphere for 2.5 h. The reaction mixture was filtered through Celite® and washed with EtOAc. The combined filtrate and washes were concentrated under reduced pressure. Purification by flash chromatography (20-50% EtOAc/hexanes eluent) provided N-(4-cyclohexylbenzyl)-N-(3-hydroxy-4-(hydroxycarbamoyl)phenyl)-1-((perfluorophenyl)sulfonyl)azetidine-3-carboxamide (62 mg, 95% yield). HRMS (ESI) m/z 654.1697 [M+H]⁺.

Example 56

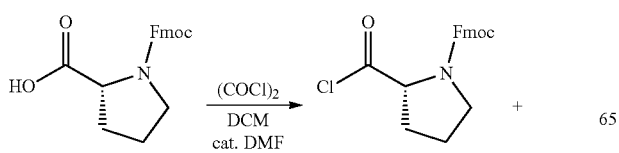

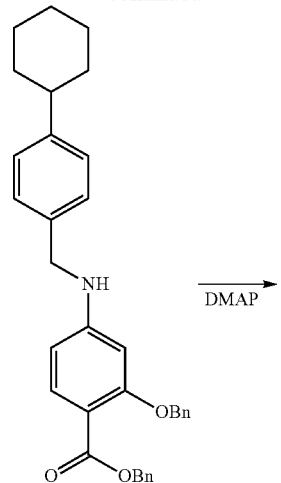

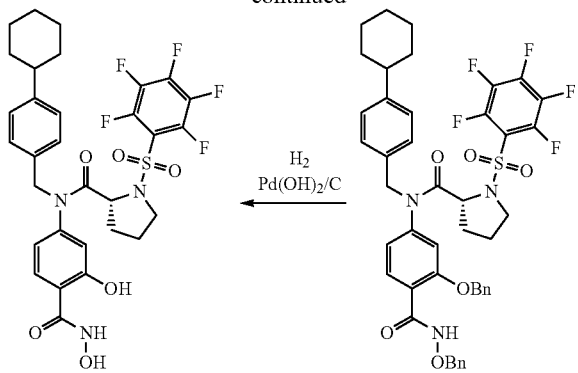

(R)—N-(4-cyclohexylbenzyl)-N-(3-hydroxy-4-(hydroxycarbamoyl)phenyl)-1-((pentafluorophenyl)sulfonyl)pyrrolidine-2-carboxamide

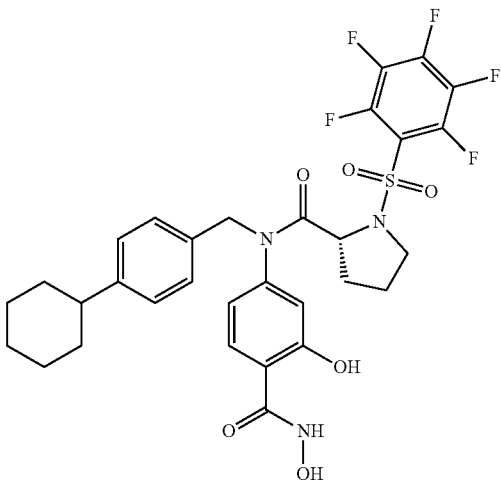 [SMILES: O=C(NO)c1ccc(N(Cc2ccc(C3CCCCC3)cc2)C(=O)[C@H]2CCCN2S(=O)(=O)c2c(F)c(F)c(F)c(F)c2F)cc1O]

Step 1: To a stirred solution of (((9H-fluoren-9-yl)methoxy)carbonyl)-D-proline (0.97 g, 2.88 mmol) in DCM (30 mL) under nitrogen was added oxalyl chloride (0.45 mL, 5.18 mmol) and DMF (2 drops). The resulting reaction solution was stirred at room temperature under nitrogen for 1.5 h and then concentrated in vacuo to provide (9H-fluoren-9-yl)methyl (R)-2-(chlorocarbonyl)pyrrolidine-1-carboxylate as a yellow foam which was used as is. To a stirred solution of the freshly generated acid chloride, (9H-fluoren-9-yl)methyl (R)-2-(chlorocarbonyl)pyrrolidine-1-carboxylate, (2.88 mmol) and benzyl 2-(benzyloxy)-4-((4-cyclohexylbenzyl)amino)benzoate (1.1 g, 2.19 mmol) in DCM (30 mL) under nitrogen was added DMAP (0.32 g, 2.63 mmol) and the resulting reaction was stirred at room temperature overnight. The reaction mixture was then poured onto water and extracted with DCM (3×). The combine organic extracts were dried over sodium sulfate, concentrated under reduced pressure and the resulting residue purified by flash chromatography (25% EtOAc/hexanes eluent) to afford (9H-fluoren-9-yl)methyl (R)-2-((3-(benzyloxy)-4-((benzyloxy)carbonyl)phenyl)(4-cyclohexylbenzyl)carbamoyl)pyrrolidine-1-carboxylate (1.62 g, 90% yield). MS (ESI) m/z 825.30 [M+H]+.

Step 2: To as stirred solution of (9H-fluoren-9-yl)methyl (R)-2-((3-(benzyloxy)-4-((benzyloxy)carbonyl)phenyl)(4-cyclohexylbenzyl)carbamoyl)pyrrolidine-1-carboxylate (390 mg, 0.47 mmol) in DCM (15 mL) under nitrogen at 0° C. was added piperidine (15 mL) and the resulting mixture was stirred at 0° C. for 2 h. The reaction was complete by LCMS. MS (ESI) m/z 603.30 [M+H]+. Concentration in vacuo provided crude benzyl (R)-2-(benzyloxy)-4-(N-(4-cyclohexylbenzyl)pyrrolidine-2-carboxamido)benzoate which was used as is. To the crude product, benzyl (R)-2-(benzyloxy)-4-(N-(4-cyclohexylbenzyl)pyrrolidine-2-carboxamido)benzoate (0.47 mmol) in methanol (9 mL) and THF (36 mL) was added 6N aqueous sodium hydroxide (9 mL) and the resulting mixture was stirred at room temperature for overnight. The reaction was complete by LCMS. MS (ESI) m/z 513.30 [M+H]+. The reaction mixture was concentrated to 15 mL, poured onto EtOAc/water and the pH was adjusted to 5 with 10% aqueous HCl and the resulting mixture extracted with EtOAc (4×). The combined organic extracts were dried over anhydrous sodium sulfate and concentrated in vacuo to provide (R)-2-(benzyloxy)-4-(N-(4-cyclohexylbenzyl)pyrrolidine-2-carboxamido)benzoic acid which was used as is. To a solution of crude (R)-2-(benzyloxy)-4-(N-(4-cyclohexylbenzyl)pyrrolidine-2-carboxamido)benzoic acid (0.47 mmol) in DCM (10 mL) at 0° C. under nitrogen was added DIPEA (0.2 mL, 1.175 mmol) followed by pentafluorobenzene sulfonyl chloride (0.14 mL, 0.94 mmol). The resulting reaction mixture was allowed to warm to room temperature and stirred at this temperature overnight. The crude reaction mixture was poured onto water and extracted with DCM (3×). The combined organic extracts were dried over anhydrous sodium sulfate, concentrated under reduced pressure and the resulting residue purified by flash chromatography (10-30% EtOAc/hexanes gradient) to provide (R)-2-(benzyloxy)-4-(N-(4-cyclohexylbenzyl)-1-((perfluorophenyl)sulfonyl)pyrrolidine-2-carboxamido)benzoic acid (137 mg, 39% yield over the 3 steps). MS (ESI) m/z 743.20 [M+H]+.

Step 3: To a stirred solution of (R)-2-(benzyloxy)-4-(N-(4-cyclohexylbenzyl)-1-((perfluorophenyl)sulfonyl)pyrrolidine-2-carboxamido)benzoic acid (137 mg, 0.18 mmol) in DCM (10 mL) under nitrogen was added oxalyl chloride (0.022 mL, 0.26 mmol) and DMF (small drop). The resulting reaction solution was stirred at room temperature under nitrogen for 2 h and then concentrated in vacuo to provide (R)-2-(benzyloxy)-4-(N-(4-cyclohexylbenzyl)-1-((perfluorophenyl)sulfonyl)pyrrolidine-2-carboxamido)benzoyl chloride which was used as is.

Step 4: To a solution of O-benzylhydroxylamine hydrochloride (40 mg, 0.25 mmol) in DMF (2 mL) was added TEA (0.065 mL, 0.47 mmol). The mixture was stirred for 15 min, then added to a solution of the crude acid chloride, (R)-2-(benzyloxy)-4-(N-(4-cyclohexylbenzyl)-1-((perfluorophenyl)sulfonyl)-pyrrolidine-2-carboxamido)benzoyl chloride (0.18 mmol), in THF (5 mL) at 0° C. under nitrogen. The resultant reaction mixture was warmed to room temperature and stirred for 1.5 h. The reaction was quenched with 10% aqueous potassium bisulfate, poured onto water and extracted with ether (3×). The combined organic extracts were washed with brine, dried over anhydrous sodium sulfate and concentrated under reduced pressure. The resulting residue was purified by flash chromatography (25-35% EtOAc/hexanes) to provide (R)—N-(3-(benzyloxy)-4-((benzyloxy)carbamoyl)phenyl)-N-(4-cyclohexylbenzyl)-1-((perfluorophenyl)sulfonyl)pyrrolidine-2-carboxamide (73 mg, 48% yield). MS (ESI) m/z 848.30 [M+H]+.

Step 5: To a stirred solution of (R)—N-(3-(benzyloxy)-4-((benzyloxy)carbamoyl)phenyl)-N-(4-cyclohexylbenzyl)-

1-((perfluorophenyl)sulfonyl)pyrrolidine-2-carboxamide (73 mg, 0.086 mmol) in methanol (2 mL) and THF (2 mL) was added 20% Pd(OH)₂/C (5 mg) and the resulting suspension was stirred at room temperature under a hydrogen atmosphere for 4 h. The reaction mixture was filtered through Celite® and washed with EtOAc. The combined filtrate and washes were concentrated under reduced pressure and residue purified by flash chromatography (30% EtOAc/hexanes eluent) to provide (R)—N-(4-cyclohexyl-benzyl)-N-(3-hydroxy-4-(hydroxycarbamoyl)phenyl)-1-((perfluorophenyl)sulfonyl)pyrrolidine-2-carboxamide (18 mg, 31% yield). MS (ESI) m/z 668.1828 [M+H]+. HRMS (ESI+) calculated for C31H30F5N3O6S: 667.1775, found 667.1768.

Example 57

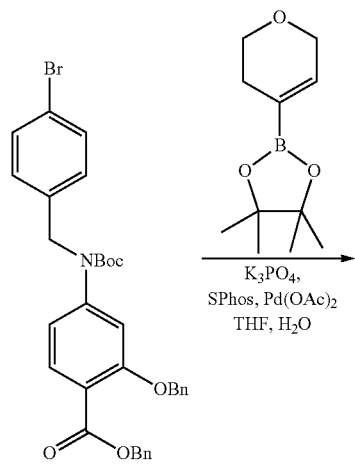

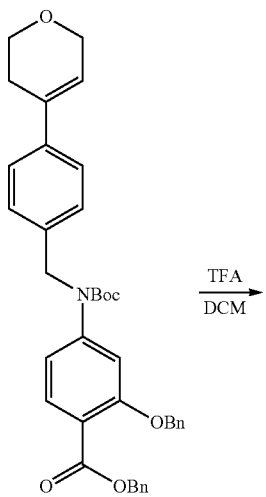

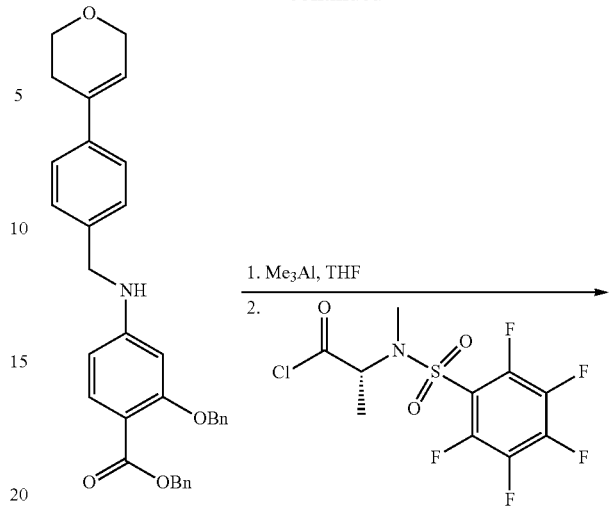

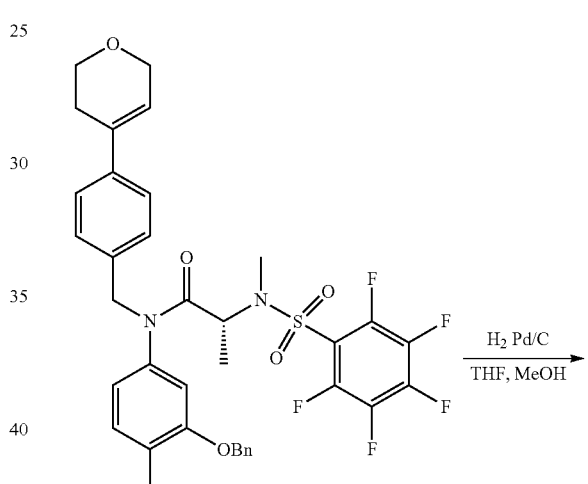

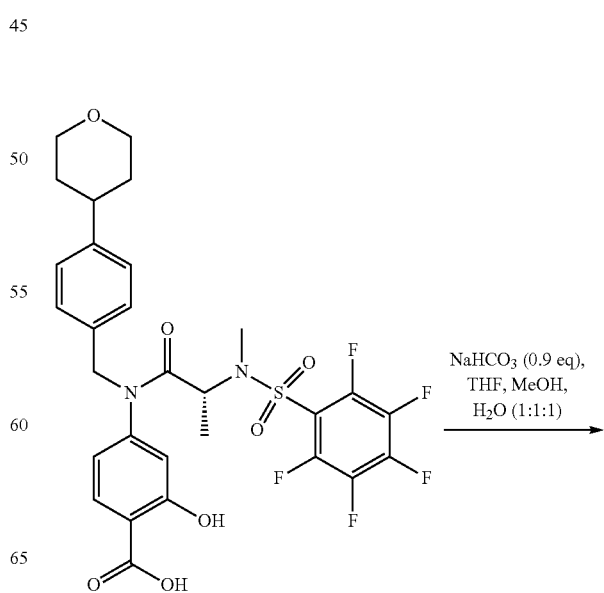

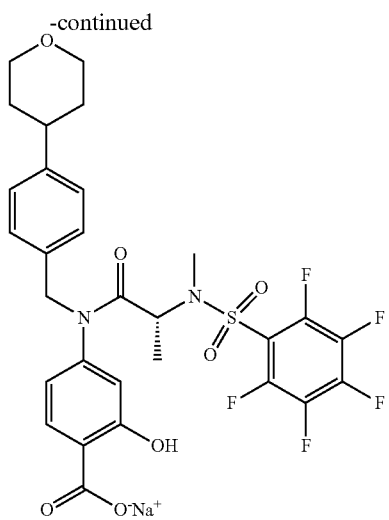

(R)-2-Hydroxy-4-(2-((2,3,4,5,6-pentafluoro-N-methylphenyl)sulfonamido)-N-(4-(tetrahydro-2H-pyran-4-yl)benzyl)propanamido)benzoic acid

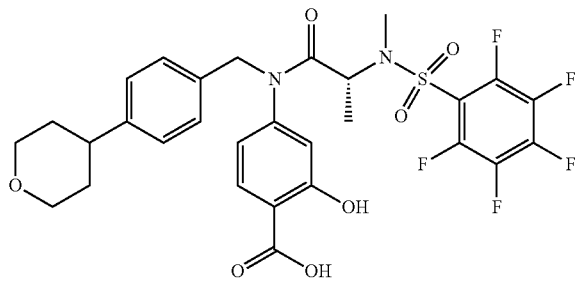 [SMILES: C[C@H](C(=O)N(Cc1ccc(C2CCOCC2)cc1)c1ccc(C(=O)O)c(O)c1)N(C)S(=O)(=O)c1c(F)c(F)c(F)c(F)c1F]

Step 1: In a dry flask under nitrogen was added benzyl 2-(benzyloxy)-4-((4-bromobenzyl)(tert-butoxycarbonyl)amino)benzoate (1.7 g, 2.82 mmol), Pd(OAc)$_2$ (32 mg, 0.141 mmol), SPhos (116 mg, 0.282 mmol), 3,6-dihydro-2H-pyran-4-boronic acid pinacol ester (592.6 mg, 2.82 mmol), potassium phosphate tribasic (1.2 g, 5.64 mmol) and water (0.1 mL). The flask was back-flushed with nitrogen, THF (36 mL) was added and the flask was heated at 45° C. for 18 h. Reaction was not complete. Additional Pd(OAc)$_2$ (32 mg, 0.141 mmol), SPhos (116 mg, 0.282 mmol) and 3,6-dihydro-2H-pyran-4-boronic acid pinacol ester (592.6 mg, 2.82 mmol) were added and the reaction was warmed to 60° C. for 27 h. The crude reaction mixture was poured onto water and extracted with EtOAc (3×). The combined extracts were washed with brine, dried over anhydrous sodium sulfate and concentrated under reduced pressure. The resulting residue purified by flash chromatography (10-20% EtOAc/hexanes) to afford benzyl 2-(benzyloxy)-4-((tert-butoxycarbonyl)-(4-(3,6-dihydro-2H-pyran-4-yl)benzyl)amino)benzoate (315 mg, 18% yield). 1H NMR (300 MHz, Chloroform-d) δ 7.80 (d, J=8.4 Hz, 1H), 7.45-7.29 (m, 12H), 7.15 (d, J=8.1 Hz, 2H), 6.87 (d, J=1.9 Hz, 1H), 6.82 (dd, J=8.4, 1.9 Hz, 1H), 6.14 (s, 1H), 5.34 (s, 2H), 5.04 (s, 2H), 4.81 (s, 2H), 4.34 (dd, J=5.5 Hz, J=2.8 Hz, 2H), 3.95 (t, J=5.6 Hz, 2H), 2.53 (t, J=5.6 Hz, 2H), 1.44 (s, 9H). MS (ESI): 628 [M+Na]+.

Step 2: A solution of benzyl 2-(benzyloxy)-4-((tert-butoxycarbonyl)(4-(3,6-dihydro-2H-pyran-4-yl)benzyl)amino)benzoate (310 mg, 0.51 mmol) in DCM (6 mL) under nitrogen was treated with TFA (1.5 mL) and the resultant reaction mixture was stirred at room temperature for 4.5 h. The mixture was poured onto saturated aqueous sodium bicarbonate with resultant pH=7 and extracted with DCM (3×). The combined organic phase was dried over sodium sulfate and concentrated to dryness. Purification by flash chromatography (70:20:10 hexanes:DCM:EtOAc eluent) provided benzyl 2-(benzyloxy)-4-((4-(3,6-dihydro-2H-pyran-4-yl)benzyl)amino) benzoate (134 mg, 73% yield) as an off-white solid. 1H NMR (300 MHz, Chloroform-d) δ 7.85 (d, J=8.6 Hz, 1H), 7.49-7.29 (m, 14H), 6.23 (dd, J=8.6, 2.2 Hz, 1H), 6.18 (d, J=2.2 Hz, 1H), 6.15 (br. s, 1H), 5.32 (s, 2H), 5.10 (s, 2H), 4.35 (d, J=2.5 Hz, 2H), 3.96 (t, J=5.3 Hz, 2H), 2.54 (dq, J=5.3, 2.9 Hz, 2H).

Step 3: To a stirred solution of benzyl 2-(benzyloxy)-4-((4-(3,6-dihydro-2H-pyran-4-yl)benzyl)amino) benzoate (131 mg, 0.26 mmol) in THF (5 mL) under nitrogen at 0° C. was added a solution of trimethylaluminum (0.33 mL of 2M in toluene, 0.66 mmol) and the mixture was warmed to room temperature over 15 min. To the resulting solution was added a solution of N-methyl-N-((pentafluorophenyl)sulfonyl)-D-alaninoyl chloride (127 mg, 0.36 mmol) in THF (4 mL). The reaction mixture was stirred at reflux temperature for 2 h, poured onto 10% KHSO$_4$/Na$_2$SO$_4$ aqueous buffer and ice and then extracted 3 times with EtOAc. The combined organic layers were washed with brine, dried over anhydrous sodium sulfate, and concentrated under reduced pressure. The resulting residue was purified by flash chromatography (5-15% EtOAc/(8:1 hexanes:DCM mixture)) as a stepwise gradient to provide benzyl (R)-2-(benzyloxy)-4-(N-(4-(3,6-dihydro-2H-pyran-4-yl)benzyl)-2-((2,3,4,5,6-pentafluoro-N-methylphenyl)sulfonamido)propanamido) benzoate (89 mg, 42% yield) as a white foam. HRMS (ESI) m/z 821.2239 [M+H]+.

Step 4: To a stirred solution of benzyl (R)-2-(benzyloxy)-4-(N-(4-(3,6-dihydro-2H-pyran-4-yl)benzyl)-2-((2,3,4,5,6-pentafluoro-N-methylphenyl)sulfonamido)propanamido) benzoate (87 mg, 0.106 mmol) in methanol (4 mL) and THF (4 mL) was added 10% Pd/C (17 mg) and the resulting suspension was stirred at room temperature under a hydrogen atmosphere until the reaction was complete as determined by LCMS (2 h). The reaction mixture was filtered through Celite® and washed with methanol (2×). The combined filtrate and washes were concentrated to provide (R)-2-hydroxy-4-(2-((2,3,4,5,6-pentafluoro-N-methylphenyl)sulfonamido)-N-(4-(tetrahydro-2H-pyran-4-yl)benzyl) propanamido)benzoic acid (68 mg, 100% yield). HRMS (ESI) m/z 643.1563 [M+H]+.

Example 58

(R)-4-(N-(4-(4,4-difluorocyclohexyl)benzyl)-2-((2,3,4,5,6-pentafluoro-N-methylphenyl)sulfonamido)propanamido)-2-hydroxybenzoic acid

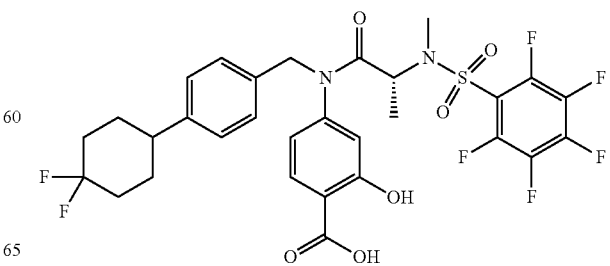

Preparation by a similar procedure to example 57, except substituting 4,4-difluorocyclohex-1-enylboronic acid pinacol ester for 3,6-dihydro-2H-pyran-4-boronic acid pinacol ester in step 1 afforded (R)-4-(N-(4-(4,4-difluorocyclohexyl)benzyl)-2-((2,3,4,5,6-pentafluoro-N-methylphenyl)sulfonamido)propanamido)-2-hydroxybenzoic acid. MS (ESI) m/z 677.1 [M+H]+.

Example 59

Sodium (R)-2-hydroxy-4-(2-((2,3,4,5,6-pentafluoro-N-methylphenyl)sulfonamido)-N-(4-(tetrahydro-2H-pyran-4-yl)benzyl)propanamido)benzoate

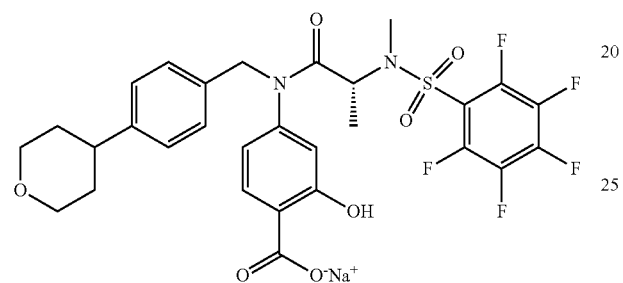

To a solution of (R)-2-hydroxy-4-(2-((2,3,4,5,6-pentafluoro-N-methylphenyl)sulfonamido)-N-(4-(tetrahydro-2H-pyran-4-yl)benzyl)propanamido)benzoic acid (68 mg, 0.106 mmol) in 3 mL of 1:1:1 THF:MeOH:H2O was added sodium bicarbonate (8 mg, 0.095 mmol) and the resultant mixture was stirred at room temperature for 4 h and then concentrated in vacuo. Trituration with ether provided sodium (R)-2-hydroxy-4-(2-((2,3,4,5,6-pentafluoro-N-methylphenyl)sulfonamido)-N-(4-(tetrahydro-2H-pyran-4-yl)benzyl)propanamido)benzoate (65 mg) as a cream colored solid. MS (ESI) m/z 643.1580 [M+H]+.

Example 60

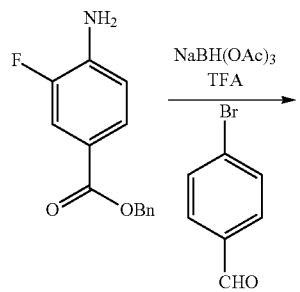

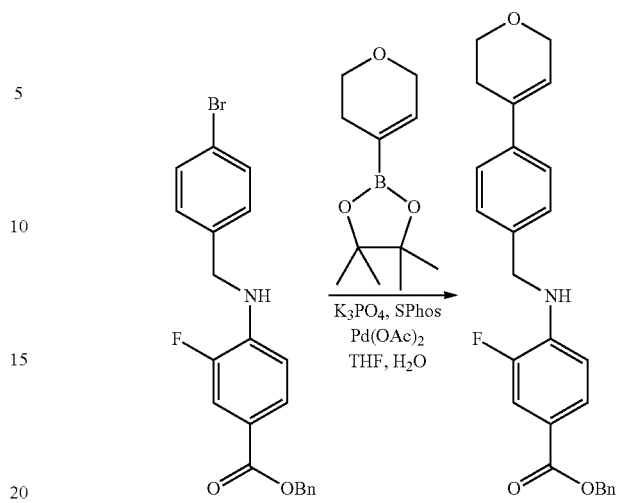

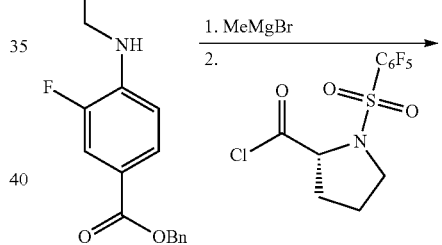

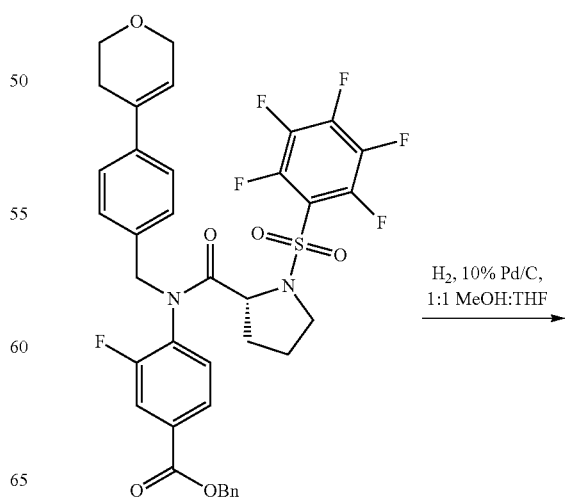

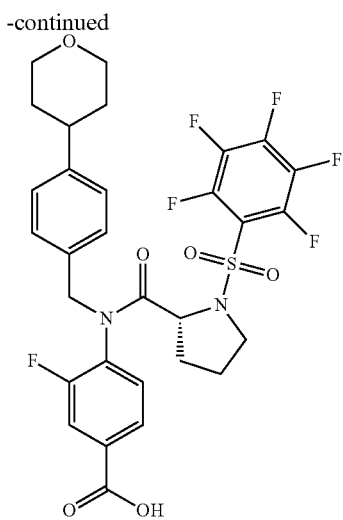

(R)-3-Fluoro-4-(1-((perfluorophenyl)sulfonyl)-N-(4-(tetrahydro-2H-pyran-4-yl)benzyl)pyrrolidine-2-carboxamido)benzoic acid

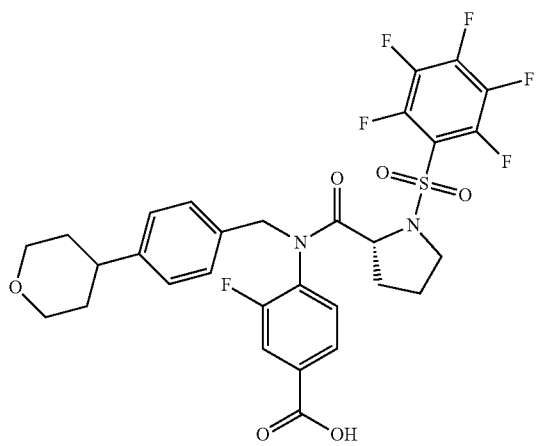 [SMILES: O=C(O)c1ccc(N(Cc2ccc(C3CCOCC3)cc2)C(=O)[C@H]2CCCN2S(=O)(=O)c2c(F)c(F)c(F)c(F)c2F)c(F)c1]

Step 1: To a solution of benzyl 4-amino-3-fluorobenzoate (318 mg, 1.30 mmol) in TFA (3.0 mL) under nitrogen at 0° C. was added sodium triacetoxyborohydride (551 mg, 2.60 mmol) portion wise. The mixture was stirred at 0° C. for 10 min before addition of 4-bromobenzaldehyde (255 mg, 1.38 mmol). The resulting reaction mixture was stirred at room temperature for 4.5 h, poured onto cold water and extracted with EtOAc (1×). The organic extracts were washed with water, then with 10% aqueous sodium bicarbonate, then with brine, dried over anhydrous sodium sulfate and concentrated under reduced pressure. The pH after the last wash was 7-8. Purification by flash chromatography (8-10% EtOAc/hexanes) provided benzyl 4-((4-bromobenzyl)amino)-3-fluorobenzoate (382 mg, 71% yield). 1H NMR (300 MHz, Chloroform-d) δ 7.80-7.66 (m, 2H), 7.55-7.31 (m, 7H), 7.24 (d, J=8.4 Hz, 2H), 6.63 (t, J=8.4 Hz, 1H), 5.32 (s, 2H), 4.41 (s, 2H).

Step 2: In a dry flask under nitrogen was added benzyl 4-((4-bromobenzyl)amino)-3-fluorobenzoate (265 mg, 0.64 mmol), Pd(OAc)$_2$ (7.2 mg, 0.0320 mmol), SPhos (26.3 mg, 0.064 mmol), 3,6-dihydro-2H-pyran-4-boronic acid pinacol ester (201.6 mg, 0.96 mmol), potassium phosphate tribasic (271.6 mg, 1.28 mmol) and water (22.8 mg, 1.27 mmol). The flask was back-flushed with nitrogen, THF (8.2 mL) was added and the flask was heated at 40° C. for 16 h. The crude reaction mixture was poured onto water and extracted with EtOAc (1×). The organic layer was washed with brine, dried over anhydrous sodium sulfate and concentrated under reduced pressure. The resulting residue was purified by flash chromatography (10-15% EtOAc/hexanes) to provide benzyl 4-((4-(3,6-dihydro-2H-pyran-4-yl)benzyl)amino)-3-fluorobenzoate (219 mg, 82% yield) as a white solid. 1H NMR (300 MHz, Chloroform-d) δ 7.80-7.64 (m, 2H), 7.51-7.29 (m, 9H), 6.69 (t, J=8.3 Hz, 1H), 6.19-6.07 (m, 1H), 5.32 (s, 2H), 4.44 (s, 2H), 4.34 (q, J=2.8 Hz, 2H), 3.95 (t, J=5.5 Hz, 2H), 2.62-2.44 (m, 2H).

Step 3: To a stirred solution of benzyl 4-((4-(3,6-dihydro-2H-pyran-4-yl)benzyl)amino)-3-fluorobenzoate (147.4 mg, 0.353 mmol) in THF (3 mL) at 0° C. under nitrogen was added a solution of methylmagnesium bromide (0.63 mL of 1.4M in THF, 0.883 mmol) and the mixture was stirred a 0° C. for 10 min before addition of ((perfluorophenyl)sulfonyl)-D-prolinoyl chloride (192.6 mg, 0.53 mmol). The reaction mixture was allowed to warm to room temperature and stirred at this temperature for 14.5 h. To the reaction mixture was added a cold solution of saturated aqueous ammonium chloride followed by water and the resultant mixture was extracted with EtOAc (2×). The combined organic extracts were washed with brine, dried over anhydrous sodium sulfate and concentrated under reduced pressure. Purification by flash chromatography (20-25% EtOAc/hexanes eluent) followed by re-purification by preparative TLC (25% EtOAc/hexanes eluent) provided benzyl (R)-4-(N-(4-(3,6-dihydro-2H-pyran-4-yl)benzyl)-1-((perfluorophenyl)sulfonyl)pyrrolidine-2-carboxamido)-3-fluorobenzoate (102.5 mg, 39% yield) as an oil. MS (ESI): 745.2 [M+H]+.

Step 4: To a stirred solution of benzyl (R)-4-(N-(4-(3,6-dihydro-2H-pyran-4-yl)benzyl)-1-((perfluorophenyl)sulfonyl)pyrrolidine-2-carboxamido)-3-fluorobenzoate (100 mg, 0.134 mmol) in methanol (1.6 mL) and THF (1.6 mL) was added 10% Pd/C (12 mg) and the resulting suspension was stirred at room temperature under a hydrogen atmosphere for 22 h. The reaction mixture was filtered through Celite® and washed with DCM/methanol (2×). The combined filtrate and washes were concentrated and the resulting residue purified by preparative TLC (1:1 hexanes:EtOAc with 0.1% acetic acid) to provide (R)-3-fluoro-4-(1-((perfluorophenyl)sulfonyl)-N-(4-(tetrahydro-2H-pyran-4-yl)benzyl)pyrrolidine-2-carboxamido)benzoic acid (18 mg, 20% yield). MS (ESI): 657.1 [M+H]+.

Example 61

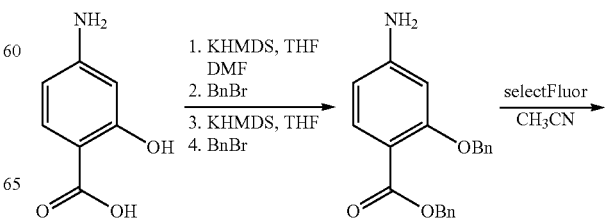

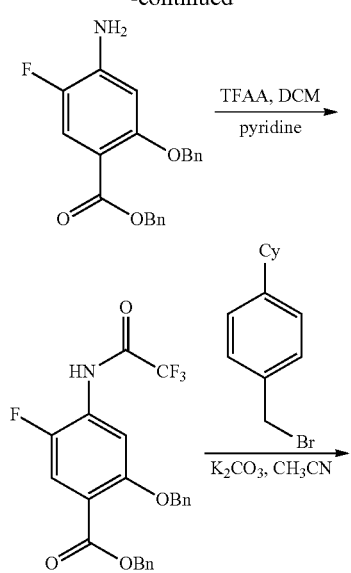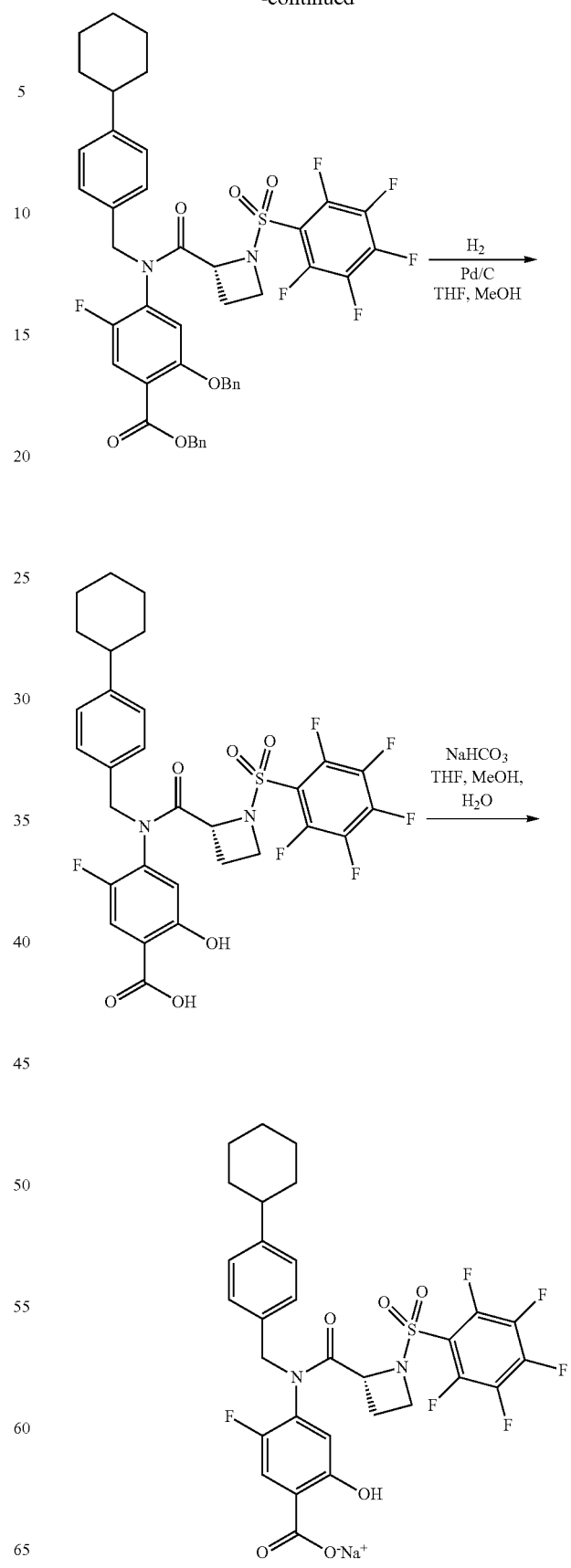

(R)-4-(N-(4-Cyclohexylbenzyl)-1-((perfluorophenyl)sulfonyl)azetidine-2-carboxamido)-5-fluoro-2-hydroxybenzoic acid

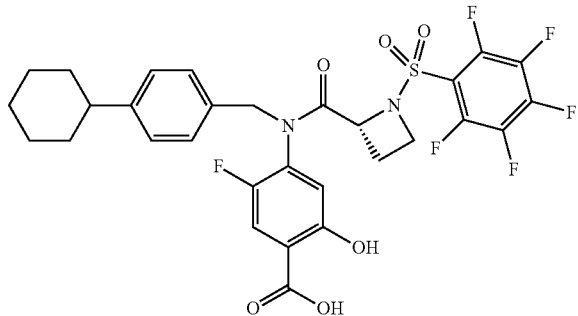 [SMILES: O=C(O)c1cc(F)c(N(Cc2ccc(C3CCCCC3)cc2)C(=O)[C@H]2CCN2S(=O)(=O)c2c(F)c(F)c(F)c(F)c2F)cc1O]

Step 1: To a stirred solution of 4-aminosalicylic acid (2.3 g, 15 mmol) in dry DMF (60 mL) under nitrogen at 0° C. was added drop wise a solution of KHMDS (16.5 mL of 1M in THF, 16.5 mmol) and the resulting mixture was stirred at 0° C. for 15 min before addition of benzyl bromide (1.96 mL, 16.5 mmol). The reaction mixture was allowed to warm to room temperature and stirred at this temperature for 4 h before cooling again to 0° C. To this stirred solution at 0° C. was added drop wise a solution of KHMDS (16.5 mL of 1M in THF, 16.5 mmol) and the resulting mixture was stirred at 0° C. for 15 min before addition of benzyl bromide (1.96 mL, 16.5 mmol). The reaction mixture was allowed to warm to room temperature and stirred at this temperature overnight. The crude reaction mixture was poured onto cold water and extracted with ether (3×200 mL). The combined ethereal extracts were washed with water, then washed with brine, dried over anhydrous sodium sulfate and concentrated under reduced pressure. Chromatography (20-40% EtOAc/hexanes) provided benzyl 4-amino-2-(benzyloxy)benzoate (3.03 g, 60% yield) as a tan solid. 1H NMR (300 MHz, Chloroform-d) δ 7.92-7.72 (m, 1H), 7.52-7.29 (m, 10H), 6.40-6.26 (m, 2H), 5.33 (s, 2H), 5.14 (s, 2H).

Step 2: To a stirred solution of benzyl 4-amino-2-(benzyloxy)benzoate (2.89 g, 8.67 mmol) in dry acetonitrile (42 mL) was added under nitrogen Selectfluor® (3.305 g, 8.67 mmol). The mixture was stirred at room temperature for 1 h, poured onto water and extracted with EtOAc (2×). The combined organic extract was washed with brine, dried over anhydrous sodium sulfate and concentrated under reduced pressure. Purification by flash chromatography (20-25% EtOAc/hexanes eluent) followed by trituration with hexanes provided benzyl 4-amino-2-(benzyloxy)-5-fluorobenzoate (988 mg, 32% yield) as a yellow solid. 1H NMR (300 MHz, Chloroform-d) δ 7.65 (d, J=11.8 Hz, 1H), 7.54-7.30 (m, 10H), 6.36 (d, J=7.3 Hz, 1H), 5.32 (s, 2H), 5.11 (s, 2H), 4.11 (br. s, 2H).

Step 3: To a stirred solution of benzyl 4-amino-2-(benzyloxy)-5-fluorobenzoate (675 mg, 1.92 mmol) in DCM (10 mL) under nitrogen at 0° C. was added pyridine (0.34 mL, 4.22 mmol) followed by TFFA (0.30 mL, 2.11 mmol). The reaction mixture was allowed to warm to room temperature and stirred at this temperature for 1.5 h. The mixture was diluted with DCM and washed with 10% aqueous KHSO$_4$/Na$_2$SO$_4$ buffer (2×), then washed with saturated aqueous sodium bicarbonate, dried over anhydrous sodium sulfate and concentrated under reduced pressure. Purification by flash chromatography (10-15% EtOAc/hexanes eluent) provided benzyl 2-(benzyloxy)-5-fluoro-4-(2,2,2-trifluoroacetamido)benzoate (766 mg, 89% yield). 1H NMR (300 MHz, Chloroform-d) δ 8.20 (d, J=6.3 Hz, 1H), 8.17 (br. s, 1H), 7.74 (d, J=11.1 Hz, 1H), 7.53-7.31 (m, 10H), 5.36 (s, 2H), 5.20 (s, 2H).

Step 4: To a stirred solution of benzyl 2-(benzyloxy)-5-fluoro-4-(2,2,2-trifluoroacetamido)benzoate (130.6 mg, 0.29 mmol) and 1-(bromomethyl)-4-cyclohexylbenzene (103.4 mg, 0.41 mmol) in acetonitrile (4 mL) was added potassium carbonate (52.2 mg, 0.38 mmol). The resulting reaction mixture was stirred at 60° C. for 3.5 h. After cooling to room temperature cold 10% aqueous KHSO$_4$/Na$_2$SO$_4$ buffer was added and the mixture was extracted with EtOAc (2×). The combined organic extract was washed with brine, dried over anhydrous sodium sulfate and concentrated under reduced pressure. The resulting residue was purified by flash chromatography (5% EtOAc/hexanes eluent) provided benzyl 2-(benzyloxy)-4-(N-(4-cyclohexylbenzyl)-2,2,2-trifluoroacetamido)-5-fluorobenzoate (161.2 mg, 89% yield as a colorless oil. 1H NMR (300 MHz, Chloroform-d) δ 7.66 (d, J=9.7 Hz, 1H), 7.47-7.29 (m, 10H), 7.14 (d, J=7.8 Hz, 2H), 7.06 (d, J=7.8 Hz, 2H), 6.33 (d, J=5.9 Hz, 1H), 5.48 (d, J=14.0 Hz, 1H), 5.35 (s, 2H), 4.85-4.63 (m, 2H), 4.20 (d, J=14.0 Hz, 1H), 2.56-2.41 (m, 1H), 1.94-1.67 (m, 6H), 1.50-1.25 (m, 4H).

Step 5: To a stirred solution of benzyl 2-(benzyloxy)-4-(N-(4-cyclohexylbenzyl)-2,2,2-trifluoroacetamido)-5-fluorobenzoate (159.4 mg, 0.257 mmol) in THF (2.0 mL) and methanol (2.0 mL) was added potassium carbonate (59.6 mg, 0.43 mmol) under nitrogen and the mixture was stirred at room temperature for 3 h. To the crude reaction mixture was added cold saturated aqueous ammonium chloride followed by water and the resulting mixture was extracted with EtOAc (2×). The combined organic extract was washed with brine, dried over anhydrous sodium sulfate and concentrated under reduced pressure. The crude residue was combined with the crude product from a 0.1 mmol scale reaction and purified by flash chromatography (7.5-9% EtOAc/hexanes eluent) to provide benzyl 2-(benzyloxy)-4-((4-cyclohexylbenzyl)amino)-5-fluorobenzoate (171.4 mg, 91% yield) as a colorless solid.

Step 6: To a stirred solution of benzyl 2-(benzyloxy)-4-((4-cyclohexylbenzyl)amino)-5-fluorobenzoate (119 mg, 0.227 mmol) in dry THF (1.8 mL) under nitrogen at 0° C. was added methylmagnesium bromide (0.406 mL of 1.4 M in THF, 0.568 mmol) and the resulting solution was stirred at 0° C. for 15 min before addition of solid (R)-1-((perfluorophenyl)sulfonyl)azetidine-2-carbonyl chloride (119.2 mg, 0.34 mmol). The resulting mixture was allowed to warm to room temperature and stirred at room temperature for 7.5 h. To the crude reaction mixture was added cold saturated aqueous ammonium chloride followed by water and the resulting mixture was extracted with EtOAc (2×). The combined organic extract was washed with brine, dried over anhydrous sodium sulfate and concentrated under reduced pressure. The crude residue was combined with the crude product from a 0.138 mmol scale reaction and purified by flash chromatography (10-15% EtOAc/hexanes eluent) followed re-purification by preparative tlc (15% EtOAc/hexanes) to provide benzyl (R)-2-(benzyloxy)-4-(N-(4-cyclohexylbenzyl)-1-((perfluorophenyl)sulfonyl)-azetidine-2-carboxamido)-5-fluorobenzoate (94 mg). MS (ESI): 837.2 [M+H]+.

Step 7: To a stirred solution of benzyl (R)-2-(benzyloxy)-4-(N-(4-cyclohexylbenzyl)-1-((perfluorophenyl)sulfonyl)-azetidine-2-carboxamido)-5-fluorobenzoate (92 mg, 0.109 mmol) in methanol (1.32 mL) and THF (1.32 mL) was added 10% Pd/C (9.8 mg) and the resulting suspension was stirred at room temperature under a hydrogen atmosphere for 22 h. The reaction mixture was filtered through Celite® and washed with methanol (2×). The combined filtrate and washes were concentrated to provide (R)-4-(N-(4-cyclohexylbenzyl)-1-((perfluorophenyl)sulfonyl)azetidine-2-carboxamido)-5-fluoro-2-hydroxybenzoic acid. MS (ESI) m/z 657.1486 [M+H]+.

Example 62

Sodium (R)-4-(N-(4-cyclohexylbenzyl)-1-((perfluorophenyl)sulfonyl)azetidine-2-carboxamido)-5-fluoro-2-hydroxybenzoate

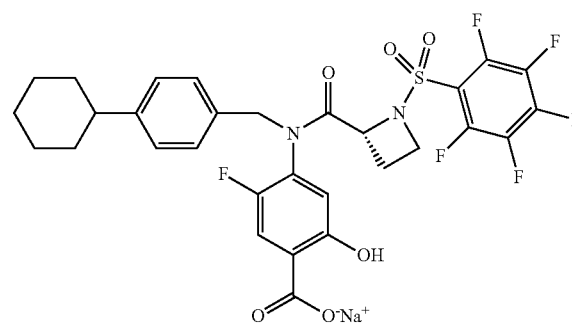

To a solution of (R)-4-(N-(4-cyclohexylbenzyl)-1-((perfluorophenyl)sulfonyl)azetidine-2-carboxamido)-5-fluoro-2-hydroxybenzoic acid (41.5 mg, 0.063 mmol) in 3 mL of 1:1:1 THF:MeOH:H2O was added sodium bicarbonate (4.8 mg, 0.057 mmol) and the resultant mixture was stirred at room temperature for 4.5 h and then concentrated in vacuo. Trituration with ether provided sodium (R)-4-(N-(4-cyclohexylbenzyl)-1-((perfluorophenyl)sulfonyl)azetidine-2-carboxamido)-5-fluoro-2-hydroxybenzoate (34 mg) as a white solid. MS (ESI) m/z 679.1288 [M+Na]+.

Example 63

(R)-5-Fluoro-2-hydroxy-4-(N-(4-isopropylbenzyl)-1-((perfluorophenyl)sulfonyl)azetidine-2-carboxamido)benzoic acid

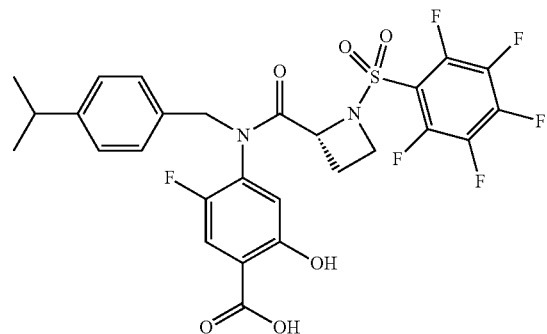 [SMILES: CC(C)c1ccc(CN(C(=O)[C@H]2CCN2S(=O)(=O)c2c(F)c(F)c(F)c(F)c2F)c2cc(O)c(C(=O)O)cc2F)cc1]

Preparation by a similar procedure to example 61, except substituting 1-(bromomethyl)-4-isopropylbenzene for 1-(bromomethyl)-4-cyclohexylbenzene in step 4 afforded (R)-5-fluoro-2-hydroxy-4-(N-(4-isopropylbenzyl)-1-((perfluorophenyl)sulfonyl)azetidine-2-carboxamido)benzoic acid. MS (ESI) m/z 617.1183 [M+H]+.

Example 64

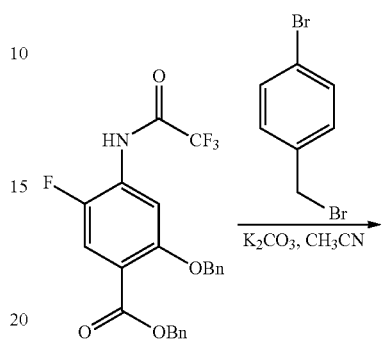

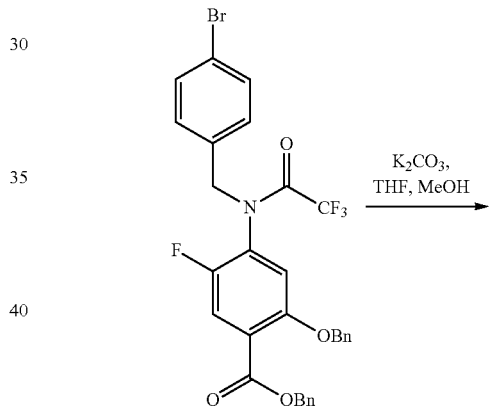

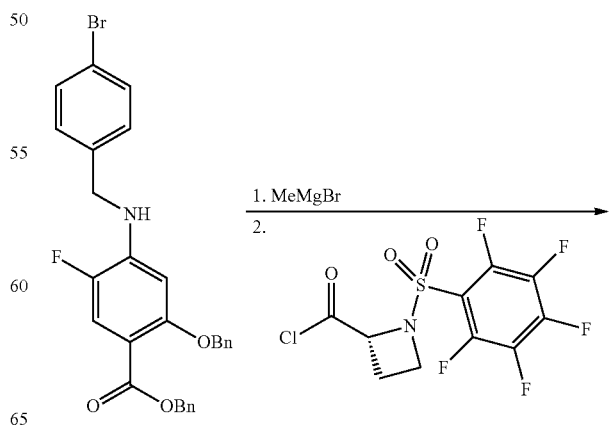

191
-continued

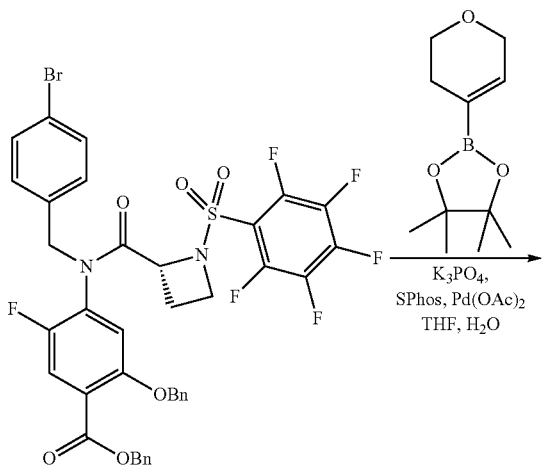

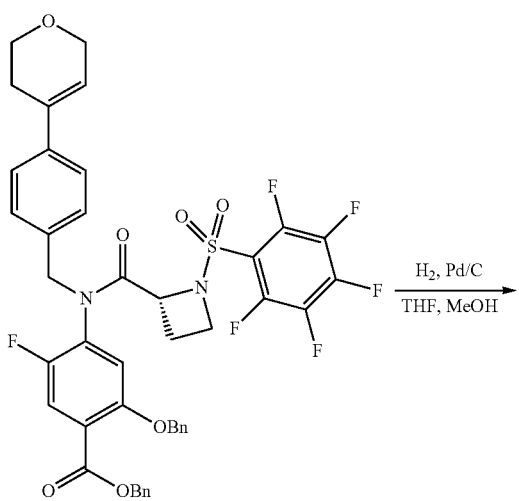

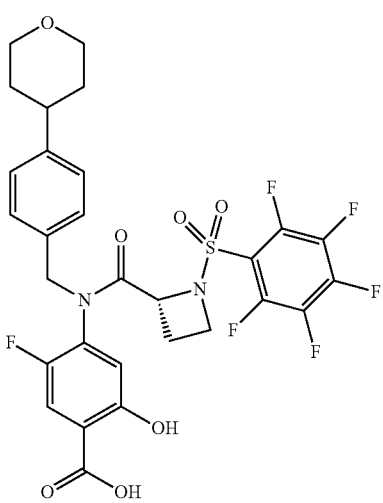

192
(R)-5-Fluoro-2-hydroxy-4-(1-((perfluorophenyl)
sulfonyl)-N-(4-(tetrahydro-2H-pyran-4-yl)benzyl)
azetidine-2-carboxamido)benzoic acid

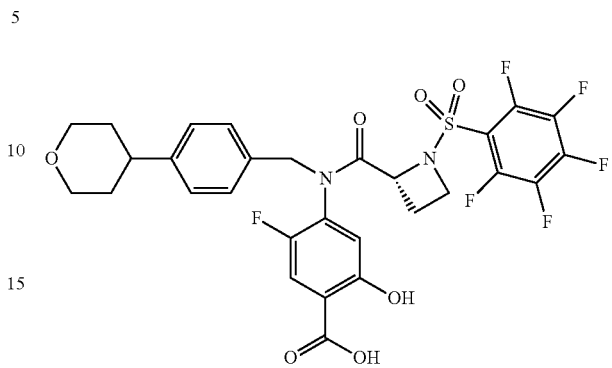

Step 1: To a stirred solution of benzyl 2-(benzyloxy)-5-fluoro-4-(2,2,2-trifluoroacetamido)benzoate (752.2 mg, 1.68 mmol) and 1-bromo-4-(bromomethyl)benzene (587.9 mg, 2.35 mmol) in acetonitrile (18 mL) was added potassium carbonate (300.5 mg, 2.18 mmol). The resulting reaction mixture was stirred at 60° C. for 3.5 h. After cooling to room temperature cold 10% aqueous KHSO$_4$/Na$_2$SO$_4$ buffer was added and the mixture was extracted with EtOAc (2×). The combined organic extract was washed with brine, dried over anhydrous sodium sulfate and concentrated under reduced pressure. The resulting residue was purified by flash chromatography (10-15% EtOAc/hexanes eluent) provided benzyl 2-(benzyloxy)-4-(N-(4-bromobenzyl)-2,2,2-trifluoroacetamido)-5-fluorobenzoate (1.01 g, 97% yield) as a colorless oil. 1H NMR (300 MHz, Chloroform-d) δ 7.65 (d, J=9.6 Hz, 1H), 7.51-7.28 (m, 12H), 7.00 (d, J=8.2 Hz, 2H), 6.44 (d, J=5.9 Hz, 1H), 5.36 (s, 2H), 5.24 (d, J=14.2 Hz, 1H), 4.91 (q, J=12.1 Hz, 2H), 4.36 (d, J=14.2 Hz, 1H).

Step 2: To a stirred solution of benzyl 2-(benzyloxy)-4-(N-(4-bromobenzyl)-2,2,2-trifluoroacetamido)-5-fluorobenzoate (649.6 mg, 1.05 mmol) in THF (5.2 mL) and methanol (6.5 mL) was added potassium carbonate (244.4 mg, 1.77 mmol) under nitrogen and the mixture was stirred at room temperature for 2 h. To the crude reaction mixture was added cold saturated aqueous ammonium chloride followed by water and the resulting mixture was extracted with EtOAc (2×). The combined organic extract was washed with brine, dried over anhydrous sodium sulfate and concentrated under reduced pressure. The crude solid residue was triturated with cold hexanes to provide benzyl 2-(benzyloxy)-4-((4-bromobenzyl)amino)-5-fluorobenzoate (534 mg, 97% yield) as a white solid. 1H NMR (300 MHz, Chloroform-d) δ 7.64 (d, J=12.4 Hz, 1H), 7.48 (d, J=8.4 Hz, 2H), 7.44-7.29 (m, 10H), 7.17 (d, J=8.4 Hz, 2H), 6.13 (d, J=7.2 Hz, 1H), 5.32 (s, 2H), 5.02 (s, 2H), 4.77 (s, 1H), 4.33 (s, 2H).

Step 3: To a stirred solution of benzyl 2-(benzyloxy)-4-((4-bromobenzyl)amino)-5-fluorobenzoate (409.4 mg, 0.787 mmol) in dry THF (6.3 mL) under nitrogen at 0° C. was added methylmagnesium bromide (1.403 mL of 1.4 M in THF, 1.97 mmol) and the resulting solution was stirred at 0° C. for 15 min before addition of solid (R)-1-((perfluorophenyl)sulfonyl)-azetidine-2-carbonyl chloride (412.5 mg, 1.18 mmol). The resulting mixture was allowed to warm to room temperature and stirred at room temperature for 3.0 h. To the crude reaction mixture was added cold saturated aqueous ammonium chloride followed by water and the resulting mixture was extracted with EtOAc (2×). The combined organic extract was washed with brine, dried over sodium sulfate and concentrated under reduced pressure. The crude residue was purified by flash chromatography (10-15% EtOAc/hexanes eluent) to provide benzyl (R)-2-(benzyloxy)-4-(N-(4-bromobenzyl)-1-((perfluorophenyl) sulfonyl)azetidine-2-carboxamido)-5-fluorobenzoate (236 mg, 40% yield). MS (ESI) m/z 833.00, 835.00 [M+H]+.

Step 4: In a dry flask under nitrogen was added benzyl (R)-2-(benzyloxy)-4-(N-(4-bromobenzyl)-1-((perfluorophenyl)sulfonyl)azetidine-2-carboxamido)-5-fluorobenzoate (272 mg, 0.327 mmol), Pd(OAc)$_2$ (3.68 mg, 0.0163 mmol), SPhos (13.4 mg, 0.0327 mmol), 3,6-dihydro-2H-pyran-4-boronic acid pinacol ester (224 mg, 0.491 mmol), potassium phosphate tribasic (138.79 mg, 0.653 mmol) and water (11.7 mg, 0.65 mmol). The flask was back-flushed with nitrogen, THF (4.2 mL) was added and the flask was heated at 40° C. for 16 h. The crude reaction mixture was poured onto water and extracted into EtOAc. The organic extract was washed with brine, dried over anhydrous sodium sulfate and concentrated under reduced pressure. The resulting residue was purified by flash chromatography (15-20% EtOAc/hexanes) to afford benzyl (R)-2-(benzyloxy)-4-(N-(4-(3,6-dihydro-2H-pyran-4-yl)benzyl)-1-((perfluorophenyl)sulfonyl)azetidine-2-carboxamido)-5-fluorobenzoate (220 mg, 80% yield). MS (ESI) m/z 837.6 [M+H]+.

Step 5: To a stirred solution of benzyl (R)-2-(benzyloxy)-4-(N-(4-(3,6-dihydro-2H-pyran-4-yl)benzyl)-1-((perfluorophenyl)sulfonyl)azetidine-2-carboxamido)-5-fluorobenzoate (100.4 mg, 0.12 mmol) in methanol (1.45 mL) and THF (1.45 mL) was added 10% Pd/C (10.79 mg) and the resulting suspension was stirred at room temperature under a hydrogen atmosphere for 16 h. The reaction mixture was filtered through Celite® and washed with methanol (2x). The combined filtrate and washes were concentrated under reduced pressure and purified by preparative TLC (60% EtOAc/hexanes with 0.2% acetic acid, run up twice). The resulting residue was dissolved in toluene and concentrated in vacuo. The resulting solid was triturate with toluene to provide (R)-5-fluoro-2-hydroxy-4-(1-((perfluorophenyl)sulfonyl)-N-(4-(tetrahydro-2H-pyran-4-yl)benzyl)azetidine-2-carboxamido)benzoic acid (32.4 mg) as a white solid. MS (ESI) m/z 659.1254 [M+H]+.

Example 65

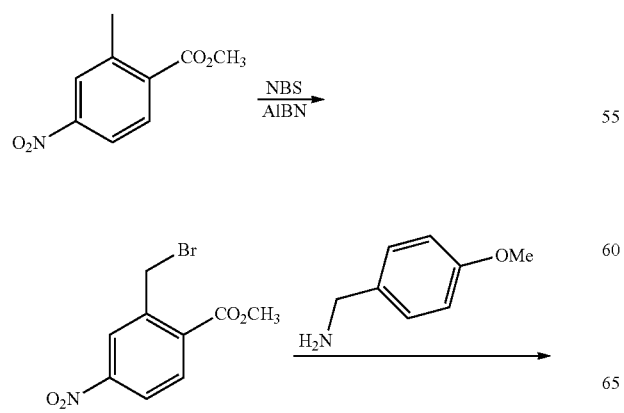

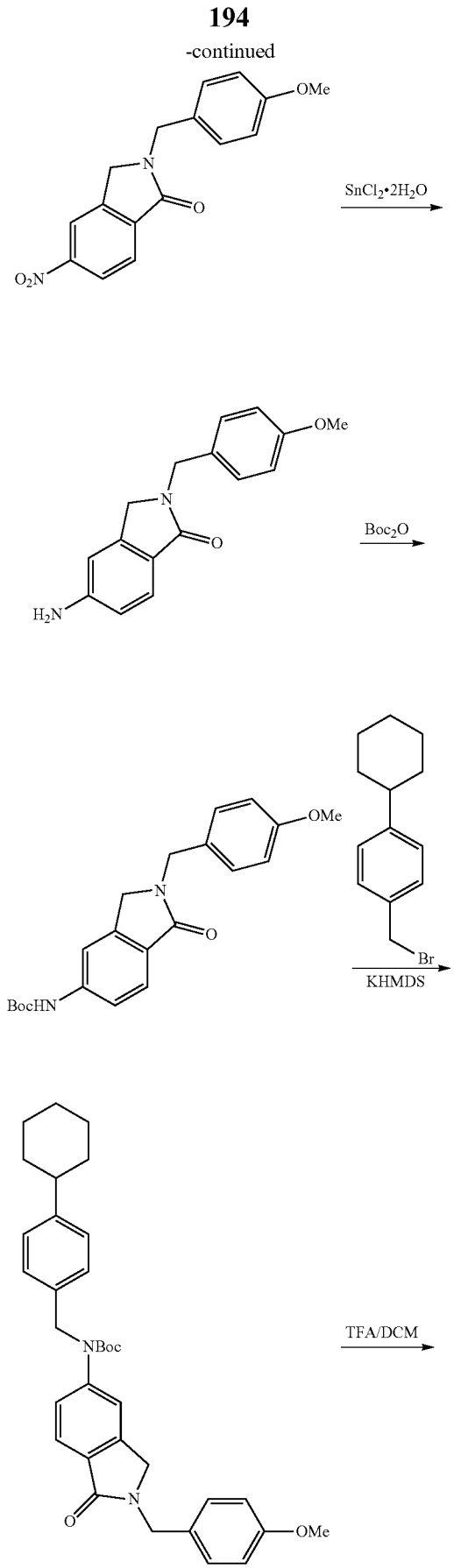

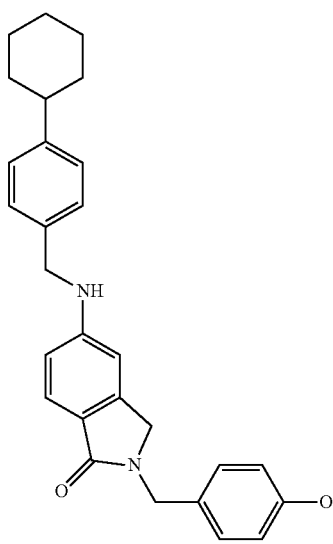
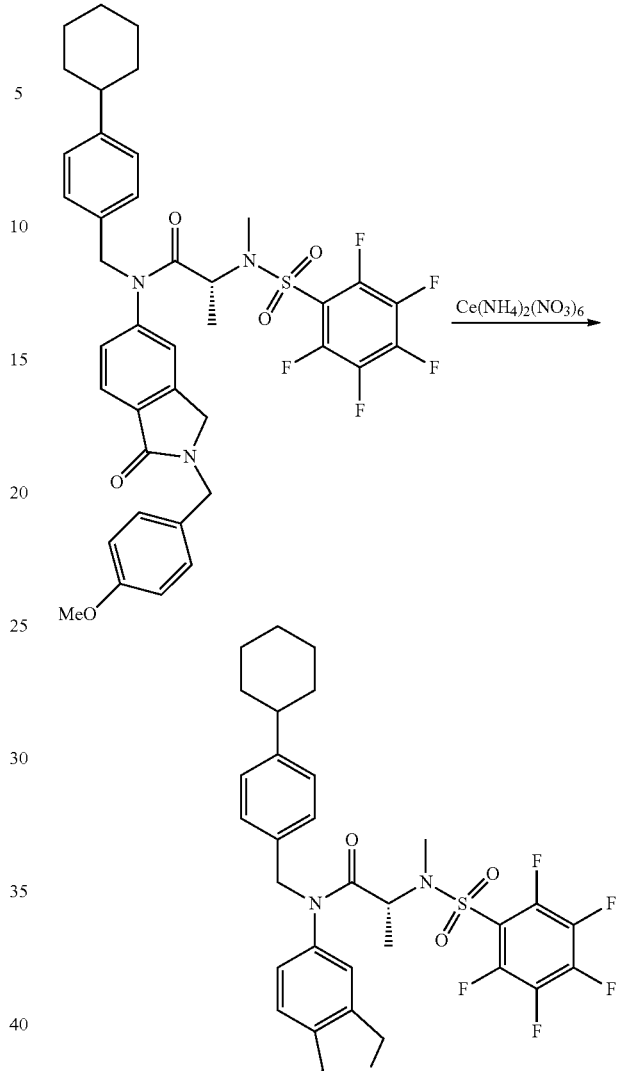
(R)—N-(4-cyclohexylbenzyl)-N-(1-oxoisoindolin-5-yl)-2-((2,3,4,5,6-pentafluoro-N-methylphenyl)sulfonamido)propanamide
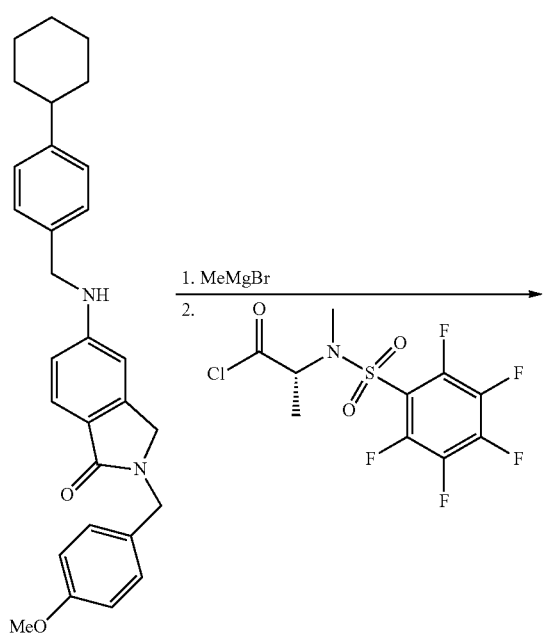
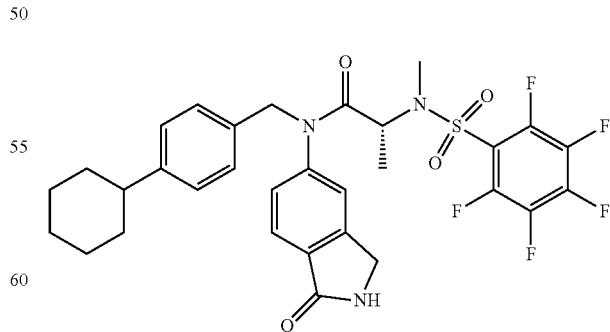
Step 1: To a solution of 2-methyl-4-nitrobenzoic acid methyl ester (2.0 g, 10.36 mmol) in carbon tetrachloride (80 mL) and 1,1'azobis(cyclohexanecarbonitrile) (0.63 g, 2.56 mmol) was added N-bromosuccinimide (2.18 g, 12.25 mmol) and the resulting solution was heated at reflux for 5 h and allowed to sit at room temperature overnight. The reaction was concentrated under reduced pressure and to the resulting residue was added DCM. The solid was filtered off and washed several times with DCM. The combined filtrate and washes were loaded onto a silica column and eluted with 10% EtOAc/hexane to provide slightly impure methyl 2-(bromomethyl)-4-nitrobenzoate (1.82 g, 65% yield) which was carried on as is to the next step.

Step 2: To methyl 2-(bromomethyl)-4-nitrobenzoate (1.82 g, 6.68 mmol) in methanol (20 mL) was added 4-methoxybenzylamine (0.87 mL, 6.68 mmol) and TEA (2.8 mL, 20 mmol) and the resulting mixture was warmed at reflux for 48 h. The reaction mixture was allowed to cool, poured onto aqueous 10% HCl and extracted with EtOAc (3×). The combined organic extracts were washed with brine, dried over anhydrous sodium sulfate and concentrated under reduced pressure. Chromatography (30% EtOAc/hexanes eluent and then 0.5% methanol in DCM eluent) followed by trituration with small volume of 20% EtOAc/hexanes afforded pure 2-(4-methoxybenzyl)-5-nitroisoindolin-1-one (989 mg, 47% yield) as a yellow solid. 1H NMR (300 MHz, Chloroform-d) δ 8.38 (dd, J=8.3, 2.1 Hz, 1H), 8.30-8.23 (m, 1H), 8.09-7.98 (m, 1H), 7.28 (d, J=8.7 Hz, 2H), 6.90 (d, J=8.7 Hz, 2H), 4.79 (s, 2H), 4.38 (s, 2H), 3.82 (s, 3H).

Step 3: To a stirred solution of crude 2-(4-methoxybenzyl)-5-nitroisoindolin-1-one (925 mg, 3.1 mmol) in EtOAc (60 mL) under nitrogen was added $SnCl_2 \cdot 2H_2O$ (3.5 g, 15.5 mmol). The resulting reaction mixture was stirred for 5 h at 80° C., cooled, and then poured onto cold water. The pH was adjusted to pH=8 using aqueous 10% sodium bicarbonate and the resulting mixture was stirred at room temperature for 1 h and then extracted with EtOAc (2×) and DCM (1×). The combined organic extracts were washed with brine, dried over anhydrous sodium sulfate and concentrated in vacuo to yield 5-amino-2-(4-methoxybenzyl)isoindolin-1-one (850 mg, 100% yield) as a yellow powder. MS (ESI) m/z 269 [M+H]+.

Step 4: To a suspension of 5-amino-2-(4-methoxybenzyl) isoindolin-1-one (400 mg, 1.5 mmol) in ethanol (20 mL) was added di-tert-butyl dicarbonate (981 mg, 4.5 mmol) and the resulting slurry was warmed at 70° C. overnight. The mixture was concentrated under reduced pressure and purified by flash chromatography to provide tert-butyl (2-(4-methoxybenzyl)-1-oxoisoindolin-5-yl)carbamate (495 mg, 90% yield). 1H NMR (300 MHz, Chloroform-d) δ 7.78 (d, J=8.2 Hz, 1H), 7.74 (br. s, 1H), 7.23 (d, J=8.9 Hz, 2H), 7.18 (dd, J=8.2 Hz, J=1.7 Hz, 1H), 6.87 (d, J=8.9 Hz, 2H), 6.77 (s, 1H), 4.73 (s, 2H), 4.21 (s, 2H), 3.80 (s, 3H), 1.53 (s, 9H).

Step 5: To a stirred solution of tert-butyl (2-(4-methoxybenzyl)-1-oxoisoindolin-5-yl)carbamate (486 mg, 1.32 mmol) in DMF (8 mL) at 0° C. under nitrogen was added KHMDS (1.58 mL of 1M in THF, 1.58 mmol). After stirring at 0° C. for 10 min, 1-(bromomethyl)-4-cyclohexylbenzene (514 mg, 1.98 mmol) was added. The reaction was allowed to warm to room temperature and stirring was continued at this temperature overnight. The reaction mixture was quenched with saturated aqueous ammonium chloride, poured onto water and extracted with ether (3×). The combined organic extracts were washed with brine, dried over anhydrous sodium sulfate and concentrated under reduced pressure. Purification by flash chromatography (20-50% EtOAc/hexanes gradient) provided tert-butyl (4-cyclohexylbenzyl)(2-(4-methoxybenzyl)-1-oxoisoindolin-5-yl)carbamate (550 mg, 77% yield). MS (ESI) m/z 541.3 [M+H]+.

Step 6: To a stirred solution of tert-butyl (4-cyclohexylbenzyl)(2-(4-methoxybenzyl)-1-oxoisoindolin-5-yl)carbamate (265 mg, 0.49 mmol) in DCM (10 mL) at 0° C. under nitrogen was added TFA (2 mL). The reaction mixture was stirred at 0° C. for 2 h and then at room temperature for 5 h. The mixture was poured onto ice water, made basic by addition of saturated aqueous sodium bicarbonate and extracted with DCM (3×). The combined organic extracts were washed with dilute aqueous sodium bicarbonate, dried over anhydrous sodium sulfate and concentrated in vacuo to provide 5-((4-cyclohexylbenzyl)amino)-2-(4-methoxybenzyl)-isoindolin-1-one (206 mg, 96% yield) as a white solid. 1H NMR (300 MHz, Chloroform-d) δ 7.67 (d, J=8.2 Hz, 1H), 7.27-7.18 (m, 4H), 6.91-6.80 (m, 2H), 6.73-6.63 (dd, J=8.2 Hz, J=2.1 Hz, 1H), 6.53 (d, J=2.1 Hz, 1H), 4.69 (s, 2H), 4.41 (t, J=5.5 Hz, 1H), 4.33 (d, J=4.5 Hz, 2H), 3.80 (s, 3H), 2.62-2.39 (m, 1H), 2.01-1.70 (m, 5H), 1.52-1.15 (m, 5H). MS (ESI) m/z 441.2 [M+H]+.

Step 7: To a stirred solution of 5-((4-cyclohexylbenzyl) amino)-2-(4-methoxybenzyl)-isoindolin-1-one (110 mg, 0.25 mmol) in THF (5 mL) under nitrogen at room temperature was added methylmagnesium bromide (0.53 mL of 1.4 M in 1:3 THF:toluene, 0.75 mmol, 3 equiv). Stirring was continued at room temperature for 5 min. The resultant solution was added drop-wise to a stirred solution of N-methyl-N-((pentafluorophenyl)sulfonyl)-D-alaninoyl chloride (132 mg, 0.375 mmol) in THF (5 mL) under nitrogen at room temperature. The resulting reaction mixture was stirred at room temperature for 2 h, quenched with saturated aqueous ammonium chloride, poured onto water and extracted with EtOAc (3×). The combined organic extracts were washed with brine, dried over anhydrous sodium sulfate and concentrated under reduced pressure. The resulting residue was purified by flash chromatography (1% methanol in DCM eluent) to afford (R)—N-(4-cyclohexylbenzyl)-N-(2-(4-methoxybenzyl)-1-oxoisoindolin-5-yl)-2-((2,3,4,5,6-pentafluoro-N-methylphenyl)sulfonamido) propanamide (144 mg, 75% yield). MS (ESI) m/z 756.2 [M+H]+.

Step 8: To a stirred solution of (R)—N-(4-cyclohexylbenzyl)-N-(2-(4-methoxybenzyl)-1-oxoisoindolin-5-yl)-2-((2,3,4,5,6-pentafluoro-N-methylphenyl)sulfonamido)propanamide (66 mg, 0.087 mmol) in acetonitrile (2 mL) and water (1 mL) was added cerric ammonium nitrate (143 mg, 0.261 mmol) and the resulting mixture was allowed to stir at room temperature overnight. An additional 50 mg of cerric ammonium nitrate was added and the reaction was stirred at room temperature for an additional 30 min. The reaction mixture was poured onto water and extracted with EtOAc (3×) and DCM (1×). The combined organic extracts were washed with brine, dried over anhydrous sodium sulfate and concentrated under reduced pressure. Purification by flash chromatography (50-100% EtOAc/hexanes gradient) provided (R)—N-(4-cyclohexylbenzyl)-N-(1-oxoisoindolin-5-yl)-2-((2,3,4,5,6-pentafluoro-N-methylphenyl)sulfonamido)propanamide (40 mg, 72% yield) as a white solid. MS (ESI) m/z 636.1 [M+H]+.

Example 66
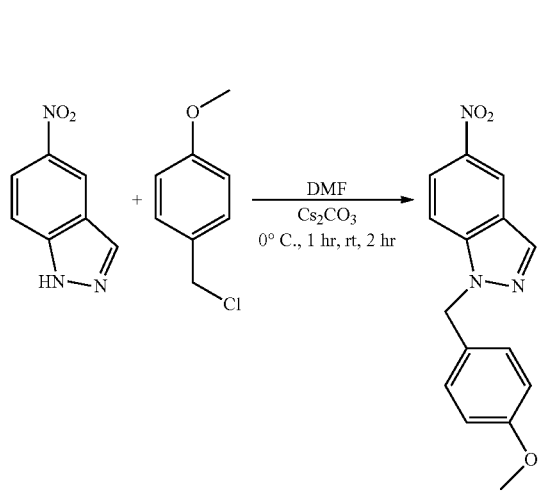
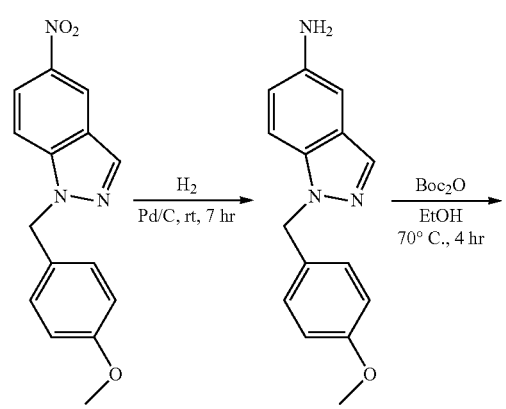
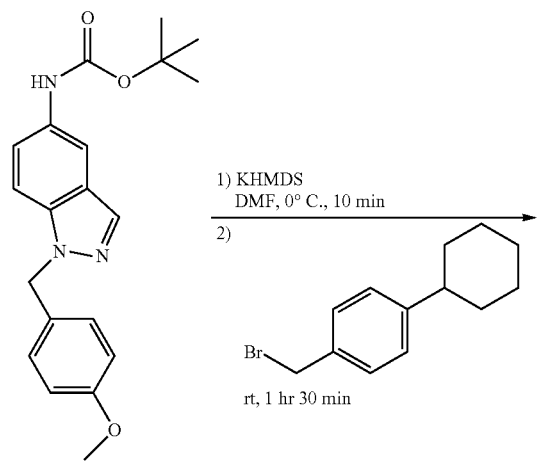
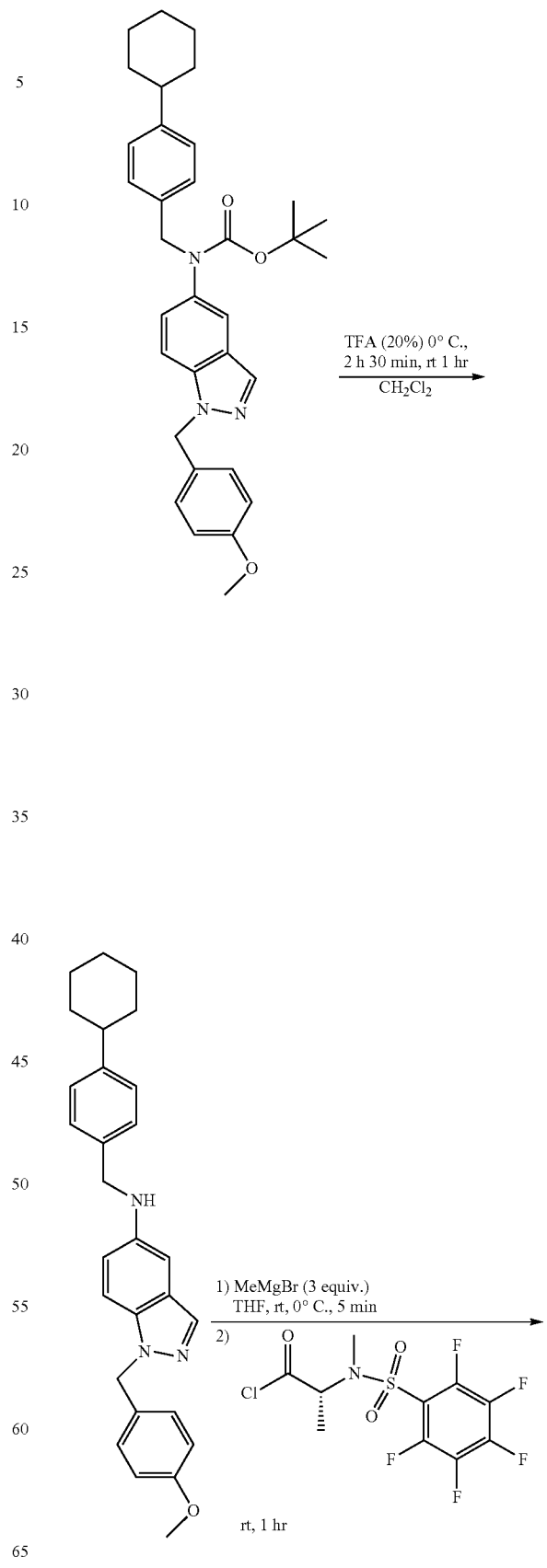

-continued

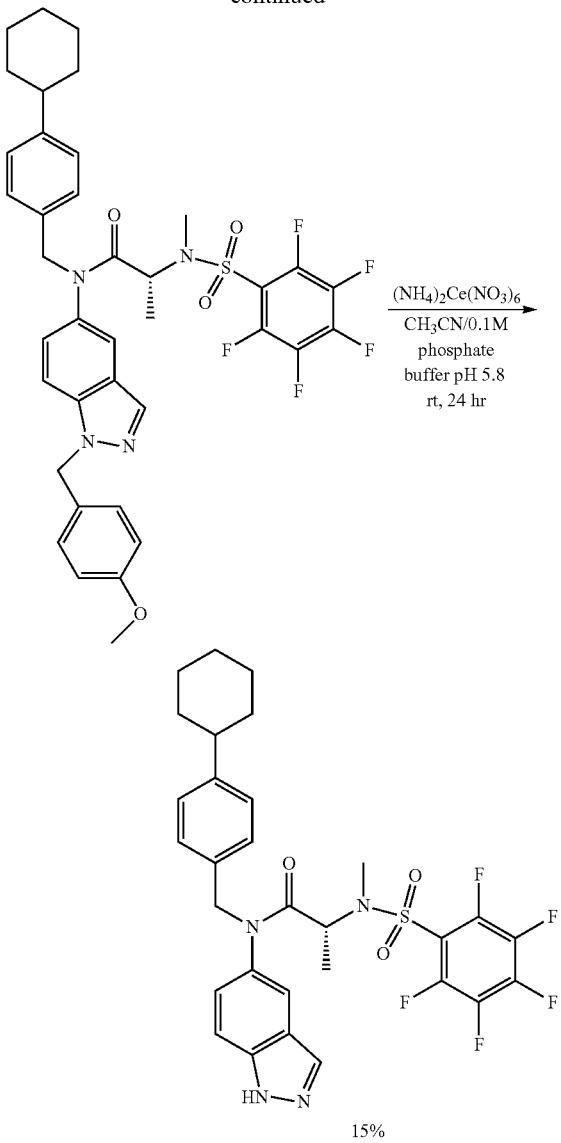

15%

(R)—N-(4-Cyclohexylbenzyl)-N-(1H-indazol-5-yl)-2-((2,3,4,5,6-pentafluoro-N-methylphenyl)sulfonamido)propanamide

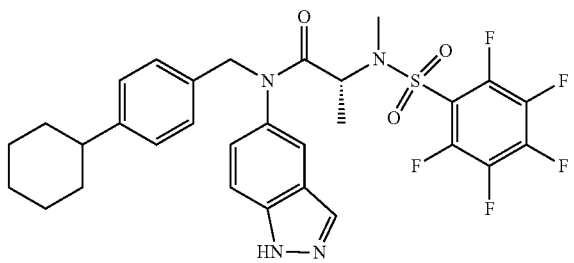 [SMILES: C[C@H](C(=O)N(Cc1ccc(C2CCCCC2)cc1)c1ccc2[nH]ncc2c1)N(C)S(=O)(=O)c1c(F)c(F)c(F)c(F)c1F]

Step 1: To a stirred solution of 5-nitro-1H-indazole (2.93 g, 18 mmol) in DMF (18 mL) under nitrogen was added cesium carbonate (6.5 g, 19.9 mmol). The solution was cooled to 0° C. p-Methoxybenzyl chloride (2.7 mL, 19.9 mmol) was added drop wise and the resulting mixture was stirred at 0° C. for 1 h and at room temperature for an additional 2 h. The reaction was quenched with saturated aqueous ammonium chloride and added to a mixture of ether and water. The aqueous phase was acidified with aqueous HCl. The precipitated solid was filtered off and washed with a small portion of DCM and dried. The filtrate and washes were added to a separatory funnel and the organic layer separated off. The aqueous phase was extracted with ether (2×). The combined organic extracts were washed with brine, dried over anhydrous sodium sulfate and concentrated under reduced pressure. The resulting residue and the solid from the filtration were combined and purified by flash chromatography (4:3:3 hexanes:DCM:EtOAc eluent) to provide 1-(4-methoxybenzyl)-5-nitro-1H-indazole (1.6 g, 31% yield) as a yellow solid. 1H NMR (300 MHz, Chloroform-d) δ 8.74 (d, J=2.1 Hz, 1H), 8.27-8.19 (m, 2H), 7.41 (d, J=9.3 Hz, 1H), 7.20 (d, J=9.3 Hz, 2H), 6.86 (d, J=8.7 Hz, 2H), 5.59 (s, 2H), 3.79 (s, 3H).

Step 2: To a stirred solution of 1-(4-methoxybenzyl)-5-nitro-1H-indazole (1.6 g, 5.6 mmol) in methanol (20 mL) and EtOAc (40 mL) under nitrogen was added 10% Pd/C (159 mg) and the suspension was place under a hydrogen atmosphere and stirred at room temperature for 7 h. The reaction mixture was filtered through Celite® and washed with methanol (2×). The combined filtrate and washes were concentrated to provide 1-(4-methoxybenzyl)-1H-indazol-5-amine (1.39 g, 96% yield). 1H NMR (300 MHz, Chloroform-d) δ 7.83 (s, 1H), 7.22-7.09 (m, 3H), 6.97-6.91 (m, 1H), 6.88-6.75 (m, 3H), 5.48 (s, 2H), 3.78 (s, 3H), 3.60 (br. s, 2H).

Step 3: To a suspension of 1-(4-methoxybenzyl)-1H-indazol-5-amine (1.39 g, 5.5 mmol) in ethanol (73 mL) was added di-tert-butyl dicarbonate (3.6 g, 16.5 mmol) and the resulting slurry was warmed at 70° C. 4 h. The mixture was concentrated under reduced pressure and purified by trituration with 10% EtOAc/hexanes to provide tert-butyl (1-(4-methoxybenzyl)-1H-indazol-5-yl)carbamate (1.78 g, 92% yield) as a tan solid. 1H NMR (300 MHz, Chloroform-d) δ 7.96 (d, J=0.8 Hz, 1H), 7.83 (s, 1H), 7.26-7.19 (m, 2H), 7.14 (d, J=8.6 Hz, 2H), 6.83 (d, J=8.6 Hz, 2H), 6.51 (s, 1H), 5.52 (s, 2H), 3.78 (s, 3H), 1.54 (s, 9H).

Step 4: To a stirred solution of tert-butyl (1-(4-methoxybenzyl)-1H-indazol-5-yl)carbamate (488 mg, 1.38 mmol) in DMF (10 mL) at 0° C. under nitrogen was added KHMDS (2.1 mL of 1M in THF, 2.1 mmol). After stirring at 0° C. for 10 min, 1-(bromomethyl)-4-cyclohexylbenzene (689 mg, 2.65 mmol) was added. The reaction was allowed to warm to room temperature and stirring was continued at this temperature for 1.5 h. The reaction mixture was, poured onto water and extracted with ether (3×). The combined organic extracts were washed with brine, dried over sodium sulfate and concentrated under reduced pressure. Purification by flash chromatography (0-20% EtOAc/hexanes gradient) provided tert-butyl (4-cyclohexylbenzyl)(1-(4-methoxybenzyl)-1H-indazol-5-yl)carbamate (647 mg, 87% yield) as a white foam. 1H NMR (300 MHz, Chloroform-d) δ 7.94 (t, J=0.6 Hz, 1H), 7.44 (s, 1H), 7.21-7.08 (m, 8H), 6.84 (d, J=8.7 Hz, 2H), 5.50 (s, 2H), 4.81 (s, 2H), 3.78 (s, 3H), 2.59-2.40 (m, 1H), 1.99-1.68 (m, 5H), 1.52-1.34 (m and overlapping s, 14H).

Step 5: To a stirred solution of tert-butyl (4-cyclohexylbenzyl)(1-(4-methoxybenzyl)-1H-indazol-5-yl)carbamate (643 mg, 1.2 mmol) in DCM (25 mL) at 0° C. under nitrogen was added TFA (5 mL). The reaction mixture was stirred at 0° C. for 2.25 h and then at room temperature for 1 h. The mixture was poured onto ice water, made basic by addition of saturated aqueous sodium bicarbonate and extracted with DCM (3×). The combined organic extracts were washed with dilute aqueous sodium bicarbonate, dried over anhydrous sodium sulfate and concentrated in vacuo to provide N-(4-cyclohexylbenzyl)-1-(4-methoxybenzyl)-1H-indazol-5-amine (576 mg, 89% yield). 1H NMR (300 MHz, Chloroform-d) δ 7.84 (d, J=0.7 Hz, 1H), 7.37-7.30 (m, 2H), 7.24-7.12 (m, 5H), 6.88-6.76 (m, 4H), 5.48 (s, 2H), 4.31 (s, 2H), 3.78 (s, 3H), 2.67-2.39 (m, 1H), 2.11-1.67 (m, 5H), 1.52-1.08 (m, 5H).

Step 6: To a stirred solution of N-(4-cyclohexylbenzyl)-1-(4-methoxybenzyl)-1H-indazol-5-amine (170 mg, 0.40 mmol) in THF (8 mL) under nitrogen at room temperature was added methylmagnesium bromide (0.86 mL of 1.4 M in 1:3 THF:toluene, 1.2 mmol, 3 equiv). Stirring was continued at room temperature for 5 min. The resultant solution was added drop-wise to a stirred solution of N-methyl-N-((pentafluorophenyl)sulfonyl)-D-alaninoyl chloride (211 mg, 0.60 mmol) in THF (8 mL) under nitrogen at room temperature. The resulting reaction mixture was stirred at room temperature for 1 h, quenched with saturated aqueous ammonium chloride, poured onto water and extracted with EtOAc (3×). The combined organic extracts were washed with brine, dried over anhydrous sodium sulfate and concentrated under reduced pressure. The resulting residue was purified by flash chromatography (20-40% EtOAc/hexanes gradient) to afford (R)—N-(4-cyclohexylbenzyl)-N-(1-(4-methoxybenzyl)-1H-indazol-5-yl)-2-((2,3,4,5,6-pentafluoro-N-methylphenyl)sulfonamido)propanamide (257 mg, 87% yield). MS (ESI) m/z 741.2 [M+H]+.

Step 7: To a stirred solution of (R)—N-(4-cyclohexylbenzyl)-N-(1-(4-methoxybenzyl)-1H-indazol-5-yl)-2-((2,3,4,5,6-pentafluoro-N-methylphenyl)sulfonamido)propanamide (206 mg, 0.279 mmol) in acetonitrile (12 mL) and 0.1 M phosphate buffer at pH=5.9 (6 mL) was added cerric ammonium nitrate (458 mg, 0.836 mmol) and the resulting mixture was allowed to stir at room temperature for 1 h. An additional 305 mg of cerric ammonium nitrate was added and the reaction was stirred at room temperature overnight. The reaction mixture was poured onto water and extracted with EtOAc (3×). The combined organic extracts were washed with brine, dried over anhydrous sodium sulfate and concentrated under reduced pressure. Purification by flash chromatography (20-40% EtOAc/hexanes gradient) provided (R)—N-(4-cyclohexylbenzyl)-N-(1H-indazol-5-yl)-2-((2,3,4,5,6-pentafluoro-N-methylphenyl) sulfonamido)-propanamide (27 mg, 15% yield) as a yellow foam. MS (ESI) m/z 621.2 [M+H]+.

Example 67

(R)—N-(4-cyclohexylbenzyl)-N-(1H-indazol-6-yl)-2-((2,3,4,5,6-pentafluoro-N-methylphenyl)sulfonamido)propanamide

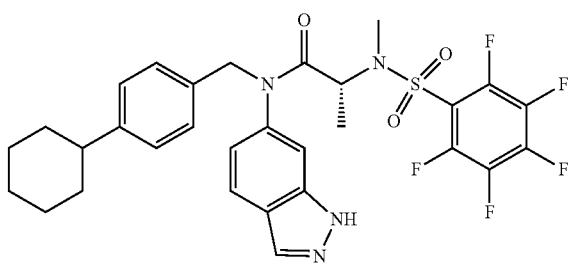 [SMILES: C[C@H](C(=O)N(Cc1ccc(C2CCCCC2)cc1)c1ccc2cn[nH]c2c1)N(C)S(=O)(=O)c1c(F)c(F)c(F)c(F)c1F]

Preparation by a similar procedure to example 66, except substituting 6-nitro-1H-indazole for 5-nitro-1H-indazole in step 1 afforded (R)—N-(4-cyclohexylbenzyl)-N-(1H-indazol-6-yl)-2-((2,3,4,5,6-pentafluoro-N-methylphenyl) sulfonamido)propanamide as a white foam. MS (ESI) m/z 621.2 [M+H]+.

Example 68

(R)-4-(1-((3-Cyano-4-fluorophenyl)sulfonyl)-N-(4-cyclohexylbenzyl)azetidine-2-carboxamido)-2-hydroxybenzoic acid

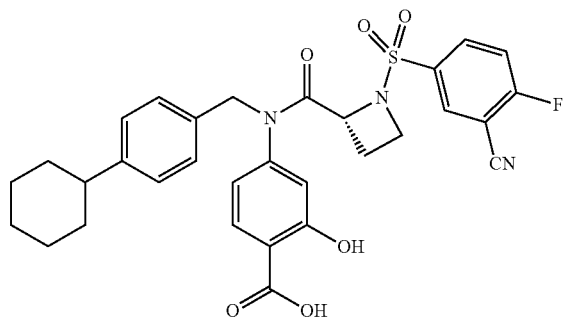 [SMILES: N#Cc1cc(S(=O)(=O)N2CC[C@@H]2C(=O)N(Cc2ccc(C3CCCCC3)cc2)c2ccc(C(=O)O)c(O)c2)ccc1F]

Preparation by a similar procedure to example 34, except substituting 3-cyano-4-fluorobenzenesulfonyl chloride for pentafluorobenzenesulfonyl chloride in step 5 afforded (R)-4-(1-((3-cyano-4-fluorophenyl)sulfonyl)-N-(4-cyclohexylbenzyl)azetidine-2-carboxamido)-2-hydroxybenzoic acid as a white foam. HRMS (ESI) m/z 592.1910 [M+H]+.

Example 69

(R)-4-(1-((4-Cyanophenyl)sulfonyl)-N-(4-cyclohexylbenzyl)azetidine-2-carboxamido)-2-hydroxybenzoic acid

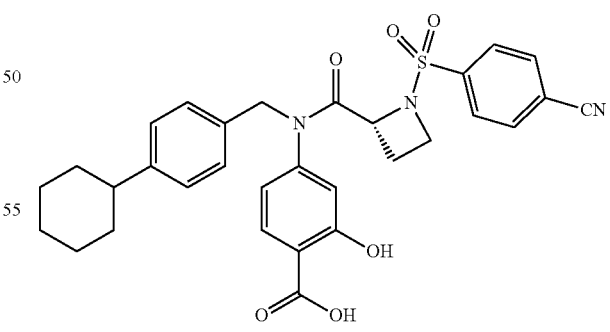

Preparation by a similar procedure to example 34, except substituting 4-cyanobenzenesulfonyl chloride for pentafluorobenzenesulfonyl chloride in step 5 afforded (R)-4-(1-((4-cyanophenyl)sulfonyl)-N-(4-cyclohexylbenzyl)azetidine-2-carboxamido)-2-hydroxybenzoic acid as a white foam. HRMS (ESI) m/z 574.2015 [M+H]+.

Example 70

(R)-4-(1-((3-Cyanophenyl)sulfonyl)-N-(4-cyclohexylbenzyl)azetidine-2-carboxamido)-2-hydroxybenzoic acid

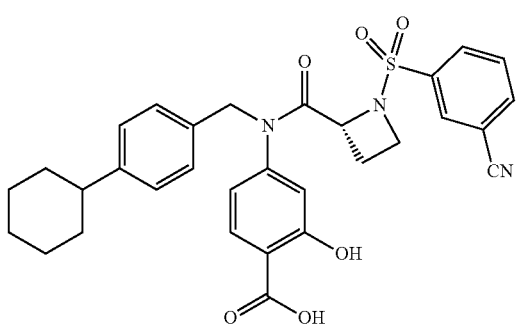 [SMILES: N#Cc1cccc(S(=O)(=O)N2CC[C@@H]2C(=O)N(Cc2ccc(C3CCCCC3)cc2)c2ccc(C(=O)O)c(O)c2)c1]

Preparation by a similar procedure to example 34, except substituting 3-cyanobenzenesulfonyl chloride for pentafluorobenzenesulfonyl chloride in step 5 afforded (R)-4-(1-((3-cyanophenyl)sulfonyl)-N-(4-cyclohexylbenzyl)azetidine-2-carboxamido)-2-hydroxybenzoic acid as a white foam. HRMS (ESI) m/z 574.2007 [M+H]+.

Example 71

(R)-4-(1-((2-Cyanophenyl)sulfonyl)-N-(4-cyclohexylbenzyl)azetidine-2-carboxamido)-2-hydroxybenzoic acid

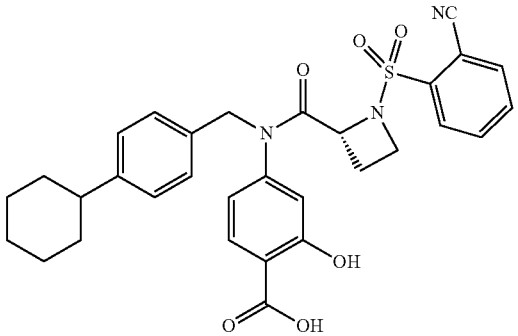 [SMILES: N#Cc1ccccc1S(=O)(=O)N1CC[C@@H]1C(=O)N(Cc1ccc(C2CCCCC2)cc1)c1ccc(C(=O)O)c(O)c1]

Preparation by a similar procedure to example 34, except substituting 2-cyanobenzenesulfonyl chloride for pentafluorobenzenesulfonyl chloride in step 5 afforded (R)-4-(1-((2-cyanophenyl)sulfonyl)-N-(4-cyclohexylbenzyl)azetidine-2-carboxamido)-2-hydroxybenzoic acid as a white foam. MS (ESI) m/z 574.2004 [M+H]+.

Examples 72-75

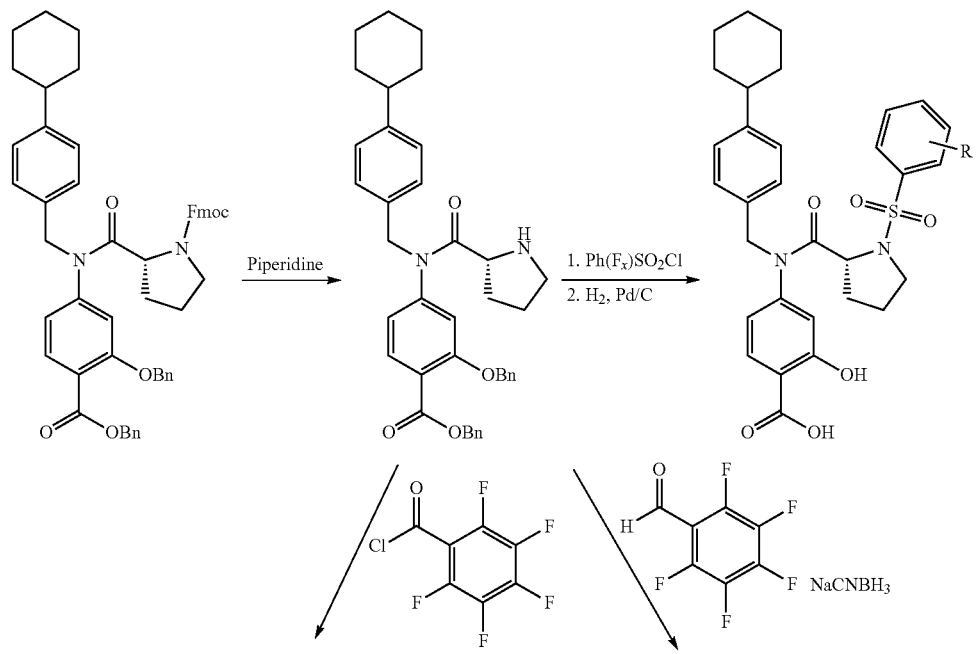

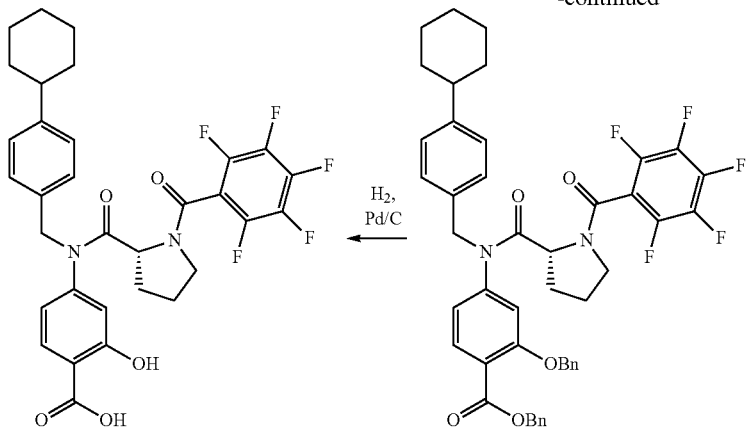
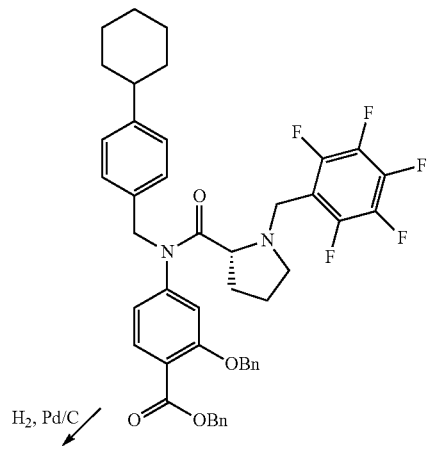
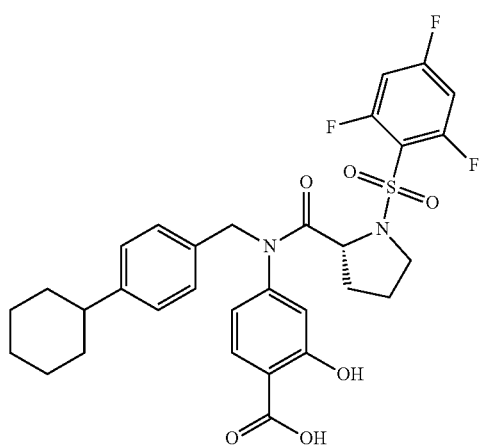 [SMILES: O=C(O)c1ccc(N(Cc2ccc(C3CCCCC3)cc2)C(=O)[C@H]2CCCN2S(=O)(=O)c2c(F)cc(F)cc2F)cc1O]

Example 72

(R)-4-(N-(4-Cyclohexylbenzyl)-1-((2,4,6-trifluorophenyl)sulfonyl)pyrrolidine-2-carboxamido)-2-hydroxybenzoic acid Step 1: To as stirred solution of (9H-fluoren-9-yl)methyl (R)-2-((3-(benzyloxy)-4-((benzyloxy)carbonyl)phenyl)(4-cyclohexylbenzyl)carbamoyl)pyrrolidine-1-carboxylate (220 mg, 0.26 mmol) in DCM (4 mL) under nitrogen at 0° C. was added piperidine (1 mL) and the resulting mixture was stirred at 0° C. for 1 h. The reaction was complete by LCMS. MS (ESI) m/z 603.30 [M+H]+. Concentration in vacuo provided crude benzyl (R)-2-(benzyloxy)-4-(N-(4-cyclohexylbenzyl)pyrrolidine-2-carboxamido)benzoate which was used as is.

Step 2: To a stirred solution of crude benzyl (R)-2-(benzyloxy)-4-(N-(4-cyclohexylbenzyl)pyrrolidine-2-carboxamido)benzoate (0.20 mmol) in DCM (3 mL) at 0° C. under nitrogen was added DIPEA (0.05 mL, 0.28 mmol) followed by 2,4,6-trifluorobenzenesulfonyl chloride (0.034 mL, 0.24 mmol). The resulting reaction mixture was allowed to warm to room temperature and stirred at this temperature overnight. The crude reaction mixture was poured onto dilute aqueous HCl and extracted with DCM (3×). The combined organic extracts were dried over anhydrous sodium sulfate, concentrated under reduced pressure and the resulting residue purified by flash chromatography (20% EtOAc/hexanes eluent) to provide benzyl (R)-2-(benzyloxy)-4-(N-(4-cyclohexylbenzyl)-1-((2,4,6-trifluorophenyl)sulfonyl)-pyrrolidine-2-carboxamido)benzoate (129 mg, 81% yield) as a white foam. MS (ESI) m/z 797.2 [M+H]+.

Step 3: To a stirred solution of benzyl (R)-2-(benzyloxy)-4-(N-(4-cyclohexylbenzyl)-1-((2,4,6-trifluorophenyl)sulfonyl)pyrrolidine-2-carboxamido)benzoate (125 mg, 0.157 mmol) in methanol (2 mL) and THF (2 mL) was added 10% Pd/C (15 mg) and the resulting suspension was stirred at room temperature under a hydrogen atmosphere for 2 h. The reaction mixture was filtered through Celite® and washed with methanol (2×). The combined filtrate and washes were concentrated to provide (R)-4-(N-(4-cyclohexylbenzyl)-1-((2,4,6-trifluorophenyl)sulfonyl)pyrrolidine-2-carboxamido)-2-hydroxybenzoic acid (98 mg, 100% yield) as a white foam. HRMS (ESI) m/z 617.1923 [M+H]+.

Example 73

(R)-4-(N-(4-Cyclohexylbenzyl)-1-((2,3,5-trifluorophenyl)sulfonyl)pyrrolidine-2-carboxamido)-2-hydroxybenzoic acid

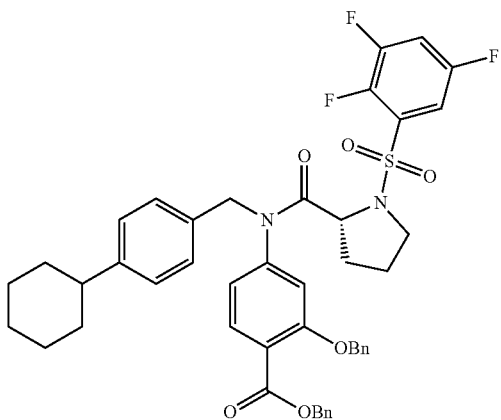 [SMILES: O=C(OCc1ccccc1)c1ccc(N(Cc2ccc(C3CCCCC3)cc2)C(=O)[C@H]2CCCN2S(=O)(=O)c2cc(F)cc(F)c2F)cc1OCc1ccccc1]

Step 1: To as stirred solution of (9H-fluoren-9-yl)methyl (R)-2-((3-(benzyloxy)-4-((benzyloxy)carbonyl)phenyl)(4-cyclohexylbenzyl)carbamoyl)pyrrolidine-1-carboxylate (1.45 g, 1.76 mmol) in DCM (15 mL) under nitrogen at 0° C. was added piperidine (15 mL) and the resulting mixture was stirred at 0° C. for 1.5 h. The reaction was complete by LCMS. MS (ESI) m/z 603.30 [M+H]+. Concentration in vacuo and purification of the resulting residue by flash chromatography (25% EtOAc/hexanes, then 5% methanol in EtOAc provided benzyl (R)-2-(benzyloxy)-4-(N-(4-cyclohexylbenzyl)pyrrolidine-2-carboxamido)benzoate (1.1 g, 100% yield) as a foam. 1H NMR (300 MHz, Chloroform-d) δ 7.83 (d, J=8.2 Hz, 1H), 7.49-7.28 (m, 10H), 7.14 (d, J=8.1 Hz, 2H), 7.08-7.02 (m, 2H), 6.72 (dd, J=8.2, 1.8 Hz, 1H), 6.57 (s, 1H), 5.36 (s, 2H), 5.09 (d, J=12.2 Hz, 1H), 4.97 (d, J=14.2 Hz, 1H), 4.83 (d, J=12.2 Hz, 1H), 4.68 (d, J=14.2 Hz, 1H), 3.87 (t, J=8.0 Hz, 1H), 3.16 (dt, J=11.0, 6.8 Hz, 1H), 2.94 (dt, J=11.0, 6.8 Hz, 1H), 2.60-2.32 (m, 1H), 1.94-1.56 (m, 8H), 1.54-1.14 (m, 6H). MS (ESI) m/z 603.3 [M+H]+.

Step 2: To a stirred solution of crude benzyl (R)-2-(benzyloxy)-4-(N-(4-cyclohexylbenzyl)pyrrolidine-2-carboxamido)benzoate (203 mg, 0.33 mmol) in DCM (5 mL) at 0° C. under nitrogen was added DIPEA (0.082 mL, 0.47 mmol) followed by 2,3,5-trifluorobenzenesulfonyl chloride (91 mg, 0.40 mmol). The resulting reaction mixture was allowed to warm to room temperature and stirred at this temperature overnight. The crude reaction mixture was poured onto water and extracted with DCM (3×). The combined organic extracts were dried over anhydrous sodium sulfate, concentrated under reduced pressure and the resulting residue purified by flash chromatography (15-25% EtOAc/hexanes eluent) to provide benzyl (R)-2-(benzyloxy)-4-(N-(4-cyclohexylbenzyl)-1-((2,3,5-trifluorophenyl)sulfonyl)pyrrolidine-2-carboxamido)benzoate (173 mg, 66% yield) as a white foam. MS (ESI) m/z 797.2 [M+H]+.

Step 3: To a stirred solution of benzyl (R)-2-(benzyloxy)-4-(N-(4-cyclohexylbenzyl)-1-((2,3,5-trifluorophenyl)sulfonyl)pyrrolidine-2-carboxamido)benzoate (155 mg, 0.19 mmol) in methanol (4 mL) and THF (4 mL) was added 10% Pd/C (18 mg) and the resulting suspension was stirred at room temperature under a hydrogen atmosphere for 1 h. The reaction mixture was filtered through Celite® and washed with methanol (2×). The combined filtrate and washes were concentrated to provide (R)-4-(N-(4-cyclohexylbenzyl)-1-((2,3,5-trifluorophenyl)sulfonyl)pyrrolidine-2-carboxamido)-2-hydroxybenzoic acid (127 mg, 100% yield) as a pink foam. HRMS (ESI) m/z 617.1918 [M+H]+.

Example 74

(R)-4-(N-(4-cyclohexylbenzyl)-1-(perfluorobenzoyl)pyrrolidine-2-carboxamido)-2-hydroxybenzoic acid

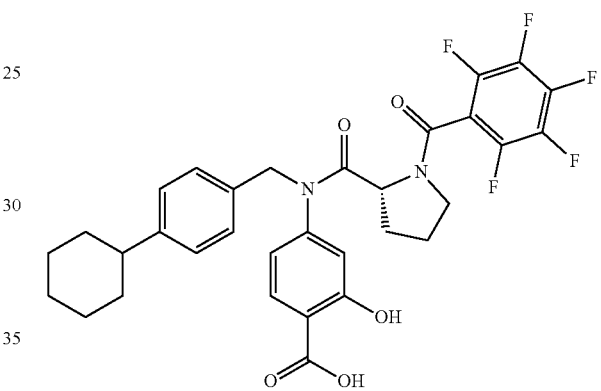

Step 1: To a stirred solution of benzyl (R)-2-(benzyloxy)-4-(N-(4-cyclohexylbenzyl)pyrrolidine-2-carboxamido)benzoate (203 mg, 0.337 mmol) in DCM (5 mL) at 0° C. under nitrogen was added DIPEA (0.088 mL, 0.50 mmol) followed by 2,3,4,5,6-pentafluorbenzoyl chloride (0.058 ml, 0.40 mmol). The resulting reaction mixture was stirred at 0° C. for 15 min before addition of saturated aqueous ammonium chloride. The crude reaction mixture was poured onto water and extracted with DCM (3×). The combined organic extracts were dried over anhydrous sodium sulfate, concentrated under reduced pressure and the resulting residue purified by flash chromatography (10-25% EtOAc/hexanes eluent) to provide benzyl (R)-2-(benzyloxy)-4-(N-(4-cyclohexylbenzyl)-1-(perfluorobenzoyl)pyrrolidine-2-carboxamido)benzoate (226 mg, 84% yield). MS (ESI) m/z 797.2 [M+H]+.

Step 2: To a stirred solution of benzyl (R)-2-(benzyloxy)-4-(N-(4-cyclohexylbenzyl)-1-(perfluorobenzoyl)pyrrolidine-2-carboxamido)benzoate (226 mg, 0.28 mmol) in methanol (5 mL) and THF (5 mL) was added 10% Pd/C (22 mg) and the resulting suspension was stirred at room temperature under a hydrogen atmosphere for 1.5 h. The reaction mixture was filtered through Celite® and washed with methanol (2×). The combined filtrate and washes were concentrated and the resulting residue purified by flash chromatography (0-2% methanol in EtOAc) to provide (R)-4-(N-(4-cyclohexylbenzyl)-1-(perfluorobenzoyl)pyrrolidine-2-carboxamido)-2-hydroxybenzoic acid (50 mg, 29% yield). HRMS (ESI) m/z 617.2071 [M+H]+.

Example 75

(R)-4-(N-(4-cyclohexylbenzyl)-1-((perfluorophenyl)methyl)pyrrolidine-2-carboxamido)-2-hydroxybenzoic acid

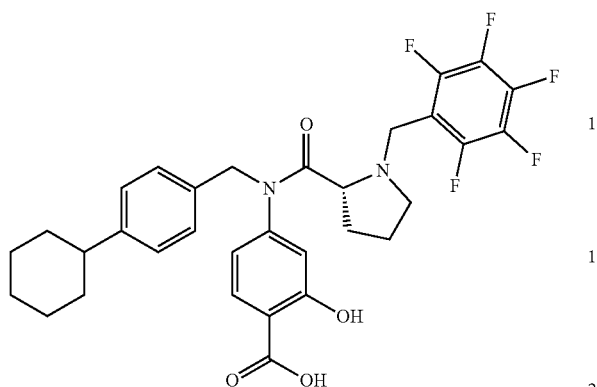

Step 1: To a stirred solution of benzyl (R)-2-(benzyloxy)-4-(N-(4-cyclohexylbenzyl)pyrrolidine-2-carboxamido)benzoate (212 mg, 0.35 mmol) in DCE (4 mL) under nitrogen was added 2,3,4,5,6-pentafluorobenzaldehyde (103 mg, 0.53 mmol) in DCE (1 mL) followed by sodium triacetoxyborohydride (97 mg, 0.45 mmol). The resulting reaction mixture was stirred at room temperature overnight. The crude reaction mixture was poured onto 10% aqueous sodium bicarbonate and extracted with DCM (3×). The combined organic extracts were dried over anhydrous sodium sulfate, concentrated under reduced pressure and the resulting residue purified by flash chromatography (10-25% EtOAc/hexanes eluent) to provide benzyl (R)-2-(benzyloxy)-4-(N-(4-cyclohexylbenzyl)-1-((perfluorophenyl)methyl)pyrrolidine-2-carboxamido)benzoate (184 mg, 67% yield). MS (ESI) m/z 783.3 [M+H]+.

Step 2: To a stirred solution of benzyl (R)-2-(benzyloxy)-4-(N-(4-cyclohexylbenzyl)-1-((perfluorophenyl)methyl)pyrrolidine-2-carboxamido)benzoate (152 mg, 0.19 mmol) in methanol (4 mL) and THF (4 mL) was added 20% Pd(OH)$_2$ on carbon (20 mg) and the resulting suspension was stirred at room temperature under a hydrogen atmosphere for 1.5 h. The reaction mixture was filtered through Celite® and washed with methanol (2×). The combined filtrate and washes were concentrated in vacuo to provide (R)-4-(N-(4-cyclohexylbenzyl)-1-((perfluorophenyl)methyl)pyrrolidine-2-carboxamido)-2-hydroxybenzoic acid (108 mg, 94% yield). HRMS (ESI) m/z 603.2285 [M+H]+.

Example 76

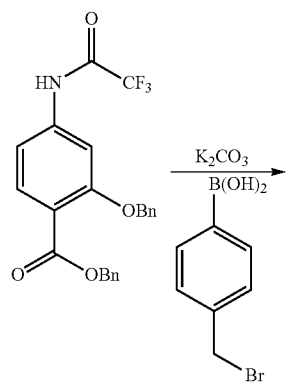

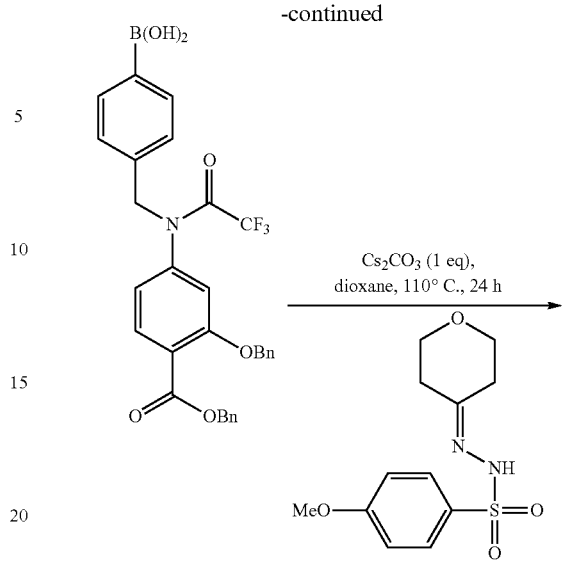

-continued

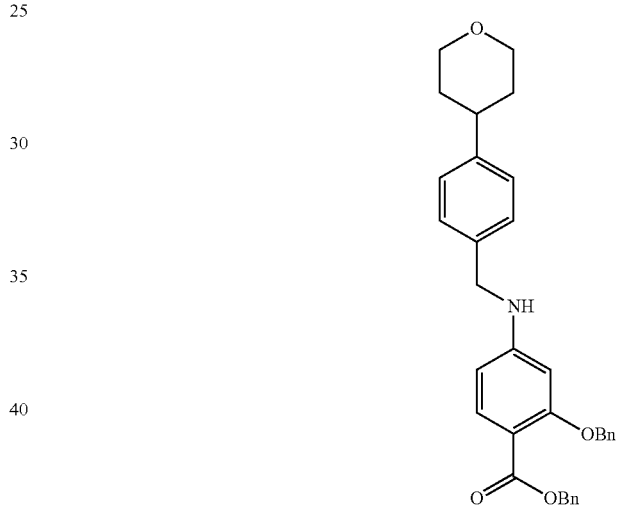

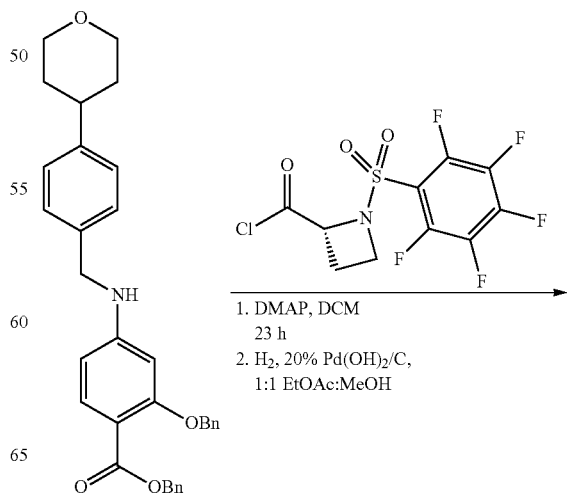

-continued

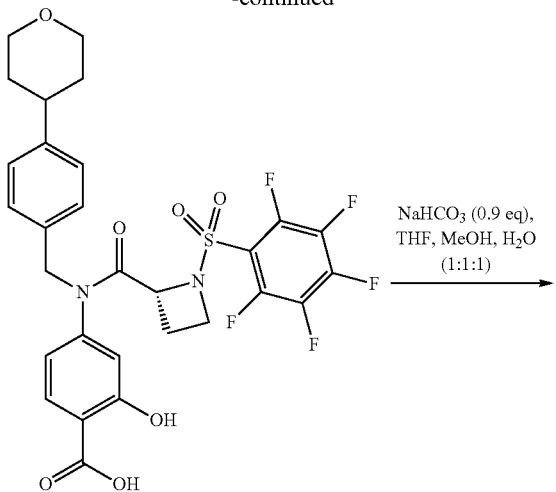

(R)-2-hydroxy-4-(1-((perfluorophenyl)sulfonyl)-N-(4-(tetrahydro-2H-pyran-4-yl)benzyl)azetidine-2-carboxamido)benzoic acid

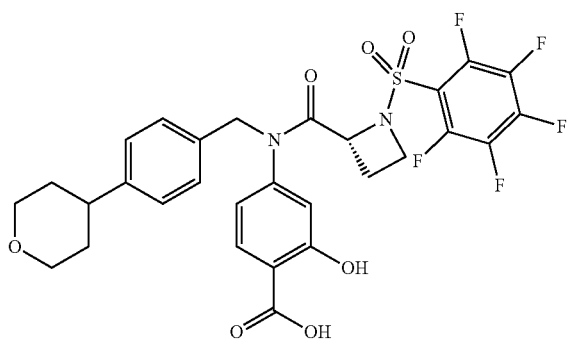 [SMILES: O=C(O)c1ccc(N(Cc2ccc(C3CCOCC3)cc2)C(=O)[C@H]2CCN2S(=O)(=O)c2c(F)c(F)c(F)c(F)c2F)cc1O]

Step 1: To a stirred solution of benzyl 2-(benzyloxy)-4-(2,2,2-trifluoroacetamido)benzoate (1.37 g, 3.2 mmol) in acetonitrile (36 mL) was added (4-(bromomethyl)phenyl)boronic acid (0.963 g, 4.48 mmol) and potassium carbonate (0.66 g, 4.8 mmol). The reaction mixture was stirred at 60° C. under nitrogen for 6 h and allowed to cool to room temperature The reaction mixture was poured onto ice with 10% aqueous potassium bisulfate/sodium sulfate buffer and extracted with EtOAc (3×). The combined organic layers were washed with brine, dried over sodium sulfate and concentrated under reduced pressure. Purification by flash chromatography (8-15% EtOAc/hexanes eluent) provided (4-((N-(3-(benzyloxy)-4-((benzyloxy)carbonyl)phenyl)-2,2,2-trifluoroacetamido)methyl)phenyl)boronic acid (1.33 g, 74% yield). HRMS (ESI) m/z 564.1760 [M+H]+.

Step 2: A stirred solution of (4-((N-(3-(benzyloxy)-4-((benzyloxy)carbonyl)phenyl)-2,2,2-trifluoroacetamido)methyl)phenyl)boronic acid (1.31 g, 2.33 mmol), 4-methoxy-N'-(tetrahydro-4H-pyran-4-ylidene)benzenesulfonohydrazide (0.66 g, 2.33 mmol) and cesium carbonate (1.14 g, 3.5 mmol) in 1.4 dioxane (12 mL) was degassed and backfilled with argon. The flask was heated to 110° C. for 24 hours. The reaction mixture was poured onto water and extracted with DCM with 0.1% methanol (3×). The combined organic layers were washed with brine, dried over anhydrous sodium sulfate and evaporated under reduced pressure. Purification by flash column chromatography (7:2:1 hexanes:DCM:EtOAc eluent) followed by trituration with 2:1 hexanes EtOAc provided benzyl 2-(benzyloxy)-4-((4-(tetrahydro-2H-pyran-4-yl)benzyl)amino)benzoate (0.27 g) as a white solid. The mother liquor and washes were purified by chromatography (20% acetone in hexanes eluent) and subsequent trituration with 1:1 ether:hexanes to provide additional product (0.185 g). Yield (38%). 1H NMR (300 MHz, Chloroform-d) δ 7.85 (d, J=8.6 Hz, 1H), 7.50-7.27 (m, 12H), 7.22 (d, J=8.2 Hz, 2H), 6.24 (dd, J=8.6, 2.2 Hz, 1H), 6.19 (d, J=2.2 Hz, 1H), 5.32 (s, 2H), 5.10 (s, 2H), 4.33 (s, 2H), 4.20-3.95 (m, 2H), 3.55 (td, J=11.3, 3.4 Hz, 2H), 2.78 (tt, J=10.9, 4.9 Hz, 1H), 1.98-1.68 (m, 4H).

Step 3: To a stirred solution of benzyl 2-(benzyloxy)-4-((4-(tetrahydro-2H-pyran-4-yl)benzyl)amino)-benzoate (0.22 g, 0.43 mmol) and (R)-1-((perfluorophenyl)sulfonyl)azetidine-2-carbonyl chloride (0.227 g, 0.65 mmol) in dry DCM (9 mL) under nitrogen was added DMAP (0.063 g, 0.52 mmol). Stirring was continued for 23 hours. The mixture was poured onto water and extracted with DCM (3×). Methanol (2-3 drops) was added to consume any excess acid chloride. The combined organic layers were dried over sodium sulfate and evaporated under reduced pressure. Purification by flash column chromatography (8-40% EtOAc/hexanes eluent) afforded benzyl (R)-2-(benzyloxy)-4-(1-((perfluorophenyl)sulfonyl)-N-(4-(tetrahydro-2H-pyran-4-yl)benzyl)azetidine-2-carboxamido)benzoate (384 mg, 100% yield). 1H NMR (300 MHz, Chloroform-d) δ 7.80 (d, J=8.2, 1H), 7.47-7.31 (m, 10H), 7.14 (d, J=8.1 Hz, 2H), 7.03 (d, J=8.1 Hz, 2H), 6.61 (dd, J=8.2, 1.8 Hz, 1H), 6.50 (s, 1H), 5.37 (s, 2H), 5.08 (d, J=12.3 Hz, 1H), 4.91 (d, J=12.3 Hz, 1H), 4.86-4.76 (m, 2H), 4.67 (d, J=14.3 Hz, 1H), 4.15-3.92 (m, 5H), 3.53 (td, J=11.3, 3.2 Hz, 2H), 2.84-2.64 (m, 1H), 2.09-1.92 (m, 1H), 1.89-1.64 (m, 4H).

Step 4: To a stirred solution of benzyl (R)-2-(benzyloxy)-4-(1-((perfluorophenyl)sulfonyl)-N-(4-(tetrahydro-2H-pyran-4-yl)benzyl)azetidine-2-carboxamido)benzoate (380 mg, 0.48 mmol) in methanol (15 mL) and EtOAc (15 mL) under nitrogen was added 20% Pd(OH)$_2$ on C (36 mg). The reaction mixture was stirred under a hydrogen atmosphere for 2 h, then filtered through Celite® and washed with EtOAc (2×). The combined filtrate and washes were concentrated in vacuo to yield (R)-2-hydroxy-4-(1-((perfluorophenyl)sulfonyl)-N-(4-(tetrahydro-2H-pyran-4-yl)benzyl)azetidine-2-carboxamido)benzoic acid as a pale pink foam (247 mg, 80% yield). HRMS (ESI) m/z 641.1382 [M+H]+.

Example 77

Sodium (R)-2-hydroxy-4-(1-((perfluorophenyl)sulfonyl)-N-(4-(tetrahydro-2H-pyran-4-yl)benzyl)azetidine-2-carboxamido)benzoate

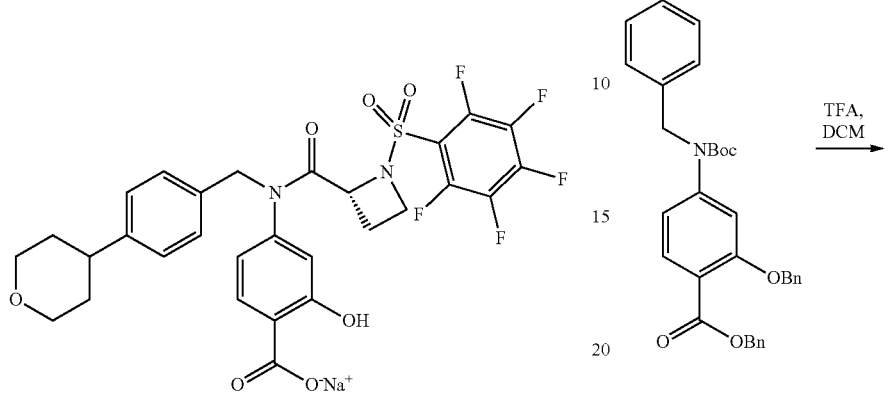

Preparation by a similar procedure to example 62, except substituting (R)-2-hydroxy-4-(1-((perfluorophenyl)sulfonyl)-N-(4-(tetrahydro-2H-pyran-4-yl)benzyl)azetidine-2-carboxamido)benzoic for (R)-4-(N-(4-cyclohexylbenzyl)-1-((perfluorophenyl)sulfonyl)azetidine-2-carboxamido)-5-fluoro-2-hydroxybenzoic acid afforded sodium (R)-2-hydroxy-4-(1-((perfluorophenyl)sulfonyl)-N-(4-(tetrahydro-2H-pyran-4-yl)benzyl)azetidine-2-carboxamido)benzoate (40 mg) as a yellow solid. HRMS (ESI) m/z 663.1196 [M+Na]+.

Example 78

Sodium (R)-5-fluoro-2-hydroxy-4-(1-((perfluorophenyl)sulfonyl)-N-(4-(tetrahydro-2H-pyran-4-yl)benzyl)azetidine-2-carboxamido)benzoate Preparation by a similar procedure to example 62, except substituting (R)-5-fluoro-2-hydroxy-4-(1-((perfluorophenyl)sulfonyl)-N-(4-(tetrahydro-2H-pyran-4-yl)benzyl)azetidine-2-carboxamido)benzoic acid for (R)-4-(N-(4-cyclohexylbenzyl)-1-((perfluorophenyl)sulfonyl)azetidine-2-carboxamido)-5-fluoro-2-hydroxybenzoic acid afforded sodium (R)-5-fluoro-2-hydroxy-4-(1-((perfluorophenyl)sulfonyl)-N-(4-(tetrahydro-2H-pyran-4-yl)benzyl)azetidine-2-carboxamido)benzoate as a light yellow solid. HRMS (ESI) m/z 681.1108 [M+Na]+.

Example 79

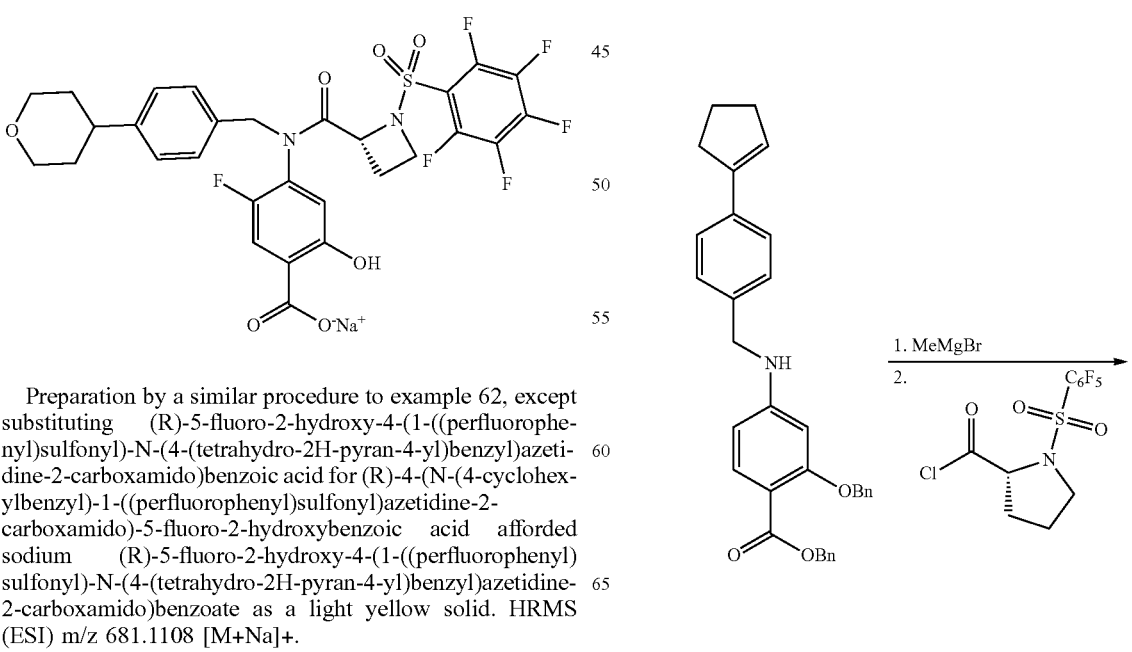

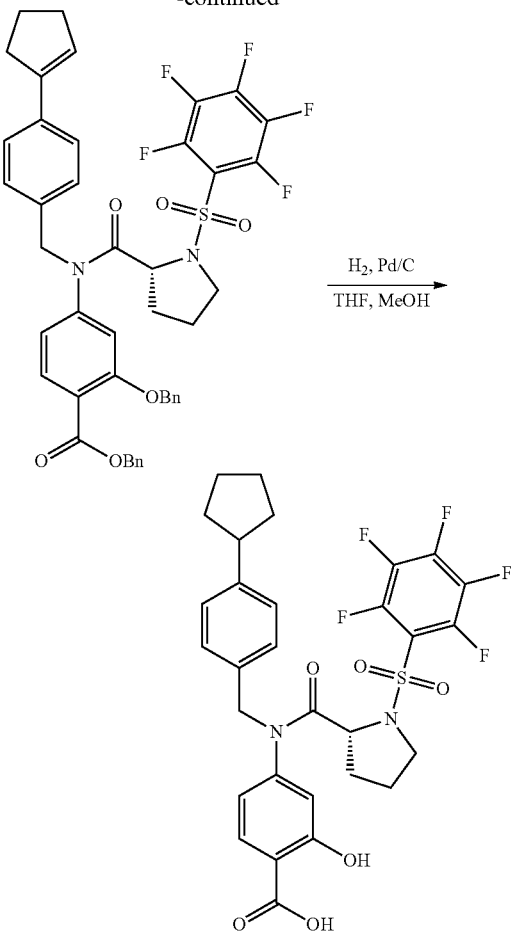

(R)-4-(N-(4-cyclopentylbenzyl)-1-((perfluorophenyl)sulfonyl)pyrrolidine-2-carboxamido)-2-hydroxybenzoic acid

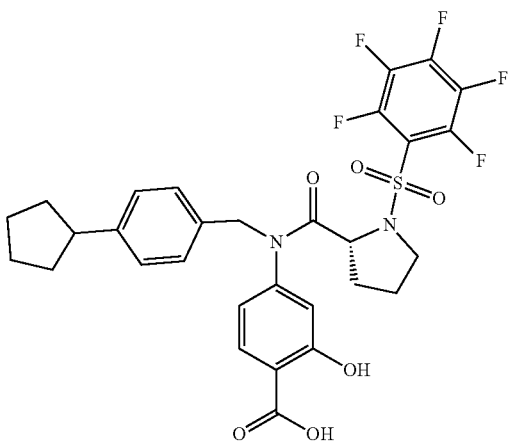 [SMILES: O=C(O)c1ccc(N(Cc2ccc(C3CCCC3)cc2)C(=O)[C@H]2CCCN2S(=O)(=O)c2c(F)c(F)c(F)c(F)c2F)cc1O]

Step 1: To a stirred solution of benzyl 2-(benzyloxy)-4-((4-bromobenzyl)(tert-butoxycarbonyl)amino)benzoate (421 mg, 0.7 mmol) in DCM (7.8 mL) under nitrogen at 0° C. was added TFA (1.56 mL) and the resultant solution was stirred at 0° C. for 2 h. The mixture was poured onto cold 10% aqueous sodium bicarbonate and after bubbling had ceased was extracted with DCM (1×). The DCM extract was dried over anhydrous sodium sulfate, concentrated under reduced pressure and resulting residue purified by flash chromatography (15-30% EtOAc/hexanes eluent) to afford benzyl 2-(benzyloxy)-4-((4-bromobenzyl)amino)benzoate (190 mg, 54% yield). 1H NMR (300 MHz, Chloroform-d) δ 7.84 (d, J=8.6, 1H), 7.47 (d, J=8.3 Hz, 2H), 7.44-7.30 (m, 10H), 7.19 (d, J=8.3 Hz, 2H), 6.21 (dd, J=8.6, 2.2 Hz, 1H), 6.14 (d, J=2.2 Hz, 1H), 5.32 (s, 2H), 5.09 (s, 2H), 4.49 (br. s, 1H), 4.32 (s, 2H).

Step 2: In a dry flask under nitrogen was added benzyl 2-(benzyloxy)-4-((4-bromobenzyl)amino)benzoate (187.1 mg, 0.37 mmol), Pd(OAc)$_2$ (4.18 mg, 0.0186 mmol), SPhos (15.3 mg, 0.037 mmol), 2-(cyclopent-1-en-1-yl)-4,4,5,5-tetramethyl-1,3,2-dioxaborolane (117.2 mg, 0.558 mmol), potassium phosphate tribasic (157.9 mg, 0.744 mmol) and water (13.3 mg, 0.744 mmol). The flask was back-flushed with nitrogen, THF (4.8 mL) was added and the flask was heated at 40° C. for 24 h. The crude reaction mixture was poured onto water and extracted with EtOAc (1×). The organic layer was washed with brine, dried over anhydrous sodium sulfate and concentrated under reduced pressure. The resulting residue was purified by flash chromatography (15% EtOAc/hexanes) followed by recrystallization from EtOAc/ether and re-purification of the mother liquors by preparative TLC to provide benzyl 2-(benzyloxy)-4-((4-(cyclopent-1-en-1-yl)benzyl)amino)benzoate (124.3 mg, 68% yield) as a white solid. 1H NMR (300 MHz, Chloroform-d) δ 7.84 (d, J=8.6 Hz, 1H), 7.53-7.23 (m, 14H), 6.30-6.12 (m, 3H), 5.32 (s, 2H), 5.10 (s, 2H), 4.45 (s, 1H), 4.33 (d, J=4.2 Hz, 2H), 2.82-2.63 (m, 2H), 2.54 (d, J=8.3 Hz, 2H), 2.04 (p, J=7.6 Hz, 2H).

Step 3: To a stirred solution of benzyl 2-(benzyloxy)-4-((4-(cyclopent-1-en-1-yl)benzyl)amino)benzoate (60.5 mg, 0.124 mmol) in THF (1 mL) at 0° C. under nitrogen was added a solution of methylmagnesium bromide (0.22 mL of 1.4M in THF, 0.309 mmol) and the mixture was stirred a 0° C. for 10 min before addition of ((perfluorophenyl)sulfonyl)-D-prolinoyl chloride (67.4 mg, 0.185 mmol). The reaction mixture was allowed to warm to room temperature and stirred at this temperature for 7.5 h. To the reaction mixture was added a cold solution of saturated aqueous ammonium chloride followed by water and the resultant mixture was extracted with EtOAc (2×). The combined organic extracts were washed with brine, dried over anhydrous sodium sulfate and concentrated under reduced pressure. Purification by flash chromatography (15-20% EtOAc/hexanes eluent) provided benzyl (R)-2-(benzyloxy)-4-(N-(4-(cyclopent-1-en-1-yl)benzyl)-1-((perfluorophenyl)sulfonyl)pyrrolidine-2-carboxamido)benzoate (93.8 mg, 93% yield) as a colorless oil. MS (ESI) m/z 817.10 [M+H]+.

Step 4: To a stirred solution of benzyl (R)-2-(benzyloxy)-4-(N-(4-(cyclopent-1-en-1-yl)benzyl)-1-((perfluorophenyl)sulfonyl)pyrrolidine-2-carboxamido)benzoate (90.7 mg, 0.111 mmol) in methanol (1.4 mL) and THF (1.4 mL) was added 10% Pd/C (10 mg) and the resulting suspension was stirred at room temperature under a hydrogen atmosphere overnight. The reaction mixture was filtered through Celite® and washed with EtOAc (2×). The combined filtrate and washes were concentrated, purified by preparative TLC (50% EtOAc/hexane with 0.1% HOAc) to provide (R)-4-(N-(4-cyclopentylbenzyl)-1-((perfluorophenyl)sulfonyl)pyrrolidine-2-carboxamido)-2-hydroxybenzoic acid (12.8 mg, 18% yield) as a foam. MS (ESI) m/z 639.1584 [M+H]+.

Example 80

(R)-4-(N-(4-Cyclopentylbenzyl)-1-((perfluorophenyl)sulfonyl)azetidine-2-carboxamido)-2-hydroxybenzoic acid

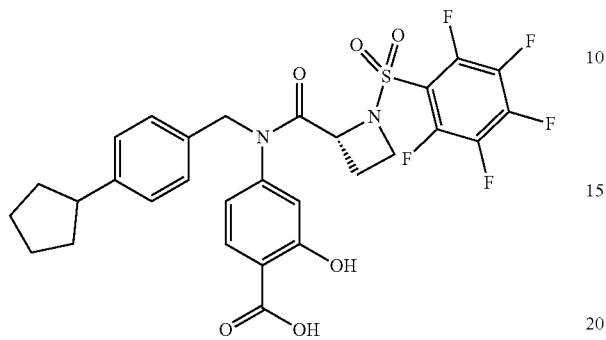

Preparation by a similar procedure to example 79, except substituting (R)-1-((perfluorophenyl)sulfonyl)azetidine-2-carbonyl chloride for ((perfluorophenyl)sulfonyl)-D-prolinoyl chloride in step 3 afforded (R)-4-(N-(4-cyclopentylbenzyl)-1-((perfluorophenyl)sulfonyl)azetidine-2-carboxamido)-2-hydroxybenzoic acid as an off-white foam. HRMS (ESI) m/z 625.1432 [M+H]+.

Example 81

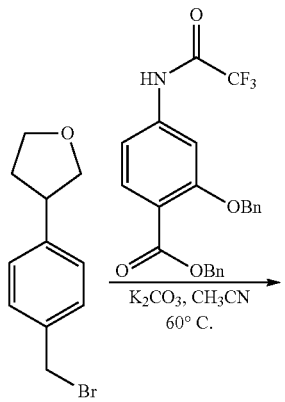

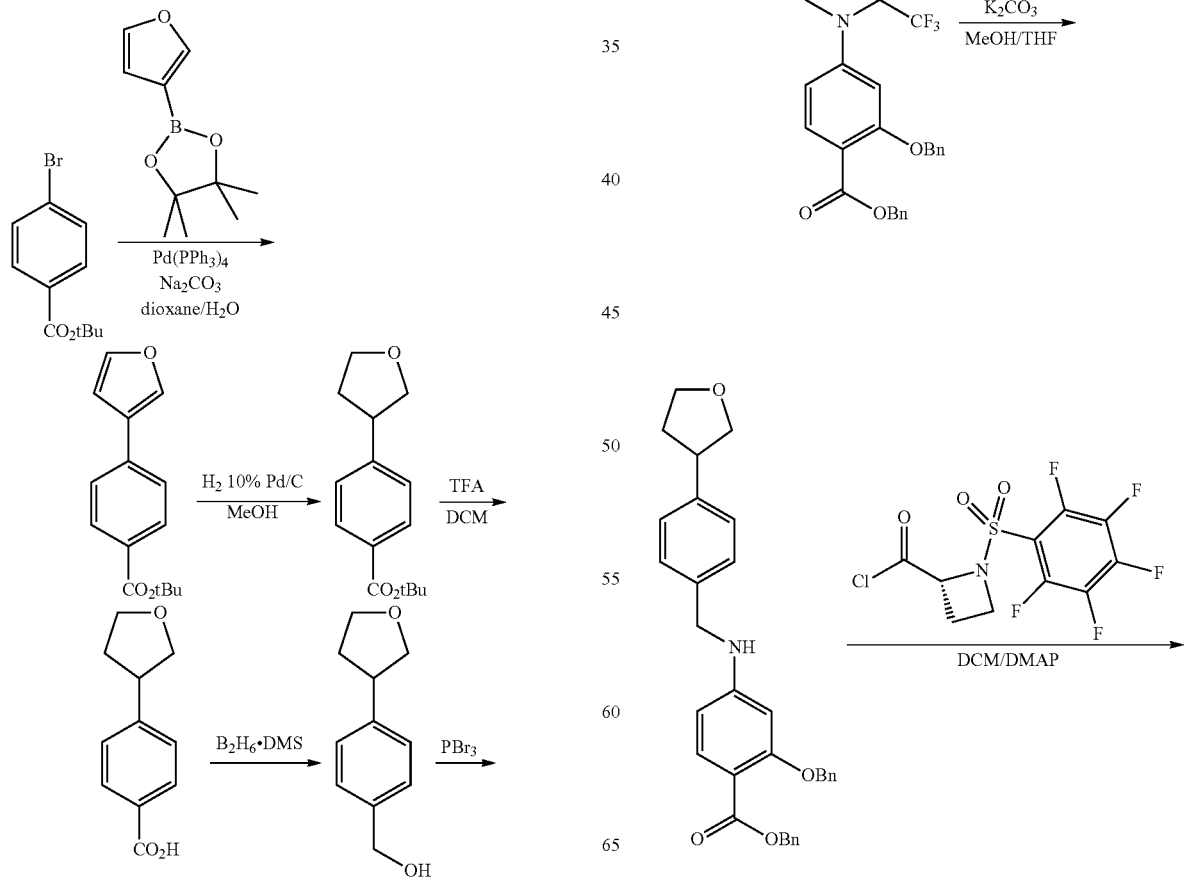

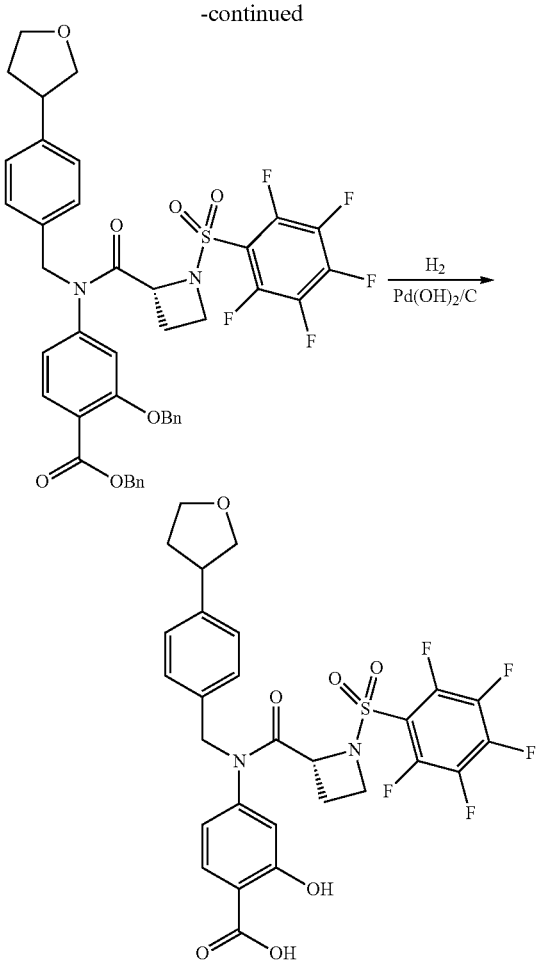

2-Hydroxy-4-((2R)-1-((perfluorophenyl)sulfonyl)-N-(4-(tetrahydrofuran-3-yl) benzyl)azetidine-2-carboxamido)benzoic acid

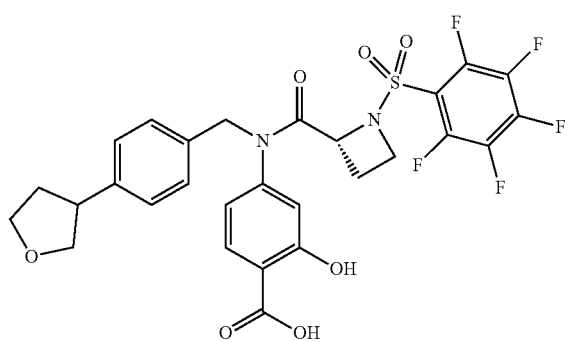 [SMILES: O=C(O)c1ccc(N(Cc2ccc(C3CCOC3)cc2)C(=O)[C@H]2CCN2S(=O)(=O)c2c(F)c(F)c(F)c(F)c2F)cc1O]

Step 1: To a stirred solution of tert-butyl 4-bromobenzoate (1.934 g, 7.53 mmol) in dioxane (62 mL) under argon was added 2-(furan-3-yl)-4,4,5,5-tetramethyl-1,3,2-dioxaborolane (1.464, 7.53 mmol), sodium carbonate (2.398 g, 22.6 mmol) and distilled water (15.5 mL). The mixture was degassed with argon before addition of palladium tetrakistriphenylphosphine (46.3 mg, 0.039 mmol). The reaction was heated at 90° C. overnight. The crude reaction mixture was poured onto water and extracted with EtOAc (3×). The combined organic extracts were washed with brine, dried over anhydrous sodium sulfate and concentrated under reduced pressure. The resulting residue was purified by flash chromatography (10-20% DCM in hexanes eluent) to provide tert-butyl 4-(furan-3-yl)benzoate (1.52 g, 83% yield) as a colorless oil. 1H NMR (300 MHz, Chloroform-d) δ 8.00 (d, J=8.7 Hz, 2H), 7.82 (dd, J=1.5, 0.9 Hz, 1H), 7.59-7.47 (m, 3H), 6.75 (dd, J=1.9, 0.9 Hz, 1H), 1.62 (s, 9H).

Step 2: To a stirred solution of tert-butyl 4-(furan-3-yl)benzoate (1.5114 g, 6.2 mmol) in methanol (76 mL) was added 10% Pd/C (151 mg) and the resulting suspension was stirred under hydrogen at room temperature for 19 h. The reaction mixture was filtered through Celite® and washed with methanol (2×). The combined filtrate and washes were concentrated in vacuo to provide tert-butyl 4-(tetrahydrofuran-3-yl)benzoate (1.466 g, 95% yield) as a colorless oil. 1H NMR (300 MHz, Chloroform-d) δ 7.94 (d, J=8.3 Hz, 2H), 7.31 (d, J=8.3 Hz, 2H), 4.20-4.03 (m, 2H), 3.93 (dt, J=8.4, 7.5 Hz, 1H), 3.76 (dd, J=8.5, 7.1 Hz, 1H), 3.46 (p, J=7.6 Hz, 1H), 2.48-2.32 (m, 1H), 2.01 (dq, J=12.4, 7.9 Hz, 1H), 1.60 (s, 9H).

Step 3: To a stirred solution of tert-butyl 4-(tetrahydrofuran-3-yl)benzoate (1.466 g, 5.91 mmol) in DCM (42 mL) under nitrogen was added TFA (8.4 mL) and the resulting mixture was stirred at room temperature for 30 min, then concentrated under reduced pressure. The resulting residue was dissolved in toluene and concentrated under reduced pressure (2×) to provide 4-(tetrahydrofuran-3-yl)benzoic acid (1.26 g). 1H NMR (300 MHz, Chloroform-d) δ 8.07 (d, J=8.3 Hz, 2H), 7.38 (d, J=8.3 Hz, 2H), 4.25-4.07 (m, 2H), 3.97 (dt, J=8.6, 7.6 Hz, 1H), 3.81 (dd, J=8.6, 7.1 Hz, 1H), 3.51 (p, J=7.6 Hz, 1H), 2.53-2.34 (m, 1H), 2.05 (dq, J=12.4, 7.9 Hz, 1H).

Step 4: To a stirred solution of 4-(tetrahydrofuran-3-yl)benzoic acid (1.26 g) in THF (7.3 mL) under nitrogen at 0° C. was added a solution of borane dimethyl sulfide complex (6.6 mL of 2M in THF, 13.1 mmol) and the resulting mixture was allowed to warm to room temperature and was stirred at this temperature overnight. Ice was added to the reaction mixture and concentrated sulfuric acid was added dropwise while stirring until pH=2. The resulting mixture was stirred at room temperature for 2 h, then poured onto water and extracted with EtOAc (3×). The combined organic extracts were washed with brine, dried over anhydrous sodium sulfate and concentrated under reduced pressure to provide (4-(tetrahydrofuran-3-yl)phenyl)methanol (1.088 g, 100% over 2 steps) as a colorless oil. 1H NMR (300 MHz, Chloroform-d) δ 7.34 (d, J=8.2 Hz, 2H), 7.27 (d, J=8.2 Hz, 2H), 4.68 (s, 2H), 4.22-4.02 (m, 2H), 3.93 (td, J=8.2, 7.3 Hz, 1H), 3.73 (dd, J=8.2, 7.5 Hz, 1H), 3.42 (p, J=7.7 Hz, 1H), 2.38 (dtd, J=12.3, 7.7, 4.5 Hz, 1H), 2.11-1.94 (m, 1H).

Step 5: To a stirred solution of (4-(tetrahydrofuran-3-yl)phenyl)methanol (517 mg, 2.9 mmol) in DCM (3.7 mL) under nitrogen at 0° C. was added phosphorous tribromide (0.125 mL, 1.32 mmol) and the resulting mixture was stirred at 0° C. for 2 h. The crude reaction mixture was poured onto ice water and extracted with DCM (3×). The combined organic extracts were washed with brine, dried over anhydrous sodium sulfate and concentrated under reduced pressure. The resulting residue was purified by flash chromatography (10-15% EtOAc/hexanes eluent) to provide 3-(4-(bromomethyl)phenyl)tetrahydrofuran (546 mg, 78% yield) as a colorless oil. 1H NMR (300 MHz, Chloroform-d) δ 7.36 (d, J=8.2 Hz, 2H), 7.25 (d, J=8.2 Hz, 2H), 4.50 (s, 2H), 4.19-4.02 (m, 2H), 3.93 (dt, J=8.4, 7.5 Hz, 1H), 3.73 (dd, J=8.4, 7.5 Hz, 1H), 3.42 (p, J=7.7 Hz, 1H), 2.45-2.31 (m, 1H), 2.01 (dq, J=12.3, 8.0 Hz, 1H).

Step 6: To a stirred solution of benzyl 2-(benzyloxy)-4-(2,2,2-trifluoroacetamido)benzoate (343 mg, 0.8 mmol) in acetonitrile (7.8 mL) under nitrogen was added 3-(4-(bromomethyl)phenyl)tetrahydrofuran (232 mg, 0.96 mmol) and potassium carbonate (166 mg, 1.2 mmol) and the resulting suspension was stirred at 60° C. for 4 h and allowed to sit at room temperature overnight. The reaction mixture was then poured onto water and 10% aqueous potassium bisulfate/sodium sulfate buffer and extracted with EtOAc (2×). The combined organic extracts were washed with brine, dried over sodium sulfate and concentrated under reduced pressure. Purification by flash chromatography (80:20:5 hexanes:DCM:EtOAc, then 70:20:10 hexanes:DCM:EtOAc eluent) provided benzyl 2-(benzyloxy)-4-(2,2,2-trifluoro-N-(4-(tetrahydrofuran-3-yl)benzyl)acetamido)benzoate (451 mg, 96% yield) as a colorless oil. 1H NMR (300 MHz, Chloroform-d) δ 7.82 (d, J=8.3 Hz, 1H), 7.44-7.31 (m, 10H), 7.18 (d, J=8.2 Hz, 2H), 7.08 (d, J=8.2 Hz, 2H), 6.68 (d, J=8.3 Hz, 1H), 6.58 (s, 1H), 5.35 (s, 2H), 4.96 (s, 2H), 4.84 (s, 2H), 4.19-4.00 (m, 2H), 3.98-3.83 (m, 1H), 3.77-3.64 (m, 1H), 3.39 (p, J=7.7 Hz, 1H), 2.43-2.27 (m, 1H), 1.96 (dq, J=12.3, 8.1 Hz, 1H).

Step 7: To a stirred solution of benzyl 2-(benzyloxy)-4-(2,2,2-trifluoro-N-(4-(tetrahydrofuran-3-yl)benzyl)acetamido)benzoate (435 mg, 0.74 mmol) in methanol (5.8 mL) and THF (5.8 mL) under nitrogen was added potassium carbonate (172 mg, 1.25 mmol) and the resulting mixture was stirred at room temperature for 2.5 h. The mixture was poured onto cold saturated aqueous ammonium chloride and water and extracted with EtOAc (2×). The combined organic extracts were washed with brine, dried over anhydrous sodium sulfate and concentrated in vacuo to give a white solid. The solid was triturated with 3:1 hexanes:ether to provide benzyl 2-(benzyloxy)-4-((4-(tetrahydrofuran-3-yl)benzyl)amino)benzoate (331 mg, 91% yield) as a white solid.

Step 8: To a stirred solution of benzyl 2-(benzyloxy)-4-((4-(tetrahydrofuran-3-yl)benzyl)amino)benzoate (0.148 g, 0.30 mmol) and (R)-1-((perfluorophenyl)sulfonyl)azetidine-2-carbonyl chloride (0.157 g, 0.45 mmol) in dry DCM (6.3 mL) under nitrogen was added DMAP (44 mg, 0.36 mmol). Stirring was continued for 20 hours. Methanol (2-3 drops) was added to consume any excess acid chloride. The mixture was poured onto water and extracted with DCM (3×). The combined organic layers were dried over sodium sulfate and evaporated under reduced pressure. Purification by flash column chromatography (15-30% EtOAc/hexanes eluent) afforded benzyl 2-(benzyloxy)-4-((2R)-1-((perfluorophenyl)sulfonyl)-N-(4-(tetrahydrofuran-3-yl)benzyl)azetidine-2-carboxamido)benzoate (233 mg, 96% yield) as a white foam. HRMS (ESI) m/z 807.2179 [M+H]+.

Step 9: To a stirred solution of benzyl 2-(benzyloxy)-4-((2R)-1-((perfluorophenyl)sulfonyl)-N-(4-(tetrahydrofuran-3-yl)benzyl)azetidine-2-carboxamido)benzoate (210 mg, 0.26 mmol) in methanol (8 mL) and EtOAc (8 mL) under nitrogen was added 20% Pd(OH)₂ on C (19.5 mg). The reaction mixture was stirred under a hydrogen atmosphere for 2 h, then filtered through Celite® and washed with EtOAc (2×). The combined filtrate and washes were concentrated in vacuo and foamed with ether to yield 2-hydroxy-4-((2R)-1-((perfluorophenyl)sulfonyl)-N-(4-(tetrahydrofuran-3-yl)benzyl)azetidine-2-carboxamido)benzoic acid as a white foam. HRMS (ESI) m/z 627.1223 [M+H]+.

Example 82

(R)-4-(N-(4-cyclohexylbenzyl)-1-((perfluorophenyl)sulfonyl)azetidine-2-carboxamido)benzoic acid

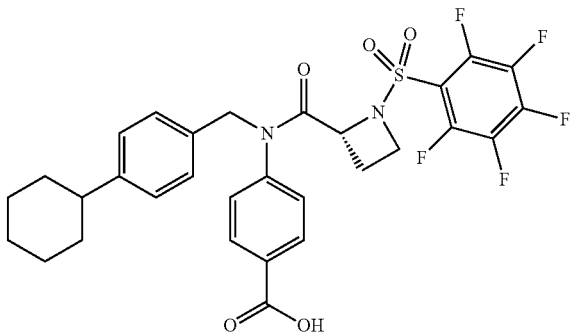 [SMILES: O=C(O)c1ccc(N(Cc2ccc(C3CCCCC3)cc2)C(=O)[C@H]2CCN2S(=O)(=O)c2c(F)c(F)c(F)c(F)c2F)cc1]

Step 1: To a solution of benzyl 4-((4-cyclohexylbenzyl)amino)benzoate (255 mg, 0.638 mmol) in DCM (6 mL) under nitrogen was added (R)-1-((perfluorophenyl)sulfonyl)azetidine-2-carbonyl chloride (245 mg, 0.702 mmol). The reaction mixture was cooled to 0° C. and DMAP (85.8 mg, 0.702 mmol) was added. The reaction was allowed to warm to room temperature and stirring was continued at room temperature for 19 hours. The mixture was poured onto water and extracted with DCM (2×). The combined organic layers were dried over sodium sulfate and evaporated under reduced pressure. Purification by flash column chromatography (20% EtOAc/hexanes eluent) afforded benzyl (R)-4-(N-(4-cyclohexylbenzyl)-1-((perfluorophenyl)sulfonyl)azetidine-2-carboxamido)benzoate (275 mg, 61% yield). 1H NMR (300 MHz, Chloroform-d) δ 8.06 (d, J=7.9, 2H), 7.52-7.35 (m, 5H), 7.05 (m, 6H), 5.39 (s, 2H), 5.00-4.80 (m, 2H), 4.72 (d, J=14.4 Hz, 1H), 4.25-3.89 (m, 2H), 2.62-2.40 (m, 1H), 2.26 (dq, J=17.0, 8.7, 8.0 Hz, 1H), 2.03-1.71 (m, 6H), 1.68-1.30 (m, 5H).

Step 2: To a stirred solution of benzyl (R)-4-(N-(4-cyclohexylbenzyl)-1-((perfluorophenyl)sulfonyl)azetidine-2-carboxamido)benzoate (256 mg, 0.36 mmol) in methanol (4.2 mL) and THF (4.2 mL) was added 10% Pd/C (32 mg) and the resulting suspension was stirred at room temperature under a hydrogen atmosphere for 5 h. The reaction mixture was filtered through Celite® and washed with EtOAc (2×). The combined filtrate and washes were concentrated to provide (R)-4-(N-(4-cyclohexylbenzyl)-1-((perfluorophenyl)sulfonyl)azetidine-2-carboxamido)benzoic acid (219 mg, 98% yield). HRMS (ESI) m/z 623.1640 [M+H]+.

Example 83

(R)—N-(4-cyclohexylbenzyl)-N-(4-(hydroxycarbamoyl)phenyl)-1-((perfluorophenyl)sulfonyl)azetidine-2-carboxamide

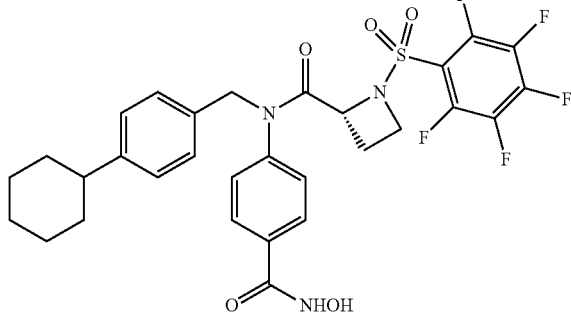

Preparation by a similar procedure to example 4, except substituting (R)-4-(N-(4-cyclohexylbenzyl)-1-((perfluorophenyl)sulfonyl)azetidine-2-carboxamido)benzoic acid for (R)-4-(N-(4-cyclohexylbenzyl)-2-((2,3,4,5,6-pentafluoro-N-methylphenyl)sulfonamido)propanamido)benzoic acid in step 1 afforded (R)—N-(4-cyclohexylbenzyl)-N-(4-(hydroxycarbamoyl)phenyl)-1-((perfluorophenyl)sulfonyl) azetidine-2-carboxamide as a white powder. HRMS (ESI+) m/z 638.1747 [M+H]+.

Example 84-85

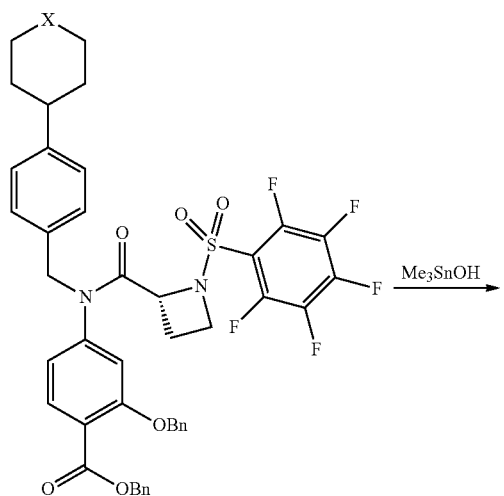

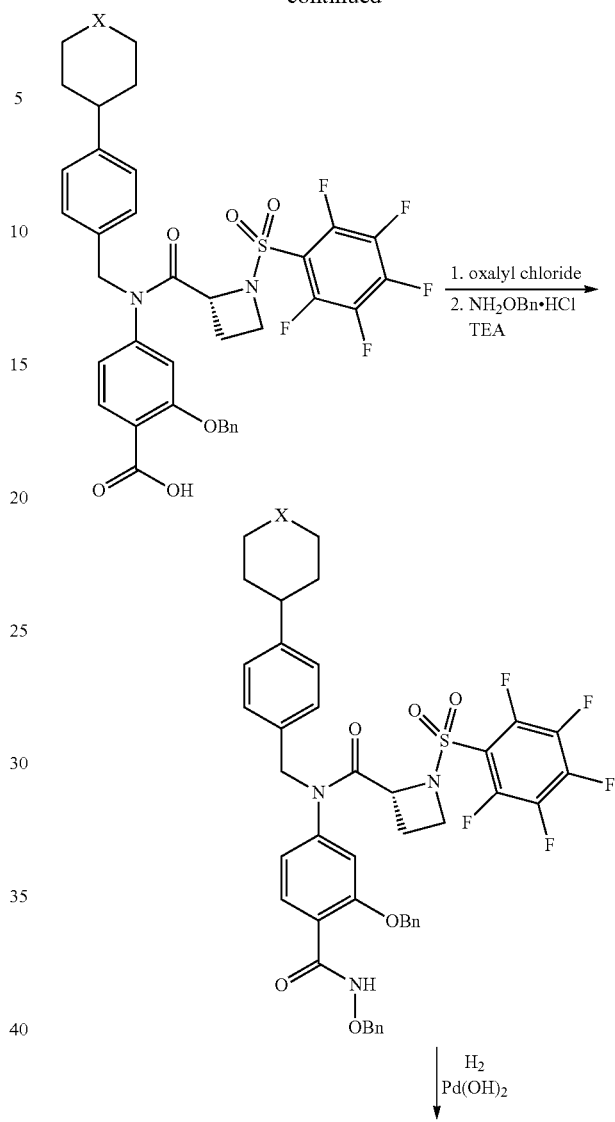

X = O, CH$_2$

Example 84

(R)—N-(3-hydroxy-4-(hydroxycarbamoyl)phenyl)-1-((perfluorophenyl)sulfonyl)-N-(4-(tetrahydro-2H-pyran-4-yl)benzyl)azetidine-2-carboxamide

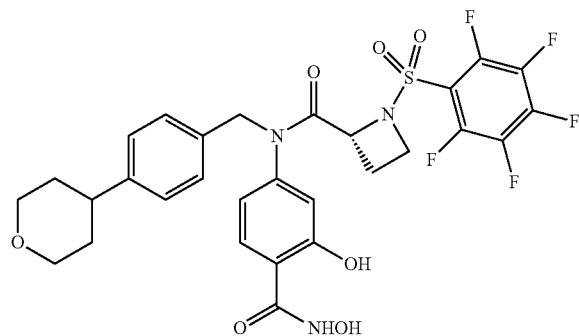

Step 1: To a stirred solution of benzyl (R)-2-(benzyloxy)-4-(1-((perfluorophenyl)sulfonyl)-N-(4-(tetrahydro-2H-pyran-4-yl)benzyl)azetidine-2-carboxamido)benzoate (285 mg, 0.35 mmol) in DCE (32 mL) under nitrogen was added trimethyltin hydroxide (503 mg, 2.78 mmol). The reaction was warmed at 85° C. for 5 days. After cooling to room temperature, the reaction mixture was poured onto 1M aqueous HCl and extracted with DCM (3×). The combined organic layers were washed with brine, dried over sodium sulfate and concentrated under reduced pressure. Purification by flash chromatography (0.5% MeOH in DCM, then 5% MeOH in DCM eluent) provided (R)-2-(benzyloxy)-4-(1-((perfluorophenyl)sulfonyl)-N-(4-(tetrahydro-2H-pyran-4-yl)benzyl)azetidine-2-carboxamido)benzoic acid (200 mg, 78% yield). LCMS (ESI+) m/z 731.10 [M+H]+.

Step 2: To a stirred solution of (R)-2-(benzyloxy)-4-(1-((perfluorophenyl)sulfonyl)-N-(4-(tetrahydro-2H-pyran-4-yl)benzyl)azetidine-2-carboxamido)benzoic acid (200 mg, 0.27 mmol) in DCM (10 mL) under nitrogen was added oxalyl chloride (0.05 mL, 0.60 mmol) and DMF (small drop). The resulting reaction solution was stirred at room temperature under nitrogen for 2 h and then concentrated in vacuo to provide (R)-2-(benzyloxy)-4-(1-((perfluorophenyl)sulfonyl)-N-(4-(tetrahydro-2H-pyran-4-yl)benzyl)azetidine-2-carboxamido)benzoyl chloride, which was used as is.

Step 3: To a solution of O-benzylhydroxylamine hydrochloride (87.8 mg, 0.55 mmol) in DMF (3 mL) was added TEA (0.115 mL, 0.82 mmol). The mixture was stirred for 5 min, then added to a solution of the crude acid chloride, (R)-2-(benzyloxy)-4-(1-((perfluorophenyl)sulfonyl)-N-(4-(tetrahydro-2H-pyran-4-yl)benzyl)azetidine-2-carboxamido)benzoyl chloride (0.27 mmol), in THF (10 mL) at 0° C. under nitrogen. The resultant reaction mixture was warmed to room temperature and stirred for 1.5 h. The reaction was quenched with 10% aqueous potassium bisulfate, poured onto water and extracted with ether (3×). The combined organic extracts were washed with brine, dried over anhydrous sodium sulfate and concentrated under reduced pressure. The resulting residue was purified by flash chromatography (25-50% EtOAc/hexanes) to provide (R)—N-(3-(benzyloxy)-4-((benzyloxy)carbamoyl)phenyl)-1-((perfluorophenyl)sulfonyl)-N-(4-(tetrahydro-2H-pyran-4-yl)benzyl)azetidine-2-carboxamide (178 mg, 79% yield). MS (ESI) m/z 836.20 [M+H]+.

Step 4: To a stirred solution of (R)—N-(3-(benzyloxy)-4-((benzyloxy)carbamoyl)phenyl)-1-((perfluorophenyl)sulfonyl)-N-(4-(tetrahydro-2H-pyran-4-yl)benzyl)azetidine-2-carboxamide (172 mg, 0.2 mmol) in methanol (5 mL) and EtOAc (5 mL) was added 20% Pd(OH)$_2$/C (17 mg) and the resulting suspension was stirred at room temperature under a hydrogen atmosphere for 1 h. The reaction mixture was filtered through Celite® and washed with EtOAc. The combined filtrate and washes were concentrated in vacuo to provide (R)—N-(3-hydroxy-4-(hydroxycarbamoyl)phenyl)-1-((perfluorophenyl)sulfonyl)-N-(4-(tetrahydro-2H-pyran-4-yl)benzyl)azetidine-2-carboxamide (135 mg, 100% yield) as a white solid. MS (ESI) m/z 656.1493 [M+H]+.

Example 85

(R)—N-(4-cyclohexylbenzyl)-N-(3-hydroxy-4-(hydroxycarbamoyl)phenyl)-1-((perfluorophenyl)sulfonyl)azetidine-2-carboxamide

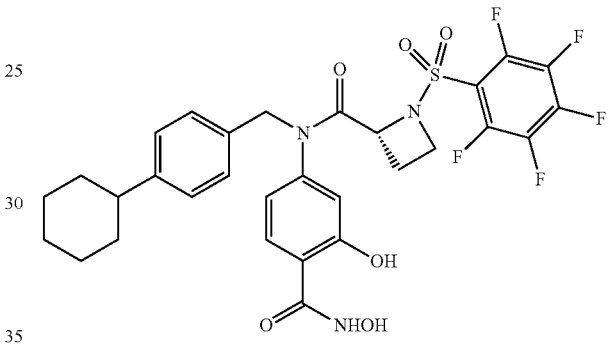

Step 1: To a stirred solution of benzyl 2-(benzyloxy)-4-((4-cyclohexylbenzyl)amino)benzoate (505 mg, 1.0 mmol) in dry THF (10 mL) under nitrogen at 0° C. was added methylmagnesium bromide (1.8 mL of 1.4 M in THF, 2.52 mmol) and the resulting solution was stirred at 0° C. for 15 min before addition of solid (R)-1-((perfluorophenyl)sulfonyl)-azetidine-2-carbonyl chloride (524 mg, 1.5 mmol). The resulting mixture was allowed to warm to room temperature and stirred at room temperature for 7 h. To the crude reaction mixture was added cold saturated aqueous ammonium chloride followed by water and the resulting mixture was extracted with EtOAc (2×). The combined organic extract was washed with brine, dried over sodium sulfate and concentrated under reduced pressure. The crude residue was purified by flash chromatography (76:10:14 hexanes:DCM:EtOAc eluent) to provide benzyl (R)-2-(benzyloxy)-4-(N-(4-cyclohexylbenzyl)-1-((perfluorophenyl)sulfonyl)azetidine-2-carboxamido)benzoate (574 mg, 70% yield). LCMS (ESI+) m/z 819.3 [M+H]+.

Step 2: To a stirred solution of benzyl (R)-2-(benzyloxy)-4-(N-(4-cyclohexylbenzyl)-1-((perfluorophenyl)sulfonyl)azetidine-2-carboxamido)benzoate (427 mg, 0.69 mmol) in DCE (58 mL) under nitrogen was added trimethyltin hydroxide (1.0 g, 5.58 mmol). The reaction was warmed at 85° C. for 3 days. After cooling to room temperature, the reaction mixture was poured onto saturated aqueous NH$_4$Cl and extracted with DCM (3×). The combined organic layers were washed with brine, dried over sodium sulfate and concentrated under reduced pressure. Purification by flash chromatography (25% EtOAc/hexanes, then 3% methanol containing 1% acetic acid in DCM eluent) provided (R)-2-

(benzyloxy)-4-(N-(4-cyclohexylbenzyl)-1-((perfluorophenyl)sulfonyl)azetidine-2-carboxamido)benzoic acid (359 mg, 71% yield). LCMS (ESI+) m/z 729.20 [M+H]+.

Step 3: To a stirred solution of (R)-2-(benzyloxy)-4-(N-(4-cyclohexylbenzyl)-1-((perfluorophenyl)sulfonyl)azetidine-2-carboxamido)benzoic acid (359 mg, 0.49 mmol) in DCM (6 mL) under nitrogen was added oxalyl chloride (0.09 mL, 1.07 mmol) and DMF (small drop). The resulting reaction solution was stirred at room temperature under nitrogen for 1.75 h and then concentrated in vacuo to provide (R)-2-(benzyloxy)-4-(N-(4-cyclohexylbenzyl)-1-((perfluorophenyl)sulfonyl)azetidine-2-carboxamido)benzoyl chloride, which was used as is.

Step 4: To a solution of O-benzylhydroxylamine hydrochloride (156 mg, 0.98 mmol) in DMF (5 mL) was added TEA (0.21 mL, 1.47 mmol). The mixture was stirred for 5 min, then added to a solution of the crude acid chloride, (R)-2-(benzyloxy)-4-(1-((perfluorophenyl)sulfonyl)-N-(4-(tetrahydro-2H-pyran-4-yl)benzyl)azetidine-2-carboxamido)benzoyl chloride (0.49 mmol), in THF (10 mL) at room temperature under nitrogen. Stirring was continued for 1 h. The reaction was quenched with 10% aqueous potassium bisulfate/sodium sulfate buffer, poured onto water and extracted with EtOAc (3×). The combined organic extracts were washed with brine, dried over anhydrous sodium sulfate and concentrated under reduced pressure. The resulting residue was purified by flash chromatography (20:15:65 EtOAc:DCM:hexanes eluent) to provide (R)—N-(3-(benzyloxy)-4-((benzyloxy)carbamoyl)phenyl)-N-(4-cyclohexylbenzyl)-1-((perfluorophenyl)sulfonyl)azetidine-2-carboxamide (188 mg, 46% yield). MS (ESI) m/z 834.30 [M+H]+.

Step 5: To a stirred solution of (R)—N-(3-(benzyloxy)-4-((benzyloxy)carbamoyl)phenyl)-N-(4-cyclohexylbenzyl)-1-((perfluorophenyl)sulfonyl)azetidine-2-carboxamide (179 mg, 0.21 mmol) in methanol (5 mL) and EtOAc (5 mL) was added 20% Pd(OH)$_2$/C (18 mg) and the resulting suspension was stirred at room temperature under a hydrogen atmosphere for 1 h. The reaction mixture was filtered through Celite® and washed with EtOAc. The combined filtrate and washes were concentrated in vacuo to provide (R)—N-(4-cyclohexylbenzyl)-N-(3-hydroxy-4-(hydroxycarbamoyl)phenyl)-1-((perfluorophenyl)sulfonyl)azetidine-2-carboxamide (130 mg, 95% yield) as a pinkish solid. HRMS (ESI) m/z 654.1696 [M+H]+.

Examples 86-87

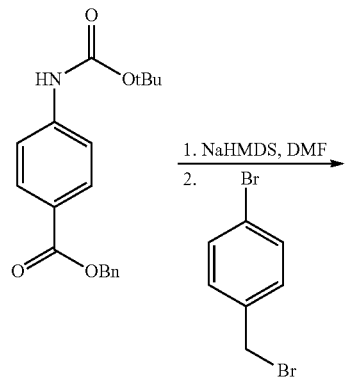

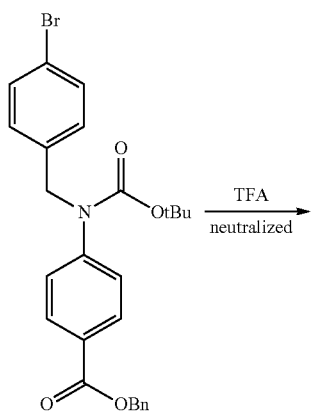

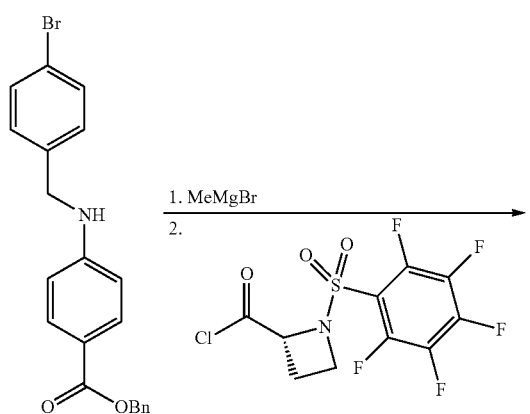

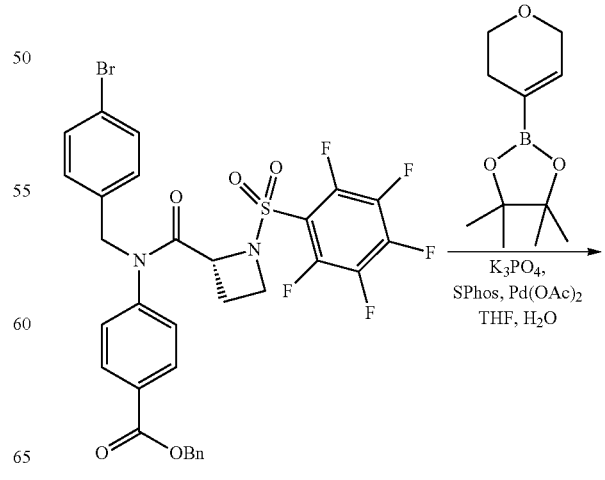

231
-continued

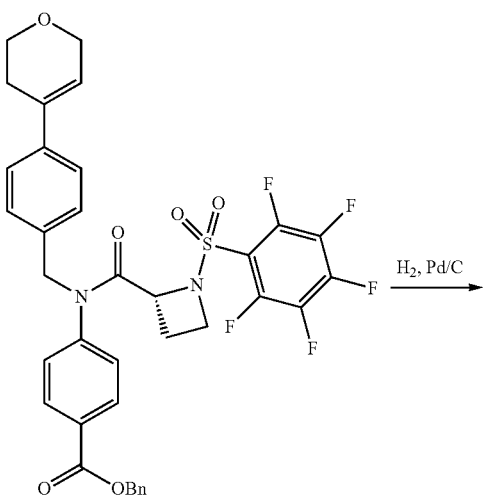

232
-continued

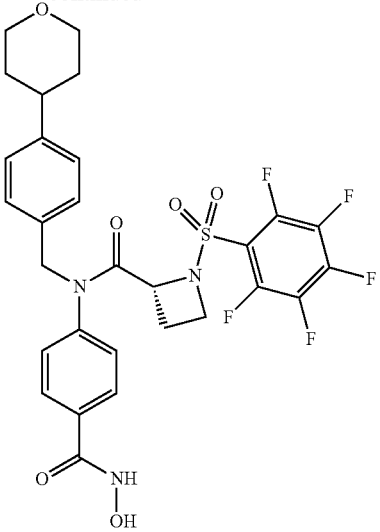

H₂, Pd/C

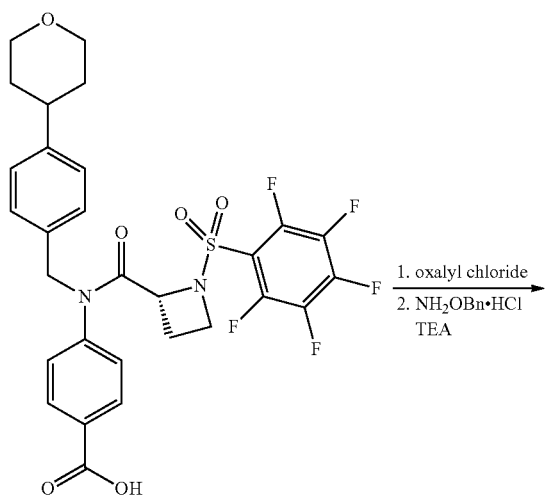

1. oxalyl chloride
2. NH₂OBn·HCl
   TEA

Example 86

(R)-4-(1-((perfluorophenyl)sulfonyl)-N-(4-(tetrahydro-2H-pyran-4-yl)benzyl)azetidine-2-carboxamido)benzoic acid

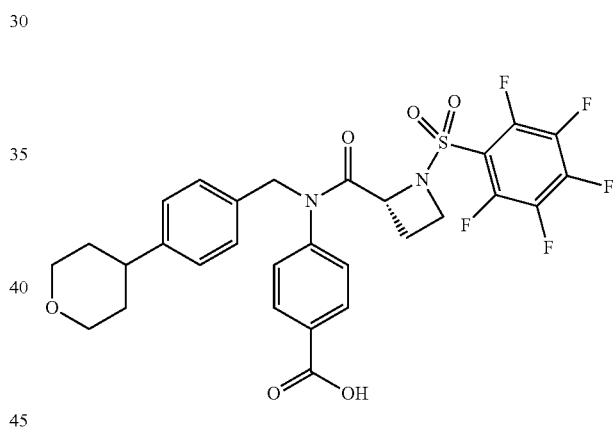

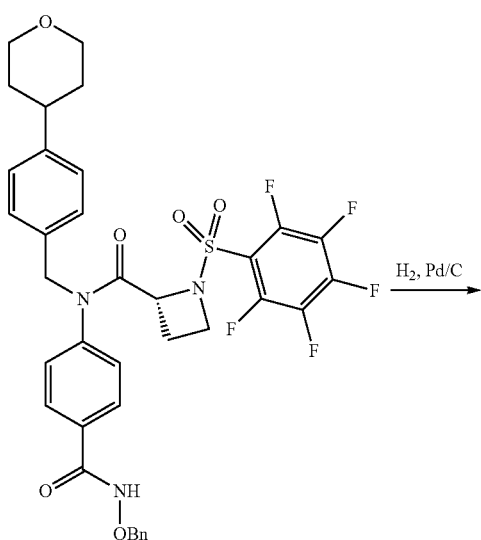

H₂, Pd/C

Step 1: To a stirred solution of benzyl 4-((tert-butoxycarbonyl)amino)benzoate (1.0 g, 3.054 mmol) in DMF (14 mL) at 0° C. under nitrogen was added NaHMDS (1.83 mL of a 2M solution in THF, 3.67 mmol). The resulting reaction mixture was stirred at 0° C. for 5-10 min before addition of 1-bromo-4-(bromomethyl)benzene (916 mg, 3.67 mmol). Stirring was continued at 0° C. for 1 h and then at room temperature for 19 h. The mixture was poured onto cold saturated aqueous ammonium chloride and the mixture was extracted with ether (2×). The combined organic extract was washed with water and then washed with brine, dried over anhydrous sodium sulfate and concentrated under reduced pressure. The resulting residue was purified by flash chromatography (10% EtOAc/hexanes eluent) to provide benzyl 4-((4-bromobenzyl)(tert-butoxycarbonyl)amino)benzoate (1.57 g, 99% yield) as a white solid. 1H NMR (300 MHz, Chloroform-d) δ 8.01 (d, J=8.9 Hz, 2H), 7.50-7.33 (m, 7H), 7.24 (d, J=8.7 Hz, 2H), 7.10 (d, J=8.3 Hz, 2H), 5.36 (s, 2H), 4.84 (s, 2H), 1.44 (s, 9H).

Step 2: To a stirred solution of benzyl 4-((4-bromobenzyl)(tert-butoxycarbonyl)amino)benzoate (1.55 g, 3.12 mmol)

in DCM (19.7 mL) under nitrogen was added TFA (6.5 mL) and the mixture was stirred at room temperature for 1 h. The crude reaction mixture was poured onto ice and aqueous sodium bicarbonate and the resulting mixture, which was confirmed to have pH=6-8, was extracted with DCM (2×). The combined organic extract was washed with aqueous sodium bicarbonate, dried over anhydrous sodium sulfate and concentrated in vacuo to provide benzyl 4-((4-bromobenzyl)amino)benzoate (1.19 g, 96% yield) as a white solid. 1H NMR (300 MHz, Chloroform-d) δ 7.92 (d, J=8.8 Hz, 2H), 7.54-7.32 (m, 7H), 7.23 (d, J=8.4 Hz, 2H), 6.58 (d, J=8.8 Hz, 2H), 5.33 (s, 2H), 4.54 (s, 1H), 4.38 (s, 2H).

Step 3: To a stirred solution of benzyl 4-((4-bromobenzyl)amino)benzoate (400 mg, 1.01 mmol) in dry THF (8 mL) under nitrogen at 0° C. was added methylmagnesium bromide (1.8 mL of 1.4 M in THF, 2.52 mmol) and the resulting solution was stirred at 0° C. for 15 min before addition of solid (R)-1-((perfluorophenyl)sulfonyl)-azetidine-2-carbonyl chloride (529.5 mg, 1.52 mmol). The resulting mixture was allowed to warm to room temperature and stirred at room temperature for 6.25 h. To the crude reaction mixture was added cold saturated aqueous ammonium chloride followed by water and the resulting organic mixture was extracted with EtOAc (2×). The combined organic extract was washed with brine, dried over sodium sulfate and concentrated under reduced pressure. The crude residue was purified by flash chromatography (20-25% EtOAc/hexanes eluent) to provide benzyl (R)-4-(N-(4-bromobenzyl)-1-((perfluorophenyl)sulfonyl)azetidine-2-carboxamido)benzoate (684 mg, 96% yield). 1H NMR (300 MHz, Chloroform-d) δ 8.08 (d, J=8.2 Hz, 2H), 7.54-7.34 (m, 7H), 7.04 (d, J=8.4 Hz, 2H), 6.99 (d, J=8.3 Hz, 2H), 5.39 (s, 2H), 4.97-4.80 (m, 2H), 4.70 (d, J=14.4 Hz, 1H), 4.31-3.84 (m, 2H), 2.32-2.13 (m, 1H), 2.02-1.84 (m, 1H).

Step 4: In a dry flask under nitrogen was added benzyl (R)-4-(N-(4-bromobenzyl)-1-((perfluorophenyl)sulfonyl)azetidine-2-carboxamido)benzoate (345.5 mg, 0.487 mmol), Pd(OAc)$_2$ (5.48 mg, 0.0243 mmol), SPhos (20 mg, 0.0488 mmol), 3,6-dihydro-2H-pyran-4-boronic acid pinacol ester (153.5 mg, 0.73 mmol), potassium phosphate tribasic (206.7 mg, 0.975 mmol) and water (17.4 mg, 0.96 mmol). The flask was back-flushed with nitrogen, THF (6.25 mL) was added and the flask was heated at 40° C. for 20 h. The crude reaction mixture was poured onto water and extracted into EtOAc. The organic extract was washed with brine, dried over anhydrous sodium sulfate and concentrated under reduced pressure. The resulting residue was purified by flash chromatography (30% EtOAc/hexanes) to afford benzyl (R)-4-(N-(4-(3,6-dihydro-2H-pyran-4-yl)benzyl)-1-((perfluorophenyl)sulfonyl)azetidine-2-carboxamido)benzoate (224 mg, 65% yield). 1H NMR (300 MHz, Chloroform-d) δ 8.07 (d, J=8.5 Hz, 2H), 7.53-7.35 (m, 5H), 7.31 (d, J=8.2, 2H), 7.11-7.00 (2 overlapping doublets, 4H), 6.14 (q, J=1.5 Hz, 1H), 5.39 (s, 2H), 4.99-4.84 (m, 2H), 4.72 (d, J=14.4 Hz, 1H), 4.39-4.28 (m, 2H), 4.21-4.01 (m, 2H), 3.94 (t, J=5.5 Hz, 2H), 2.51 (m, 2H), 2.25 (dt, J=16.7, 7.7 Hz, 1H), 2.02-1.83 (m, 1H).

Step 5: To a stirred solution of benzyl (R)-4-(N-(4-(3,6-dihydro-2H-pyran-4-yl)benzyl)-1-((perfluorophenyl)sulfonyl)azetidine-2-carboxamido)benzoate (219.5 mg, 0.309 mmol) in methanol (3.6 mL) and EtOAc (3.6 mL) was added 10% Pd/C (27.5 mg) and the resulting suspension was stirred at room temperature under a hydrogen atmosphere for 16.5 h. The reaction mixture was filtered through Celite® and washed with EtOAc (2×). The combined filtrate and washes were concentrated in vacuo to provide (R)-4-(1-((perfluorophenyl)sulfonyl)-N-(4-(tetrahydro-2H-pyran-4-yl)benzyl) azetidine-2-carboxamido)benzoic acid (186.7 mg) as a white foam. HRMS (ESI) m/z 625.1433 [M+H]+.

Example 87

(R)—N-(4-(hydroxycarbamoyl)phenyl)-1-((perfluorophenyl)sulfonyl)-N-(4-(tetrahydro-2H-pyran-4-yl)benzyl)azetidine-2-carboxamide

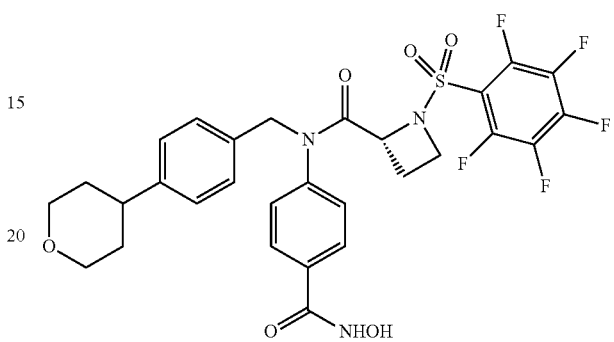

Step 1: To a stirred solution of (R)-4-(1-((perfluorophenyl)sulfonyl)-N-(4-(tetrahydro-2H-pyran-4-yl)benzyl)azetidine-2-carboxamido)benzoic acid (173.2 mg, 0.277 mmol) in DCM (4.2 mL) under nitrogen was added oxalyl chloride (0.031 mL, 0.36 mmol) and DMF (small drop). The resulting reaction solution was stirred at room temperature under nitrogen for 2 h and then concentrated in vacuo to provide (R)-4-(1-((perfluorophenyl)sulfonyl)-N-(4-(tetrahydro-2H-pyran-4-yl)benzyl)azetidine-2-carboxamido)-benzoyl chloride (175.1 mg), which was used as is.

Step 3: To a solution of O-benzylhydroxylamine hydrochloride (86.78 mg, 0.544 mmol) in DMF (4.8 mL) was added TEA (0.151 mL, 1.09 mmol). The mixture was stirred for 15 min, then added to a solution of (R)-4-(1-((perfluorophenyl)sulfonyl)-N-(4-(tetrahydro-2H-pyran-4-yl)benzyl)azetidine-2-carboxamido)-benzoyl chloride (175.1 mg, 0.272 mmol) in THF (4.8 mL) at 0° C. under nitrogen. The resultant reaction mixture was warmed to room temperature and stirred for 1.5 h. The reaction was quenched with 10% aqueous potassium bisulfate/10% sodium sulfate buffer, poured onto water and extracted with EtOAc (2×). The combined organic extracts were washed with brine, dried over anhydrous sodium sulfate and concentrated under reduced pressure. The resulting residue was purified by flash chromatography (50% EtOAc/hexanes) to provide (R)—N-(4-((benzyloxy)carbamoyl)phenyl)-1-((perfluorophenyl)sulfonyl)-N-(4-(tetrahydro-2H-pyran-4-yl)benzyl)azetidine-2-carboxamide (119 mg, 60% yield). MS (ESI) m/z 730.10 [M+H]+.

Step 4: To a stirred solution of (R)—N-(4-((benzyloxy)carbamoyl)phenyl)-1-((perfluorophenyl)sulfonyl)-N-(4-(tetrahydro-2H-pyran-4-yl)benzyl)azetidine-2-carboxamide (111.7 mg, 0.153 mmol) in methanol (5.1 mL) and EtOAc (5.1 mL) was added 10% Pd/C (13.2 mg) and the resulting suspension was stirred at room temperature under a hydrogen atmosphere for 2 h. The reaction mixture was filtered through Celite® and washed with EtOAc. The combined filtrate and washes were concentrated under reduced pressure. Purification by preparative TLC (1:1 hexanes:acetone) provided (R)—N-(4-(hydroxycarbamoyl)phenyl)-1-((perfluorophenyl)sulfonyl)-N-(4-(tetrahydro-2H-pyran-4-yl)

benzyl)azetidine-2-carboxamide (53 mg, 54% yield) as a light pink solid. HRMS (ESI) m/z 640.1540 [M+H]+.

Example 88

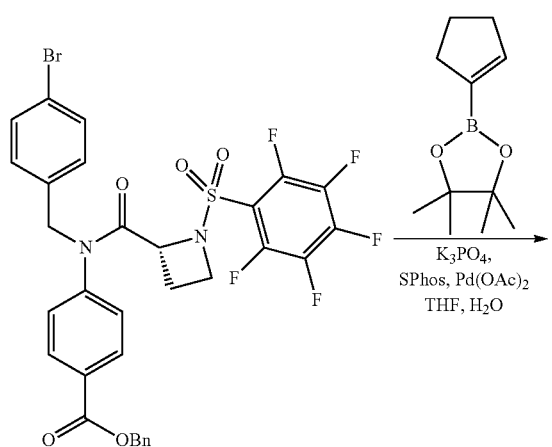

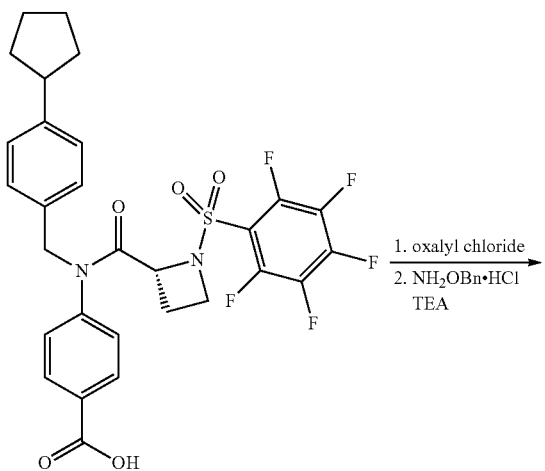

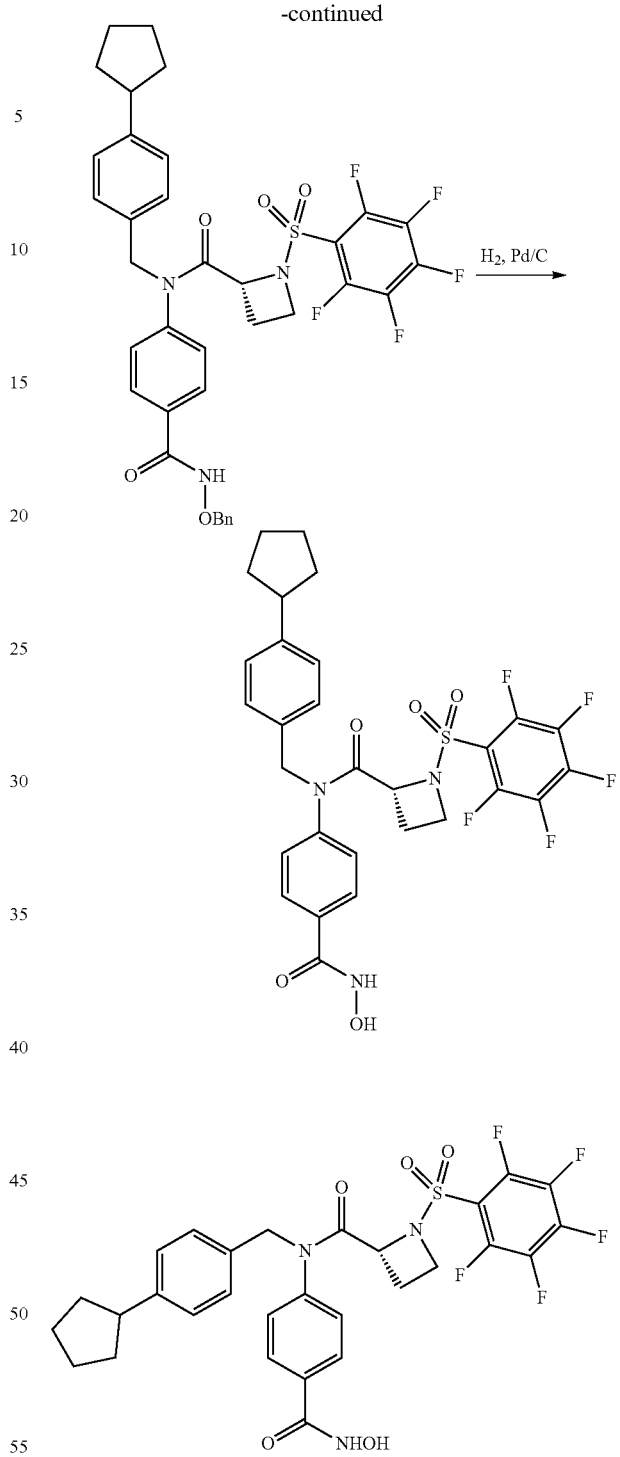

Step 1: In a dry flask under nitrogen was added benzyl (R)-4-(N-(4-bromobenzyl)-1-((perfluorophenyl)-sulfonyl)azetidine-2-carboxamido)benzoate (314.4 mg, 0.443 mmol), Pd(OAc)$_2$ (4.98 mg, 0.022 mmol), SPhos (18.19 mg, 0.044 mmol), 2-(cyclopent-1-en-1-yl)-4,4,5,5-tetramethyl-1,3,2-dioxaborolane (129.0 mg, 0.665 mmol), potassium phosphate tribasic (188 mg, 0.887 mmol) and water (15.8 mg, 0.87 mmol). The flask was back-flushed with nitrogen, THF (5.7 mL) was added and the flask was heated at 40° C. for 26 h. The crude reaction mixture was poured onto water and extracted into EtOAc. The organic extract was washed with brine, dried over anhydrous sodium sulfate and concentrated under reduced pressure. The resulting residue was purified by flash chromatography (22.5% EtOAc/hexanes) to afford benzyl (R)-4-(N-(4-(cyclopent-1-en-1-yl)benzyl)-1-((perfluorophenyl)sulfonyl)azetidine-2-carboxamido)benzoate (197 mg, 64% yield) as a white solid. 1H NMR (300 MHz, Chloroform-d) δ 8.06 (d, J=8.3 Hz, 2H), 7.57-7.30 (m, 7H), 7.14-6.93 (m, 4H), 6.30-6.10 (m, 1H), 5.38 (s, 2H), 4.97-4.81 (m, 2H), 4.75 (d, J=14.4 Hz, 1H), 4.25-3.98 (m, 2H), 2.80-2.64 (m, 2H), 2.62-2.45 (m, 2H), 2.38-2.15 (m, 1H), 2.04-1.80 (m, 3H).

Step 2: To a stirred solution of benzyl (R)-4-(N-(4-(cyclopent-1-en-1-yl)benzyl)-1-((perfluorophenyl)sulfonyl) azetidine-2-carboxamido)benzoate (188.2 mg, 0.270 mmol) in methanol (3.2 mL) and EtOAc (3.2 mL) was added 10% Pd/C (24.1 mg) and the resulting suspension was stirred at room temperature under a hydrogen atmosphere overnight. The reaction mixture was filtered through Celite® and washed with EtOAc (2×). The combined filtrate and washes were concentrated in vacuo to provide (R)-4-(N-(4-cyclopentylbenzyl)-1-((perfluorophenyl)sulfonyl)azetidine-2-carboxamido)benzoic acid (159 mg, 97% yield). HRMS (ESI) m/z 609.1486 [M+H]+.

Step 3: To a stirred solution of (R)-4-(N-(4-cyclopentylbenzyl)-1-((perfluorophenyl)sulfonyl)azetidine-2-carboxamido)benzoic acid (151.9 mg, 0.25 mmol) in DCM (3.8 mL) under nitrogen was added oxalyl chloride (0.028 mL, 0.324 mmol) and DMF (small drop). The resulting reaction solution was stirred at room temperature under nitrogen for 2 h and then concentrated in vacuo to provide (R)-4-(N-(4-cyclopentylbenzyl)-1-((perfluorophenyl)sulfonyl)azetidine-2-carboxamido)benzoyl chloride (185.3 mg), which was used as is.

Step 4: To a solution of O-benzylhydroxylamine hydrochloride (79.8 mg, 0.5 mmol) in DMF (4.4 mL) was added TEA (0.139 mL, 1.00 mmol). The mixture was stirred for 15 min, then added to a solution of (R)-4-(N-(4-cyclopentylbenzyl)-1-((perfluorophenyl)sulfonyl)azetidine-2-carboxamido)benzoyl chloride (185.3 mg, 0.296 mmol) in THF (4.4 mL) at room temperature under nitrogen. Stirring was continued for 1.5 h. The reaction was quenched with 10% aqueous potassium bisulfate/10% sodium sulfate buffer, poured onto water and extracted with EtOAc (2×). The combined organic extracts were washed with brine, dried over anhydrous sodium sulfate and concentrated under reduced pressure. The resulting residue was purified by flash chromatography (40% EtOAc/hexanes) followed by re-purification by preparative TLC (50% EtOAc/hexanes eluent) to provide (R)—N-(4-((benzyloxy)carbamoyl)phenyl)-N-(4-cyclopentylbenzyl)-1-((perfluorophenyl)sulfonyl)azetidine-2-carboxamide (100.4 mg, 48% yield).

1H NMR (300 MHz, Chloroform-d) δ 8.45 (s, 1H), 7.66 (d, J=8.4 Hz, 2H), 7.51-7.36 (m, 5H), 7.14 (d, J=7.9 Hz, 2H), 7.04 (d, J=7.9 Hz, 2H), 6.99 (d, J=8.4 Hz, 2H), 5.06 (s, 2H), 4.92-4.78 (m, 2H), 4.71 (d, J=14.4 Hz, 1H), 4.14-3.98 (m, 2H), 2.97 (p, J=8.1 Hz, 1H), 2.25 (t, J=9.5 Hz, 1H), 2.13-1.45 (m, 9H).

Step 5: To a stirred solution of (R)—N-(4-((benzyloxy)carbamoyl)phenyl)-N-(4-cyclopentylbenzyl)-1-((perfluorophenyl)sulfonyl)azetidine-2-carboxamide (96.1 mg, 0.135 mmol) in methanol (4.5 mL) and EtOAc (4.5 mL) was added 10% Pd/C (11.6 mg) and the resulting suspension was stirred at room temperature under a hydrogen atmosphere for 2 h. The reaction mixture was filtered through Celite® and washed with EtOAc. The combined filtrate and washes were concentrated under reduced pressure. Purification by preparative TLC (1:1 hexanes:acetone) provided (R)—N-(4-cyclopentylbenzyl)-N-(4-(hydroxycarbamoyl)phenyl)-1-((perfluorophenyl)sulfonyl) azetidine-2-carboxamide (49.5 mg, 59% yield) as an off-white solid. HRMS (ESI) m/z 624.1589 [M+H]+.

Example 89

(R)—N-(2-fluoro-5-hydroxy-4-(hydroxycarbamoyl)phenyl)-1-((perfluorophenyl)sulfonyl)-N-(4-(tetrahydro-2H-pyran-4-yl)benzyl)azetidine-2-carboxamide

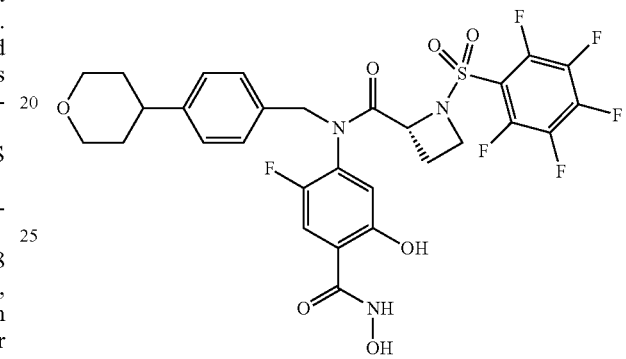

Preparation by a similar procedure to example 84, except substituting benzyl (R)-2-(benzyloxy)-4-(N-(4-(3,6-dihydro-2H-pyran-4-yl)benzyl)-1-((perfluorophenyl)sulfonyl) azetidine-2-carboxamido)-5-fluorobenzoate for benzyl (R)-2-(benzyloxy)-4-(1-((perfluorophenyl)sulfonyl)-N-(4-(tetrahydro-2H-pyran-4-yl)benzyl)azetidine-2-carboxamido)benzoate in step 1 and substituting 10% Pd/C for 20% Pd(OH)₂/C in step 4 afforded (R)—N-(2-fluoro-5-hydroxy-4-(hydroxycarbamoyl)phenyl)-1-((perfluorophenyl)sulfonyl)-N-(4-(tetrahydro-2H-pyran-4-yl)benzyl)azetidine-2-carboxamide as a brown solid. HRMS (ESI+) m/z 674.1398 [M+H]⁺.

Example 90

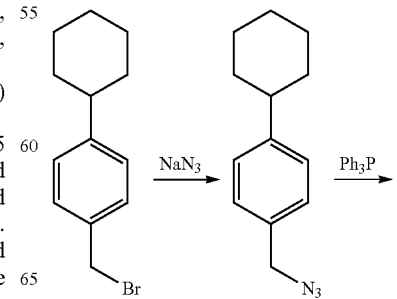

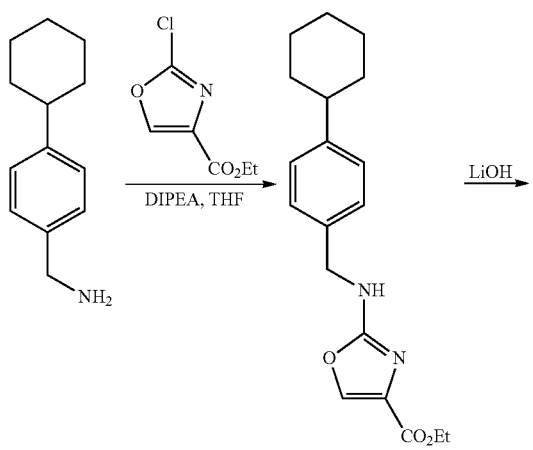

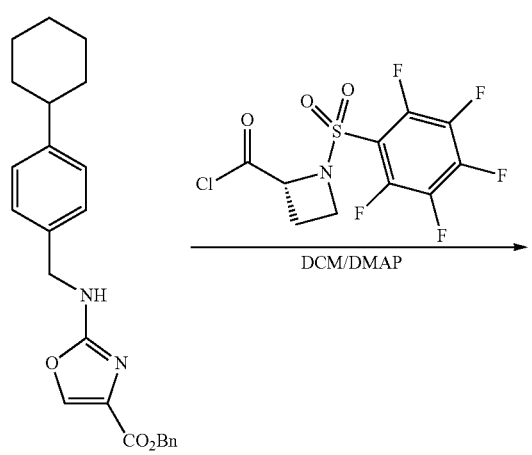

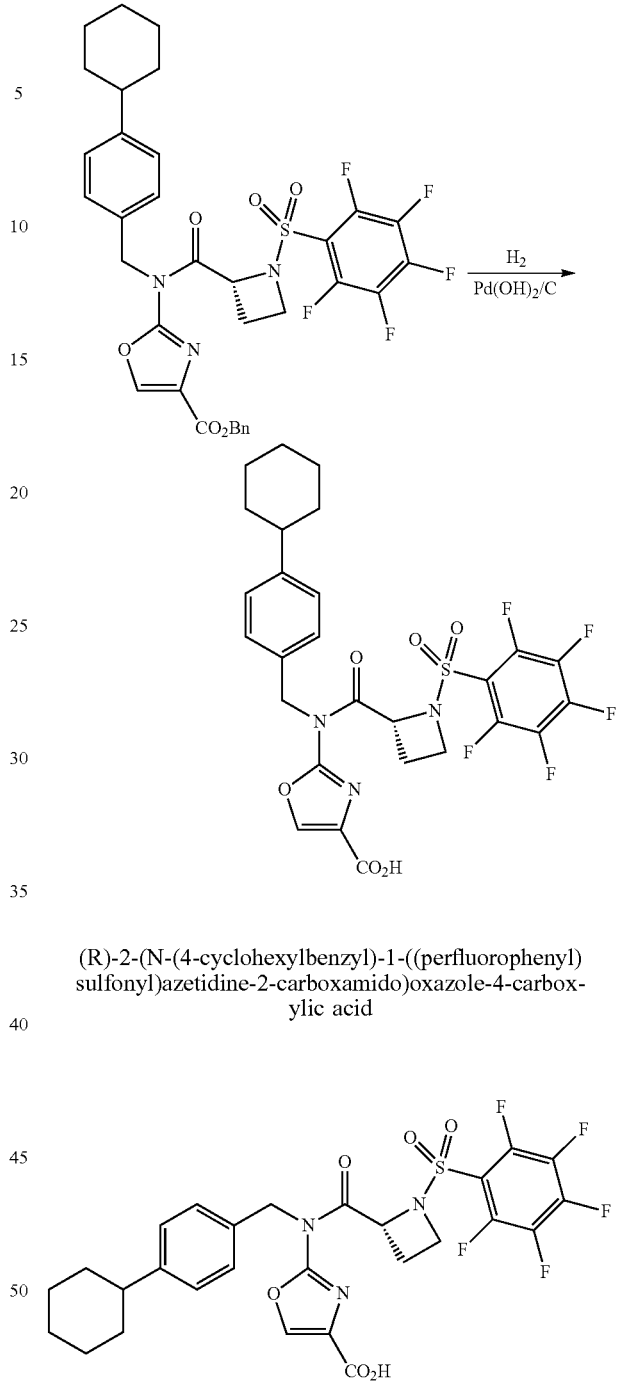

(R)-2-(N-(4-cyclohexylbenzyl)-1-((perfluorophenyl)sulfonyl)azetidine-2-carboxamido)oxazole-4-carboxylic acid Step 1: To a stirred solution of 1-(bromomethyl)-4-cyclohexylbenzene (2.02 g, 8 mmol) in DMF (9 mL) under nitrogen was added sodium azide (572 mg, 8.8 mmol) and the resultant mixture was stirred at 65° C. for 2.5 h. The reaction was allowed to cool to room temperature. Cold water was added and the mixture was extracted with ether (3×). The combined ethereal extracts were washed with water and then with brine, dried over sodium sulfate and concentrated in vacuo to provide 1-(azidomethyl)-4-cyclohexylbenzene (1.823 g, 100% yield) as a colorless oil. $^1$H NMR (300 MHz, Chloroform-d) δ 7.27-7.21 (m, 4H), 4.32 (s, 2H), 2.64-2.42 (m, 1H), 2.00-1.69 (m, 5H), 1.54-1.16 (m, 5H).

Step 2: To a solution 1-(azidomethyl)-4-cyclohexylbenzene (1.823 g, 8 mmol) in THF (23.5 mL) under nitrogen was added triphenylphosphine (2.67 g, 10.2 mmol) and the resulting mixture was stirred at room temperature for 30 min. Water (7.7 mL) was added and the mixture was heated at reflux for 5.5 h. The reaction was allowed to cool to room temperature and was left overnight. Water was added and the mixture was extracted with DCM (3×). The combined organic extracts were dried over sodium sulfate and concentrated under reduced pressure. Purification by flash chromatography (97:3:0.2 DCM:MeOH NH$_4$OH, then 85:15:1 DCM:MeOH NH$_4$OH) provided (4-cyclohexylphenyl)methanamine (827 mg, 52% yield). $^1$H NMR (300 MHz, Chloroform-d) δ 7.28-7.14 (m, 4H), 3.85 (s, 2H), 2.62-2.41 (m, 1H), 1.99-1.66 (m, 6H), 1.52-1.16 (m, 4H).

Step 3: To a solution of (4-cyclohexylphenyl)methanamine (827 mg, 4.4 mmol) in THF (18 mL) under nitrogen was added ethyl 2-chlorooxazole-4-carboxylate (1.08 g, 6.16 mmol) followed by DIPEA (0.92 mL, 5.28 mmol) and the resultant mixture was heated with stirring at 55° C. for 22 h. After cooling to room temperature, water was added and the mixture was extracted with EtOAc (2×). The combined extract was washed with brine and concentrated under reduced pressure. The resultant crude product was triturated with ether to provide ethyl 2-((4-cyclohexylbenzyl)amino)oxazole-4-carboxylate (998 mg, 69% yield). $^1$H NMR (300 MHz, Chloroform-d) δ 7.76 (s, 1H), 7.27 (d, J=8.2 Hz, 2H), 7.21 (d, J=8.2 Hz, 2H), 5.13-4.94 (m, 1H), 4.55 (d, J=5.8 Hz, 2H), 4.37 (q, J=7.1 Hz, 2H), 2.60-2.38 (m, 1H), 1.97-1.70 (m, 6H), 1.51-1.10 (m and overlapping t, J=7.1 Hz, 7H).

Step 4: To a solution of ethyl 2-((4-cyclohexylbenzyl)amino)oxazole-4-carboxylate (998 mg, 3.04 mmol) in THF (17 mL) and methanol (17 mL) was added water (4.2 mL) followed by lithium hydroxide hydrate (182 mg, 4.3 mmol) and the mixture was stirred at room temperature for 24 h. Aqueous 10% KHSO$_4$/Na$_2$SO$_4$ buffer was added and the mixture was extracted with EtOAc (3×). The combined organic extract was washed with brine, dried over sodium sulfate and concentrated in vacuo to provide 2-((4-cyclohexylbenzyl)amino)oxazole-4-carboxylic acid (674 mg, 73% yield). $^1$H NMR (300 MHz, Chloroform-d) δ 8.42 (br s, 1H), 7.64 (s, 1H), 7.42-6.96 (m, 4H), 4.51 (s, 2H), 2.62-2.42 (m, 1H), 2.02-1.58 (m, 5H), 1.56-1.08 (m, 5H).

Step 5: To a stirred suspension of 2-((4-cyclohexylbenzyl)amino)oxazole-4-carboxylic acid (674 mg, 2.25 mmol) in DMF (22 mL) was added cesium carbonate (795 mg) under nitrogen. After 10 min benzyl bromide (0.26 mL, 2.18 mmol) was added. The mixture was stirred at room temperature for 23 h. Cold water was added and the mixture was extracted with EtOAc (3×). The combined organic extracts were washed with water and then with brine, dried over sodium sulfate and concentrated under reduced pressure. Purification by flash chromatography (60% EtOAc in hexanes eluent) provided benzyl 2-((4-cyclohexylbenzyl)amino)oxazole-4-carboxylate (540 mg, 61% yield). $^1$H NMR (300 MHz, Chloroform-d) δ 7.76 (s, 1H), 7.49-7.31 (m, 5H), 7.32-7.12 (m, 4H), 5.35 (s, 2H), 5.13 (t, J=6.1 Hz, 1H), 4.54 (d, J=5.9 Hz, 2H), 2.63-2.40 (m, 1H), 1.96-1.60 (m, 6H), 1.51-1.19 (m, 4H).

Step 6: To a solution of benzyl 2-((4-cyclohexylbenzyl)amino)oxazole-4-carboxylate (85 mg, 0.22 mmol) in DCM (0.6 mL) under nitrogen was added (R)-1-((perfluorophenyl)sulfonyl)azetidine-2-carbonyl chloride (115 mg, 0.33 mmol). To the reaction mixture DMAP (32 mg, 0.26 mmol) was added. The reaction was stirred at room temperature for 23 hours. A few drops of methanol was added and stirred for 15 min. The mixture was poured onto water and extracted with DCM (2×). The combined organic layers were dried over sodium sulfate and evaporated under reduced pressure. Purification by flash column chromatography (30% EtOAc/hexanes eluent) afforded benzyl (R)-2-(N-(4-cyclohexylbenzyl)-1-((perfluorophenyl)sulfonyl)azetidine-2-carboxamido)oxazole-4-carboxylate (70 mg, 45% yield) as a white solid. MS (ESI) m/z 726.2 [M+Na]+.

Step 7: To a stirred solution of benzyl (R)-2-(N-(4-cyclohexylbenzyl)-1-((perfluorophenyl)sulfonyl)azetidine-2-carboxamido)oxazole-4-carboxylate (70 mg, 0.1 mmol) in methanol (2.5 mL) and EtOAc (2.5 mL) was added 20% Pd(OH)$_2$/C (8 mg) and the resulting suspension was stirred at room temperature under a hydrogen atmosphere for 4.5 h. The reaction mixture was filtered through Celite® and washed with EtOAc (2×). The combined filtrate and washes were concentrated under reduced pressure. Purification by flash chromatography (80:20 EtOAc:hexanes eluent) provided (R)-2-(N-(4-cyclohexylbenzyl)-1-((perfluorophenyl)sulfonyl)azetidine-2-carboxamido)oxazole-4-carboxylic acid (11 mg, 19% yield). HRMS (ESI) m/z 614.1375 [M+H]+.

Example 91

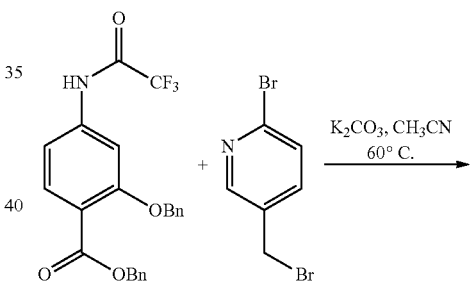

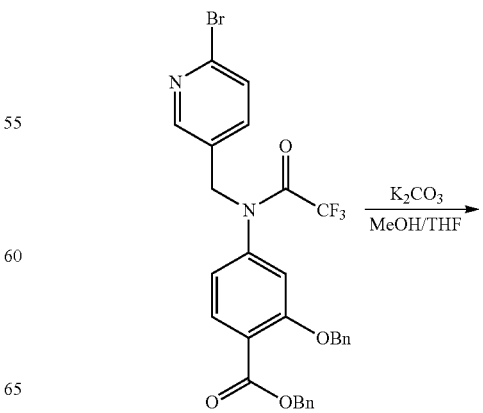

243
-continued

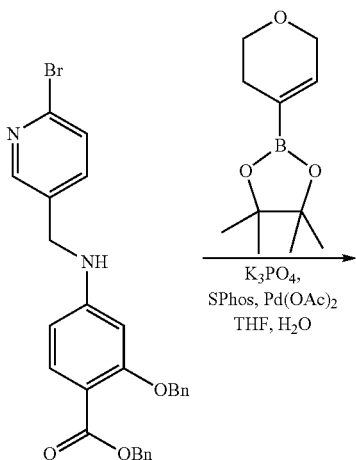

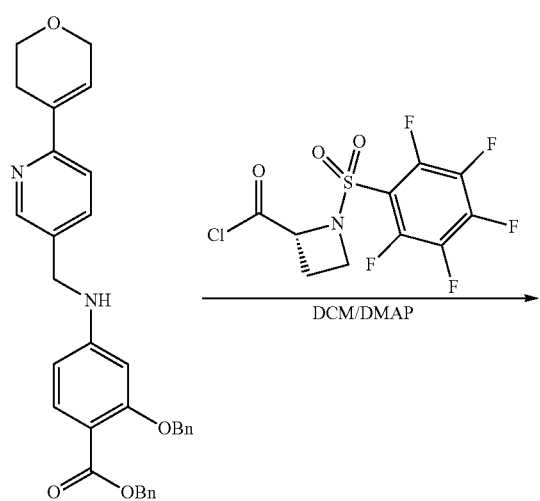

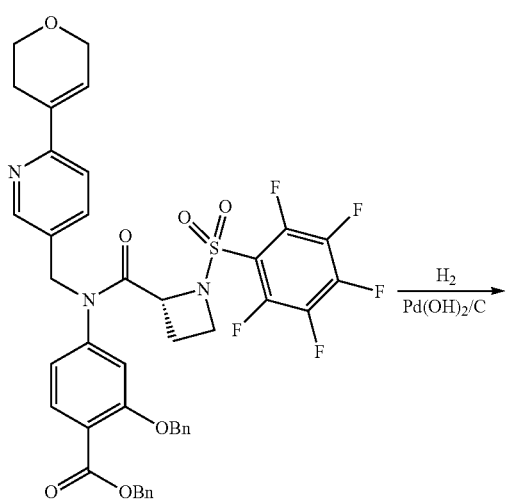

244
-continued

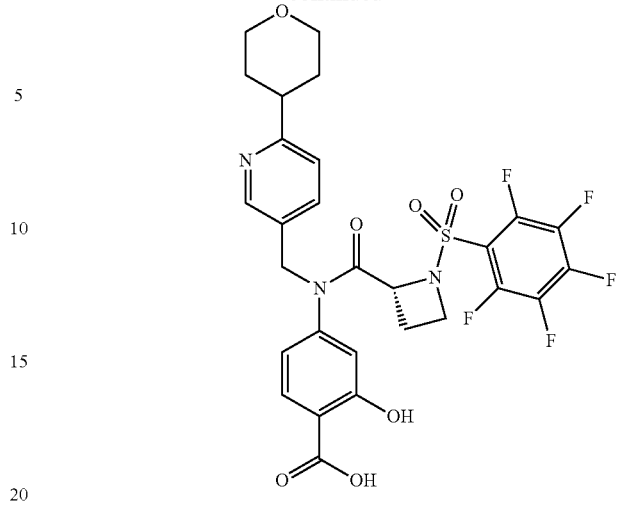

(R)-2-hydroxy-4-(1-((perfluorophenyl)sulfonyl)-N-((6-(tetrahydro-2H-pyran-4-yl)pyridin-3-yl)methyl)azetidine-2-carboxamido)benzoic acid Step 1: Step 1: To a stirred suspension of benzyl 2-(benzyloxy)-4-(2,2,2-trifluoroacetamido)benzoate (1.0 g, 2.33 mmol) and potassium carbonate (483 mg, 3.5 mmol) in acetonitrile (25 mL) was added 2-bromo-5-(bromomethyl)pyridine (703 mg, 2.8 mmol). The resulting reaction mixture under nitrogen was stirred at 60° C. for 6 h. After cooling to room temperature the reaction mixture was poured onto 1:1 saturated aqueous ammonium chloride:water and extracted with EtOAc (3×). The combined organic extract was washed with brine, dried over anhydrous sodium sulfate and concentrated under reduced pressure. The resulting residue was purified by flash chromatography (10-25% EtOAc/hexanes eluent) to provide benzyl 2-(benzyloxy)-4-(N-((6-bromopyridin-3-yl)methyl)-2,2,2-trifluoroacetamido)benzoate (1.092 g, 78% yield) as a colorless oil. MS (ESI) m/z 599.1, 601.1 [M+H]+.

Step 2: To a stirred solution of benzyl 2-(benzyloxy)-4-(N-((6-bromopyridin-3-yl)methyl)-2,2,2-trifluoroacetamido)benzoate (1.092 g, 1.82 mmol) in THF (14 mL) and methanol (14 mL) was added potassium carbonate (428 mg, 3.1 mmol) under nitrogen and the mixture was stirred at room temperature for 2 h. To the crude reaction mixture was added cold saturated aqueous ammonium chloride followed by water and the resulting mixture was extracted with EtOAc (3×). The combined organic extract was washed with brine, dried over anhydrous sodium sulfate and concentrated under reduced pressure to provide benzyl 2-(benzyloxy)-4-(((6-bromopyridin-3-yl)methyl)amino)benzoate (929 mg, 100% yield). MS (ESI) m/z 525.1, 527.1 [M+Na]+.

Step 3: In a dry flask under nitrogen was added benzyl 2-(benzyloxy)-4-(((6-bromopyridin-3-yl)methyl)amino)benzoate (526 mg, 1.04 mmol), SPhos (41 mg, 0.1 mmol), 2-cyclohexyl-4,4,5,5-tetramethyl-1,3,2-dioxaborolane (329 mg, 1.57 mmol), potassium phosphate tribasic (441 mg, 2.08 mmol), THF (14 mL), Pd(OAc)₂ (11.2 mg, 0.05 mmol), and HPLC-grade water (0.037 mL). Reaction mixture was thoroughly flushed with nitrogen. The mixture was stirred at 50-60° C. for 19 h. Water was added and the mixture was extracted with EtOAc (2×). The combined organic extract was washed with brine, dried over sodium sulfate and concentrated under reduced pressure. Purification by flash column (10-30% EtOAc in hexanes eluent) provided benzyl 2-(benzyloxy)-4-(((6-(3,6-dihydro-2H-pyran-4-yl)pyridin-3-yl)methyl)amino)benzoate (348 mg, 66% yield). MS (ESI+) m/z 507.3 [M+H]⁺.

Step 4: To a stirred solution of benzyl 2-(benzyloxy)-4-(((6-(3,6-dihydro-2H-pyran-4-yl)pyridin-3-yl)methyl)amino)benzoate (200 mg, 0.395 mmol) and (R)-1-((perfluorophenyl)sulfonyl)azetidine-2-carbonyl chloride (207 mg, 0.59 mmol) in dry DCM (10 mL) under nitrogen was added DMAP (58 mg, 0.47 mmol). Stirring was continued overnight. The mixture was poured onto water and extracted with DCM (3×). Methanol (2-3 drops) was added to consume any excess acid chloride. The combined organic layers were dried over sodium sulfate and evaporated under reduced pressure. Purification by flash column chromatography (20-50% EtOAc/hexanes eluent) afforded benzyl (R)-2-(benzyloxy)-4-(N-((6-(3,6-dihydro-2H-pyran-4-yl)pyridin-3-yl)methyl)-1-((perfluorophenyl)sulfonyl)azetidine-2-carboxamido)benzoate (152 mg, 47% yield). MS (ESI+) m/z 820.3 [M+H]⁺.

Step 5: To a stirred solution of benzyl (R)-2-(benzyloxy)-4-(N-((6-(3,6-dihydro-2H-pyran-4-yl)pyridin-3-yl)methyl)-1-((perfluorophenyl)sulfonyl)azetidine-2-carboxamido)benzoate (95 mg, 0.116 mmol) in methanol (1 mL) and EtOAc (1 mL) under nitrogen was added 20% Pd(OH)₂ on C (10 mg). The reaction mixture was stirred under a hydrogen atmosphere for 5 h, then filtered through Celite® and washed with EtOAc (2×). The combined filtrate and washes were concentrated in vacuo to yield (R)-2-hydroxy-4-(1-((perfluorophenyl)sulfonyl)-N-((6-(tetrahydro-2H-pyran-4-yl)pyridin-3-yl)methyl)azetidine-2-carboxamido)benzoic acid as a grey solid (69 mg, 93% yield). HRMS (ESI) m/z 642.1326 [M+H]+.

Example 92

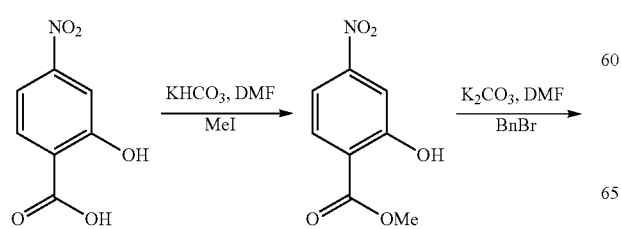

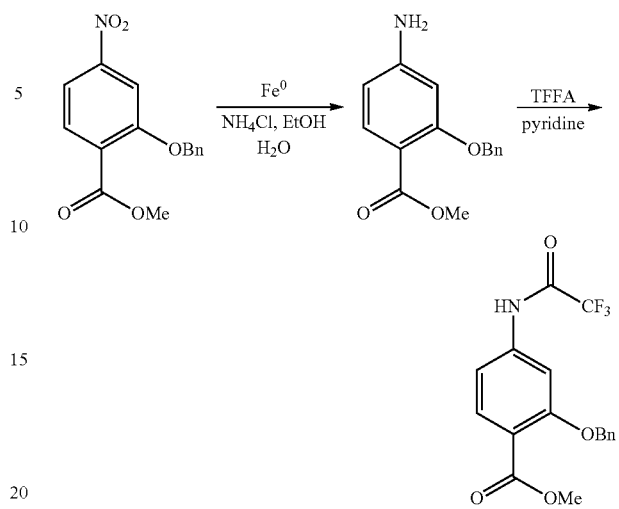

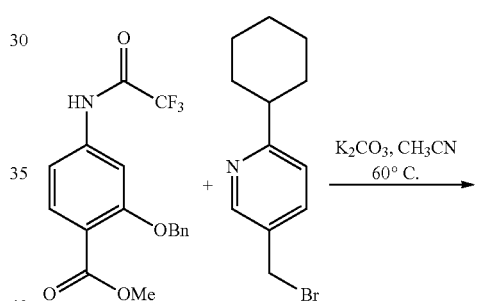

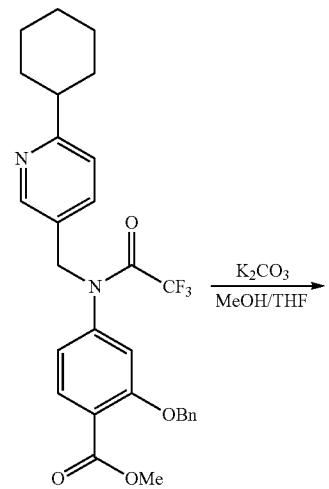

247
-continued

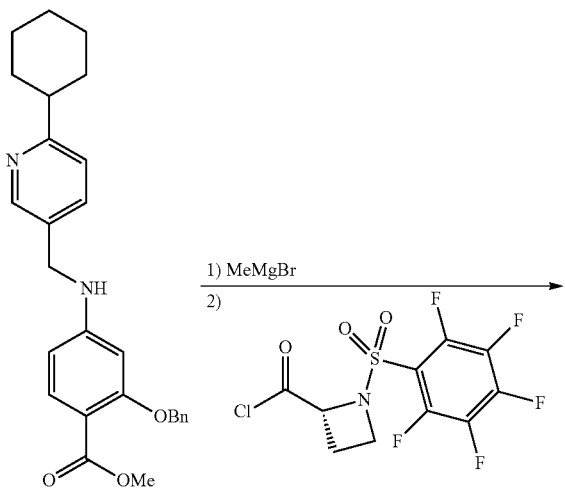

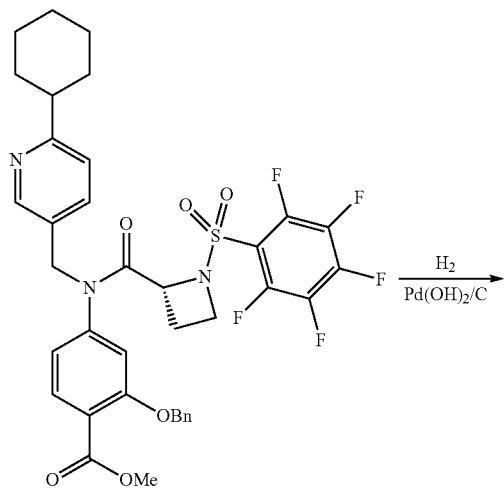

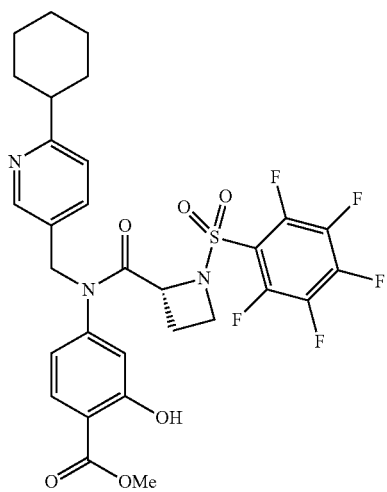

248
Methyl (R)-4-(N-((6-cyclohexylpyridin-3-yl)methyl)-1-((perfluorophenyl)sulfonyl)azetidine-2-carboxamido)-2-hydroxybenzoate

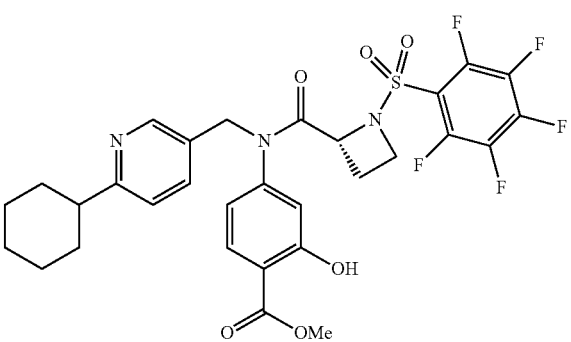 [SMILES: COC(=O)c1ccc(N(Cc2ccc(C3CCCCC3)nc2)C(=O)[C@H]2CCN2S(=O)(=O)c2c(F)c(F)c(F)c(F)c2F)cc1O]

Step 1: To a solution of 2-hydroxy-4-nitrobenzoic acid (1.83 g, 10 mmol) in 35 mL of dry DMF under nitrogen was added potassium bicarbonate (1.3 g, 13 mmol). After stirring at room temperature for 10 min, methyl iodide (1.55 mL, 24 mmol) was added. Stirring was continued at room temperature for 4 h. The reaction mixture was poured onto water and ethyl acetate and extracted into ethyl acetate (3×). The combined organic extracts were washed with water and then brine, dried over anhydrous sodium sulfate and concentrated under reduced pressure to provide methyl 2-hydroxy-4-nitrobenzoate (1.73 g, 88% yield). $^1$H NMR (300 MHz, Chloroform-d) δ 10.99 (s, 1H), 8.04 (d, J=8.7 Hz, 1H), 7.84 (d, J=2.3 Hz, 1H), 7.72 (dd, J=8.7, 2.3 Hz, 1H), 4.04 (s, 3H).

Step 2: To a stirred solution of methyl 2-hydroxy-4-nitrobenzoate (1.73 g, 8.78 mmol) and potassium carbonate (1.45 g, 10.5 mmol) in dry DMF (32 mL) under nitrogen at 0° C. was added benzyl bromide (1.15 mL, 9.66 mmol). The stirred reaction mixture was allowed to warm to room temperature and was stirred at this temperature for 5 h before being poured onto waster and extracted into ethyl acetate (3×). The combined organic extracts were washed with water, then brine, dried over anhydrous sodium sulfate and concentrated under reduced pressure. The resulting solid was triturated with 5-10% ether in hexanes, filtered and the filter cake washed with 5% ether in hexanes to provide methyl 2-(benzyloxy)-4-nitrobenzoate (2.01 g, 80% yield) as a tan solid. $^1$H NMR (300 MHz, Chloroform-d) δ 7.98-7.91 (m, 1H), 7.91-7.82 (m, 2H), 7.57-7.31 (m, 5H), 5.30 (s, 2H), 3.96 (s, 3H).

Step 3: To a suspension of methyl 2-(benzyloxy)-4-nitrobenzoate (2.0 g, 7 mmol) in ethanol (25.4 mL) and water (12.7 mL) was added ammonium chloride (3.8 g). The suspension was put under nitrogen and iron powder (2.73 g, 49 mmol) was added. The reaction was stirred at 66° C. overnight. Celite® was added and the mixture was filtered through a pad of Celite® and the filtercake was washed several times with ethyl acetate. The filtrate and washes were transferred to a separatory funnel. Water was added. The mixture was extracted with ethyl acetate (3×). The combined organic extract was washed with brine, dried over anhydrous sodium sulfate and concentrated to give a solid. The solid was washed with 10% ethyl acetate in hexanes and purified further by chromatography (80:20:20 hexane:DCM:EtOAc to 80:20:25 hexane:DCM:EtOAc) to provide methyl 4-amino-2-(benzyloxy)benzoate (1.22 g, 68% yield) as an off-white solid. $^1$H NMR (300 MHz, Chloroform-d) δ 7.82-

7.76 (m, 1H), 7.57-7.49 (m, 2H), 7.46-7.29 (m, 3H), 6.32-6.20 (m, 2H), 5.15 (s, 2H), 4.02 (s, 2H), 3.86 (s, 3H).

Step 4: To a stirred solution of methyl 4-amino-2-(benzyloxy)benzoate (1.21 g, 4.71 mmol) in DCM (26 mL) under nitrogen at 0° C. was added pyridine (0.46 mL, 5.65 mmol) followed by TFFA (0.73 mL, 5.18 mmol). The reaction mixture was allowed to warm to room temperature and stirred at this temperature for 1.5 h. The mixture was diluted with DCM and washed with 10% aqueous $KHSO_4$/$Na_2SO_4$ buffer (2×), then washed with saturated aqueous sodium bicarbonate, dried over anhydrous sodium sulfate and concentrated under reduced pressure. Trituration with 10% ether in hexane provided methyl 2-(benzyloxy)-4-(2,2,2-trifluoroacetamido)benzoate (1.74 g, 100% yield) as a white solid. $^1$H NMR (300 MHz, Chloroform-d) δ 8.00 (br s, 1H), 7.91 (d, J=8.5 Hz, 1H), 7.64 (d, J=2.1 Hz, 1H), 7.56-7.48 (m, 2H), 7.46-7.30 (m, 3H), 7.01 (dd, J=8.5, 2.1 Hz, 1H), 5.22 (s, 2H), 3.92 (s, 3H).

Step 5: To a stirred solution of methyl 2-(benzyloxy)-4-(2,2,2-trifluoroacetamido)benzoate (452 mg, 1.3 mmol) and 5-(bromomethyl)-2-cyclohexylpyridine (358 mg, 1.4 mmol) in acetonitrile (14 mL) was added potassium carbonate (270 mg, 1.95 mmol). The resulting reaction mixture under nitrogen was stirred at 60° C. for 4 h. After cooling to room temperature the reaction mixture was poured onto water and extracted with EtOAc (3×). The combined organic extract was washed with brine, dried over anhydrous sodium sulfate and concentrated under reduced pressure. The resulting residue was purified by flash chromatography (5-25% EtOAc/hexanes eluent) to provide methyl 2-(benzyloxy)-4-(N-((6-cyclohexylpyridin-3-yl)methyl)-2,2,2-trifluoroacetamido)benzoate (612 mg, 89% yield) as a colorless film. $^1$H NMR (300 MHz, Chloroform-d) δ 8.29-8.23 (m, 1H), 7.83 (d, J=8.2 Hz, 1H), 7.53-7.30 (m, 6H), 7.12 (dd, J=8.1, 0.9 Hz, 1H), 6.70 (dd, J=8.5, 1.8 Hz, 1H), 6.58 (s, 1H), 5.01 (s, 2H), 4.84 (s, 2H), 3.93 (s, 3H), 2.80-2.58 (m, 1H), 2.02-1.68 (m, 6H), 1.57-1.09 (m, 4H).

Step 6: To methyl 2-(benzyloxy)-4-(N-((6-cyclohexylpyridin-3-yl)methyl)-2,2,2-trifluoroacetamido)benzoate (609 mg, 1.15 mmol) in THF (10 mL) and MeOH (10 mL) under nitrogen was added potassium carbonate (350 mg, 2.5 mmol) under nitrogen. Stirring was continued for 1.5 h before the reaction mixture was poured onto cold saturated aqueous ammonium chloride and extracted with EtOAc (3×). The combined organic extracts were washed with brine, dried over anhydrous sodium sulfate and concentrated in vacuo to provide methyl 2-(benzyloxy)-4-(((6-cyclohexylpyridin-3-yl)methyl)amino)benzoate (485 mg, 98% yield) as a colorless film. $^1$H NMR (300 MHz, Chloroform-d) δ 8.56-8.47 (m, 1H), 7.81 (d, J=8.6 Hz, 1H), 7.57 (dd, J=8.0, 2.4 Hz, 1H), 7.53-7.46 (m, 2H), 7.44-7.30 (m, 3H), 7.15 (d, J=8.0 Hz, 1H), 6.24 (dd, J=8.6, 2.2 Hz, 1H), 6.18 (d, J=2.2 Hz, 1H), 5.12 (s, 2H), 4.41 (t, J=5.5 Hz, 1H), 4.33 (d, J=5.3 Hz, 2H), 3.86 (d, J=0.6 Hz, 3H), 2.72 (tt, J=11.6, 3.4 Hz, 1H), 2.03-1.70 (m, 5H), 1.60-1.14 (m, 5H).

Step 7: To a stirred solution of methyl 2-(benzyloxy)-4-(((6-cyclohexylpyridin-3-yl)methyl)amino)benzoate (485 mg, 1.12 mmol) in dry THF (19 mL) under nitrogen at 0° C. was added methylmagnesium bromide (2.4 mL of 1.4 M in THF, 3.37 mmol) and the resulting solution was stirred at 0° C. for 5 min and room temperature for 10 min before addition of solid (R)-1-((perfluorophenyl)sulfonyl)-azetidine-2-carbonyl chloride (681 mg, 1.95 mmol). The resulting mixture was allowed to warm to room temperature and stirred at room temperature for 2.5 h. A few drops of methanol were added and then the crude reaction mixture was poured onto water and extracted with EtOAc (3×) and then with DCM (3×). The combined organic extract was dried over sodium sulfate and concentrated under reduced pressure. The crude residue was purified by flash chromatography (30-40% EtOAc in hexanes eluent) to provide methyl (R)-2-(benzyloxy)-4-(N-((6-cyclohexylpyridin-3-yl)methyl)-1-((perfluorophenyl)sulfonyl)azetidine-2-carboxamido)benzoate (719 mg, 86% yield). MS (ESI+) m/z 744.3 [M+H]$^+$.

Step 8: To a stirred solution of methyl (R)-2-(benzyloxy)-4-(N-((6-cyclohexylpyridin-3-yl)methyl)-1-((perfluorophenyl)sulfonyl)azetidine-2-carboxamido)benzoate (175 mg, 0.23 mmol) in methanol (7 mL) and EtOAc (7 mL) was added 20% Pd(OH)$_2$/C (18 mg) and the resulting suspension was stirred at room temperature under a hydrogen atmosphere for 4.5 h. Allowed to sit overnight. The reaction mixture was filtered through Celite® and washed with EtOAc. The combined filtrate and washes were concentrated in vacuo and then foamed with ether to provide (R)-4-(N-((6-cyclohexylpyridin-3-yl)methyl)-1-((perfluorophenyl)sulfonyl)azetidine-2-carboxamido)-2-hydroxybenzoic acid (46 mg, 98% yield) as a white foam. HRMS (ESI+) m/z 654.1688 [M+H]$^+$.

Example 93

Methyl (R)-4-(N-(4-cyclohexylbenzyl)-1-((perfluorophenyl)sulfonyl) azetidine-2-carboxamido)-3-fluorobenzoate

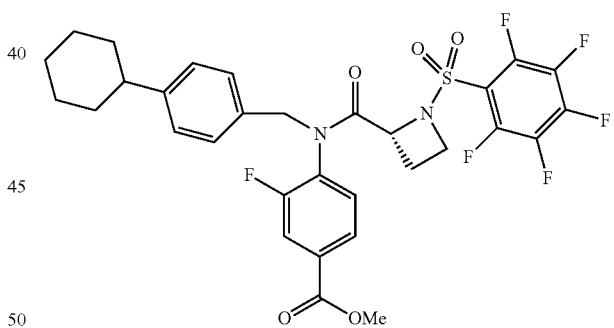

To (R)-4-(N-(4-cyclohexylbenzyl)-1-((perfluorophenyl)sulfonyl)azetidine-2-carboxamido)-3-fluorobenzoic acid (Example 49, 100 mg, 0.156 mmol) in dry DMF (0.4 mL) under nitrogen was added potassium carbonate (32 mg, 0.23 mmol). Stirring was continued at room temperature for 10 min before addition of 4 drops of methyl iodide. Stirring was continued for 30 min at room temperature. The reaction mixture was poured onto water and ether and extracted with ether (3×). The combined ether layer was dried over anhydrous sodium sulfate and concentrated under reduced pressure before foaming with ether and hexane (3×) and drying under vacuum to provide methyl (R)-4-(N-(4-cyclohexylbenzyl)-1-((perfluorophenyl)sulfonyl) azetidine-2-carboxamido)-3-fluorobenzoate (100 mg) as a foam. MS (ESI+) m/z 677.1 [M+Na]$^+$.

Example 94
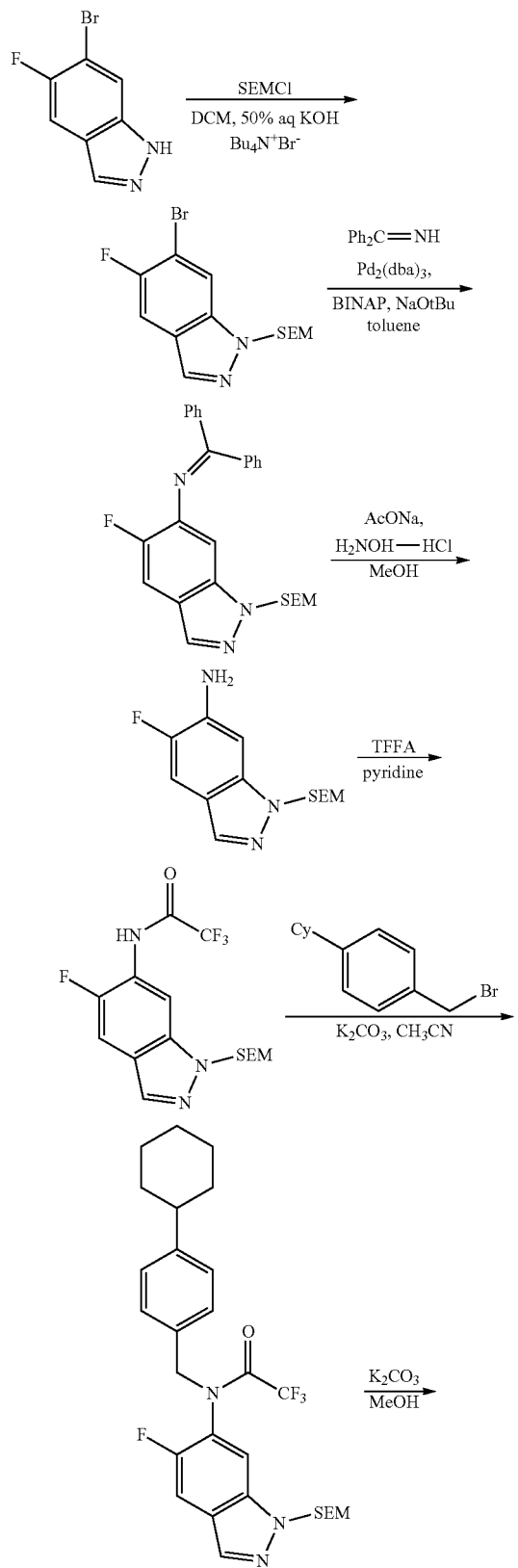
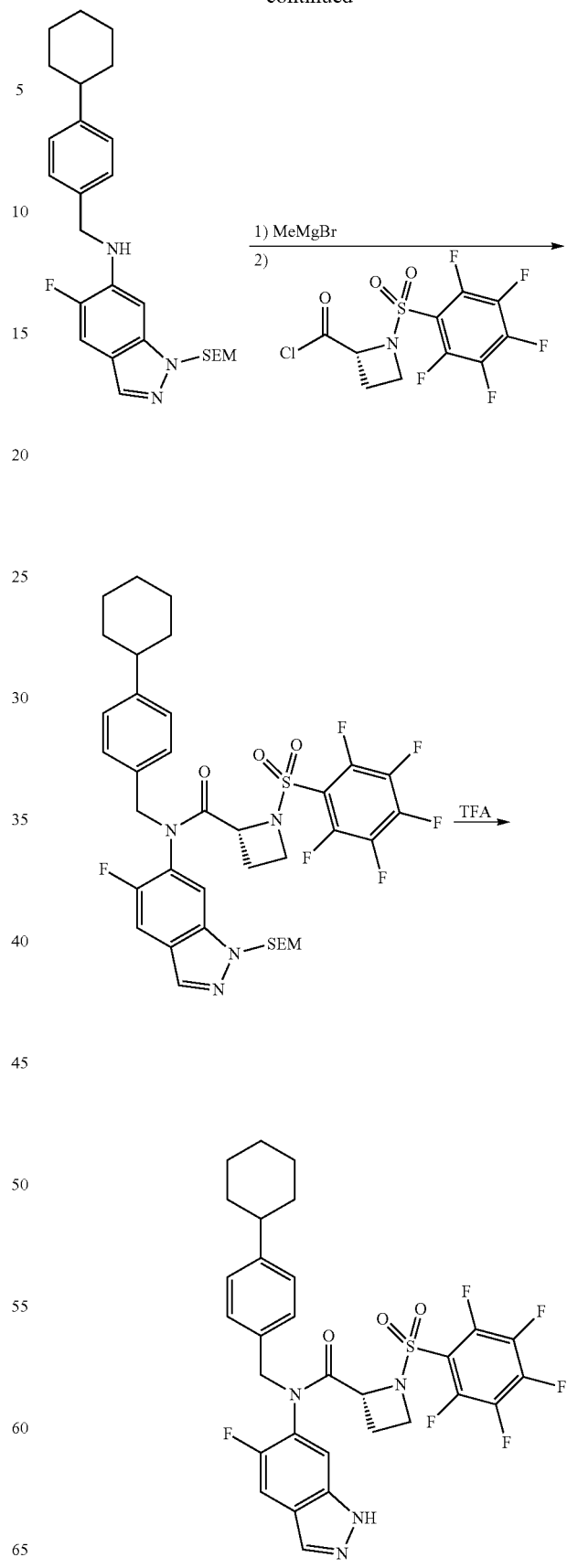

(R)—N-(4-cyclohexylbenzyl)-N-(5-fluoro-1H-indazol-6-yl)-1-((perfluorophenyl)sulfonyl)azetidine-2-carboxamide

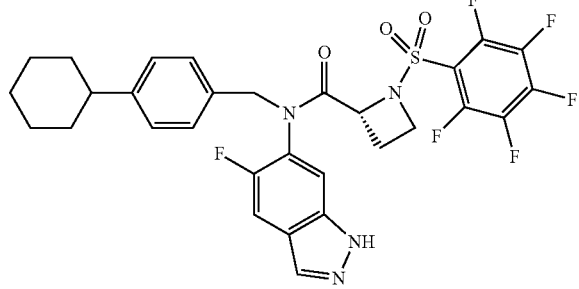

Step 1: To a suspension of 6-bromo-5-fluoro-1H-indazole (1.0 g, 4.65 mmol) and Bu$_4$N$^1$Br (15 mg, 0.046 mmol) in DCM (40 mL) under a nitrogen atmosphere at 0° C. was added 50% KOH in water (20 mL). To the rapidly stirred biphasic mixture was added SEMCl (0.91 mL, 5.11 mmol) by dropwise addition. The reaction mixture was allowed to stir at 0° C. for 1 hour and then at room temperature for 1.5 hours. The reaction mixture was poured onto water/DCM and extracted with DCM (2×). The combined DCM extracts were washed with brine, dried over anhydrous sodium sulfate, and concentrated under reduced pressure. The crude product was purified by flash chromatography (5-10% EtOAc in hexane eluent) to provide 6-bromo-5-fluoro-1-((2-(trimethylsilyl)ethoxy)methyl)-1H-indazole (1.02 g, 100% yield). $^1$H NMR (300 MHz, Chloroform-d) δ 7.97 (s, 1H), 7.85 (d, J=5.4 Hz, 1H), 7.46 (d, J=8.2 Hz, 1H), 5.71 (s, 2H), 3.63-3.45 (m, 2H), 1.02-0.80 (m, 2H), −0.04 (s, 9H).

Step 2: A dry 2-neck flask was evacuated and backflushed with argon (3×). Sodium t-butoxide (313 mg, 3.27 mmol), (+/−)BINAP (54 mg, 0.0877 mmol), and Pd$_2$(dba)$_3$ (26 mg, 0.0292 mmol) were added to the flask. A solution of 6-bromo-5-fluoro-1-((2-(trimethylsilyl)ethoxy)methyl)-1H-indazole (810 mg, 2.34 mmol) in toluene (15 mL) was then added to the flask followed by benzophenone imine (0.47 mL, 2.81 mmol). The reaction mixture was stirred at 80° C. for 2 hours and then allowed to cool to room temperature. The reaction mixture was poured onto water and EtOAc and extracted with EtOAc (3×). The combined organic extract was washed with brine, dried over anhydrous sodium sulfate and concentrated under reduced pressure. The reaction was 98% complete by LCMS. The crude product was combined with a previous small scale reaction to provide intermediate, N-(5-fluoro-1-((2-(trimethylsilyl)ethoxy)methyl)-1H-indazol-6-yl)-1,1-diphenylmethanimine (approx. 2.93 mmol), which was used as is for the next reaction. MS (ESI+) m/z 446.3 [M+H]$^+$.

Step 3: To a solution intermediate, N-(5-fluoro-1-((2-(trimethylsilyl)ethoxy)methyl)-1H-indazol-6-yl)-1,1-diphenylmethanimine, (approx. 2.93 mmol) in methanol (29 mL) under a nitrogen atmosphere was added potassium acetate (682 mg, 7 mmol) and hydroxylamine hydrochloride (363 mg, 5.2 mmol). The reaction mixture was stirred at room temperature for 1.5 h. The reaction was not complete. Additional potassium acetate (682 mg, 7 mmol) and hydroxylamine hydrochloride (363 mg, 5.2 mmol) were added. The reaction mixture was stirred for an additional 45 min at room temperature. The reaction mixture was poured onto 1% aqueous KOH and DCM and extracted with DCM (3×). The combined organic extracts were washed with water, dried over anhydrous sodium sulfate and concentrated under reduced pressure. Purification by flash chromatography provided 538 mg of 5-fluoro-1-((2-(trimethylsilyl)ethoxy)methyl)-1H-indazol-6-amine in 66% overall yield for the 2 steps. $^1$H NMR (300 MHz, Chloroform-d) δ 7.83 (s, 1H), 7.29 (d, J=10.7 Hz, 1H), 6.85 (d, J=7.2 Hz, 1H), 5.63 (s, 2H), 4.03 (br. s, 2H), 3.61-3.43 (m, 2H), 1.00-0.79 (m, 2H), −0.05 (s, 9H).

Step 4: To a stirred solution of 5-fluoro-1-((2-(trimethylsilyl)ethoxy)methyl)-1H-indazol-6-amine (530 mg, 1.88 mmol) in DCM (10 mL) under nitrogen at 0° C. was added pyridine (0.18 mL, 2.25 mmol) followed by TFFA (0.29 mL, 2.07 mmol). The reaction mixture was allowed to warm to room temperature and stirred at this temperature for 1.5 h. The reaction mixture was diluted with DCM, poured onto 10% aqueous KHSO$_4$/Na$_2$SO$_4$ buffer and extracted with DCM (3×). The organic extracts were washed with saturated aqueous sodium bicarbonate, dried over anhydrous sodium sulfate and concentrated under reduced pressure to provide 2,2,2-trifluoro-N-(5-fluoro-1-((2-(trimethylsilyl)ethoxy)methyl)-1H-indazol-6-yl)acetamide (820 mg, 100% yield) as a orange solid. $^1$H NMR (300 MHz, Chloroform-d) δ 7.83 (s, 1H), 7.43-7.09 (m, 4H), 6.85 (d, J=7.2 Hz, 1H), 5.63 (s, 2H), 4.03 (s, 5H), 3.61-3.43 (m, 2H), 1.00-0.79 (m, 2H), −0.05 (s, 9H).

Step 5: To a stirred solution of 2,2,2-trifluoro-N-(5-fluoro-1-((2-(trimethylsilyl)ethoxy)methyl)-1H-indazol-6-yl)acetamide (820 mg, 2.1 mmol) and 1-(bromomethyl)-4-cyclohexylbenzene (637 mg, 2.52 mmol) in acetonitrile (22 mL) was added potassium carbonate (434 mg, 3.15 mmol). The resulting reaction mixture under nitrogen was stirred at 60° C. for 2.5 h. After cooling to room temperature the reaction mixture was poured onto water and extracted with EtOAc (3×). The combined organic extract was washed with brine, dried over anhydrous sodium sulfate and concentrated under reduced pressure. The resulting residue was purified by flash chromatography (0-10% EtOAc/hexanes eluent) to provide N-(4-cyclohexylbenzyl)-2,2,2-trifluoro-N-(5-fluoro-1-((2-(trimethylsilyl)ethoxy)methyl)-1H-indazol-6-yl)acetamide (1.1 g, 95% yield). $^1$H NMR (300 MHz, Chloroform-d) δ 8.02 (s, 1H), 7.50 (d, J=9.2 Hz, 1H), 7.20-6.96 (m, 5H), 5.67-5.45 (m, 3H), 4.29 (d, J=14.1 Hz, 1H), 3.52-3.36 (m, 2H), 2.48 (m, 1H), 2.00-1.67 (m, 5H), 1.52-1.17 (m, 5H), 0.82 (dd, J=9.3, 7.2 Hz, 2H), −0.06 (s, 9H).

Step 6: To N-(4-cyclohexylbenzyl)-2,2,2-trifluoro-N-(5-fluoro-1-((2-(trimethylsilyl)ethoxy)methyl)-1H-indazol-6-yl)acetamide (1.03 g, 1.87 mmol) in THF (18 mL) and MeOH (18 mL) under nitrogen was added potassium carbonate (460 mg, 3.36 mmol). Stirring was continued for 7 h before the reaction mixture was poured onto cold saturated aqueous ammonium chloride and water and extracted with EtOAc (3×). The combined organic extracts were washed with water and then with brine, dried over anhydrous sodium sulfate and concentrated in vacuo to provide N-(4-cyclohexylbenzyl)-5-fluoro-1-((2-(trimethylsilyl)ethoxy)methyl)-1H-indazol-6-amine (861 mg, 100% yield). MS (ESI+) m/z 476.2 [M+Na]$^+$. $^1$H NMR (300 MHz, Chloroform-d) δ 7.82 (s, 1H), 7.41-7.19 (m, 5H), 6.68 (d, J=6.9 Hz, 2H), 5.63 (s, 2H), 4.55 (br. s, 1H), 4.43-4.35 (m, 2H), 3.59-3.50 (m, 2H), 2.62-2.44 (m, 1H), 2.00-1.72 (m, 5H), 1.54-1.32 (m, 5H), 0.93-0.85 (m, 2H), −0.04 (s, 9H).

Step 7: To a stirred solution of N-(4-cyclohexylbenzyl)-5-fluoro-1-((2-(trimethylsilyl)ethoxy)methyl)-1H-indazol-6-amine (250 mg, 0.55 mmol) in dry THF (8 mL) under nitrogen at 0° C. was added methylmagnesium bromide (0.98 mL of 1.4 M in THF, 1.38 mmol) and the resulting solution was stirred at 0° C. for 5 min and room temperature for 10 min before addition of solid (R)-1-((perfluorophenyl)sulfonyl)-azetidine-2-carbonyl chloride (288 mg, 0.825 mmol). The resulting mixture was allowed to warm to room temperature and stirred at room temperature for 3.5 h. A few drops of methanol were added and then the crude reaction mixture was poured onto water and extracted with DCM (3×). The combined organic extract was dried over sodium sulfate and concentrated under reduced pressure. The crude residue was purified by flash chromatography (8-20% EtOAc in hexanes eluent) to provide (R)—N-(4-cyclohexylbenzyl)-N-(5-fluoro-1-((2-(trimethylsilyl)ethoxy)methyl)-1H-indazol-6-yl)-1-((perfluorophenyl)sulfonyl)azetidine-2-carboxamide (145 mg, 34% yield) as a white foam. MS (ESI+) m/z 767.2 [M+H]+.

Step 8: To a stirred solution of (R)—N-(4-cyclohexylbenzyl)-N-(5-fluoro-1-((2-(trimethylsilyl)ethoxy)methyl)-1H-indazol-6-yl)-1-((perfluorophenyl)sulfonyl)azetidine-2-carboxamide (137 mg, 0.18 mmol) in DCM under a nitrogen atmosphere was added TFA (4 mL) and the resulting solution was allowed to stir at room temperature overnight. The reaction mixture was poured onto aqueous sodium bicarbonate and extracted with DCM (3×). The combined organic extracts were dried over anhydrous sodium sulfate and concentrated under reduced pressure. LCMS analysis showed 37% desired product and 60% (R)—N-(4-cyclohexylbenzyl)-N-(5-fluoro-1-(hydroxymethyl)-1H-indazol-6-yl)-1-((perfluorophenyl)sulfonyl)azetidine-2-carboxamide. Chromatography (50% EtOAc/hexanes eluent) and collection of a center cut of the upper spot provided pure (R)—N-(4-cyclohexylbenzyl)-N-(5-fluoro-1H-indazol-6-yl)-1-((perfluorophenyl)sulfonyl)azetidine-2-carboxamide (32 mg, 28% yield) as a white foam. HRMS (ESI+) m/z 637.1698 [M+H]+.

Example 95

(R)—N-(4-cyclohexylbenzyl)-N-(5-fluoro-1H-indazol-6-yl)-2-((2,3,4,5,6-pentafluoro-N-methylphenyl)sulfonamido)propanamide

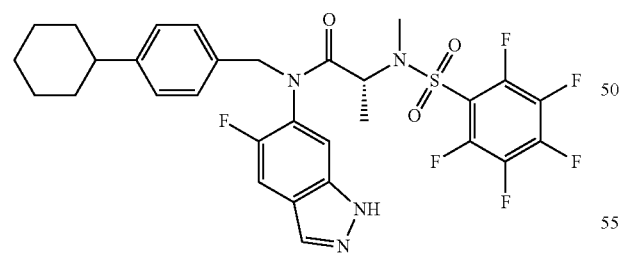

Preparation by a similar procedure to example 94, except substituting N-methyl-N-((perfluorophenyl)sulfonyl)-D-alaninoyl chloride for (R)-1-((perfluorophenyl)sulfonyl)-azetidine-2-carbonyl chloride in step 7 afforded (R)—N-(4-cyclohexylbenzyl)-N-(5-fluoro-1H-indazol-6-yl)-2-((2,3,4,5,6-pentafluoro-N-methylphenyl)sulfonamido)propanamide as a white solid. HRMS (ESI) m/z 639.1854 [M+H]+.

Example 96

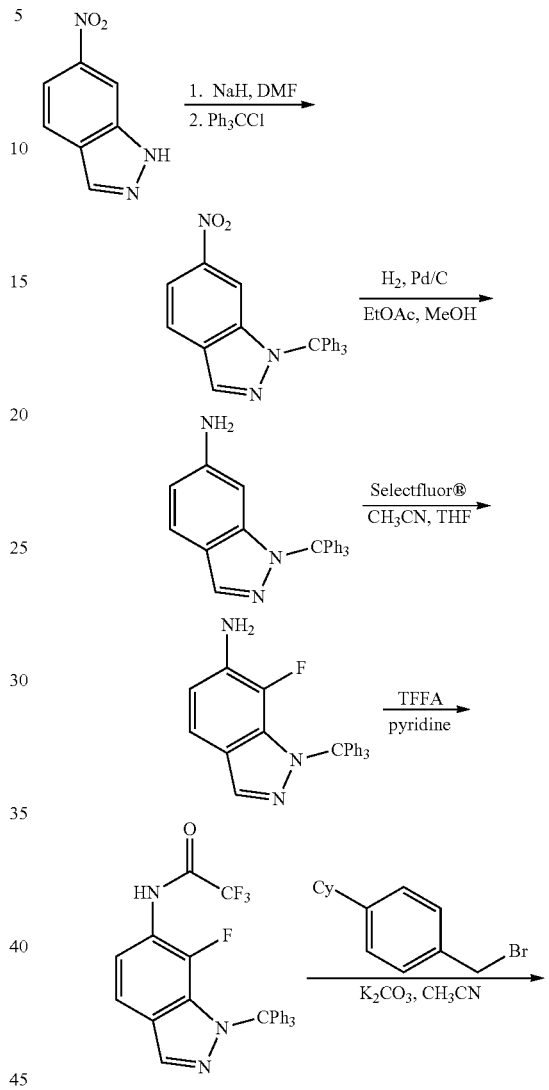

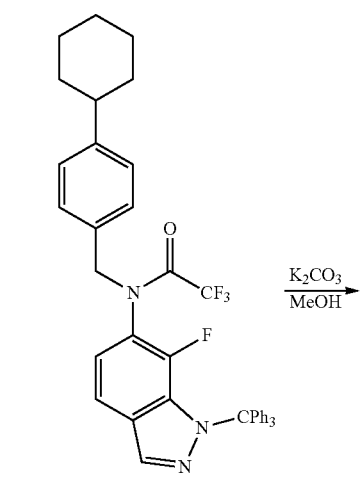

257
-continued

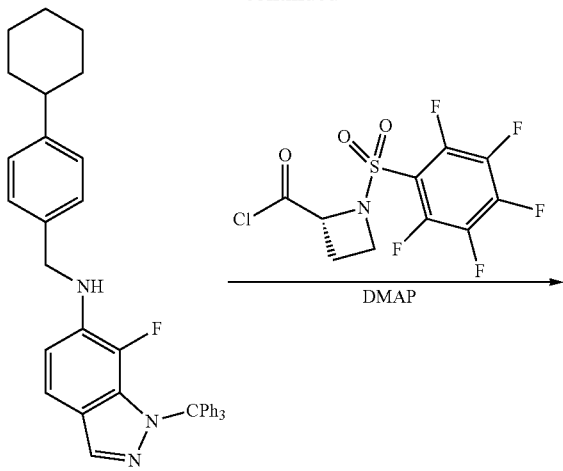

258

(R)—N-(4-cyclohexylbenzyl)-N-(7-fluoro-1H-indazol-6-yl)-1-((perfluorophenyl)sulfonyl)azetidine-2-carboxamide

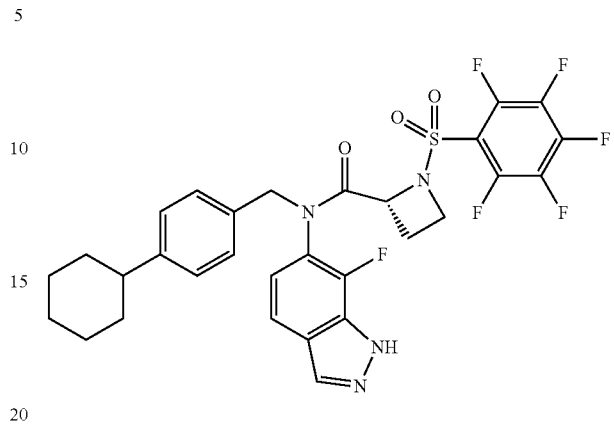

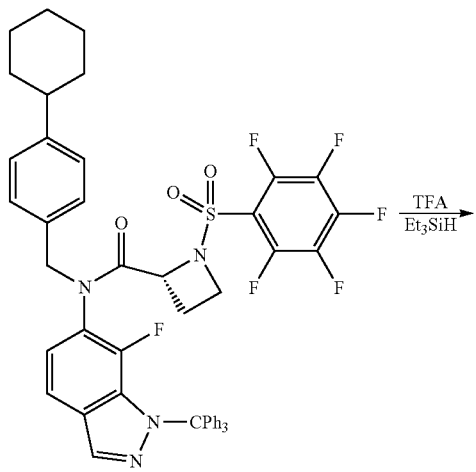

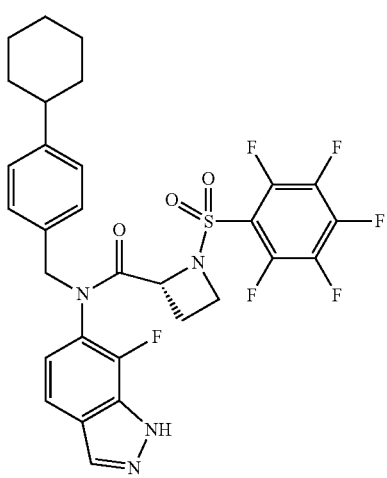

Step 1: To a suspension of sodium hydride (0.8 g of a 60% oil dispersion, 20 mmol) in THF (50 mL) under a nitrogen atmosphere at 0° C. was added a slurry of 6-nitro-1H-indazole (2.69 g, 16 mmol) in THF (15 mL) by dropwise addition. The mixture was stirred at 0° C. for 10 min. Triphenylmethylchloride (4.80 g, 17.6 mmol) in THF (20 mL) was added to the flask. The ice bath was removed and the mixture was allowed to warm to room temperature and stirred at that temperature overnight. The reaction mixture was cooled in an ice bath and quenched with saturated aqueous ammonium chloride. In a separatory funnel, the reaction mixture was poured onto water and extracted with ethyl acetate twice. The combined organic extracts were washed with brine, dried over anhydrous sodium sulfate, and concentrated under reduced pressure to get the crude product. The crude mixture was slurried in DCM and filtered. The solid was washed several times with small volumes of DCM. The combined filtrate and washes were added to a large column and eluted with 70:30 hexane:DCM. The fractions containing pure product were collected to provide 6-nitro-1-(triphenylmethyl)-1H-indazole (3.5 g, 54% yield). MS (ESI+) m/z 428.1 [M+Na]+. $^1$H NMR (300 MHz, Chloroform-d) δ 8.22 (d, J=1.0 Hz, 1H), 7.94 (dd, J=8.8, 1.9 Hz, 1H), 7.82 (d, J=8.9 Hz, 1H), 7.42-7.29 (m, 10H), 7.27-7.14 (m, 6H).

Step 2: To a stirred suspension of 6-nitro-1-(triphenylmethyl)-1H-indazole (3.06 g, 7.55 mmol) in ethyl acetate (50 mL) and methanol (25 mL), 10% Pd/C was added. The reaction was stirred under a hydrogen atmosphere for 7 h. The reaction mixture was filtered through Celite® and washed with ethyl acetate (3×). The combined filtrate and washes were concentrated under reduced pressure. The crude product was purified by flash chromatography (70:20 hexane:DCM, then with 70:20:10 hexane:DCM:EtOAc, and finally with 70:20:15 hexane:DCM:EtOAc eluents) to provide 6-amino-1-(triphenylmethyl)-1H-indazole (1.7 g, 60% yield). $^1$H NMR (300 MHz, Chloroform-d) δ 7.93 (d, J=0.9 Hz, 1H), 7.47 (dd, J=8.5, 0.7 Hz, 1H), 7.36-7.17 (m, 15H), 6.51 (dd, J=8.5, 1.9 Hz, 1H), 5.72-5.63 (m, 1H).

Step 3: To a suspension of 6-amino-1-(triphenylmethyl)-1H-indazole (375 mg, 1 mmol) in acetonitrile (8 mL) and THF (2 mL) under a nitrogen atmosphere was added sodium bicarbonate (252 mg, 3 mmol). To the resulting solution was added Selectfluor® (390 mg, 1.1 mmol) by portionwise addition over 10 min. After 1.5 hours, water was added to the mixture and the mixture was extracted with ethyl acetate (3×). The combined ethyl acetate extracts were dried with anhydrous sodium sulfate and concentration under reduced pressure to get the crude product. The LCMS showed that reaction went 90% to completion. This reaction was combined with other trial reactions and purified by a column eluting with 70:20:5 hexane:$CH_2Cl_2$:EtOAc and then with 70:20:15 hexane:$CH_2Cl_2$:EtOAc to provide 7-fluoro-1-trityl-1H-indazol-6-amine (170 mg, 45% yield). $^1$H NMR (300 MHz, Chloroform-d) δ 7.92 (d, J=2.4 Hz, 1H), 7.36-7.15 (m, 16H), 6.66 (dd, J=8.4, 6.7 Hz, 1H).

Step 4: To a stirred solution of 7-fluoro-1-trityl-1H-indazol-6-amine (297 mg, 0.76 mmol) in DCM (6 mL) under nitrogen at 0° C. was added pyridine (0.073 mL, 0.91 mmol) followed by TFFA (0.12 mL, 0.83 mmol). The reaction mixture was allowed to warm to room temperature and stirred at this temperature for 0.5 h. The reaction mixture was diluted with DCM, poured onto 10% aqueous $KHSO_4$/$Na_2SO_4$ buffer and extracted with DCM (3×). The organic extracts were washed with saturated aqueous sodium bicarbonate, dried over anhydrous sodium sulfate and concentrated under reduced pressure to provide 2,2,2-trifluoro-N-(7-fluoro-1-trityl-1H-indazol-6-yl)acetamide (385 mg, 100% yield) as a orange foam. $^1$H NMR (300 MHz, Chloroform-d) δ 8.09 (d, J=2.5, 1H), 8.02 (dd, J=8.8, 5.8 Hz, 1H), 7.81 (br. s, 1H), 7.59 (d, J=8.8 Hz, 1H), 7.37-7.24 (m, 9H), 7.23-7.13 (m, 6H).

Step 5: To a stirred solution of 2,2,2-trifluoro-N-(7-fluoro-1-trityl-1H-indazol-6-yl)acetamide (382 mg, 0.76 mmol) and 1-(bromomethyl)-4-cyclohexylbenzene (257 mg, 0.99 mmol) in acetonitrile (10 mL) was added potassium carbonate (157 mg, 1.14 mmol). The resulting reaction mixture under nitrogen was stirred at 60° C. for 2 h. After cooling to room temperature the reaction mixture was poured onto water and extracted with EtOAc (3×). The combined organic extract was washed with brine, dried over anhydrous sodium sulfate and concentrated under reduced pressure. The resulting residue was purified by flash chromatography (0-10% EtOAc/hexanes eluent) to provide N-(4-cyclohexylbenzyl)-2,2,2-trifluoro-N-(7-fluoro-1-trityl-1H-indazol-6-yl)acetamide (436 mg, 87% yield). $^1$H NMR (300 MHz, Chloroform-d) δ 8.06 (d, J=2.2 Hz, 1H), 7.37-7.22 (m, 9H), 7.21-7.12 (m, 7H), 7.04 (d, J=8.1 Hz, 2H), 6.82 (d, J=8.1 Hz, 2H), 6.55-6.44 (m, 1H), 5.29 (d, J=14.0 Hz, 1H), 3.72 (d, J=14.0 Hz, 1H), 2.56-2.34 (m, 1H), 1.97-1.68 (m, 5H), 1.53-1.16 (m, 5H).

Step 6: To N-(4-cyclohexylbenzyl)-2,2,2-trifluoro-N-(7-fluoro-1-trityl-1H-indazol-6-yl)acetamide (427 mg, 0.65 mmol) in THF (7 mL) and MeOH (7 mL) under nitrogen was added potassium carbonate (160 mg, 1.16 mmol). Stirring was continued for 3 days before the reaction mixture was poured onto cold saturated aqueous ammonium chloride and water and extracted with EtOAc (3×). The combined organic extracts were washed with water and then with brine, dried over anhydrous sodium sulfate and concentrated under reduced pressure. The crude product was taken up in ether and product was allowed to slowly precipitate out. The ether was decanted off and solid was washed with ether (1×) and dried under vacuum to provide N-(4-cyclohexylbenzyl)-7-fluoro-1-trityl-1H-indazol-6-amine (260 mg, 71% yield) as a white solid. $^1$H NMR (300 MHz, Chloroform-d) δ 7.91 (d, J=2.4 Hz, 1H), 7.34 (d, J=8.6 Hz, 1H), 7.31-7.12 (m, 15H), 6.70 (dd, J=8.6, 6.5 Hz, 1H), 4.27 (s, 2H), 3.99 (br. s, 1H), 2.61-2.37 (m, 1H), 1.98-1.68 (m, 5H), 1.52-1.21 (m, 5H).

Step 7: To a stirred solution of N-(4-cyclohexylbenzyl)-7-fluoro-1-trityl-1H-indazol-6-amine (230 mg, 0.41 mmol) in dry DCM (5 mL) under nitrogen was added (R)-1-((perfluorophenyl)sulfonyl)-azetidine-2-carbonyl chloride (199 mg, 0.57 mmol) followed by DMAP (60 mg, 0.49 mmol). The resulting mixture was stirred at room temperature for 4.5 h. The crude reaction mixture was poured onto water and extracted with DCM (3×). The combined organic extract was dried over sodium sulfate and concentrated under reduced pressure to provide crude product, (R)—N-(4-cyclohexylbenzyl)-N-(7-fluoro-1-trityl-1H-indazol-6-yl)-1-((perfluorophenyl)sulfonyl)azetidine-2-carboxamide which was used as is for the next step. MS (ESI+) m/z 879 [M+H]$^+$.

Step 8: To a stirred solution of (R)—N-(4-cyclohexylbenzyl)-N-(7-fluoro-1-trityl-1H-indazol-6-yl)-1-((perfluorophenyl)sulfonyl)azetidine-2-carboxamide (0.41 mmol) in DCM (5 mL) under a nitrogen atmosphere was added triethylsilane (91 uL, 1.5 equiv) followed by TFA (1 mL) and the resulting solution was allowed to stir at room temperature for 2 h. The reaction mixture was concentrated under reduced pressure. Purification by flash chromatography (30:15:55 EtOAc:DCM:hexane eluent) followed by repurification by chromatography (25% EtOAc/hexanes eluent) provided (R)—N-(4-cyclohexylbenzyl)-N-(7-fluoro-1H-indazol-6-yl)-1-((perfluorophenyl)sulfonyl)azetidine-2-carboxamide (200 mg, 77% yield for the 2 steps) as a white foam. HRMS (ESI+) m/z 637.1707 [M+H]$^1$.

Example 97

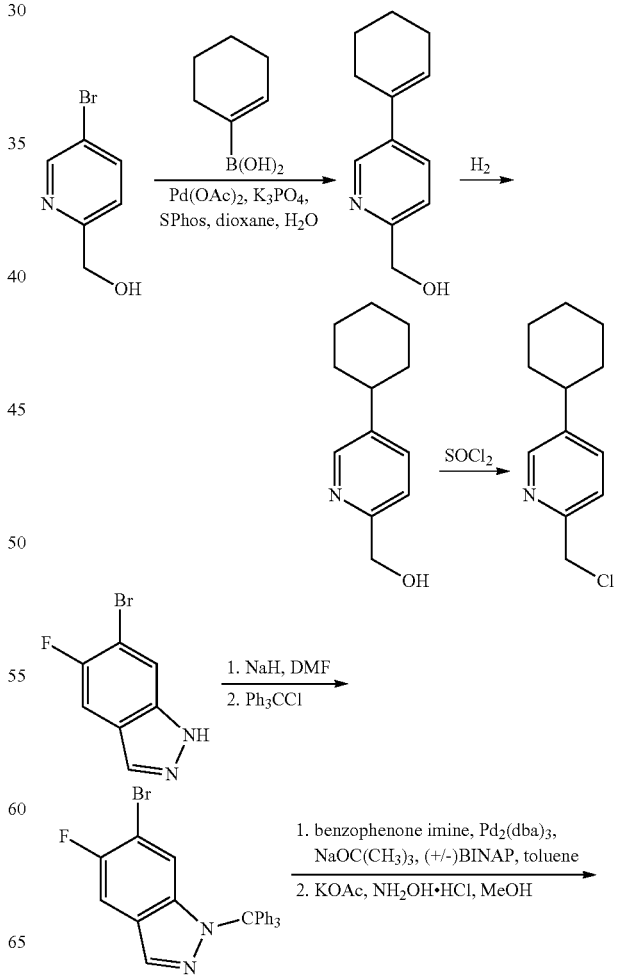

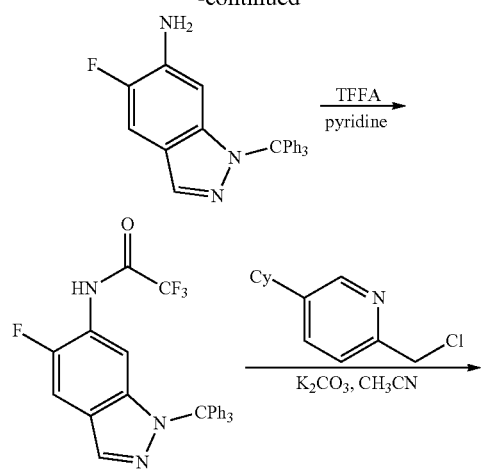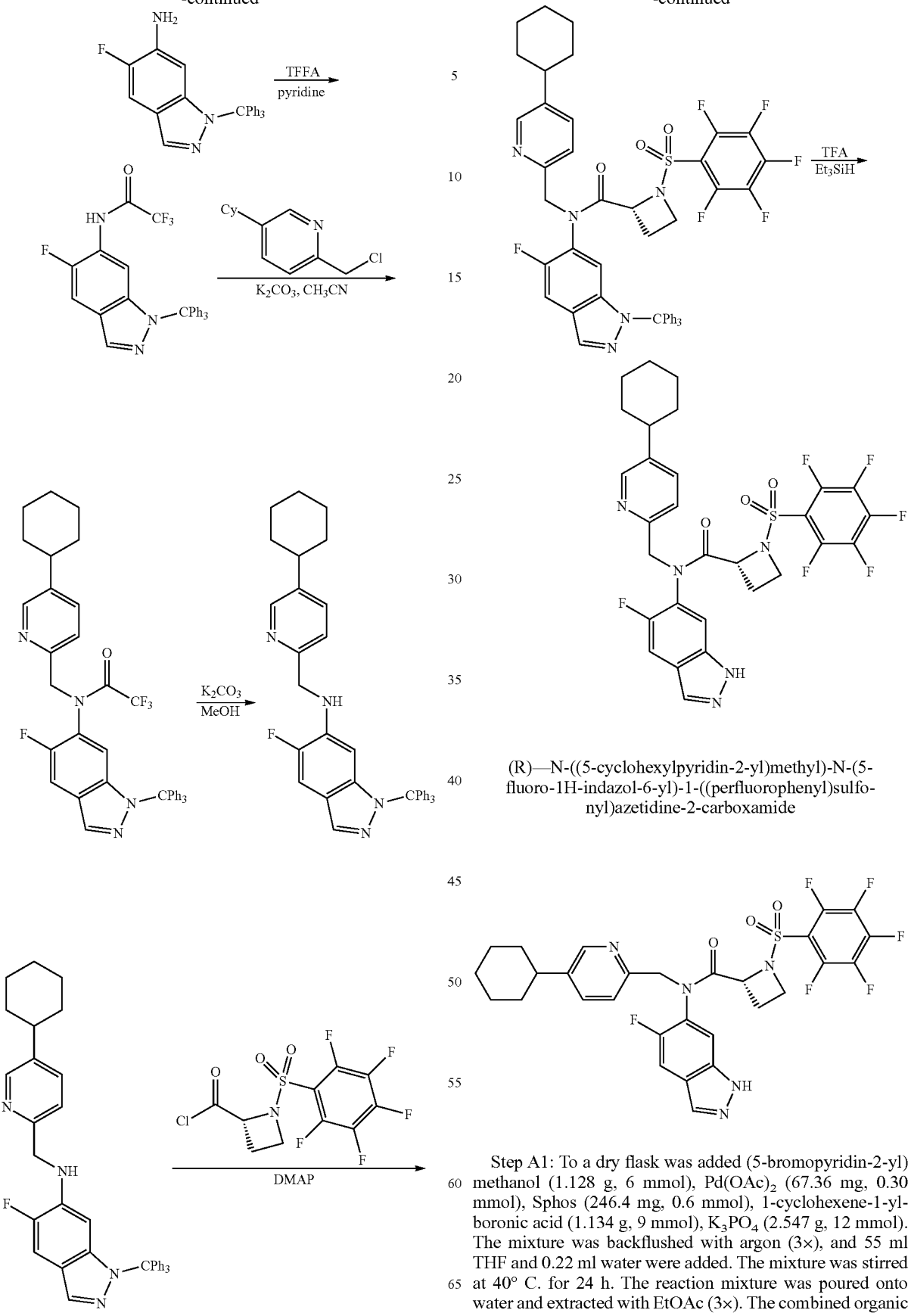

(R)—N-((5-cyclohexylpyridin-2-yl)methyl)-N-(5-fluoro-1H-indazol-6-yl)-1-((perfluorophenyl)sulfonyl)azetidine-2-carboxamide Step A1: To a dry flask was added (5-bromopyridin-2-yl)methanol (1.128 g, 6 mmol), Pd(OAc)$_2$ (67.36 mg, 0.30 mmol), Sphos (246.4 mg, 0.6 mmol), 1-cyclohexene-1-yl-boronic acid (1.134 g, 9 mmol), K$_3$PO$_4$ (2.547 g, 12 mmol). The mixture was backflushed with argon (3×), and 55 ml THF and 0.22 ml water were added. The mixture was stirred at 40° C. for 24 h. The reaction mixture was poured onto water and extracted with EtOAc (3×). The combined organic layer was washed with brine, dried with Na$_2$SO$_4$, concentrated under vacuum and purified by chromatography providing (5-(cyclohex-1-en-1-yl)pyridin-2-yl)methanol (1.08 g, 95% yield) as a yellowish solid. $^1$H NMR (300 MHz, cdcl$_3$) δ 8.54 (s, 1H), 7.65 (dd, J=8.1, 2.2 Hz, 1H), 7.22 (d, J=8.1 Hz, 1H), 6.20-6.10 (m, 1H), 4.74 (s, 2H), 2.44-2.33 (m, 2H), 2.27-2.17 (m, 2H), 1.85-1.74 (m, 2H), 1.73-1.62 (m, 2H).

Step A2: To a two-neck flask under an argon atmosphere was added (5-(cyclohex-1-en-1-yl)pyridin-2-yl)methanol (1 g, 5.29 mmol) and 10 w % PtO$_2$. The flask was evacuated under vacuum and backflushed with hydrogen (3×). To the flask EtOAc (8 mL) and methanol (8 mL) and the mixture was stirred in the RT for 4 h. After the reaction was completed, the PtO$_2$ was filtered. The filtrate was concentrated in vacuo to provide (5-cyclohexylpyridin-2-yl)methanol (1 g, 99% yield). $^1$H NMR (300 MHz, Chloroform-d) δ 8.42 (d, J=2.4 Hz, 1H), 7.53 (dd, J=8.0, 2.4 Hz, 1H), 7.19 (d, J=8.0 Hz, 1H), 4.74 (s, 2H), 2.73-2.31 (m, 1H), 2.00-1.68 (m, 5H), 1.58-1.14 (m, 5H).

Step A3: To a solution of (5-cyclohexylpyridin-2-yl)methanol (143.3 mg, 0.75 mmol) in DCM (3 mL) under a nitrogen atmosphere at 0° C. was added thionyl chloride (0.083 mL, 1.15 mmol). The reaction mixture was stirred at room temperature for 3 h before being poured onto saturated aqueous sodium bicarbonate and extracted with DCM (2×). The combined organic extract was washed with 10% aqueous sodium bicarbonate, dried over anhydrous sodium sulfate and concentrated in vacuo to provide 0.75 mmol of 2-(chloromethyl)-5-cyclohexylpyridine which was used immediately as is. $^1$H NMR (300 MHz, Chloroform-d) δ 8.45 (d, J=2.4 Hz, 1H), 7.56 (dd, J=8.2, 2.4 Hz, 1H), 7.40 (d, J=8.2 Hz, 1H), 4.67 (s, 2H), 2.71-2.30 (m, 1H), 2.10-1.72 (m, 5H), 1.55-1.03 (m, 5H).

Step 1: A round-bottomed flask was evacuated and back-flushed with argon (3×). To the flask was added 6-bromo-5-fluoro-1H-indazole (965 mg, 4.49 mmol, Synthonix) and 50.0 mL of dry THF. The flask was cooled to 0° C. and then was added NaH (252 mg, 6.29 mmol). The reaction mixture was stirred at 0° C. for 5 min., then stirred at room temperature for 10 min. A solution of trityl chloride (1.37 g, 4.94 mmol) in THF (10.0 mL) was added dropwise and the resulting reaction mixture was allowed to stir overnight at room temperature. The reaction mixture was quenched with 2 mL of saturated aqueous ammonium chloride solution, poured into deionized water, and extracted with EtOAc (3×). The combined organic extracts were washed with brine, dried over anhydrous sodium sulfate, and concentrated in vacuo yielding the crude product as an orange oil. The crude product was taken up in DCM/MeOH and purified twice by flash column chromatography: first, using a step-wise gradient (Hexane/DCM 4:1, Hexane/DCM/EtOAc 20:5:1) followed subsequently by purification using (Hexane/EtOAc 19:1) eluent to provide 6-bromo-5-fluoro-1-trityl-1H-indazole (1.26 g, 61%) as a white powder. $^1$H NMR (300 MHz, Chloroform-d) δ 8.04 (s, 1H), 7.39 (d, J=8.1 Hz, 1H), 7.36-7.29 (m, 9H), 7.24-7.16 (m, 6H), 6.61 (d, J=5.3 Hz, 1H). MS (ESI+) m/z 479.0, 481.0 [M+Na]$^+$.

Step 2: To a flask, that was evacuated and back-flushed with argon (3×), containing 6-bromo-5-fluoro-1-trityl-1H-indazole (625 mg, 1.37 mmol) was added sodium t-butoxide (184 mg, 1.92 mmol), Pd$_2$(dba)$_3$ (16.0 mg, 0.017 mmol) and (±) BINAP (32.0 mg). The flask was evacuated again and put under argon. To the flask was added 12 mL of dry toluene and benzophenone imine (0.28 mL 1.64 mmol). The reaction mixture was stirred at 80° C. overnight, then poured into deionized water, and extracted with EtOAc (3×). The organic extracts were combined, washed with brine, dried over anhydrous sodium sulfate, and concentrated in vacuo yielding the crude product, N-(5-fluoro-1-trityl-1H-indazol-6-yl)-1,1-diphenylmethanimine, as a green solid. This procedure was conducted a second time and the same scale. The crude products of both reactions were combined and carried on to the next reaction without further purification. MS (ESI+) m/z 558.0 [M+H]$^+$. To a slurry of the crude N-(5-fluoro-1-trityl-1H-indazol-6-yl)-1,1-diphenylmethanimine (approx. 2.73 mmol) in methanol (60 mL) under a nitrogen atmosphere was added anhydrous potassium acetate (647 mg, 6.60 mmol) and hydroxylamine hydrochloride (343 mg, 4.90 mmol). The reaction mixture was stirred overnight at 60° C. after which it was allowed to cool and then poured onto deionized water. A few mL of 1N aqueous KOH solution was added to ensure the aqueous phase was not acidic and then the mixture was extracted with DCM (3×). The organic extracts were combined, washed with brine, dried over anhydrous sodium sulfate, and concentrated in vacuo yielding the crude product as a solid brown powder. The crude product was taken up in DCM and purified twice by flash column chromatography: first column using isocratic conditions (Hexane/DCM/EtOAc 16:3:1) followed by a second column using a step-wise gradient (DCM/Hexane 1:1, DCM/Hexane 3:2, DCM/Hexane/EtOAc 3:2:1) to provide 5-fluoro-1-trityl-1H-indazol-6-amine (911 mg, 85% yield over the 2 steps) as a white powder. $^1$H NMR (300 MHz, Chloroform-d) δ 7.91 (d, J=1.0 Hz, 1H), 7.37-7.11 (m, 16H), 5.75 (dd, J=7.5, 1.0 Hz, 1H), 3.63 (s, 2H). MS (ESI+) m/z 394.0 [M+H]$^+$.

Step 3: To a stirred solution of 5-fluoro-1-trityl-1H-indazol-6-amine (905 mg, 2.3 mmol) in DCM (13 mL) under nitrogen at 0° C. was added pyridine (0.22 mL, 2.76 mmol) followed by TFFA (0.36 mL, 2.53 mmol). The reaction mixture was allowed to warm to room temperature and stirred at this temperature for 2 h. The reaction mixture was diluted with DCM, poured onto 10% aqueous KHSO$_4$/Na$_2$SO$_4$ buffer and extracted with DCM (3×). The organic extracts were washed with saturated aqueous sodium bicarbonate, dried over anhydrous sodium sulfate and concentrated under reduced pressure to provide 2,2,2-trifluoro-N-(5-fluoro-1-trityl-1H-indazol-6-yl)acetamide (1.13 g, 100% yield) as a white solid. $^1$H NMR (300 MHz, Chloroform-d) δ 8.06 (d, J=1.0 Hz, 1H), 8.00 (br. s, 1H), 7.62-7.54 (m, 1H), 7.43 (dd, J=10.2, 0.5 Hz, 1H), 7.34-7.28 (m, 9H), 7.28-7.21 (m, 6H).

Step 4: To a stirred solution of 2,2,2-trifluoro-N-(5-fluoro-1-trityl-1H-indazol-6-yl)acetamide (245 mg, 0.5 mmol) and 2-(chloromethyl)-5-cyclohexylpyridine (Example 96 step A3, 0.75 mmol) in acetonitrile (6 mL) was added potassium carbonate (105 mg, 0.75 mmol) followed by catalytic sodium iodide (7.5 mg, 0.05 mmol). The resulting reaction mixture under nitrogen was stirred at 60° C. overnight. After cooling to room temperature the reaction mixture was poured onto water and extracted with EtOAc (3×). The combined organic extract was washed with brine, dried over anhydrous sodium sulfate and concentrated under reduced pressure. The resulting residue was purified by flash chromatography (83:10:7 hexane:DCM:EtOAc eluent) to provide N-((5-cyclohexylpyridin-2-yl)methyl)-2,2,2-trifluoro-N-(5-fluoro-1-trityl-1H-indazol-6-yl)acetamide (285.5 mg, 86% yield) as a white solid. MS (ESI+) m/z 663.2 [M+H]$^+$.

Step 5: To N-((5-cyclohexylpyridin-2-yl)methyl)-2,2,2-trifluoro-N-(5-fluoro-1-trityl-1H-indazol-6-yl)acetamide (275 mg, 0.415 mmol) in THF (5 mL) and MeOH (5 mL) under nitrogen was added potassium carbonate (103 mg, 0.75 mmol). Stirring was continued for 2.5 h before the reaction mixture was poured onto cold saturated aqueous ammonium chloride and water and extracted with EtOAc (3×). The combined organic extracts were washed with water and then with brine, dried over anhydrous sodium sulfate and concentrated under reduced pressure to provide N-((5-cyclohexylpyridin-2-yl)methyl)-5-fluoro-1-trityl-1H-indazol-6-amine (230 mg, 98% yield) as a cream-colored solid.

Step 6: To a stirred solution of N-((5-cyclohexylpyridin-2-yl)methyl)-5-fluoro-1-trityl-1H-indazol-6-amine (221 mg, 0.39 mmol) in dry DCM (5 mL) under nitrogen was added (R)-1-((perfluorophenyl)sulfonyl)-azetidine-2-carbonyl chloride (191 mg, 0.55 mmol) followed by DMAP (57 mg, 0.47 mmol). The resulting mixture was stirred at room temperature for 3 days. A few drops of methanol were added. The crude reaction mixture was poured onto water and extracted with DCM (3×). The combined organic extract was dried over sodium sulfate and concentrated under reduced pressure to provide crude product. The crude product was purified by flash chromatography (10-25% EtOAc/hexanes eluent) to provide (R)—N-cyclohexylpyridin-2-yl)methyl)-N-(5-fluoro-1-trityl-1H-indazol-6-yl)-1-((perfluorophenyl)sulfonyl)azetidine-2-carboxamide (192 mg, 56% yield). MS (ESI+) m/z 880.3 [M+H]⁺.

Step 7: To a stirred solution of (R)—N-((5-cyclohexylpyridin-2-yl)methyl)-N-(5-fluoro-1-trityl-1H-indazol-6-yl)-1-((perfluorophenyl)sulfonyl)azetidine-2-carboxamide (185 mg, 0.21 mmol) in DCM (5 mL) under a nitrogen atmosphere was added triethylsilane (40 uL, 1.5 equiv) followed by TFA (1 mL) and the resulting solution was allowed to stir at room temperature for 0.5 h. The reaction mixture was concentrated under reduced pressure. Toluene was added and the reaction mixture was concentrated again under reduced pressure. The crude product was taken up in DCM, washed with aqueous sodium bicarbonate, dried over anhydrous sodium sulfate and concentrated under reduced pressure. Purification by flash chromatography (30-100% EtOAc/hexane eluent) provided (R)—N-((5-cyclohexylpyridin-2-yl)methyl)-N-(5-fluoro-1H-indazol-6-yl)-1-((perfluorophenyl) sulfonyl)azetidine-2-carboxamide (123 mg, 92% yield) as a white foam. HRMS (ESI+) m/z 638.1754 [M+H]⁺.

Example 98

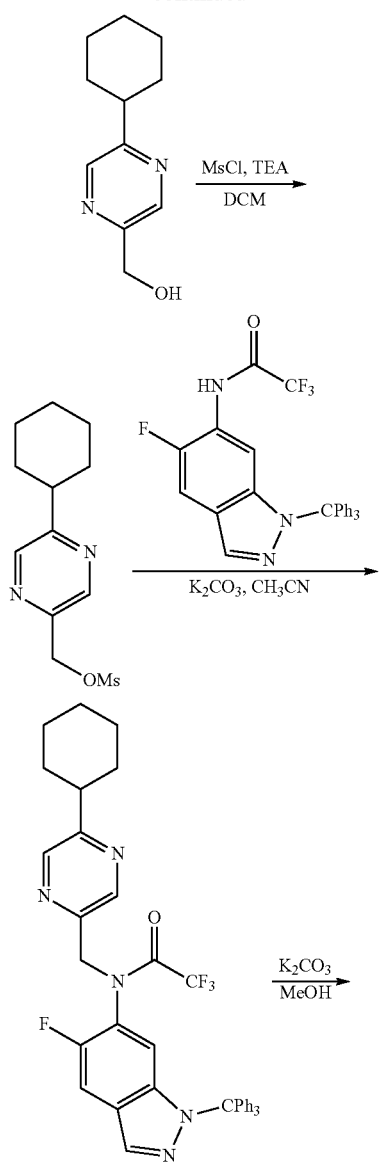

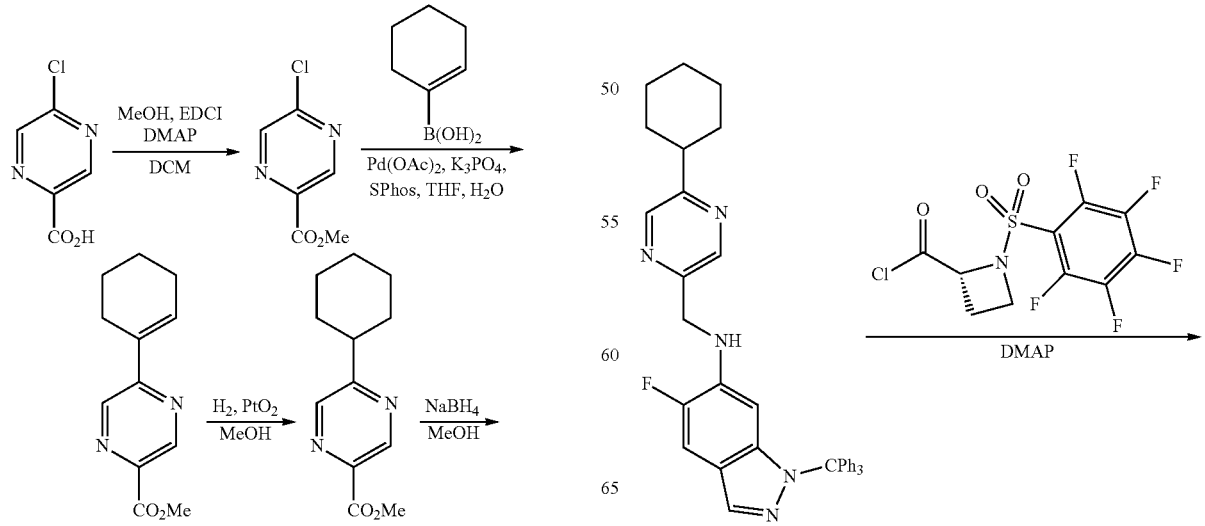

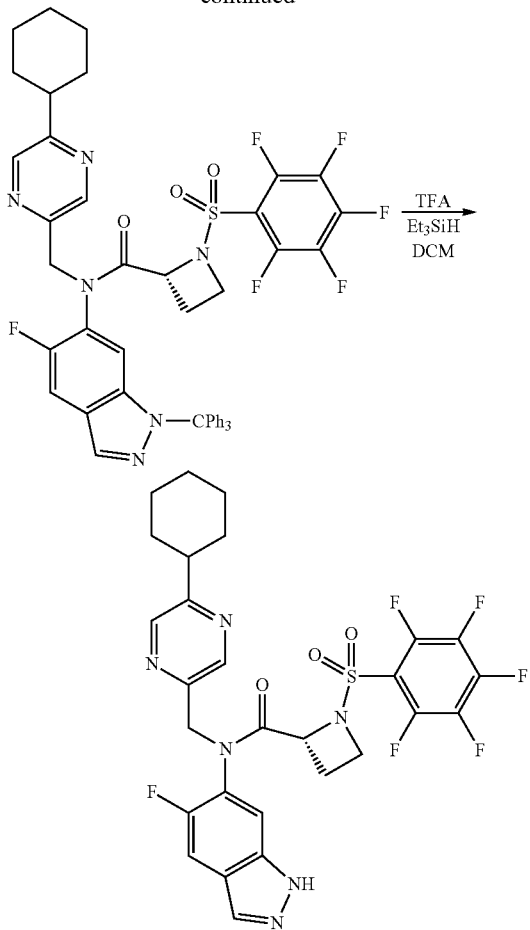

(R)—N-((5-cyclohexylpyrazin-2-yl)methyl)-N-(5-fluoro-1H-indazol-6-yl)-1-((perfluorophenyl)sulfonyl)azetidine-2-carboxamide

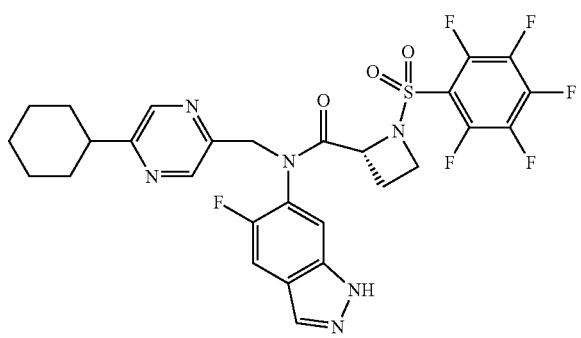 [SMILES: O=C([C@H]1CCN1S(=O)(=O)c1c(F)c(F)c(F)c(F)c1F)N(Cc1cnc(C2CCCCC2)cn1)c1cc2[nH]ncc2cc1F]

Step 1: To a solution of 5-chloropyrazine-2-carboxylic acid (1.00 g, 6.31 mmol) in CH$_2$Cl$_2$ (10 mL) was added EDCI (1.34 g, 7.03 mmol), DMAP (39 mg, 0.32 mmol) and MeOH (0.51 mL, 13 mmol) at room temperature. After stirring for 2.5 h, the reaction was quenched by adding saturated aqueous ammonium chloride solution. The crude products were extracted with CH$_2$Cl$_2$ (3×), and the combined organic extracts were washed with brine, dried (MgSO$_4$), and concentrated in vacuo. The residue was purified by flash column chromatography (hexane/EtOAc=9/1 to 7/1) to afford methyl 5-chloropyrazine-2-carboxylate (631 mg, 58%) as a white solid. $^1$H NMR (300 MHz, CDCl$_3$) δ 9.12 (d, J=1.8 Hz, 1H), 8.73 (d, J=1.8 Hz, 1H), 4.07 (s, 3H).

Step 2: To a solution of methyl 5-chloropyrazine-2-carboxylate (601 mg, 3.48 mmol) in THF (11.6 mL) was added 1-cyclohexene-1-yl-boronic acid (656 mg, 5.21 mmol), K$_3$PO$_4$ (1.47 g, 6.91 mmol), Pd(OAc)$_2$ (39.2 mg, 0.175 mmol), SPhos (144 mg, 0.350 mmol) and H$_2$O (0.13 mL, 7.2 mmol) at room temperature. After stirring for 15 h at 40° C., the reaction was quenched by adding water. The crude products were extracted with EtOAc (3×), and the combined organic extracts were washed with brine, dried (MgSO$_4$), and concentrated in vacuo. The residue was purified by flash column chromatography (hexane/EtOAc=9/1 to 4/1) to afford methyl 5-(cyclohex-1-en-1-yl)pyrazine-2-carboxylate (736 mg, 97%) as a pale yellow solid. $^1$H NMR (300 MHz, CDCl$_3$) δ 9.21 (d, J=1.2 Hz, 1H), 8.81 (d, J=1.2 Hz, 1H), 6.98-7.01 (m, 1H), 4.05 (s, 3H), 2.55-2.60 (m, 2H), 2.34-2.38 (m, 2H), 1.81-1.89 (m, 2H), 1.70-1.77 (m, 2H).

Step 3: To a solution of methyl 5-(cyclohex-1-en-1-yl)pyrazine-2-carboxylate (716 mg, 3.28 mmol) in EtOAc (16 mL) was added PtO$_2$ (109 mg, 0.478 mmol) and the reaction mixture was stirred under a H$_2$ atmosphere at room temperature. After stirring for 3 h, the reaction mixture was filtered through Celite® pad and the pad was washed with EtOAc. The combined filtrate and washes were concentrated in vacuo. The residue was purified by flash column chromatography (hexane/EtOAc=8/1 to 5/1) to provide methyl 5-cyclohexylpyrazine-2-carboxylate (595 mg, 82%) as a pale yellow solid. $^1$H NMR (300 MHz, CDCl$_3$) δ 9.23 (d, J=1.8 Hz, 1H), 8.59 (d, J=1.8 Hz, 1H), 4.05 (s, 3H), 2.82-2.91 (m, 1H), 1.31-1.99 (m, 10H).

Step 4: To a solution of methyl 5-cyclohexylpyrazine-2-carboxylate (556 mg, 2.52 mmol) in MeOH (12.6 mL) was added NaBH$_4$ (304 mg, 8.04 mmol) at 0° C. After stirring for 25 min at room temperature, another portion of NaBH$_4$ (192 mg, 5.08 mmol) was added. After stirring for 35 min, the reaction mixture was evaporated to half volume before the addition of water and EtOAc. The crude products were extracted with EtOAc (3×), and the combined organic extracts were washed with brine, dried (MgSO$_4$), and concentrated in vacuo. The residue was purified by flash column chromatography (hexane/EtOAc=4/1 to 2/1) to afford (5-cyclohexylpyrazin-2-yl)methanol (464 mg, 96%) as a pale yellow oil. $^1$H NMR (300 MHz, CDCl$_3$) δ 8.57 (d, J=1.2 Hz, 1H), 8.45 (d, J=1.2 Hz, 1H), 4.84 (s, 2H), 3.10 (brs, 1H, OH), 2.76-2.85 (m, 1H), 1.28-1.98 (m, 10H).

Step 5: To a solution of (5-cyclohexylpyrazin-2-yl)methanol (160 mg, 0.83 mmol) in CH$_2$Cl$_2$ (8 mL) was added Et$_3$N (0.35 mL, 2.5 mmol) and MsCl (0.097 mL, 1.25 mmol) at 0° C. After stirring for 30 min, the reaction mixture was poured onto saturated aqueous sodium bicarbonate and DCM and extracted with DCM (2×). The combined organic extracts were washed with brine, dried over anhydrous sodium sulfate and concentrated in vacuo to afford (5-cyclohexylpyrazin-2-yl)methyl methanesulfonate (220 mg, 100%), which was used directly in the next reaction.

$^1$H NMR (300 MHz, CDCl$_3$) δ 8.65 (d, J=1.2 Hz, 1H), 8.50 (d, J=1.2 Hz, 1H), 5.36 (s, 2H), 3.14 (s, 3H), 2.77-2.86 (m, 1H), 1.26-1.98 (m, 10H).

Step 6: To a stirred solution of 2,2,2-trifluoro-N-(5-fluoro-1-trityl-1H-indazol-6-yl)acetamide (245 mg, 0.5 mmol) and (5-cyclohexylpyrazin-2-yl)methyl methanesulfonate (0.83 mmol) in acetonitrile (6 mL) was added potassium carbonate (115 mg, 0.83 mmol) followed by catalytic sodium iodide (7 mg, 0.05 mmol). The resulting reaction mixture under nitrogen was stirred at 60° C. overnight. After cooling to room temperature the reaction mixture was poured onto water and extracted with EtOAc (3×). The combined organic extract was washed with brine, dried over anhydrous sodium sulfate and concentrated under reduced pressure. The resulting residue was purified by flash chromatography (20% EtOAc/hexane eluent) to provide N-((5-cyclohexylpyrazin-2-yl)methyl)-2,2,2-trifluoro-N-(5-fluoro-1-trityl-1H-indazol-6-yl)acetamide (287 mg, 86% yield) as a white solid. $^1$H NMR (300 MHz, Chloroform-d) δ 8.32 (d, J=1.4 Hz, 1H), 8.13 (d, J=1.4 Hz, 1H), 8.09 (s, 1H), 7.43 (d, J=9.0 Hz, 1H), 7.28-7.07 (m, 15H), 6.46 (d, J=6.2 Hz, 1H), 5.18 (d, J=15.2 Hz, 1H), 4.44 (d, J=15.2 Hz, 1H), 2.82-2.60 (m, 1H), 2.03-1.71 (m, 7H), 1.57-1.26 (m, 3H).

Step 7: To N-((5-cyclohexylpyrazin-2-yl)methyl)-2,2,2-trifluoro-N-(5-fluoro-1-trityl-1H-indazol-6-yl)acetamide (281 mg, 0.42 mmol) in THF (5 mL) and MeOH (5 mL) under nitrogen was added potassium carbonate (103 mg, 0.75 mmol). Stirring was continued for 1.5 h before the reaction mixture was poured onto cold saturated aqueous ammonium chloride and water and extracted with EtOAc (3×). The combined organic extracts were washed with water and then with brine, dried over anhydrous sodium sulfate and concentrated under reduced pressure to provide N-((5-cyclohexylpyrazin-2-yl)methyl)-5-fluoro-1-trityl-1H-indazol-6-amine (257 mg, 100% yield) as a white foam. $^1$H NMR (300 MHz, Chloroform-d) δ 8.34 (d, J=1.5 Hz, 1H), 8.27 (s, 1H), 7.90 (d, J=1.0 Hz, 1H), 7.27-7.11 (m, 15H), 5.54 (d, J=7.2 Hz, 1H), 4.93-4.82 (m, 1H), 3.97 (d, J=5.1 Hz, 2H), 2.88-2.66 (m, 1H), 2.04-1.74 (m, 4H), 1.70-1.30 (m, 6H).

Step 8: To a stirred solution of N-((5-cyclohexylpyrazin-2-yl)methyl)-5-fluoro-1-trityl-1H-indazol-6-amine (240 mg, 0.42 mmol) in dry DCM (6 mL) under nitrogen was added (R)-1-((perfluorophenyl)sulfonyl)-azetidine-2-carbonyl chloride (205 mg, 0.58 mmol) followed by DMAP (61 mg, 0.50 mmol). The resulting mixture was stirred at room temperature for 3.5 h. A few drops of methanol were added and the reaction mixture was concentrated under reduced pressure to provide crude product. The crude product was purified by flash chromatography (6:0.8:3 hexane:EtOAc:DCM eluent followed by 6:1.2:3 hexane:EtOAc:DCM eluent followed by 25% EtOAc/hexanes eluent) to provide (R)—N-((5-cyclohexylpyrazin-2-yl)methyl)-N-(5-fluoro-1-trityl-1H-indazol-6-yl)-1-((perfluorophenyl)sulfonyl)azetidine-2-carboxamide (298 mg, 81% yield). HRMS (ESI+) m/z 881.2724 [M+H]$^+$.

Step 9: To a stirred solution of (R)—N-((5-cyclohexylpyrazin-2-yl)methyl)-N-(5-fluoro-1-trityl-1H-indazol-6-yl)-1-((perfluorophenyl)sulfonyl)azetidine-2-carboxamide (289 mg, 0.32 mmol) in DCM (7.5 mL) under a nitrogen atmosphere was added triethylsilane (60 uL, 1.5 equiv) followed by TFA (1.5 mL) and the resulting solution was allowed to stir at room temperature for 20 min. The reaction mixture was concentrated under reduced pressure. Toluene was added and the reaction mixture was concentrated again under reduced pressure. Purification by flash chromatography (30-100% EtOAc/hexane eluent) provided (R)—N-((5-cyclohexylpyrazin-2-yl)methyl)-N-(5-fluoro-1H-indazol-6-yl)-1-((perfluorophenyl) sulfonyl)azetidine-2-carboxamide (192 mg, 94% yield) as a white foam. HRMS (ESI+) m/z 639.1713 [M+H]$^+$.

Example 99

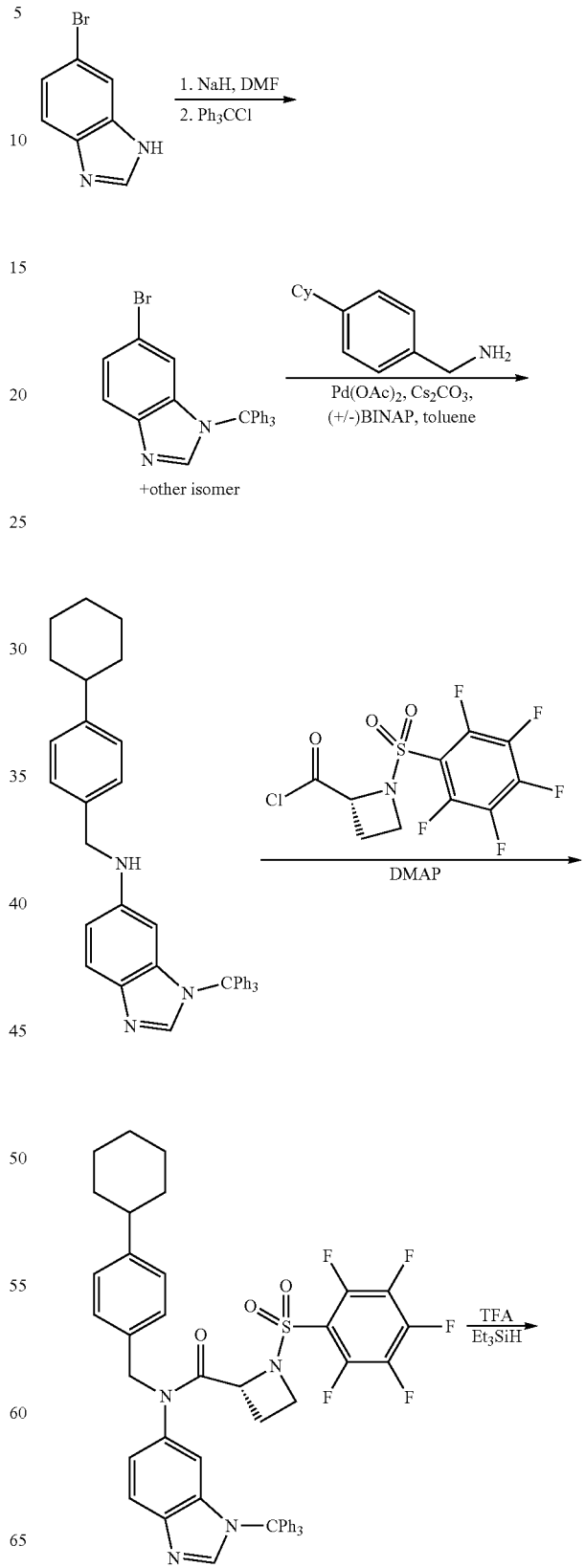

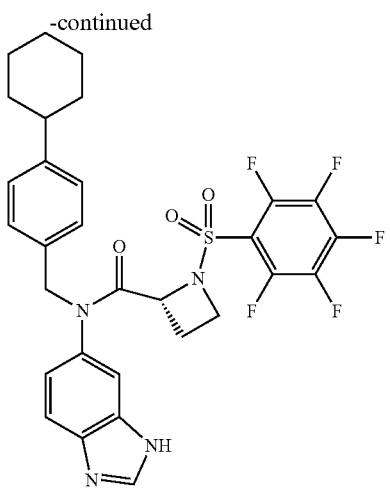

(R)—N-(M-benzo[d]imidazol-6-yl)-N-(4-cyclohexylbenzyl)-1-((perfluorophenyl)sulfonyl)azetidine-2-carboxamide

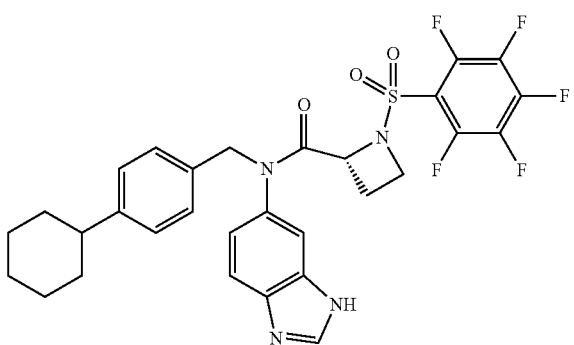 [SMILES: O=C([C@H]1CCN1S(=O)(=O)c1c(F)c(F)c(F)c(F)c1F)N(Cc1ccc(C2CCCCC2)cc1)c1ccc2nc[nH]c2c1]

Step 1: A round-bottomed flask was evacuated and backflushed with argon (3x). The flask was charged with 6-bromo-1H-benzo[d]imidazole (2.00 g, 10.15 mmol, Combi Blocks) followed by 50.0 mL of dry THF which was allowed to stir until the starting material dissolved fully. The flask was placed in an ice bath and solid NaH (487 mg, 12.18 mmol) was added in two portions. The reaction mixture was allowed to stir at room temperature for 30 min before triphenylmethylchloride (3.67 g, 13.2 mmol) was added as a solid in 1 portion. To the flask was then added tetrabutylammonium iodide (187 mg, 0.51 mmol) The resulting reaction mixture was allowed to stir at room temperature for an additional 30 min. under argon. The reaction mixture was quenched with aqueous saturated NH$_4$Cl solution, poured into a mixture of deionized water with a few mL of aqueous saturated NH$_4$Cl solution added, and extracted with EtOAc (3x). The organic extracts were combined, washed with deionized water, washed with brine, dried over anhydrous sodium sulfate, and concentrated in vacuo. The crude product was taken up in DCM/MeOH and purified by flash column chromatography using a step-wise gradient (79:21 hexane/EtOAc, then 19:6 hexane/EtOAc and then 13:7 hexane/EtOAc) affording 6-bromo-1-trityl-1H-benzo[d]imidazole (1.68 g) and 5-bromo-1-trityl-1H-benzo[d]imidazole (1.65 g), with a combined yield of 75%. For 6-Bromo-1-trityl-1H-benzo[d]imidazole: $^1$H NMR (300 MHz, Chloroform-d) δ 7.89 (s, 1H), 7.65 (d, J=8.6, 1H), 7.42-7.32 (m, 8H), 7.31-7.25 (m, 1H), 7.24-7.14 (m, 7H), 6.60 (d, J=1.9 Hz, 1H). For 5-bromo-1-trityl-1H-benzo[d]imidazole: $^1$H NMR (300 MHz, Chloroform-d) δ 7.94 (d, J=1.9 Hz, 1H), 7.89 (s, 1H), 7.41-7.29 (m, 9H), 7.24-7.11 (m, 6), 7.02 (dd, J=8.8, 1.9 Hz, 1H), 6.35 (d, J=8.8 Hz, 1H).

Step 2: To a solution of (4-cyclohexylphenyl)methanamine (238 mg, 1.26 mmol) in toluene (10 mL) under an argon atmosphere was added 6-bromo-1-trityl-1H-benzo[d]imidazole (394 mg, 0.9 mmol), cesium carbonate (410 mg, 1.26 mmol), and (+/−)BINAP (56 mg, 0.09 mmol). The reaction mixture was degassed under vacuum and backflushed with argon and then Pd(OAc)$_2$ (20 mg, 0.09 mmol) was added. The reaction mixture was heated for 18 h at 110° C., allowed to cool to room temperature, poured onto water and extracted with EtOAc (2x). The combined organic extract was washed with brine, dried over anhydrous sodium sulfate and concentrated under reduced pressure. The crude product was purified by chromatography (20-30% EtOAc/hexane gradient) to provide N-(4-cyclohexylbenzyl)-1-trityl-1H-benzo[d]imidazol-6-amine (114 mg, 23% yield). HRMS (ESI+) m/z 548.3528 [M+H]$^+$.

Step 3: To a stirred solution of N-(4-cyclohexylbenzyl)-1-trityl-1H-benzo[d]imidazol-6-amine (110 mg, 0.20 mmol) in dry DCM (4 mL) under nitrogen was added (R)-1-((perfluorophenyl)sulfonyl)-azetidine-2-carbonyl chloride (112 mg, 0.32 mmol) followed by DMAP (29 mg, 0.24 mmol). The resulting mixture was stirred at room temperature overnight. A few drops of methanol were added and the reaction mixture was concentrated under reduced pressure to provide crude product. The crude product was purified by flash chromatography to provide (R)—N-(4-cyclohexylbenzyl)-1-((perfluorophenyl)sulfonyl)-N-(1-trityl-1H-benzo[d]imidazol-6-yl)azetidine-2-carboxamide (48 mg, 28% yield). HRMS (ESI+) m/z 883.2995 [M+Na]$^+$.

Step 4: To a stirred solution of (R)—N-(4-cyclohexylbenzyl)-1-((perfluorophenyl)sulfonyl)-N-(1-trityl-1H-benzo[d]imidazol-6-yl)azetidine-2-carboxamide (45 mg, 0.05 mmol) in DCM (4 mL) under a nitrogen atmosphere was added triethylsilane (2 drops) followed by TFA (10 drops) and the resulting solution was allowed to stir at room temperature for 20 min. The reaction mixture was concentrated under reduced pressure. Toluene was added and the reaction mixture was concentrated again under reduced pressure. Purification by flash chromatography (50-100% EtOAc/hexane eluent) provided (R)—N-(1H-benzo[d]imidazol-6-yl)-N-(4-cyclohexylbenzyl)-1-((perfluorophenyl)sulfonyl)azetidine-2-carboxamide (31 mg, 99% yield) as a white powder. HRMS (ESI+) m/z 619.1833 [M+H]$^+$.

Example 100

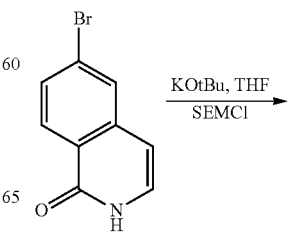

273
-continued
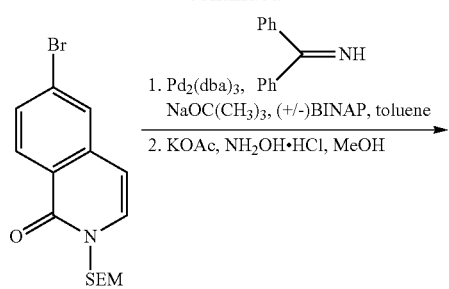
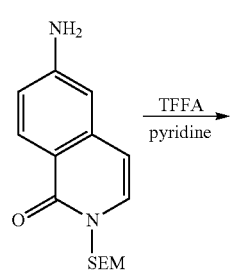
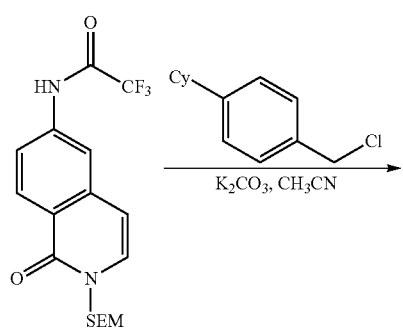
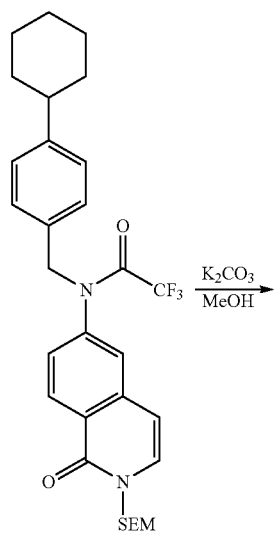
274
-continued
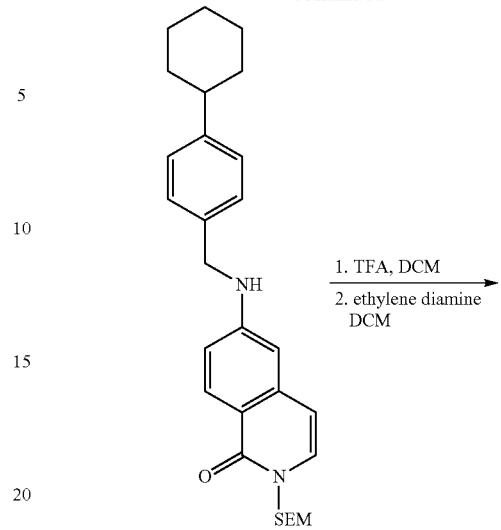
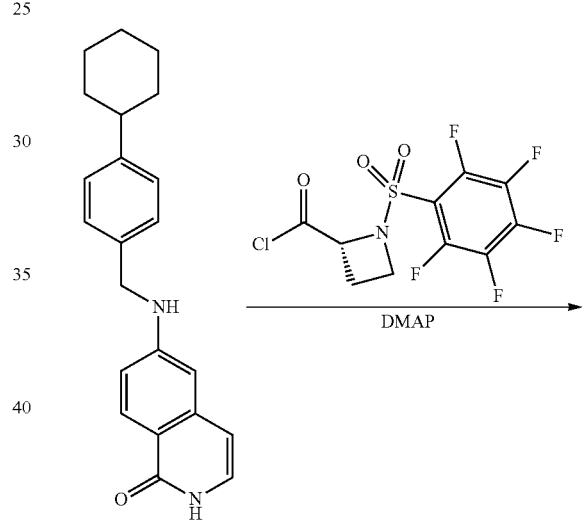
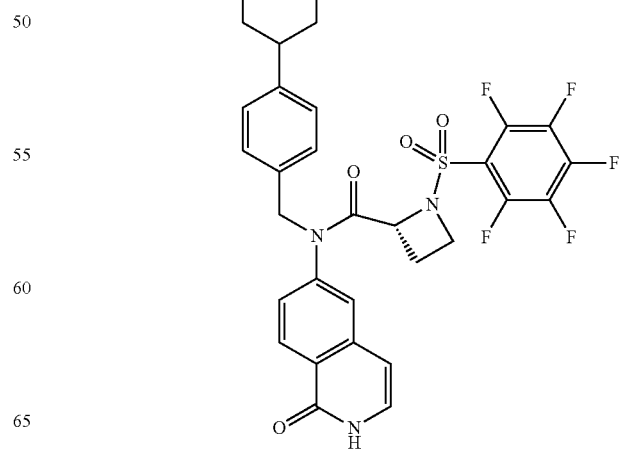

(R)—N-(4-cyclohexylbenzyl)-N-(1-oxo-1,2-dihydroisoquinolin-6-yl)-1-((perfluorophenyl)sulfonyl)azetidine-2-carboxamide

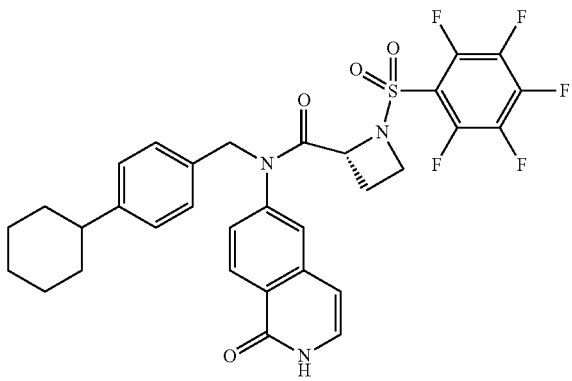 [SMILES: O=C([C@H]1CCN1S(=O)(=O)c1c(F)c(F)c(F)c(F)c1F)N(Cc1ccc(C2CCCCC2)cc1)c1ccc2c(=O)[nH]ccc2c1]

Step 1: To a stirred suspension of 6-bromo-2H-isoquinolin-1-one (2.0 g, 8.92 mmol) in THF (77 mL) under nitrogen at 0° C. was added a solution of potassium t-butoxide (9.81 mL of a 1M solution in THF, 9.81 mmol) by dropwise addition. The mixture was stirred at this temperature for 10 min. To the resulting reaction solution was added (2-(chloromethoxy)ethyl)trimethylsilane (1.58 mL, 8.92 mmol). The reaction was mixture allowed to stir for 30 min before being poured into water and EtOAc and extracted with EtOAc (3×). The combined organic layer was washed with brine, dried over anhydrous sodium sulfate and concentrated under reduced pressure. Purification by chromatography (0:15:85 EtOAc:DCM:hexane eluent followed by 5:15:85 EtOAc:DCM:hexane eluent followed by 10:10:80 EtOAc:DCM:hexane eluent as a stepwise gradient) provided 6-bromo-2-((2-(trimethylsilyl)ethoxy)methyl)isoquinolin-1(2H)-one (2.512 g, 80% yield) as a yellow solid. $^1$H NMR (300 MHz, Chloroform-d) δ 8.30 (d, J=8.6, 1H), 7.70 (d, J=1.9 Hz, 1H), 7.64-7.56 (m, 1H), 7.25 (d, J=7.5 Hz, 1H), 6.45 (d, J=7.5 Hz, 1H), 5.43 (s, 2H), 3.74-3.53 (m, 2H), 1.07-0.85 (m, 2H), 0.00 (s, 9H).

Step 2: A dry 2-neck flask was evacuated and backflushed with argon (3×). Sodium t-butoxide (570 mg, 5.94 mmol), 6-bromo-2-((2-(trimethylsilyl)ethoxy)methyl)isoquinolin-1(2H)-one (1.5 g, 4.24 mmol) and (+/−)BINAP (99 mg, 0.159 mmol) were added to the flask. Toluene (28 mL) was then added and the mixture was degassed with stirring under vacuum and backflushed with argon (3×). Benzophenone imine (0.853 mL, 5.09 mmol) was added followed by Pd$_2$(dba)$_3$ (48.5 mg, 0.053 mmol). The reaction mixture was stirred at 80° C. for 2.5 hours and then allowed to cool to room temperature. The reaction mixture was poured onto water and EtOAc and extracted with EtOAc (3×). The combined organic extract was washed with brine, dried over anhydrous sodium sulfate and concentrated under reduced pressure to provide intermediate, 6-((diphenylmethylene)amino)-2-((2-(trimethylsilyl)ethoxy)methyl)isoquinolin-1(2H)-one (approx. 4.24 mmol), which was used as is for the next reaction. MS (ESI+) m/z 455.3 [M+H]$^+$.

To a solution of intermediate, 6-((diphenylmethylene)amino)-2-((2-(trimethylsilyl)ethoxy)methyl)isoquinolin-1(2H)-one, (approx. 4.24 mmol) in methanol (40 mL) under a nitrogen atmosphere was added potassium acetate (2.0 g, 20.35 mmol) and hydroxylamine hydrochloride (1.06 g, 15.26 mmol). The reaction mixture was stirred at room temperature for 2 h. The reaction was complete by TLC. The reaction mixture was poured onto 0.1% aqueous KOH and DCM and extracted with DCM (3×). The combined organic extracts were washed with water, dried over anhydrous sodium sulfate and concentrated under reduced pressure. Purification by flash chromatography (25-40% EtOAc/hexane eluent) provided 6-amino-2-((2-(trimethylsilyl)ethoxy)methyl)isoquinolin-1(2H)-one (1.206 g, 98% overall yield for the 2 steps) as a yellow solid. $^1$H NMR (300 MHz, Chloroform-d) δ 8.24 (d, J=8.7 Hz, 1H), 7.12 (d, J=7.5 Hz, 1H), 6.81 (dd, J=8.6, 2.3 Hz, 1H), 6.64 (d, J=2.3 Hz, 1H), 6.34 (d, J=7.5 Hz, 1H), 5.40 (s, 2H), 4.13 (br. s, 2H), 3.72-3.41 (m, 1H), 1.01-0.89 (m, 2H), −0.01 (s, 9H).

Step 3: To a stirred solution of 6-amino-2-((2-(trimethylsilyl)ethoxy)methyl)isoquinolin-1(2H)-one (1.2 g, 4.12 mmol) in DCM (20 mL) under nitrogen at 0° C. was added pyridine (0.40 mL, 4.96 mmol) followed by TFFA (0.64 mL, 4.54 mmol). The reaction mixture was allowed to warm to room temperature and was stirred at this temperature for 1 h. The reaction mixture was diluted with DCM, poured onto 10% aqueous KHSO$_4$/Na$_2$SO$_4$ buffer and extracted with DCM (3×). The organic extracts were washed with saturated aqueous sodium bicarbonate, dried over anhydrous sodium sulfate and concentrated in vacuo to provide 2,2,2-trifluoro-N-(1-oxo-2-((2-(trimethylsilyl)ethoxy)methyl)-1,2-dihydroisoquinolin-6-yl)acetamide (1.60 g, 100% yield) as a cream-colored solid. $^1$H NMR (300 MHz, Chloroform-d) δ 8.44 (d, J=8.7 Hz, 1H), 8.33 (s, 1H), 8.07 (d, J=2.1 Hz, 1H), 7.47 (dd, J=8.7, 2.1 Hz, 1H), 7.27 (d, J=7.5 Hz, 1H), 6.55 (d, J=7.5 Hz, 1H), 5.44 (s, 2H), 3.76-3.48 (m, 2H), 1.04-0.85 (m, 2H), −0.00 (s, 9H).

Step 4: To a stirred solution of 2,2,2-trifluoro-N-(1-oxo-2-((2-(trimethylsilyl)ethoxy)methyl)-1,2-dihydroisoquinolin-6-yl)acetamide (510 mg, 1.32 mmol) in acetonitrile (14 mL) under a nitrogen atmosphere was added potassium carbonate (273 mg, 1.98 mmol) followed by 1-(bromomethyl)-4-cyclohexylbenzene (0.33 mL, 1.72 mmol). The resulting reaction mixture was stirred at 60° C. for 4 h. After cooling to room temperature, the reaction mixture was poured onto water and extracted with EtOAc (3×). The combined organic extract was washed with brine, dried over anhydrous sodium sulfate and concentrated under reduced pressure. The resulting residue was purified by flash chromatography (10-15% EtOAc/hexanes eluent) to provide some impure fractions and pure N-(4-cyclohexylbenzyl)-2,2,2-trifluoro-N-(1-oxo-2-((2-(trimethylsilyl)ethoxy)methyl)-1,2-dihydroisoquinolin-6-yl)acetamide (540 mg) as a colorless film. $^1$H NMR (300 MHz, Chloroform-d) δ 8.41 (d, J=8.4 Hz, 1H), 7.25 (d, J=7.5 Hz, 1H), 7.18-6.99 (m, 6H), 6.42 (d, J=7.5 Hz, 1H), 5.43 (s, 2H), 4.94 (s, 2H), 3.75-3.54 (m, 2H), 2.61-2.39 (m, 1H), 1.98-1.67 (m, 6H), 1.51-1.14 (m, 4H), 1.06-0.86 (m, 2H), 0.01 (s, 8H).

Step 5: To N-(4-cyclohexylbenzyl)-2,2,2-trifluoro-N-(1-oxo-2-((2-(trimethylsilyl)ethoxy)methyl)-1,2-dihydroisoquinolin-6-yl)acetamide (540 mg, 0.96 mmol) in THF (10 mL) and MeOH (10 mL) under nitrogen was added potassium carbonate (235 mg, 1.7 mmol). Stirring was continued for 1.5 h before the reaction mixture was poured onto cold saturated aqueous ammonium chloride and water and extracted with EtOAc (3×). The combined organic extracts were washed with water and then with brine, dried over anhydrous sodium sulfate and concentrated in vacuo to provide 6-((4-cyclohexylbenzyl)amino)-2-((2-(trimethylsilyl)ethoxy)methyl)isoquinolin-1(2H)-one (445 mg, 100% yield) as a white solid.

Step 6: To a stirred solution of 6-((4-cyclohexylbenzyl)amino)-2-((2-(trimethylsilyl)ethoxy)methyl)isoquinolin-1

(2H)-one (170 mg, 0.37 mmol) in DCM (6 mL) under a nitrogen atmosphere was added TFA (2.5 mL) and the resulting reaction solution was stirred for 1 h. The starting material was consumed as judged by TLC. The reaction mixture was concentrated in vacuo. The resulting residue was dissolved in DCM (6 mL) and placed under a nitrogen atmosphere. Ethylene diamine (5-6 drops) was added and the resulting mixture was stirred at room temperature for 2 h. Reaction was complete as judged by LCMS. The reaction mixture was poured onto dilute aqueous sodium bicarbonate and extracted with DCM (3×). The combined organic phase was washed with water and then with brine, dried over anhydrous sodium sulfate and concentrated in vacuo to provide 6-((4-cyclohexylbenzyl)amino)isoquinolin-1(2H)-one (approx. 0.37 mmol) which was used as is in the next step. MS (ESI+) m/z 333.2 [M+H]$^+$.

Step 7: To a stirred solution of 6-((4-cyclohexylbenzyl)amino)isoquinolin-1(2H)-one (approx. 0.37 mmol) and (R)-1-((perfluorophenyl)sulfonyl)azetidine-2-carbonyl chloride (184 mg, 0.53 mmol) in dry DCM (5 mL) under nitrogen was added DMAP (55 mg, 0.45 mmol). Stirring was continued at room temperature for 2 h. The reaction was 80% complete as judged by LCMS. An additional 68 mg of (R)-1-((perfluorophenyl)sulfonyl)azetidine-2-carbonyl chloride was added followed by 20 mg of DMAP and the reaction mixture was stirred for an additional 2 h. A few drops of methanol was added and the mixture was allowed to stir for 5 min. The mixture was poured onto water and extracted with DCM (3×). The combined organic layers were dried over sodium sulfate and evaporated under reduced pressure. Purification by flash column chromatography (65:20:15 hexane:EtOAc:DCM eluent) and isolation of the center cut of the product peak afforded 50 mg of slightly impure material. This was purified again by flash chromatography (50% EtOAc/hexane eluent) to provide pure product, (R)—N-(4-cyclohexylbenzyl)-N-(1-oxo-1,2-dihydroisoquinolin-6-yl)-1-((perfluorophenyl)sulfonyl)azetidine-2-carboxamide (25 mg). $^1$H NMR (300 MHz, Chloroform-d) δ 10.72 (s, 1H), 8.39 (d, J=8.5 Hz, 1H), 7.24-6.92 (m, 7H), 6.47 (d, J=7.2 Hz, 1H), 5.08-4.68 (m, 3H), 4.21-3.96 (m, 2H), 2.58-2.39 (m, 1H), 2.37-2.20 (m, 1H), 2.04-1.70 (m, 5H), 1.58-1.14 (m, 6H). HRMS (ESI+) m/z 646.1826 [M+H]$^+$.

Example 101

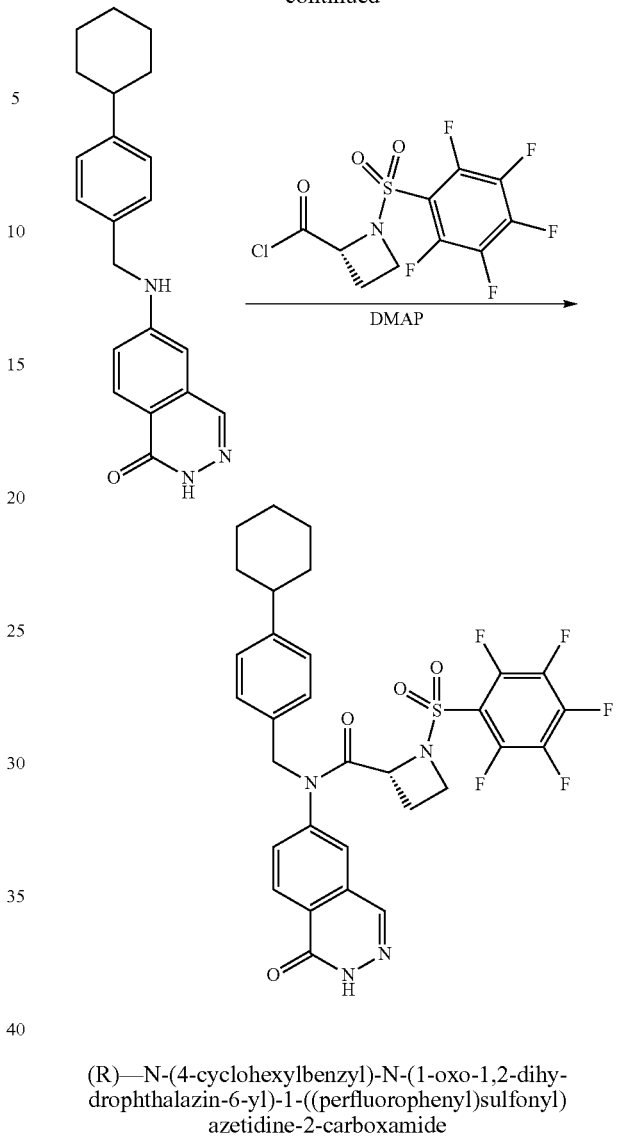

(R)—N-(4-cyclohexylbenzyl)-N-(1-oxo-1,2-dihydrophthalazin-6-yl)-1-((perfluorophenyl)sulfonyl)azetidine-2-carboxamide

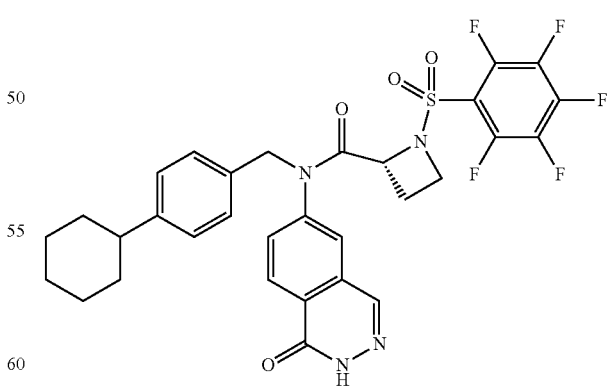

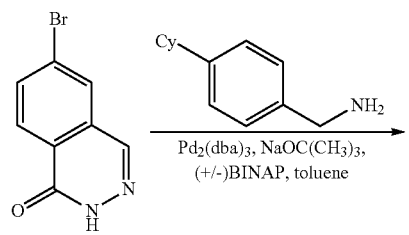

Step 1: A dry 2-neck flask was evacuated and backflushed with argon (3×). Sodium t-butoxide (360 mg, 3.75 mmol), 6-bromophthalazin-1(2H)-one (338 mg, 1.5 mmol), (4-cyclohexylphenyl)methanamine (340 mg, 1.8 mmol), (+/−) BINAP (280 mg, 0.45 mmol) and Pd$_2$(dba)$_3$ (137 mg, 0.15 mmol) were added to the flask. Toluene (30 mL) was then added and the mixture was degassed with stirring under vacuum and backflushed with argon (3×). The reaction mixture was stirred at reflux for 3 hours and then allowed to cool to room temperature. The reaction mixture was poured onto water and EtOAc and extracted with EtOAc (3×) and then extracted with DCM (2×). The combined organic extract was washed with brine, dried over anhydrous sodium sulfate and concentrated under reduced pressure. The crude residue was slurred in DCM and filtered and the solid cake washed several times with DCM. The combined filtrate and washes were concentrated in vacuo to provide crude product, 6-((4-cyclohexylbenzyl)amino)phthalazin-1(2H)-one, as an off-white powder (118 mg).

Step 2: To the crude product above (approx. 0.35 mmole) and (R)-1-((perfluorophenyl)sulfonyl)azetidine-2-carbonyl chloride (175 mg, 0.50 mmol) in dry DCM (10 mL) under nitrogen was added DMAP (52 mg, 0.42 mmol). The reaction was stirred at room temperature overnight. The reaction had only gone to 10% conversion as determined by LCMS. Another portion of each (R)-1-((perfluorophenyl)sulfonyl)azetidine-2-carbonyl chloride (175 mg, 0.50 mmol) and DMAP (52 mg, 0.42 mmol) were added and the reaction was warmed at 50° C. for 4 days. The reaction had only gone to 30% conversion as determined by LCMS. The liquid was decanted from the resulting suspension and the solid washed with DCM (3×) and similarly separated by decanting. To the combined turbid liquid and washes was added 1 mL of methanol and the resulting mixture was concentrated and added to a preparative TLC plate. The plate was eluted with 5% methanol in DCM. The band that contained product was removed and washed from the silica with 10% methanol in DCM to provide a mixture of starting aniline and product. This mixture was resubjected to above reaction conditions with no progress. Purification by chromatography (3% methanol in DCM) followed by purification by preparatory TLC provided pure product, (R)—N-(4-cyclohexylbenzyl)-N-(1-oxo-1,2-dihydrophthalazin-6-yl)-1-((perfluorophenyl)sulfonyl)azetidine-2-carboxamide (35 mg, 0.2% yield) as a yellow foam. ¹H NMR (300 MHz, Chloroform-d) δ 10.68 (s, 1H), 8.42 (d, J=8.3 Hz, 1H), 8.08 (s, 1H), 7.49-7.30 (m, 2H), 7.13 (d, J=7.8 Hz, 2H), 7.01 (d, J=7.8 Hz, 2H), 5.07-4.67 (m, 3H), 4.23-3.98 (m, 2H), 2.58-2.42 (m, 1H), 2.42-2.22 (m, 1H), 2.04-1.66 (m, 6H), 1.53-1.17 (m, 5H). HRMS (ESI+) m/z 647.1745 [M+H]⁺.

Example 102

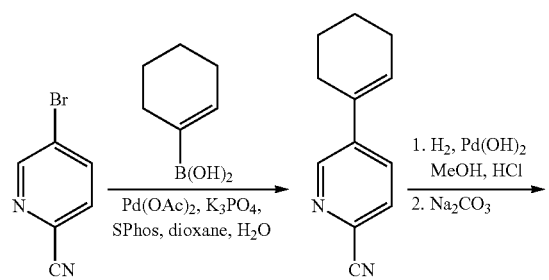

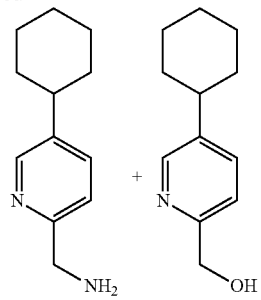

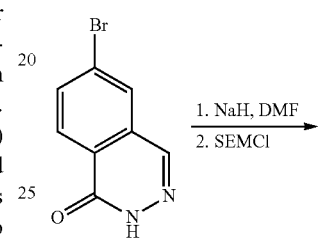

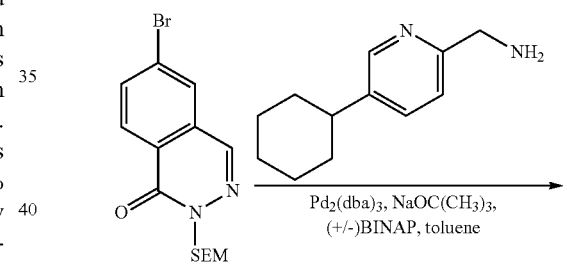

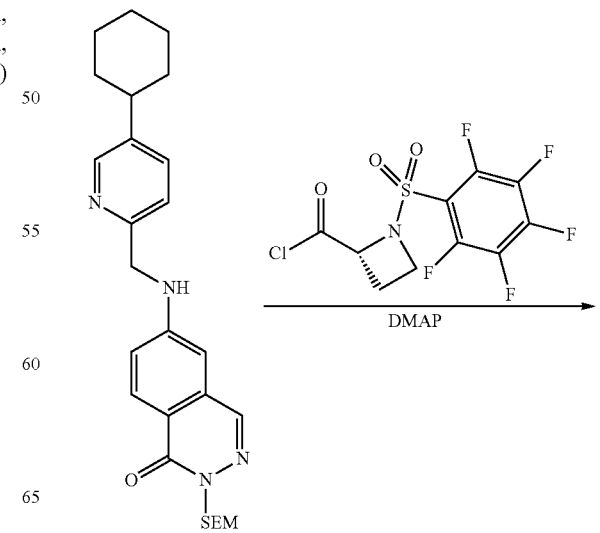

281
-continued

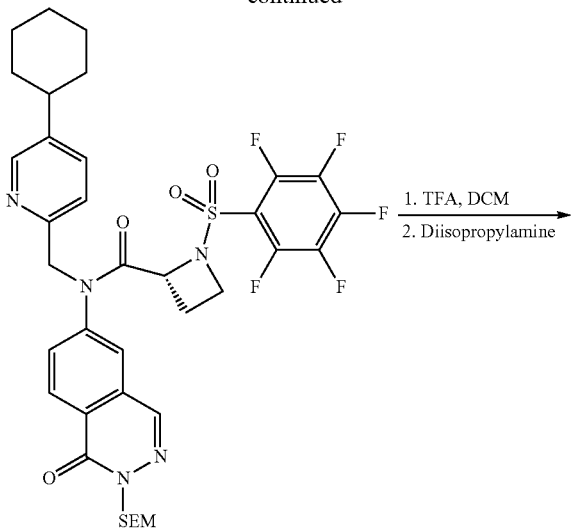

1. TFA, DCM
2. Diisopropylamine 282
(R)—N-((5-cyclohexylpyridin-2-yl)methyl)-N-(1-oxo-1,2-dihydrophthalazin-6-yl)-1-((perfluorophenyl)sulfonyl)azetidine-2-carboxamide Step 1: In a dry flask under argon was added 5-bromo-2-cyanopyridine (1.83 g, 10 mmol), SPhos (410 mg, 1.0 mmol), cyclohexene-1-yl boronic acid (1.76 g, 14 mmol) and potassium phosphate tribasic (6.37 g, 30 mmol). The flask flushed with argon. Dioxane (30 mL) and water (4 mL) were added and the mixture was degassed with vacuum and backflushed with argon. Pd(OAc)$_2$ (112 mg, 0.5 mmol) was added and the reaction was degassed again. The reaction mixture was stirred at 115° C. for 18 h. The crude reaction mixture was cooled, poured onto water and extracted with EtOAc (3×). The organic layers were washed with water and then brine, dried over anhydrous sodium sulfate and concentrated under reduced pressure. Purification by chromatography (0-20% EtOAc in hexanes) followed by re-purification by chromatography (5-8% EtOAc/hexanes) provided 5-(cyclohex-1-en-1-yl)picolinonitrile (1.22 g, 65% yield). $^1$H NMR (300 MHz, Chloroform-d) δ 8.75 (d, J=2.2 Hz, 1H), 7.76 (dd, J=8.2, 2.2 Hz, 1H), 7.64 (d, J=8.2 Hz, 1H), 6.43-6.30 (m, 1H), 2.48-2.35 (m, 2H), 2.35-2.23 (m, 2H), 1.92-1.78 (m, 2H), 1.77-1.66 (m, 2H).

Step 2: To a mixture of 5-(cyclohex-1-en-1-yl)picolinonitrile (196 mg, 1.06 mmol) in methanol (9 mL) was added concentrated HCl (0.7 mL) and palladium hydroxide (20% on C, 75 mg). The reaction was stirred under a balloon of hydrogen overnight. The mixture was filtered through Celite® and the filtercake was washed several times with methanol. The combined filtrate and washes were concentrated under reduced pressure and taken up in DCM and 10% aqueous sodium carbonate. The mixture was extracted with DCM (3×). The organic extracts were combined and dried over anhydrous sodium sulfate and concentrated under reduced pressure.

The reaction was repeated using 658 mg of 5-(cyclohex-1-en-1-yl)picolinonitrile and the crude products were combined. Purification by flash chromatography [5% (5% NH$_4$OH in MeOH) in DCM] to [10% (5% NH$_4$OH in MeOH) in DCM] gradient provided (5-cyclohexylpyridin-2-yl)methanamine (424 mg, 48% yield) and (5-cyclohexylpyridin-2-yl)methanol (270 mg, 30% yield). For (5-cyclohexylpyridin-2-yl)methanamine: $^1$H NMR (300 MHz, Chloroform-d) δ 8.41 (d, J=2.3 Hz, 1H), 7.49 (dd, J=8.0, 2.3 Hz, 1H), 7.20 (d, J=8.0 Hz, 1H), 3.94 (s, 2H), 2.65-2.40 (m, 1H), 2.04-1.66 (m, 7H), 1.54-1.10 (m, 5H).

For (5-cyclohexylpyridin-2-yl)methanol: $^1$H NMR (300 MHz, Chloroform-d) δ 8.43 (d, J=2.2 Hz, 1H), 7.54 (dd, J=8.0, 2.2 Hz, 1H), 7.18 (d, J=8.0 Hz, 1H), 4.75 (s, 2H), 3.77 (br. s, 1H), 2.67-2.43 (m, 1H), 2.04-1.73 (m, 6H), 1.57-1.27 (m, 4H).

Step 3: To a suspension of 6-bromophthalazine-1-(2H)-one (563 mg, 2.5 mmol) in DMF (25 mL) under an argon atmosphere was added sodium hydride (140 mg of 60% oil dispersion, 3.5 mmol) and the resulting mixture was allowed to stir at room temperature for 15 min. before addition of (2-(chloromethoxy)ethyl)trimethylsilane (0.53 mL, 3 mmol). The reaction mixture was stirred at room temperature overnight, then poured onto water and ether and extracted with ether (3×). The combined organic layer was washed with water, then brine, dried over anhydrous sodium sulfate and concentrated under reduced pressure. The resulting residue was slurried in DCM and filtered. The solid was washed with DCM. The combined filtrate and wash was purified by chromatography to provide 6-bromo-2-((2-(trimethylsilyl)ethoxy)methyl)phthalazin-1(2H)-one (625 mg, 70% yield) as a white solid. $^1$H NMR (300 MHz, Chloroform-d) δ 8.37-8.29 (m, 1H), 8.12 (s, 1H), 7.93-7.85 (m, 2H), 5.57 (s, 2H), 3.84-3.62 (m, 2H), 1.10-0.89 (m, 1H), 0.01 (s, 9H).

Step 4: A dry 2-neck flask was evacuated and backflushed with argon (3×). A solution of (5-cyclohexylpyridin-2-yl)methanamine (342 mg, 1.69 mmol) in toluene (12 mL) was added to the flask. To the flask was then added 6-bromo-2-((2-(trimethylsilyl)ethoxy)methyl)phthalazin-1(2H)-one (462 mg, 1.3 mmol), sodium t-butoxide (175 mg, 1.82 mmol) and (+/−)BINAP (30 mg, 0.049 mmol) and the mixture was degassed with stirring under vacuum and backflushed with argon (3×). Pd$_2$(dba)$_3$ (14.9 mg, 0.016 mmol) were added to the flask. The reaction mixture was stirred at 85-90° C. overnight and then allowed to cool to room temperature. The reaction mixture was poured onto water and EtOAc and extracted with EtOAc (3×). The combined organic extract was washed with brine, dried over anhydrous sodium sulfate and concentrated under reduced pressure. Purification by chromatography (20-30% acetone in hexanes gradient) provided pure 6-(((5-cyclohexylpyridin-2-yl)methyl)amino)-2-((2-(trimethylsilyl)ethoxy) methyl)phthalazin-1(2H)-one (392 mg, 65% yield). $^1$H NMR (300 MHz, Chloroform-d) δ 8.47 (d, J=2.2 Hz, 1H), 8.23 (d, J=8.8 Hz, 1H), 8.01 (s, 1H), 7.54 (dd, J=8.0, 2.2 Hz, 1H), 7.25 (d, J=8.0 Hz, 1H), 7.09 (dd, J=8.8, 2.2 Hz, 1H), 6.68 (d, J=2.3 Hz, 1H), 5.74 (t, J=5.0 Hz, 1H), 5.54 (s, 2H), 4.53 (d, J=4.9 Hz, 2H), 3.74 (dd, J=8.7, 8.0 Hz, 2H), 2.67-2.48 (m, 1H), 2.03-1.73 (m, 5H), 1.58-1.19 (m, 5H), 1.00 (dd, J=8.7, 8.0 Hz, 2H), 0.00 (s, 9H).

Step 5: To a stirred solution of 6-(((5-cyclohexylpyridin-2-yl)methyl)amino)-2-((2-(trimethylsilyl)ethoxy)methyl)phthalazin-1(2H)-one (383 mg, 0.825 mmol) in dry DCM (10 mL) under nitrogen was added (R)-1-((perfluorophenyl)sulfonyl)-azetidine-2-carbonyl chloride (404 mg, 1.16 mmol) followed by DMAP (121 mg, 0.99 mmol). The resulting mixture was stirred at room temperature for 5 h. A few drops of methanol were added and the reaction mixture was poured onto water and extracted with DCM (3×). The combined organic extracts were dried over anhydrous sodium sulfate and concentrated under reduced pressure. The crude product was purified by flash chromatography (5:2:3 hexane:DCM:EtOAc eluent and then 1:1 EtOAc: hexane eluent) to provide (R)—N-((5-cyclohexylpyridin-2-yl)methyl)-N-(1-oxo-2-((2-(trimethylsilyl)ethoxy)methyl)-1,2-dihydrophthalazin-6-yl)-1-((perfluorophenyl)sulfonyl) azetidine-2-carboxamide (476 mg, 74% yield). HRMS (ESI+) m/z 778.2611 [M+H]$^+$.

Step 6: To a stirred solution of (R)—N-((5-cyclohexylpyridin-2-yl)methyl)-N-(1-oxo-2-((2-(trimethylsilyl) ethoxy)methyl)-1,2-dihydrophthalazin-6-yl)-1-((perfluorophenyl)sulfonyl)azetidine-2-carboxamide (468 mg, 0.6 mmol) in DCM (6 mL) under a nitrogen atmosphere was added TFA (2 mL). The reaction mixture was stirred at room temperature for 30 minutes until complete consumption of starting material as judged by LCMS. The mixture was concentrated in vacuo. Toluene was added and the mixture was concentrated in vacuo. The crude residue was dissolved in DCM, poured onto saturated aqueous sodium bicarbonate and extracted into DCM (3×). The combined organic extract was dried over anhydrous sodium sulfate and concentrated under reduced pressure to provide intermediate, (R)—N-((5-cyclohexylpyridin-2-yl)methyl)-N-(2-(hydroxymethyl)-1-oxo-1,2-dihydrophthalazin-6-yl)-1-((perfluorophenyl) sulfonyl)azetidine-2-carboxamide (400 mg). MS (ESI+) m/z 678.3 [M+H]$^+$.

Step 7: To intermediate, (R)—N-((5-cyclohexylpyridin-2-yl)methyl)-N-(2-(hydroxymethyl)-1-oxo-1,2-dihydrophthalazin-6-yl)-1-((perfluorophenyl)sulfonyl)azetidine-2-carboxamide (240 mg, approx. 0.35 mmol) in DCM (10 mL) was added diisopropylamine (1 mL) and the resulting mixture was stirred at room temperature for 3 days and then concentrated in vacuo. Purification by chromatography followed by taking the center cut (110 mg) provided product and intermediate in an 85:15 ratio. Trituration with 50% EtOAc in hexanes provided 95% pure (R)—N-((5-cyclohexylpyridin-2-yl)methyl)-N-(1-oxo-1,2-dihydrophthalazin-6-yl)-1-((perfluorophenyl)sulfonyl)azetidine-2-carboxamide (60 mg) as a white solid. HRMS (ESI+) m/z 648.1850 [M+H]$^+$.

Example 103

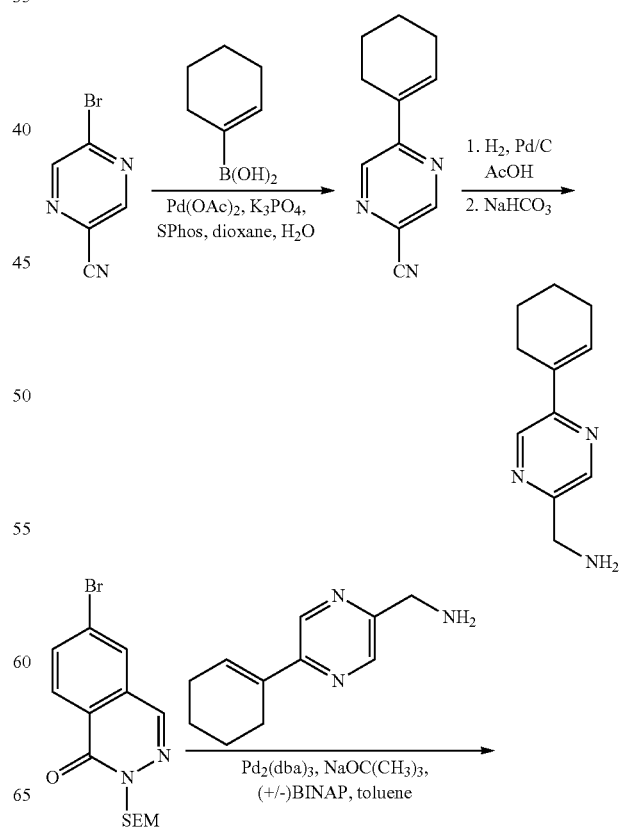

285
-continued

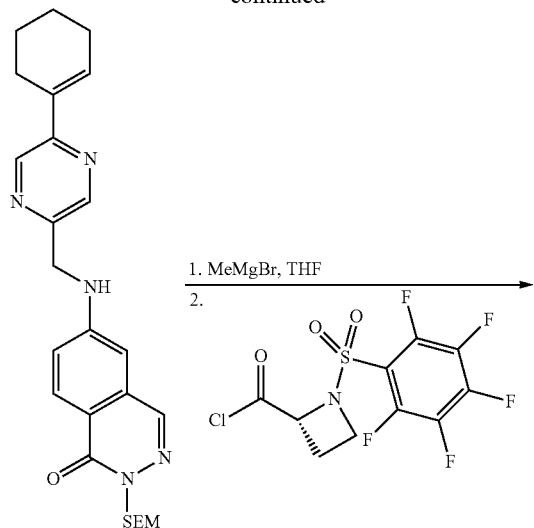

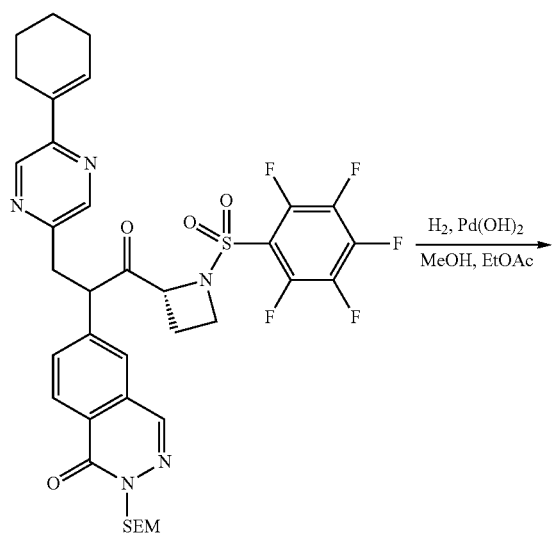

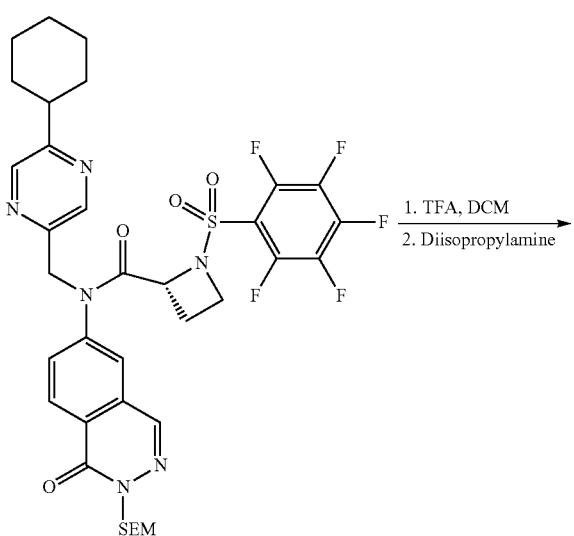

286
-continued

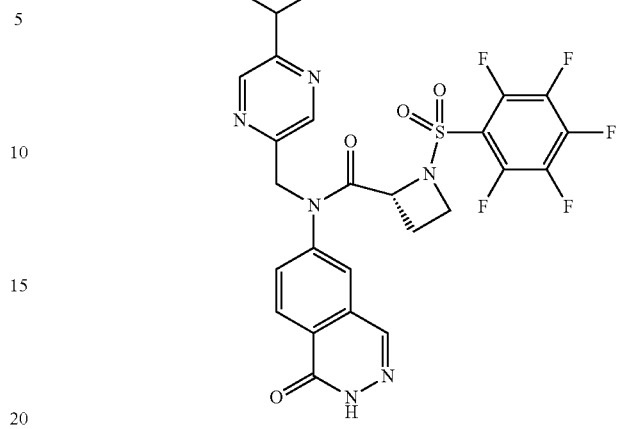

(R)—N-((5-cyclohexylpyrazin-2-yl)methyl)-N-(1-oxo-1,2-dihydrophthalazin-6-yl)-1-((perfluorophenyl)sulfonyl)azetidine-2-carboxamide

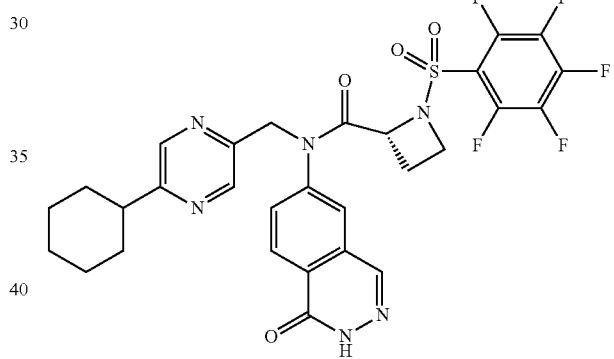

Step 1: In a dry flask under argon was added 2-bromo-5-cyanopyrazine (1.84 g, 10 mmol), SPhos (410 mg, 1.0 mmol), cyclohexene-1-yl boronic acid (1.76 g, 14 mmol) and potassium phosphate tribasic (6.37 g, 30 mmol). The flask flushed with argon. Dioxane (30 mL) and water (4 mL) were added and the mixture was degassed with vacuum and backflushed with argon. Pd(OAc)$_2$ (112 mg, 0.5 mmol) was added and the reaction was degassed again. The reaction mixture was stirred at 95° C. for overnight. The crude reaction mixture was cooled, poured onto water and extracted with EtOAc (3×). The organic layers were washed with brine, dried over anhydrous sodium sulfate and concentrated under reduced pressure. Purification by chromatography (80:15:5 hexane:DCM:EtOAc eluent) provided 5-(cyclohex-1-en-1-yl)pyrazine-2-carbonitrile (1.3 g, 68%). $^1$H NMR (300 MHz, Chloroform-d) δ 8.87-8.70 (m, 2H), 7.10-6.98 (m, 1H), 2.61-2.49 (m, 2H), 2.43-2.31 (m, 2H), 1.93-1.79 (m, 2H), 1.78-1.68 (m, 2H).

Step 2: To a solution of 5-(cyclohex-1-en-1-yl)pyrazine-2-carbonitrile (370 mg, 2 mmol) in glacial acetic acid (15 mL) under nitrogen was added 10% palladium on carbon (70 mg) and the reaction was stirred under a hydrogen balloon for 2 h until no starting material remained by tlc. The reaction mixture was filtered through Celite® and the filtercake was washed several times with ethanol and concentrated in vacuo. The residue was slurried in DCM and shaken with saturated aqueous sodium bicarbonate, then extracted with DCM (2×). The combined organic layer was dried over anhydrous sodium sulfate and concentrated in vacuo to provide (5-(cyclohex-1-en-1-yl)pyrazin-2-yl)methanamine (290 mg, 77% yield) which was used as is. $^1$H NMR (300 MHz, Chloroform-d) δ 8.63 (d, J=1.5 Hz, 1H), 8.47 (d, J=1.5 Hz, 1H), 6.78-6.70 (m, 1H), 4.00 (s, 2H), 2.59-2.47 (m, 2H), 2.35-2.23 (m, 2H), 1.89-1.62 (m, 6H).

Step 3: A dry 2-neck flask was evacuated and backflushed with argon (3×). To the flask was then added (5-(cyclohex-1-en-1-yl)pyrazin-2-yl)methanamine (252 mg, 1.33 mmol), 6-bromo-2-((2-(trimethylsilyl)ethoxy)methyl)phthalazin-1(2H)-one (337 mg, 0.95 mmol), sodium t-butoxide (128 mg, 1.33 mmol), (+/−)BINAP (22 mg, 0.0356 mmol) and toluene (11 mL). The mixture was degassed with stirring under vacuum and backflushed with argon (3×). Pd$_2$(dba)$_3$ (10.9 mg, 0.0118 mmol) was added to the flask. The reaction mixture was stirred at 85-90° C. for 2 h and then allowed to cool to room temperature. The reaction mixture was poured onto water and EtOAc and extracted with EtOAc (3×). The combined organic extract was washed with brine, dried over anhydrous sodium sulfate and concentrated under reduced pressure. Purification by chromatography (40% EtOAc/hexanes eluent) provided 6-(((5-(cyclohex-1-en-1-yl)pyrazin-2-yl)methyl)amino)-2-((2-(trimethylsilyl)ethoxy)methyl)phthalazin-1(2H)-one (398 mg, 90% yield). $^1$H NMR (300 MHz, Chloroform-d) δ 8.68 (s, 1H), 8.56 (s, 1H), 8.25 (d, J=8.8 Hz, 1H), 8.01 (s, 1H), 7.10 (dd, J=8.8, 2.4 Hz, 1H), 6.87-6.77 (m, 1H), 6.70 (d, J=2.4 Hz, 1H), 5.54 (s, 2H), 4.65-4.54 (m, 2H), 3.83-3.66 (m, 2H), 2.65-2.45 (m, 2H), 2.41-2.25 (m, 2H), 1.90-1.78 (m, 2H), 1.78-1.67 (m, 2H), 1.15-0.90 (m, 2H), 0.00 (s, 9H).

Step 4: To a stirred solution of 6-(((5-(cyclohex-1-en-1-yl)pyrazin-2-yl)methyl)amino)-2-((2-(trimethylsilyl)ethoxy)methyl)phthalazin-1(2H)-one (125 mg, 0.26 mmol) in dry THF (6 mL) under nitrogen at 0° C. was added methylmagnesium bromide (0.46 mL of 1.4 M in THF, 0.65 mmol) and the resulting solution was stirred at 0° C. for 5 min and room temperature for 10 min before addition of solid (R)-1-((perfluorophenyl)sulfonyl)-azetidine-2-carbonyl chloride (136 mg, 0.39 mmol). The resulting mixture was allowed to warm to room temperature and stirred at room temperature overnight. The reaction was quenched by addition of a saturated aqueous ammonium chloride (1 mL) and then the crude reaction mixture was poured onto water and extracted with EtOAc (3×). The combined organic extract was washed with brine, dried over sodium sulfate and concentrated under reduced pressure. The crude residue was purified by flash chromatography (30-50% EtOAc in hexanes eluent) to provide (R)—N-((5-(cyclohex-1-en-1-yl)pyrazin-2-yl)methyl)-N-(1-oxo-2-((2-(trimethylsilyl)ethoxy)methyl)-1,2-dihydrophthalazin-6-yl)-1-((perfluorophenyl)sulfonyl)azetidine-2-carboxamide (125 mg, 62% yield). MS (ESI+) m/z 777.3 [M+H]$^+$.

Step 5: To a stirred solution of (R)—N-((5-(cyclohex-1-en-1-yl)pyrazin-2-yl)methyl)-N-(1-oxo-2-((2-(trimethylsilyl)ethoxy)methyl)-1,2-dihydrophthalazin-6-yl)-1-((perfluorophenyl)sulfonyl)azetidine-2-carboxamide (125 mg, 0.16 mmol) in methanol (3 mL) and EtOAc (3 mL) was added 20% Pd(OH)$_2$/C (25 mg) and the resulting suspension was stirred at room temperature under a hydrogen atmosphere for 4 h. The reaction mixture was filtered through Celite® and washed with EtOAc. The combined filtrate and washes were concentrated in vacuo to provide (R)—N-((5-cyclohexylpyrazin-2-yl)methyl)-N-(1-oxo-2-((2-(trimethylsilyl)ethoxy)methyl)-1,2-dihydrophthalazin-6-yl)-1-((perfluorophenyl)sulfonyl)azetidine-2-carboxamide (125 mg) which was used as is in the next reaction. MS (ESI+) m/z 779.3 [M+H]$^+$.

Step 6: To a stirred solution of (R)—N-((5-cyclohexylpyrazin-2-yl)methyl)-N-(1-oxo-2-((2-(trimethylsilyl)ethoxy)methyl)-1,2-dihydrophthalazin-6-yl)-1-((perfluorophenyl)sulfonyl)azetidine-2-carboxamide (125 mg, 0.16 mmol) in DCM (3 mL) under a nitrogen atmosphere was added TFA (1.5 mL). The reaction mixture was stirred at room temperature for 2 h until complete consumption of starting material as judged by LCMS. The mixture was concentrated in vacuo to provide intermediate, (R)—N-((5-cyclohexylpyrazin-2-yl)methyl)-N-(2-(hydroxymethyl)-1-oxo-1,2-dihydrophthalazin-6-yl)-1-((perfluorophenyl)sulfonyl)azetidine-2-carboxamide. MS (ESI+) m/z 679.2 [M+H]$^+$.

Step 7: To intermediate, (R)—N-((5-cyclohexylpyrazin-2-yl)methyl)-N-(2-(hydroxymethyl)-1-oxo-1,2-dihydrophthalazin-6-yl)-1-((perfluorophenyl)sulfonyl)azetidine-2-carboxamide (approx. 0.16 mmol) in THF (2 mL) was added diisopropylamine (1 mL) and the resulting mixture was stirred at room temperature for 18 h and then concentrated in vacuo. Purification by chromatography (50-70% EtOAc in hexanes eluent) twice and taking front cut each time provided 95% pure (R)—N-((5-cyclohexylpyrazin-2-yl)methyl)-N-(1-oxo-1,2-dihydrophthalazin-6-yl)-1-((perfluorophenyl)sulfonyl)azetidine-2-carboxamide (12 mg). HRMS (ESI+) m/z 649.1687 [M+H]$^+$.

Example 104

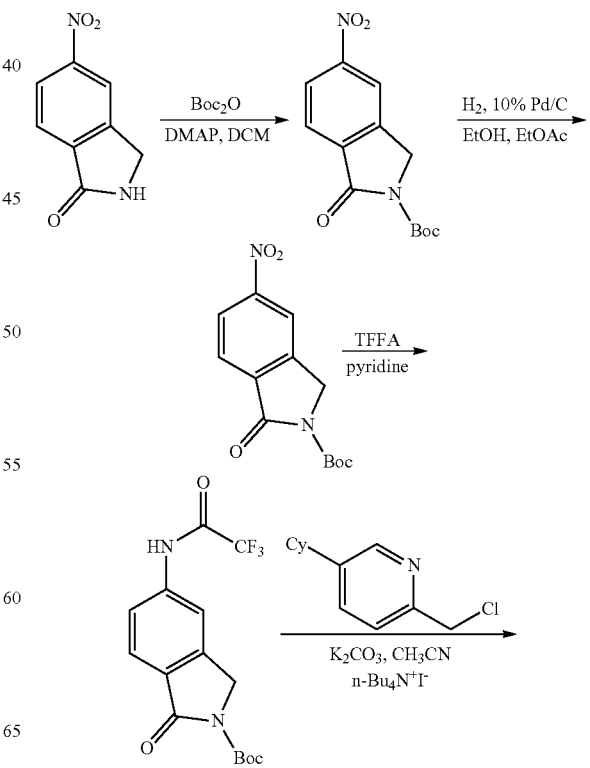

289
-continued

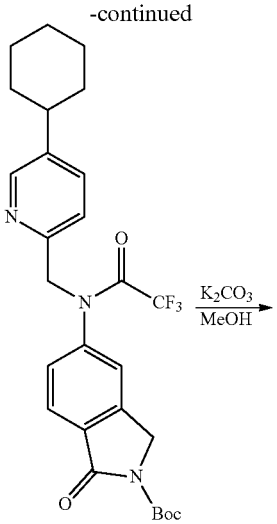

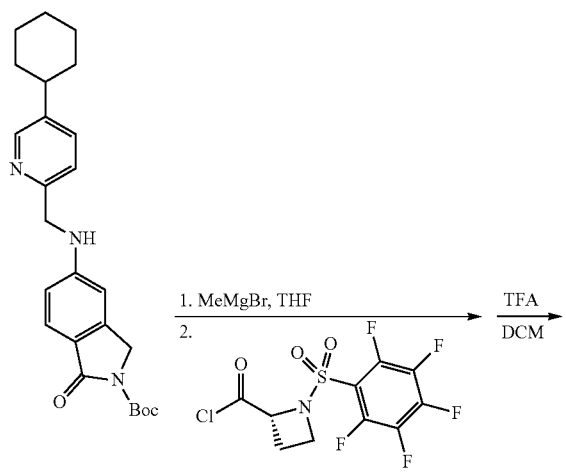

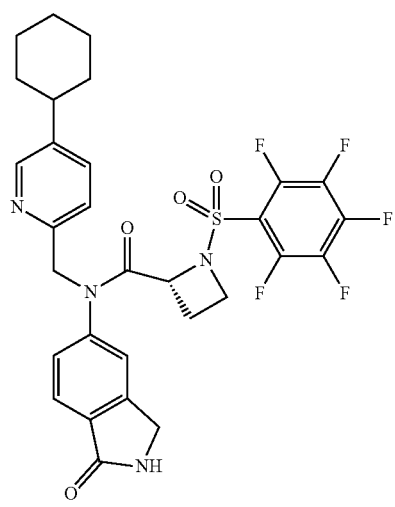

290
(R)—N-((5-cyclohexylpyridin-2-yl)methyl)-N-(1-oxoisoindolin-5-yl)-1-((perfluorophenyl)sulfonyl)azetidine-2-carboxamide

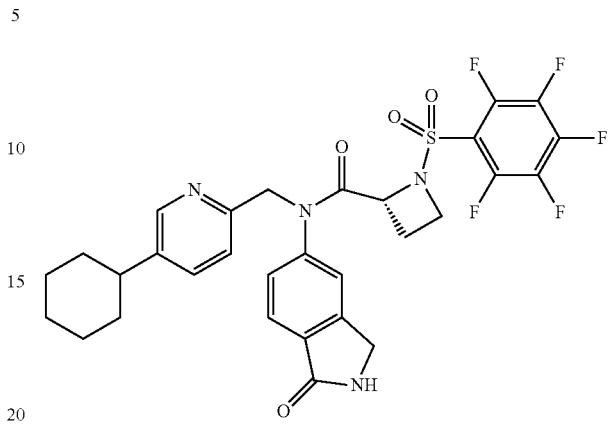

Step 1: To a solution of 5-nitroisoindolin-1-one (600 mg, 3.37 mmol) in dioxane (30 mL) under a nitrogen atmosphere was added DMAP (616 mg, 5.05 mmol) followed by di-tert-butyl dicarbonate (1.16 mL, 5.05 mmol). The resulting reaction mixture was stirred at room temperature overnight, then poured onto water and extracted with EtOAc (3×). The combined organic layer was washed with brine, dried over anhydrous sodium sulfate and concentrated under reduced pressure. The crude residue was purified by chromatography (20% EtOAc in hexanes eluent followed by 20:20:80 DCM:EtOAc:hexane eluent) to provide tert-butyl 5-nitro-1-oxoisoindoline-2-carboxylate (576 mg, 61% yield) as a white solid. $^1$H NMR (300 MHz, Chloroform-d) δ 8.43-8.35 (m, 2H), 8.10 (d, J=8.9 Hz, 1H), 4.90 (s, 2H), 1.64 (s, 9H).

Step 2: To a stirred solution of tert-butyl 5-nitro-1-oxoisoindoline-2-carboxylate (570 mg, 2.05 mmol) in ethanol (30 mL) and EtOAc (30 mL) under nitrogen was added 10% palladium on carbon (111 mg) and the reaction mixture was placed under a hydrogen atmosphere under a balloon of hydrogen and stirred at room temperature for 2 h. The reaction mixture was filtered through Celite® and washed with EtOAc and methanol (3×). The combined filtrate and washes were concentrated in vacuo to provide tert-butyl 5-amino-1-oxoisoindoline-2-carboxylate (538 mg, 100% yield) as an amber foam. $^1$H NMR (300 MHz, Chloroform-d) δ 7.68 (d, J=8.3 Hz, 1H), 6.71 (dd, J=8.3, 2.0 Hz, 1H), 6.63 (d, J=2.0 Hz, 1H), 4.64 (s, 2H), 4.22 (br. s, 2H), 1.60 (s, 9H).

Step 3: To a stirred solution of tert-butyl 5-amino-1-oxoisoindoline-2-carboxylate (530 mg, 2.05 mmol) in DCM (20 mL) under nitrogen at 0° C. was added pyridine (0.20 mL, 2.46 mmol) followed by TFFA (0.32 mL, 2.25 mmol). The reaction mixture was allowed to warm to room temperature and was stirred at this temperature for 1.5 h. The reaction mixture was diluted with DCM, poured onto 10% aqueous KHSO$_4$/Na$_2$SO$_4$ buffer and extracted with DCM (3×). The organic extracts were washed with saturated aqueous sodium bicarbonate, dried over anhydrous sodium sulfate and concentrated in vacuo to provide tert-butyl 1-oxo-5-(2,2,2-trifluoroacetamido)isoindoline-2-carboxylate (664 mg, 100% yield) as an amber solid. $^1$H NMR (300 MHz, Chloroform-d) δ 8.58 (br. s, 1H), 8.11 (d, J=1.8 Hz, 1H), 7.92 (d, J=8.3 Hz, 1H), 7.53 (dd, J=8.3, 1.8 Hz, 1H), 4.80 (s, 2H), 1.62 (s, 9H).

Step 4: To a stirred solution of tert-butyl 1-oxo-5-(2,2,2-trifluoroacetamido)isoindoline-2-carboxylate (179 mg, 0.52 mmol) in acetonitrile (6 mL) under a nitrogen atmosphere was added potassium carbonate (107 mg, 0.78 mmol) followed by 2-(chloromethyl)-5-cyclohexylpyridine (freshly prepared as in example 97, step A3, 0.78 mmol) and then catalytic tetra-n-butylammonium iodide (12 mg). The resulting reaction mixture was stirred at 60° C. for 20 h. After cooling to room temperature, the reaction mixture was poured onto water and extracted with EtOAc (3×). The combined organic extract was washed with brine, dried over anhydrous sodium sulfate and concentrated under reduced pressure. The resulting residue was purified by flash chromatography (15% acetone in hexanes eluent) to provide tert-butyl 5-(N-((5-cyclohexylpyridin-2-yl)methyl)-2,2,2-trifluoroacetamido)-1-oxoisoindoline-2-carboxylate (61 mg, 23% yield). MS (ESI+) m/z 518.4 [M+H]$^+$.

Step 5: To tert-butyl 5-(N-((5-cyclohexylpyridin-2-yl)methyl)-2,2,2-trifluoroacetamido)-1-oxoisoindoline-2-carboxylate (61 mg, 0.118 mmol) in THF (1.0 mL) and MeOH (1.0 mL) under nitrogen was added potassium carbonate (29 mg, 0.21 mmol). Stirring was continued for 0.5 h before the reaction mixture was poured onto cold saturated aqueous ammonium chloride and water and extracted with EtOAc (3×). The combined organic extracts were washed with water and then with brine, dried over anhydrous sodium sulfate and concentrated in vacuo to provide tert-butyl 5-(((5-cyclohexylpyridin-2-yl)methyl)amino)-1-oxoisoindoline-2-carboxylate (51 mg, 100% yield) as a pale yellow solid. $^1$H NMR (300 MHz, Chloroform-d) δ 8.46 (s, 1H), 7.69 (d, J=8.4 Hz, 1H), 7.53 (dd, J=8.1, 2.2 Hz, 1H), 7.24 (d, J=8.1 Hz, 1H), 6.75 (d, J=8.4 Hz, 1H), 6.59 (s, 1H), 5.55 (br. s, 1H), 4.64 (s, 2H), 4.48 (d, J=4.2 Hz, 2H), 2.66-2.45 (m, 1H), 2.02-1.73 (m, 6H), 1.60 (s, 9H), 1.50-1.31 (m, 4H).

Step 6 To a stirred solution of tert-butyl 5-(((5-cyclohexylpyridin-2-yl)methyl)amino)-1-oxoisoindoline-2-carboxylate (51 mg, 0.118 mmol) in dry THF (3 mL) under nitrogen at 0° C. was added methylmagnesium bromide (0.21 mL of 1.4 M in THF, 0.295 mmol) and the resulting solution was stirred at 0° C. for 5 min and room temperature for 10 min before addition of solid (R)-1-((perfluorophenyl)sulfonyl)-azetidine-2-carbonyl chloride (62 mg, 0.177 mmol). The resulting mixture was stirred at room temperature for 1.0 h. The crude reaction mixture was quenched with saturate aqueous ammonium chloride, poured onto water and extracted with EtOAc (3×). The combined organic extract was washed with brine, dried over sodium sulfate and concentrated under reduced pressure. The crude residue was analyzed by LCMS and found to be a 7:3 mixture of tert-butyl (R)-5-(N-((5-cyclohexylpyridin-2-yl)methyl)-1-((perfluorophenyl)sulfonyl)azetidine-2-carboxamido)-1-oxoisoindoline-2-carboxylate [MS (ESI+) m/z 735.4 [M+H]$^+$] and the deprotected product, (R)—N-((5-cyclohexylpyridin-2-yl)methyl)-N-(1-oxoisoindolin-5-yl)-1-((perfluorophenyl)sulfonyl)azetidine-2-carboxamide [MS (ESI+) m/z 635.4 [M+H]$^+$]. To a stirred solution of the above residue in DCM (1 mL) under a nitrogen atmosphere was added TFA (0.4 mL) and the resulting solution was allowed to stir at room temperature for 5 min. The reaction mixture was poured onto aqueous sodium bicarbonate and extracted with DCM (3×). The combined organic extracts were dried over anhydrous sodium sulfate and concentrated under reduced pressure. Purification by chromatography (50% EtOAc/hexanes eluent, then 100% EtOAc and then 5% methanol in EtOAc) provided pure (R)—N-((5-cyclohexylpyridin-2-yl)methyl)-N-(1-oxoisoindolin-5-yl)-1-((perfluorophenyl)sulfonyl)azetidine-2-carboxamide (39 mg, 52% yield). HRMS (ESI+) m/z 635.1975 [M+H]$^+$.

Example 105

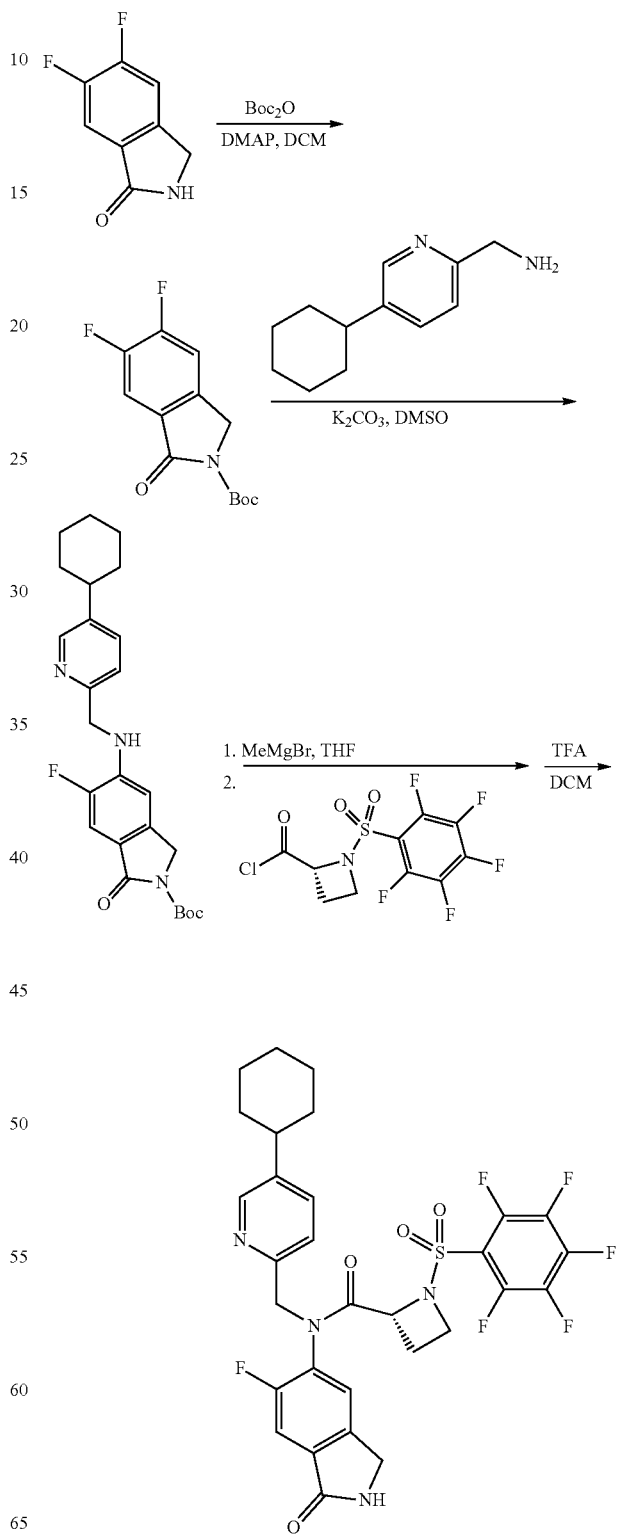

(R)—N-((5-cyclohexylpyridin-2-yl)methyl)-N-(6-fluoro-1-oxoisoindolin-5-yl)-1-((perfluorophenyl)sulfonyl)azetidine-2-carboxamide

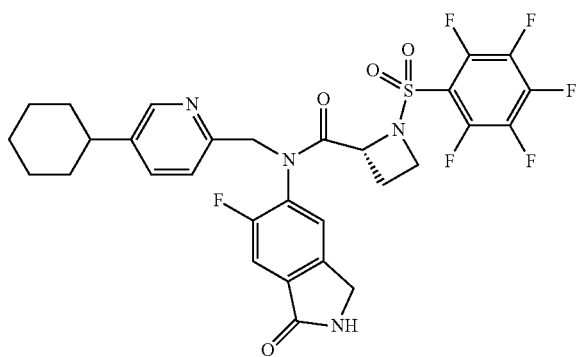 [SMILES: O=C1NCc2cc(N(Cc3ccc(C4CCCCC4)cn3)C(=O)[C@H]3CCN3S(=O)(=O)c3c(F)c(F)c(F)c(F)c3F)c(F)cc21]

Step 1: To a solution of 5,6-difluoroisoindolin-1-one (275 mg, 1.63 mmol) in DCM (20 mL) under a nitrogen atmosphere was added DMAP (20 mg, 0.163 mmol) followed by di-tert-butyl dicarbonate (approx. 355 mg, 1.63 mmol). The resulting reaction mixture was stirred at room temperature overnight, then poured onto water and extracted with DCM (3×). The combined organic layer was washed with brine, dried over anhydrous sodium sulfate and concentrated under reduced pressure. The crude residue was purified by chromatography (30-50% EtOAc in hexane eluent) to provide tert-butyl 5,6-difluoro-1-oxoisoindoline-2-carboxylatecarboxylate (413 mg, 94% yield) as a fluffy white solid. $^1$H NMR (300 MHz, Chloroform-d) δ 7.71 (dd, J=8.6, 7.2 Hz, 1H), 7.35-7.28 (m, 1H), 4.74 (s, 2H), 1.62 (s, 9H).

Step 2: A solution of tert-butyl 5,6-difluoro-1-oxoisoindoline-2-carboxylatecarboxylate (100 mg, 0.37 mmol), (5-cyclohexylpyridin-2-yl)methanamine (300 mg, 1.58 mmol) and potassium carbonate (102 mg, 0.74 mmol) in DMSO (2.1 mL) under argon was heated at 100° C. for 20 h. The reaction mixture was allowed to cool, was diluted with DCM, poured onto water and extracted with DCM (3×). The combined organic extract was dried over anhydrous sodium sulfate, filtered and concentrated under reduced pressure. Combined with 2 trial reaction done on a 10 mg scale each for purification. Purification by chromatography (1-2% methanol in DCM eluent) followed by repurification by chromatography (20-30% EtOAc in hexanes eluent) provided impure product as a yellow film. This yellow film was triturated with ether to provide pure product, tert-butyl 5-(((5-cyclohexylpyridin-2-yl)methyl)amino)-6-fluoro-1-oxoisoindoline-2-carboxylate as a white solid. $^1$H NMR (300 MHz, Chloroform-d) δ 8.48 (d, J=2.2 Hz, 1H), 7.54 (dd, J=8.0, 2.2 Hz, 1H), 7.47 (d, J=10.4 Hz, 1H), 7.27-7.22 (m, 1H), 6.62 (d, J=7.1 Hz, 1H), 5.79-5.64 (m, 1H), 4.62 (s, 2H), 4.52 (d, J=5.1 Hz, 2H), 2.67-2.47 (m, 1H), 2.02-1.71 (m, 6H), 1.60 (s, 9H), 1.53-1.31 (m, 4H). MS (ESI+) m/z 440.4 [M+H]$^+$.

Step 3: To a stirred solution of tert-butyl 5-(((5-cyclohexylpyridin-2-yl)methyl)amino)-6-fluoro-1-oxoisoindoline-2-carboxylate (40 mg, 0.0887 mmol) in dry THF (2 mL) under nitrogen at 0° C. was added methylmagnesium bromide (0.16 mL of 1.4 M in THF, 0.222 mmol) and the resulting solution was stirred at 0° C. for 5 min and room temperature for 10 min before addition of solid (R)-1-((perfluorophenyl)sulfonyl)-azetidine-2-carbonyl chloride (47 mg, 0.133 mmol). The resulting mixture was stirred at room temperature for 2 h. The crude reaction mixture was quenched with saturate aqueous ammonium chloride, poured onto water and extracted with EtOAc (3×). The combined organic extract was washed with brine, dried over sodium sulfate and concentrated under reduced pressure. The crude residue was analyzed by LCMS and found to be a 3:2 mixture of tert-butyl (R)-5-(N-((5-cyclohexylpyridin-2-yl)methyl)-1-((perfluorophenyl)sulfonyl)azetidine-2-carboxamido)-6-fluoro-1-oxoisoindoline-2-carboxylate [MS (ESI+) m/z 753.4 [M+H]$^+$] and the deprotected product, (R)—N-((5-cyclohexylpyridin-2-yl)methyl)-N-(6-fluoro-1-oxoisoindolin-5-yl)-1-((perfluorophenyl)sulfonyl)azetidine-2-carboxamide [MS (ESI+) m/z 653.3 [M+H]$^+$] and some starting aniline. To a stirred solution of the above residue in DCM (1 mL) under a nitrogen atmosphere was added TFA (0.3 mL) and the resulting solution was allowed to stir at room temperature for 10 min. The reaction mixture was poured onto aqueous sodium bicarbonate and extracted with DCM (3×). The combined organic extracts were dried over anhydrous sodium sulfate and concentrated under reduced pressure. Purification by chromatography (50% EtOAc/hexanes eluent, then 100% EtOAc and then 5% methanol in EtOAc) provided product with 12% deprotected aniline, 5-(((5-cyclohexylpyridin-2-yl)methyl)amino)-6-fluoroisoindolin-1-one. The mixture was triturated with EtOAc/hexanes and the resulting white solid was removed by filtration. Concentration of the filtrate provide (R)—N-((5-cyclohexylpyridin-2-yl)methyl)-N-(6-fluoro-1-oxoisoindolin-5-yl)-1-((perfluorophenyl)sulfonyl)azetidine-2-carboxamide (22 mg, 38% yield) as a yellow solid in 96% purity by LCMS. HRMS (ESI+) m/z 653.1682 [M+H]$^+$.

Example 106

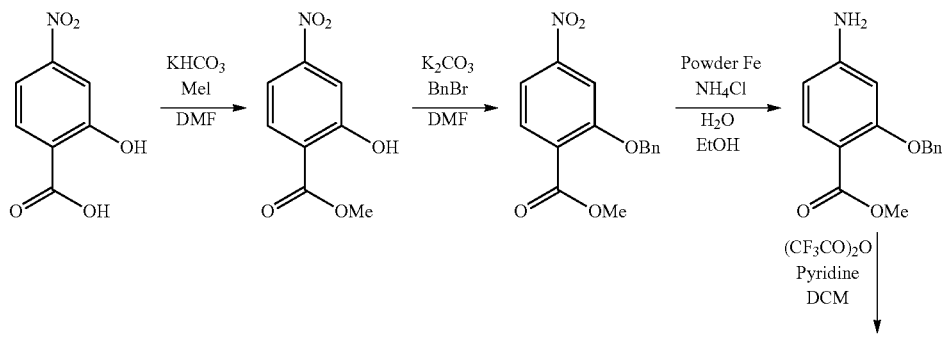

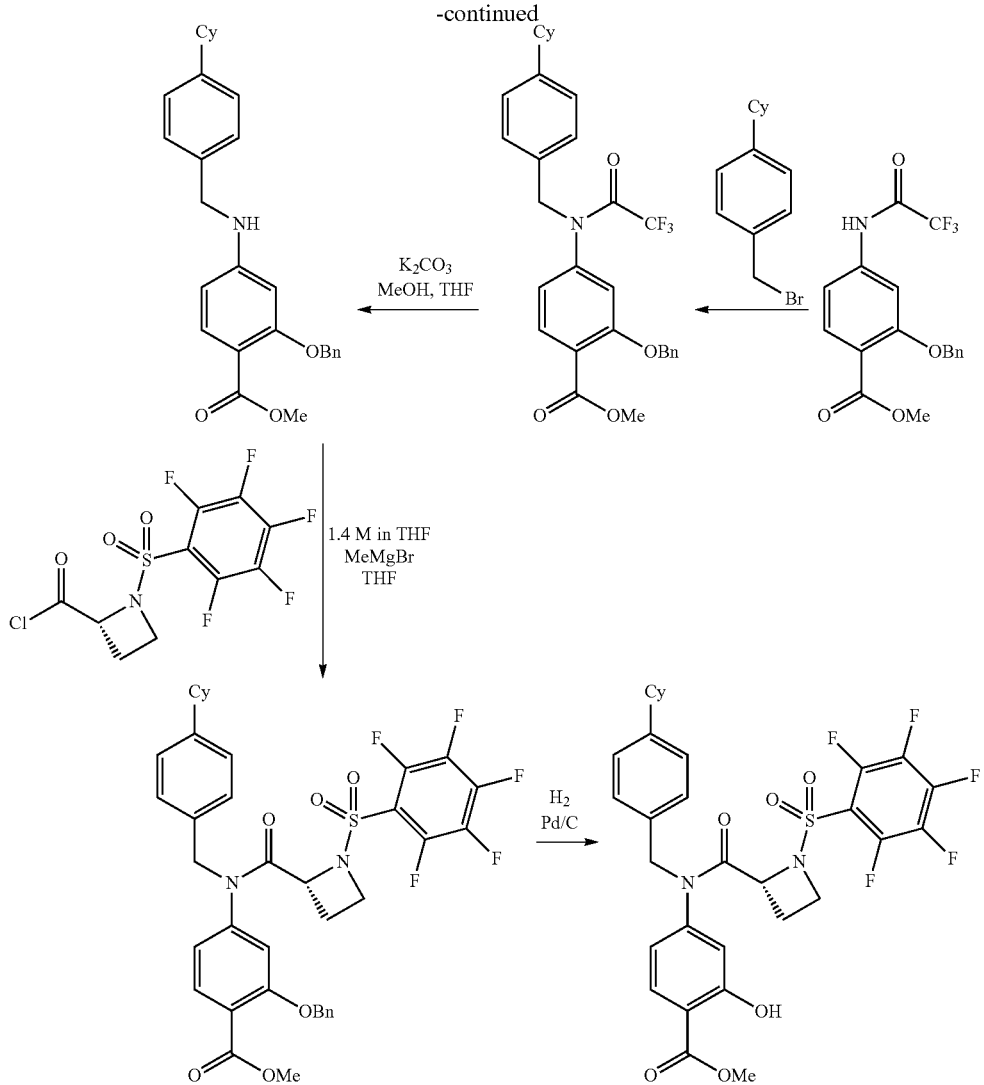

Methyl (R)-4-(N-(4-cyclohexylbenzyl)-1-((perfluorophenyl)sulfonyl)azetidine-2-carboxamido)-2-hydroxybenzoate

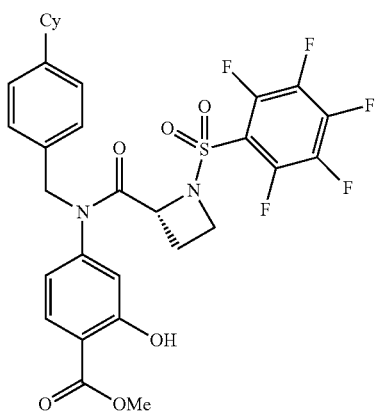

Step 1. To a solution of 2-hydroxy-4-nitrobenzoic acid (1.12 g, 6.12 mmol) in DMF (22 mL) was added potassium bicarbonate (794 mg, 7.93 mmol) under nitrogen. The mixture was stirred for 10 minutes. Methyl iodide (0.95 mL, 15.3 mmol) was added, and the mixture was stirred for 6 hours at rt. The mixture was poured onto cold water, and extracted with EtOAc (2×). The extract was washed with water (2×), brine, dried (sodium sulfate) and concentrated to dryness to obtain methyl 2-hydroxy-4-nitrobenzoate as light brown solid (1.06 g, 90% yield). $^1$H NMR (300 MHz, Chloroform-d) δ 10.99 (s, 1H), 8.04 (d, J=8.7 Hz, 1H), 7.84 (d, J=2.2 Hz, 1H), 7.72 (dd, J=8.7, 2.2 Hz, 1H), 4.04 (s, 3H).

Step 2. To a solution of methyl 2-hydroxy-4-nitrobenzoate (249 mg, 1.30 mmol) in DMF (6.5 mL) was added potassium carbonate (216 mg, 1.56 mmol) under nitrogen. The mixture was stirred for 10 minutes. Benzyl bromide (0.165 mL, 1.37 mmol) was added, and the mixture was stirred at rt for 5 hours. The mixture was poured onto cold water, and extracted with EtOAc (2×). The extract was washed with water (2×), brine, dried (sodium sulfate) and concentrated to dryness. Hexane trituration gave methyl 2-(benzyloxy)-4-nitrobenzoate as cream solid (329 mg, 88% yield). $^1$H NMR (300 MHz, Chloroform-d) δ 7.99-7.81 (m, 3H), 7.57-7.25 (m, 5H), 5.30 (s, 2H), 3.96 (s, 3H).

Step 3. To methyl 2-(benzyloxy)-4-nitrobenzoate (1.7 g, 5.9 mmol) and ammonium chloride (3.23 g, 60.4 mmol) were added ethanol (22 mL) and HPLC water (11 mL) under nitrogen. Iron powder (2.32 g, 41.5 at Eq) was added, and the mixture was stirred vigorously at 66° C. overnight. After cooling, the mixture was filtered through celite. The cake was washed with EtOAc. Water was added to the filtrate, which was extracted with EtOAc (2×). The extract was washed with brine, dried (sodium sulfate) and concentrated to dryness to obtain methyl 4-amino-2-(benzyloxy)benzoate (1.5 g, 98% yield). $^1$H NMR (300 MHz, Chloroform-d) δ 7.80 (d, J=8.6 Hz, 1H), 7.54 (m, 2H), 7.47-7.25 (m, 5H), 6.27 (m, 2H), 5.16 (s, 2H), 4.06-3.99 (m, 2H), 3.87 (s, 3H).

Step 4. Preparation by a similar procedure to Example 52, step 4b, starting from methyl 4-amino-2-(benzyloxy)benzoate to obtain methyl 2-(benzyloxy)-4-(2,2,2-trifluoroacetamido)benzoate. $^1$H NMR (300 MHz, Chloroform-d) δ 7.99 (s, 1H), 7.91 (d, J=8.4 Hz, 1H), 7.64 (d, J=2.0 Hz, 1H), 7.53 (m, 2H), 7.49-7.20 (m, 3H), 7.01 (dd, J=8.5, 2.0 Hz, 1H), 5.22 (s, 2H), 4.02-3.82 (s, 3H).

Step 5. Preparation by a similar procedure to Example 61, step 4, starting from methyl 2-(benzyloxy)-4-(2,2,2-trifluoroacetamido)benzoate to obtain methyl 2-(benzyloxy)-4-(N-(4-cyclohexylbenzyl)-2,2,2-trifluoroacetamido)benzoate. $^1$H NMR (300 MHz, Chloroform-d) δ 7.81 (d, J=8.2 Hz, 1H), 7.43-7.30 (m, 5H), 7.14 (d, J=8.2 Hz, 2H) 7.05 (d, J=8.2 Hz, 2H), 6.72 (d, J=8.2 Hz, 1H), 6.49 (s, 1H), 4.93 (s, 2H), 4.84 (s, 2H), 3.92 (s, 3H), 2.57-2.41 (m, 1H), 1.98-1.69 (m, 5H), 1.2-1.5 (m, 5H).

Step 6. Preparation by a similar procedure to Example 61, step 5, starting from methyl 2-(benzyloxy)-4-(2,2,2-trifluoroacetamido)benzoate to obtain methyl 2-(benzyloxy)-4-((4-cyclohexylbenzyl)amino)benzoate. $^1$H NMR (300 MHz, Chloroform-d) δ 7.81 (d, J=8.5 Hz, 1H), 7.51 (d, J=7.4 Hz, 2H), 7.46-7.16 (m, 7H), 6.29 (dd, J=8.5, 2.4 Hz, 1H), 6.17 (d, J=2.4 Hz, 1H), 5.12 (s, 2H), 4.41 (br, 1H), 4.31 (s, 2H), 3.86 (s, 3H), 2.52 (m, 1H), 1.98-1.69 (m, 5H), 1.50-1.19 (m, 5H).

Step 7. Preparation by a similar procedure to Example 61, step 6, starting from methyl 2-(benzyloxy)-4-((4-cyclohexylbenzyl)amino)benzoate to obtain methyl (R)-2-(benzyloxy)-4-(N-(4-cyclohexylbenzyl)-1-((perfluorophenyl)sulfonyl)azetidine-2-carboxamido)benzoate. MS (ESI): [M+H]+ m/z 743.2

Step 8. Preparation by a similar procedure to Example 61, step 7, starting from methyl (R)-2-(benzyloxy)-4-(N-(4-cyclohexylbenzyl)-1-((perfluorophenyl)sulfonyl)azetidine-2-carboxamido)benzoate to obtain the compound of Example 106 methyl (R)-4-(N-(4-cyclohexylbenzyl)-1-((perfluorophenyl)sulfonyl)azetidine-2-carboxamido)-2-hydroxybenzoate. HRMS (ESI+) m/z 653.1732 [M+H]+

Example 107

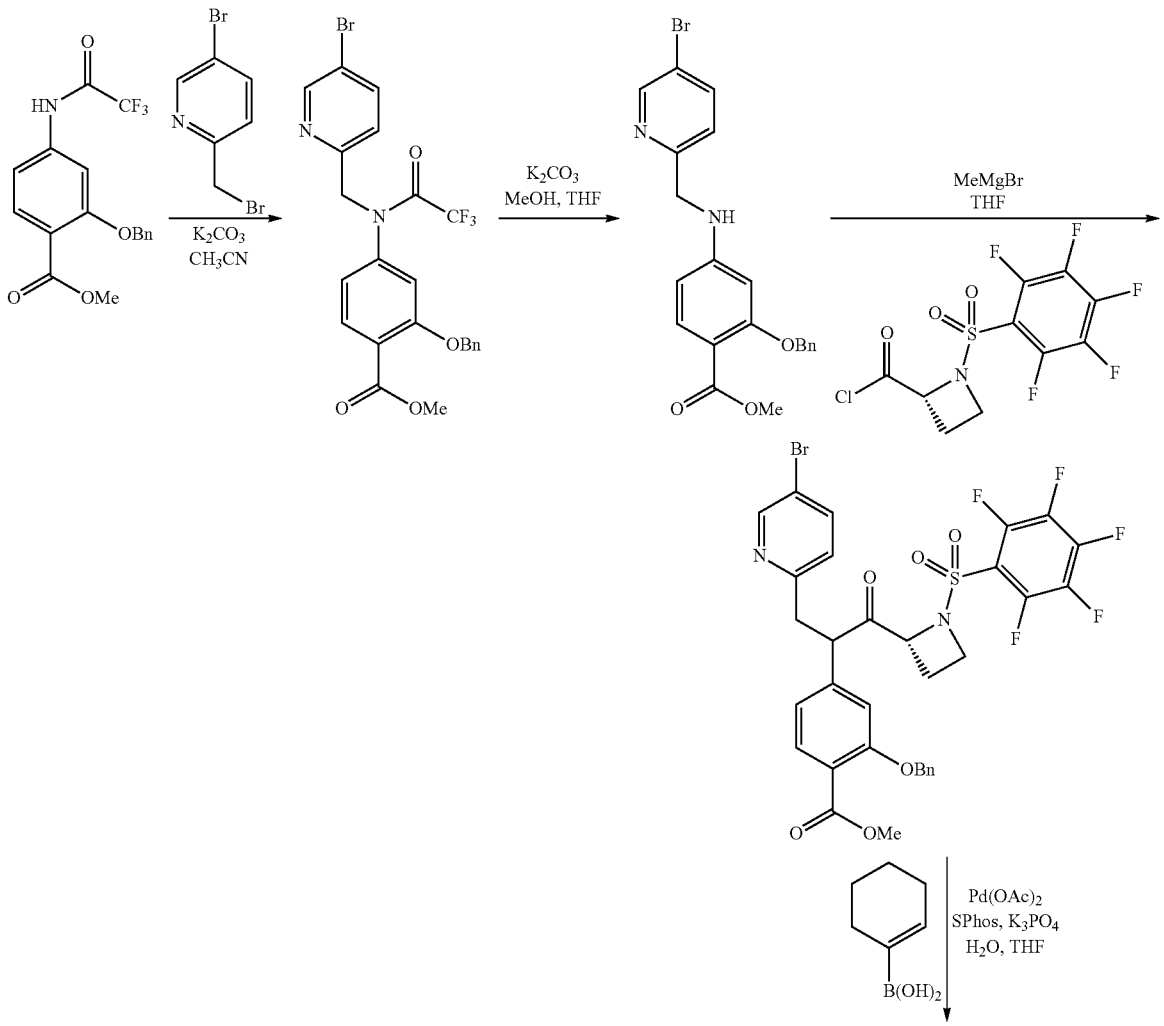

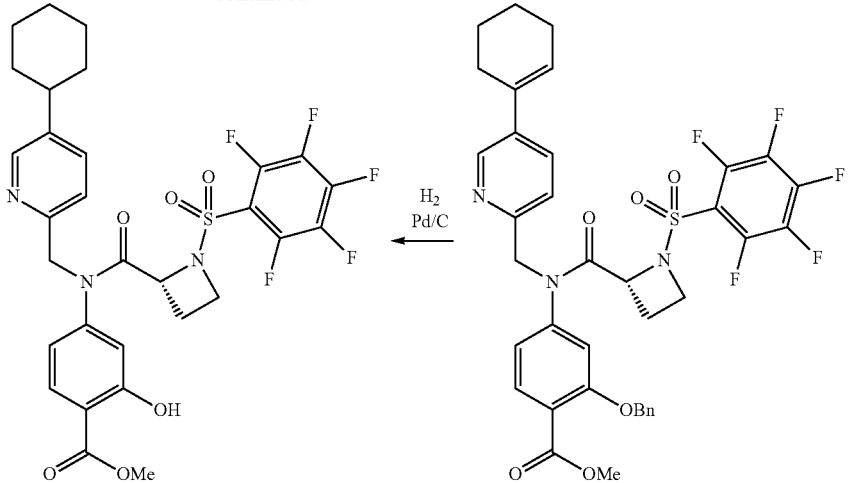

Methyl (R)-4-(N-((5-cyclohexylpyridin-2-yl)methyl)-1-((perfluorophenyl)sulfonyl)azetidine-2-carboxamido)-2-hydroxybenzoate

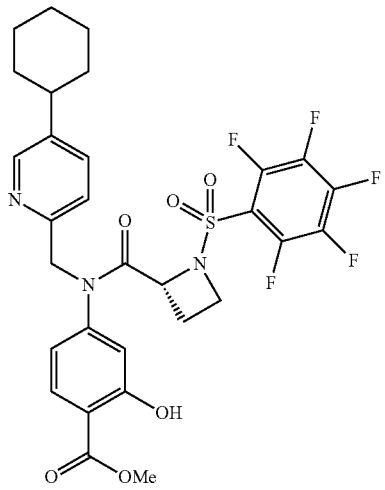 [SMILES: COC(=O)c1ccc(N(Cc2ccc(C3CCCCC3)cn2)C(=O)[C@H]2CCN2S(=O)(=O)c2c(F)c(F)c(F)c(F)c2F)cc1O]

Step 1. Preparation by a similar procedure to Example 53, step 1, starting from methyl 2-(benzyloxy)-4-(2,2,2-trifluoroacetamido)benzoate to obtain methyl 2-(benzyloxy)-4-(N-((5-bromopyridin-2-yl)methyl)-2,2,2-trifluoroacetamido)benzoate. $^1$H NMR (300 MHz, Chloroform-d) δ 8.57 (d, J=1.7 Hz, 1H), 7.83 (d, J=8.3, 1H), 7.78 (dd, J=8.2, 2.3, 1H), 7.47-7.31 (m, 5H), 7.18 (d, J=8.2 Hz, 1H), 6.96 (d, J=1.8 Hz, 1H), 6.90 (dd, J=8.3, 1.8 Hz, 1H), 5.13 (s, 3H), 4.94 (s, 3H), 3.93 (s, 3H).

Step 2. Preparation by a similar procedure to Example 53, step 2, starting from methyl 2-(benzyloxy)-4-(N-((5-bromopyridin-2-yl)methyl)-2,2,2-trifluoroacetamido)benzoate to obtain methyl 2-(benzyloxy)-4-(((5-bromopyridin-2-yl)methyl)amino)benzoate. $^1$H NMR (300 MHz, Chloroform-d) δ 8.66 (d, J=2.4 Hz, 1H), 7.83 (d, J=8.3, 1H), 7.78 (dd, J=8.2, 2.4, 1H), 7.55-7.46 (m, 2H), 7.44-7.26 (m, 3H), 7.18 (d, J=8.2 Hz, 1H), 6.26 (dd, J=8.3, 2.2, 1H), 6.20 (d, J=2.2 Hz, 1H), 5.25 (br, 1H), 5.15 (s, 2H), 4.44 (d, J=4.4 Hz, 2H), 3.86 (s, 3H).

Step 3. Preparation by a similar procedure to Example 53, step 3, starting from methyl 2-(benzyloxy)-4-(((5-bromopyridin-2-yl)methyl)amino)benzoate to obtain methyl (R)-2-(benzyloxy)-4-(N-((5-bromopyridin-2-yl)methyl)-1-((perfluorophenyl)sulfonyl)azetidine-2-carboxamido)benzoate. $^1$H NMR (300 MHz, Chloroform-d) δ 8.53 (m, 1H), 7.98-7.66 (m, 2H), 7.62-7.05 (m, 6H), 7.01-6.69 (m, 2H), 5.4-5.06 (m, 2H), 5.05-4.70 (m, 3H), 4.28-3.70 (m, 5H), 1.94-1.43 (m, 2H).

Step 4. Methyl (R)-2-(benzyloxy)-4-(N-((5-bromopyridin-2-yl)methyl)-1-((perfluorophenyl)sulfonyl)azetidine-2-carboxamido)benzoate (354.6 mg, 0.479 mmol), palladium acetate (5.37 mg), SPhos (19.6 mg), cyclohex-1-en-1-ylboronic acid (90.4 mg), potassium phosphate (203 mg) and HPLC quality water (17 mg) were mixed under N$_2$. The mixture was further thoroughly flushed with N$_2$, capped, and a N$_2$ balloon was set. THF (7.2 mL) was added through a septum. The mixture was stirred at 40° C. for 20 h. Water was added and the mixture was extracted with EtOAc (2×). The extract was washed with brine, dried (Na$_2$SO$_4$) and concentrated. Purification by SiO$_2$ flash column (85:15 Hexane/EtOAc) gave methyl (R)-2-(benzyloxy)-4-(N-((5-(cyclohex-1-en-1-yl)pyridin-2-yl)methyl)-1-((perfluorophenyl)sulfonyl)azetidine-2-carboxamido)benzoate (194 mg, 55% yield) as a white solid. MS (ESI): [M+H]+ m/z 742.2

Step 5. Preparation by a similar procedure to Example 53, step, starting from methyl (R)-2-(benzyloxy)-4-(N-((5-(cyclohex-1-en-1-yl)pyridin-2-yl)methyl)-1-((perfluorophenyl)sulfonyl)azetidine-2-carboxamido)benzoate to obtain the compound of Example 107 methyl (R)-4-(N-((5-cyclohexylpyridin-2-yl)methyl)-1-((perfluorophenyl)sulfonyl)azetidine-2-carboxamido)-2-hydroxybenzoate. MS (ESI): [M+H]+ m/z 654.3

Example 108
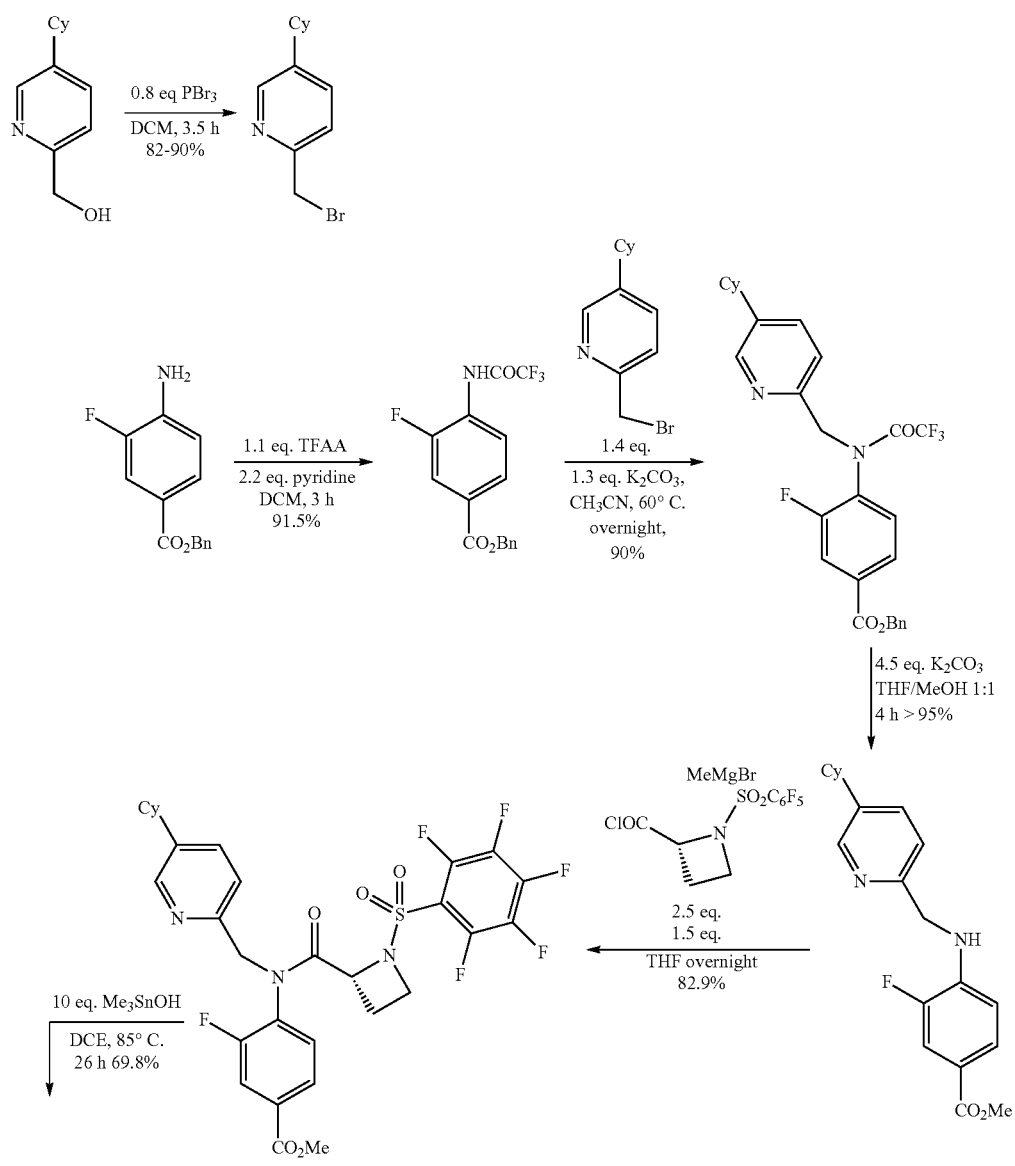
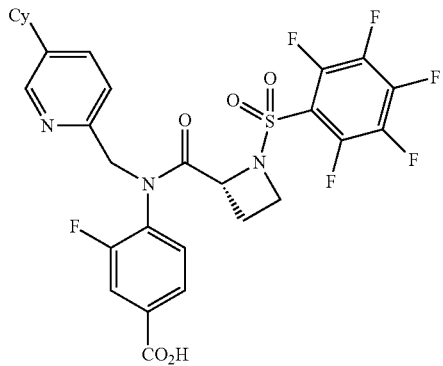

(R)-4-(N-((5-cyclohexylpyridin-2-yl)methyl)-1-((perfluorophenyl)sulfonyl)azetidine-2-carboxamido)-3-fluorobenzoic acid

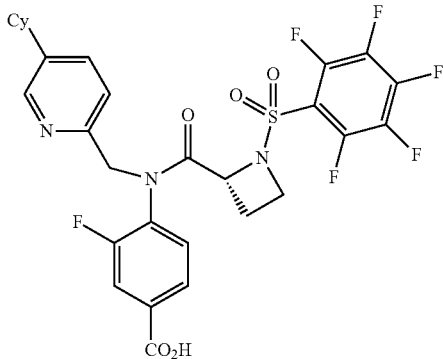

Step A1. 2-(Bromomethyl)-5-cyclohexylpyridine. Phosphorous tribromide (0.05 ml) was added to (5-cyclohexylpyridin-2-yl)methanol (167.6 mg) (see Example 97) in DCM (5 ml) in 0° C. under Argon. The mixture was allowed to reach rt and stirred for 3.5 h. Ice water (3 mL) was added to quench the reaction. The mixture was extracted with DCM (2 times), and the organic layer was washed with brine and dried with $Na_2SO_4$. Then the organic layer was concentrated to dryness giving 2-(bromomethyl)-5-cyclohexylpyridine (182 mg, 82%) as purple oil. $^1$H NMR (300 MHz, $CDCl_3$) δ 8.42 (d, J=2.2 Hz, 1H), 7.50 (dd, J=8.0, 2.2 Hz, 1H), 7.34 (d, J=8.0 Hz, 1H), 4.53 (s, 2H), 2.64-2.38 (m, 1H), 1.91-1.71 (m, 5H), 1.50-1.25 (m, 5H).

Step 1. Preparation by a similar procedure to Example 61, step 3, except substituting benzyl 4-amino-2-(benzyloxy)-5-fluorobenzoate for benzyl 4-amino-3-fluorobenzoate afforded benzyl 3-fluoro-4-(2,2,2-trifluoroacetamido)benzoate. NMR (300 MHz, $CDCl_3$) δ 8.49-8.33 (m, 1H), 8.20 (br, 1H), 8.03-7.79 (m, 2H), 7.55-7.18 (m, 5H), 5.39 (s, 2H).

Step 2. Benzyl 4-(N-((5-cyclohexylpyridin-2-yl)methyl)-2,2,2-trifluoroacetamido)-3-fluorobenzoate. To benzyl 3-fluoro-4-(2,2,2-trifluoroacetamido)benzoate (176.7 mg, 0.518 mmol) and 2-(bromomethyl)-5-cyclohexylpyridine (182 mg, 0.725 mmol) was added acetonitrile (5 mL) under $N_2$. To the resulting solution was added potassium carbonate (93 mg, 0.673 mmol), and the mixture was heated at 60° C. overnight. After cooling to rt, pH 2 solution (10% aqueous $KHSO_4$/$Na_2SO_4$) was added. The mixture was extracted with EtOAc (2×). The extract was washed sat. $NaHCO_3$, brine, dried ($Na_2SO_4$) and concentrated. Purification by column chromatography gave benzyl 4-(N-((5-cyclohexylpyridin-2-yl)methyl)-2,2,2-trifluoroacetamido)-3-fluorobenzoate (238.7 mg, 89.5%). $^1$H NMR (300 MHz, $CDCl_3$) δ 8.36 (d, J=2.0 Hz, 1H), 7.90-7.79 (m, 2H), 7.50 (dd, J=8.0, 2.0 Hz, 1H), 7.47-7.35 (m, 5H), 7.35-7.26 (m, 2H), 5.42 (d, J=14.6 Hz, 1H), 5.37 (s, 2H), 4.58 (d, J=14.6 Hz, 1H), 2.61-2.42 (m, 1H), 1.92-1.72 (m, 5H), 1.52-1.29 (m, 5H).

Step 3. Preparation by a similar procedure to Example 53, step 2, starting from benzyl 4-(N-((5-cyclohexylpyridin-2-yl)methyl)-2,2,2-trifluoroacetamido)-3-fluorobenzoate to obtain methyl 4-(((5-cyclohexylpyridin-2-yl)methyl)amino)-3-fluorobenzoate. $^1$H NMR (300 MHz, $CDCl_3$) δ 8.47 (d, J=2.1 Hz, 1H), 7.73 (d, J=8.4 Hz, 1H), 7.71-7.63 (m, 1H), 7.52 (dd, J=8.0, 2.1 Hz, 1H), 7.24 (d, J=8.0 Hz, 1H), 6.66 (m, 1H), 5.51 (br, 1H), 4.52 (d, J=5.3 Hz, 2H), 3.87 (s, 3H), 2.56 (s, 1H), 1.96-1.76 (m, 5H), 1.53-1.35 (m, 5H).

Step 4. Preparation by a similar procedure to Example 53, step 3, starting from methyl 4-(((5-cyclohexylpyridin-2-yl)methyl)amino)-3-fluorobenzoate to obtain methyl (R)-4-(N-((5-cyclohexylpyridin-2-yl)methyl)-1-((perfluorophenyl)sulfonyl)azetidine-2-carboxamido)-3-fluorobenzoate. $^1$H NMR (300 MHz, $CDCl_3$) δ 8.24 (s, 1H), 7.85-7.69 (m, 2H), 7.51-7.38 (m, 1H), 7.34-7.12 (m, 2H), 5.26 (d, J=14.9 Hz, 1H), 4.90 (t, J=7.8 Hz, 1H), 4.45 (d, J=14.9 Hz, 1H), 4.18-3.95 (m, 3H), 3.91 (s, 3H), 4.03-3.85 (m, 1H), 2.55-2.38 (m, 1H), 2.36-2.15 (m, 1H), 1.96-1.65 (m, 6H), 1.46-1.17 (m, 5H).

Step 5. Methyl (R)-4-(N-((5-cyclohexylpyridin-2-yl)methyl)-1-((perfluorophenyl)sulfonyl)azetidine-2-carboxamido)-3-fluorobenzoate (70 mg, 0.107 mmol) and trimethyltin hydroxide (193.1 mg, 1.07 mmol) were flushed thoroughly with nitrogen. Dichloroethane (3 mL) was added and the mixture was heated at 85° C. for 26 h. The mixture was concentrated and the residue was taken up in EtOAc. The organic solution was washed with pH2 buffer (3×), brine, dried (sodium sulfate) and concentrated. Purification by column chromatography gave Example 108 (R)-4-(N-((5-cyclohexylpyridin-2-yl)methyl)-1-((perfluorophenyl)sulfonyl)azetidine-2-carboxamido)-3-fluorobenzoic acid. MS (ESI): [M+H]+ m/z 642.2

Example 109

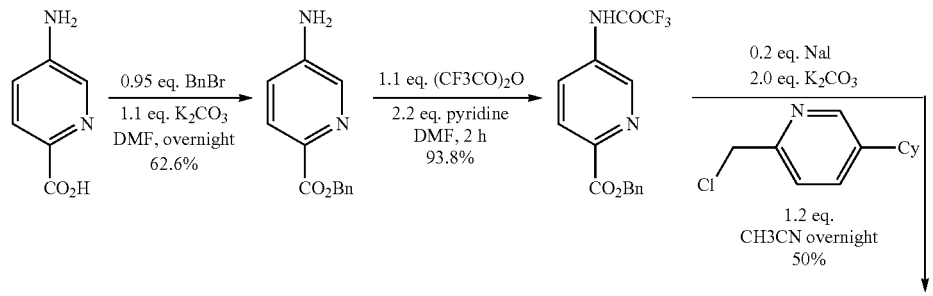

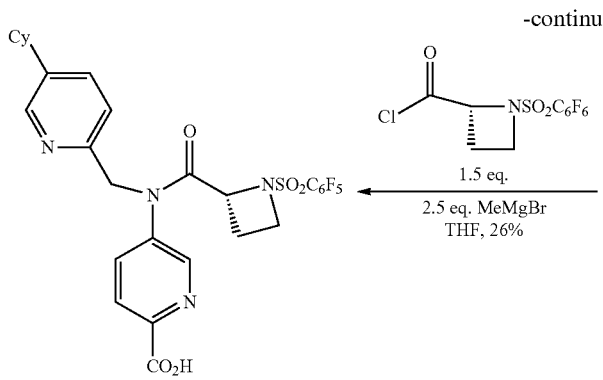
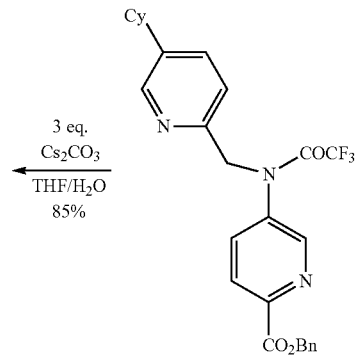

(R)-5-(N-((5-cyclohexylpyridin-2-yl)methyl)-1-((perfluorophenyl)sulfonyl)azetidine-2-carboxamido)picolinic acid

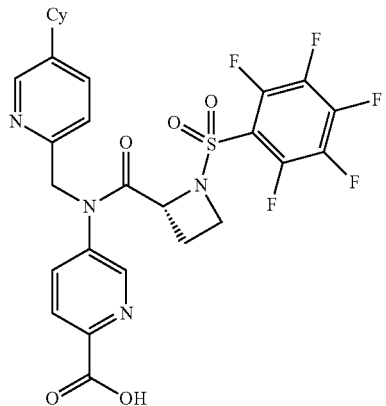

Step 1. Preparation by a similar procedure to Example 48, step 3, starting from 5-aminopicolinic acid to obtain benzyl 5-aminopicolinate. $^1$H NMR (300 MHz, CDCl$_3$) δ 8.16 (d, J=2.8 Hz, 1H), 7.99-7.92 (m, 1H), 7.52-7.44 (m, 2H), 7.41-7.30 (m, 3H), 6.96 (dd, J=8.5, 2.8 Hz, 1H), 5.42 (s, 2H), 4.14 (s, 2H).

Step 2. Preparation by a similar procedure to Example 52, step 4b, starting from benzyl 5-aminopicolinate to obtain benzyl 5-(2,2,2-trifluoroacetamido)picolinate. $^1$H NMR (300 MHz, CDCl$_3$) δ 8.78 (d, J=2.1 Hz, 1H), 8.54-8.37 (m, 2H), 8.22 (d, J=8.6 Hz, 1H), 7.55-7.45 (m, 2H), 7.45-7.34 (m, 3H), 5.47 (s, 2H).

Step 3. Preparation by a similar procedure to Example 116, step 4 starting from benzyl 5-(2,2,2-trifluoroacetamido)picolinate to obtain benzyl 5-(N-((5-cyclohexylpyridin-2-yl)methyl)-2,2,2-trifluoroacetamido)picolinate. $^1$H NMR (300 MHz, CDCl$_3$) δ 8.63 (d, J=2.3 Hz, 1H), 8.37 (d, J=2.2 Hz, 1H), 8.17 (d, J=8.3 Hz, 1H), 7.82 (dd, J=8.3, 2.3 Hz, 1H), 7.53-7.46 (m, 3H), 7.43-7.33 (m, 3H), 7.23 (d, J=7.9 Hz, 1H), 5.46 (s, 2H), 5.02 (s, 2H), 2.59-2.46 (m, 1H), 1.94-1.77 (m, 5H), 1.49-1.34 (m, 5H).

Step 4. In a dry flask, benzyl 5-(N-((5-cyclohexylpyridin-2-yl)methyl)-2,2,2-trifluoroacetamido)picolinate (192.4 mg, 0.387 mmol) and Cs$_2$CO$_3$ (409.3 mg, 1.16 mmol) was added. Then water (3 mL) and THF (10 mL) were added to the flask, and the mixture was stirred at rt overnight. After the reaction was completed, water was added. The mixture was extracted with ether acetate (2×). The combined organic phase was dried over sodium sulfate, and evaporated under reduced pressure. The crude product was purified by column chromatography to give benzyl 5-(((5-cyclohexylpyridin-2-yl)methyl)amino)picolinate (132.5 mg, 85% yield). $^1$H NMR (300 MHz, CDCl$_3$) δ 8.44 (s, 1H), 8.20 (d, J=2.7 Hz, 1H), 7.98 (d, J=8.6 Hz, 1H), 7.58-7.30 (m, 6H), 7.22 (d, J=8.0 Hz, 1H), 6.90 (dd, J=8.6, 2.7 Hz, 1H), 5.66 (br, 1H), 5.41 (s, 2H), 4.46 (d, J=4.9 Hz, 2H), 2.57-2.45 (m, 1H), 1.99-1.79 (m, 5H), 1.53-1.32 (m, 5H).

Step 5. To a solution of benzyl 5-(((5-cyclohexylpyridin-2-yl)methyl)amino)picolinate (100 mg, 0.249 mmol) in THF (2.5 mL) was added at 0° C. 1.4 M in THF methylmagnesium bromide (0.45 mL, 0.63 mmol) under N$_2$. The mixture was stirred 5-10 min at 0° C. Powder (R)-1-((perfluorophenyl)sulfonyl)azetidine-2-carbonyl chloride (130.6 mg, 0.374 mmol) was added at 0° C. The mixture was allowed to reach rt and stirred for overnight. Cold saturated ammonium chloride was added followed by water. The mixture was extracted with EtOAc (2×). The extract was washed with brine, dried (sodium sulfate) and concentrated. Purification by column chromatography gave Example 109 (R)-5-(N-((5-cyclohexylpyridin-2-yl)methyl)-1-((perfluorophenyl)sulfonyl)azetidine-2-carboxamido)picolinic acid (40 mg, 26%) as a white solid. MS (ESI): [M+H]+ m/z 625.2.

Example 110

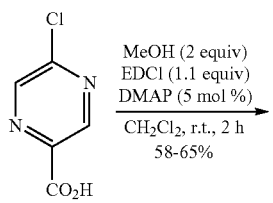

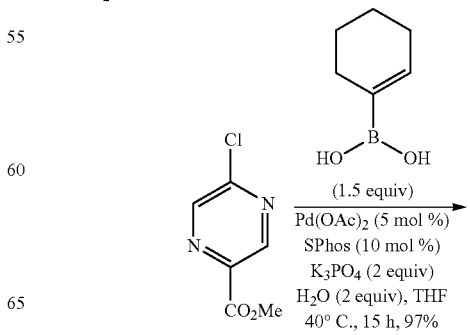

-continued

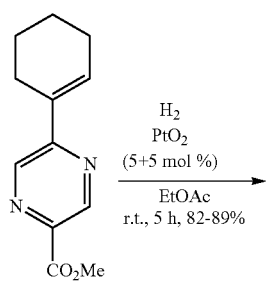

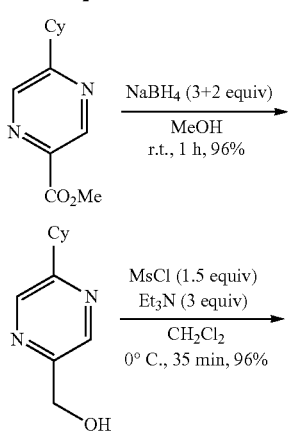

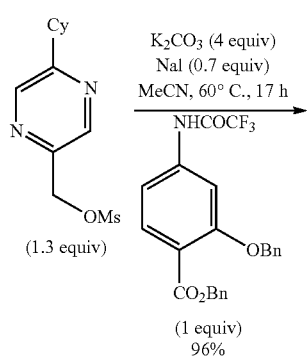

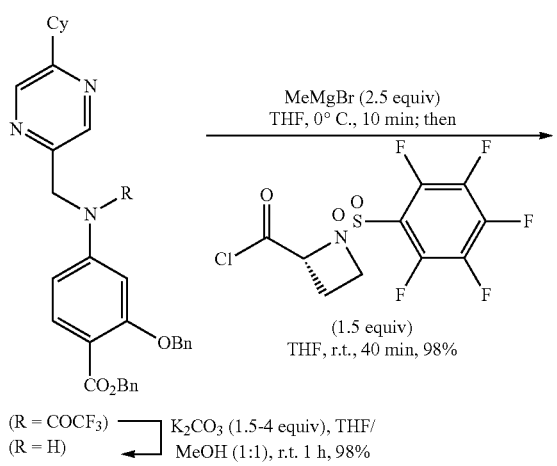

-continued

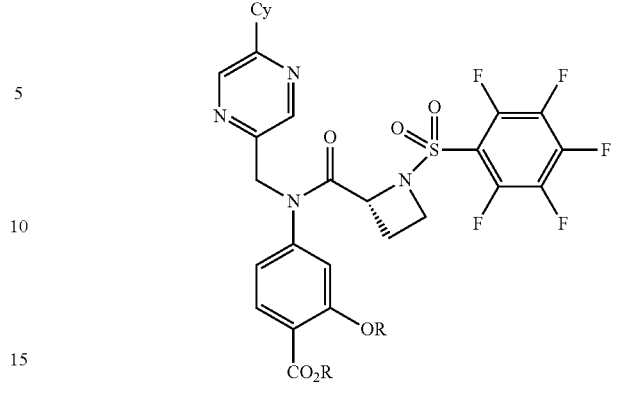

(R)-4-(N-((5-cyclohexylpyrazin-2-yl)methyl)-1-((perfluorophenyl)sulfonyl)azetidine-2-carboxamido)-2-hydroxybenzoic acid

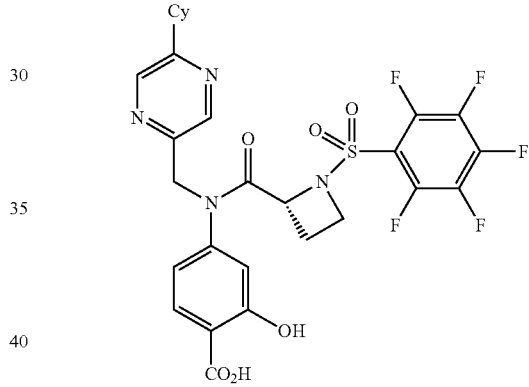

Step 1. To a solution of 5-chloropyrazine-2-carboxylic acid (300 mg, 1.89 mmol) in CH2Cl2 (3.8 mL) was added EDCI (401 mg, 2.09 mmol), DMAP (12.5 mg, 0.102 mmol) and MeOH (0.15 mL, 3.7 mmol) at room temperature. After stirring for 2 h, the reaction was quenched by adding saturated NH4Cl solution. The crude products were extracted with CH2Cl2 (×3), and the combined organic extracts were washed with brine, dried (MgSO4), and concentrated in vacuo. The residue was purified by flash column chromatography (hexane/EtOAc=9/1 to 7/1) to afford methyl 5-chloropyrazine-2-carboxylate (213 g, 65%) as a white solid. $^1$H NMR (300 MHz, CDCl$_3$) δ 9.12 (d, J=1.8 Hz, 1H), 8.73 (d, J=1.8 Hz, 1H), 4.07 (s, 3H).

Step 2. To a solution of methyl 5-chloropyrazine-2-carboxylate (601 mg, 3.48 mmol) in THF (11.6 mL) was added 1-cyclohexene-1-yl-boronic acid (656 mg, 5.21 mmol), K$_3$PO$_4$ (1.47 g, 6.91 mmol), Pd(OAc)$_2$ (39.2 mg, 0.175 mmol), SPhos (144 mg, 0.350 mmol) and H$_2$O (0.13 mL, 7.2 mmol) at room temperature. After stirring for 15 h at 40° C., the reaction was quenched by adding water. The crude products were extracted with EtOAc (×3), and the combined organic extracts were washed with brine, dried (MgSO$_4$), and concentrated in vacuo. The residue was purified by flash column chromatography (hexane/

EtOAc=9/1 to 4/1) to afford methyl 5-(cyclohex-1-en-1-yl)pyrazine-2-carboxylate (736 mg, 97%) as a pale yellow solid. ¹H NMR (300 MHz, CDCl₃) δ 9.21 (d, J=1.2 Hz, 1H), 8.81 (d, J=1.2 Hz, 1H), 6.98-7.01 (m, 1H), 4.05 (s, 3H), 2.55-2.60 (m, 2H), 2.34-2.38 (m, 2H), 1.81-1.89 (m, 2H), 1.70-1.77 (m, 2H).

Step 3. A solution of methyl 5-(cyclohex-1-en-1-yl)pyrazine-2-carboxylate (347 mg, 1.59 mmol) in EtOAc (16 mL) was added PtO2 (18 mg, 0.080 mmol) and stirred under H₂ atmosphere at room temperature. After stirring for 4 h, another PtO₂ (20 mg, 0.089 mmol) was added. After stirring for 1 h, the reaction mixture was filtered through Celite® pad (washed with EtOAc) and concentrated in vacuo. The residue was purified by flash column chromatography (hexane/EtOAc=9/1 to 4/1) to methyl 5-cyclohexylpyrazine-2-carboxylate (311 mg, 89%) as a pale yellow solid. ¹H NMR (300 MHz, CDCl₃) δ 9.23 (d, J=1.8 Hz, 1H), 8.59 (d, J=1.8 Hz, 1H), 4.05 (s, 3H), 2.82-2.91 (m, 1H), 1.31-1.99 (m, 10H).

Step 4. To a solution of methyl 5-cyclohexylpyrazine-2-carboxylate (556 mg, 2.52 mmol) in MeOH (12.6 mL) was added NaBH₄ (304 mg, 8.04 mmol) at 0° C. After stirring for 25 min at room temperature, another NaBH₄ (192 mg, 5.08 mmol) was added. After stirring for 35 min, the reaction mixture was evaporated to half volume and added water and EtOAc. The crude products were extracted with EtOAc (×3), and the combined organic extracts were washed with brine, dried (MgSO4), and concentrated in vacuo. The residue was purified by flash column chromatography (hexane/EtOAc=4/1 to 2/1) to afford (5-cyclohexylpyrazin-2-yl)methanol (464 mg, 96%) as a pale yellow oil. ¹H NMR (300 MHz, CDCl₃) δ 8.57 (d, J=1.2 Hz, 1H), 8.45 (d, J=1.2 Hz, 1H), 4.84 (s, 2H), 3.10 (brs, 1H, OH), 2.76-2.85 (m, 1H), 1.28-1.98 (m, 10H).

Step 5. To a solution of (5-cyclohexylpyrazin-2-yl)methanol (243 mg, 1.26 mmol) in CH2Cl2 (6.4 mL) was added Et3N (0.53 mL, 3.8 mmol) and MsCl (0.18 mL, 1.9 mmol) at 0° C. After stirring for 35 min, the reaction was quenched by the addition of saturated NaHCO3 solution. The crude products were extracted with CH2Cl2 (×3), and the combined organic extracts were washed with brine, dried (MgSO4), and concentrated in vacuo. The residue was purified by flash column chromatography (hexane/EtOAc=9/1 to 3/1) to afford (5-cyclohexylpyrazin-2-yl)methyl methanesulfonate (329 mg, 96%) as a purple solid. ¹H NMR (300 MHz, CDCl₃) δ 8.65 (d, J=1.2 Hz, 1H), 8.50 (d, J=1.2 Hz, 1H), 5.36 (s, 2H), 3.14 (s, 3H), 2.77-2.86 (m, 1H), 1.26-1.98 (m, 10H).

Step 6. Preparation by a similar procedure to Example 149, step 2, starting from (5-cyclohexylpyrazin-2-yl)methyl methanesulfonate to obtain benzyl 2-(benzyloxy)-4-(N-((5-cyclohexylpyrazin-2-yl)methyl)-2,2,2-trifluoroacetamido)benzoate. ¹H NMR (300 MHz, CDCl₃) δ 8.48 (s, 1H), 8.40 (d, J=1.2 Hz, 1H), 7.86 (d, J=8.1 Hz, 1H), 7.33-7.41 (m, 10H), 6.99 (s, 1H), 6.93 (d, J=8.1 Hz, 1H), 5.35 (s, 2H), 5.09 (s, 2H), 4.99 (s, 2H), 2.72-2.81 (m, 1H), 1.26-1.96 (m, 10H).

Step 7. Preparation by a similar procedure to Example 136, step 5, starting from benzyl 2-(benzyloxy)-4-(N-((5-cyclohexylpyrazin-2-yl)methyl)-2,2,2-trifluoroacetamido)benzoate to obtain benzyl 2-(benzyloxy)-4-(((5-cyclohexylpyrazin-2-yl)methyl)amino)benzoate. ¹H NMR (300 MHz, CDCl₃) δ 8.52 (d, J=1.2 Hz, 1H), 8.43 (d, J=1.2 Hz, 1H), 7.87 (d, J=9.0 Hz, 1H), 7.28-7.50 (m, 10H), 6.27-6.31 (m, 2H), 5.32 (s, 2H), 5.15-5.19 (m, 3H), 4.48 (d, J=4.5 Hz, 2H), 2.73-2.81 (m, 1H), 1.28-1.97 (m, 10H).

Step 8. Preparation by a similar procedure to Example 136, step 6, starting from benzyl 2-(benzyloxy)-4-(((5-cyclohexylpyrazin-2-yl)methyl)amino)benzoate to obtain benzyl (R)-2-(benzyloxy)-4-(N-((5-cyclohexylpyrazin-2-yl)methyl)-1-((perfluorophenyl)sulfonyl)azetidine-2-carboxamido)benzoate. ¹H NMR (300 MHz, CDCl₃) δ 8.39 (s, 1H), 8.35 (s, 1H), 7.84 (d, J=8.4 Hz, 1H), 7.33-7.44 (m, 10H), 6.92 (d, J=1.8 Hz, 1H), 6.82 (dd, J=1.8, 8.4 Hz, 1H), 5.37 (s, 2H), 5.21 (d, J=12.3 Hz, 1H), 5.12 (d, J=12.3 Hz, 1H), 4.99 (d, J=15.9 Hz, 1H), 4.88-4.94 (m, 1H), 4.76 (d, J=15.9 Hz, 1H), 4.01-4.09 (m, 1H), 3.88-3.98 (m, 1H), 2.69-2.78 (m, 1H), 1.26-2.10 (m, 12H).

Step 9. Preparation by a similar procedure to Example 61, step 7, starting from benzyl 2-(benzyloxy)-4-(((5-cyclohexylpyrazin-2-yl)methyl)amino)benzoate to obtain the compound of Example 110 (R)-4-(N-((5-cyclohexylpyrazin-2-yl)methyl)-1-((perfluorophenyl)sulfonyl)azetidine-2-carboxamido)-2-hydroxybenzoic acid. ¹H NMR (300 MHz, CDCl₃) δ 11.23 (brs, 1H, OH), 8.83 (s, 1H), 8.43 (s, 1H), 7.70 (d, J=8.4 Hz, 1H), 6.69 (dd, J=1.8, 8.4 Hz, 1H), 6.61 (d, J=1.8 Hz, 1H), 4.95-5.07 (m, 3H), 4.10-4.18 (m, 1H), 3.96-4.05 (m, 1H), 2.79-2.90 (m, 1H), 2.20-2.31 (m, 1H), 1.25-2.08 (m, 11H). MS (ESI+) m/z 641.0 [M+H]+.

Example 111

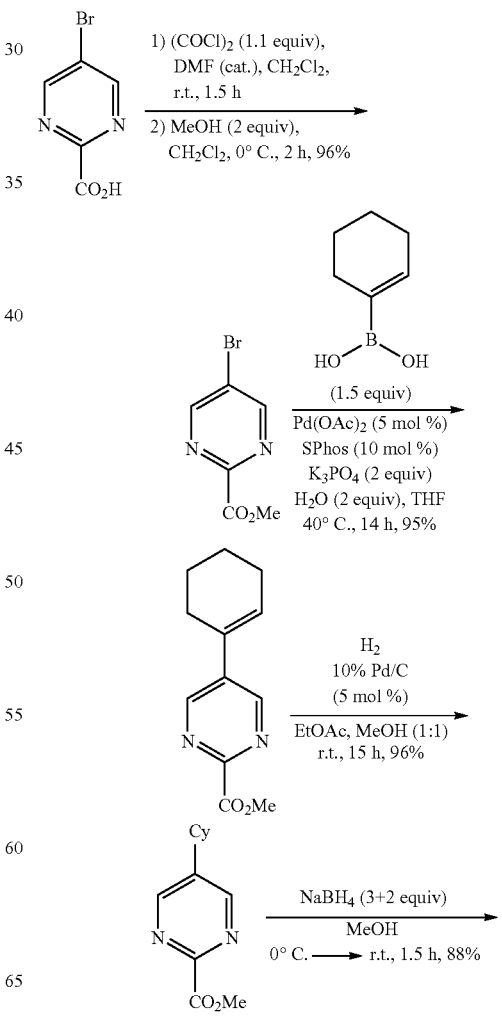

311
-continued

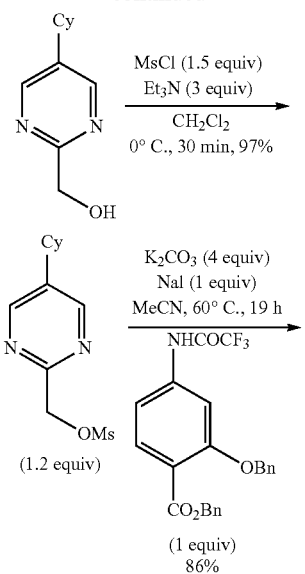

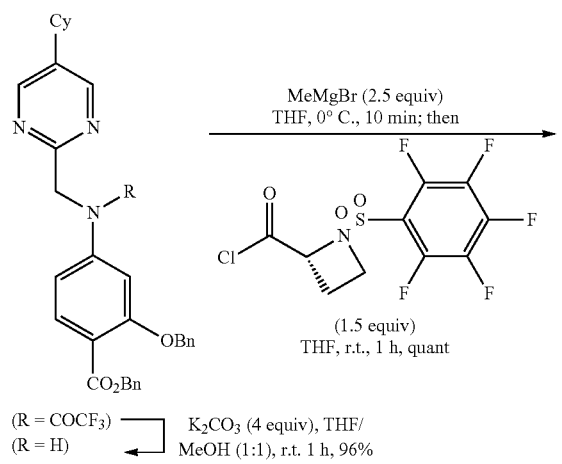

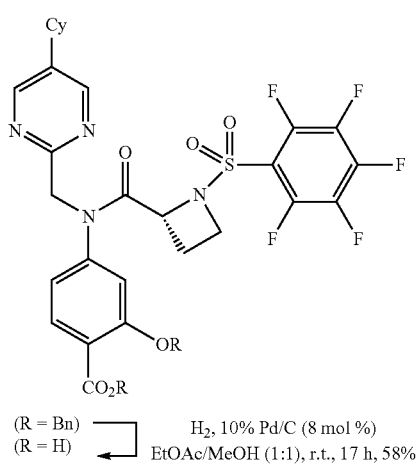

312

(R)-4-(N-((5-cyclohexylpyrimidin-2-yl)methyl)-1-((perfluorophenyl)sulfonyl) azetidine-2-carboxamido)-2-hydroxybenzoic acid

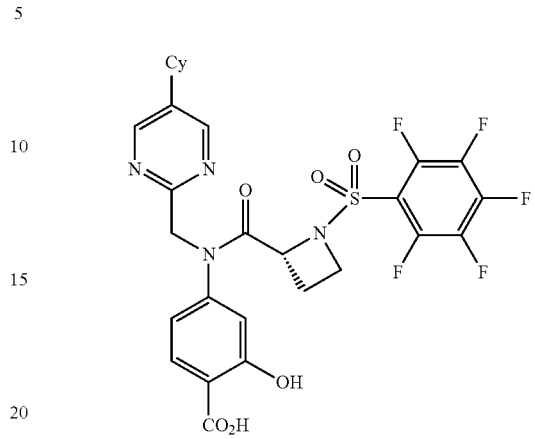

Step 1. To a solution of 5-bromopyrimidine-2-carboxylic acid (500 mg, 2.47 mmol) in DCM (5.0 mL), in a two-necked flask equipped with a bubbler, was added oxalyl chloride (0.23 mL, 2.72 mmol) and two drops of DMF at room temperature. After stirring for 1.5 h, the solvent was removed in vacuo. The acyl chloride was dissolved in CH2Cl2 (5.0 mL) and added MeOH (0.20 mL, 4.93 mmol) at 0° C. After stirring for 2 h, the reaction mixture was quenched by adding saturated NaHCO$_3$ solution. The crude products were extracted with CH2Cl2 (×3), and the combined organic extracts were washed with brine, dried (MgSO4), and concentrated in vacuo. The residue was purified by flash column chromatography (hexane/EtOAc=3/1 to 2/1) to afford desired methyl 5-bromopyrimidine-2-carboxylate (294 mg, 90%) as a white solid. $^1$H NMR (300 MHz, CDCl$_3$) δ 9.01 (s, 2H), 4.10 (s, 3H).

Step 2. Preparation by a similar procedure to Example 110, step 2, starting from methyl 5-bromopyrimidine-2-carboxylate to obtain methyl 5-(cyclohex-1-en-1-yl)pyrimidine-2-carboxylate. $^1$H NMR (300 MHz, CDCl$_3$) δ 8.91 (s, 2H), 6.42-6.44 (m, 1H), 4.09 (s, 3H), 2.43-2.48 (m, 2H), 2.28-2.34 (m, 2H), 1.84-1.88 (m, 2H), 1.71-1.76 (m, 2H).

Step 3. Preparation by a similar procedure to Example 110, step 3, starting from methyl 5-(cyclohex-1-en-1-yl)pyrimidine-2-carboxylate to obtain methyl 5-cyclohexylpyrimidine-2-carboxylate. $^1$H NMR (300 MHz, CDCl$_3$) δ 8.78 (s, 2H), 4.08 (s, 3H), 2.61-2.70 (m, 1H), 1.25-1.96 (m, 10H).

Step 4. Preparation by a similar procedure to Example 110, step 4, starting from methyl 5-cyclohexylpyrimidine-2-carboxylate to obtain (5-cyclohexylpyrimidin-2-yl)methanol. $^1$H NMR (300 MHz, CDCl$_3$) δ 8.59 (s, 2H), 4.83 (s, 2H), 3.71 (brs, 1H, OH), 2.53-2.62 (m, 1H), 1.77-1.97 (m, 5H), 1.25-1.54 (m, 5H).

Step 5. Preparation by a similar procedure to Example 110, step 4, starting from (5-cyclohexylpyrimidin-2-yl)methanol to obtain (5-cyclohexylpyrimidin-2-yl)methyl methanesulfonate. $^1$H NMR (300 MHz, CDCl$_3$) δ 8.63 (s, 2H), 5.43 (s, 2H), 3.22 (s, 3H), 2.54-2.63 (m, 1H), 1.76-1.98 (m, 5H), 1.25-1.54 (m, 5H).

Step 6. Preparation by a similar procedure to Example 149, step 2, starting from (5-cyclohexylpyrimidin-2-yl)methyl methanesulfonate to obtain benzyl 2-(benzyloxy)-4-(N-((5-cyclohexylpyrimidin-2-yl)methyl)-2,2,2-trifluoroacetamido)benzoate. $^1$H NMR (300 MHz, CDCl$_3$) δ 8.52 (s, 2H), 7.86 (d, J=8.1 Hz, 1H), 7.32-7.42 (m, 10H), 7.23 (d, J=1.2 Hz, 1H), 7.11 (dd, J=1.2, 8.1 Hz, 1H), 5.35 (s, 2H), 5.13 (s, 2H), 5.07 (s, 2H), 2.48-2.58 (m, 1H), 1.76-1.96 (m, 5H), 1.24-1.53 (m, 5H).

Step 7. Preparation by a similar procedure to Example 136, step 5, starting from (5-cyclohexylpyrimidin-2-yl) methyl methanesulfonate to obtain benzyl 2-(benzyloxy)-4-(((5-cyclohexylpyrimidin-2-yl)methyl)amino)benzoate. $^1$H NMR (300 MHz, CDCl$_3$) δ 8.59 (s, 2H), 7.88 (d, J=9.3 Hz, 1H), 7.49-7.52 (m, 2H), 7.30-7.43 (m, 8H), 6.31-6.35 (m, 2H), 5.58 (t, J=5.4 Hz, 1H, NH), 5.33 (s, 2H), 5.18 (s, 2H), 4.56 (d, J=5.4 Hz, 2H), 2.52-2.61 (m, 1H), 1.77-1.98 (m, 5H), 1.26-1.54 (m, 5H).

Step 8. Preparation by a similar procedure to Example 136, step 6, starting from benzyl 2-(benzyloxy)-4-(((5-cyclohexylpyrimidin-2-yl)methyl)amino)benzoate to obtain benzyl (R)-2-(benzyloxy)-4-(N-((5-cyclohexylpyrimidin-2-yl)methyl)-1-((perfluorophenyl)sulfonyl) azetidine-2-carboxamido)benzoate. $^1$H NMR (300 MHz, CDCl$_3$) δ 8.49 (s, 2H), 7.83 (d, J=8.4 Hz, 1H), 7.32-7.45 (m, 10H), 7.15 (d, J=1.8 Hz, 1H), 6.98 (dd, J=1.8, 8.4 Hz, 1H), 5.37 (s, 2H), 5.25 (d, J=12.6 Hz, 1H), 5.16 (d, J=12.6 Hz, 1H), 5.09 (d, J=17.1 Hz, 1H), 4.98-5.04 (m, 1H), 4.82 (d, J=17.1 Hz, 1H), 3.94-4.13 (m, 2H), 2.47-2.56 (m, 2H), 2.11-2.21 (m, 1H), 1.24-1.95 (m, 11H).

Step 9. Preparation by a similar procedure to Example 61, step 7, starting from benzyl benzyl (R)-2-(benzyloxy)-4-(N-((5-cyclohexylpyrimidin-2-yl)methyl)-1-((perfluorophenyl) sulfonyl) azetidine-2-carboxamido)benzoate to obtain the compound of Example 111 (R)-4-(N-((5-cyclohexylpyrimidin-2-yl)methyl)-1-((perfluorophenyl)sulfonyl)azetidine-2-carboxamido)-2-hydroxybenzoic acid. $^1$H NMR (300 MHz, CDCl$_3$) δ 11.08 (brs, 1H, OH), 8.63 (s, 2H), 7.83 (d, J=8.4 Hz, 1H), 6.82-6.91 (m, 2H), 5.12-5.32 (m, 3H), 4.90 (d, J=17.1 Hz, 1H), 4.02-4.23 (m, 2H), 2.53-2.64 (m, 1H), 2.35-2.46 (m, 1H), 1.76-2.20 (m, 6H), 1.24-1.54 (m, 5H). MS (ESI+) m/z 641.1 [M+H]+.

Example 112

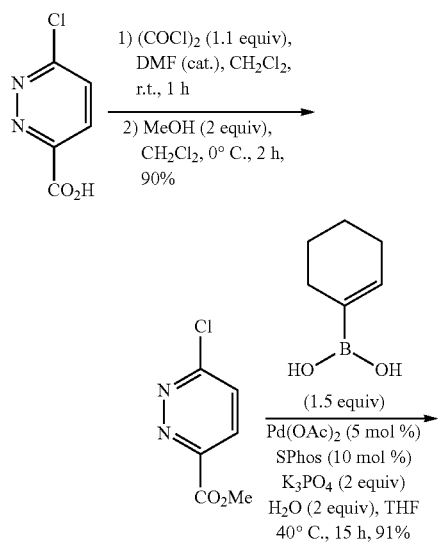

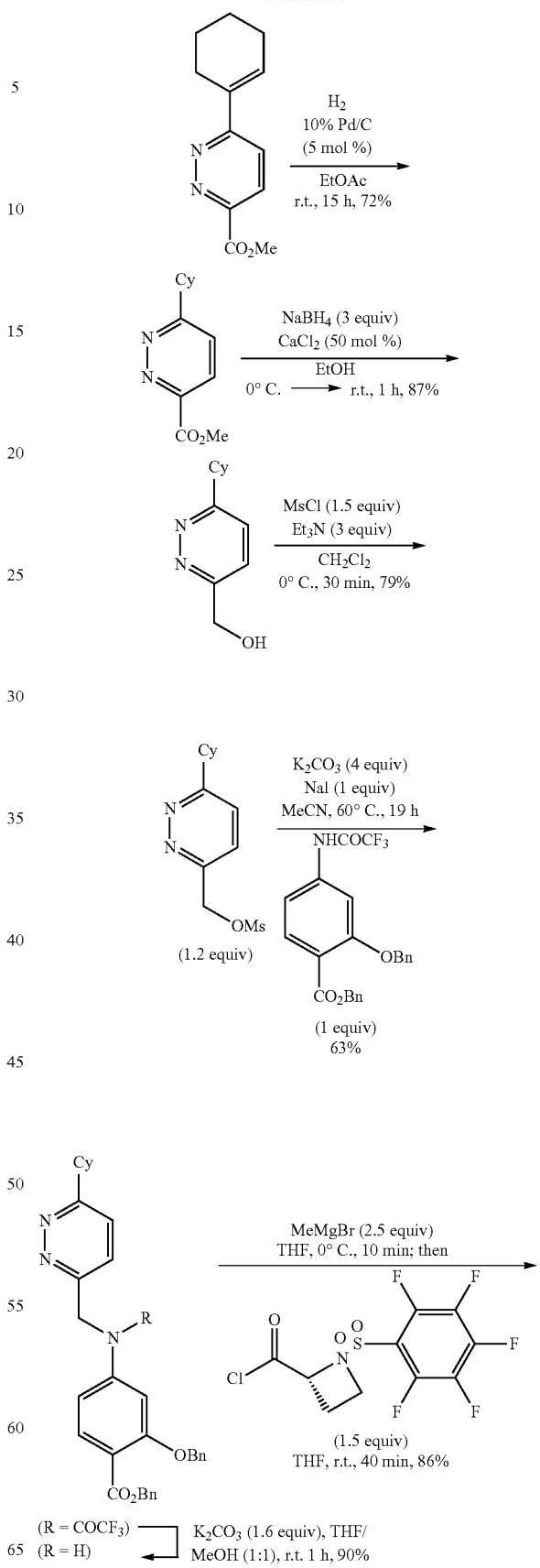

-continued

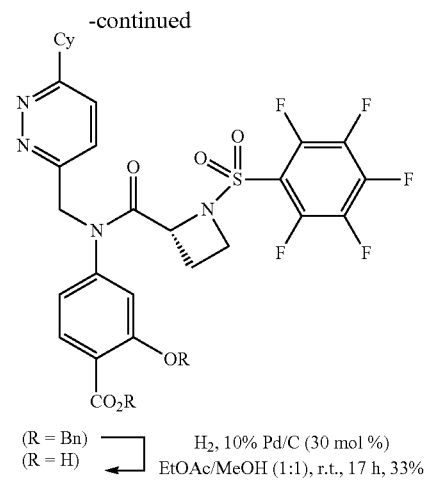

(R)-4-(N-((6-cyclohexylpyridazin-3-yl)methyl)-1-
((perfluorophenyl)sulfonyl)azetidine-2-carbox-
amido)-2-hydroxybenzoic acid

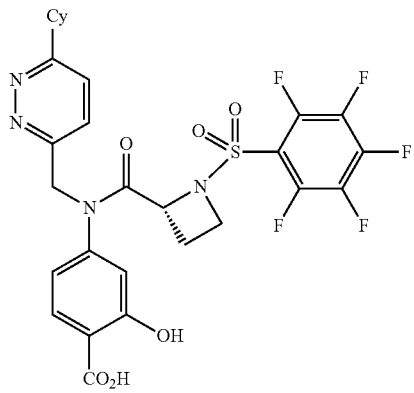

Step 1. Preparation by a similar procedure to Example 111, step 1, starting from 6-chloropyridazine-3-carboxylic acid to obtain methyl 6-chloropyridazine-3-carboxylate. $^1$H NMR (300 MHz, CDCl$_3$) δ 8.18 (d, J=8.7 Hz, 1H), 7.69 (d, J=8.7 Hz, 1H), 4.09 (s, 3H).

Step 2. Preparation by a similar procedure to Example 110, step 2, starting from methyl 6-chloropyridazine-3-carboxylate to obtain methyl 6-(cyclohex-1-en-1-yl)pyridazine-3-carboxylate. $^1$H NMR (300 MHz, CDCl$_3$) δ 8.11 (d, J=8.7 Hz, 1H), 7.67 (d, J=8.7 Hz, 1H), 6.95-6.98 (m, 1H), 4.08 (s, 3H), 2.65-2.72 (m, 2H), 2.32-2.40 (m, 2H), 1.82-1.91 (m, 2H), 1.70-1.79 (m, 2H).

Step 3. Preparation by a similar procedure to Example 110, step 3, starting from methyl 6-(cyclohex-1-en-1-yl)pyridazine-3-carboxylate to obtain methyl 6-cyclohexylpyridazine-3-carboxylate. $^1$H NMR (300 MHz, CDCl$_3$) δ 8.12 (d, J=8.7 Hz, 1H), 7.48 (d, J=8.7 Hz, 1H), 4.08 (s, 3H), 3.06-3.17 (m, 1H), 2.00-2.09 (m, 2H), 1.88-1.98 (m, 2H), 1.78-1.86 (m, 2H), 1.27-1.68 (m, 5H).

Step 4. To a solution of methyl 6-cyclohexylpyridazine-3-carboxylate (90 mg, 0.41 mmol) and CaCl$_2$ (24 mg, 0.22 mmol) in EtOH (4.0 mL) was added NaBH4 (47 mg, 1.3 mmol) at 0° C. After stirring for 1 h at room temperature, the reaction mixture quenched by adding saturated NaHCO3 solution. The crude products were extracted with EtOAc (×3), and the combined organic extracts were washed with brine, dried (MgSO$_4$), and concentrated in vacuo. The residue was purified by flash column chromatography (hexane/EtOAc=2/1 to 1/2) to afford (6-cyclohexylpyridazin-3-yl)methanol (68 mg, 87%) as a colorless oil. $^1$H NMR (300 MHz, CDCl$_3$) δ 7.42 (d, J=9.0 Hz, 1H), 7.36 (d, J=9.0 Hz, 1H), 4.95 (s, 2H), 3.59 (brs, 1H, OH), 2.93-3.03 (m, 1H), 1.98-2.06 (m, 2H), 1.87-1.95 (m, 2H), 1.25-1.86 (m, 6H).

Step 5. Preparation by a similar procedure to Example 110, step 4, starting from (6-cyclohexylpyridazin-3-yl) methanol to obtain (6-cyclohexylpyridazin-3-yl)methyl methanesulfonate. $^1$H NMR (300 MHz, CDCl$_3$) δ 7.62 (d, J=9.0 Hz, 1H), 7.43 (d, J=9.0 Hz, 1H), 5.54 (s, 2H), 3.15 (s, 3H), 2.97-3.06 (m, 1H), 1.98-2.06 (m, 2H), 1.88-1.96 (m, 2H), 1.78-1.86 (m, 1H), 1.27-1.68 (m, 5H).

Step 6. Preparation by a similar procedure to Example 149, step 2, starting from (6-cyclohexylpyridazin-3-yl) methyl methanesulfonate to obtain benzyl 2-(benzyloxy)-4-(N-((6-cyclohexylpyridazin-3-yl)methyl)-2,2,2-trifluoroacetamido)benzoate. $^1$H NMR (300 MHz, CDCl$_3$) δ 7.86 (d, J=8.1 Hz, 1H), 7.31-7.48 (m, 12H), 7.05 (d, J=1.8 Hz, 1H), 6.96 (dd, J=1.8, 8.1 Hz, 1H), 5.35 (s, 2H), 5.13 (s, 2H), 5.10 (s, 2H), 2.94-3.02 (m, 1H), 1.97-2.05 (m, 2H), 1.86-1.94 (m, 2H), 1.26-1.84 (m, 6H).

Step 7. Preparation by a similar procedure to Example 136, step 5, starting from benzyl 2-(benzyloxy)-4-(N-((6-cyclohexylpyridazin-3-yl)methyl)-2,2,2-trifluoroacetamido) benzoate to obtain benzyl 2-(benzyloxy)-4-(((6-cyclohexylpyridazin-3-yl)methyl)amino)benzoate. $^1$H NMR (300 MHz, CDCl$_3$) δ 7.87 (d, J=8.4 Hz, 1H), 7.29-7.49 (m, 12H), 6.25-6.30 (m, 2H), 5.49 (t, J=5.4 Hz, 1H, NH), 5.32 (s, 2H), 5.13 (s, 2H), 4.64 (d, J=5.4 Hz, 2H), 2.92-3.02 (m, 1H), 1.98-2.05 (m, 2H), 1.87-1.96 (m, 2H), 1.77-1.85 (m, 1H), 1.28-1.68 (m, 5H).

Step 8. Preparation by a similar procedure to Example 136, step 6, starting from benzyl 2-(benzyloxy)-4-(((6-cyclohexylpyridazin-3-yl)methyl)amino)benzoate to obtain benzyl (R)-2-(benzyloxy)-4-(N-((6-cyclohexylpyridazin-3-yl)methyl)-1-((perfluorophenyl)sulfonyl)azetidine-2-carboxamido)benzoate. $^1$H NMR (300 MHz, CDCl$_3$) δ 7.83 (d, J=8.4 Hz, 1H), 7.30-7.43 (m, 12H), 6.93 (d, J=1.8 Hz, 1H), 6.89 (dd, J=1.8, 8.4 Hz, 1H), 5.37 (s, 2H), 5.19 (d, J=12.3 Hz, 1H), 5.06-5.14 (m, 2H), 4.90-5.00 (m, 2H), 3.90-4.08 (m, 2H), 2.91-3.01 (m, 1H), 1.24-2.13 (m, 12H)

Step 9. Preparation by a similar procedure to Example 61, step 7, starting from benzyl (R)-2-(benzyloxy)-4-(N-((6-cyclohexylpyridazin-3-yl)methyl)-1-((perfluorophenyl) sulfonyl)azetidine-2-carboxamido)benzoate to obtain the compound of Example 112 (R)-4-(N-((6-cyclohexylpyridazin-3-yl)methyl)-1-((perfluorophenyl)sulfonyl)azetidine-2-carboxamido)-2-hydroxybenzoic acid. $^1$H NMR (300 MHz, CDCl$_3$) δ 11.29 (brs, 1H, OH), 7.94 (d, J=8.1 Hz, 1H), 7.78 (d, J=8.4 Hz, 1H), 7.59 (d, J=8.4 Hz, 1H), 6.55-6.63 (m, 2H), 5.33 (d, J=13.8 Hz, 1H), 5.11 (d, J=13.8 Hz, 1H), 4.97 (t, J=7.8 Hz, 1H), 3.94-4.15 (m, 2H), 3.03-3.14 (m, 1H), 1.26-2.28 (m, 12H). HRMS (ESI+) m/z 641.1491 [M+H]+.

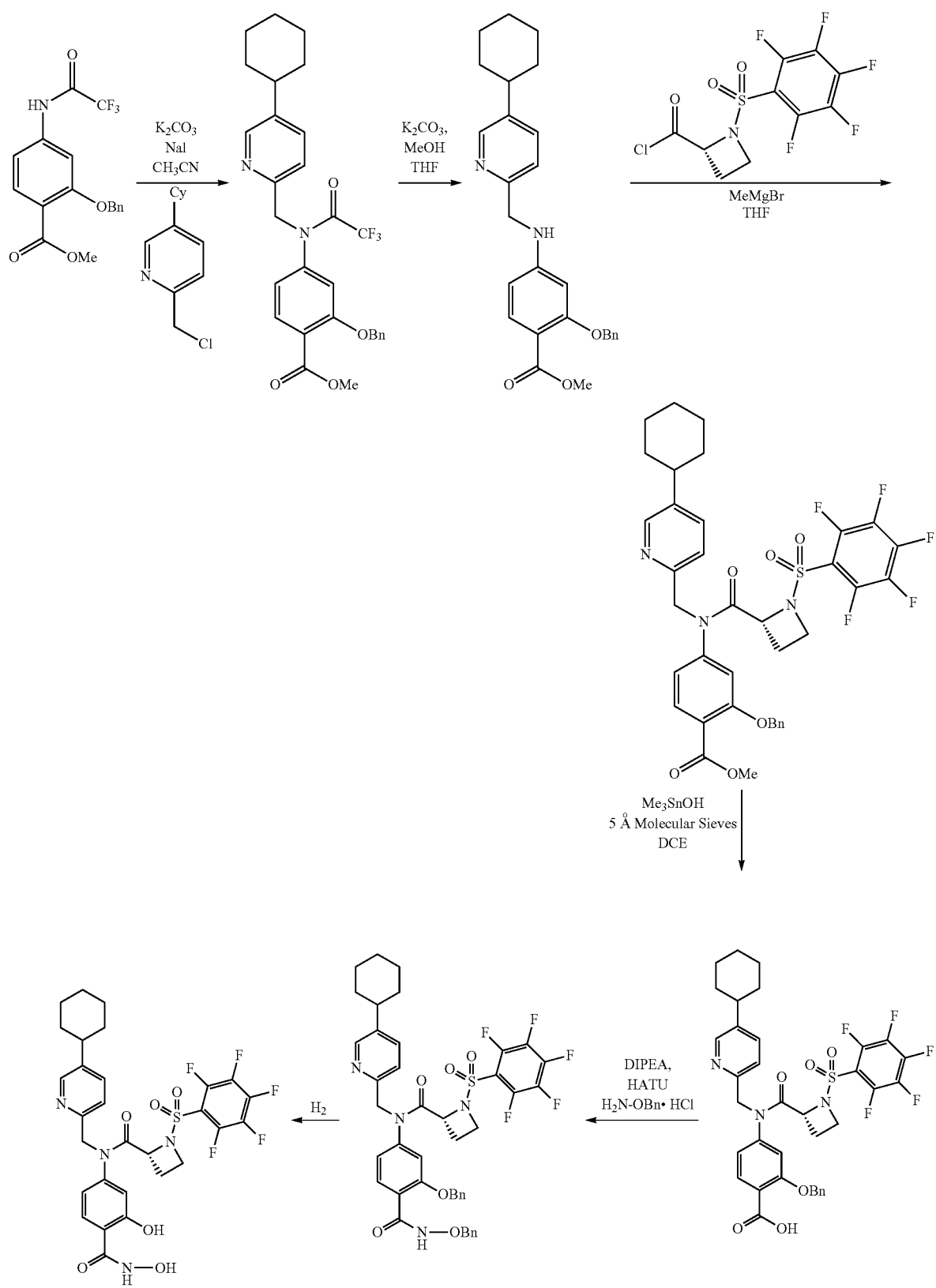
Example 113

(R)—N-((5-cyclohexylpyridin-2-yl)methyl)-N-(3-hydroxy-4-(hydroxycarbamoyl)phenyl)-1-((perfluorophenyl)sulfonyl)azetidine-2-carboxamide

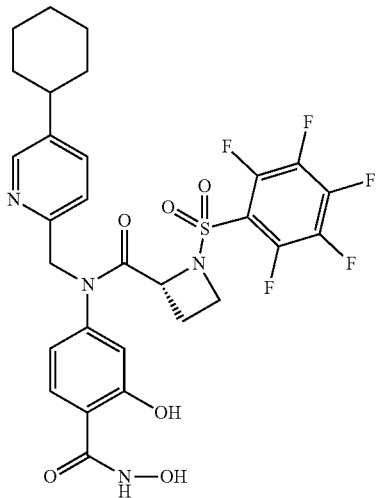 [SMILES: O=C(NO)c1ccc(N(Cc2ccc(C3CCCCC3)cn2)C(=O)[C@H]2CCN2S(=O)(=O)c2c(F)c(F)c(F)c(F)c2F)cc1O]

Step 1. Starting from methyl 2-(benzyloxy)-4-(2,2,2-trifluoroacetamido)benzoate (see Example 106 for preparation) to obtain methyl 2-(benzyloxy)-4-(N-((5-cyclohexylpyridin-2-yl)methyl)-2,2,2-trifluoroacetamido)benzoate. $^1$H NMR (300 MHz, CDCl$_3$) δ 8.39 (d, J=2.3 Hz, 1H), 7.81 (d, J=8.2 Hz, 1H), 7.57-7.24 (m, 6H), 7.19 (d, J=8.0 Hz, 1H), 6.93 (d, J=2.0 Hz, 1H), 6.89 (dd, J=8.2, 2.0 Hz, 1H), 5.06 (s, 2H), 4.99 (s, 3H), 3.91 (s, 3H), 2.60-2.47 (m, 1H), 1.96-1.71 (m, 5H), 1.52-1.33 (m, 5H).

Step 2. Preparation by a similar procedure to Example 53, step 2, starting from methyl 2-(benzyloxy)-4-(N-((5-cyclohexylpyridin-2-yl)methyl)-2,2,2-trifluoroacetamido)benzoate to obtain methyl 2-(benzyloxy)-4-(((5-cyclohexylpyridin-2-yl)methyl)amino)benzoate. $^1$H NMR (300 MHz, CDCl$_3$) δ 8.45 (d, J=2.2 Hz, 1H), 7.82 (dd, J=8.5, 0.7 Hz, 1H), 7.60-7.46 (m, 3H), 7.45-7.26 (m, 3H), 7.25-7.17 (m, 1H), 6.38-6.15 (m, 2H), 5.35 (br, 1H), 5.14 (s, 2H), 4.45 (s, 2H), 3.86 (s, 3H), 2.63-2.48 (m, 1H), 1.97-1.71 (m, 5H), 1.53-1.31 (m, 5H)

Step 3. Preparation by a similar procedure to Example 53, step 3, starting from methyl 2-(benzyloxy)-4-(((5-cyclohexylpyridin-2-yl)methyl)amino)benzoate to obtain methyl (R)-2-(benzyloxy)-4-(N-((5-cyclohexylpyridin-2-yl)methyl)-1-((perfluorophenyl)sulfonyl)azetidine-2-carboxamido)benzoate. $^1$H NMR (300 MHz, CDCl$_3$) δ 8.35 (d, J=2.2 Hz, 1H), 7.83-7.76 (m, 1H), 7.53-7.30 (m, 6H), 7.13 (d, J=8.1 Hz, 1H), 6.83 (d, J=1.9 Hz, 1H), 6.81-6.73 (m, 1H), 5.18 (d, J=12.6 Hz, 1H), 5.07 (d, J=12.6 Hz, 1H), 4.99-4.80 (m, 3H), 4.20-3.85 (m, 2H), 3.94 (s, 3H), 2.58-2.45 (m, 1H), 2.14-1.98 (m, 1H), 1.96-1.51 (m, 6H), 1.51-1.28 (m, 5H).

Step 4. Methyl (R)-2-(benzyloxy)-4-(N-((5-cyclohexylpyridin-2-yl)methyl)-1-((perfluorophenyl)sulfonyl)azetidine-2-carboxamido)benzoate (0.780 g, 1.05 mmol) and trimethyltin hydroxide (1.9 g, 10.5 mmol) were thoroughly flushed with N2. DCE (26 mL) was added followed by powdered 5 Å molecular sieves (0.53 g). The mixture was heated at 85° C. for 77 h. The mixture was concentrated and the residue was taken up in EtOAc. The organic solution was washed with pH2 buffer (3×), brine, dried (sodium sulfate) and concentrated. Purification by column chromatography gave the desired product (R)-2-(benzyloxy)-4-(N-((5-cyclohexylpyridin-2-yl)methyl)-1-((perfluorophenyl)sulfonyl)azetidine-2-carboxamido)benzoic acid (0.47 g, 61%) and recovered starting material (0.16 g). MS (ESI): [M+H]+ m/z 730.3.

Step 5. To a solution of (R)-2-(benzyloxy)-4-(N-((5-cyclohexylpyridin-2-yl)methyl)-1-((perfluorophenyl)sulfonyl)azetidine-2-carboxamido)benzoic acid (139.1 mg, 0.19 mmol) in DCM (5 mL) was added DIPEA (0.063 mL, 0.36 mmol) followed by HATU (79.1 mg 0.21 mmol) at 0° C. under N$_2$. The mixture was allowed to reach rt and stirred for 75 min before H$_2$NOBn.HCl (34.2 mg, 0.214 mmol) was added. The mixture was stirred for 5.5 h. Aqueous 10% sodium bicarbonate was added, and the mixture was extracted with DCM. The extract was dried (sodium sulfate) and concentrated. Purification by column chromatography gave (R)—N-(3-(benzyloxy)-4-((benzyloxy)carbamoyl)phenyl)-N-((5-cyclohexylpyridin-2-yl)methyl)-1-((perfluorophenyl)sulfonyl)azetidine-2-carboxamide (109 mg, 68% yield). MS (ESI): [M+H]+ m/z 834.9.

Preparation by a similar procedure to Example 4, step 3, starting from (R)—N-(3-(benzyloxy)-4-((benzyloxy)carbamoyl)phenyl)-N-((5-cyclohexylpyridin-2-yl)methyl)-1-((perfluorophenyl)sulfonyl)azetidine-2-carboxamide to obtain the compound of Example 113 (R)—N-((5-cyclohexylpyridin-2-yl)methyl)-N-(3-hydroxy-4-(hydroxycarbamoyl)phenyl)-1-((perfluorophenyl)sulfonyl)azetidine-2-carboxamide. MS (ESI): [M+H]+ m/z 654.9.

Example 114

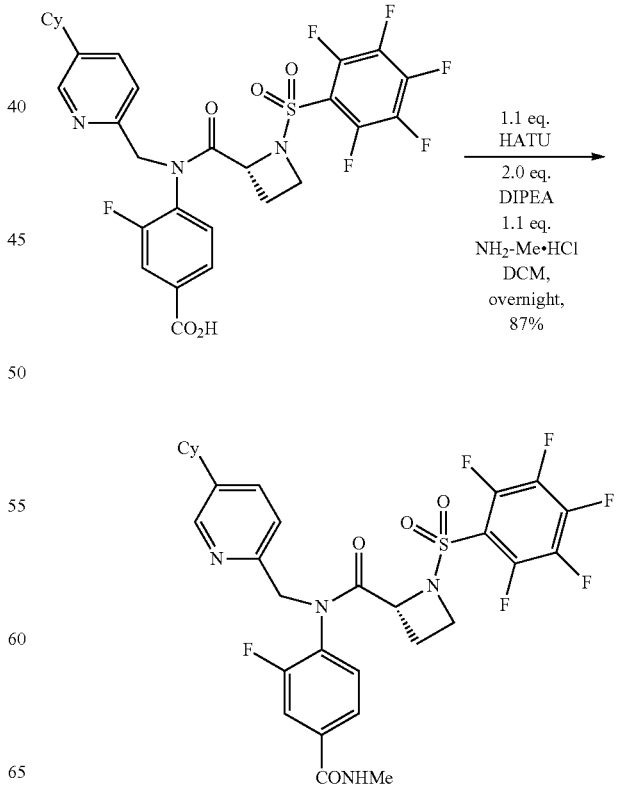

321

(R)—N-((5-cyclohexylpyridin-2-yl)methyl)-N-(2-fluoro-4-(methylcarbamoyl)phenyl)-1-((perfluorophenyl)sulfonyl)azetidine-2-carboxamide

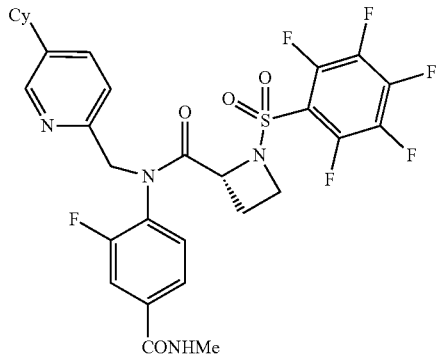

Step 1. Preparation by a similar procedure to Example 113, step 5, starting from (R)-4-(N-((5-cyclohexylpyridin-2-yl)methyl)-1-((perfluorophenyl)sulfonyl)azetidine-2-carboxamido)-3-fluorobenzoic acid to obtain the compound of Example 114 (R)—N-((5-cyclohexylpyridin-2-yl)methyl)-N-(2-fluoro-4-(methylcarbamoyl)phenyl)-1-((perfluorophenyl)sulfonyl)azetidine-2-carboxamide. MS (ESI): [M+H]+ m/z 654.9.

Example 115

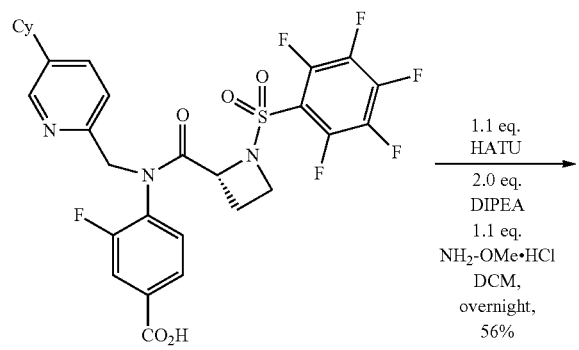

322

-continued

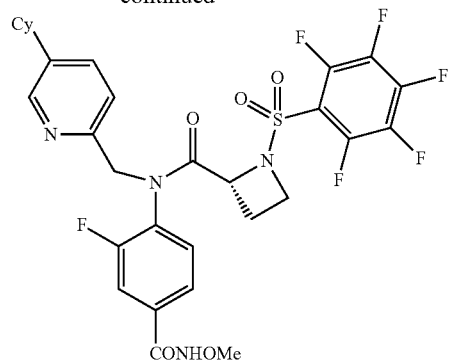

(R)—N-((5-cyclohexylpyridin-2-yl)methyl)-N-(2-fluoro-4-(methoxycarbamoyl)phenyl)-1-((perfluorophenyl)sulfonyl)azetidine-2-carboxamide

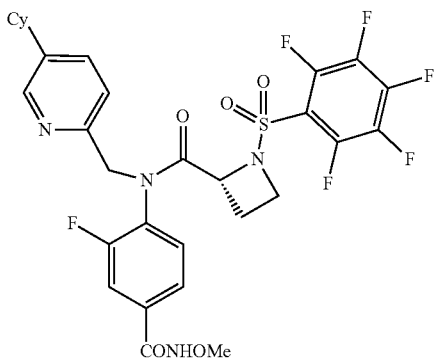

Step 1. Preparation by a similar procedure to Example 113, step 5, starting from (R)-4-(N-((5-cyclohexylpyridin-2-yl)methyl)-1-((perfluorophenyl)sulfonyl)azetidine-2-carboxamido)-3-fluorobenzoic acid to obtain the compound of Example 115 (R)—N-((5-cyclohexylpyridin-2-yl)methyl)-N-(2-fluoro-4-(methoxy carbamoyl)phenyl)-1-((perfluorophenyl)sulfonyl)azetidine-2-carboxamide. MS (ESI): [M+H]+ m/z m/z=671.0.

Example 116

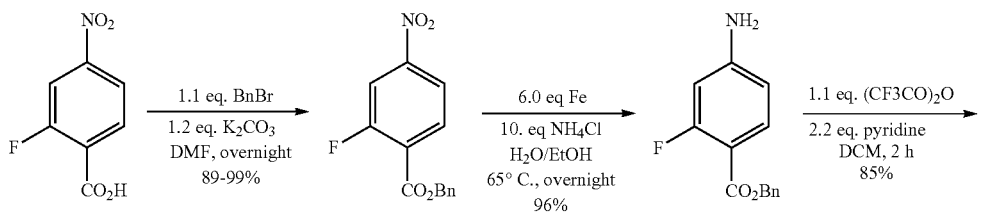

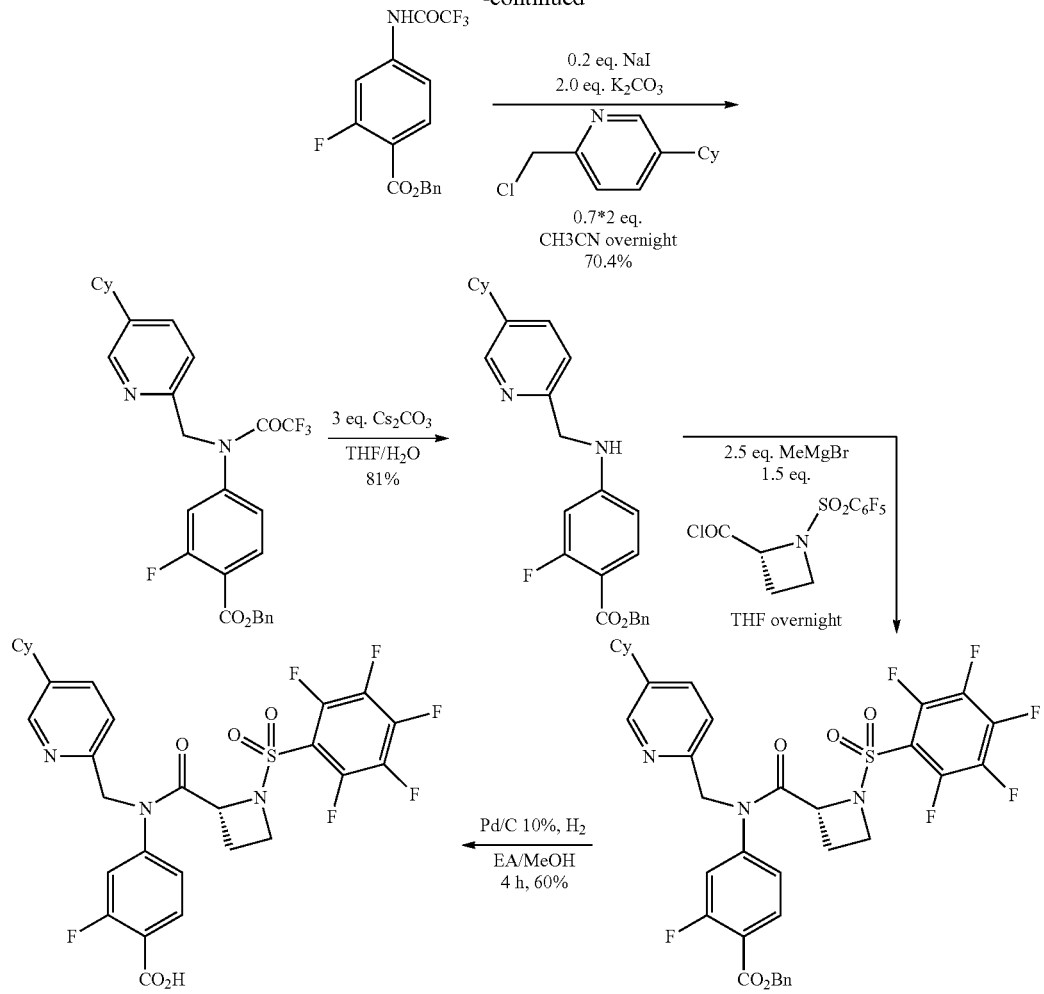

(R)-4-(N-((5-cyclohexylpyridin-2-yl)methyl)-1-((perfluorophenyl)sulfonyl)azetidine-2-carboxamido)-2-fluorobenzoic acid

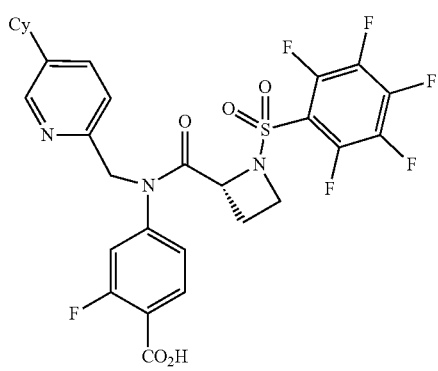

Step 1. Preparation by a similar procedure to Example 37, step 1, starting from 2-fluoro-4-nitrobenzoic acid to obtain benzyl 2-fluoro-4-nitrobenzoate. ¹H NMR (300 MHz, CDCl₃) δ 8.21-8.00 (m, 3H), 7.52-7.35 (m, 5H), 5.45 (s, 2H).

Step 2. Preparation by a similar procedure to Example 106, step 3, starting from benzyl 2-fluoro-4-nitrobenzoate to obtain benzyl 4-amino-2-fluorobenzoate. ¹H NMR (300 MHz, CDCl₃) δ 7.81 (dd, J=7.8 Hz, 8.4 Hz, 1H), 7.55-7.29 (m, 5H), 6.47-6.29 (m, 2H), 5.35 (s, 2H), 4.17 (s, 2H).

Step 3. Preparation by a similar procedure to Example 61, step 3, starting from benzyl 4-amino-2-fluorobenzoate to obtain benzyl 2-fluoro-4-(2,2,2-trifluoroacetamido)benzoate. ¹H NMR (300 MHz, CDCl₃) δ 8.04 (dd, J=8.3, 8.2 Hz, 1H), 7.97 (s, 1H), 7.67 (dd, J=11.9, 2.0 Hz, 1H), 7.51-7.35 (m, 5H), 7.33-7.28 (m, 1H), 5.40 (s, 2H).

Step 4. To a dry two-neck flask, NaI (0.2 eq), K₂CO₃ (2.0 eq) and benzyl 2-fluoro-4-(2,2,2-trifluoroacetamido)benzoate (160 mg, 0.47 mmol) was added under Argon. 2-(chloromethyl)-5-cyclohexylpyridine (0.7 eq) in acetonitrile (6 mL) was added. The mixture was stirred at 65° C. After 6 h, additional 2-(chloromethyl)-5-cyclohexylpyridine (0.7 eq) in acetonitrile (3 mL) was added, and the mixture was stirred at 65° C. overnight. Water (ca. 5 mL) was added, and the mixture was extracted with ethyl acetate (2×10 ml). The combined organic phase was dried over Na₂SO₄, and evaporated under reduced pressure. The crude product was purified by column chromatography (DCM/hexane=2:1) to give benzyl 4-(N-((5-cyclohexylpyridin-2-yl)methyl)-2,2,2-trifluoroacetamido)-2-fluorobenzoate (170 mg, 70% yield). ¹H NMR (300 MHz, CDCl₃) δ 8.41 (s, 1H), 7.99 (m, 1H), 7.65-6.95 (m, 9H), 5.40 (s, 2H), 5.02 (s, 2H), 2.65-2.53 (m, 1H), 2.05-1.65 (m, 5H), 1.56-1.20 (m, 5H).

Step 5. Preparation by a similar procedure to Example 109, step 4, starting from benzyl 4-(N-((5-cyclohexylpyridin-2-yl)methyl)-2,2,2-trifluoroacetamido)-2-fluorobenzoate to obtain benzyl 4-(((5-cyclohexylpyridin-2-yl)methyl)amino)-2-fluorobenzoate. $^1$H NMR (300 MHz, CDCl$_3$) δ 8.44 (d, J=1.2 Hz, 1H), 7.81 (dd, J=8.7 Hz, 8.4 Hz, 1H), 7.54-7.41 (m, 4H), 7.40-7.29 (m, 3H), 6.45 (d, J=8.9 Hz, 1H), 6.33 (d, J=13.5 Hz, 1H), 5.63 (s, 1H), 5.33 (s, 2H), 4.42 (s, 2H), 2.64-2.52 (m, 1H), 1.98-1.69 (m, 5H), 1.58-1.22 (m, 5H).

Step 6. Preparation by a similar procedure to Example 53, step 3, starting from benzyl 4-(((5-cyclohexylpyridin-2-yl)methyl)amino)-2-fluorobenzoate to obtain benzyl (R)-4-(N-((5-cyclohexylpyridin-2-yl)methyl)-1-((perfluorophenyl)sulfonyl)azetidine-2-carboxamido)-2-fluorobenzoate. $^1$H NMR (300 MHz, CDCl$_3$) δ 8.35 (s, 1H), 7.98 (dd, J=8.2 Hz, 8.0 Hz, 1H), 7.55-7.34 (m, 6H), 7.21-7.05 (m, 3H), 5.39 (s, 2H), 5.04 (m, 1H), 4.91 (s, 2H), 4.26-3.99 (m, 2H), 2.64-2.46 (m, 1H), 2.46-2.22 (m, 1H), 1.94-1.70 (m, 6H), 1.51-1.33 (m, 5H).

Step 7. Preparation by a similar procedure to Example 37, example 5, starting from benzyl (R)-4-(N-((5-cyclohexylpyridin-2-yl)methyl)-1-((perfluorophenyl)sulfonyl)azetidine-2-carboxamido)-2-fluorobenzoate to obtain the compound of Example 116 (R)-4-(N-((5-cyclohexylpyridin-2-yl)methyl)-1-((perfluorophenyl)sulfonyl)azetidine-2-carboxamido)-2-fluorobenzoic acid. MS (ESI): [M+H]+ m/z 641.9.

Example 117

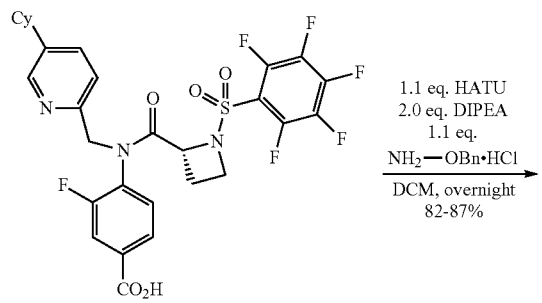

1.1 eq. HATU
2.0 eq. DIPEA
1.1 eq.
NH$_2$—OBn·HCl
DCM, overnight
82-87%

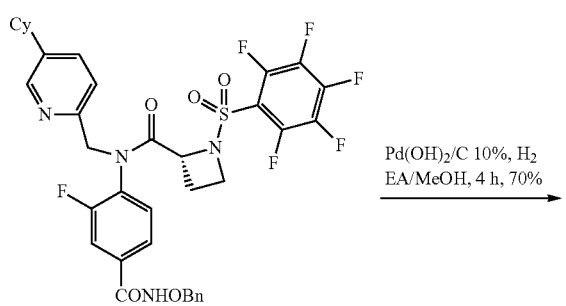

Pd(OH)$_2$/C 10%, H$_2$
EA/MeOH, 4 h, 70%

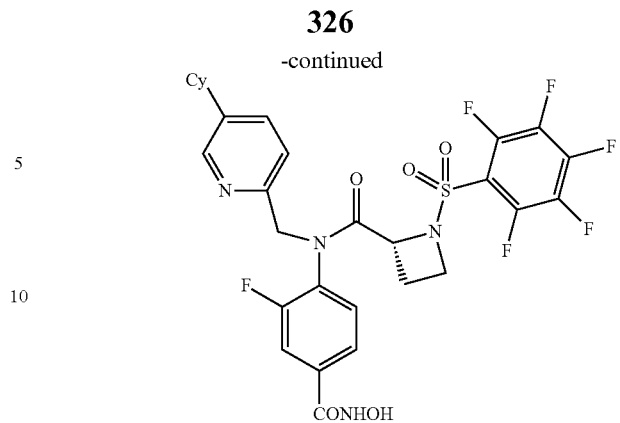

(R)—N-((5-cyclohexylpyridin-2-yl)methyl)-N-(2-fluoro-4-(hydroxycarbamoyl) phenyl)-1-((perfluorophenyl)sulfonyl)azetidine-2-carboxamide

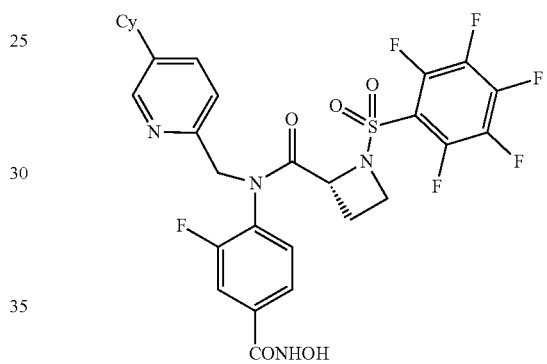

Step 1. Preparation by a similar procedure to Example 113, step 5, starting from (R)-4-(N-((5-cyclohexylpyridin-2-yl)methyl)-1-((perfluorophenyl)sulfonyl)azetidine-2-carboxamido)-3-fluorobenzoic acid to obtain (R)—N-(4-((benzyloxy)carbamoyl)-2-fluorophenyl)-N-((5-cyclohexylpyridin-2-yl)methyl)-1-((perfluorophenyl)sulfonyl)azetidine-2-carboxamide. $^1$H NMR (300 MHz, CDCl$_3$) δ 9.56 (s, 1H), 8.19 (s, 1H), 7.59-7.31 (m, 8H), 7.26-7.03 (m, 2H), 5.19 (d, J=14.8 Hz, 1H), 4.99 (s, 2H), 4.80-4.92 (m, 1H), 4.47 (d, J=14.8 Hz, 1H), 4.17-4.06 (m, 1H), 4.06-3.90 (m, 1H), 2.60-2.35 (m, 1H), 2.34-2.10 (m, 1H), 2.00-1.69 (m, 6H), 1.54-1.26 (m, 5H).

Step 2. To a stirred solution of (R)—N-(4-((benzyloxy)carbamoyl)-2-fluorophenyl)-N-((5-cyclohexylpyridin-2-yl)methyl)-1-((perfluorophenyl)sulfonyl)azetidine-2-carboxamide (50 mg, 0.067 mmol) in methanol (3 mL) and EtOAc (3 mL) was added 20% Pd(OH)$_2$/C (17 mg) and the resulting suspension was stirred at room temperature under a hydrogen atmosphere for 4 h. The reaction mixture was filtered through Celite® and washed with EtOAc. The combined filtrate and washes were concentrated. Purification by column chromatography gave Example 117 (R)—N-((5-cyclohexylpyridin-2-yl)methyl)-N-(2-fluoro-4-(hydroxycarbamoyl)phenyl)-1-((perfluorophenyl)sulfonyl)azetidine-2-carboxamide. MS (ESI): [M+H]+ m/z 656.9.

Example 118

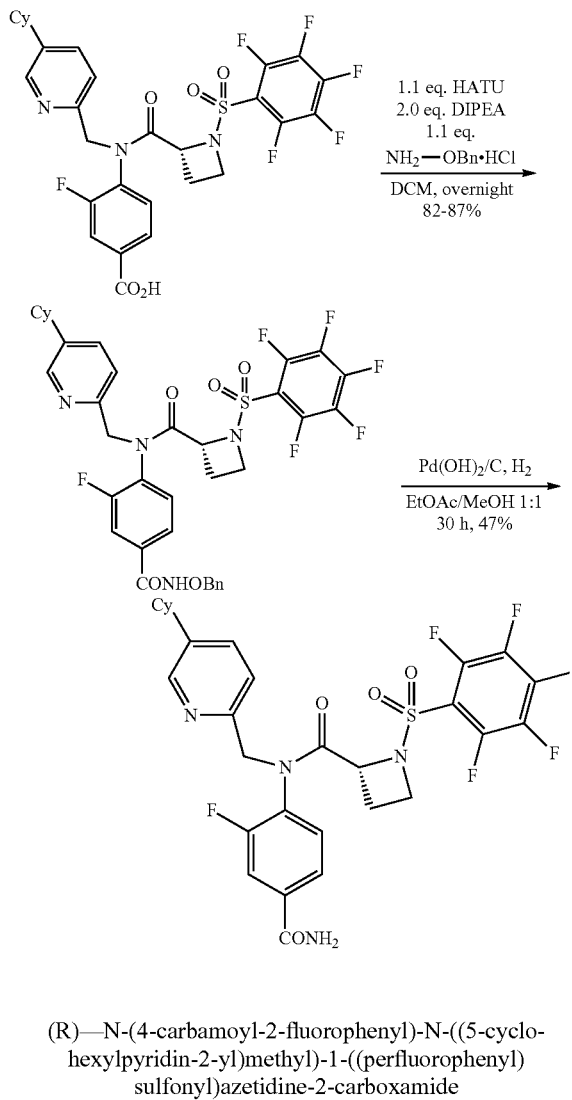

(R)-N-(4-carbamoyl-2-fluorophenyl)-N-((5-cyclohexylpyridin-2-yl)methyl)-1-((perfluorophenyl)sulfonyl)azetidine-2-carboxamide Step 1. Preparation by a similar procedure to Example 113, step 5, starting from (R)-4-(N-((5-cyclohexylpyridin-2-yl)methyl)-1-((perfluorophenyl)sulfonyl)azetidine-2-carboxamido)-3-fluorobenzoic acid to obtain (R)—N-(4-((benzyloxy)carbamoyl)-2-fluorophenyl)-N-((5-cyclohexylpyridin-2-yl)methyl)-1-((perfluorophenyl)sulfonyl)azetidine-2-carboxamide. $^1$H NMR (300 MHz, CDCl$_3$) δ 9.56 (s, 1H), 8.19 (s, 1H), 7.59-7.31 (m, 8H), 7.26-7.03 (m, 2H), 5.19 (d, J=14.8 Hz, 1H), 4.99 (s, 2H), 4.80-4.92 (m, 1H), 4.47 (d, J=14.8 Hz, 1H), 4.17-4.06 (m, 1H), 4.06-3.90 (m, 1H), 2.60-2.35 (m, 1H), 2.34-2.10 (m, 1H), 2.00-1.69 (m, 6H), 1.54-1.26 (m, 5H).

Step 2. To a stirred solution of (R)—N-(4-((benzyloxy)carbamoyl)-2-fluorophenyl)-N-((5-cyclohexylpyridin-2-yl)methyl)-1-((perfluorophenyl)sulfonyl)azetidine-2-carboxamide (50 mg, 0.067 mmol) in methanol (3 mL) and EtOAc (3 mL) was added 20% Pd(OH)$_2$/C (17 mg) and the resulting suspension was stirred at room temperature under a hydrogen atmosphere for 30 h. The reaction mixture was filtered through Celite® and washed with EtOAc. The combined filtrate and washes were concentrated. Purification by column chromatography gave Example 118 (R)—N-(4-carbamoyl-2-fluorophenyl)-N-((5-cyclohexylpyridin-2-yl)methyl)-1-((perfluorophenyl)sulfonyl)azetidine-2-carboxamide. MS (ESI): [M+H]+ 641.0.

Example 119

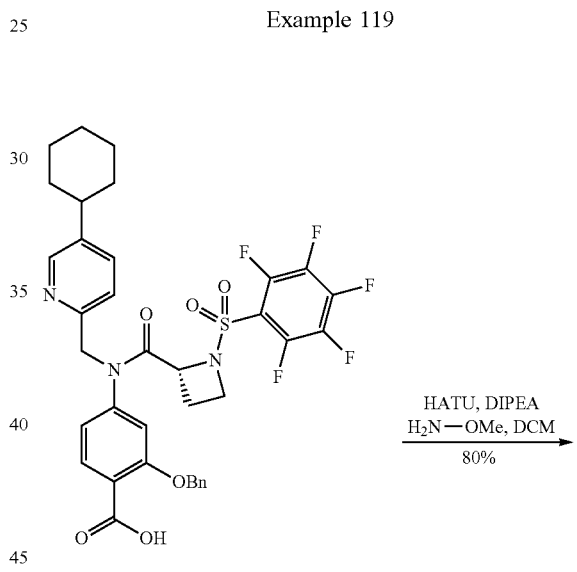

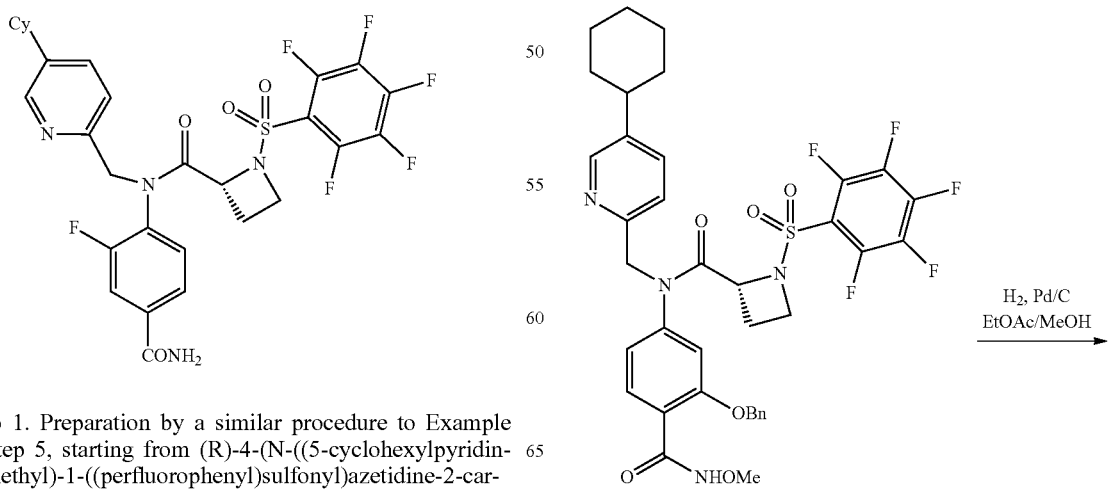

-continued

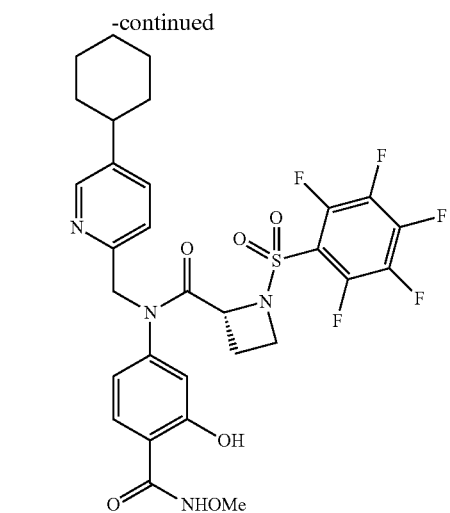

(R)—N-((5-cyclohexylpyridin-2-yl)methyl)-N-(3-hydroxy-4-(methoxycarbamoyl)phenyl)-1-((perfluorophenyl)sulfonyl)azetidine-2-carboxamide

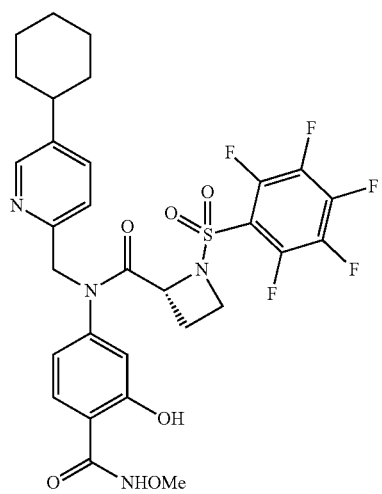

Step 1. Preparation by a similar procedure to Example 113, step 5, starting from (R)-2-(benzyloxy)-4-(N-((5-cyclohexylpyridin-2-yl)methyl)-1-((perfluorophenyl)sulfonyl)azetidine-2-carboxamido)benzoic acid (see preparation in Example 113, step 4) to obtain (R)—N-(3-(benzyloxy)-4-(methoxycarbamoyl)phenyl)-N-((5-cyclohexylpyridin-2-yl)methyl)-1-((perfluorophenyl)sulfonyl)azetidine-2-carboxamide. ¹H NMR (300 MHz, CDCl₃) δ 10.12 (s, 1H), 8.35 (d, J=2.2 Hz, 1H), 8.20 (d, J=8.3 Hz, 1H), 7.56-7.35 (m, 6H), 7.16 (d, J=8.0 Hz, 1H), 7.00 (d, J=1.9 Hz, 1H), 6.86 (dd, J=8.3, 1.9 Hz, 1H), 5.22 (d, J=11.4 Hz, 1H), 5.11 (d, J=11.4 Hz, 1H), 5.02-4.76 (m, 3H), 4.26-3.90 (m, 2H), 3.80 (s, 3H), 2.66-2.42 (m, 1H), 2.31-2.00 (m, 1H), 1.96-1.69 (m, 6H), 1.57-1.15 (m, 5H).

Step 2. Preparation by a similar procedure to Example 53, step 5, starting from (R)—N-(3-(benzyloxy)-4-(methoxycarbamoyl)phenyl)-N-((5-cyclohexylpyridin-2-yl)methyl)-1-((perfluorophenyl)sulfonyl)azetidine-2-carboxamide to obtain the compound of Example 119 (R)—N-((5-cyclohex-ylpyridin-2-yl)methyl)-N-(3-hydroxy-4-(methoxy carbamoyl)phenyl)-1-((perfluorophenyl)sulfonyl)azetidine-2-carboxamide. MS (ESI+) m/z 759.0 [M+H]+.

Example 120

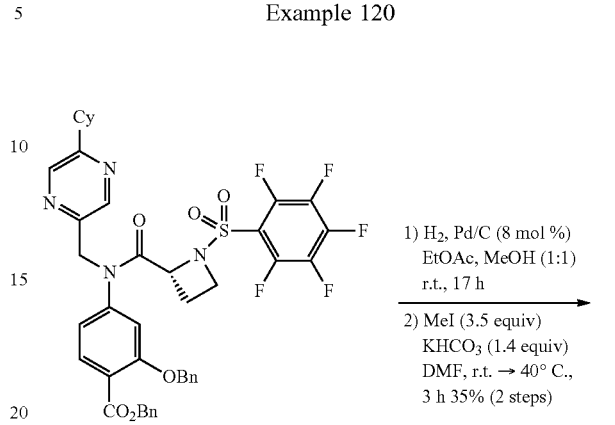

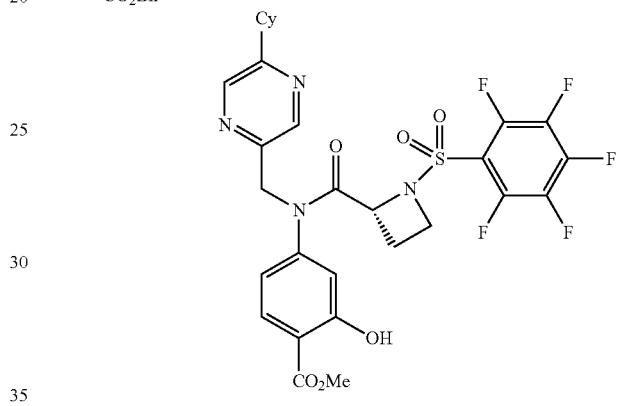

methyl (R)-4-(N-((5-cyclohexylpyrazin-2-yl)methyl)-1-((perfluorophenyl)sulfonyl)azetidine-2-carboxamido)-2-hydroxybenzoate

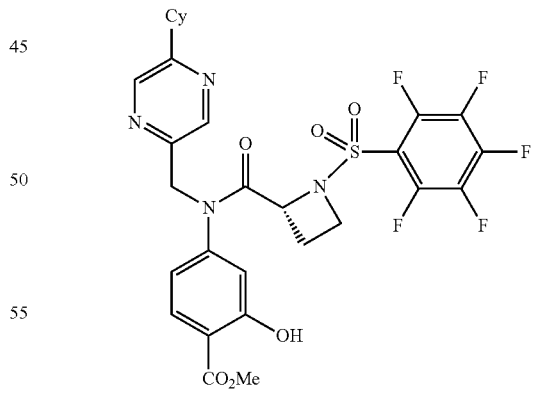

Step 1. Preparation by a similar procedure to Example 106, step 1, starting from (R)-4-(N-((5-cyclohexylpyrazin-2-yl)methyl)-1-((perfluorophenyl)sulfonyl)azetidine-2-carboxamido)-2-hydroxybenzoic acid to obtain the compound of Example 120 methyl (R)-4-(N-((5-cyclohexylpyrazin-2-yl)methyl)-1-((perfluorophenyl)sulfonyl)azetidine-2-carboxamido)-2-hydroxybenzoate. ¹H NMR (300 MHz, CDCl₃) δ 10.91 (s, 1H, OH), 8.42 (d, J=1.2 Hz, 1H), 8.37 (d, J=1.2 Hz, 1H), 7.89 (d, J=8.4 Hz, 1H), 6.86 (d, J=2.4 Hz, 1H), 6.80 (dd, J=2.4, 8.4 Hz, 1H), 5.02-5.12 (m, 2H), 4.80 (d, J=15.3 Hz, 1H), 4.12-4.20 (m, 1H), 3.93-4.07 (m, 4H), 2.68-2.78 (m, 1H), 2.27-2.38 (m, 1H), 2.04-2.14 (m, 1H), 1.84-1.98 (m, 4H), 1.73-1.82 (m, 1H), 1.27-1.58 (m, 5H). HRMS (ESI+) m/z 655.1646 [M+H]+.

Example 121

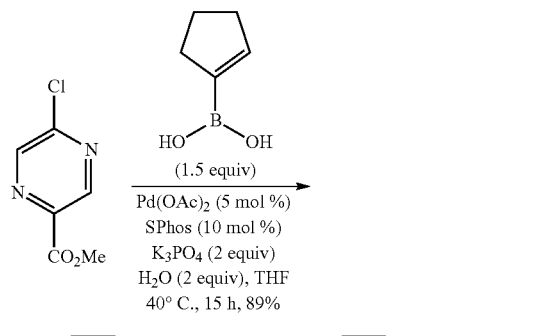

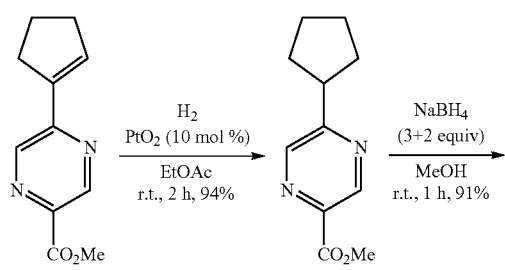

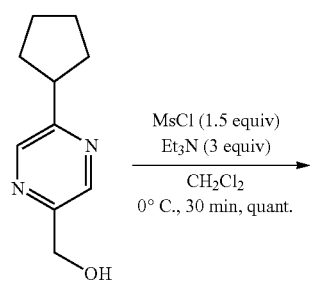

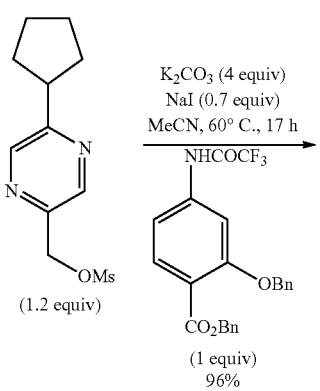

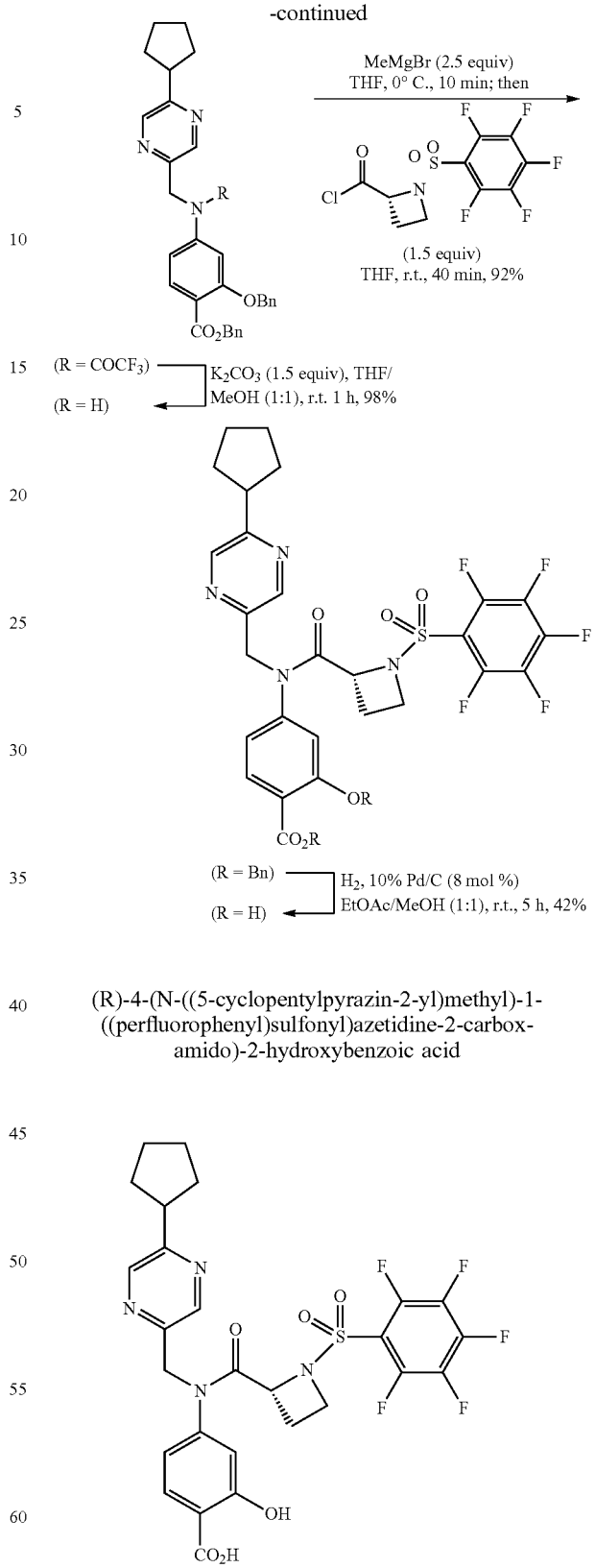

(R)-4-(N-((5-cyclopentylpyrazin-2-yl)methyl)-1-((perfluorophenyl)sulfonyl)azetidine-2-carboxamido)-2-hydroxybenzoic acid Step 1. Preparation by a similar procedure to Example 110, step 2, starting from methyl 5-chloropyrazine-2-carboxylate to obtain methyl 5-(cyclopent-1-en-1-yl)pyrazine-2-carboxylate. $^1$H NMR (300 MHz, CDCl$_3$) δ 9.23 (d, J=1.5

Hz, 1H), 8.80 (d, J=1.5 Hz, 1H), 6.92-6.95 (m, 1H), 4.05 (s, 3H), 2.84-2.91 (m, 2H), 2.64-2.71 (m, 2H), 2.06-2.17 (m, 2H).

Step 2. Preparation by a similar procedure to Example 110, step 3, starting from methyl 5-(cyclopent-1-en-1-yl)pyrazine-2-carboxylate to obtain methyl 5-cyclopentylpyrazine-2-carboxylate. $^1$H NMR (300 MHz, CDCl$_3$) δ 9.23 (d, J=1.5 Hz, 1H), 8.59 (d, J=1.5 Hz, 1H), 4.05 (s, 3H), 3.28-3.38 (m, 1H), 2.11-2.19 (m, 2H), 1.72-1.94 (m, 6H).

Step 3. Preparation by a similar procedure to Example 110, step 4, starting from methyl 5-cyclopentylpyrazine-2-carboxylate to obtain (5-cyclopentylpyrazin-2-yl)methanol. $^1$H NMR (300 MHz, CDCl$_3$) δ 8.54 (d, J=1.8 Hz, 1H), 8.44 (d, J=1.8 Hz, 1H), 4.82 (d, J=4.2 Hz, 2H), 3.19-3.30 (m, 1H), 3.07 (t, J=4.2 Hz, 1H, OH), 2.08-2.16 (m, 2H), 1.71-1.91 (m, 6H).

Step 4. Preparation by a similar procedure to Example 110, step 5, starting from (5-cyclopentylpyrazin-2-yl)methanol to obtain (5-cyclopentylpyrazin-2-yl)methyl methanesulfonate. $^1$H NMR (300 MHz, CDCl$_3$) δ 8.65 (d, J=1.2 Hz, 1H), 8.50 (d, J=1.2 Hz, 1H), 5.35 (s, 2H), 3.22-3.32 (m, 1H), 3.13 (s, 3H), 2.07-2.16 (m, 2H), 1.71-1.92 (m, 6H).

Step 5. Preparation by a similar procedure to Example 149, step 2, starting from (5-cyclopentylpyrazin-2-yl)methanol to obtain (5-cyclopentylpyrazin-2-yl)methyl methanesulfonate to obtain benzyl 2-(benzyloxy)-4-(N-((5-cyclopentylpyrazin-2-yl)methyl)-2,2,2-trifluoroacetamido)benzoate. $^1$H NMR (300 MHz, CDCl$_3$) δ 8.48 (s, 1H), 8.39 (d, J=1.8 Hz, 1H), 7.87 (d, J=8.7 Hz, 1H), 7.32-7.42 (m, 10H), 7.00 (s, 1H), 6.93 (d, J=8.7 Hz, 1H), 5.35 (s, 2H), 5.09 (s, 2H), 4.98 (s, 2H), 3.16-3.27 (m, 1H), 2.05-2.14 (m, 2H), 1.69-1.90 (m, 6H).

Step 6. Preparation by a similar procedure to Example 136, step 5, starting from benzyl 2-(benzyloxy)-4-(N-((5-cyclopentylpyrazin-2-yl)methyl)-2,2,2-trifluoroacetamido)benzoate to obtain benzyl 2-(benzyloxy)-4-(((5-cyclopentylpyrazin-2-yl)methyl)amino)benzoate. $^1$H NMR (300 MHz, CDCl$_3$) δ 8.52 (d, J=1.2 Hz, 1H), 8.44 (d, J=1.2 Hz, 1H), 7.87 (d, J=8.4 Hz, 1H), 7.29-7.50 (m, 10H), 6.26-6.31 (m, 2H), 5.32 (s, 2H), 5.17 (t, J=5.4 Hz, 1H, NH), 5.15 (s, 2H), 4.48 (d, J=5.4 Hz, 2H), 3.18-3.28 (m, 1H), 2.10-2.15 (m, 2H), 1.70-1.91 (m, 6H).

Step 7. Preparation by a similar procedure to Example 136, step 6, starting from benzyl 2-(benzyloxy)-4-(((5-cyclopentylpyrazin-2-yl)methyl)amino)benzoate to obtain benzyl (R)-2-(benzyloxy)-4-(N-((5-cyclopentylpyrazin-2-yl)methyl)-1-((perfluorophenyl)sulfonyl)azetidine-2-carboxamido)benzoate. $^1$H NMR (300 MHz, CDCl$_3$) δ 8.39 (s, 1H), 8.35 (d, J=1.8 Hz, 1H), 7.84 (d, J=8.4 Hz, 1H), 7.33-7.44 (m, 10H), 6.93 (d, J=1.8 Hz, 1H), 6.82 (dd, J=1.8, 8.4 Hz, 1H), 5.37 (s, 2H), 5.21 (d, J=12.6 Hz, 1H), 5.13 (d, J=12.6 Hz, 1H), 4.88-5.01 (m, 2H), 4.76 (d, J=15.0 Hz, 1H), 4.00-4.10 (m, 1H), 3.89-3.98 (m, 1H), 3.15-3.25 (m, 1H), 2.01-2.13 (m, 3H), 1.67-1.89 (m, 7H).

Step 8. Preparation by a similar procedure to Example 61, step 7, starting from benzyl (R)-2-(benzyloxy)-4-(N-((5-cyclopentylpyrazin-2-yl)methyl)-1-((perfluorophenyl)sulfonyl)azetidine-2-carboxamido)benzoate to obtain the compound of Example 121 (R)-4-(N-((5-cyclopentylpyrazin-2-yl)methyl)-1-((perfluorophenyl)sulfonyl)azetidine-2-carboxamido)-2-hydroxybenzoic acid. $^1$H NMR (300 MHz, CDCl$_3$) δ 11.29 (brs, 1H, OH), 8.86 (s, 1H), 8.44 (s, 1H), 7.69 (d, J=8.4 Hz, 1H), 6.69 (d, J=8.4 Hz, 1H), 6.60 (s, 1H), 4.95-5.08 (m, 3H), 4.10-4.18 (m, 1H), 3.98-4.05 (m, 1H), 3.25-3.37 (m, 1H), 1.72-2.29 (m, 10H). MS (ESI+) m/z 627.0 [M+H]+.

Example 122

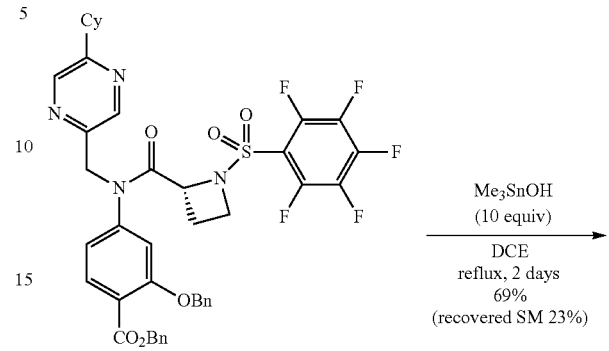

335

(R)—N-((5-cyclohexylpyrazin-2-yl)methyl)-N-(3-hydroxy-4-(hydroxycarbamoyl)phenyl)-1-((perfluorophenyl)sulfonyl)azetidine-2-carboxamide

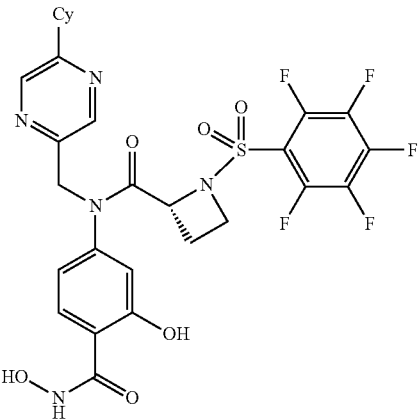

Step 1. Preparation by a similar procedure to Example 84, step 1, starting from benzyl (R)-2-(benzyloxy)-4-(N-((5-cyclohexylpyrazin-2-yl)methyl)-1-((perfluorophenyl)sulfonyl)azetidine-2-carboxamido)benzoate to obtain (R)-2-(benzyloxy)-4-(N-((5-cyclohexylpyrazin-2-yl)methyl)-1-((perfluorophenyl)sulfonyl)azetidine-2-carboxamido)benzoic acid. $^1$H NMR (300 MHz, CDCl$_3$) δ 8.43 (d, J=1.2 Hz, 1H), 8.36 (d, J=1.2 Hz, 1H), 8.21 (d, J=8.1 Hz, 1H), 7.44-7.48 (m, 5H), 7.23 (d, J=1.5 Hz, 1H), 6.98 (dd, J=1.5, 8.1 Hz, 1H), 5.39 (d, J=11.4 Hz, 1H), 5.29 (d, J=11.4 Hz, 1H), 4.94-5.03 (m, 2H), 4.80 (d, J=15.6 Hz, 1H), 4.00-4.15 (m, 2H), 2.70-2.80 (m, 1H), 2.12-2.22 (m, 1H), 1.25-1.98 (m, 11H).

Step 2. Preparation by a similar procedure to Example 113, step 5, starting from (R)-2-(benzyloxy)-4-(N-((5-cyclohexylpyrazin-2-yl)methyl)-1-((perfluorophenyl)sulfonyl)azetidine-2-carboxamido)benzoic acid to obtain (R)—N-(3-(benzyloxy)-4-((benzyloxy)carbamoyl)phenyl)-N-((5-cyclohexylpyrazin-2-yl)methyl)-1-((perfluorophenyl)sulfonyl)azetidine-2-carboxamide. $^1$H NMR (300 MHz, CDCl$_3$) δ 10.07 (s, 1H, NH), 8.40 (s, 1H), 8.34 (s, 1H), 8.24 (d, J=8.4 Hz, 1H), 7.35-7.42 (m, 8H), 7.21-7.25 (m, 2H), 7.00 (d, J=1.8 Hz, 1H), 6.89 (dd, J=1.8, 8.4 Hz, 1H), 5.13 (d, J=12.0 Hz, 1H), 4.87-5.06 (m, 5H), 4.75 (d, J=15.3 Hz, 1H), 3.95-4.12 (m, 2H), 2.69-2.78 (m, 1H), 2.07-2.15 (m, 1H), 1.25-1.97 (m, 11H).

Step 3. Preparation by a similar procedure to Example 85, step 5, starting from (R)—N-(3-(benzyloxy)-4-((benzyloxy)carbamoyl)phenyl)-N-((5-cyclohexylpyrazin-2-yl)methyl)-1-((perfluorophenyl)sulfonyl)azetidine-2-carboxamide to obtain the compound of Example 122 (R)—N-((5-cyclohexylpyrazin-2-yl)methyl)-N-(3-hydroxy-4-(hydroxycarbamoyl)phenyl)-1-((perfluorophenyl)sulfonyl)azetidine-2-carboxamide. 1H NMR (300 MHz, CDCl$_3$) □ 11.61 (brs, 1H, OH), 10.35 (brs, 1H, OH), 8.47 (s, 1H), 8.39 (s, 1H), 7.56 (d, J=7.8 Hz, 1H), 6.85 (s, 1H), 6.74 (d, J=7.8 Hz, 1H), 5.08-5.15 (m, 1H), 4.96 (s, 2H), 3.99-4.19 (m, 2H), 2.69-2.80 (m, 1H), 2.26-2.38 (m, 1H), 1.23-2.17 (m, 11H). MS (ESI+) m/z 656.0 [M+H]+.

Example 123

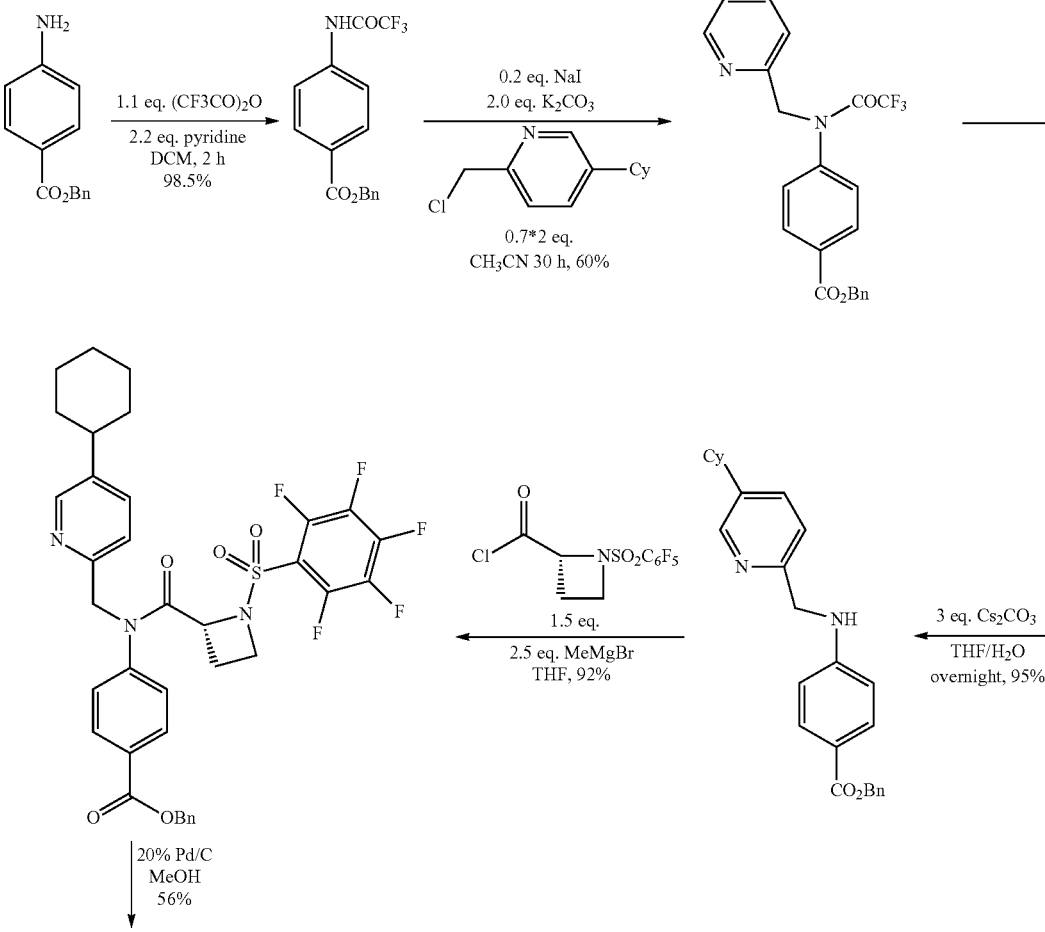

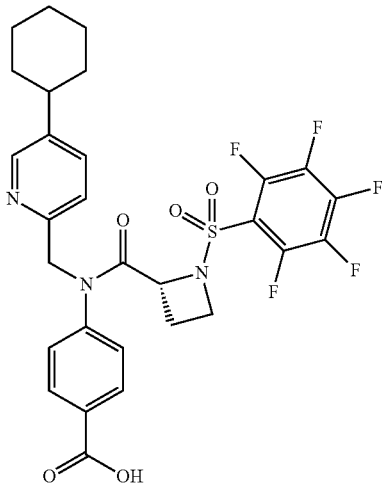

(R)-4-(N-((5-cyclohexylpyridin-2-yl)methyl)-1-((perfluorophenyl)sulfonyl)azetidine-2-carbox-amido)benzoic acid

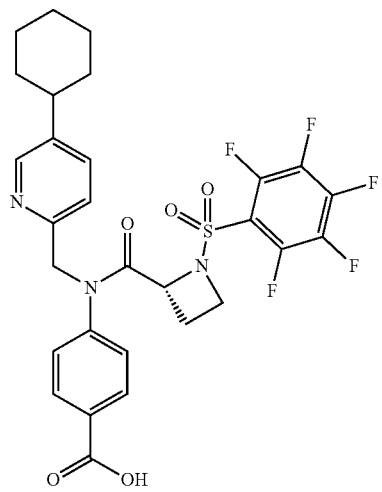 [SMILES: O=C(O)c1ccc(N(Cc2ccc(C3CCCCC3)cn2)C(=O)[C@H]2CCN2S(=O)(=O)c2c(F)c(F)c(F)c(F)c2F)cc1]

Step 1. Preparation by a similar procedure to Example 61, step 3, starting from benzyl 4-aminobenzoate to obtain benzyl 4-(2,2,2-trifluoroacetamido)benzoate. ¹H NMR (300 MHz, CDCl₃) δ 8.18-8.11 (m, 2H), 7.99 (s, 1H), 7.73-7.66 (m, 2H), 7.51-7.34 (m, 5H), 5.39 (s, 2H).

Step 2. Preparation by a similar procedure to Example 116, step 4, starting from benzyl 4-(2,2,2-trifluoroacetamido)benzoate to obtain benzyl 4-(N-((5-cyclohexylpyridin-2-yl)methyl)-2,2,2-trifluoroacetamido)benzoate. Taken a such to next step Step 3. Preparation by a similar procedure to Example 109, step 4, starting from benzyl 4-(N-((5-cyclohexylpyridin-2-yl)methyl)-2,2,2-trifluoroacetamido)benzoate to obtain benzyl 4-(((5-cyclohexylpyridin-2-yl)methyl)amino)benzoate. Taken as such to next step.

Step 4. Preparation by a similar procedure to Example 53, step 3, starting from benzyl 4-(((5-cyclohexylpyridin-2-yl)methyl)amino)benzoate to obtain benzyl (R)-4-(N-((5-cyclohexylpyridin-2-yl)methyl)-1-((perfluorophenyl)sulfonyl)azetidine-2-carboxamido)benzoate. ¹H NMR (300 MHz, CDCl₃) δ 8.32 (s, 1H), 8.07 (d, J=8.5 Hz, 2H), 7.52-7.34 (m, 6H), 7.25 (d, J=8.5 Hz, 2H), 7.18 (d, J=8.0 Hz, 1H), 5.37 (s, 2H), 5.04-4.95 (m, 1H), 4.95-4.84 (m, 2H), 4.18-4.08 (m, 1H), 4.08-4.00 (m, 1H), 2.58-1.44 (m, 1H), 2.38-2.23 (m, 1H), 1.97-1.77 (m, 6H), 1.50-1.31 (m, 5H).

Step 5. Preparation by a similar procedure to Example 37, example 5, starting from benzyl (R)-4-(N-((5-cyclohexylpyridin-2-yl)methyl)-1-((perfluorophenyl)sulfonyl)azetidine-2-carboxamido)benzoate to obtain the compound of Example 123 (R)-4-(N-((5-cyclohexylpyridin-2-yl)methyl)-1-((perfluorophenyl)sulfonyl)azetidine-2-carboxamido)benzoic acid. MS (ESI+) m/z 624.0 [M+H]+.

Example 124

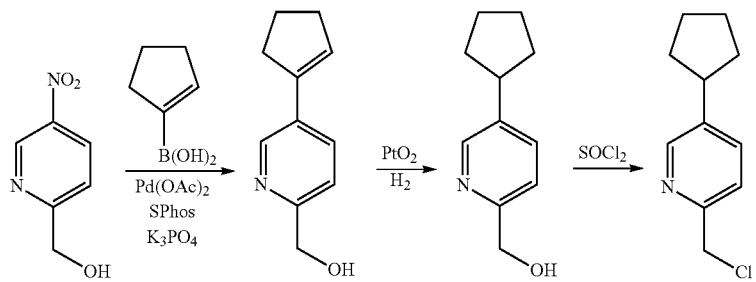

-continued
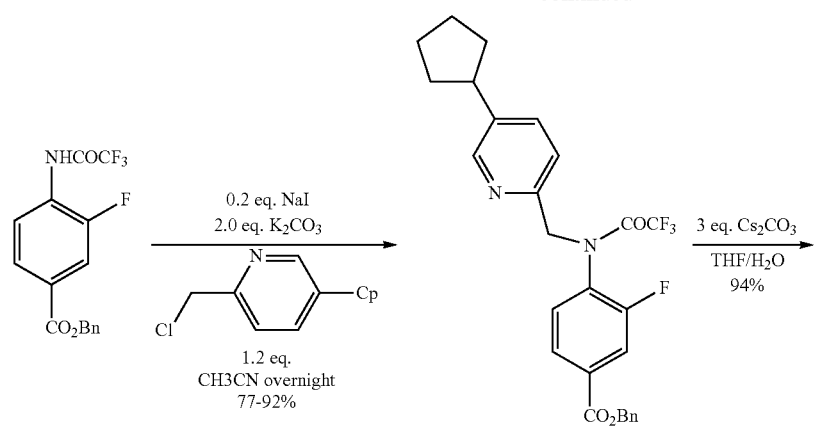
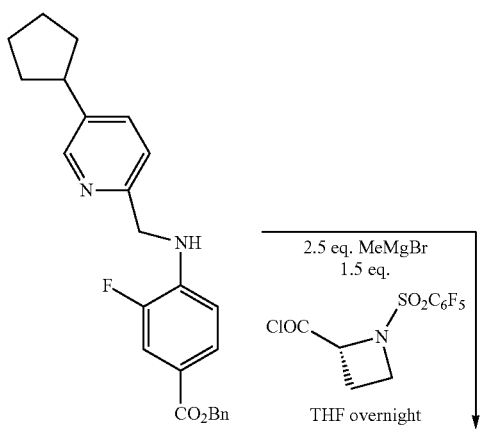
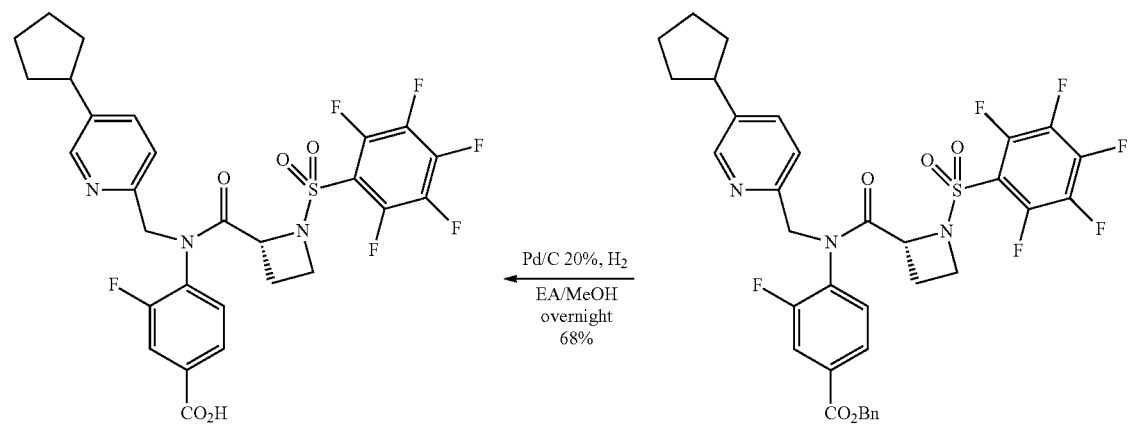

(R)-4-(N-((5-cyclopentylpyridin-2-yl)methyl)-1-((perfluorophenyl)sulfonyl)azetidine-2-carboxamido)-3-fluorobenzoic acid

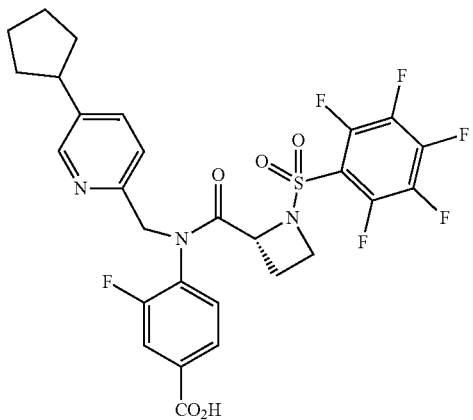 [SMILES: O=C(O)c1ccc(N(Cc2ccc(C3CCCC3)cn2)C(=O)[C@H]2CCN2S(=O)(=O)c2c(F)c(F)c(F)c(F)c2F)c(F)c1]

Step A1. Preparation by a similar procedure to Example 97, step A1, starting from (5-bromopyridin-2-yl)methanol and cyclopent-1-en-1-ylboronic acid to obtain (5-(cyclopent-1-en-1-yl)pyridin-2-yl)methanol. $^1$H NMR (300 MHz, CDCl$_3$) δ 8.50 (s, 1H), 7.75-7.53 (m, 1H), 7.41-7.11 (m, 1H), 6.34-6.06 (m, 1H), 4.70 (s, 2H), 2.89-2.31 (m, 4H), 2.03-1.98 (m, 2H).

Step A2. Preparation by a similar procedure to Example 97, step A2, starting from (5-(cyclopent-1-en-1-yl)pyridin-2-yl)methanol to obtain (5-cyclopentylpyridin-2-yl)methanol. $^1$H NMR (300 MHz, CDCl$_3$) δ 8.41 (d, J=1.8 Hz, 1H), 7.53 (dd, J=8.0, 1.8 Hz, 1H), 7.19 (d, J=8.0 Hz, 1H), 4.73 (s, 2H), 2.61-2.47 (m, 1H), 1.91-1.79 (m, 4H), 1.48-1.33 (m, 4H).

Step A3. Preparation by a similar procedure to Example 97, step A2, starting from (5-cyclopentylpyridin-2-yl)methanol to obtain 2-(chloromethyl)-5-cyclopentylpyridine. $^1$H NMR (300 MHz, CDCl$_3$) δ 8.46 (s, 1H), 7.69-7.46 (m, 1H), 7.46-7.17 (m, 1H), 4.65 (s, 2H), 3.10-2.90 (m, 1H), 2.27-1.40 (m, 8H).

Step 1. Preparation by a similar procedure to Example 116, step 4, starting from benzyl 3-fluoro-4-(2,2,2-trifluoroacetamido)benzoate (see Example 108, step 1) and 2-(chloromethyl)-5-cyclopentylpyridine to obtain benzyl 4-(N-((5-cyclopentylpyridin-2-yl)methyl)-2,2,2-trifluoroacetamido)-3-fluorobenzoate. Taken as such to next step Step 2. Preparation by a similar procedure to Example 109, step 4, starting from benzyl 4-(N-((5-cyclopentylpyridin-2-yl)methyl)-2,2,2-trifluoroacetamido)-3-fluorobenzoate to obtain benzyl 4-(((5-cyclopentylpyridin-2-yl)methyl)amino)-3-fluorobenzoate. $^1$H NMR (300 MHz, CDCl$_3$) δ 8.49 (d, J=2.2 Hz, 1H), 7.77 (dd, J=8.4, 1.7 Hz, 1H), 7.71 (dd, J=12.3, 1.7 Hz, 1H), 7.54 (dd, J=8.0, 2.2 Hz, 1H), 7.47-7.30 (m, 5H), 7.23 (d, J=8.0 Hz, 1H), 6.65 (dd, J=8.5, 8.4 Hz, 1H), 5.57 (s, 1H), 5.32 (s, 2H), 4.51 (m, 2H), 3.08-2.95 (m, 1H), 2.17-2.07 (m, 2H), 1.86-1.68 (m, 4H), 1.63-1.53 (m 2H).

Step 3. Preparation by a similar procedure to Example 53, step 3, starting from benzyl 4-(((5-cyclopentylpyridin-2-yl)methyl)amino)-3-fluorobenzoate to obtain benzyl benzyl (R)-4-(N-((5-cyclopentylpyridin-2-yl)methyl)-1-((perfluorophenyl)sulfonyl)azetidine-2-carboxamido)-3-fluorobenzoate. $^1$H NMR (300 MHz, CDCl$_3$) δ 8.31 (s, 1H), 7.91-7.77 (m, 2H), 7.52 (d, J=7.8 Hz, 1H), 7.47-7.29 (m, 6H), 7.26-7.20 (m, 1H), 5.37 (s, 2H), 5.35-5.24 (m 1H), 4.98-4.89 (m, 1H), 4.49 (d, J=14.8 Hz, 1H), 4.17-4.04 (m, 2H), 3.04-2.89 (m, 1H), 2.39-2.19 (m, 1H), 2.14-2.02 (m, 1H), 1.94-1.65 (m, 6H), 1.60-1.46 (m 2H).

Step 4. Preparation by a similar procedure to Example 37, example 5, starting from benzyl (R)-4-(N-((5-cyclopentylpyridin-2-yl)methyl)-1-((perfluorophenyl)sulfonyl)azetidine-2-carboxamido)-3-fluorobenzoate to obtain the compound of Example 124 (R)-4-(N-((5-cyclopentylpyridin-2-yl)methyl)-1-((perfluorophenyl)sulfonyl)azetidine-2-carboxamido)-3-fluorobenzoic acid. MS (ESI+): [M+H]+ m/z 627.9.

Example 125

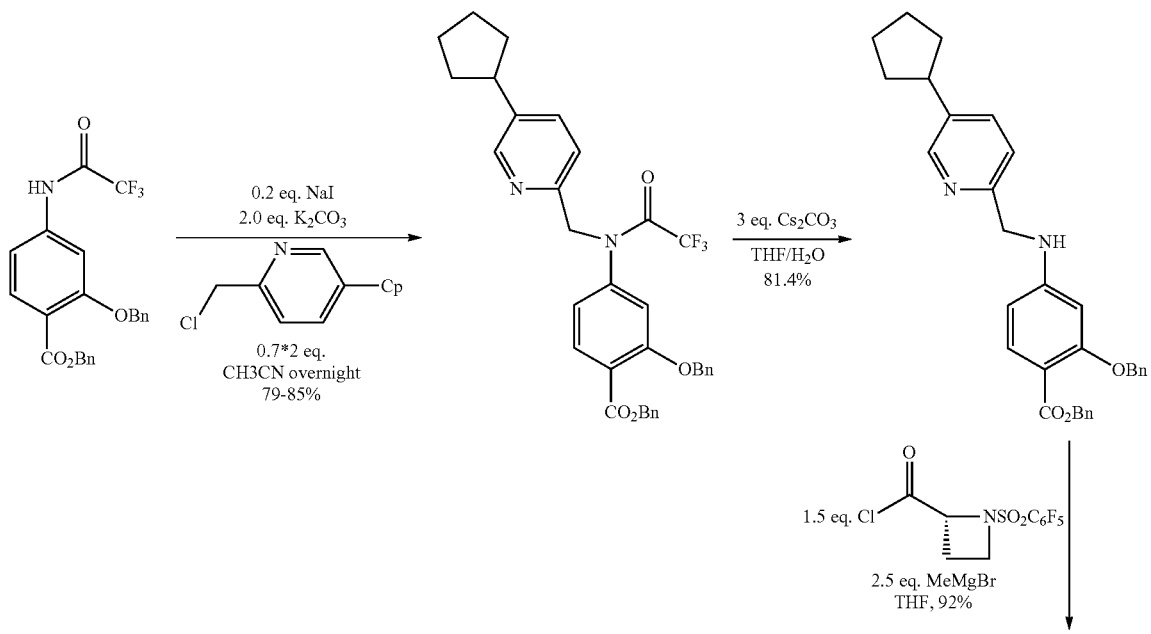

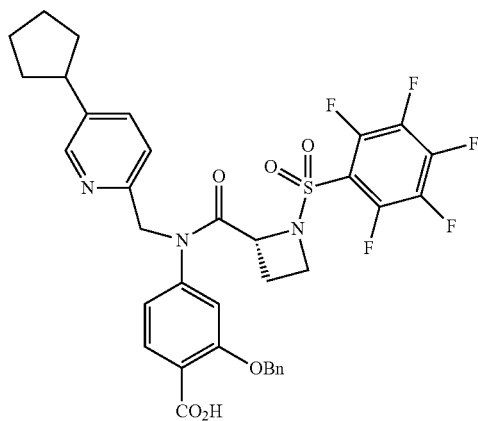

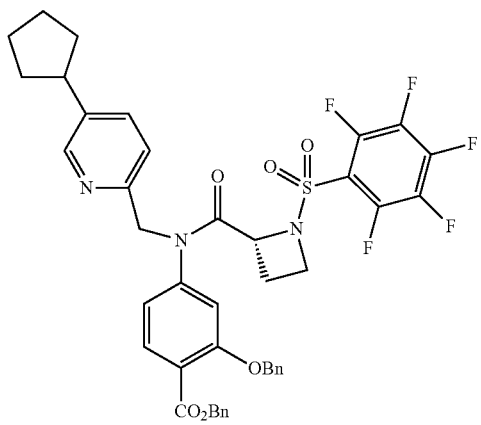

(R)-4-(N-((5-cyclopentylpyridin-2-yl)methyl)-1-((perfluorophenyl)sulfonyl)azetidine-2-carbox-amido)-2-hydroxybenzoic acid Step 1. Preparation by a similar procedure to Example 116, step 4, starting from benzyl 2-(benzyloxy)-4-(2,2,2-trifluoroacetamido)benzoate and 2-(chloromethyl)-5-cyclopentylpyridine (see Example 124, step A3) to obtain benzyl 2-(benzyloxy)-4-(N-((5-cyclopentylpyridin-2-yl)methyl)-2,2,2-trifluoroacetamido)benzoate. $^1$H NMR (300 MHz, CDCl$_3$) δ 8.42 (d, J=1.8 Hz, 1H), 7.86 (d, J=8.3 Hz, 1H), 7.52 (dd, J=8.0, 1.8 Hz, 1H), 7.43-7.30 (m, 10H), 7.19 (d, J=7.9 Hz, 1H), 6.98 (s, 1H), 6.90 (d, J=8.3 Hz, 1H), 5.35 (s, 2H), 5.05 (s, 2H), 4.99 (s, 2H), 3.07-2.92 (m, 1H), 2.15-2.07 (m, 2H), 1.88-1.68 (m, 4H), 1.63-1.51 (m, 2H).

Step 2. Preparation by a similar procedure to Example 109, step 4, starting from benzyl 2-(benzyloxy)-4-(N-((5-cyclopentylpyridin-2-yl)methyl)-2,2,2-trifluoroacetamido)benzoate to obtain benzyl 2-(benzyloxy)-4-(((5-cyclopentylpyridin-2-yl)methyl)amino)benzoate. $^1$H NMR (300 MHz, CDCl$_3$) δ 8.47 (d, J=1.8 Hz, 1H), 7.87 (d, J=8.4 Hz, 1H), 7.57-7.23 (m, 11H), 7.19 (d, J=7.9 Hz, 1H), 6.30-6.22 (m, 2H), 5.39 (s, 1H), 5.32 (s, 2H), 5.12 (s, 2H), 4.43 (s, 2H), 3.07-2.94 (m, 1H), 2.18-2.07 (m, 2H), 1.88-1.68 (m, 4H), 1.63-1.51 (m, 2H).

Step 3. Preparation by a similar procedure to Example 53, step 3, starting from benzyl 2-(benzyloxy)-4-(((5-cyclopentylpyridin-2-yl)methyl)amino)benzoate to obtain benzyl (R)-2-(benzyloxy)-4-(N-((5-cyclopentylpyridin-2-yl)methyl)-1-((perfluorophenyl)sulfonyl)azetidine-2-carbox-amido)benzoate. $^1$H NMR (300 MHz, CDCl$_3$) δ 8.36 (s, 1H), 7.86-7.75 (m, 1H), 7.53-7.46 (m, 1H), 7.44-7.39 (m, 10H), 7.15-7.07 (m, 1H), 6.87 (s, 1H), 6.82-6.73 (m, 1H), 5.35 (s, 2H), 5.20-5.10 (m, 1H), 5.10-5.02 (m, 1H), 4.97-4.82 (m, 3H), 4.11-3.89 (m, 2H), 3.06-2.90 (m, 1H), 2.12-2.04 (m, 2H), 1.88-1.48 (m, 8H).

Step 4. Preparation by a similar procedure to Example 53, step 5, starting from benzyl (R)-2-(benzyloxy)-4-(N-((5-cyclopentylpyridin-2-yl)methyl)-1-((perfluorophenyl)sulfonyl)azetidine-2-carboxamido)benzoate to obtain the compound of Example 125 (R)-4-(N-((5-cyclopentylpyridin-2-yl)methyl)-1-((perfluorophenyl)sulfonyl)azetidine-2-carboxamido)-2-hydroxybenzoic acid. MS (ESI+): [M+H]+ m/z 626.0.

Example 126

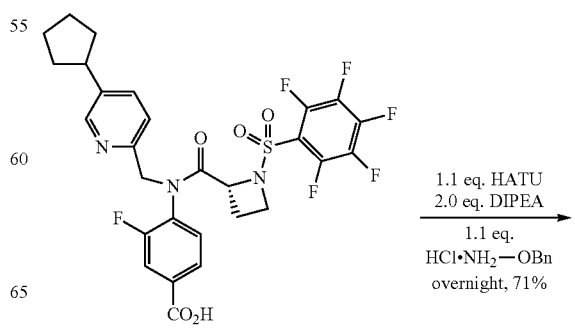

-continued

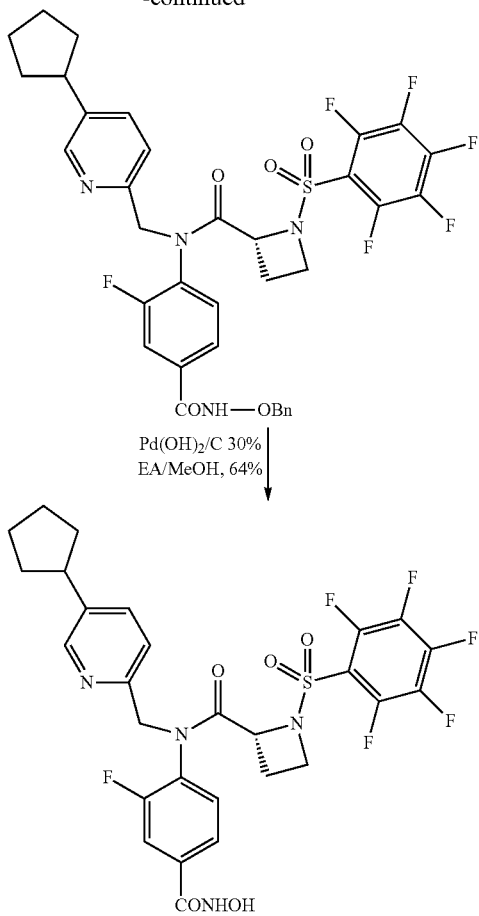

(R)—N-((5-cyclopentylpyridin-2-yl)methyl)-N-(2-fluoro-4-(hydroxycarbamoyl) phenyl)-1-((perfluorophenyl)sulfonyl)azetidine-2-carboxamide

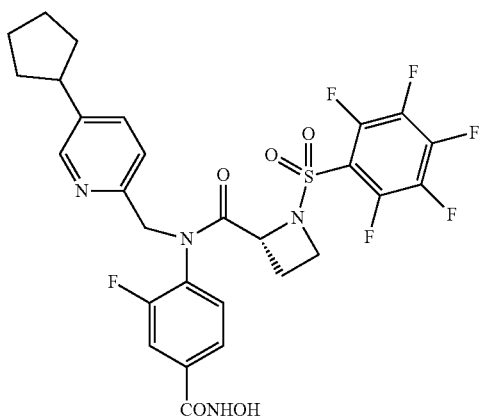

Step 1. Preparation by a similar procedure to Example 113, step 5, starting from (R)-4-(N-((5-cyclopentylpyridin-2-yl)methyl)-1-((perfluorophenyl)sulfonyl)azetidine-2-carboxamido)-3-fluorobenzoic acid to obtain (R)—N-(4-((benzyloxy)carbamoyl)-2-fluorophenyl)-N-((5-cyclopentylpyridin-2-yl)methyl)-1-((perfluorophenyl)sulfonyl)azetidine-2-carboxamide. Taken as such to next step Step 2. Preparation by a similar procedure to Example 85, step 5, starting from (R)—N-(4-((benzyloxy)carbamoyl)-2-fluorophenyl)-N-((5-cyclopentylpyridin-2-yl)methyl)-1-((perfluorophenyl)sulfonyl)azetidine-2-carboxamide to obtain the compound of Example 126 (R)—N-((5-cyclopentylpyridin-2-yl)methyl)-N-(2-fluoro-4-(hydroxycarbamoyl)phenyl)-1-((perfluorophenyl)sulfonyl)azetidine-2-carboxamide. MS (ESI+): [M+H]+ m/z 643.1.

Example 127

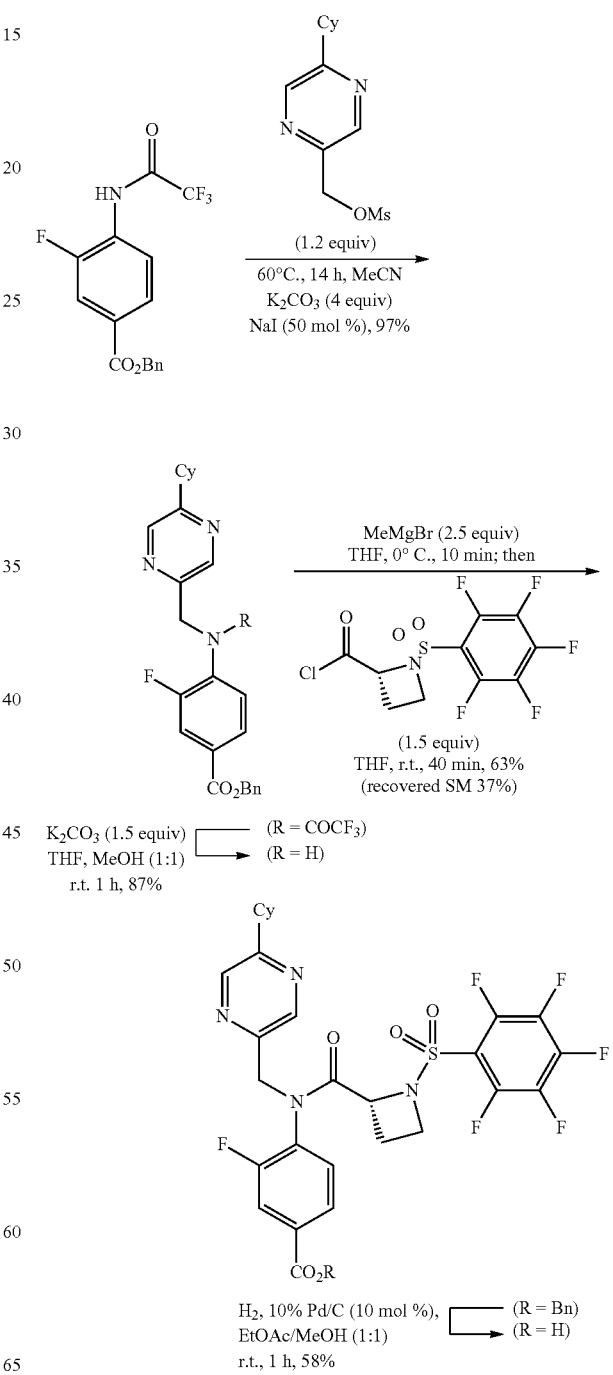

(R)-4-(N-((5-cyclohexylpyrazin-2-yl)methyl)-1-((perfluorophenyl)sulfonyl)azetidine-2-carboxamido)-3-fluorobenzoic acid Example 128

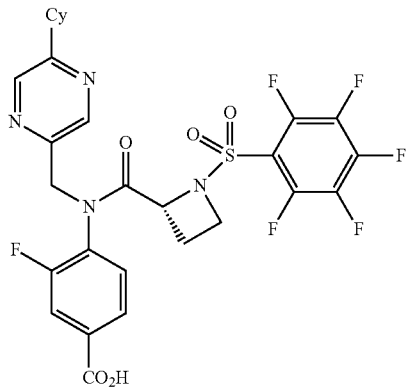

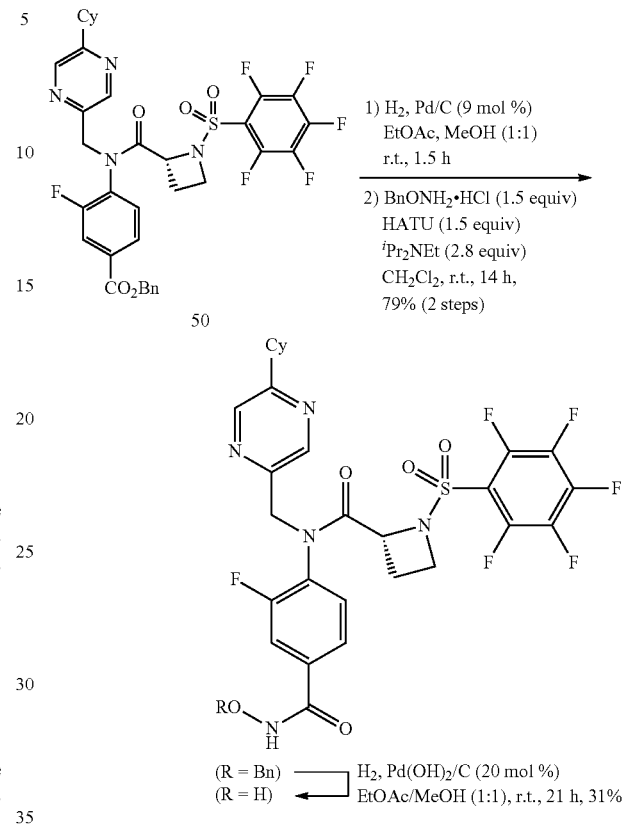

Step 1. Preparation by a similar procedure to Example 149, step 2, starting from benzyl 3-fluoro-4-(2,2,2-trifluoroacetamido)benzoate to obtain benzyl 4-(N-((5-cyclohexylpyrazin-2-yl)methyl)-2,2,2-trifluoroacetamido)-3-fluorobenzoate. $^1$H NMR (300 MHz, CDCl$_3$) δ 8.53 (s, 1H), 8.37 (s, 1H), 7.84-7.89 (m, 2H), 7.33-7.47 (m, 6H), 5.39 (d, J=14.4 Hz, 1H), 5.38 (s, 2H), 4.62 (d, J=14.4 Hz, 1H), 2.70-2.80 (m, 1H), 1.85-1.98 (m, 4H), 1.74-1.82 (m, 1H), 1.26-1.61 (m, 5H).

Step 2. Preparation by a similar procedure to Example 136, step 5, starting from benzyl 4-(N-((5-cyclohexylpyrazin-2-yl)methyl)-2,2,2-trifluoroacetamido)-3-fluorobenzoate to obtain benzyl 4-(((5-cyclohexylpyrazin-2-yl)methyl)amino)-3-fluorobenzoate. $^1$H NMR (300 MHz, CDCl$_3$) δ 8.54 (s, 1H), 8.46 (d, J=1.2 Hz, 1H), 7.79 (dd, J=2.1, 9.0 Hz, 1H), 7.72 (dd, J=2.1, JHF=12.0 Hz, 1H), 7.34-7.46 (m, 5H), 6.70 (dd, J=9.0, JHF=9.0 Hz, 1H), 5.39-5.44 (m, 1H, NH), 5.33 (s, 2H), 4.56 (d, J=5.4 Hz, 2H), 2.72-2.82 (m, 1H), 1.86-2.00 (m, 4H), 1.76-1.82 (m, 1H), 1.28-1.65 (m, 5H).

Step 3. Preparation by a similar procedure to Example 136, step 6, starting from benzyl 4-(((5-cyclohexylpyrazin-2-yl)methyl)amino)-3-fluorobenzoate to obtain benzyl (R)-4-(N-((5-cyclohexylpyrazin-2-yl)methyl)-1-((perfluorophenyl)sulfonyl)azetidine-2-carboxamido)-3-fluorobenzoate. $^1$H NMR (300 MHz, CDCl$_3$) δ 8.46 (s, 1H), 8.32 (s, 1H), 7.81-7.94 (m, 2H), 7.38-7.49 (m, 6H), 5.39 (s, 2H), 5.17 (d, J=15.6 Hz, 1H), 4.91-4.98 (m, 1H), 4.66 (d, J=15.6 Hz, 1H), 3.96-4.19 (m, 2H), 2.68-2.78 (m, 1H), 2.25-2.36 (m, 1H), 1.26-2.00 (m, 11H).

Step 4. Preparation by a similar procedure to Example 82, step 2, starting from benzyl (R)-4-(N-((5-cyclohexylpyrazin-2-yl)methyl)-1-((perfluorophenyl)sulfonyl)azetidine-2-carboxamido)-3-fluorobenzoate to obtain the compound of Example 127 (R)-4-(N-((5-cyclohexylpyrazin-2-yl)methyl)-1-((perfluorophenyl)sulfonyl)azetidine-2-carboxamido)-3-fluorobenzoic acid. $^1$H NMR (300 MHz, CDCl$_3$) δ 8.83 (s, 1H), 8.43 (s, 1H), 7.65-7.75 (m, 2H), 7.25-7.31 (m, 1H), 5.18 (d, J=14.7 Hz, 1H), 4.87-4.96 (m, 1H), 4.80 (d, J=14.7 Hz, 1H), 4.10-4.18 (m, 1H), 3.96-4.05 (m, 1H), 2.78-2.89 (m, 1H), 2.12-2.21 (m, 1H), 1.24-2.04 (m, 11H). HRMS (ESI+) m/z 643.1447 [M+H]+.

(R)—N-((5-cyclohexylpyrazin-2-yl)methyl)-N-(2-fluoro-4-(hydroxycarbamoyl) phenyl)-1-((perfluorophenyl)sulfonyl)azetidine-2-carboxamide

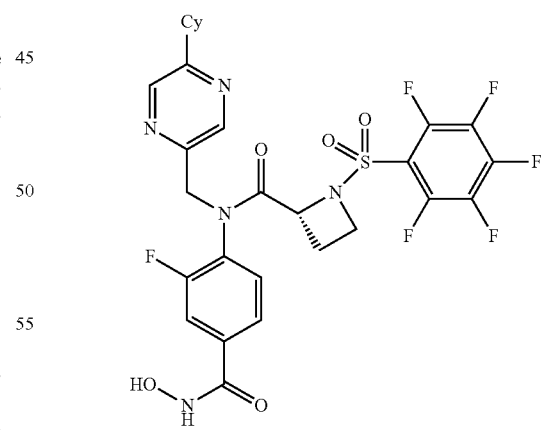

Step 1. Preparation by a similar procedure to Example 113, step 5, starting from (R)-4-(N-((5-cyclohexylpyrazin-2-yl)methyl)-1-((perfluorophenyl)sulfonyl)azetidine-2-carboxamido)-3-fluorobenzoic acid to obtain (R)—N-(4-((benzyloxy)carbamoyl)-2-fluorophenyl)-N-((5-cyclohexylpyrazin-2-yl)methyl)-1-((perfluorophenyl)sulfonyl)azetidine-2-carboxamide. $^1$H NMR (300 MHz,

349

CDCl₃) δ 8.46 (s, 1H), 8.31 (s, 1H), 7.40-7.59 (m, 8H), 5.14 (d, J=15.3 Hz, 1H), 5.05 (s, 2H), 4.88-4.95 (m, 1H), 4.65 (d, J=15.3 Hz, 1H), 3.86-4.19 (m, 2H), 2.68-2.77 (m, 1H), 2.24-2.35 (m, 1H), 1.25-1.96 (m, 11H).

Step 2. Preparation by a similar procedure to Example 85, step 5, starting from (R)—N-(4-((benzyloxy)carbamoyl)-2-fluorophenyl)-N-((5-cyclohexylpyrazin-2-yl)methyl)-1-((perfluorophenyl)sulfonyl)azetidine-2-carboxamide to obtain the compound of Example 128 (R)—N-((5-cyclohexylpyrazin-2-yl)methyl)-N-(2-fluoro-4-(hydroxycarbamoyl)phenyl)-1-((perfluorophenyl)sulfonyl)azetidine-2-carboxamide. ¹H NMR (300 MHz, CDCl₃) δ 8.48 (s, 1H), 8.33 (s, 1H), 7.46-7.67 (m, 3H), 5.18 (d, J=14.7 Hz, 1H), 4.90-4.99 (m, 1H), 4.66 (d, J=14.7 Hz, 1H), 3.96-4.22 (m, 2H), 2.69-2.80 (m, 1H), 2.27-2.38 (m, 1H), 1.26-2.07 (m, 11H). HRMS (ESI+) m/z 658.1555 [M+H]+.

Example 129

350 methyl (R)-4-(N-((5-cyclohexylpyrazin-2-yl)methyl)-1-((perfluorophenyl)sulfonyl)azetidine-2-carboxamido)-3-fluorobenzoate

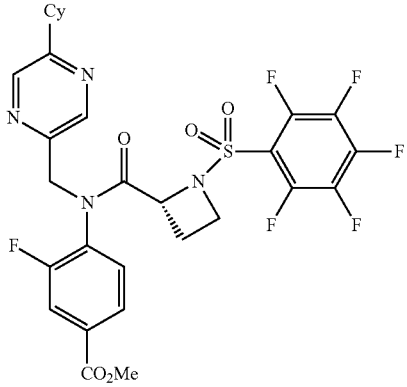

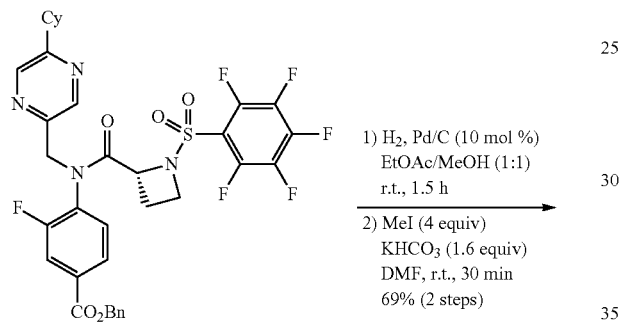

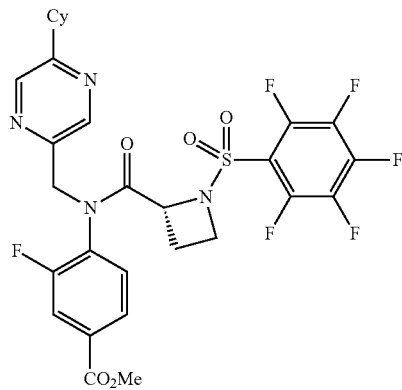

Step 1. Preparation by a similar procedure to Example 106, step 1, starting from (R)-4-(N-((5-cyclohexylpyrazin-2-yl)methyl)-1-((perfluorophenyl)sulfonyl)azetidine-2-carboxamido)-3-fluorobenzoic acid to obtain the compound of Example 129 methyl (R)-4-(N-((5-cyclohexylpyrazin-2-yl)methyl)-1-((perfluorophenyl)sulfonyl)azetidine-2-carboxamido)-3-fluorobenzoate. ¹H NMR (300 MHz, CDCl₃) δ 8.46 (s, 1H), 8.32 (s, 1H), 7.79-7.90 (m, 2H), 7.47 (dd, J=7.8, JHF=7.8 Hz, 1H), 5.17 (d, J=15.0 Hz, 1H), 4.93-4.99 (m, 1H), 4.66 (d, J=15.0 Hz, 1H), 4.12-4.20 (m, 1H), 3.93-4.08 (m, 4H), 2.68-2.78 (m, 1H), 2.26-2.36 (m, 1H), 1.84-2.00 (m, 5H), 1.74-1.82 (m, 1H), 1.26-1.64 (m, 5H). HRMS (ESI+) m/z 657.1604 [M+H]+.

Example 130

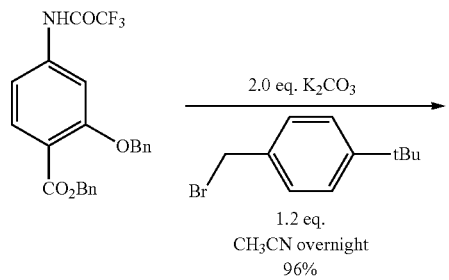

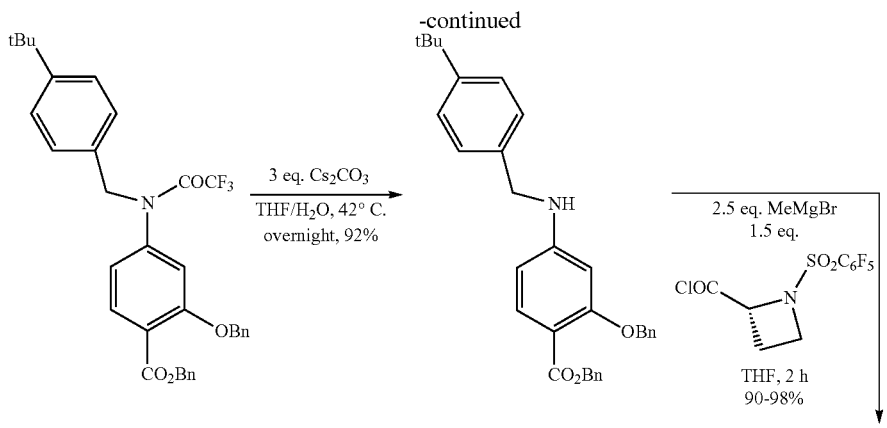

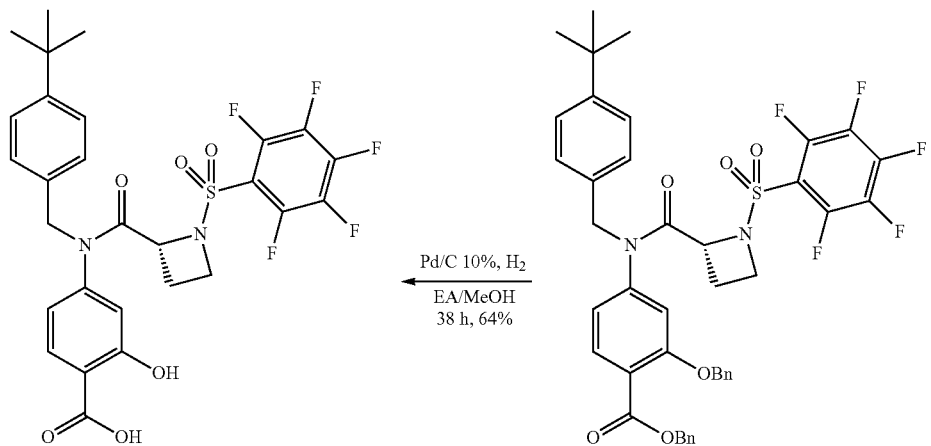

(R)-4-(N-(4-(tert-butyl)benzyl)-1-((perfluorophenyl)sulfonyl)azetidine-2-carboxamido)-2-hydroxybenzoic acid

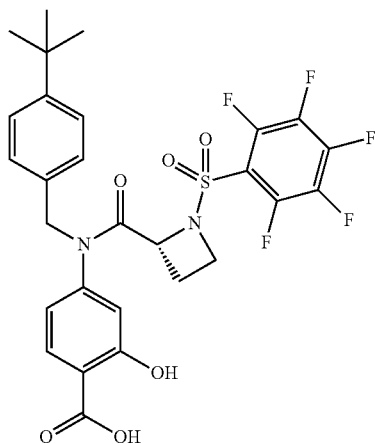 [SMILES: CC(C)(C)c1ccc(CN(C(=O)[C@H]2CCN2S(=O)(=O)c2c(F)c(F)c(F)c(F)c2F)c2ccc(C(=O)O)c(O)c2)cc1]

Step 1. Preparation by a similar procedure to Example 61, step 4, starting from benzyl 2-(benzyloxy)-4-(2,2,2-trifluoroacetamido)benzoate to obtain benzyl 2-(benzyloxy)-4-(N-(4-(tert-butyl)benzyl)-2,2,2-trifluoroacetamido)benzoate.
$^1$H NMR (300 MHz, CDCl$_3$) δ 7.86 (d, J=8.2 Hz, 1H), 7.43-7.32 (m, 12H), 7.10 (d, J=8.3 Hz, 2H), 6.74 (d, J=8.2 Hz, 1H), 6.55 (s, 1H), 5.37 (s, 2H), 4.92 (s, 2H), 4.86 (s, 2H), 1.32 (s, 9H).

Step 2. Preparation by a similar procedure to Example 109, step 4, starting from benzyl 2-(benzyloxy)-4-(N-(4-(tert-butyl)benzyl)-2,2,2-trifluoroacetamido)benzoate to obtain benzyl 2-(benzyloxy)-4-((4-(tert-butyl)benzyl)amino)benzoate. $^1$H NMR (300 MHz, CDCl$_3$) δ 7.87 (d, J=8.7 Hz, 1H), 7.49-7.26 (m, 14H), 6.29-6.13 (m, 2H), 5.34 (s, 2H), 5.12 (s, 2H), 4.45 (s, 1H), 4.33 (d, J=5.0 Hz, 2H), 1.36 (s, 9H).

Step 3. Preparation by a similar procedure to Example 53, step 3, starting from benzyl 2-(benzyloxy)-4-((4-(tert-butyl)benzyl)amino)benzoate to obtain benzyl (R)-2-(benzyloxy)-4-(N-(4-(tert-butyl)benzyl)-1-((perfluorophenyl)sulfonyl)azetidine-2-carboxamido)benzoate. $^1$H NMR (300 MHz, CDCl$_3$) δ 7.88-7.76 (m, 1H), 7.45-7.24 (m, 12H), 7.08-6.96 (m, 2H), 6.69-6.59 (m, 1H), 6.50 (s, 1H), 5.37 (s, 2H), 5.13-5.01 (m, 1H), 4.94-4.78 (m, 2H), 4.74 (s, 2H), 4.19-3.92 (m, 2H), 2.09-1.70 (m, 2H), 1.31 (s, 9H).

Step 4. Preparation by a similar procedure to Example 53, step 5, starting from benzyl (R)-2-(benzyloxy)-4-(N-(4-(tert-butyl)benzyl)-1-((perfluorophenyl)sulfonyl)azetidine-2-carboxamido)benzoate to obtain the compound of Example 130 (R)-4-(N-(4-(tert-butyl)benzyl)-1-((perfluorophenyl)sulfonyl)azetidine-2-carboxamido)-2-hydroxybenzoic acid. MS (ESI+): [M+H]+ m/z 613.0.

Example 131

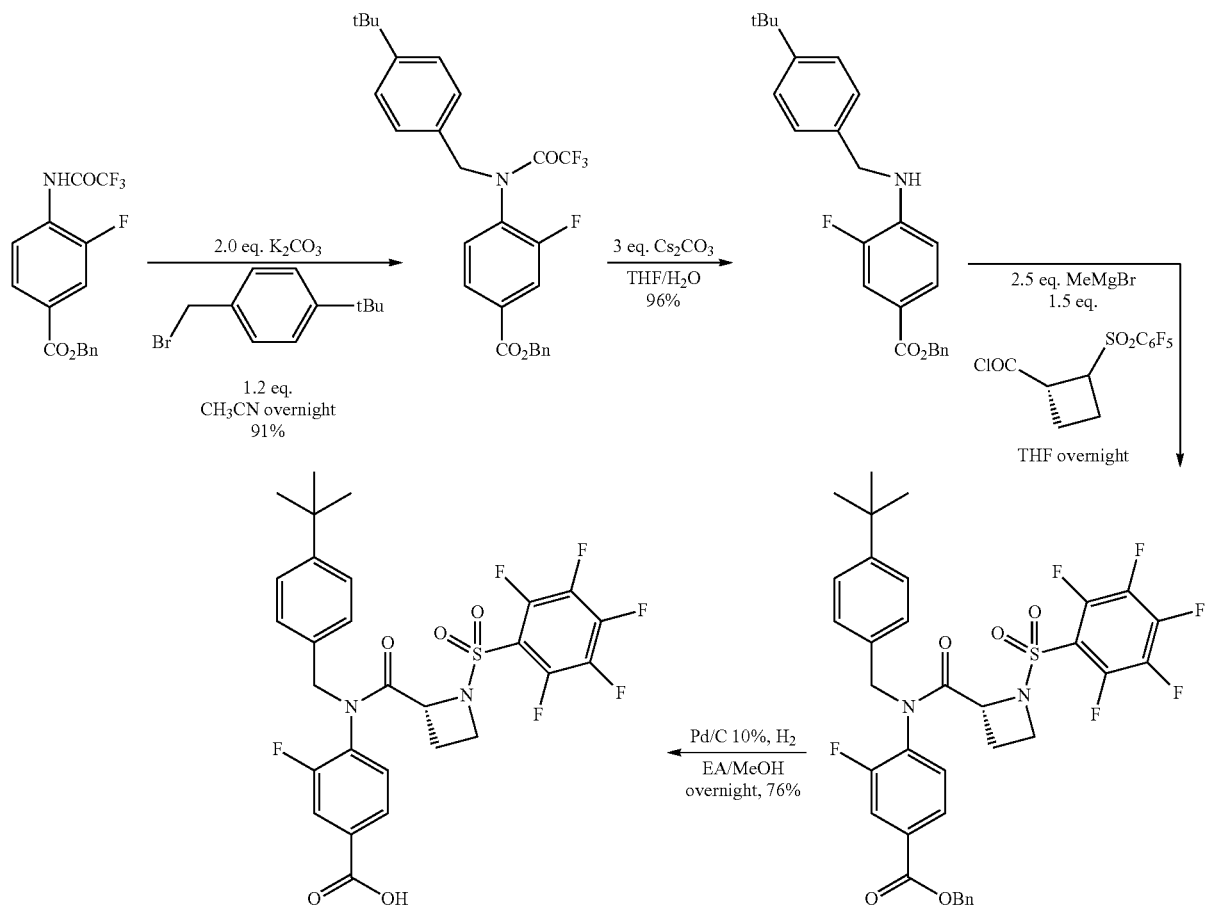

(R)-4-(N-(4-(tert-butyl)benzyl)-1-((perfluorophenyl)sulfonyl)azetidine-2-carboxamido)-3-fluorobenzoic acid

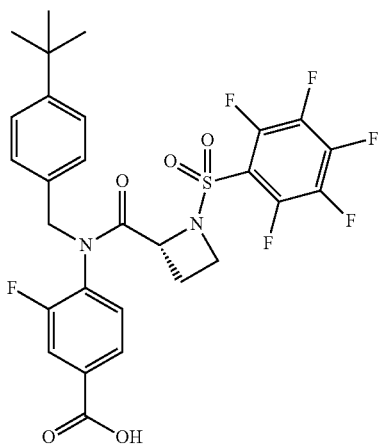 [SMILES: CC(C)(C)c1ccc(CN(C(=O)[C@H]2CCN2S(=O)(=O)c2c(F)c(F)c(F)c(F)c2F)c2ccc(C(=O)O)cc2F)cc1]

Step 1. Preparation by a similar procedure to Example 61, step 4, starting from benzyl 3-fluoro-4-(2,2,2-trifluoroacetamido)benzoate to obtain benzyl 4-(N-(4-(tert-butyl)benzyl)-2,2,2-trifluoroacetamido)-3-fluorobenzoate. Taken as such to next step.

Step 2. Preparation by a similar procedure to Example 109, step 4, starting from benzyl 4-(N-(4-(tert-butyl)benzyl)-2,2,2-trifluoroacetamido)-3-fluorobenzoate to obtain benzyl 4-((4-(tert-butyl)benzyl)amino)-3-fluorobenzoate. $^1$H NMR (300 MHz, CDCl$_3$) δ 7.86-7.68 (m, 2H), 7.52-7.27 (m, 9H), 6.75-6.63 (m, 1H), 5.37 (s, 2H), 4.82 (s, 1H), 4.43 (s, 2H), 1.38 (s, 9H).

Step 3. Preparation by a similar procedure to Example 53, step 3, starting from benzyl 4-((4-(tert-butyl)benzyl)amino)-3-fluorobenzoate to obtain benzyl (R)-4-(N-(4-(tert-butyl)benzyl)-1-((perfluorophenyl)sulfonyl)azetidine-2-carboxamido)-3-fluorobenzoate. $^1$H NMR (300 MHz, CDCl$_3$) δ 7.87-7.74 (m, 2H), 7.47-7.30 (m, 5H), 7.27-7.23 (m, 2H), 7.10-6.95 (m, 3H), 5.36 (s, 2H), 5.28 (d, J=14.4 Hz, 1H), 5.13-4.94 (m, 1H), 4.91-4.81 (m, 1H), 4.35-4.20 (m, 1H), 4.06-3.99 (m, 1H), 2.48-2.24 (m, 1H), 1.97-1.80 (m, 1H), 1.27 (s, 9H).

Step 4. Preparation by a similar procedure to Example 37, example 5, starting from benzyl (R)-4-(N-(4-(tert-butyl)benzyl)-1-((perfluorophenyl)sulfonyl)azetidine-2-carboxamido)-3-fluorobenzoate to obtain the compound of Example 131 (R)-4-(N-(4-(tert-butyl)benzyl)-1-((perfluorophenyl)sulfonyl)azetidine-2-carboxamido)-3-fluorobenzoic acid. MS (ESI+): [M+H]+ m/z 615.1.

Example 132

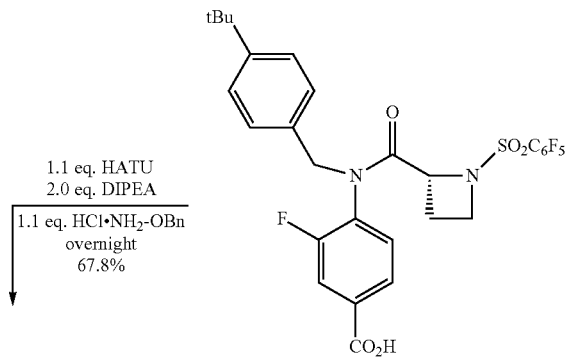

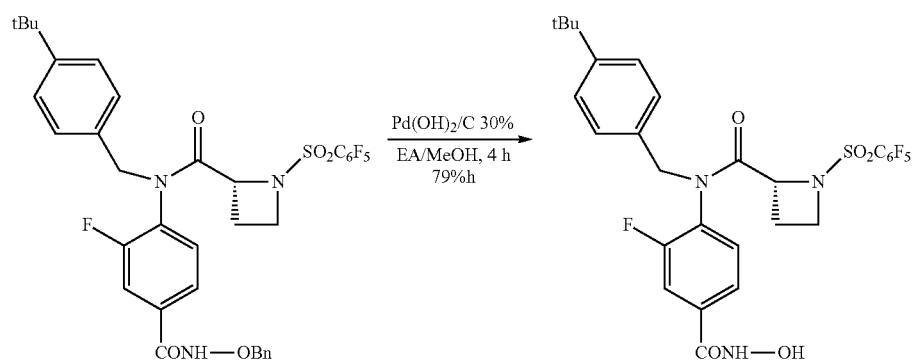

(R)—N-(4-(tert-butyl)benzyl)-N-(2-fluoro-4-(hydroxycarbamoyl)phenyl)-1-((perfluorophenyl)sulfonyl)azetidine-2-carboxamide

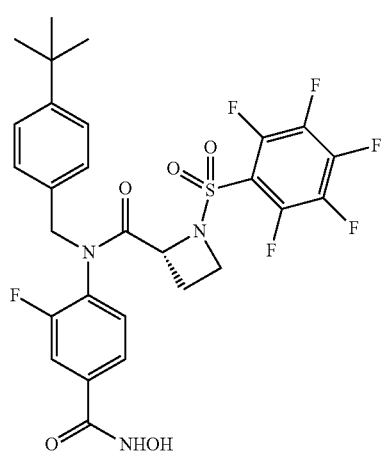

Step 1. Preparation by a similar procedure to Example 113, step 5, starting from (R)-4-(N-(4-(tert-butyl)benzyl)-1-((perfluorophenyl)sulfonyl)azetidine-2-carboxamido)-3-fluorobenzoic acid to obtain (R)—N-(4-((benzyloxy)carbamoyl)-2-fluorophenyl)-N-(4-(tert-butyl)benzyl)-1-((perfluorophenyl)sulfonyl)azetidine-2-carboxamide. $^1$H NMR (300 MHz, CDCl$_3$) δ 9.20-8.95 (m, 1H), 7.69-7.53 (m, 1H), 7.45-7.38 (m, 5H), 7.35-7.25 (m, 3H), 7.08-6.96 (m, 3H), 5.28-5.15 (m, 1H), 5.02 (s, 2H), 4.88-4.79 (m, 1H), 4.36-4.17 (m, 1H), 4.18-3.98 (m, 2H), 2.39-2.22 (m, 1H), 2.02-1.87 (m, 1H), 1.29 (s, 9H).

Step 2. Preparation by a similar procedure to Example 85, step 5, starting from (R)—N-(4-((benzyloxy)carbamoyl)-2-fluorophenyl)-N-(4-(tert-butyl)benzyl)-1-((perfluorophenyl)sulfonyl)azetidine-2-carboxamide to obtain the compound of Example 132 (R)—N-(4-(tert-butyl)benzyl)-N-(2-fluoro-4-(hydroxycarbamoyl)phenyl)-1-((perfluorophenyl)sulfonyl)azetidine-2-carboxamide. MS (ESI+): [M+H]+ m/z 630.1.

Example 133

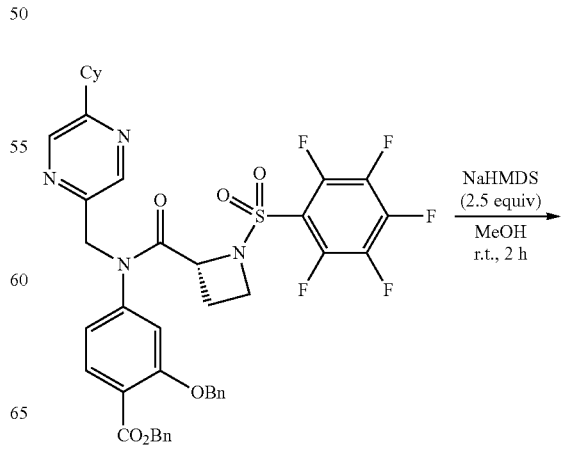

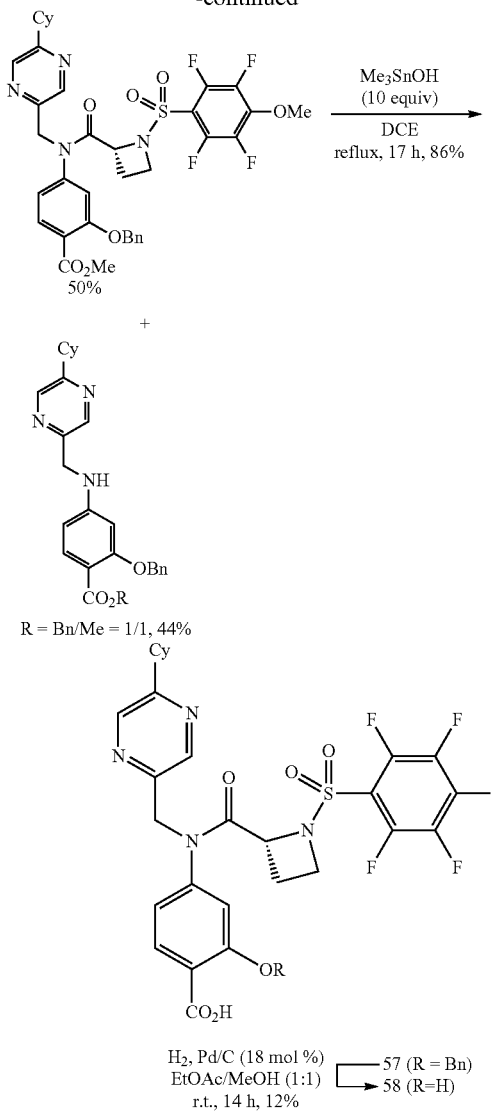

(R)-4-(N-((5-cyclohexylpyrazin-2-yl)methyl)-1-((2,3,5,6-tetrafluoro-4-methoxyphenyl)sulfonyl)azetidine-2-carboxamido)-2-hydroxybenzoic acid

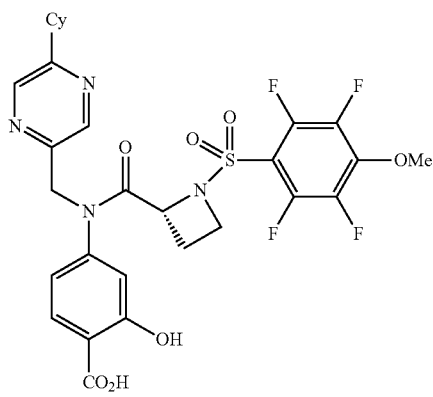

Step 1. To a solution of benzyl (R)-2-(benzyloxy)-4-(N-((5-cyclohexylpyrazin-2-yl)methyl)-1-((perfluorophenyl)sulfonyl)azetidine-2-carboxamido)benzoate (34 mg, 0.042 mmol) in MeOH (0.80 mL) was added NaHMDS (1 M in THF, 0.10 mL, 0.10 mmol) at room temperature. After stirring for 2 h, the reaction was quenched by adding water. The crude products were extracted with EtOAc (×3), and the combined organic extracts were washed with brine, dried (MgSO4), and concentrated in vacuo. The residue was purified by flash column chromatography (hexane/EtOAc=5/1 to 1/1) to afford methyl (R)-2-(benzyloxy)-4-(N-((5-cyclohexylpyrazin-2-yl)methyl)-1-((2,3,5,6-tetrafluoro-4-methoxyphenyl)sulfonyl)azetidine-2-carboxamido)benzoate (15.9 mg, 50%) as a colorless oil. $^1$H NMR (300 MHz, CDCl$_3$) δ 8.43 (s, 1H), 8.35 (d, J=1.2 Hz, 1H), 7.81 (d, J=8.1 Hz, 1H), 7.33-7.48 (m, 5H), 6.94 (d, J=1.8 Hz, 1H), 6.84 (dd, J=1.8, 8.1 Hz, 1H), 5.23 (d, J=12.6 Hz, 1H), 5.13 (d, J=12.6 Hz, 1H), 5.04 (d, J=15.3 Hz, 1H), 4.87-4.93 (m, 1H), 4.76 (d, J=15.3 Hz, 1H), 4.19 (t, JHF=1.8 Hz, 3H), 3.87-4.05 (m, 5H), 2.69-2.79 (m, 1H), 2.04-2.15 (m, 1H), 1.24-1.98 (m, 11H).

Step 2. Preparation by a similar procedure to Example 108, step 5, starting from methyl (R)-2-(benzyloxy)-4-(N-((5-cyclohexylpyrazin-2-yl)methyl)-1-((2,3,5,6-tetrafluoro-4-methoxyphenyl)sulfonyl)azetidine-2-carboxamido)benzoate to obtain (R)-2-(benzyloxy)-4-(N-((5-cyclohexylpyrazin-2-yl)methyl)-1-((2,3,5,6-tetrafluoro-4-methoxyphenyl)sulfonyl)azetidine-2-carboxamido)benzoic acid. $^1$H NMR (300 MHz, CDCl$_3$) δ 8.48 (d, J=1.2 Hz, 1H), 8.36 (d, J=1.2 Hz, 1H), 8.17 (d, J=8.7 Hz, 1H), 7.43-7.47 (m, 5H), 7.23 (d, J=1.8 Hz, 1H), 6.97 (dd, J=1.8, 8.7 Hz, 1H), 5.38 (d, J=11.4 Hz, 1H), 5.27 (d, J=11.4 Hz, 1H), 5.06 (d, J=15.3 Hz, 1H), 4.92-4.99 (m, 1H), 4.81 (d, J=15.3 Hz, 1H), 4.20 (t, JHF=1.8 Hz, 3H), 3.96-4.20 (m, 2H), 2.70-2.80 (m, 1H), 2.17-2.25 (m, 1H), 1.75-1.98 (m, 6H), 1.26-1.64 (m, 5H).

Step 3. Preparation by a similar procedure to Example 53, step 5, starting from (R)-2-(benzyloxy)-4-(N-((5-cyclohexylpyrazin-2-yl)methyl)-1-((2,3,5,6-tetrafluoro-4-methoxyphenyl)sulfonyl)azetidine-2-carboxamido)benzoic acid to obtain the compound of Example 133 (R)-4-(N-((5-cyclohexylpyrazin-2-yl)methyl)-1-((2,3,5,6-tetrafluoro-4-methoxyphenyl)sulfonyl)azetidine-2-carboxamido)-2-hydroxybenzoic acid. $^1$H NMR (300 MHz, CDCl$_3$) δ 8.67 (s, 1H), 8.37 (s, 1H), 7.68-7.79 (m, 1H), 6.58-6.72 (m, 2H), 4.81-5.14 (m, 3H), 4.20 (brs, 3H), 3.90-4.09 (m, 2H), 2.71-2.83 (m, 1H), 1.28-2.29 (m, 12H). HRMS (ESI+) m/z 653.1686 [M+H]+.

Example 134

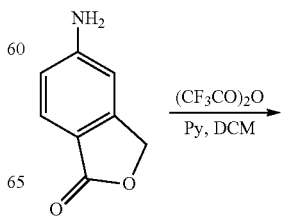

359
-continued

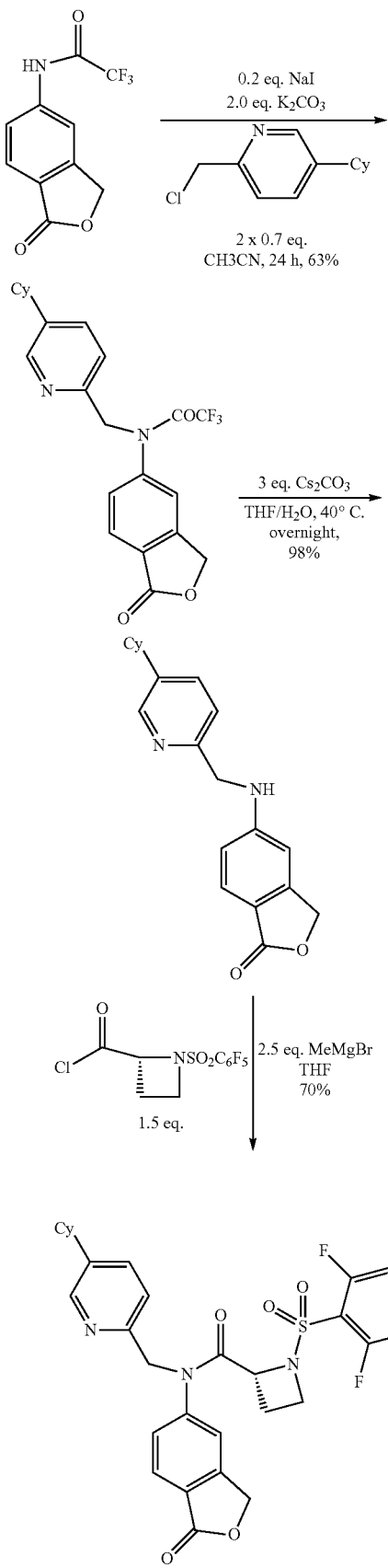

360

(R)—N-((5-cyclohexylpyridin-2-yl)methyl)-N-(1-oxo-1,3-dihydroisobenzofuran-5-yl)-1-((perfluorophenyl)sulfonyl)azetidine-2-carboxamide

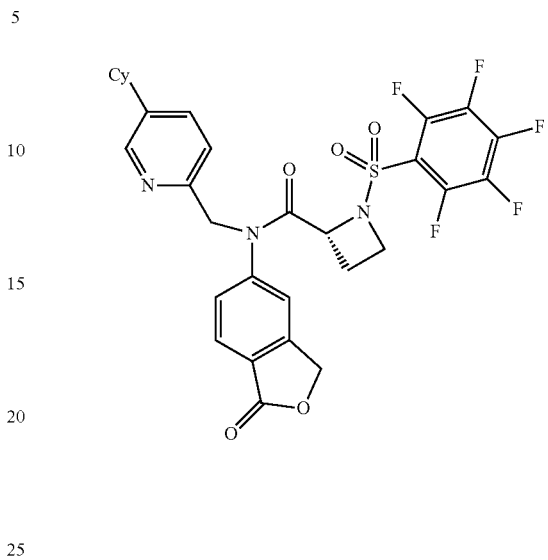

Step 1. To a suspension of 5-aminoisobenzofuran-1(3H)-one (147 mg, 0.99 mmol) in DCM (5 mL) was added at 0° C. pyridine (0.17 mL, 2.16 mmol) and trifluoroacetic anhydride (0.15 mL, 1.1 mmol) under argon. The mixture was allowed to reach rt and stirred for 2 hours. The mixture was diluted with DCM and washed with aqueous pH 2 solution (10% $KHSO_4/Na_2SO_4$), saturated sodium bicarbonate, dried (sodium sulfate) and concentrated to dryness to obtain a solid. Trituration with hexane gave 2,2,2-trifluoro-N-(1-oxo-1,3-dihydroisobenzofuran-5-yl)acetamide (220 mg, 91% yield). $^1$H NMR (300 MHz, $CDCl_3$) δ 8.20 (br, 1H), 8.13 (d, J=1.8 Hz, 1H), 7.97 (d, J=8.2 Hz, 1H), 7.56-7.47 (m, 1H), 5.37 (s, 2H).

Step 2. Preparation by a similar procedure to Example 116, step 4, starting from 2,2,2-trifluoro-N-(1-oxo-1,3-dihydroisobenzofuran-5-yl)acetamide to obtain N-((5-cyclohexylpyridin-2-yl)methyl)-2,2,2-trifluoro-N-(1-oxo-1,3-dihydroisobenzofuran-5-yl)acetamide. $^1$H NMR (300 MHz, $CDCl_3$) δ 8.37 (d, J=1.8 Hz, 1H), 7.91 (d, J=8.2 Hz, 1H), 7.53-7.45 (m, 2H), 7.42 (d, J=8.2 Hz, 1H), 7.28-7.24 (m, 1H), 5.30 (m, 2H), 5.02 (s, 2H), 2.60-2.43 (m, 1H), 1.92-1.72 (m, 5H), 1.49-1.29 (m, 5H).

Step 3. Preparation by a similar procedure to Example 109, step 4, starting from N-((5-cyclohexylpyridin-2-yl)methyl)-2,2,2-trifluoro-N-(1-oxo-1,3-dihydroisobenzofuran-5-yl)acetamide to obtain 5-(((5-cyclohexylpyridin-2-yl)methyl)amino)isobenzofuran-1(3H)-one. $^1$H NMR (300 MHz, $CDCl_3$) δ 8.43 (s, 1H), 7.65 (d, J=8.4, 1H), 7.56-7.46 (m, 1H), 7.23 (d, J=8.0, 1H), 6.75 (d, J=8.4 Hz, 1H), 6.56 (s, 1H), 5.84 (s, 1H), 5.14 (s, 2H), 4.47 (s, 2H), 2.62-2.42 (m, 1H), 1.94-1.72 (m, 5H), 1.51-1.28 (m, 5H).

Step 4. Preparation by a similar procedure to Example 53, step 3, starting from 5-(((5-cyclohexylpyridin-2-yl)methyl)amino)isobenzofuran-1(3H)-one to obtain the compound of Example 134 (R)—N-((5-cyclohexylpyridin-2-yl)methyl)-N-(1-oxo-1,3-dihydroisobenzofuran-5-yl)-1-((perfluorophenyl)sulfonyl)azetidine-2-carboxamide. MS (ESI+): [M+H]+ m/z 636.17.

Example 135

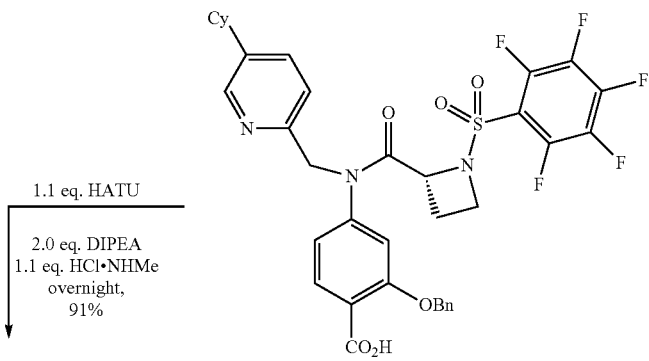

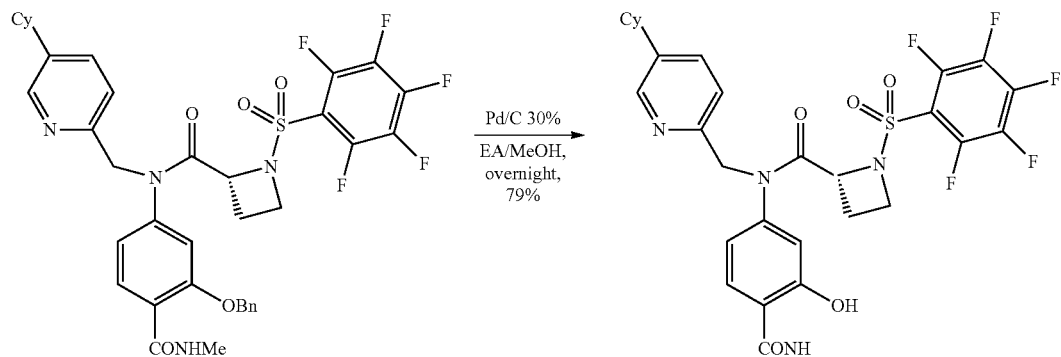

(R)—N-((5-cyclohexylpyridin-2-yl)methyl)-N-(3-hydroxy-4-(methylcarbamoyl) phenyl)-1-((perfluorophenyl)sulfonyl)azetidine-2-carboxamide

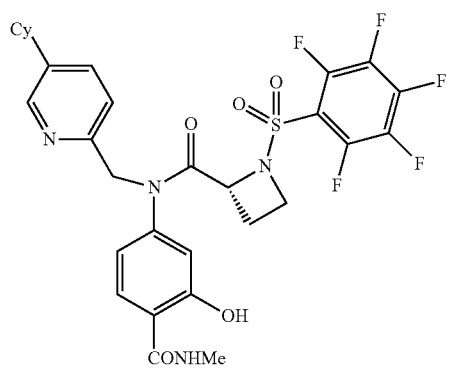

Step 1. Preparation by a similar procedure to Example 113, step 5, starting from (R)-2-(benzyloxy)-4-(N-((5-cyclohexylpyridin-2-yl)methyl)-1-((perfluorophenyl)sulfonyl) azetidine-2-carboxamido)benzoic acid (See Example 113 for preparation) to obtain (R)—N-(3-(benzyloxy)-4-(methylcarbamoyl)phenyl)-N-((5-cyclohexylpyridin-2-yl) methyl)-1-((perfluorophenyl)sulfonyl)azetidine-2-carboxamide. $^1$H NMR (300 MHz, CDCl$_3$) δ 8.33 (s, 1H), 8.24-8.16 (m, 1H), 7.80 (s, 1H), 7.50-7.36 (m, 6H), 7.20-7.10 (m, 1H), 6.95 (d, J=2.2 Hz, 1H), 6.87-6.76 (m, 1H), 5.24-5.15 (m, 1H), 5.14-5.05 (m, 1H), 4.99-4.83 (m, 3H), 4.15-3.94 (m, 2H), 2.93 (s, 3H), 2.60-2.42 (m, 1H), 2.21-2.12 (m, 1H), 2.02-1.93 (m, 1H), 1.92-1.72 (m, 5H), 1.51-1.27 (m, 5H).

Step 2. Preparation by a similar procedure to Example 53, step 5, starting from (R)—N-(3-(benzyloxy)-4-(methylcarbamoyl)phenyl)-N-((5-cyclohexylpyridin-2-yl)methyl)-1-((perfluorophenyl)sulfonyl)azetidine-2-carboxamide to obtain the compound of Example 135 (R)—N-((5-cyclohexylpyridin-2-yl)methyl)-N-(3-hydroxy-4-(methylcarbamoyl) phenyl)-1-((perfluorophenyl)sulfonyl)azetidine-2-carboxamide. MS (ESI+): [M+H]+ m/z 653.2.

Example 136
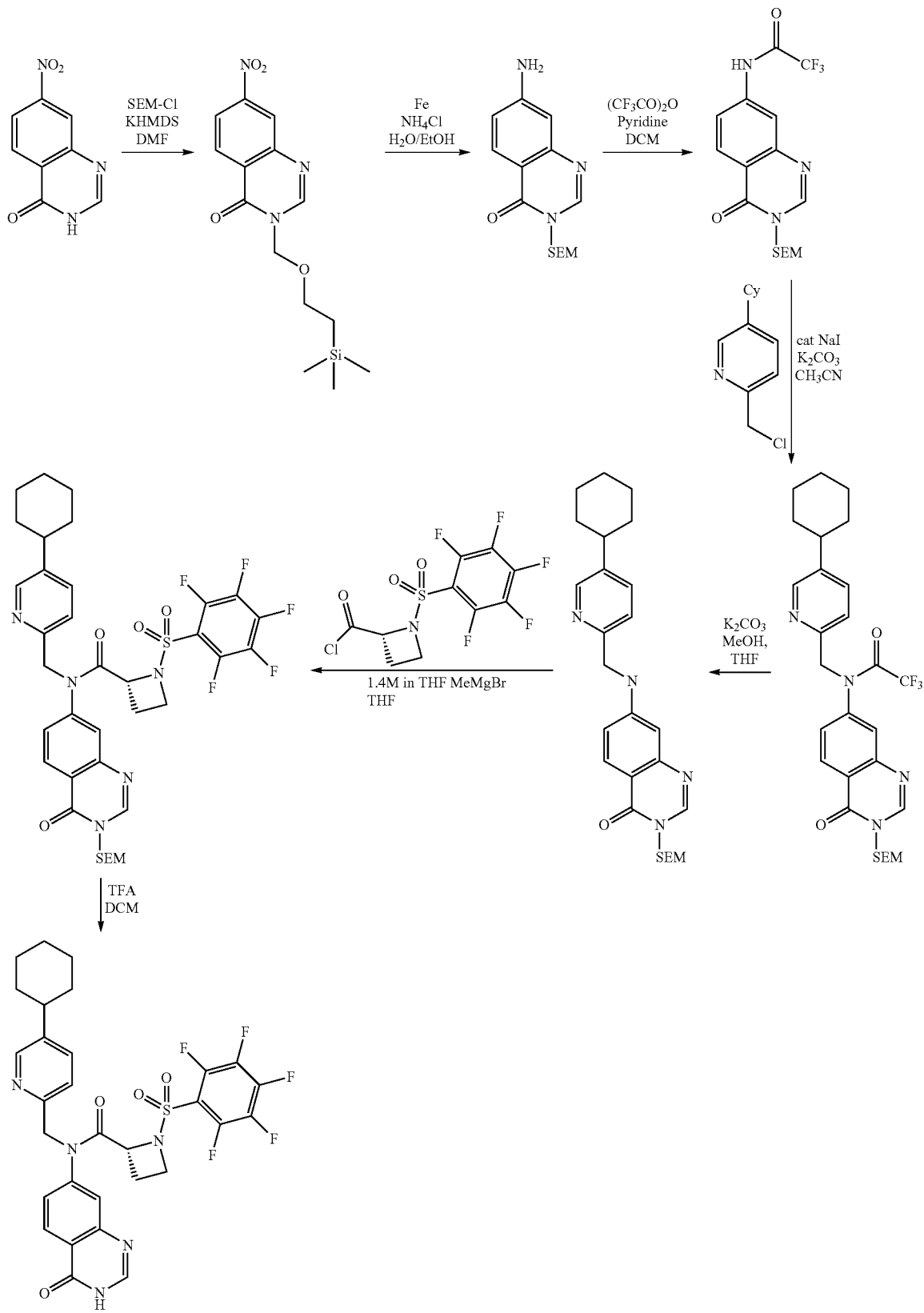

(R)—N-((5-cyclohexylpyridin-2-yl)methyl)-N-(4-oxo-3,4-dihydroquinazolin-7-yl)-1-((perfluorophenyl)sulfonyl)azetidine-2-carboxamide

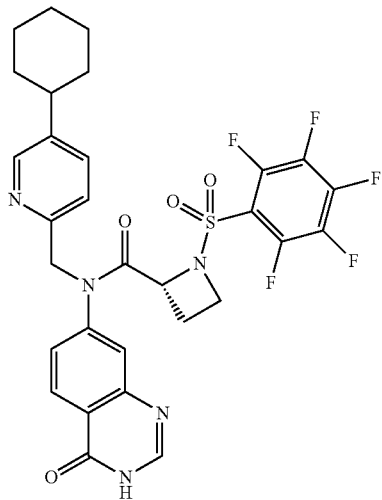 [SMILES: O=C([C@H]1CCN1S(=O)(=O)c1c(F)c(F)c(F)c(F)c1F)N(Cc1ccc(C2CCCCC2)cn1)c1ccc2c(=O)[nH]cnc2c1]

Step 1. To a suspension of 7-nitroquinazolin-4(3H)-one (98 mg, 0.51 mmol) in DMF (4 mL) was added at 0° C. KHMDS (1M in THF, 0.61 mL) under nitrogen. After 5-10 min at 0° C., SEM-Cl (0.11 mL, 0.61 mmol) was added dropwise. The resulting homogeneous mixture was allowed to reach rt and stirred for 3 hours. Cold saturated ammonium chloride was added followed by water. The mixture was extracted with EtOAc (2×). The extract was washed with water, brine, dried (sodium sulfate) and concentrated. Purification by column chromatography gave 7-nitro-3-((2-(trimethylsilyl)ethoxy)methyl)quinazolin-4(3H)-one as yellow solid (114 mg, 70% yield). $^1$H NMR (300 MHz, CDCl$_3$) δ 8.59 (m, 1H), 8.51 (d, J=8.8 Hz, 1H), 8.37-8.22 (m, 2H), 5.48 (s, 2H), 3.83-3.62 (m, 2H), 1.08-0.92 (m, 2H), 0.07-0.03 (m, 9H).

Step 2. Preparation by a similar procedure to Example 106, step 3, starting from 7-nitro-3-((2-(trimethylsilyl)ethoxy)methyl)quinazolin-4(3H)-one to obtain 7-amino-3-((2-(trimethylsilyl)ethoxy)methyl)quinazolin-4(3H)-one. $^1$H NMR (300 MHz, CDCl$_3$) δ 8.17-8.04 (m, 2H), 6.91-6.76 (m, 2H), 5.41 (s, 2H), 4.53-3.92 (m, 2H), 3.78-3.60 (m, 2H), 1.06-0.89 (m, 2H), −0.01 (s, 9H).

Step 3. Preparation by a similar procedure to Example 61, step 3, starting from 7-amino-3-((2-(trimethylsilyl)ethoxy)methyl)quinazolin-4(3H)-one to obtain 2,2,2-trifluoro-N-(4-oxo-3-((2-(trimethylsilyl)ethoxy)methyl)-3,4-dihydroquinazolin-7-yl)acetamide. $^1$H NMR (300 MHz, CDCl$_3$) δ 8.37 (d, J=8.7 Hz, 1H), 8.18 (m, 2H), 8.02 (d, J=2.1 Hz, 1H), 7.75 (dd, J=8.7, 2.1 Hz, 1H), 5.45 (s, 2H), 3.81-3.60 (m, 2H), 1.07-0.91 (m, 2H), 0.09-0.03 (m, 9H)

Step 4. Preparation by a similar procedure to Example 116, step 4, starting from 2,2,2-trifluoro-N-(4-oxo-3-((2-(trimethylsilyl)ethoxy)methyl)-3,4-dihydroquinazolin-7-yl)acetamide to obtain N-((5-cyclohexylpyridin-2-yl)methyl)-2,2,2-trifluoro-N-(4-oxo-3-((2-(trimethylsilyl)ethoxy) methyl)-3,4-dihydroquinazolin-7-yl)acetamide. $^1$H NMR (300 MHz, CDCl$_3$) δ 8.40 (d, J=2.3 Hz, 1H), 8.33 (d, J=8.3 Hz, 1H), 8.18 (s, 1H), 7.65 (d, J=2.3 Hz, 1H), 7.55 (d, J=8.3 Hz, 1H), 7.47-7.36 (m, 1H), 7.36-7.27 (m, 1H), 5.44 (s, 2H), 5.10 (s, 2H), 3.80-3.60 (m, 2H), 2.67-2.45 (m, 1H), 2.1-1.6 (m, 5H), 1.55-1.15 (m, 5H), 1.07-0.88 (m, 2H), 0.02 (s, 9H).

Step 5. To a solution of N-((5-cyclohexylpyridin-2-yl)methyl)-2,2,2-trifluoro-N-(4-oxo-3-((2-(trimethylsilyl)ethoxy) methyl)-3,4-dihydroquinazolin-7-yl)acetamide (149 mg, 0.27 mmol) in THF (1.4 mL) and methanol (1.7 mL) was added potassium carbonate (93 mg, 0.67 mmol) under nitrogen. The mixture was stirred at rt for 2 hours. Cold saturated ammonium chloride was added followed by water. The mixture was extracted with EtOAc (2×). The extract was washed with brine, dried (sodium sulfate), and concentrated. Purification by column chromatography gave 7-(((5-cyclohexylpyridin-2-yl)methyl)amino)-3-((2-(trimethylsilyl)ethoxy)methyl)quinazolin-4(3H)-one (117 mg, 95% yield). $^1$H NMR (300 MHz, CDCl$_3$) δ 8.46 (d, J=2.2 Hz, 1H), 8.10 (m, 2H), 7.58 (dd, J=8.0, 2.2 Hz, 1H), 7.32 (d, J=8.0 Hz, 1H), 6.88 (dd, J=8.8, 2.3 Hz, 1H), 6.77 (d, J=2.3 Hz, 1H), 5.89-5.69 (br, 1H), 5.40 (s, 2H), 4.56 (s, 2H), 3.77-3.61 (m, 2H), 2.66-2.46 (m, 1H), 2.0-1.70 (m, 5H), 1.58-1.14 (m, 5H), 1.05-0.86 (m, 2H), 0.07 (s, 9H)

Step 6. To a solution of 7-(((5-cyclohexylpyridin-2-yl)methyl)amino)-3-((2-(trimethylsilyl)ethoxy)methyl)quinazolin-4(3H)-one (129 mg, 0.28 mmol) in THF (2.2 mL) was added at 0° C. MeMgBr (1.4 M in THF, 0.50 mL) under argon. After 5-10 minutes, powder (R)-1-((perfluorophenyl)sulfonyl)azetidine-2-carbonyl chloride (146 mg, 0.42 mmol) was added at 0° C. The mixture was allowed to reach rt and stirred for 1 hour. Cold ammonium chloride was added followed by water. The mixture was extracted with EtOAc (2×). The extract was washed with brine, dried (sodium sulfate), and concentrated. Purification by column chromatography gave (R)—N-((5-cyclohexylpyridin-2-yl)methyl)-N-(4-oxo-3-((2-(trimethylsilyl)ethoxy)methyl)-3,4-dihydroquinazolin-7-yl)-1-((perfluorophenyl)sulfonyl)azetidine-2-carboxamide (185 mg, 86% yield). $^1$H NMR (300 MHz, CDCl$_3$) δ 8.43-8.26 (m, 2H), 8.18 (s, 1H), 7.55 (s, 1H), 7.42-7.10 (m, 3H), 5.45 (s, 2H), 5.21-4.90 (m, 3H), 4.27-3.97 (m, 2H), 3.84-3.51 (m, 2H), 2.66-2.48 (m, 1H), 2.48-2.27 (m, 1H), 1.96-1.71 (m, 6H), 1.54-1.13 (m, 5H), 1.10-0.89 (m, 2H), 0.03 (s, 9H).

Step 7. To a solution of (R)—N-((5-cyclohexylpyridin-2-yl)methyl)-N-(4-oxo-3-((2-(trimethylsilyl)ethoxy)methyl)-3,4-dihydroquinazolin-7-yl)-1-((perfluorophenyl)sulfonyl) azetidine-2-carboxamide (183 mg, 0.24 mmol) in dichloromethane (1 mL) was added trifluoroacetic acid (1 mL) under argon. The mixture was stirred at rt for 2 hours. Additional dichloromethane was added, and the mixture was poured onto cold saturated sodium bicarbonate. After separation of phases, the aqueous layer was extracted with additional dichloromethane. The combined organics was washed with additional saturated sodium bicarbonate, dried (sodium sulfate) and concentrated. Purification by column chromatography gave Example 136 (R)—N-((5-cyclohexylpyridin-2-yl)methyl)-N-(4-oxo-3,4-dihydroquinazolin-7-yl)-1-((perfluorophenyl)sulfonyl)azetidine-2-carboxamide (128 mg, 84% yield). HRMS (ESI+) m/z 648.1847 [M+H]+.

Example 137
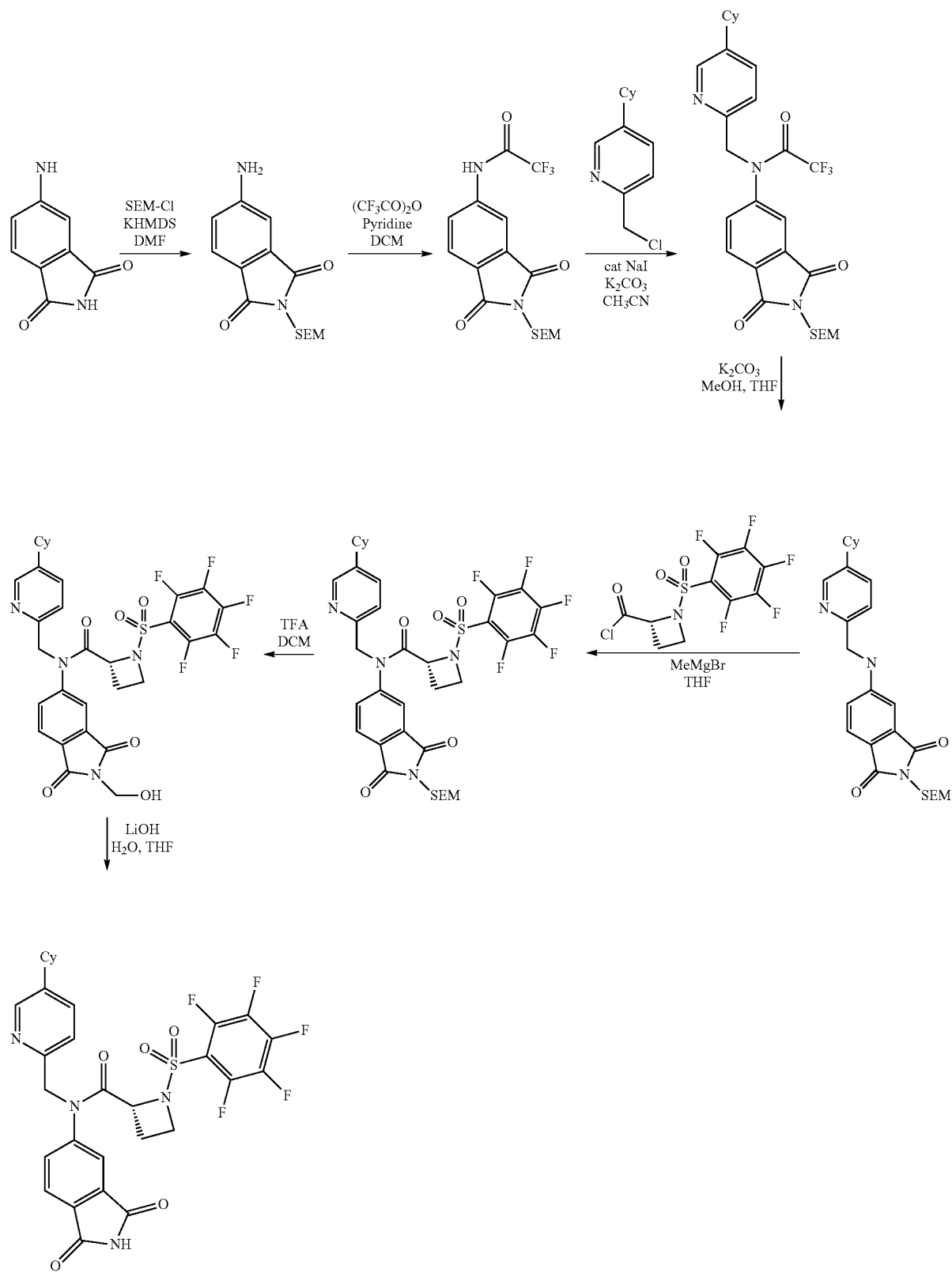

(R)—N-((5-cyclohexylpyridin-2-yl)methyl)-N-(1,3-dioxoisoindolin-5-yl)-1-((perfluorophenyl)sulfonyl)azetidine-2-carboxamide

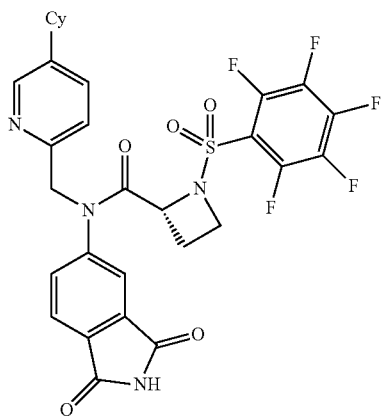

Step 1. Preparation by a similar procedure to Example 136, step 1, starting from 5-aminoisoindoline-1,3-dione to obtain 5-amino-2-((2-(trimethylsilyl)ethoxy)methyl)isoindoline-1,3-dione. $^1$H NMR (300 MHz, CDCl$_3$) δ 7.67 (d, J=8.1 Hz, 1H), 7.09 (d, J=2.1 Hz, 1H), 6.88 (dd, J=8.1, 2.1 Hz, 1H), 5.07 (s, 2H), 4.41 (br, 2H), 3.74-3.53 (m, 2H), 1.05-0.87 (m, 2H), 0.09-0.04 (m, 9H).

Step 2. Preparation by a similar procedure to Example 61, step 3, starting from 5-amino-2-((2-(trimethylsilyl)ethoxy)methyl)isoindoline-1,3-dione to obtain N-(1,3-dioxo-2-((2-(trimethylsilyl)ethoxy)methyl)isoindolin-5-yl)-2,2,2-trifluoroacetamide. $^1$H NMR (300 MHz, CDCl$_3$) δ 8.48 (s, 1H), 8.21 (d, J=2.0 Hz, 1H), 8.09 (dd, J=8.2, 2.0 Hz, 1H), 7.97 (d, J=8.2 Hz, 1H), 5.13 (s, 2H), 3.76-3.60 (m, 2H), 1.08-0.88 (m, 2H), 0.06-0.04 (m, 9H).

Step 3. Preparation by a similar procedure to Example 116, step 4, starting from N-(1,3-dioxo-2-((2-(trimethylsilyl)ethoxy)methyl)isoindolin-5-yl)-2,2,2-trifluoroacetamide to obtain N-((5-cyclohexylpyridin-2-yl)methyl)-N-(1,3-dioxo-2-((2-(trimethylsilyl)ethoxy)methyl)isoindolin-5-yl)-2,2,2-trifluoroacetamide. $^1$H NMR (300 MHz, CDCl$_3$) δ 8.39 (d, J=2.3 Hz, 1H), 7.93 (d, J=7.9 Hz, 1H), 7.83 (s, 1H), 7.68 (d, J=7.9 Hz, 1H), 7.53 (dd, J=7.9, 2.3 Hz, 1H), 7.36-7.21 (m, 1H), 5.12 (s, 2H), 5.05 (s, 2H), 3.76-3.56 (m, 2H), 1.99-1.71 (m, 5H), 1.50-1.19 (m, 5H), 1.08-0.83 (m, 2H), 0.08-0.05 (m, 9H).

Step 4. Preparation by a similar procedure to Example 136, step 5, starting from N-((5-cyclohexylpyridin-2-yl)methyl)-N-(1,3-dioxo-2-((2-(trimethylsilyl)ethoxy)methyl)isoindolin-5-yl)-2,2,2-trifluoroacetamide to obtain 5-(((5-cyclohexylpyridin-2-yl)methyl)amino)-2-((2-(trimethylsilyl)ethoxy)methyl)isoindoline-1,3-dione.

Step 5. Preparation by a similar procedure to Example 136, step 6, starting from 5-(((5-cyclohexylpyridin-2-yl)methyl)amino)-2-((2-(trimethylsilyl)ethoxy)methyl)isoindoline-1,3-dione to obtain (R)—N-((5-cyclohexylpyridin-2-yl)methyl)-N-(1,3-dioxo-2-((2-(trimethylsilyl)ethoxy)methyl) isoindolin-5-yl)-1-((perfluorophenyl)sulfonyl)azetidine-2-carboxamide. $^1$H NMR (300 MHz, CDCl$_3$) δ 8.35 (s, 1H), 7.94 (d, J=8.0 Hz, 1H), 7.75 (d, J=2.0 Hz, 1H), 7.70-7.59 (m, 1H), 7.52 (dd, J=8.0, 2.0 Hz, 1H), 7.27-7.15 (m, 1H), 5.12 (s, 2H), 5.07-4.88 (m, 3H), 3.79-3.52 (m, 2H), 2.61-2.46 (m, 1H), 1.97-1.70 (m, 5H), 1.50-1.30 (m, 5H), 1.05-0.85 (m, 2H), 0.02 (s, 9H).

Step 6. To a solution of (R)—N-((5-cyclohexylpyridin-2-yl)methyl)-N-(1,3-dioxo-2-((2-(trimethylsilyl)ethoxy)methyl) isoindolin-5-yl)-1-((perfluorophenyl)sulfonyl)azetidine-2-carboxamide (182 mg (0.23 mmol) in dichloromethane (1 mL) was added TFA (1 mL) under nitrogen. The mixture was stirred at rt for 5.5 h, then poured onto aqueous 10% sodium bicarbonate, dried (sodium sulfate) and concentrated. Purification by column chromatography gave (R)—N-((5-cyclohexylpyridin-2-yl)methyl)-N-(2-(hydroxymethyl)-1,3-dioxoisoindolin-5-yl)-1-((perfluorophenyl)sulfonyl)azetidine-2-carboxamide (105 mg, 66% yield). $^1$H NMR (300 MHz, CDCl$_3$) δ 8.33 (m, 1H), 7.87 (d, J=7.9 Hz, 1H), 7.79 (d, J=1.8 Hz, 1H), 7.60 (dd, J=7.9, 1.8 Hz, 1H), 7.53 (dd, J=8.1, 2.3 Hz, 1H), 7.35-7.07 (m, 1H), 5.17 (s, 2H), 5.09-4.83 (m, 3H), 4.13-3.93 (m, 2H), 2.61-2.42 (m, 1H), 2.42-2.21 (m, 1H), 1.94-1.64 (m, 6H), 1.54-1.29 (m, 5H).

Step 7. To (R)—N-((5-cyclohexylpyridin-2-yl)methyl)-N-(2-(hydroxymethyl)-1,3-dioxoisoindolin-5-yl)-1-((perfluorophenyl)sulfonyl)azetidine-2-carboxamide (24.6 mg, 0.036 mmol) and LiOH.H$_2$O (1.37 mg, 0.033 mmol) were added water (0.3 mL0 and THF (1 mL). The mixture was stirred at rt for 1 hour, then pH 2 buffer (10% aqueous KHSO$_4$/Na$_2$SO$_4$) was added, and the mixture was extracted with EtOAc (2×). The extract was washed with water, brine, dried (sodium sulfate) and concentrated. Purification by preparative TLC gave Example 137 (R)—N-((5-cyclohexylpyridin-2-yl)methyl)-N-(1,3-dioxoisoindolin-5-yl)-1-((perfluorophenyl) sulfonyl)azetidine-2-carboxamide (6 mg, 26% yield) as colorless film. HRMS (ESI+) m/z 649.1563 [M+H]+.

Example 138

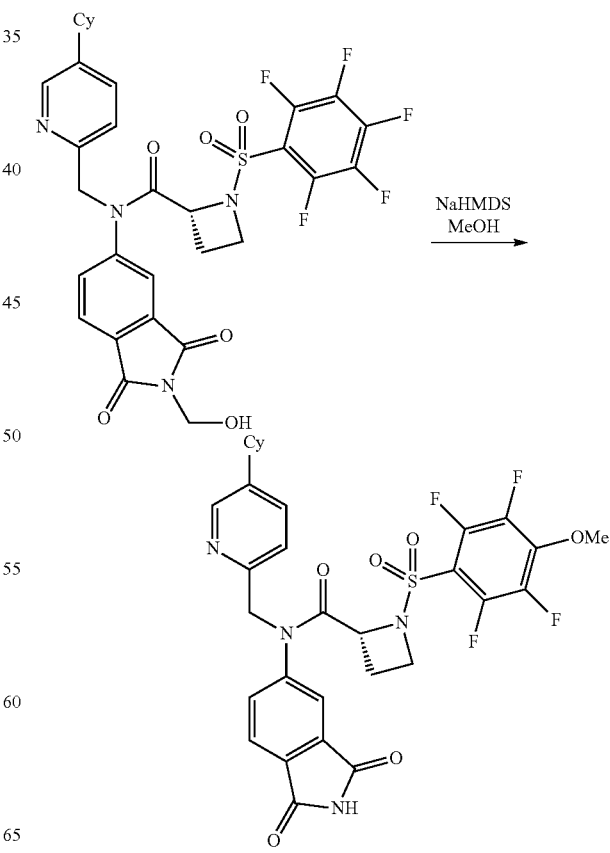

371

(R)—N-((5-cyclohexylpyridin-2-yl)methyl)-N-(1,3-dioxoisoindolin-5-yl)-1-((2,3,5,6-tetrafluoro-4-methoxyphenyl)sulfonyl)azetidine-2-carboxamide

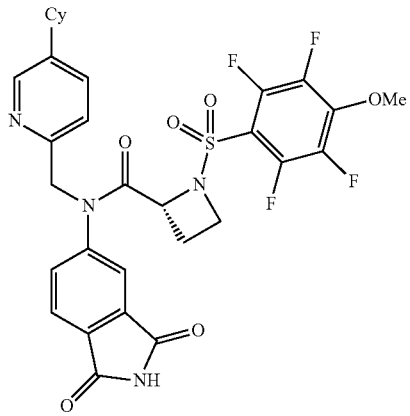

Step 1. To a solution of (R)—N-((5-cyclohexylpyridin-2-yl)methyl)-N-(2-(hydroxymethyl)-1,3-dioxoisoindolin-5-yl)-1-((perfluorophenyl)sulfonyl)azetidine-2-carboxamide (100 mg, 0.15 mmol) in methanol (1.2 mL) was added at 0° C. NaHMDS (1M in THF, 0.18 mL) under nitrogen. The mixture was allowed to reach rt, and stirred for 2 hours. Cold pH 2 buffer (10% aqueous KHSO$_4$/Na$_2$SO$_4$) was added, and the mixture was extracted with EtOAc (2×). The extract was washed with water, brine, dried (sodium sulfate) and concentrated. Purification by preparative TLC gave Example 138 (R)—N-((5-cyclohexylpyridin-2-yl)methyl)-N-(1,3-dioxoisoindolin-5-yl)-1-((2,3,5,6-tetrafluoro-4-methoxyphenyl)sulfonyl)azetidine-2-carboxamide (51 mg, 53% yield). MS (ESI+) m/z 661.0 [M+H]+.

Example 139

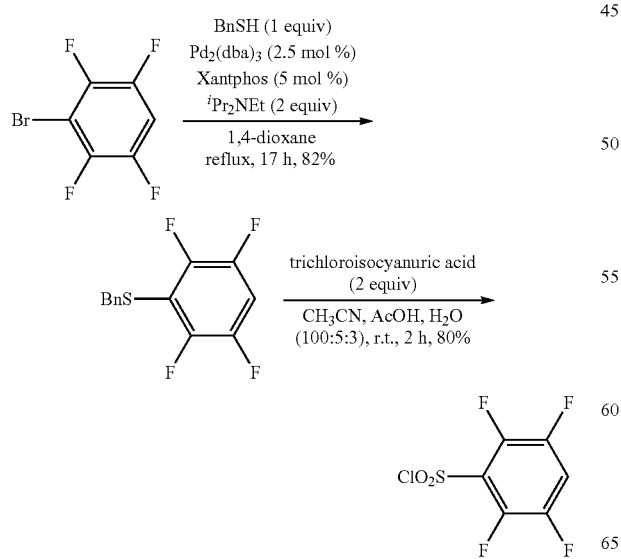

-continued

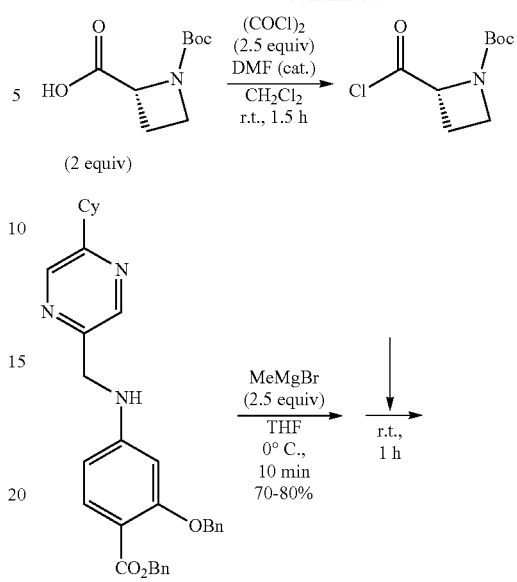

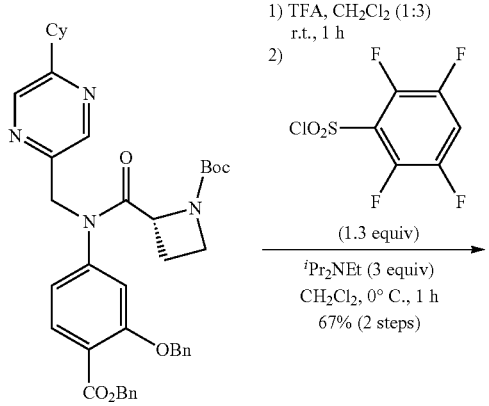

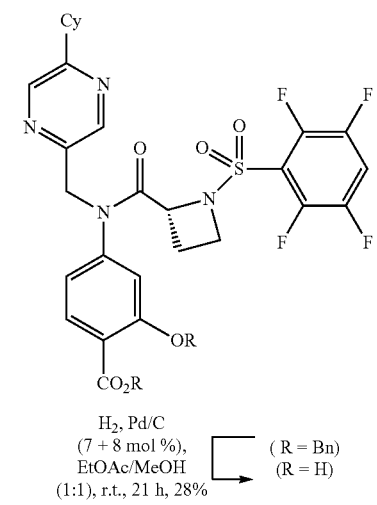

(R)-4-(N-((5-cyclohexylpyrazin-2-yl)methyl)-1-((2,3,5,6-tetrafluorophenyl)sulfonyl)azetidine-2-carboxamido)-2-hydroxybenzoic acid

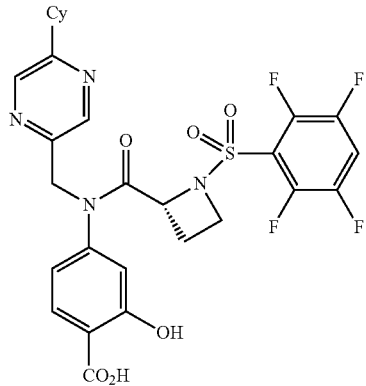

Step 1. To a solution of 2,3,5,6-tetrafluorobromobenzene (59) (0.50 mL, 4.1 mmol) in 1,4-dioxane (9.0 mL) was added Pd$_2$(dba)$_3$ (93.1 mg, 0.102 mmol), Xantphos (118 mg, 0.204 mmol), iPr2NEt (1.4 mL, 8.0 mmol) and BnSH (0.50 mL, 4.3 mmol) at room temperature. The reaction mixture degassed and refluxed for 17 h. After cooling to room temperature, the reaction mixture was filtered through Celite® pad (washed with EtOAc) and concentrated in vacuo. The residue was purified by flash column chromatography (hexane to hexane/EtOAc=24/1) to afford benzyl (2,3,5,6-tetrafluorophenyl)sulfane (921 mg, 82%) as a white solid. $^1$H NMR (300 MHz, CDCl$_3$) δ 7.24-7.29 (m, 5H), 6.95-7.06 (m, 1H), 4.15 (s, 2H).

Step 2. To a solution of benzyl(2,3,5,6-tetrafluorophenyl) sulfane (29.0 mg, 0.107 mmol) in the mixed solvent [MeCN (1.0 mL), AcOH (0.05 mL), H$_2$O (0.03 mL)] was added trichloroisocyanuric acid (47.8 mg, 0.206 mmol) at room temperature. After stirring for 2 h, water and EtOAc were added. The crude products were extracted with EtOAc (×3), and the combined organic extracts were washed with brine, dried (MgSO4), and concentrated in vacuo. The residue was purified by flash column chromatography (hexane to hexane/EtOAc=11/1) to afford 2,3,5,6-tetrafluorobenzenesulfonyl chloride (21.4 mg, 80%) as a white solid. $^1$H NMR (300 MHz, CDCl$_3$) δ 7.48-7.58 (m, 1H).

Step 3. To a solution of Boc-d-azetidine-2-carboxylic acid (81.3 mg, 0.404 mmol) in DCM (2.0 mL), in a two-necked flask equipped with a bubbler, was added oxalyl chloride (0.04 mL, 0.47 mmol) and a drop of DMF at room temperature. After stirring for 1.5 h, the solvent was removed in vacuo to obtain the corresponding acid chloride. To a solution of benzyl 2-(benzyloxy)-4-(((5-cyclohexylpyrazin-2-yl)methyl)amino)benzoate (98.7 mg, 0.194 mmol), which was azeotropically dried with toluene (1 mL×3), in THF (2.0 mL) was added MeMgBr (1.4 M in THF/toluene, 0.35 mL, 0.49 mmol) at 0° C. After stirring for 10 min at 0° C., the acid chloride in THF (2.0 mL) was added. After stirring for 1 h at room temperature, the reaction mixture was quenched by adding water. The crude products were extracted with EtOAc (×3), and the combined organic extracts were washed with brine, dried (MgSO4), and concentrated in vacuo. The residue was purified by flash column chromatography (hexane/EtOAc=3/1 to 1/1) to afford tert-butyl (R)-2-((3-(benzyloxy)-4-((benzyloxy)carbonyl)phenyl)((5-cyclohexylpyrazin-2-yl)methyl)carbamoyl)azetidine-1-carboxylate (126 mg, 94%) as a yellow oil. $^1$H NMR (300 MHz, CDCl$_3$) δ 8.59 (s, 1H), 8.33 (s, 1H), 7.84 (d, J=8.1 Hz, 1H), 7.31-7.43 (m, 10H), 6.82-6.93 (m, 2H), 5.36 (s, 2H), 5.07-5.19 (m, 4H), 4.54-4.64 (m, 1H), 3.99-4.07 (m, 1H), 3.69-3.77 (m, 1H), 2.68-2.79 (m, 1H), 1.26-2.13 (m, 21H).

Step 4. tert-butyl (R)-2-((3-(benzyloxy)-4-((benzyloxy)carbonyl)phenyl)((5-cyclohexylpyrazin-2-yl)methyl)carbamoyl)azetidine-1-carboxylate (73.5 mg, 0.106 mmol) was dissolved in mixed solvent [DCM (1.0 mL) and TFA (0.3 mL)] at room temperature. After stirring for 1 h, the solvent was removed in vacuo, and then water and EtOAc were added to the residue. The crude products were extracted with EtOAc (×3), and the combined organic extracts were washed with brine, dried (MgSO4), and concentrated in vacuo. The residue was purified by flash column chromatography to afford deprotected azetidine (65.1 mg), which included some impurity. This free azetidine was dissolved in DCM (0.5 mL), then iPr$_2$NEt (0.06 mL, 0.34 mmol) and 2,3,5,6-tetrafluorobenzenesulfonyl chloride (35.7 mg, 0.14 mmol) in DCM (1.0 mL) were added at 0° C. After stirring for 1 h at 0° C., the reaction mixture was quenched by adding saturated NaHCO$_3$ solution. The crude products were extracted with DCM (×3), and the combined organic extracts were washed with brine, dried (MgSO4), and concentrated in vacuo. The residue was purified by flash column chromatography (hexane/EtOAc=5/1 to 2/1) to afford benzyl (R)-2-(benzyloxy)-4-(N-((5-cyclohexylpyrazin-2-yl)methyl)-1-((2,3,5,6-tetrafluorophenyl)sulfonyl)azetidine-2-carboxamido)benzoate (57.4 mg, 67%, 2 steps) as a colorless oil. $^1$H NMR (300 MHz, CDCl$_3$) δ 8.45 (s, 1H), 8.40 (s, 1H), 7.84 (d, J=8.1 Hz, 1H), 7.34-7.44 (m, 10H), 7.21-7.28 (m, 1H), 6.96 (d, J=1.8 Hz, 1H), 6.84 (dd, J=1.8, 8.1 Hz, 1H), 5.37 (s, 2H), 5.22 (d, J=12.9 Hz, 1H), 5.13 (d, J=12.9 Hz, 1H), 5.01 (d, J=15.3 Hz, 1H), 4.90-4.95 (m, 1H), 4.79 (d, J=15.3 Hz, 1H), 3.93-4.09 (m, 2H), 2.74-2.84 (m, 1H), 1.26-2.14 (m, 12H).

Step 5. Preparation by a similar procedure to Example 61, step 7, starting from (R)-2-(benzyloxy)-4-(N-((5-cyclohexylpyrazin-2-yl)methyl)-1-((2,3,5,6-tetrafluorophenyl)sulfonyl)azetidine-2-carboxamido)benzoate to obtain the compound of Example 139 (R)-4-(N-((5-cyclohexylpyrazin-2-yl)methyl)-1-((2,3,5,6-tetrafluorophenyl)sulfonyl)azetidine-2-carboxamido)-2-hydroxybenzoic acid. $^1$H NMR (300 MHz, CDCl$_3$) δ 11.4 (brs, 1H, OH), 8.88 (s, 1H), 8.51 (s, 1H), 7.71 (d, J=7.5 Hz, 1H), 7.25-7.35 (m, 1H), 6.64-6.72 (m, 2H), 4.98-5.10 (m, 3H), 4.00-4.19 (m, 2H), 2.86-2.97 (m, 1H), 2.22-2.33 (m, 1H), 1.26-2.11 (m, 11H). HRMS (ESI+) m/z 623.1577 [M+H]+.

Example 140
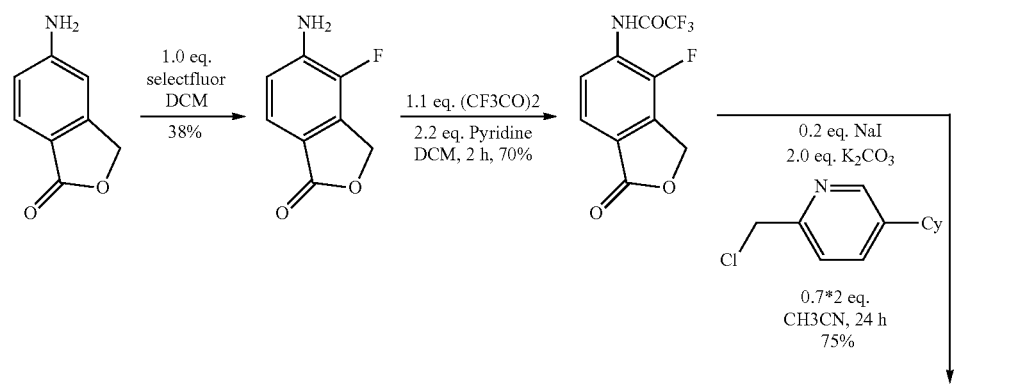
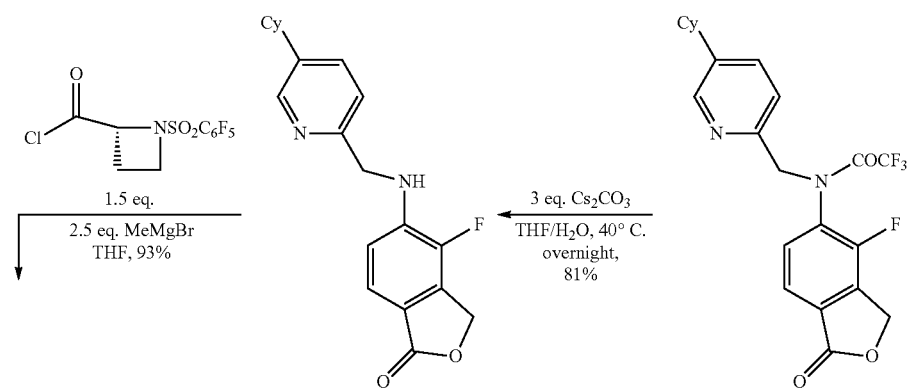
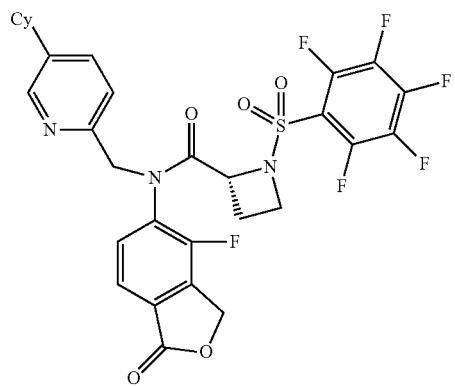

(R)—N-((5-cyclohexylpyridin-2-yl)methyl)-N-(4-fluoro-1-oxo-1,3-dihydroisobenzofuran-5-yl)-1-((perfluorophenyl)sulfonyl)azetidine-2-carboxamide

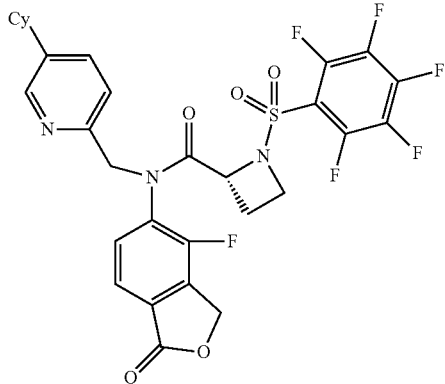

Step 1. Preparation by a similar procedure to Example 61, step 2, starting from 5-aminoisobenzofuran-1(3H)-one to obtain 5-amino-4-fluoroisobenzofuran-1(3H)-one. $^1$H NMR (300 MHz, CDCl$_3$) δ 7.54 (d, J=8.1 Hz, 1H), 6.89 (dd, J=8.0, 7.7 Hz, 1H), 5.30 (s, 2H), 4.35 (s, 2H).

Step 2. Preparation by a similar procedure to Example 61, step 3, starting from 5-amino-4-fluoroisobenzofuran-1(3H)-one to obtain 2,2,2-trifluoro-N-(4-fluoro-1-oxo-1,3-dihydroisobenzofuran-5-yl)acetamide. $^1$H NMR (300 MHz, CDCl$_3$) δ 8.62-8.38 (m, 2H), 7.87-7.71 (m, 1H), 5.42 (s, 2H)

Step 3. Preparation by a similar procedure to Example 116, step 4, starting from 2,2,2-trifluoro-N-(4-fluoro-1-oxo-1,3-dihydroisobenzofuran-5-yl)acetamide to obtain N-((5-cyclohexylpyridin-2-yl)methyl)-2,2,2-trifluoro-N-(4-fluoro-1-oxo-1,3-dihydroisobenzofuran-5-yl)acetamide. $^1$H NMR (300 MHz, CDCl$_3$) δ 8.34 (d, J=2.0 Hz, 1H), 7.68 (d, J=8.0 Hz, 1H), 7.53 (dd, J=8.0, 2.0 Hz, 1H), 7.46-7.39 (m, 1H), 7.32 (d, J=8.0 Hz, 1H), 5.50-5.37 (m, 3H), 4.58 (d, J=14.5 Hz, 1H), 2.61-2.47 (m, 1H), 1.95-1.75 (m, 5H), 1.53-1.28 (m, 5H).

Step 4. Preparation by a similar procedure to Example 109, step 4, starting from N-((5-cyclohexylpyridin-2-yl)methyl)-2,2,2-trifluoro-N-(4-fluoro-1-oxo-1,3-dihydroisobenzofuran-5-yl)acetamide to obtain 5-(((5-cyclohexylpyridin-2-yl)methyl)amino)-4-fluoroisobenzofuran-1(3H)-one. $^1$H NMR (300 MHz, CDCl$_3$) δ 8.47 (d, J=2.0 Hz, 1H), 7.59-7.51 (m, 2H), 7.24 (d, J=8.0 Hz, 1H), 6.82 (dd, J=7.8, 7.7 Hz, 1H), 5.79 (s, 1H), 5.29 (s, 2H), 4.53 (m, 2H), 2.63-2.48 (m, 1H), 1.97-1.78 (m, 5H), 1.51-1.25 (m, 5H).

Step 5. Preparation by a similar procedure to Example 136, step 6, starting from 5-(((5-cyclohexylpyridin-2-yl)methyl)amino)-4-fluoroisobenzofuran-1(3H)-one to obtain the compound of Example 140 (R)—N-((5-cyclohexylpyridin-2-yl)methyl)-N-(4-fluoro-1-oxo-1,3-dihydroisobenzofuran-5-yl)-1-((perfluorophenyl)sulfonyl)azetidine-2-carboxamide. MS (ESI+): [M+H]+ m/z 654.3.

Example 141

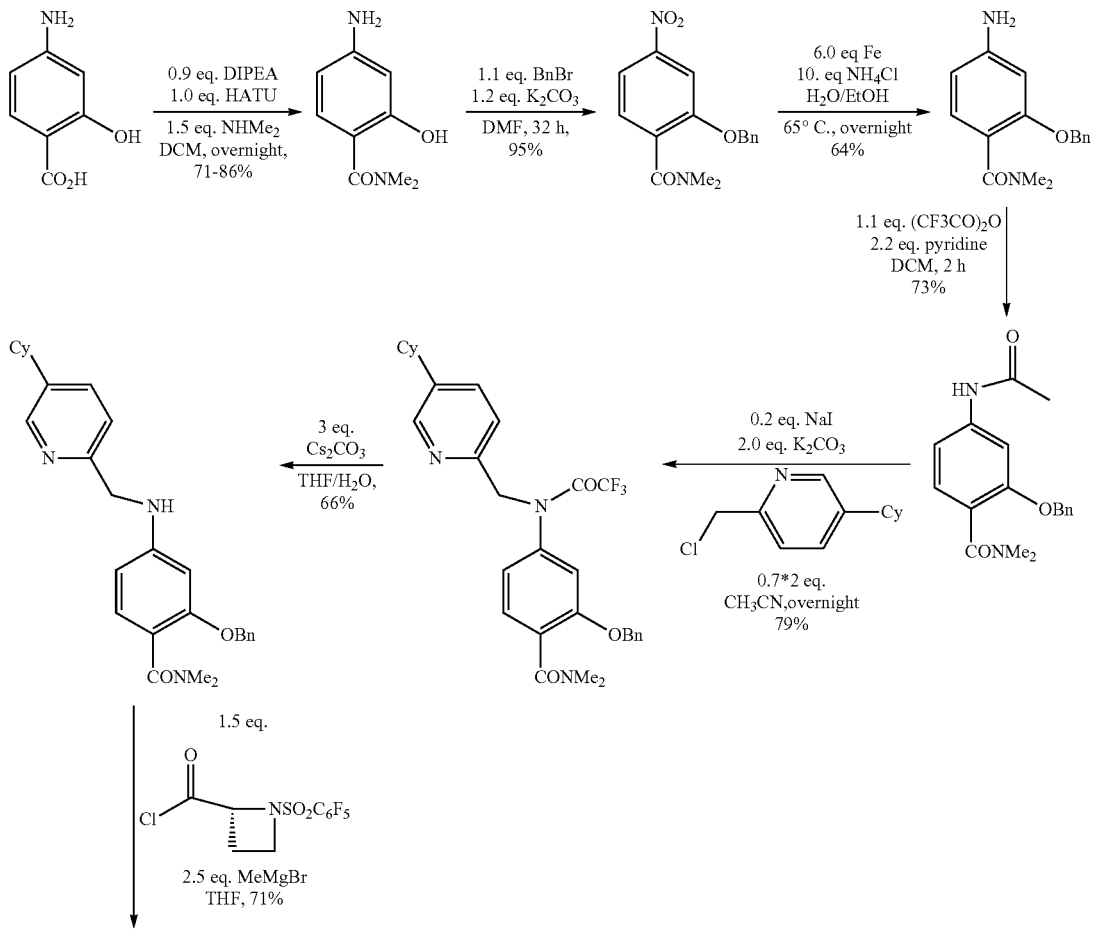

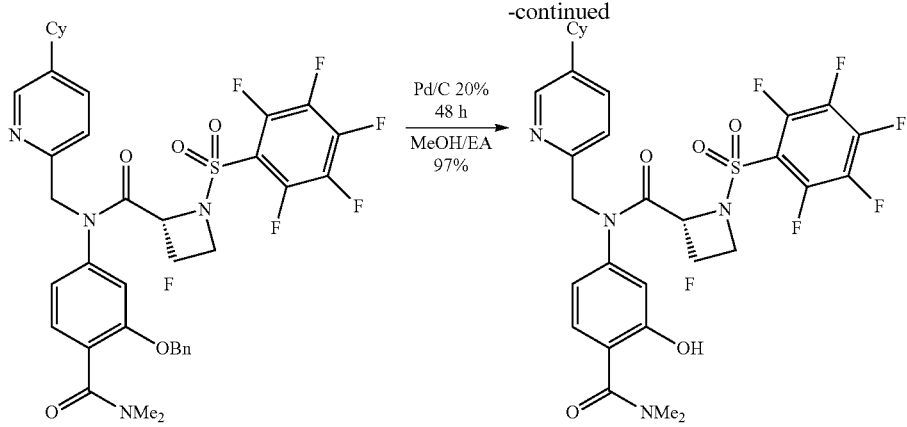

(R)—N-((5-cyclohexylpyridin-2-yl)methyl)-N-(4-(dimethylcarbamoyl)-3-hydroxyphenyl)-1-((perfluorophenyl)sulfonyl)azetidine-2-carboxamide

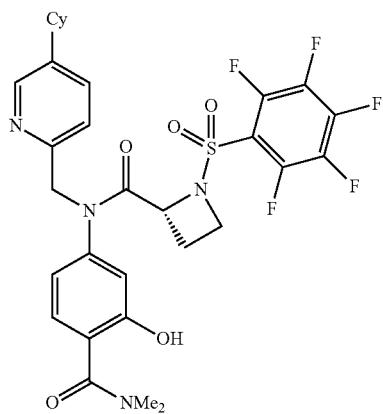

Step 1. To a solution of 105 mg of 2-hydroxy-4-nitrobenzoic acid in 6 ml DCM at 0° C., 0.9 eq. DIPEA and 1.0 eq. HATU were added. The mixture was allowed to warm to RT, and stirring for 1.5 h, then 1.5 eq. dimethyl amine was added, and the mixture was stirred overnight. After the reaction was completed, 5 ml H2O was added. The mixture was extracted with DCM 2 times, and the organic layer was washed with brine and dried over $Na_2SO_4$. The organic layer was concentrated under vacuum, and purified by column chromatography to obtain 2-hydroxy-N,N-dimethyl-4-nitrobenzamide (86 mg. 71% yield). $^1$H NMR (300 MHz, $CDCl_3$) δ 10.15 (s, 1H), 7.85 (d, J=2.3 Hz, 1H), 7.73 (dd, J=8.5, 2.3 Hz, 1H), 7.49 (d, J=8.5 Hz, 1H), 3.21 (s, 6H).

Step 2. Preparation by a similar procedure to Example 106, step 2, starting from 2-hydroxy-N,N-dimethyl-4-nitrobenzamide to obtain 2-(benzyloxy)-N,N-dimethyl-4-nitrobenzamide. $^1$H NMR (300 MHz, $CDCl_3$) δ 7.91 (dd, J=8.2, 2.0 Hz, 1H), 7.85 (d, J=2.0 Hz, 1H), 7.45 (d, J=8.2 Hz, 1H), 7.43-7.34 (m, 5H), 5.23 (s, 2H), 3.13 (s, 3H), 2.85 (s, 3H).

Step 3. Preparation by a similar procedure to Example 106, step 3, starting from 2-(benzyloxy)-N,N-dimethyl-4-nitrobenzamide to obtain 4-amino-2-(benzyloxy)-N,N-dimethylbenzamide. $^1$H NMR (300 MHz, $CDCl_3$) δ 7.44-7.30 (m, 5H), 7.09 (d, J=8.0 Hz, 1H), 6.28 (dd, J=8.0, 2.0 Hz, 1H), 6.24 (d, J=2.0 Hz, 1H), 5.03 (s, 2H), 3.47 (br s, 2H), 3.07 (s, 3H), 2.88 (s, 3H).

Step 4. Preparation by a similar procedure to Example 61, step 3, starting from 4-amino-2-(benzyloxy)-N,N-dimethylbenzamide to obtain 2-(benzyloxy)-N,N-dimethyl-4-(2,2,2-trifluoroacetamido)benzamide. $^1$H NMR (300 MHz, $CDCl_3$) δ 8.78 (s, 1H), 7.43-7.31 (m, 6H), 7.18 (d, J=8.1 Hz, 1H), 6.95 (dd, J=8.1, 1.9 Hz, 1H), 5.04 (s, 2H), 3.12 (s, 3H), 2.86 (s, 3H).

Step 5. Preparation by a similar procedure to Example 116, step 4, starting from 2-(benzyloxy)-N,N-dimethyl-4-(2,2,2-trifluoroacetamido)benzamide to obtain 2-(benzyloxy)-4-(N-((5-cyclohexylpyridin-2-yl)methyl)-2,2,2-trifluoroacetamido)-N,N-dimethylbenzamide. $^1$H NMR (300 MHz, $CDCl_3$) δ 8.39-8.35 (m, 1H), 7.50-7.43 (m, 1H), 7.37-7.26 (m, 5H), 7.26-7.20 (m, 1H), 7.19-7.12 (m, 1H), 6.92-6.85 (m, 2H), 4.97 (s, 4H), 3.07 (s, 3H), 2.79 (s, 3H), 2.58-2.43 (m, 1H), 1.70-1.70 (m 5H), 1.45-1.30 (m, 5H).

Step 6. Preparation by a similar procedure to Example 109, step 4, starting from 2-(benzyloxy)-4-(N-((5-cyclohexylpyridin-2-yl)methyl)-2,2,2-trifluoroacetamido)-N,N-dimethylbenzamide to obtain 2-(benzyloxy)-4-(((5-cyclohexylpyridin-2-yl)methyl)amino)-N,N-dimethylbenzamide. $^1$H NMR (300 MHz, $CDCl_3$) δ 8.42 (m, 1H), 7.47 (m, 1H), 7.40-7.25 (m, 5H), 7.20 (m, 1H), 7.12 (m, 1H), 6.33-6.22 (m, 2H), 5.15-4.98 (m, 3H), 4.38 (s, 2H), 3.06 (s, 3H), 2.87 (s, 3H), 2.60-2.46 (m, 1H), 1.92-1.73 (m, 5H), 1.51-1.31 (m, 5H).

Step 7. Preparation by a similar procedure to Example 136, step 6, starting from 2-(benzyloxy)-4-(((5-cyclohexylpyridin-2-yl)methyl)amino)-N,N-dimethylbenzamide to obtain (R)—N-(3-(benzyloxy)-4-(dimethylcarbamoyl)phenyl)-N-((5-cyclohexylpyridin-2-yl)methyl)-1-((perfluorophenyl)sulfonyl)azetidine-2-carboxamide. $^1$H NMR (300 MHz, $CDCl_3$) δ 8.32 (d, J=2.0 Hz, 1H), 7.47 (dd, J=8.0, 2.0 Hz, 1H), 7.42-7.29 (m, 5H), 7.24 (d, J=8.2 Hz, 1H), 7.14 (d, J=8.0 Hz, 1H), 6.81-6.74 (m, 2H), 5.15-4.82 (m, 5H), 4.07-3.91 (m, 2H), 3.10 (s, 3H), 2.85 (s, 3H), 2.58-2.43 (m, 1H), 2.15-2.05 (m, 1H), 1.80-1.68 (m, 6H), 1.50-1.29 (m, 5H).

Step 8. Preparation by a similar procedure to Example 53, step 5, starting from (R)—N-(3-(benzyloxy)-4-(dimethylcarbamoyl)phenyl)-N-((5-cyclohexylpyridin-2-yl)methyl)-1-((perfluorophenyl)sulfonyl)azetidine-2-carboxamide to obtain the compound of Example 141 (R)—N-((5-cyclohexylpyridin-2-yl)methyl)-N-(4-(dimethylcarbamoyl)-3-hydroxy phenyl)-1-((perfluorophenyl)sulfonyl)azetidine-2-carboxamide. MS (ESI+): [M+H]+ m/z 667.4.

Example 142

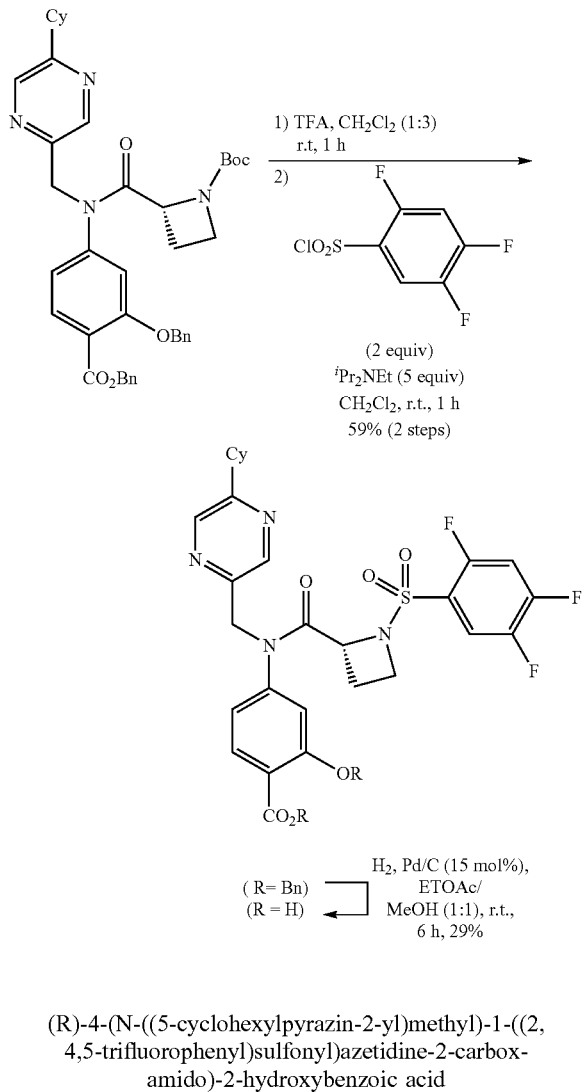

(R)-4-(N-((5-cyclohexylpyrazin-2-yl)methyl)-1-((2,4,5-trifluorophenyl)sulfonyl)azetidine-2-carboxamido)-2-hydroxybenzoic acid Step 1. Tert-butyl (R)-2-((3-(benzyloxy)-4-((benzyloxy)carbonyl)phenyl)((5-cyclohexylpyrazin-2-yl)methyl)carbamoyl)azetidine-1-carboxylate (77.8 mg, 0.113 mmol) was dissolved in a mixed solvent [DCM (0.9 mL) and TFA (0.3 mL)] at room temperature. After stirring for 50 min, the solvent was removed in vacuo, then saturated NaHCO3 solution and EtOAc were added to the residue. The crude products were extracted with EtOAc (×3), and the combined organic extracts were washed with brine, dried (MgSO4), and concentrated in vacuo. The resulting free azetidine was dissolved in DCM (0.5 mL), then iPr2NEt (0.10 mL, 0.29 mmol) and 2,4,5-trifluorobenzenesulfonyl chloride (0.03 mL, 0.215 mmol) in DCM (1.0 mL) were added at 0° C. After stirring for 1.5 hours at rt, the reaction mixture was quenched by adding saturated NaHCO3 solution. The crude products were extracted with DCM (×3), and the combined organic extracts were washed with brine, dried (MgSO4), and concentrated in vacuo. The residue was purified by flash column chromatography (hexane/EtOAc=5/1 to 2/1) to afford benzyl (R)-2-(benzyloxy)-4-(N-((5-cyclohexylpyrazin-2-yl)methyl)-1-((2,4,5-trifluorophenyl)sulfonyl)azetidine-2-carboxamido)benzoate (52.2 mg, 59%, 2 steps) as a colorless oil. $^1$H NMR (300 MHz, CDCl$_3$) δ 8.49 (s, 1H), 8.38 (s, 1H), 7.86 (d, J=8.1 Hz, 1H), 7.69-7.77 (m, 1H), 7.33-7.44 (m, 10H), 7.01-7.09 (m, 1H), 6.95 (d, J=1.8 Hz, 1H), 6.84 (dd, J=1.8, 8.1 Hz, 1H), 5.38 (s, 2H), 5.21 (d, J=12.6 Hz, 1H), 5.11 (d, J=12.6 Hz, 1H), 5.00 (d, J=15.3 Hz, 1H), 4.83-4.92 (m, 2H), 3.94-4.02 (m, 1H), 3.79-3.86 (m, 1H), 2.73-2.83 (m, 1H), 2.11-2.18 (m, 1H), 1.26-1.99 (m, 11H).

Step 2. Preparation by a similar procedure to Example 61, step 7, starting from benzyl (R)-2-(benzyloxy)-4-(N-((5-cyclohexylpyrazin-2-yl)methyl)-1-((2,4,5-trifluorophenyl)sulfonyl)azetidine-2-carboxamido)benzoate to obtain the compound of Example 142 (R)-4-(N-((5-cyclohexylpyrazin-2-yl)methyl)-1-((2,4,5-trifluorophenyl)sulfonyl)azetidine-2-carboxamido)-2-hydroxybenzoic acid. 1H NMR (300 MHz, CDCl3) □ 11.14 (brs, 1H, OH), 8.92 (s, 1H), 8.49 (s, 1H), 7.68-7.78 (m, 2H), 7.05-7.14 (m, 1H), 6.63-6.75 (m, 2H), 5.09 (s, 2H), 4.90-4.98 (m, 1H), 4.01-4.10 (m, 1H), 3.88-3.96 (m, 1H), 2.86-2.98 (m, 1H), 1.28-2.61 (m, 12H). MS (ESI+) m/z 605.3 [M+H]+.

Example 143

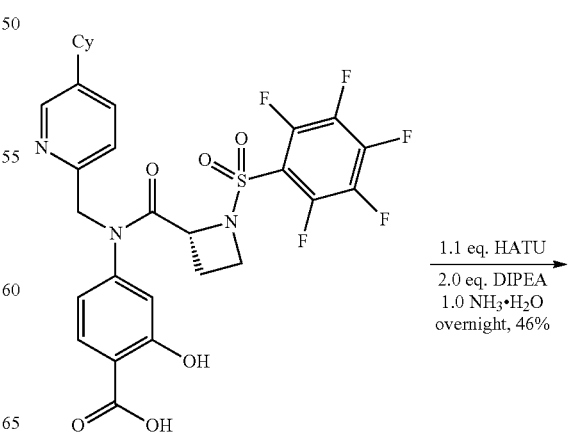

383

-continued

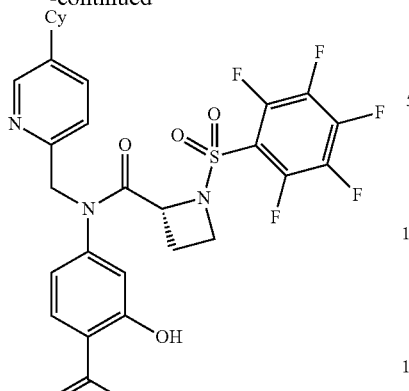

(R)—N-(4-carbamoyl-3-hydroxyphenyl)-N-((5-cy-clohexylpyridin-2-yl)methyl)-1-((perfluorophenyl)sulfonyl)azetidine-2-carboxamide

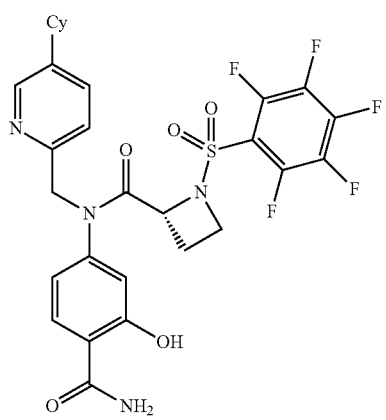

Step 1. To a flask, 1.0 eq. DIPEA and 1.0 eq. HATU was added to a solution of 80 mg of (R)-4-(N-((5-cyclohexylpyridin-2-yl)methyl)-1-((perfluorophenyl)sulfonyl)azetidine-2-carboxamido)-2-hydroxybenzoic acid in 4 mL DMF at 0° C. under Argon. The mixture allowed to warm to RT and stirred for 1.5 h. Then 1.0 eq. ammonium hydroxide in DMF was added and stirred overnight. After the reaction was complete, water was added, and the mixture was extracted with EA for 2 times. The extract was dried with Na$_2$SO$_4$. Solvent was removed under vacuum. Purification by column Chromatography gave Example 143 (R)—N-(4-carbamoyl-3-hydroxyphenyl)-N-((5-cyclohexylpyridin-2-yl)methyl)-1-((perfluorophenyl)sulfonyl)azetidine-2-carboxamide (37 mg, 46%). $^1$H NMR (300 MHz, CDCl$_3$) δ 12.46 (s, 1H), 8.34 (d, J=1.9 Hz, 1H), 7.51 (dd, J=8.0, 1.9 Hz, 1H), 7.46 (d, J=8.4 Hz, 1H), 7.19 (d, J=8.0 Hz, 1H), 6.76 (d, J=2.0 Hz, 1H), 6.72 (dd, J=8.4, 2.1 Hz, 1H), 5.18-5.04 (m, 1H), 4.98-4.79 (m, 2H), 4.13-4.01 (m, 2H), 2.58-2.45 (m, 1H), 2.43-2.27 (m, 1H), 2.22-2.08 (m, 1H), 1.92-1.72 (m, 5H), 1.49-1.31 (m, 5H). MS (ESI+): [M+H]+ m/z 639.4.

384

Example 144

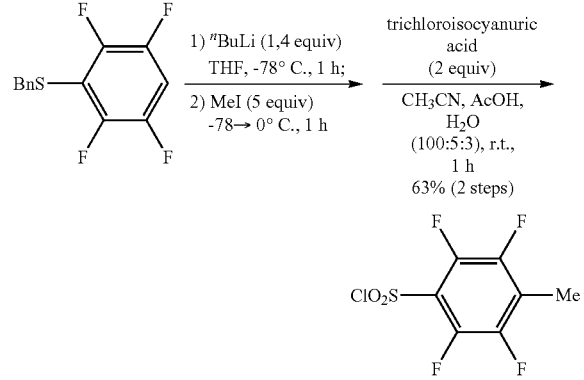

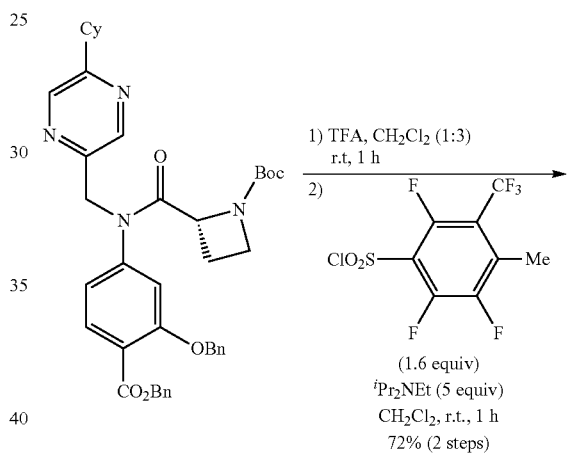

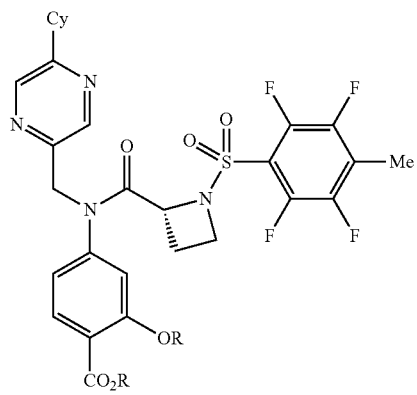

(R)-4-(N-((5-cyclohexylpyrazin-2-yl)methyl)-1-((2, 3,5,6-tetrafluoro-4-methylphenyl)sulfonyl)azetidine-2-carboxamido)-2-hydroxybenzoic acid

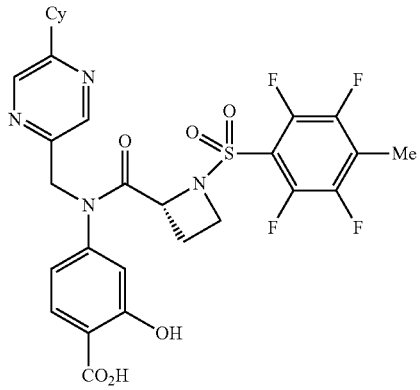

Step 1. To a solution of benzyl(2,3,5,6-tetrafluorophenyl)sulfane (50.9 mg, 0.187 mmol), which was azeotropically dried with toluene (1 mL×3), in THF (1.9 mL) was added nBuLi (2.6 M in hexane, 0.10 mL, 0.26 mmol) at −78° C. After stirring for 1 h, MeI (0.06 mL, 0.96 mmol) was added and the reaction mixture was gradually warmed to 0° C. for 30 min. After stirring for 30 min at 0° C., the reaction mixture was quenched by adding water. The crude products were extracted with EtOAc (×3), and the combined organic extracts were washed with brine, dried (MgSO4), and concentrated in vacuo. The residue dissolved in the mixed solvent [MeCN (1.0 mL), AcOH (0.05 mL), H$_2$O (0.03 mL)], then trichloroisocyanuric acid (85.7 mg, 0.369 mmol) was added at room temperature. After stirring for 1 h, water and EtOAc were added. The crude products were extracted with EtOAc (×3), and the combined organic extracts were washed with brine, dried (MgSO4), and concentrated in vacuo. The residue was purified by flash column chromatography (hexane to hexane/EtOAc=49/1) to afford 2,3,5,6-tetrafluoro-4-methylbenzenesulfonyl chloride (31.0 mg, 63%, 2 steps) as a white solid. $^1$H NMR (300 MHz, CDCl$_3$) δ 2.43 (t, JHF=2.1 Hz, 3H).

Step 2. Preparation by a similar procedure to Example 142, step 1, starting from 2,3,5,6-tetrafluoro-4-methylbenzenesulfonyl chloride to obtain benzyl (R)-2-(benzyloxy)-4-(N-((5-cyclohexylpyrazin-2-yl)methyl)-1-((2,3,5,6-tetrafluoro-4-methylphenyl)sulfonyl)azetidine-2-carboxamido)benzoate. $^1$H NMR (300 MHz, CDCl$_3$) δ 8.44 (s, 1H), 8.38 (s, 1H), 7.84 (d, J=8.1 Hz, 1H), 7.34-7.44 (m, 10H), 6.97 (s, 1H), 6.83 (d, J=8.1 Hz, 1H), 5.37 (s, 2H), 5.22 (d, J=12.9 Hz, 1H), 5.12 (d, J=12.9 Hz, 1H), 5.03 (d, J=15.0 Hz, 1H), 4.88-4.95 (m, 1H), 4.78 (d, J=15.0 Hz, 1H), 3.93-4.05 (m, 2H), 2.73-2.84 (m, 1H), 1.28-2.34 (m, 15H).

Step 3. Preparation by a similar procedure to Example 61, step 7, starting from benzyl (R)-2-(benzyloxy)-4-(N-((5-cyclohexylpyrazin-2-yl)methyl)-1-((2,3,5,6-tetrafluoro-4-methylphenyl)sulfonyl)azetidine-2-carboxamido)benzoate to obtain the compound of Example 144 (R)-4-(N-((5-cyclohexylpyrazin-2-yl)methyl)-1-((2,3,5,6-tetrafluoro-4-methylphenyl)sulfonyl)azetidine-2-carboxamido)-2-hydroxybenzoic acid. $^1$H NMR (300 MHz, CDCl$_3$) δ 11.17 (brs, 1H, OH), 8.88 (s, 1H), 8.47 (s, 1H), 7.71 (d, J=8.1 Hz, 1H), 6.70 (d, J=8.1 Hz, 1H), 6.64 (s, 1H), 5.11 (d, J=14.1 Hz, 1H), 4.97-5.02 (m, 2H), 3.97-4.18 (m, 2H), 2.83-2.94 (m, 1H), 2.23-2.40 (m, 4H), 1.26-2.07 (m, 11H). HRMS (ESI+) m/z 637.1739 [M+H]+.

Example 145

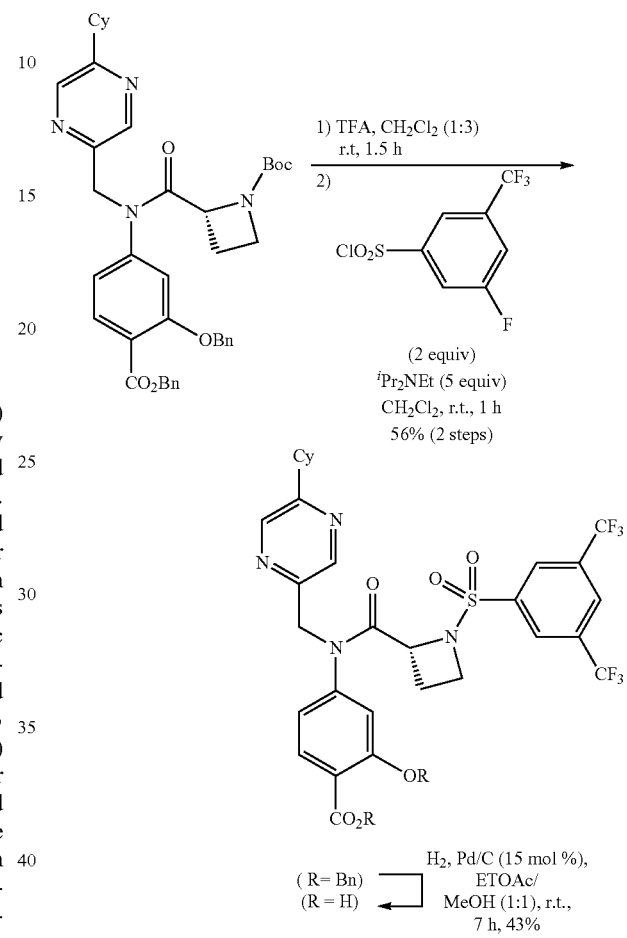

(R)-4-(1-((3,5-bis(trifluoromethyl)phenyl)sulfonyl)-N-((5-cyclohexylpyrazin-2-yl)methyl)azetidine-2-carboxamido)-2-hydroxybenzoic acid

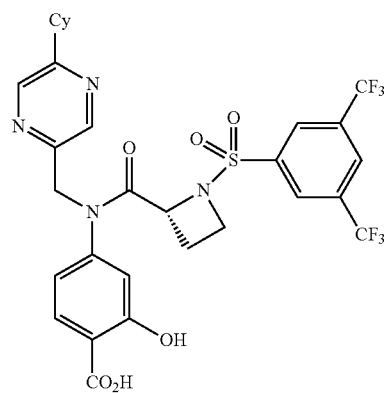

Step 1. Preparation by a similar procedure to Example 142, step 1, starting from tert-butyl (R)-2-((3-(benzyloxy)-4-((benzyloxy)carbonyl)phenyl)((5-cyclohexylpyrazin-2-yl)methyl)carbamoyl)azetidine-1-carboxylate to obtain benzyl (R)-2-(benzyloxy)-4-(1-((3,5-bis(trifluoromethyl)phenyl)sulfonyl)-N-((5-cyclohexylpyrazin-2-yl)methyl)azetidine-2-carboxamido)benzoate. $^1$H NMR (300 MHz, CDCl$_3$) δ 8.50 (s, 1H), 8.46 (s, 2H), 8.38 (s, 1H), 8.06 (s, 1H), 7.87 (d, J=8.4 Hz, 1H), 7.34-7.44 (m, 10H), 6.98 (d, J=1.8 Hz, 1H), 6.87 (dd, J=1.8, 8.4 Hz, 1H), 5.38 (s, 2H), 5.22 (d, J=12.6 Hz, 1H), 5.06-5.14 (m, 2H), 4.93-4.99 (m, 1H), 4.83 (d, J=15.3 Hz, 1H), 3.92-3.99 (m, 1H), 3.56-3.63 (m, 1H), 2.72-2.83 (m, 1H), 1.26-2.16 (m, 12H)

Step 2. Preparation by a similar procedure to Example 61, step 7, starting from benzyl (R)-2-(benzyloxy)-4-(1-((3,5-bis(trifluoromethyl)phenyl)sulfonyl)-N-((5-cyclohexylpyrazin-2-yl)methyl)azetidine-2-carboxamido)benzoate to obtain the compound of Example 145 (R)-4-(1-((3,5-bis(trifluoromethyl)phenyl)sulfonyl)-N-((5-cyclohexylpyrazin-2-yl)methyl)azetidine-2-carboxamido)-2-hydroxybenzoic acid. $^1$H NMR (300 MHz, CDCl$_3$) δ 11.20 (brs, 1H, OH), 8.97 (s, 1H), 8.47 (s, 3H), 8.10 (s, 1H), 7.72 (d, J=8.4 Hz, 1H), 6.70 (d, J=8.4 Hz, 1H), 6.65 (s, 1H), 5.19 (d, J=12.3 Hz, 1H), 4.97-5.08 (m, 2H), 3.98-4.07 (m, 1H), 3.66-3.74 (m, 1H), 2.85-2.97 (m, 1H), 2.26-2.36 (m, 1H), 1.26-2.08 (m, 11H). HRMS (ESI+) m/z 687.1691 [M+H]+.

Example 146

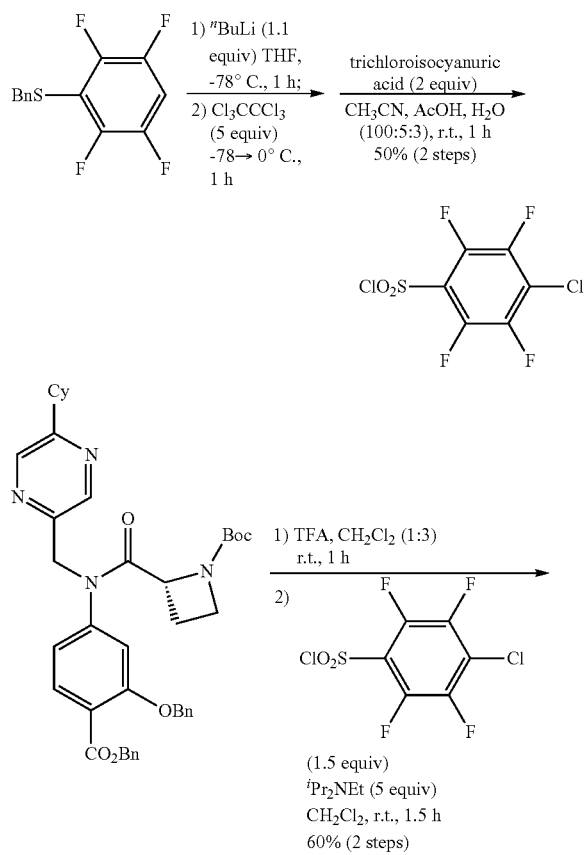

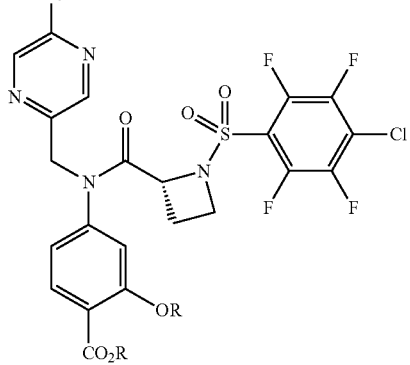

(R)-4-(1-((4-chloro-2,3,5,6-tetrafluorophenyl)sulfonyl)-N-((5-cyclohexylpyrazin-2-yl)methyl)azetidine-2-carboxamido)-2-hydroxybenzoic acid

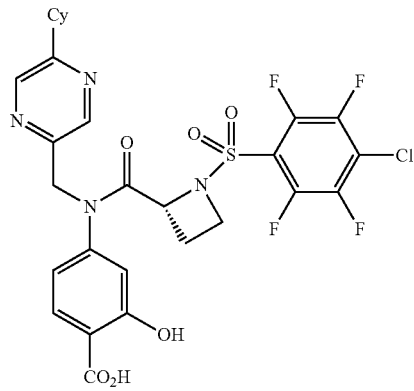

Step 1. To a solution of benzyl(2,3,5,6-tetrafluorophenyl)sulfane (51.1 mg, 0.188 mmol), which was azeotropically dried with toluene (1 mL×3), in THF (1.8 mL) was added nBuLi (2.6 M in hexane, 0.080 mL, 0.21 mmol) at −78° C. After stirring for 1 h, hexachloroethane (221 mg, 0.931 mmol) was added and the reaction mixture was gradually warmed to 0° C. for 20 min. After stirring for 40 min at 0° C., the reaction mixture was quenched by adding water. The crude products were extracted with EtOAc (×3), and the combined organic extracts were washed with brine, dried (MgSO4), and concentrated in vacuo. The residue dissolved in the mixed solvent [CH3CN (1.0 mL), AcOH (0.05 mL), H2O (0.03 mL)], then trichloroisocyanuric acid (86.7 mg, 0.373 mmol) was added at room temperature. After stirring for 1 h, water and EtOAc were added. The crude products were extracted with EtOAc (×3), and the combined organic extracts were washed with brine, dried (MgSO4), and concentrated in vacuo. The residue was purified by flash column chromatography (hexane to hexane/EtOAc=49/1) to afford 4-chloro-2,3,5,6-tetrafluorobenzenesulfonyl chloride (26.7 mg, 50%, 2 steps) as a white solid. $^{19}$H NMR (282 MHz, CDCl3) δ −134.1, −135.4.

Step 2. Preparation by a similar procedure to Example 142, step 1, starting from tert-butyl (R)-2-((3-(benzyloxy)-

4-((benzyloxy)carbonyl)phenyl)((5-cyclohexylpyrazin-2-yl)methyl)carbamoyl)azetidine-1-carboxylate to obtain benzyl (R)-2-(benzyloxy)-4-(1-((4-chloro-2,3,5,6-tetrafluorophenyl)sulfonyl)-N-((5-cyclohexylpyrazin-2-yl)methyl)azetidine-2-carboxamido)benzoate. ¹H NMR (300 MHz, CDCl₃) δ 8.43 (s, 1H), 8.40 (s, 1H), 7.84 (d, J=8.1 Hz, 1H), 7.34-7.44 (m, 10H), 6.94 (s, 1H), 6.83 (d, J=8.1 Hz, 1H), 5.38 (s, 2H), 5.22 (d, J=12.6 Hz, 1H), 5.14 (d, J=12.6 Hz, 1H), 5.01 (d, J=15.6 Hz, 1H), 4.90-4.95 (m, 1H), 4.79 (d, J=15.6 Hz, 1H), 3.91-4.10 (m, 2H), 2.74-2.85 (m, 1H), 1.26-2.83 (m, 12H).

Step 3. Preparation by a similar procedure to Example 27, step 5, starting from benzyl (R)-2-(benzyloxy)-4-(1-((4-chloro-2,3,5,6-tetrafluorophenyl)sulfonyl)-N-((5-cyclohexylpyrazin-2-yl)methyl)azetidine-2-carboxamido)benzoate to obtain the compound of Example 146 (R)-4-(1-((4-chloro-2,3,5,6-tetrafluorophenyl)sulfonyl)-N-((5-cyclohexylpyrazin-2-yl)methyl)azetidine-2-carboxamido)-2-hydroxybenzoic acid. ¹H NMR (300 MHz, CDCl₃) δ 11.13 (brs, 1H, OH), 8.84 (s, 1H), 8.49 (s, 1H), 7.72 (d, J=7.5 Hz, 1H), 6.64-6.72 (m, 2H), 4.98-5.11 (m, 3H), 4.11-4.20 (m, 1H), 4.00-4.08 (m, 1H), 2.85-2.97 (m, 1H), 2.22-2.33 (m, 1H), 1.26-2.13 (m, 11H). HRMS (ESI+) m/z 657.1190 [M+H]+.

Example 147

(R)-4-(N-((5-cyclohexylpyrazin-2-yl)methyl)-1-((3,4,5-trifluorophenyl)sulfonyl)azetidine-2-carboxamido)-2-hydroxybenzoic acid

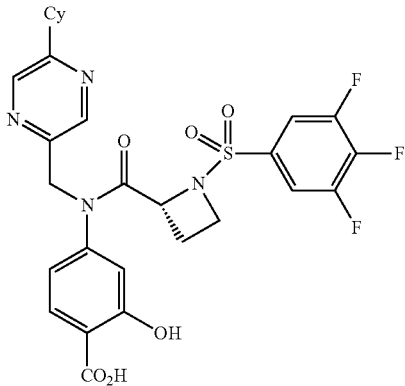

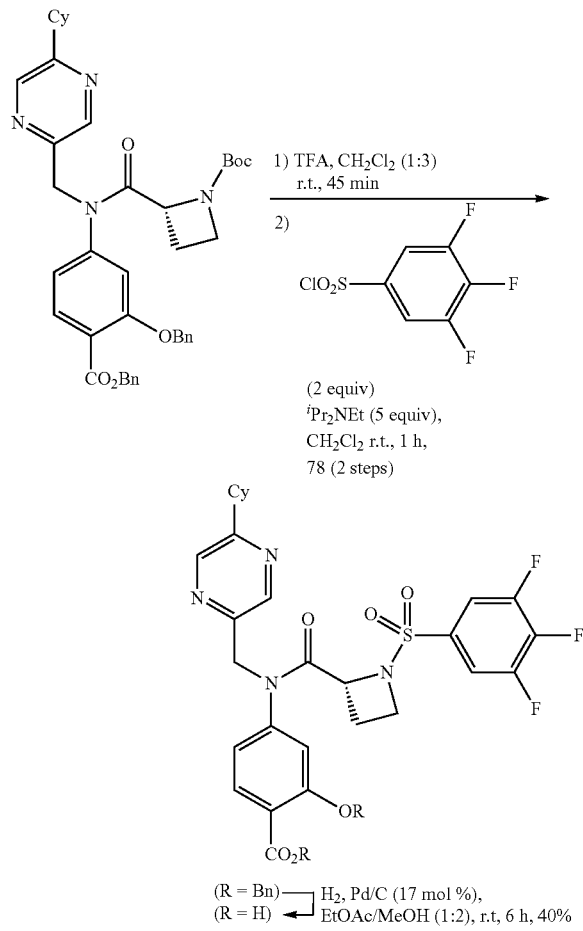

Step 1. Preparation by a similar procedure to Example 142, step 1, starting from tert-butyl (R)-2-((3-(benzyloxy)-4-((benzyloxy)carbonyl)phenyl)((5-cyclohexylpyrazin-2-yl)methyl)carbamoyl)azetidine-1-carboxylate to obtain benzyl (R)-2-(benzyloxy)-4-(N-((5-cyclohexylpyrazin-2-yl)methyl)-1-((3,4,5-trifluorophenyl)sulfonyl)azetidine-2-carboxamido)benzoate. ¹H NMR (300 MHz, CDCl₃) δ 8.68 (s, 1H), 8.62 (s, 1H), 7.89 (d, J=8.1 Hz, 1H), 7.55-7.63 (m, 2H), 7.34-7.45 (m, 10H), 7.08 (s, 1H), 6.90 (d, J=8.1 Hz, 1H), 5.39 (s, 2H), 5.27 (d, J=12.3 Hz, 1H), 5.14-5.20 (m, 2H), 4.98 (d, J=15.9 Hz, 1H), 4.84-4.89 (m, 1H), 3.79-3.87 (m, 1H), 3.54-3.62 (m, 1H), 2.98-3.08 (m, 1H), 1.26-2.45 (m, 12H).

Step 2. Preparation by a similar procedure to Example 61, step 7, starting from benzyl (R)-2-(benzyloxy)-4-(N-((5-cyclohexylpyrazin-2-yl)methyl)-1-((3,4,5-trifluorophenyl)sulfonyl)azetidine-2-carboxamido)benzoate to obtain the compound of Example 147 (R)-4-(N-((5-cyclohexylpyrazin-2-yl)methyl)-1-((3,4,5-trifluorophenyl)sulfonyl)azetidine-2-carboxamido)-2-hydroxybenzoic acid. 1H NMR (300 MHz, CDCl3) □ 11.19 (brs, 1H, OH), 9.01 (s, 1H), 8.54 (s, 1H), 7.75 (d, J=8.4 Hz, 1H), 7.56-7.62 (m, 2H), 6.67-6.74 (m, 2H), 5.27 (d, J=14.7 Hz, 1H), 5.05 (d, J=14.7 Hz, 1H), 4.85-4.90 (m, 1H), 3.84-3.92 (m, 1H), 3.65-3.73 (m, 1H), 2.89-3.00 (m, 1H), 2.31-2.43 (m, 1H), 1.26-2.09 (m, 11H). MS (ESI+) m/z 603.3 [M+H]+.

Example 148
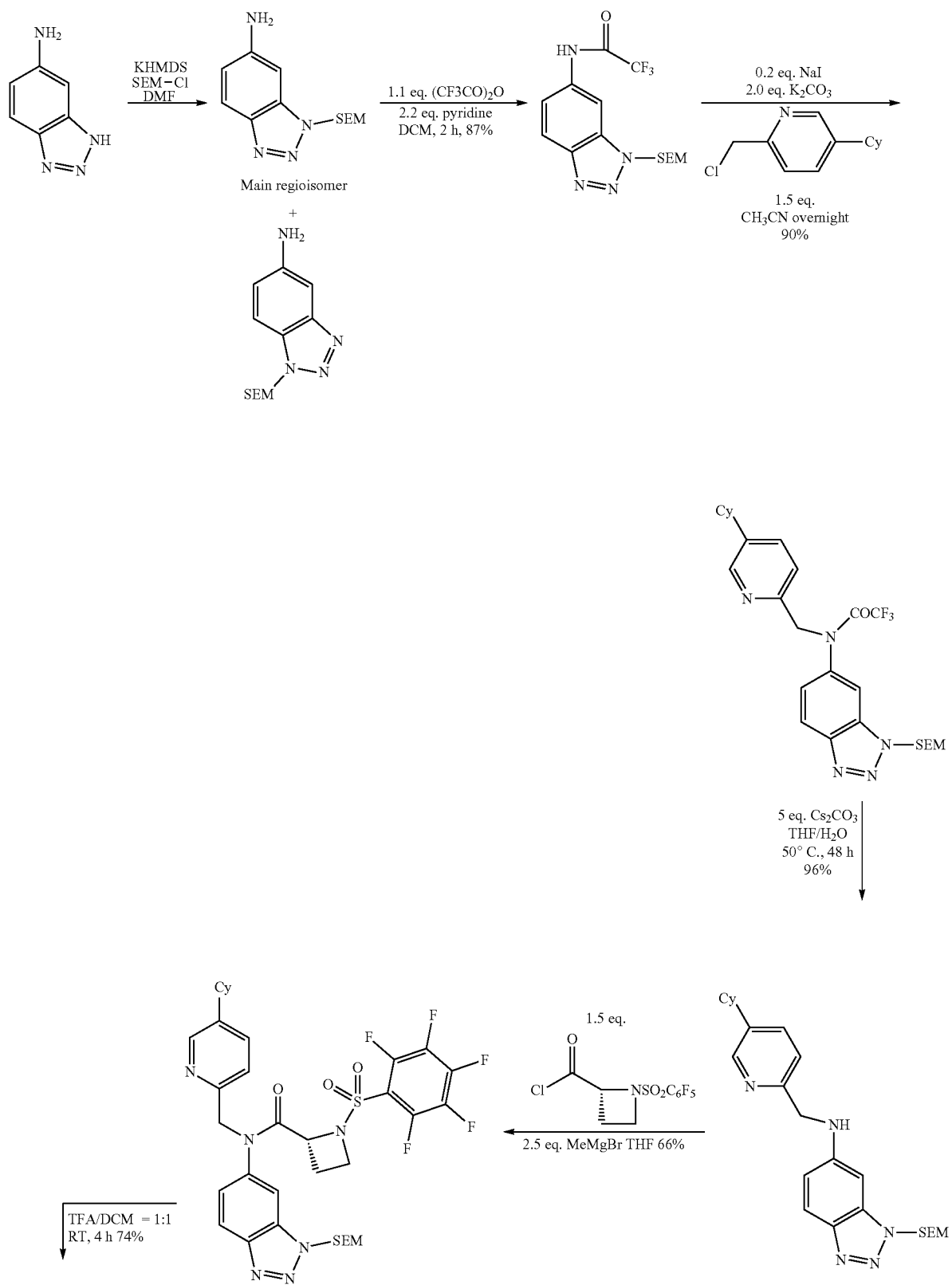

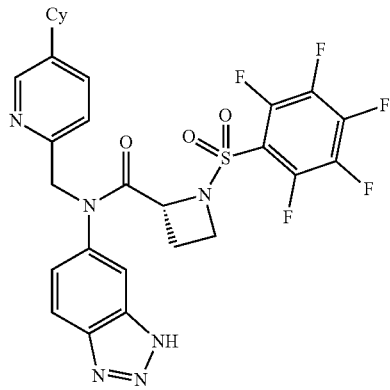

(R)—N-(1H-benzo[d][1,2,3]triazol-6-yl)-N-((5-cyclohexylpyridin-2-yl)methyl)-1-((perfluorophenyl)sulfonyl)azetidine-2-carboxamide

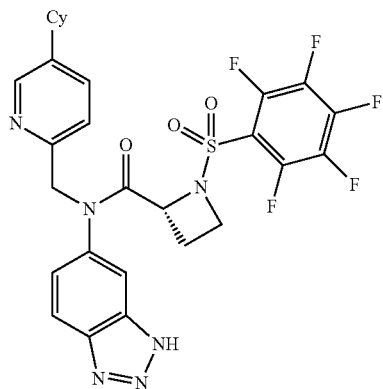

Step 1. Preparation by a similar procedure to Example 136, step 1, starting from 1H-benzo[d][1,2,3]triazol-6-amine to obtain 1-((2-(trimethylsilyl)ethoxy)methyl)-1H-benzo[d][1,2,3]triazol-6-amine as the main regioisomer (29% yield, $^1$H NMR (300 MHz, CDCl$_3$) δ 7.79 (d, J=8.8, 1H), 6.86-6.67 (m, 2H), 5.83 (s, 2H), 5.48-5.04 (m, 2H), 3.65-3.41 (m, 2H), 0.97-0.77 (m, 2H), −0.02−−0.17 (m, 9H)), and 1-((2-(trimethylsilyl)ethoxy)methyl)-1H-benzo[d]imidazol-5-amine (18% yield, $^1$H NMR (300 MHz, CDCl$_3$) δ 7.47 (dd, J=8.7, 0.8 Hz, 1H), 7.23 (dd, J=2.1, 0.8 Hz, 1H), 6.97 (dd, J=8.7, 2.1 Hz, 1H), 5.90 (s, 2H), 5.12 (br s, 2H), 3.63-3.46 (m, 2H), 0.98-0.80 (m, 2H), −0.08 (s, 9H)).

Step 2. Preparation by a similar procedure to Example 61, step 3, starting from 1-((2-(trimethylsilyl)ethoxy)methyl)-1H-benzo[d][1,2,3]triazol-6-amine to obtain 2,2,2-trifluoro-N-(1-((2-(trimethylsilyl)ethoxy)methyl)-1H-benzo[d][1,2,3]triazol-6-yl)acetamide. $^1$H NMR (300 MHz, CDCl$_3$) δ 9.46 (s, 1H), 8.47 (s, 1H), 8.02 (d, J=8.9 Hz, 1H), 7.47 (d, J=8.9, 1H), 5.99 (s, 2H), 3.59 (t, J=8.4 Hz, 2H), 0.91 (t, J=8.4 Hz, 2H), −0.06 (s, 9H).

Step 3. Preparation by a similar procedure to Example 116, step 4, starting from 2,2,2-trifluoro-N-(1-((2-(trimethylsilyl)ethoxy)methyl)-1H-benzo[d][1,2,3]triazol-6-yl)acetamide to obtain N-((5-cyclohexylpyridin-2-yl)methyl)-2,2,2-trifluoro-N-(1-((2-(trimethylsilyl)ethoxy)methyl)-1H-benzo[d][1,2,3]triazol-6-yl)acetamide. $^1$H NMR (300 MHz, CDCl$_3$) δ 8.38 (s, 1H), 8.06 (d, J=8.8 Hz, 1H), 7.66 (s, 1H), 7.51 (d, J=8.0 Hz, 1H), 7.34-7.24 (m, 2H), 5.95 (s, 2H), 5.07 (s, 2H), 3.55 (t, J=8.4 Hz, 2H), 2.59-2.43 (m, 1H), 1.88-1.72 (m, 5H), 1.49-1.29 (m, 5H), 0.92-0.82 (t, J=8.4 Hz, 2H), −0.08 (s, 9H)

Step 4. Preparation by a similar procedure to Example 109, step 4, starting from N-((5-cyclohexylpyridin-2-yl)methyl)-2,2,2-trifluoro-N-(1-((2-(trimethylsilyl)ethoxy)methyl)-1H-benzo[d][1,2,3]triazol-6-yl)acetamide to obtain N-((5-cyclohexylpyridin-2-yl)methyl)-1-((2-(trimethylsilyl)ethoxy)methyl)-1H-benzo[d][1,2,3]triazol-6-amine. $^1$H NMR (300 MHz, CDCl$_3$) δ 8.43 (d, J=2.1 Hz, 1H), 7.75 (d, J=9.0 Hz, 1H), 7.48 (dd, J=8.0, 2.1 Hz, 1H), 7.23 (d, J=8.0 Hz, 1H), 6.82 (dd, J=9.0, 1.9 Hz, 1H), 6.55 (d, J=1.9 Hz, 1H), 5.81 (s, 2H), 5.50 (s, 1H), 4.44 (s, 2H), 3.60-3.47 (m, 2H), 2.61-2.44 (m, 1H), 1.89-1.70 (m, 5H), 1.47-1.29 (m, 5H), 0.92-0.79 (m, 2H), −0.09 (s, 9H).

Step 5. Preparation by a similar procedure to Example 136, step 6, starting from N-((5-cyclohexylpyridin-2-yl)methyl)-1-((2-(trimethylsilyl)ethoxy)methyl)-1H-benzo[d][1,2,3]triazol-6-amine to obtain (R)—N-((5-cyclohexylpyridin-2-yl)methyl)-1-((perfluorophenyl)sulfonyl)-N-(1-((2-(trimethylsilyl)ethoxy)methyl)-1H-benzo[d][1,2,3]triazol-6-yl)azetidine-2-carboxamide. $^1$H NMR (300 MHz, CDCl$_3$) δ 8.32 (d, J=2.0 Hz, 1H), 8.05 (d, J=8.7 Hz, 1H), 7.60 (s, 1H), 7.50 (dd, J=8.0, 2.0 Hz, 1H), 7.25-7.18 (m, 2H), 5.94 (s, 2H), 5.02-4.92 (m, 3H), 4.09-4.01 (m, 2H), 3.64-3.52 (m, 2H), 2.56-2.42 (m, 1H), 2.40-2.27 (m, 1H), 2.00-1.69 (m, 6H), 1.50-1.24 (m, 5H), 0.96-0.80 (m, 2H), −0.06 (s, 9H)

Step 6. Preparation by a similar procedure to Example 136, step 7, starting from (R)—N-((5-cyclohexylpyridin-2-yl)methyl)-1-((perfluorophenyl)sulfonyl)-N-(1-((2-(trimethylsilyl)ethoxy)methyl)-1H-benzo[d][1,2,3]triazol-6-yl)azetidine-2-carboxamide to obtain the compound of Example 148 (R)—N-(1H-benzo[d][1,2,3]triazol-6-yl)-N-((5-cyclohexylpyridin-2-yl)methyl)-1-((perfluorophenyl)sulfonyl)azetidine-2-carboxamide. MS (ESI+): [M+H]+ m/z 621.3.

Example 149
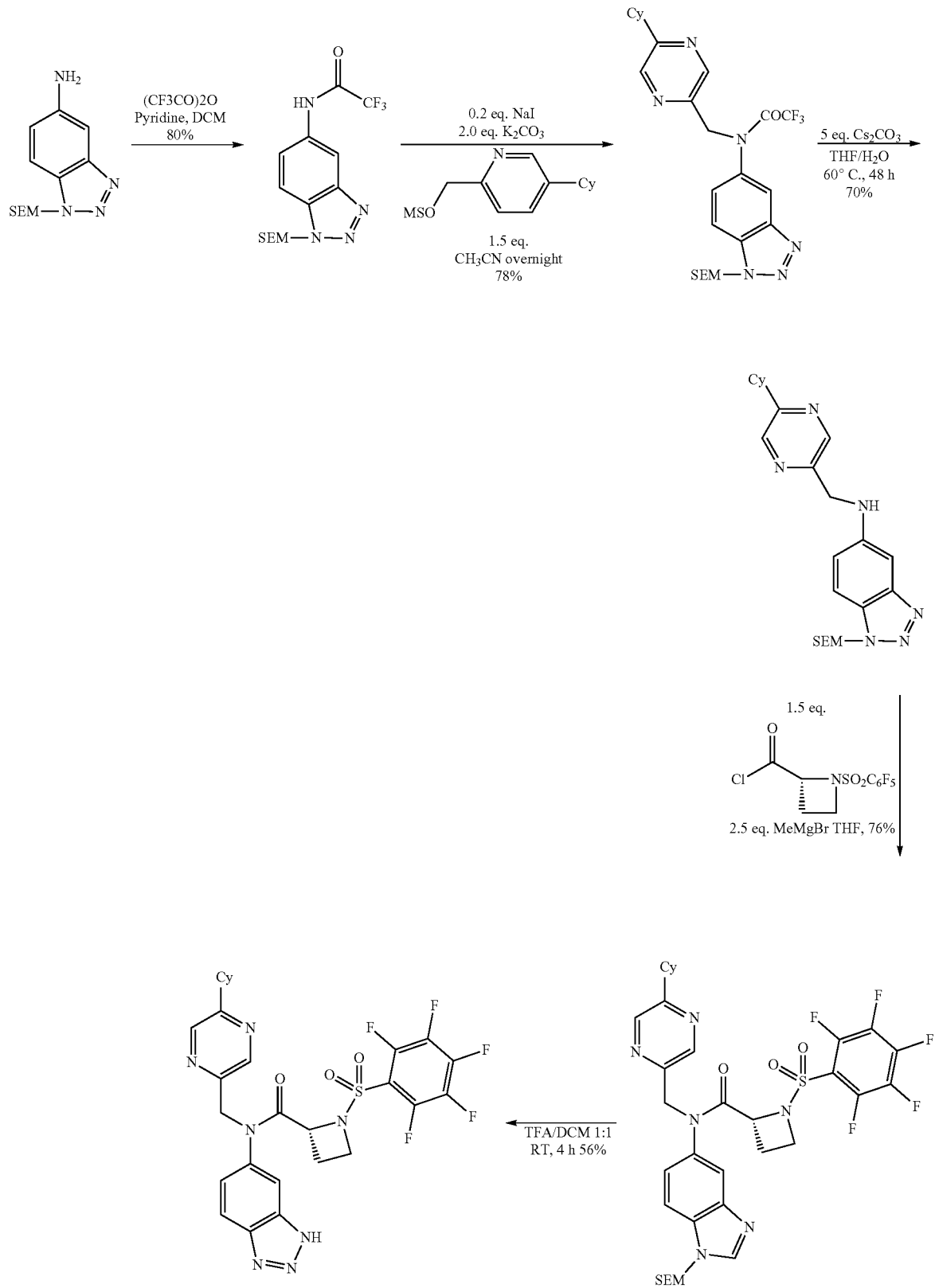

(R)—N-(1H-benzo[d][1,2,3]triazol-6-yl)-N-((5-cyclohexylpyrazin-2-yl)methyl)-1-((perfluorophenyl)sulfonyl)azetidine-2-carboxamide

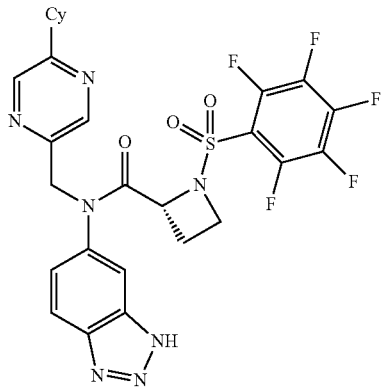

Step 1. Preparation by a similar procedure to Example 61, step 3, starting from 2,2,2-trifluoro-N-(1-((2-(trimethylsilyl)ethoxy)methyl)-1H-benzo[d][1,2,3]triazol-5-yl)acetamide to obtain 2,2,2-trifluoro-N-(1-((2-(trimethylsilyl)ethoxy)methyl)-1H-benzo[d][1,2,3]triazol-5-yl)acetamide. $^1$H NMR (300 MHz, CDCl$_3$) δ 9.71 (s, 1H), 8.42 (d, J=1.7 Hz, 1H), 7.84 (dd, J=8.9, 1.7 Hz, 1H), 7.70 (d, J=8.9 Hz, 1H), 5.98 (s, 2H), 3.57 (t, J=8.2 Hz, 2H), 0.89 (t, J=8.2 Hz, 2H), −0.08 (s, 9H).

Step 2. To a dry flask, 72 mg of 2,2,2-trifluoro-N-(1-((2-(trimethylsilyl)ethoxy)methyl)-1H-benzo[d][1,2,3]triazol-5-yl)acetamide, 0.2 eq. NaI and 2.0 eq. K$_2$CO$_3$ were added under Argon. A solution of 1.5 eq. (5-cyclohexylpyrazin-2-yl)methyl methanesulfonate in 4 ml CH3CN was added to the mixture, which was then stirred overnight at 65° C. After the reaction was complete, 5 ml water was added. The mixture was extracted with EA for 3 times. The combined organic layer was washed with brine and dried with Na$_2$SO$_4$. The organic layer was concentrated under vacuum and purified by column chromatography to obtain N-((5-cyclohexylpyrazin-2-yl)methyl)-2,2,2-trifluoro-N-(1-((2-(trimethylsilyl)ethoxy)methyl)-1H-benzo[d][1,2,3]triazol-5-yl)acetamide (84 mg, 78% yield). $^1$H NMR (300 MHz, CDCl$_3$) δ 8.52 (s, 1H), 8.43 (s, 1H), 8.04 (s, 1H), 7.72 (d, J=8.7 Hz, 1H), 7.49 (d, J=8.7 Hz, 1H), 6.00 (s, 2H), 5.08 (s, 2H), 3.66-3.52 (m, 2H), 2.83-2.68 (m, 1H), 2.00-1.71 (m, 5H), 1.63-1.32 (m, 5H), 0.96-0.84 (m, 2H), −0.07 (s, 9H).

Step 3. Preparation by a similar procedure to Example 109, step 4, starting from N-((5-cyclohexylpyrazin-2-yl)methyl)-2,2,2-trifluoro-N-(1-((2-(trimethylsilyl)ethoxy)methyl)-1H-benzo[d][1,2,3]triazol-5-yl)acetamide to obtain N-((5-cyclohexylpyrazin-2-yl)methyl)-1-((2-(trimethylsilyl)ethoxy)methyl)-1H-benzo[d][1,2,3]triazol-5-amine. $^1$H NMR (300 MHz, CDCl$_3$) δ 8.56 (d, J=1.3 Hz, 1H), 8.42 (d, J=1.3 Hz, 1H), 7.47 (d, J=8.7 Hz, 1H), 7.10-6.99 (m, 2H), 5.89 (s, 2H), 4.51 (s, 2H), 3.59-3.48 (m, 2H), 2.81-2.67 (m, 1H), 1.97-1.77 (m, 5H), 1.64-1.31 (m, 5H), 0.93-0.83 (m, 2H), −0.07 (s, 9H).

Step 4. Preparation by a similar procedure to Example 136, step 6, starting from N-((5-cyclohexylpyrazin-2-yl)methyl)-1-((2-(trimethylsilyl)ethoxy)methyl)-1H-benzo[d][1,2,3]triazol-5-amine to obtain (R)—N-((5-cyclohexylpyrazin-2-yl)methyl)-1-((perfluorophenyl)sulfonyl)-N-(1-((2-(trimethylsilyl)ethoxy)methyl)-1H-benzo[d]imidazol-5-yl)azetidine-2-carboxamide. $^1$H NMR (300 MHz, CDCl$_3$) δ 8.43 (d, J=1.2 Hz, 1H), 8.37 (d, J=1.2 Hz, 1H), 7.92 (s, 1H), 7.75 (d, J=8.7 Hz, 1H), 7.48 (d, J=8.7 Hz, 1H), 5.99 (s, 2H), 5.15 (d, J=15.3 Hz, 1H), 4.99-4.90 (m, 1H), 4.79 (d, J=15.3 Hz, 1H), 4.08-3.95 (m, 2H), 3.64-3.57 (m, 2H), 2.79-2.65 (m, 1H), 2.41-2.27 (m, 1H), 1.98-1.76 (m, 6H), 1.63-1.30 (m, 5H), 0.98-0.86 (m, 2H), −0.05 (s, 9H).

Step 5. Preparation by a similar procedure to Example 136, step 7, starting from (R)—N-((5-cyclohexylpyrazin-2-yl)methyl)-1-((perfluorophenyl)sulfonyl)-N-(1-((2-(trimethylsilyl)ethoxy)methyl)-1H-benzo[d]imidazol-5-yl)azetidine-2-carboxamide to obtain the compound of Example 149 (R)—N-(1H-benzo[d][1,2,3]triazol-6-yl)-N-((5-cyclohexylpyrazin-2-yl)methyl)-1-((perfluorophenyl)sulfonyl)azetidine-2-carboxamide. MS (ESI+): [M+H]+ m/z 622.3.

Example 150

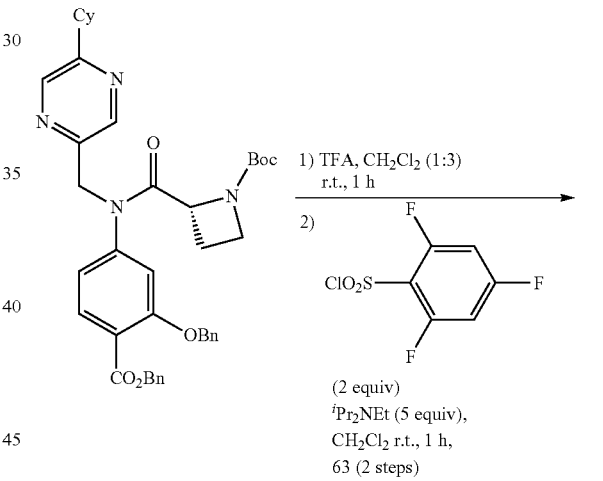

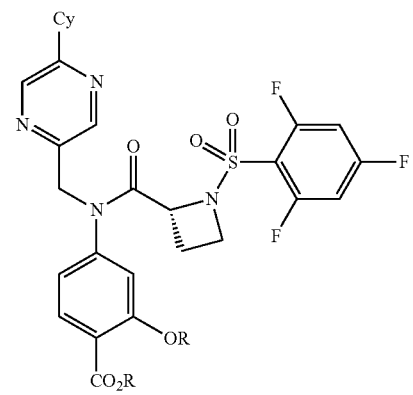

399

(R)-4-(N-((5-cyclohexylpyrazin-2-yl)methyl)-1-((2,4,6-trifluorophenyl)sulfonyl)azetidine-2-carboxamido)-2-hydroxybenzoic acid

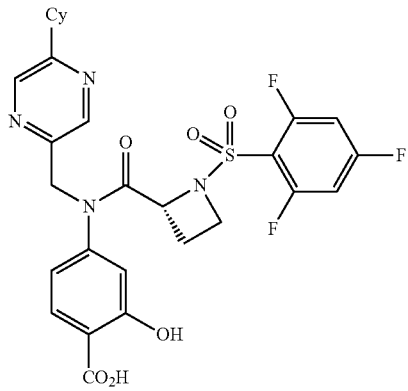

Step 1. Preparation by a similar procedure to Example 142, step 1, starting from tert-butyl (R)-2-((3-(benzyloxy)-4-((benzyloxy)carbonyl)phenyl)((5-cyclohexylpyrazin-2-yl)methyl)carbamoyl)azetidine-1-carboxylate to obtain benzyl (R)-2-(benzyloxy)-4-(N-((5-cyclohexylpyrazin-2-yl)methyl)-1-((2,4,6-trifluorophenyl)sulfonyl)azetidine-2-carboxamido)benzoate. $^1$H NMR (300 MHz, CDCl$_3$) δ 8.55 (s, 1H), 8.48 (s, 1H), 7.85 (d, J=8.1 Hz, 1H), 7.33-7.45 (m, 10H), 6.99 (d, J=1.8 Hz, 1H), 6.85 (dd, J=1.8, 8.1 Hz, 1H), 6.73-6.81 (m, 2H), 5.38 (s, 2H), 5.24 (d, J=12.6 Hz, 1H), 5.14 (d, J=12.6 Hz, 1H), 4.99 (d, J=15.9 Hz, 1H), 4.88-4.95 (m, 2H), 3.97-4.05 (m, 1H), 3.87-3.94 (m, 1H), 2.87-2.97 (m, 1H), 1.26-2.38 (m, 12H).

Step 2. Preparation by a similar procedure to Example 61, step 7, starting from benzyl (R)-2-(benzyloxy)-4-(N-((5-cyclohexylpyrazin-2-yl)methyl)-1-((2,4,6-trifluorophenyl)sulfonyl)azetidine-2-carboxamido)benzoate to obtain the compound of Example 150 (R)-4-(N-((5-cyclohexylpyrazin-2-yl)methyl)-1-((2,4,6-trifluorophenyl)sulfonyl)azetidine-2-carboxamido)-2-hydroxybenzoic acid. $^1$H NMR (300 MHz, CDCl$_3$) δ 11.13 (brs, 1H, OH), 8.90 (s, 1H), 8.52 (s, 1H), 7.70 (d, J=8.7 Hz, 1H), 6.76-6.84 (m, 2H), 6.65-6.70 (m, 2H), 5.15 (d, J=14.7 Hz, 1H), 4.96-5.04 (m, 2H), 4.06-4.13 (m, 1H), 3.93-4.01 (m, 1H), 2.89-3.01 (m, 1H), 2.24-2.35 (m, 1H), 1.26-2.10 (m, 11H). MS (ESI+) m/z 605.3 [M+H]+.

Example 151

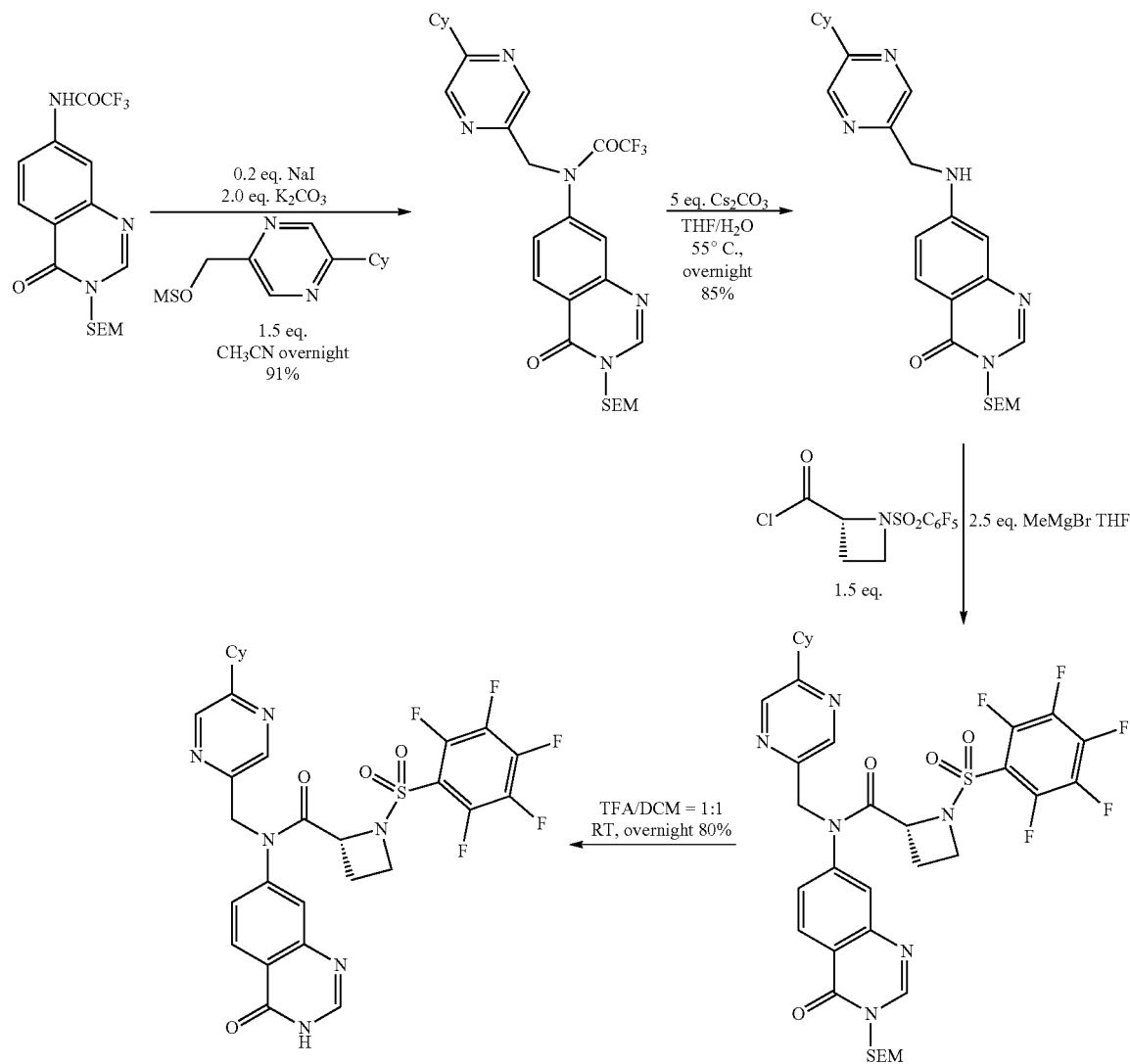

(R)—N-((5-cyclohexylpyrazin-2-yl)methyl)-N-(4-oxo-3,4-dihydroquinazolin-7-yl)-1-((perfluorophenyl)sulfonyl)azetidine-2-carboxamide

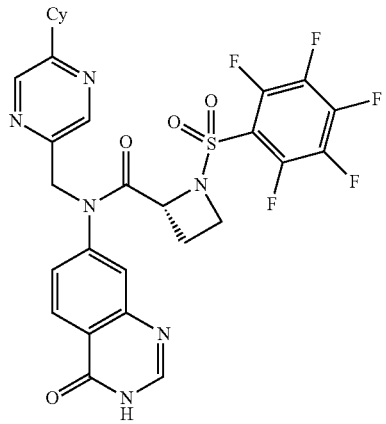

Step 1. Preparation by a similar procedure to Example 149, step 2, starting from 2,2,2-trifluoro-N-(4-oxo-3-((2-(trimethylsilyl)ethoxy)methyl)-3,4-dihydroquinazolin-7-yl)acetamide to obtain N-((5-cyclohexylpyrazin-2-yl)methyl)-2,2,2-trifluoro-N-(4-oxo-3-((2-(trimethylsilyl)ethoxy)methyl)-3,4-dihydroquinazolin-7-yl)acetamide. $^1$H NMR (300 MHz, CDCl$_3$) δ 8.45 (s, 1H), 8.36 (s, 1H), 8.27 (d, J=8.5 Hz, 1H), 8.14 (s, 1H), 7.64 (d, J=1.6 Hz, 1H), 7.38 (dd, J=8.5, 1.6 Hz, 1H), 5.37 (s, 2H), 4.98 (s, 2H), 3.63-3.49 (m, 2H), 2.69-2.53 (m, 1H), 1.85-1.55 (m, 5H), 1.51-1.18 (m, 5H), 0.93-0.77 (m, 2H), −0.13 (s, 9H).

Step 2. Preparation by a similar procedure to Example 109, step 4, starting from N-((5-cyclohexylpyrazin-2-yl)methyl)-2,2,2-trifluoro-N-(4-oxo-3-((2-(trimethylsilyl)ethoxy) methyl)-3,4-dihydroquinazolin-7-yl)acetamide to obtain 7-(((5-cyclohexylpyrazin-2-yl)methyl)amino)-3-((2-(trimethylsilyl)ethoxy)methyl)quinazolin-4(3H)-one. $^1$H NMR (300 MHz, CDCl$_3$) δ 8.56 (s, 1H), 8.46 (s, 1H), 8.17-8.07 (m, 2H), 6.92-6.85 (m 1H), 6.81 (m, 1H), 5.51-5.38 (m, 3H), 4.59 (s, 2H), 3.75-3.62 (m, 2H), 2.85-2.71 (m, 1H), 2.00-1.77 (m, 5H), 1.52-1.24 (m, 5H), 1.03-0.92 (m, 2H), 0.00 (s, 9H)

Step 3. Preparation by a similar procedure to Example 136, step 6, starting from 7-(((5-cyclohexylpyrazin-2-yl)methyl)amino)-3-((2-(trimethylsilyl)ethoxy)methyl)quinazolin-4(3H)-one to obtain (R)—N-((5-cyclohexylpyrazin-2-yl)methyl)-N-(4-oxo-3-((2-(trimethylsilyl)ethoxy)methyl)-3,4-dihydroquinazolin-7-yl)-1-((perfluorophenyl)sulfonyl)azetidine-2-carboxamide. $^1$H NMR (300 MHz, CDCl$_3$) δ 8.44 (s, 1H), 8.39-8.33 (m, 2H), 8.18 (s, 1H), 7.61 (d, J=1.6 Hz, 1H), 7.42 (dd, J=8.5, 1.6 Hz, 1H), 5.44 (s, 2H), 5.17-5.01 (m, 2H), 4.86 (d, J=15.5 Hz, 1H), 4.18-3.99 (m, 2H), 3.75-3.65 (m, 2H), 2.80-2.66 (m, 1H), 2.45-2.25 (m, 1H), 1.98-1.67 (m, 6H), 1.63-1.34 (m, 5H), 1.02-0.95 (m, 2H), 0.02 (s, 9H).

Step 4. Preparation by a similar procedure to Example 136, step 7, starting from (R)—N-((5-cyclohexylpyrazin-2-yl)methyl)-N-(4-oxo-3-((2-(trimethylsilyl)ethoxy)methyl)-3,4-dihydroquinazolin-7-yl)-1-((perfluorophenyl)sulfonyl) azetidine-2-carboxamide to obtain the compound of Example 151 (R)—N-((5-cyclohexylpyrazin-2-yl)methyl)-N-(4-oxo-3,4-dihydroquinazolin-7-yl)-1-((perfluorophenyl)sulfonyl)azetidine-2-carboxamide. MS (ESI+): [M+H]+ m/z 649.2.

Example 152

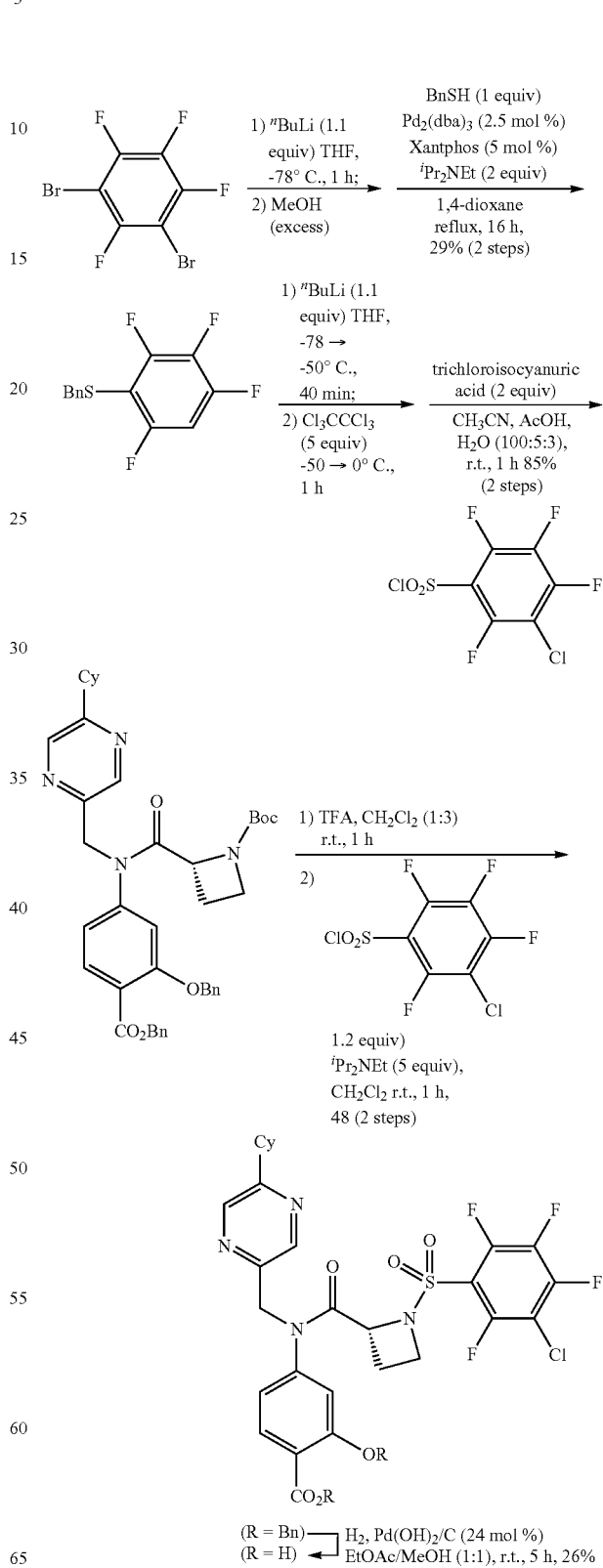

(R)-4-(1-((3-chloro-2,4,5,6-tetrafluorophenyl)sulfonyl)-N-((5-cyclohexylpyrazin-2-yl)methyl)azetidine-2-carboxamido)-2-hydroxybenzoic acid

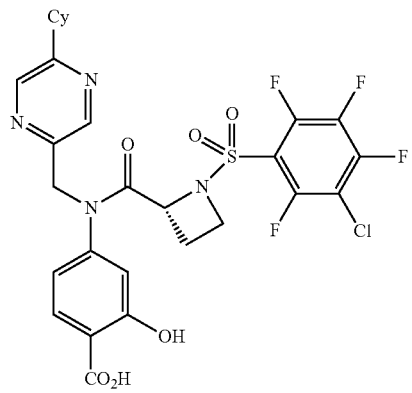

Step 1. To a solution of 1,3-dibromo-2,4,5,6-tetrafluorobenzene (600 mg, 1.95 mmol) in THF (9.6 mL) was added nBuLi (3.2 M in hexane, 0.68 mL, 2.2 mmol) at −78° C. After stirring for 1 h, MeOH (1.0 mL) was added and the reaction mixture was gradually warmed to room temperature, then added water. The crude products were extracted with EtOAc (×3), and the combined organic extracts were washed with brine, dried (MgSO4), and concentrated in vacuo. The residue dissolved in 1,4-dioxane (5.0 mL) and was added Pd$_2$(dba)$_3$ (46 mg, 0.050 mmol), Xantphos (57 mg, 0.098 mmol), iPr$_2$NEt (0.68 mL, 3.9 mmol) and BnSH (0.20 mL, 1.7 mmol) at room temperature. The reaction mixture degassed and refluxed for 16 h. After cooling to room temperature, the reaction mixture was filtered through Celite® pad (washed with EtOAc) and concentrated in vacuo. The residue was purified by flash column chromatography (hexane to hexane/EtOAc=24/1) to afford benzyl (2,3,4,6-tetrafluorophenyl)sulfane (153 mg, 29%) as a colorless oil. $^1$H NMR (300 MHz, CDCl$_3$) δ 7.20-7.39 (m, 1H), 6.72-6.81 (m, 1H), 4.04 (s, 2H).

Step 2. Preparation by a similar procedure to Example 146, step 1, starting from benzyl(2,3,4,6-tetrafluorophenyl) sulfane to obtain 3-chloro-2,4,5,6-tetrafluorobenzenesulfonyl chloride. $^{19}$F NMR (282 MHz, CDCl3) δ −109.8, −117.8, −128.2, −156.7.

Step 3. Preparation by a similar procedure to Example 142, step 1, starting from tert-butyl (R)-2-((3-(benzyloxy)-4-((benzyloxy)carbonyl)phenyl)((5-cyclohexylpyrazin-2-yl)methyl)carbamoyl)azetidine-1-carboxylate to obtain benzyl (R)-2-(benzyloxy)-4-(1-((3-chloro-2,4,5,6-tetrafluorophenyl)sulfonyl)-N-((5-cyclohexylpyrazin-2-yl)methyl)azetidine-2-carboxamido)benzoate. $^1$H NMR (300 MHz, CDCl$_3$) δ 8.44 (s, 1H), 8.40 (s, 1H), 7.84 (d, J=8.1 Hz, 1H), 7.34-7.44 (m, 10H), 6.94 (d, J=1.5 Hz, 1H), 6.83 (dd, J=1.5, 8.1 Hz, 1H), 5.38 (s, 2H), 5.22 (d, J=12.3 Hz, 1H), 5.13 (d, J=12.3 Hz, 1H), 5.02 (d, J=15.3 Hz, 1H), 4.89-4.94 (m, 1H), 4.78 (d, J=15.3 Hz, 1H), 4.01-4.09 (m, 1H), 3.91-3.98 (m, 1H), 2.74-2.85 (m, 1H), 1.26-2.13 (m, 12H).

Step 4. Preparation by a similar procedure to Example 27, step 5, starting from benzyl (R)-2-(benzyloxy)-4-(1-((3-chloro-2,4,5,6-tetrafluorophenyl)sulfonyl)-N-((5-cyclohexylpyrazin-2-yl)methyl)azetidine-2-carboxamido)benzoate to obtain the compound of Example 152 (R)-4-(1-((3-chloro-2,4,5,6-tetrafluorophenyl)sulfonyl)-N-((5-cyclohexylpyrazin-2-yl)methyl)azetidine-2-carboxamido)-2-hydroxybenzoic acid. $^1$H NMR (300 MHz, CDCl$_3$) δ 11.09 (brs, 1H, OH), 8.83 (s, 1H), 8.50 (s, 1H), 7.73 (d, J=8.4 Hz, 1H), 6.66-6.72 (m, 2H), 4.97-5.09 (m, 3H), 4.10-4.19 (m, 1H), 3.99-4.07 (m, 1H), 2.87-2.96 (m, 1H), 1.26-2.45 (m, 12H). MS (ESI+) m/z 657.2 [M+H]+.

Example 153

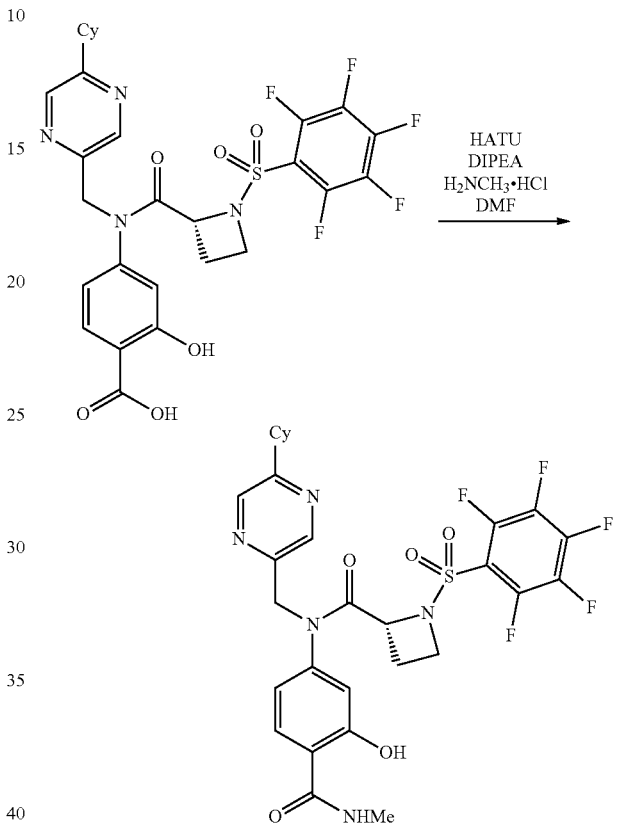

(R)—N-((5-cyclohexylpyrazin-2-yl)methyl)-N-(3-hydroxy-4-(methylcarbamoyl)phenyl)-1-((perfluorophenyl)sulfonyl)azetidine-2-carboxamide

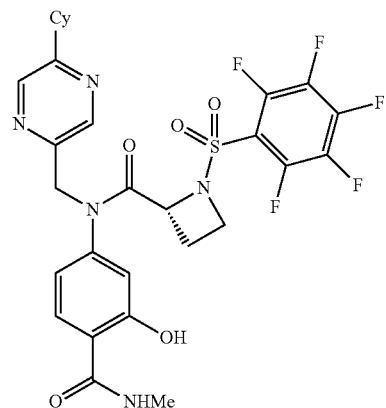

Step 1. To a solution of (R)-4-(N-((5-cyclohexylpyrazin-2-yl)methyl)-1-((perfluorophenyl)sulfonyl)azetidine-2-carboxamido)-2-hydroxybenzoic acid (35.5 mg, 0.055 mmol) in DMF (1.2 mL) was added at 0° C. DIPEA (0.0092 mL, 0.055 mmol) and HATU (21.1 mg, 0.055 mmol) under argon. The mixture was allowed to reach rt and stirred for 1.5 hours. A solution of H₂NMe.HCl (3.7 mg, 0.055 mmol) and DIPEA (0.0092 mL, 0.055 mmol) in DMF (1.2 mL) was added. The mixture was stirred overnight. Cold water was added, and the mixture was extracted with EtOAc (2×). The extract was washed with water, brine, dried (sodium sulfate) and concentrated. Purification by preparative TLC gave Example 153 (R)—N-((5-cyclohexylpyrazin-2-yl)methyl)-N-(3-hydroxy-4-(methylcarbamoyl)phenyl)-1-((perfluorophenyl)sulfonyl)azetidine-2-carboxamide. HRMS (ESI+) m/z 654.1919 [M+H]+.

Example 154

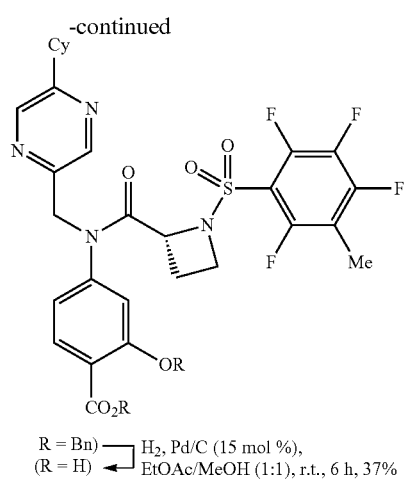

(R)-4-(N-((5-cyclohexylpyrazin-2-yl)methyl)-1-((2,3,4,6-tetrafluoro-5-methylphenyl)sulfonyl)azetidine-2-carboxamido)-2-hydroxybenzoic acid

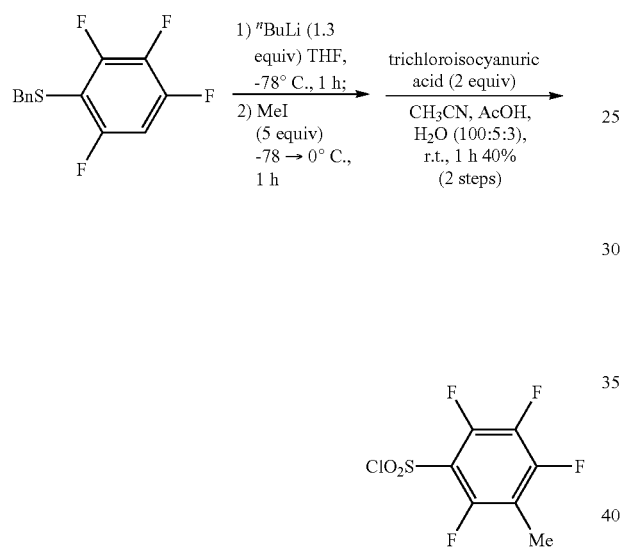

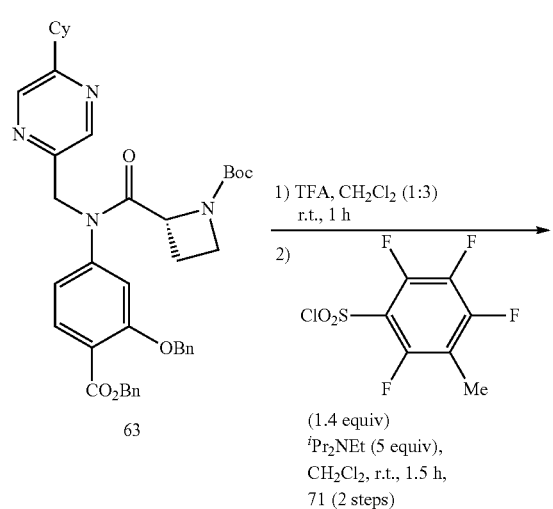

Step 1. Preparation by a similar procedure to Example 144, step 1, starting from benzyl(2,3,4,6-tetrafluorophenyl)sulfane to obtain 2,3,4,6-tetrafluoro-5-methylbenzenesulfonyl chloride. ¹H NMR (300 MHz, CDCl₃) δ 2.32-2.34 (m, 3H).

Step 2. Preparation by a similar procedure to Example 142, step 1, starting from tert-butyl (R)-2-((3-(benzyloxy)-4-((benzyloxy)carbonyl)phenyl)((5-cyclohexylpyrazin-2-yl)methyl)carbamoyl)azetidine-1-carboxylate to obtain benzyl (R)-2-(benzyloxy)-4-(N-((5-cyclohexylpyrazin-2-yl)methyl)-1-((2,3,4,6-tetrafluoro-5-methylphenyl)sulfonyl)azetidine-2-carboxamido)benzoate. ¹H NMR (300 MHz, CDCl₃) δ 8.47 (s, 1H), 8.40 (s, 1H), 7.84 (d, J=8.1 Hz, 1H), 7.33-7.44 (m, 10H), 6.96 (d, J=1.8 Hz, 1H), 6.83 (d, J=1.8, 8.1 Hz, 1H), 5.37 (s, 2H), 5.22 (d, J=12.6 Hz, 1H), 5.12 (d, J=12.6 Hz, 1H), 5.03 (d, J=15.3 Hz, 1H), 4.88-4.95 (m, 1H), 4.81 (d, J=15.3 Hz, 1H), 3.88-4.06 (m, 2H), 2.74-2.85 (m, 1H), 2.22 (s, 3H), 1.26-2.15 (m, 12H).

Step 3. Preparation by a similar procedure to Example 61, step 7, starting from benzyl (R)-2-(benzyloxy)-4-(N-((5-cyclohexylpyrazin-2-yl)methyl)-1-((2,3,4,6-tetrafluoro-5-methyl phenyl)sulfonyl)azetidine-2-carboxamido)benzoate to obtain the compound of Example 154 (R)-4-(N-((5-cyclohexylpyrazin-2-yl)methyl)-1-((2,3,4,6-tetrafluoro-5- methylphenyl)sulfonyl)azetidine-2-carboxamido)-2-hydroxybenzoic acid. $^1$H NMR (300 MHz, CDCl$_3$) δ 11.11 (brs, 1H, OH), 8.88 (s, 1H), 8.49 (s, 1H), 7.71 (d, J=8.7 Hz, 1H), 6.65-6.71 (m, 2H), 5.10 (d, J=14.1 Hz, 1H), 4.96-5.05 (m, 2H), 4.06-4.15 (m, 1H), 3.95-4.02 (m, 1H), 2.86-2.96 (m, 1H), 2.26 (s, 3H), 1.26-2.09 (m, 12H). HRMS (ESI+) m/z 637.1726 [M+H]+.

Example 155

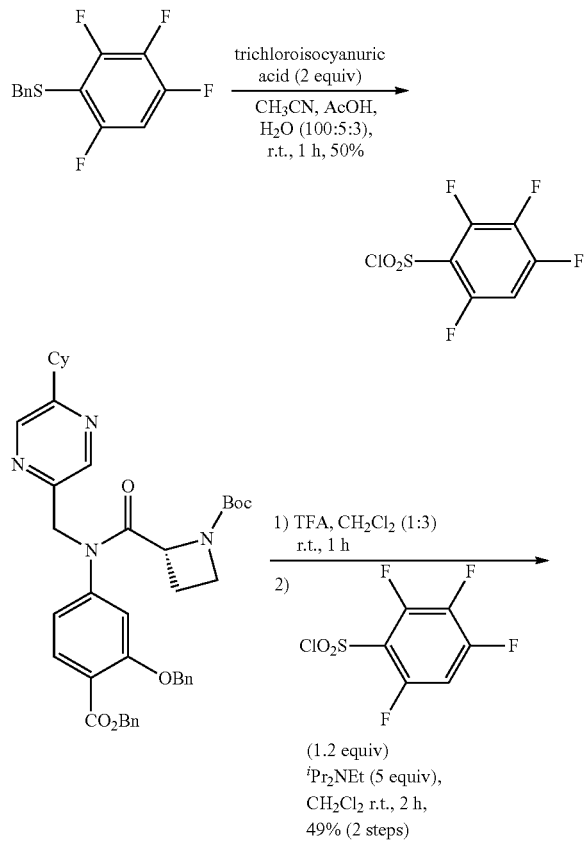

408

(R)-4-(N-((5-cyclohexylpyrazin-2-yl)methyl)-1-((2,3,4,6-tetrafluorophenyl)sulfonyl)azetidine-2-carboxamido)-2-hydroxybenzoic acid

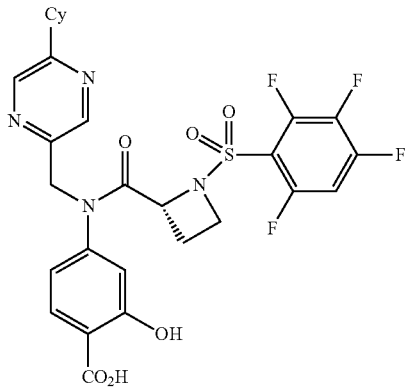

Step 1. Preparation by a similar procedure to Example 139, step 2, starting from benzyl(2,3,4,6-tetrafluorophenyl)sulfane (see Example 152, step 1) to obtain 2,3,4,6-tetrafluorobenzenesulfonyl chloride. $^1$H NMR (300 MHz, CDCl$_3$) δ 7.02-7.11 (m, 1H).

Step 2. Preparation by a similar procedure to Example 142, step 1, starting from tert-butyl (R)-2-((3-(benzyloxy)-4-((benzyloxy)carbonyl)phenyl)((5-cyclohexylpyrazin-2-yl)methyl)carbamoyl)azetidine-1-carboxylate to obtain benzyl (R)-2-(benzyloxy)-4-(N-((5-cyclohexylpyrazin-2-yl)methyl)-1-((2,3,4,6-tetrafluorophenyl)sulfonyl)azetidine-2-carboxamido)benzoate. $^1$H NMR (300 MHz, CDCl$_3$) δ 8.45 (s, 1H), 8.39 (s, 1H), 7.84 (d, J=8.1 Hz, 1H), 7.33-7.44 (m, 10H), 6.81-6.95 (m, 3H), 5.37 (s, 2H), 5.22 (d, J=12.6 Hz, 1H), 5.12 (d, J=12.6 Hz, 1H), 4.89-5.00 (m, 2H), 4.83 (d, J=15.3 Hz, 1H), 3.99-4.07 (m, 1H), 3.88-3.95 (m, 1H), 2.74-2.84 (m, 1H), 1.26-2.20 (m, 12H).

Step 3. Preparation by a similar procedure to Example 61, step 7, starting from benzyl (R)-2-(benzyloxy)-4-(N-((5-cyclohexylpyrazin-2-yl)methyl)-1-((2,3,4,6-tetrafluorophenyl)sulfonyl)azetidine-2-carboxamido)benzoate to obtain the compound of Example 155 (R)-4-(N-((5-cyclohexylpyrazin-2-yl)methyl)-1-((2,3,4,6-tetrafluorophenyl)sulfonyl)azetidine-2-carboxamido)-2-hydroxybenzoic acid. $^1$H NMR (300 MHz, CDCl$_3$) δ 11.10 (brs, 1H, OH), 8.50 (s, 1H), 8.49 (s, 1H), 7.72 (d, J=7.5 Hz, 1H), 6.88-6.97 (m, 1H), 6.65-6.71 (m, 2H), 4.98-5.11 (m, 3H), 4.09-4.18 (m, 1H), 3.96-4.04 (m, 1H), 2.85-2.98 (m, 1H), 1.26-2.32 (m, 12H). HRMS (ESI+) m/z 623.1584 [M+H]+.

Example 156

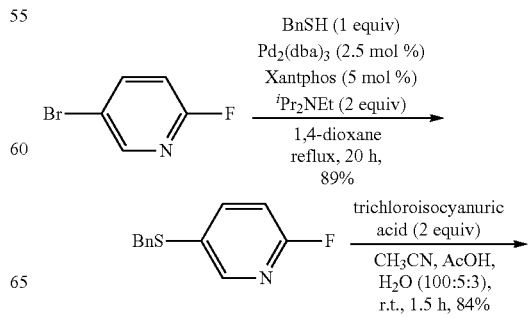

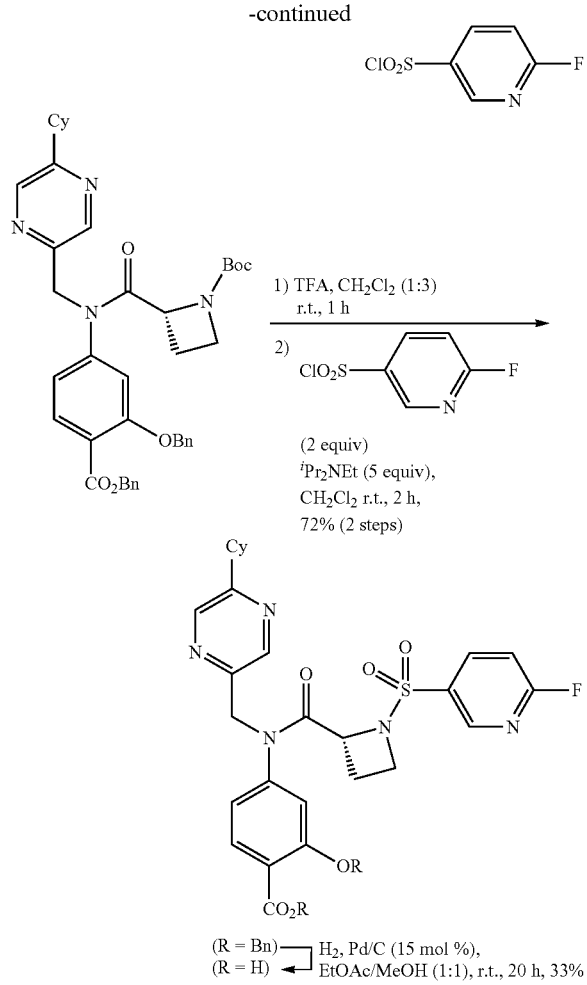

(R)-4-(N-((5-cyclohexylpyrazin-2-yl)methyl)-1-((6-fluoropyridin-3-yl)sulfonyl)azetidine-2-carboxamido)-2-hydroxybenzoic acid

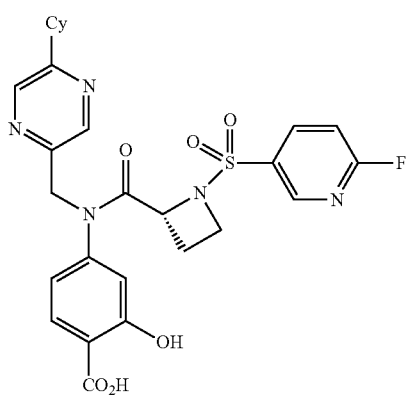

Step 1. Preparation by a similar procedure to Example 139, step 1, starting from 5-bromo-2-fluoropyridine to obtain 5-(benzylthio)-2-fluoropyridine. ¹H NMR (300 MHz, CDCl₃) δ 8.12 (d, J=2.1 Hz, 1H), 7.64 (ddd, J=2.1, 8.4, 8.4 Hz, 1H), 7.18-7.33 (m, 5H), 6.82 (dd, J=3.0, 8.4 Hz, 1H), 4.04 (s, 2H).

Step 2. Preparation by a similar procedure to Example 139, step 2, starting from 5-(benzylthio)-2-fluoropyridine to obtain 6-fluoropyridine-3-sulfonyl chloride. ¹H NMR (300 MHz, CDCl₃) δ 8.96 (d, J=2.1 Hz, 1H), 8.45 (ddd, J=2.1, 6.6, 9.0 Hz, 1H), 7.23 (dd, J=9.0, 3.0 Hz, 1H).

Step 3. Preparation by a similar procedure to Example 142, step 1, starting from tert-butyl (R)-2-((3-(benzyloxy)-4-((benzyloxy)carbonyl)phenyl)((5-cyclohexylpyrazin-2-yl)methyl)carbamoyl)azetidine-1-carboxylate to obtain benzyl (R)-2-(benzyloxy)-4-(N-((5-cyclohexylpyrazin-2-yl)methyl)-1-((6-fluoropyridin-3-yl)sulfonyl)azetidine-2-carboxamido)benzoate. ¹H NMR (300 MHz, CDCl₃) δ 8.73 (d, J=1.8 Hz, 1H), 8.50 (s, 1H), 8.34-8.38 (m, 2H), 7.86 (d, J=8.7 Hz, 1H), 7.32-7.42 (m, 10H), 7.04 (dd, J=3.0, 9.0 Hz, 1H), 6.97 (s, 1H), 6.86 (d, J=8.7 Hz, 1H), 5.38 (s, 2H), 5.21 (d, J=12.3 Hz, 1H), 5.03-5.13 (m, 2H), 4.82-4.93 (m, 2H), 3.86-3.94 (m, 1H), 3.54-3.60 (m, 1H), 2.71-2.82 (m, 1H), 1.26-2.40 (m, 12H).

Step 4. Preparation by a similar procedure to Example 61, step 7, starting from benzyl (R)-2-(benzyloxy)-4-(N-((5-cyclohexylpyrazin-2-yl)methyl)-1-((6-fluoropyridin-3-yl)sulfonyl)azetidine-2-carboxamido)benzoate to obtain the compound of Example 156 (R)-4-(N-((5-cyclohexylpyrazin-2-yl)methyl)-1-((6-fluoropyridin-3-yl)sulfonyl)azetidine-2-carboxamido)-2-hydroxybenzoic acid. ¹H NMR (300 MHz, CDCl₃) δ 11.19 (brs, 1H, OH), 8.94 (s, 1H), 8.74 (d, J=2.4 Hz, 1H), 8.47 (s, 1H), 8.37-8.43 (m, 1H), 7.73 (d, J=8.4 Hz, 1H), 7.10 (dd, J=2.4, 8.4 Hz, 1H), 6.70 (d, J=8.1 Hz, 1H), 6.66 (s, 1H), 5.16 (d, J=14.7 Hz, 1H), 4.92-5.03 (m, 2H), 3.94-4.02 (m, 1H), 3.63-3.70 (m, 1H), 2.84-2.92 (m, 1H), 1.25-2.38 (m, 12H). HRMS (ESI+) m/z 570.1820 [M+H]+.

Example 157

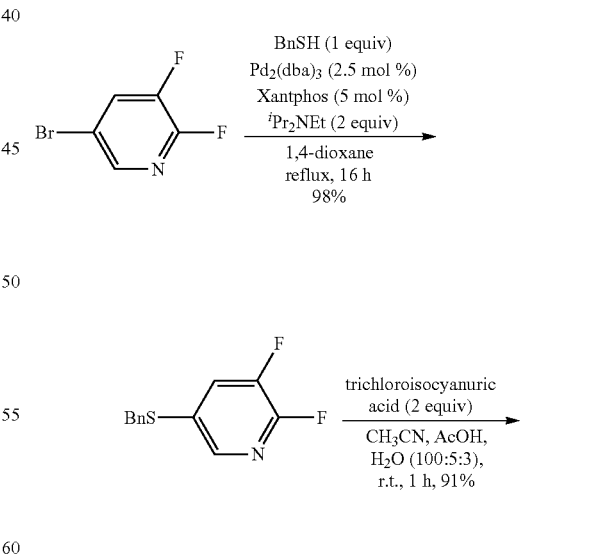

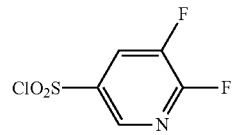

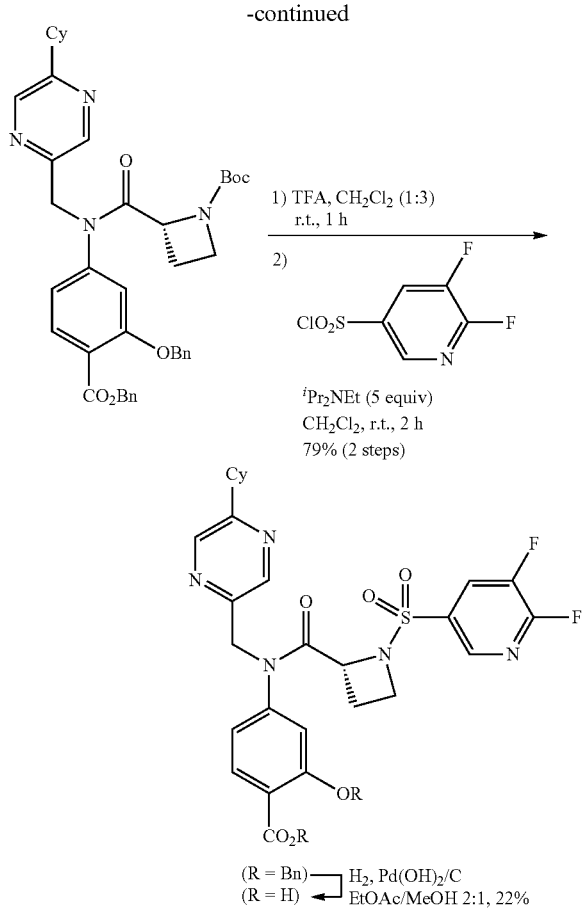

(R)-4-(N-((5-cyclohexylpyrazin-2-yl)methyl)-1-((5,6-difluoropyridin-3-yl)sulfonyl)azetidine-2-carboxamido)-2-hydroxybenzoic acid

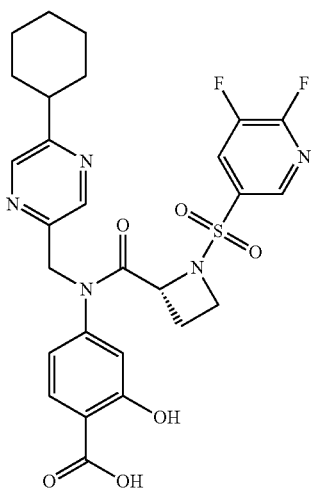 [SMILES: O=C(O)c1ccc(N(Cc2cnc(C3CCCCC3)cn2)C(=O)[C@H]2CCN2S(=O)(=O)c2cnc(F)c(F)c2)cc1O]

Step 1. Preparation by a similar procedure to Example 139, step 1, starting from 5-bromo-2,3-difluoropyridine to obtain 5-(benzylsulfanyl)-2,3-difluoropyridine. $^1$H NMR (300 MHz, CDCl$_3$) δ 7.86-7.88 (m, 1H), 7.22-7.48 (m, 6H), 4.08 (s, 2H).

Step 2. Preparation by a similar procedure to Example 139, step 2, starting from 5-(benzylsulfanyl)-2,3-difluoropyridine to obtain 5,6-difluoropyridine-3-sulfonyl chloride. $^1$H NMR (300 MHz, CDCl$_3$) δ 8.73 (s, 1H), 8.19-8.25 (m, 1H).

Step 3. Preparation by a similar procedure to Example 142, step 1, starting from tert-butyl (R)-2-((3-(benzyloxy)-4-((benzyloxy)carbonyl)phenyl)((5-cyclohexylpyrazin-2-yl)methyl)carbamoyl)azetidine-1-carboxylate to obtain benzyl (R)-2-(benzyloxy)-4-(N-((5-cyclohexylpyrazin-2-yl)methyl)-1,6-difluoropyridin-3-yl)sulfonyl)azetidine-2-carboxamido)benzoate. $^1$H NMR (300 MHz, CDCl$_3$) δ 8.48-8.50 (m, 2H), 8.40 (d, J=1.2 Hz, 1H), 8.23-8.29 (m, 1H), 7.84 (d, J=8.1 Hz, 1H), 7.30-7.44 (m, 10H), 6.96 (d, J=1.8 Hz, 1H), 6.86 (dd, J=1.8, 8.1 Hz, 1H), 5.38 (s, 2H), 5.21 (d, J=12.3 Hz, 1H), 5.04-5.14 (m, 2H), 4.91-4.96 (m, 1H), 4.86 (d, J=15.9 Hz, 1H), 3.90-3.98 (m, 1H), 3.54-3.61 (m, 1H), 2.74-2.84 (m, 1H), 2.05-2.15 (m, 1H), 1.85-2.00 (m, 5H), 1.75-1.82 (m, 1H), 1.26-1.66 (m, 5H).

Step 4. Preparation by a similar procedure to Example 27, step 5, starting from benzyl (R)-2-(benzyloxy)-4-(N-((5-cyclohexylpyrazin-2-yl)methyl)-1,6-difluoropyridin-3-yl)sulfonyl)azetidine-2-carboxamido)benzoate to obtain the compound of Example 157 (R)-4-(N-((5-cyclohexylpyrazin-2-yl)methyl)-1-((5,6-difluoropyridin-3-yl)sulfonyl)azetidine-2-carboxamido)-2-hydroxybenzoic acid. $^1$H NMR (300 MHz, CDCl$_3$) δ 11.14 (brs, 1H, OH), 8.94 (s, 1H), 8.51 (s, 1H), 8.47 (s, 1H), 8.23-8.29 (m, 1H), 7.74 (d, J=8.4 Hz, 1H), 6.67-6.71 (m, 2H), 5.18 (d, J=14.1 Hz, 1H), 4.95-5.02 (m, 2H), 3.96-4.05 (m, 1H), 3.64-3.71 (m, 1H), 2.82-2.92 (m, 1H), 2.26-2.37 (m, 1H), 1.26-2.07 (m, 11H). MS (ESI): [M+H]+ m/z 588.3.

Example 158

Design and In Vitro Testing of Select Stat3 Compounds of the Present Invention

In Silico Compound Design.

Ligand structures were drawn and converted to three-dimensional coordinates in MarvinSketch (ChemAxon). The structure was then minimized in energy in Avogadro (Hanwell M D, et al., (2012) *J. Cheminformatics* 4:17) using the MMFF94 force field (Halgren T A (1996) *J. Comput. Chem.* 17: 490-519). The structure of Stat3 monomer (PDB 1bg1) with K591 mutated to Ala in silico was prepared for docking in UCSF Chimera (Pettersen E F, et al., (2004) *J. Comput. Chem.* 25:1605-1612). The K591A mutant was used due to the difficulty of reliably modeling K591, which is flexible and extends over the putative ligand binding site. Ligands were docked against five structures of Stat3 with alternate side chain conformations using Yasara (Krieger E, et al., (2014) *Bioinformatics* 30:2981-2982) which uses a docking and scoring algorithm based on Autodock Vina (Trott O, et al., *J. Comput. Chem.* 31:455-461). Manual inspection supported the highest scoring model from Yasara as that most chemically reasonable and consistent with SAR data. Residue 591 was then mutated back to Lys, and the side chain rotamer was optimized to fit the docked model in Yasara using the SCWRL rotamer library (Shapovalov M V, et al., (2007) *Proteins* 66:279-303)). The final model was energy minimized in Yasara with the Nova force field (Krieger E, et al., (2002) *Proteins* 47:393-402; Krieger E, et al. (2009) *Proteins* 77 Suppl 9:114-122). The two dimensional ligand interaction diagram was created with Schrodinger Maestro.

Cell Lines and Reagents.

Normal mouse fibroblast (NIH3T3), and the human breast cancer MDA-MB-231, MDA-MB-468, and MCF-7 cell lines have been reported previously (Zhang X, et al., (2010) Biochem Pharmacol 79:1398-409; Zhang X, et al., (2012) Proc Natl Acad Sci USA 109:9623-8; Garcia R, et al., (1997) Cell Growth Diff 8:1267-1276; Garcia R, et al., (2001) Oncogene 20:2499-2513). The Stat3 knockout mouse embryonic fibroblasts line (MEFStat3-/-) was generous gift from Dr. Valerie Poli (University of Turin) and have been previously reported (Yue P, et al., (2016) Cancer Res. 76:652-63). Cells were grown in Dulbecco's modified Eagle's medium (DMEM) containing 10% heat-inactivated fetal bovine serum (for human cells) or bovine calf serum (for mouse cells). Human metastatic melanoma C8161, 1205Lu, UACC903 cell lines, C81-61, an early stage melanoma from the same patient as the late stage C8161 cells, have been reported [40, 41] and were maintained in RPMI with 10% FBS. The immortalized normal human melanocytes, AR7119 line was maintained in Medium 254 supplemented with human growth factors (GIBCO).

Glioblastoma-Derived Neurospheres and Culture.

All of the work related to human tissues performed at The University of California at Los Angeles, The University of Texas M.D. Anderson Cancer Center, The Ohio State University, and The University of Alabama at Birmingham was under the institutional review board-approved protocols, according to National Institute of Health (NIH) guidelines. Glioblastoma (GBM) neurospheres derived from GBM samples. Freshly resected glioma tumor samples were dissociated into single cells using both mechanical (gently pipet neurospheres with P1000 pipet tips four to five times) and enzymatic methods (TrypLE Express; Invitrogen). The dissociated tumor cells were cultured in defined serum-free medium: DMEM/F12/Glutamax (Invitrogen) supplemented with B27 (Invitrogen) (1:50), heparin (5 mg/mL), basic FGF (bFGF) (20 ng/mL), and EGF (20 ng/mL) (PeproTech, Rocky Hill, N.J.). Growth factors (bFGF and EGF) were added twice a week. After two to four weeks, free floating neurospheres were collected and thereafter routinely cultured in the above mentioned neurosphere media, with dissociation to single cells every 5-6 days. All of the neurospheres analyzed in this study were cultured <20 passages.

Antibodies against Stat3, pStat3, Src, pSrc Jak, pJak, Erk$^{MAPK}$, and pErk$^{MAPK}$ were purchased from Cell Signaling Technology y, Inc. (Danvers, Mass.). Tubulin was purchased from (Santa Cruz Biotechnology, Inc., Dallas, Tex.).

Nuclear Extract Preparation, Gel Shift Assays, and Densitometric Analysis.

Nuclear extract preparations and DNA-binding activity/electrophoretic mobility shift assay (EMSA) were carried out as previously described (Zhang X, et al., (2010) Biochem Pharmacol 79:1398-409; Zhang X, et al., (2012) Proc Natl Acad Sci USA 109:9623-8). The $^{32}$P-labeled oligonucleotide probes used were hSIE (high affinity sis-inducible element from the c-fos gene, m67 variant, 5'-AGCTTCAT-TTCCCGTAAATCCCTA) (SEQ ID NO: 1) that binds Stat1 and Stat3 and MGFe (mammary gland factor element from the bovine β-casein gene promoter, 5'-AGATTTCTAG-GAATTCAA) (SEQ ID NO: 2) for Stat1 and Stat5 binding. Except where indicated, nuclear extracts were pre-incubated with compound for 30 min at room temperature prior to incubation with the radiolabeled probe for 30 min at 30° C. before subjecting to EMSA analysis. Where appropriate, bands corresponding to Stat3:DNA complexes were scanned and quantified for each concentration of compound using ImageJ and plotted as percent of control (DMSO) against concentration of compound, from which the IC$_{50}$ values were derived.

Immunoblotting Analysis.

Whole cell lysate preparation and immunoblotting analysis were performed as previously reported (Zhang X, et al., (2010) Biochem Pharmacol 79:1398-409; Zhang X, et al., (2012) Proc Natl Acad Sci USA 109:9623-8). All antibodies tested were purchased from Cell Signaling Technology.

Cell Proliferation and Viability Assay.

Studies were conducted as previously reported (Zhang X, et al., (2010) Biochem Pharmacol 79:1398-409; Zhang X, et al., (2012) Proc Natl Acad Sci USA 109:9623-8; Siddiquee K, et al., (2007) Proc Natl Acad Sci USA 104:7391-6; Siddiquee K A, et al., (2007) ACS Chem Biol 2:787-98). Cells in 6-well or 96-well plates were treated with or without compounds for the indicated concentrations and time, and subjected to MTT assay or CyQuant cell proliferation assay (Invitrogen/ThermoFisher Scientific), or harvested and the viable cells were counted by trypan blue exclusion with phase-contrast microscopy.

Clonogenic Survival Assays.

Colony survival assay was performed as previously reported (Zhang X, et al., (2010) Biochem Pharmacol 79:1398-409; Zhang X, et al., (2012) Proc Natl Acad Sci USA 109:9623-8). Briefly, cells were seeded as single-cell cultures in 6-cm dishes (250 cells per dish), treated once the next day with compounds at the indicated concentrations and allowed to culture until large colonies were visible. Colonies were stained with crystal violet for 4 h, counted and photographed.

Scratch Assay for Cell Migration.

Studies were performed as previously reported (Yue P, et al., (2016) Cancer Res. 76:652-63). Briefly, wounds were made in 95-100% confluent cultures of cells in six-well plates using pipette tips. Subsequently, cells were treated with or without compounds at the designated concentrations and allowed to migrate into the denuded area over 22 h. The migration of cells was visualized at a 10× magnification using an Axiovert 300 Inverted Fluorescence Microscope (Zeiss, Göttingen Germany), with pictures taken using a mounted Canon Powershot A640 digital camera (Canon USA, Lake Success, N.Y.).

Formulae I-VIII were designed around a core scaffold to develop potent Stat3 inhibitor compounds with appropriate physicochemical properties. The inhibitory activities of the representative analogs against in vitro Stat3 DNA-binding activity, as measured by electrophoretic mobility shift assay (EMSA) for selected compounds from the Examples above are shown in FIG. 1 and summarized in Table 2.

TABLE 2

Stat3 DNA-binding activity in vitro of selected compounds of the present invention, as measured by electrophoretic mobility shift assay (EMSA). The inhibition metrics are presented in units of micromolar (μM).

| Example | EMSA IC$_{50}$ (μM) | Example (compound) | EMSA IC$_{50}$ (μM) |
|---|---|---|---|
| 1 | 3.0 ± 0.9 | 80 | 0.711 ± 0.11 |
| 2 | 6.4 ± 2.0 | 81 | 1.50 ± 0.12 |
| 3 | 9.3 ± 5.0 | 82 | 3.04 ± 0.14 |
| 4 | 5.3 ± 1.8 | 83 | 2.51 ± 0.23 |
| 5 | 5.0 ± 0.2 | 84 | 2.07 ± 0.12 |
| 6 | 10.0 ± 2.6 | 85 | 1.32 ± 0.36 |
| 7 | 6.8 ± 3.7 | 86 | 3.94 ± 0.43 |
| 8 | 10.0 ± 4.7 | 87 | 2.92 ± 0.12 |

TABLE 2-continued

Stat3 DNA-binding activity in vitro of selected compounds of the present invention, as measured by electrophoretic mobility shift assay (EMSA). The inhibition metrics are presented in units of micromolar (μM).

| Example | EMSA IC$_{50}$ (μM) | Example (compound) | EMSA IC$_{50}$ (μM) |
|---|---|---|---|
| 9 | 6.9 ± 3.2 | 88 | 2.25 ± 0.72 |
| 10 | 12.8 ± 4.3 | 89 | 2.11 ± 0.24 |
| 11 | 22.4 ± 1.4 | 90 | >5 |
| 12 | 8.5 ± 1.3 | 91 | 0.900 ± 0.143 |
| 13 | 12.9 ± 4.5 | 92 | 1.052 ± 0.125 |
| 14 | 7.4 ± 4.4 | 93 | >4 |
| 15 | 23.1 ± 1.7 | 94 | 1.896 ± 0.370 |
| 16 | >30 | 95 | >10 |
| 17 | 20.0 ± 2.4 | 96 | 2.960 ± 0.112 |
| 18 | 14.2 ± 3.4 | 97 | 1.798 ± 0.094 |
| 19 | 17.6 ± 2.2 | 98 | 1.416 ± 0.102 |
| 20 | 19.6 ± 1.4 | 99 | 2.350 ± 0.546 |
| 21 | 11.6 ± 2.2 | 100 | 1.866 ± 0.172 |
| 22 | 27.4 ± 4.2 | 101 | 1.796 ± 0.149 |
| 23 | >30 | 102 | 0.663 ± 0.182 |
| 24 | 30.0 ± 11.2 | 103 | 2.452 ± 0.020 |
| 25 | 2.4 ± 0.4 | 104 | 0.642 ± 0.118 |
| 26 | 7.2 ± 3.4 | 105 | 1.085 ± 0.148 |
| 27 | 5.4 | 106 | >4 |
| 28 | 7 | 107 | 0.998 ± 0.333 |
| 29 | 4.5 ± 1.0 | 108 | 0.755 ± 0.110 |
| 30 | 6.5 ± 2.5 | 109 | >2 |
| 31 | 6.9 ± 1.9 | 110 | 0.458 ± 0.054 |
| 32 | 5.4 ± 1.6 | 111 | 0.456 ± 0.045 |
| 33 | 7.0 ± 0.4 | 112 | 0.702 ± 0.026 |
| 34 | 0.546 ± 0.014 | 113 | 0.337 ± 0.017 |
| 35 | 0.583 ± 0.055 | 114 | 1.906 ± 0.027 |
| 36 | 2.22 ± 0.49 | 115 | 1.956 ± 0.154 |
| 37 | 2.2 ± 0.9 | 116 | 0.856 ± 0.112 |
| 38 | 3.4 ± 1.7 | 117 | 0.889 ± 0.183 |
| 39 | 5.3 ± 0.4 | 118 | >2 |
| 40 | 4.1 ± 0.6 | 119 | 0.511 ± 0.021 |
| 41 | 3.5 ± 0.6 | 120 | >2 |
| 42 | 5.7 ± 1.4 | 121 | 0.775 ± 0.056 |
| 43 | 6.6 ± 0.8 | 122 | 0.534 ± 0.047 |
| 44 | 4.6 ± 0.5 | 123 | 1.089 ± 0.297 |
| 45 | 3.6 ± 0.2 | 124 | 1.177 ± 0.187 |
| 46 | 3.8 ± 0.8 | 125 | 0.628 ± 0.074 |
| 47 | 4.2 ± 0.7 | 126 | 1.937 ± 0.158 |
| 48 | 4.1 ± 0.2 | 127 | 1.715 ± 0.035 |
| 49 | 1.08 ± 0.2 | 128 | >2 |
| 50 | 1.75 ± 0.19 | 129 | >2 |
| 51 | 1.36 ± 0.096 | 130 | 2.172 ± 0.298 |
| 52 | 0.656 ± 0.057 | 131 | 3.546 ± 0.097 |
| 53 | 0.384 ± 0.024 | 132 | 3.957 ± 0.056 |
| 54 | >2 | 133 | >4 |
| 55 | >2 | 134 | 1.791 ± 0.107 |
| 56 | 5.4 ± 1.4 | 135 | 0.773 ± 0.152 |
| 57 | 5.0 ± 0.8 | 136 | 0.978 ± 0.054 |
| 58 | 8.3 ± 0.3 | 137 | 1.180 ± 0.415 |
| 59 | 11.6 ± 0.6 | 138 | >4 |
| 60 | 7.4 ± 2.5 | 139 | >10 |
| 61 | 0.659 ± 0.07 | 140 | >4 |
| 62 | 0.562 ± 0.07 | 141 | 1.718 ± 0.205 |
| 63 | 1.282 ± 0.16 | 142 | >30 |
| 64 | 0.809 ± 0.16 | 143 | 0.664 ± 0.167 |
| 65 | 10.8 ± 3.4 | 144 | >30 |
| 66 | >30 | 145 | >30 |
| 67 | 18.2 ± 6.9 | 146 | >30 |
| 68 | 21.9 ± 1.7 | 147 | >30 |
| 69 | >30 | 148 | 0.612 ± 0.037 |
| 70 | >30 | 149 | 0.628 ± 0.006 |
| 71 | >30 | 150 | >30 |
| 72 | >10 | 151 | 1.465 ± 0.151 |
| 73 | >10 | 152 | 0.422 ± 0.052 |
| 74 | >10 | 153 | 1.896 ± 0.017 |
| 75 | >10 | 154 | 16.28 ± 2.29 |
| 76 | 1.09 ± 1.25 | 155 | >30 |
| 77 | 1.25 ± 0.82 | 156 | >30 |
| 78 | 1.63 ± 0.22 | 157 | 29.41 ± 0.25 |
| 79 | 3.6 ± 0.3 | | |

Figure 2A:
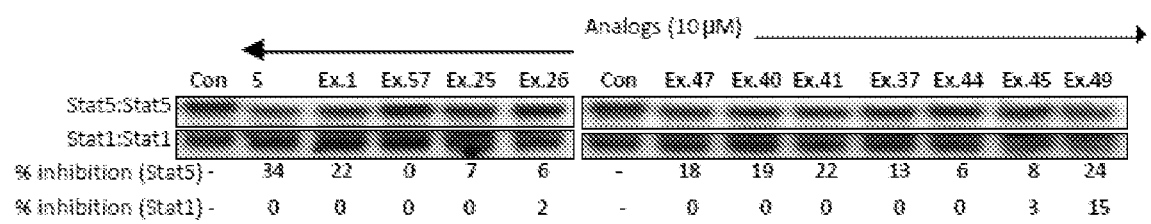
FIG. 2. Effects of select compounds of the present invention on Stat1 and Stat5 DNA-binding activity. EMSA analysis of Stat1 and Stat5 DNA-binding activity in nuclear extracts of equal total protein containing activated Stat1 and Stat5 pre-incubated with 10 µM (FIG. 2A), or with 0-30 µM (FIG. 2B) of each compound for 30 min at room temperature prior to incubation with the radiolabeled MGFe probe that binds both Stat1 and Stat5. Positions of Stat:DNA complexes in gel are labeled; control lanes (0 or Con) represent nuclear extracts pre-treated with 10% DMSO. Data are representative of 1-3 independent determinations.
Figure 2B:
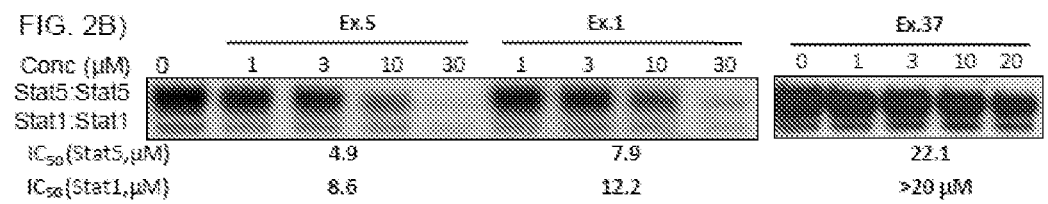

Select Analogs Disrupt the DNA-Binding Activities of Both Stat3 and Stat5, But Not That of Stat1 In Vitro In order to determine the specificity of select new analogs active against Stat3 activity, the inventors investigated the effects on the inhibition of other STAT family members, including Stat1 and Stat5 DNA-binding activity in vitro. It was surprisingly found from EMSA analysis that many of the compounds of the present invention, including the compound of Example 1, which potently inhibited Stat3 DNA-binding activity also disrupted Stat5 DNA-binding activity, but only weakly affected the activity of Stat1 (FIG. 2A). By contrast, Example 37 had no measureable effect on Stat5 or Stat1 DNA-binding activity (FIG. 2B, Example 37). For Example 1, the inhibition of Stat5 DNA-binding activity was concentration-dependent (FIG. 2B, "Ex. 1" (the compound of Example 1)), while a non-specific effect on Stat1 DNA-binding activity was only observed at 30 μM (FIG. 2A, FIG. 6, 10 vs 30 μM, FIG. 2B). Example 5, which is the (S)-enantiomer of the Ala analog compound of Example 1, showed relatively stronger inhibitory effect on Stat5 DNA binding activity, with IC$_{50}$ of 4.9 μM, and it also inhibited Stat1 activity to a moderate extent, compared to its (R)-antipode, Example 1 (FIG. 2A, FIG. 2B). Moreover, Example 57, the tetrahydropyran (THP) analog of Example 1, showed minimum effect on Stat5 DNA binding activity at the lowest concentration that inhibits Stat3 DNA-binding activity in vitro (FIG. 2A, the compounds of Example 57 vs. Example 1).

New Analogs Inhibited Constitutive Stat3 Activation and Function in Cancer Cells, With Minimal Effects on Other Signaling Proteins.

Select compounds of the invention were investigated for their inhibitory effects of the active analogs on intracellular Stat3 signaling. Human breast cancer cells, MDA-MB-231 were treated with 10 μM the compounds of Example 5 or Example 1 for 1, 3, or 24 h. Nuclear extracts were prepared and subjected to EMSA analysis for Stat3 DNA-binding activity. Results show inhibition of Stat3 DNA-binding activity. Stat3 DNA-binding activity in MDA-MB-231 cells was inhibited by both Examples 1 and 5 following treatment at 3 h, with little change at 1 h (FIG. 3A). At the 24 h time point, however, only Example 5 treatment, but not Example 1 inhibited Stat3 DNA-binding activity (FIG. 3A, 24 h).

Select compounds of the invention were analyzed for their ability to inhibit constitutive Stat3 tyrosine phosphorylation in the human breast cancer, MDA-MB-231 and MDA-MB-468 cells. Treatment for 1 h with Example 37 strongly inhibited constitutive pY705Stat3 levels in both MDA-MB-231 and MDA-MB-468 lines (FIGS. 3B and 3C), while 1 h treatment with 5 μM of Examples 1, 25 and 26 only inhibited pY705Stat3 levels in MDA-MB-231 (FIG. 3C). Constitutive Stat3 Tyr705 phosphorylation in the three metastatic melanoma cells, C8161, 1205LU, and UACC903, is also strongly inhibited by treatment with Example 1 at 10 or 20 μM for 1 and 3 h (FIG. 3D). By contrast, immunoblotting analysis shows that 24 h treatment of MDA-MB-231 cells with 5 μM of Examples 40 and 42 had little effect on pJak2, pSrc, pERK1/2 (FIG. 4), suggesting that at concentrations that inhibit Stat3 Tyr705 phosphorylation and Stat3 DNA-binding activity, these compounds have little effect on other signaling proteins. Altogether, the new analogs show strong, albeit variable degrees of inhibition of constitutive Stat3 DNA-binding activity and Tyr phosphorylation in human tumor cells.

Novel Active Analogs Decreased the Growth of Human Cancer Cells Harboring Persistently Active Stat3

Figure 5C:
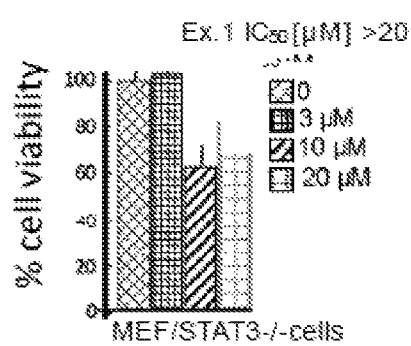
FIG. 5C shows cultures of Stat3 null mouse embryonic fibroblasts (MEF/Stat3–/–) treated with compound of Example 1 for 48-72 h.
Figure 5D:
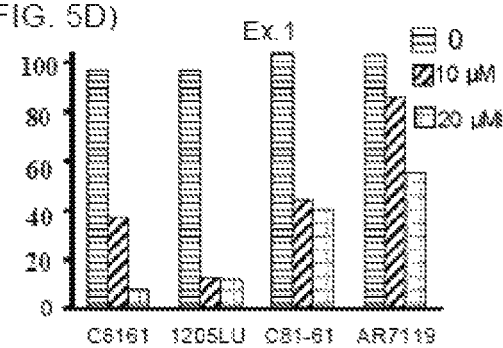
FIG. 5D. shows the cultures of melanoma cells harboring aberrantly-active Stat3 (C8161, 1305LU, and C81-61) and counterpart that does not (AR7119), treated with the compound of Example 1 at concentrations of 0, 10 micromolar, and 20 micromolar.
Figure 5E:
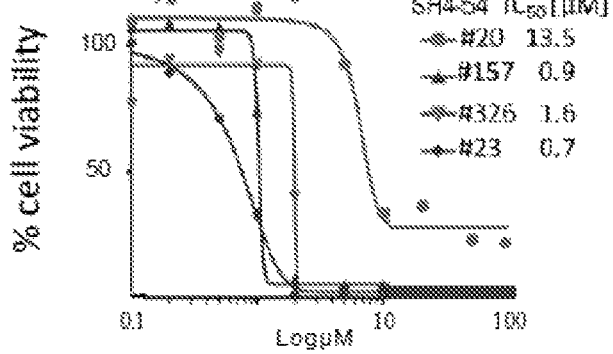
FIG. 5E shows the human GBM patient-derived xenograft stem cells harboring constitutively-active Stat3 (#20, #157, #326, and #23) treated with 0-100 µM SH4-54 for 48 h.
Figure 6A:
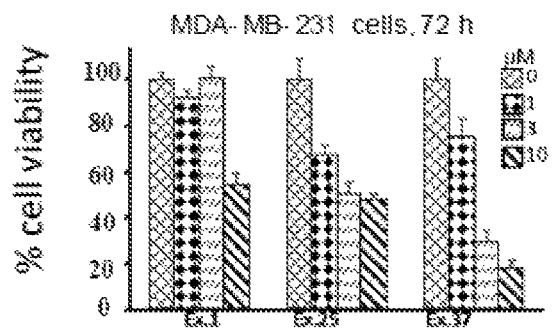
FIG. 6A shows human breast cancer cells MDA-MB-231 harboring aberrantly-active Stat3 or that do not grow in the presence of compounds of Examples 1, 25, and 37.
Figure 6B:
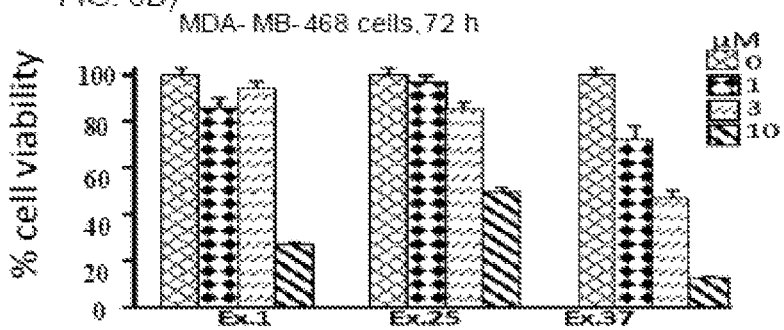
FIG. 6B shows MDA-MB-468 cells harboring aberrantly-active Stat3 or MCF-7 cells that do not grow in the presence of compounds of Examples 1, 25, and 37.
Figure 6C:
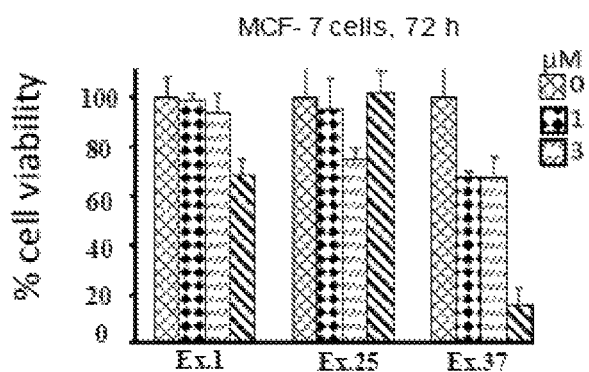
FIG. 6C shows MCF-7 cells harboring aberrantly-active Stat3 or MCF-7 cells that do not grow in the presence of compounds of Examples 1, 25, and 37. Cells were first grown in 6-well plates then were treated once with 0-10 µM of the indicated compounds for 72 h. Viable cells were assayed using CyQuant cell proliferation kit and plotted as % cell viability against concentration. Control (0) represents 0.05% DMSO-treated cells. Values, mean ± S.D. of 2-3 independent determinations.

Constitutive Stat3 activity promotes tumor cell growth and proliferation and survival (Darnell J E (2005) *Nat Med.* 11:595-6; Bowman T, et al., (2000) *Oncogene* 19:2474-2488). Some of the compounds of the present invention were tested against tumor cells harboring constitutively-active Stat3. The compounds of Example 37, and to a lower extent, Example 25, suppressed the human breast cancer lines MDA-MB-231 and/or MDA-MB-468 cell growth in a time- or dose-dependent manner, as measured by trypan blue exclusion-phase contrast microscopy (FIGS. 5A, B, left), with $IC_{50}$ of 3.9 μM for the effects of Example 37 against MDA-MB-231 (FIG. 5B, left). Treatment with the compounds of Examples 1, 25, or 37 also suppressed the viability of the same cells, as measured by CyQuant cell viability assay (FIGS. 6, A, B). By contrast 72 h treatment with Example 37 of normal NIH3T3 mouse fibroblasts that do not harbor aberrantly-active Stat3 showed relatively weaker inhibitory effects on effects cell growth, as measured by trypan blue exclusion-phase contrast microscopy, with $IC_{50}$ of 5.1 μM (FIG. 5B, right). Similarly, the viability of the breast cancer line, MCF7, which does not harbor aberrantly-active Stat3, was only weakly or not inhibited by the 72 h treatment with the compounds of Examples 25, or 37, except at 10 μM for Example 37, which showed general toxicity (FIGS. 6, C). The compound of Example 1 also only weakly inhibited the viability of the Stat3 null mouse embryonic fibroblasts (MEF/Stat3−/−) (FIG. 5C). Moreover, treatment with the compound of Example 1 for 48 h strongly inhibited the viability of human metastatic melanoma C8161, 1205LU, and C81-61 cell lines that harbor constitutively-active Stat3, compared to the relatively weaker activity against the immortalized human normal melanocyte, AR7119 line that does not harbor aberrant Stat3 activation (FIG. 5D). At concentrations (<10 μM) that inhibit Stat3 activity in tumor cells, the tested compounds showed relative preferential effects against the viability of tumor cells that harbor constitutive Stat3 activation over cells that do not, except for the effects of compound of Example 37 at 10 μM. Treatment with increasing concentration of compound SH4-54 strongly and variably suppressed the viability of patient-derived xenografts (pdx) cells (#20, #157, #326, #23), with $IC_{50}$ of 13.5, 0.9, 1.6, and 0.7 μM, respectively (FIG. 5E). These results indicate that GBM pdx cells show increased sensitivity to the inhibition of Stat3 activation.

Example 159

Pharmacokinetic Evaluation of Select Compounds of the Invention

General Methods.

Assessment of Physicochemical Properties.

Solubility, cell membrane permeability, and human and mouse liver microsomal studies were perform by Eurofins Cerep Panlabs and Eurofin Discovery Services.

In vitro assessment of aqueous solubility, cell membrane permeability (Caco-2 cells assay), and mouse and human liver microsomal (MLM and HLM) metabolic stability studies were conducted. Results indicate that the carboxylic acid sodium salts, the compounds of Examples 2, 28 and 59 are moderately soluble in simulated intestinal fluid (SIF, 127, 129, and 117 μg/mL, respectively) and PBS buffer pH 7.4 (127, 132, and 123 μg/mL, respectively) (Table 1). However, compound SH4-54, which was tested as the free carboxylic acid (i.e., no sodium salt), has only limited solubility (14 μg/mL in SIF and 7.6 μg/mL in PBS). On the other hand, the benzohydroxamic acids, compounds SH5-07 and of Example 38, present good solubility in SIF (74 and 72 μg/mL, respectively), but not in PBS pH 7.4 (0.3 and 4.7 μg/mL, respectively). All compounds tested in simulated gastric fluid (SGF) present very limited solubility (<2.2 μg/mL), possibly because at the SGF pH of 1.2, all the compounds are completely un-ionized. Both Ala-based analogs show lower metabolic stability compared to Gly-based compounds. For example, the Ala-linker Examples 2 and 59 have lower metabolic stability (RLM and HLM $t_{1/2}$≤5 min) than the Gly-based compounds, SH4-54 and SH5-07 (RLM and HLM $t_{1/2}$≥17 min) (Table 1). However, the Pro-based compounds gained back reasonable metabolic stability (e.g., Example 60, HLM and MLM $t_{1/2}$ of 54 and 26 min, respectively, and Example 28, HLM and MLM $t_{1/2}$ 15 and 18 min, respectively).

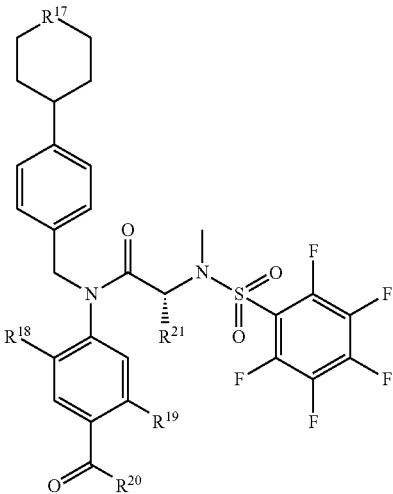

Formula V

SH4-54: $R^{20}$=OH, $R^{21}$=H, $R^{19}$=H, $R^{17}$=CH$_2$, $R^{18}$=H

SH5-07: $R^{20}$=NHOH, $R^{21}$=H, $R^{19}$=H, $R^{17}$=CH$_2$, $R^{18}$=H

Example 2: $R^{20}$=ONa, $R^{21}$=CH$_3$, $R^{19}$=OH, $R^{17}$=CH$_2$, $R^{18}$=H Example 38: $R^{20}$=NHOH, $R^{21}$=CH$_3$, $R^{19}$=H, $R^{17}$=CH$_2$, $R^{18}$=F Example 59: $R^{20}$=ONa, $R^{21}$=CH$_3$, $R^{19}$=OH, $R^{17}$=O, $R^{18}$=H

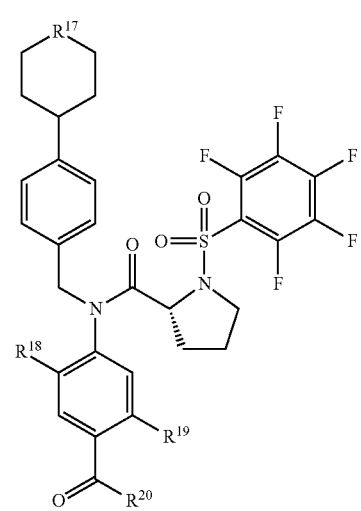

Formula VI

Example 60: $R^{20}$=OH, $R^{19}$=H, $R^{18}$=F, $R^{17}$=O
Example 28: $R^{20}$=ONa, $R^{19}$=OH, $R^{18}$=H, $R^{17}$=O

TABLE 1

Initial analyses of solubility, metabolic stability, and cell membrane permeability of lead Stat3 inhibitors and their analogs

| Compound | Solubility (micrograms/milliliter) | | | Metabolic Stability Half-Life (min) | | Caco-2 Cells Permeability ($10^{-6}$ cm/s)/Recovery (%) | |
|---|---|---|---|---|---|---|---|
| | PBS | SGF | SIF | MLM | HLM | A to B | B to A |
| SH4-54 | 7.6 | 1.2 | 14 | 26 | 37 | 0/7 | 0/29 |
| SH5-07 | 0.3 | 2.2 | 74 | 17 | 19 | 0/2 | 0/8 |
| Example 2 | 127 | 1.3 | 127 | 5 | 4 | 0/6 | 0/2 |
| Example 38 | 4.7 | 0.8 | 72 | | | | |
| Example 59 | 132 | 1.5 | 129 | 4 | 5 | 0/31 | 0.7/40 |
| Example 60 | | | | 26 | 54 | 0.1/8 | 0.1/67 |
| Example 28 | 123 | 0.4 | 117 | 18 | 15 | 0.2/34 | 0.2/60 |

Caco-2 cells studies show that incorporation of the THP group instead of the lipophilic cyclohexyl ring gives better permeability (Table 1). For example, the THP compounds of Examples 28 and 60, (Table 1), show detectable apical (A) to basolateral (B) relative permeability ($P_{Caco-2}$ 0.1 and 0.2 $10^{-6}$ cm/sec, respectively). Moreover, the other THP compound in Table 1, the compound of Example 59, shows increased B to A permeability ($P_{Caco-2}$ 0.7 $10^{-6}$ cm/sec). However, compounds containing the lipophilic cyclohexyl group instead of the THP ring show no appreciable permeability (compounds SH4-54, SH5-07, and the compound of Example 2, Table 1).

Discussion

The inventors designed a series of potent Stat3 inhibitor compounds with appropriate physicochemical properties while minimizing or lowering lipophilicity and molecular weight (MW). A thorough exploration of substitution at the methylene Gly-linker led to compounds with promising properties. For example, replacement to the Ala-linker, especially enantiomers with the (R)-configuration led to some analogs with improved potency (compounds of Examples 1-4, $IC_{50}$ 3.0-9.3 µM), notably the compound of Example 1 with $IC_{50}$ 3.0 µM, which compares well with the $IC_{50}$ 6.8 µM of the parent BP-1-102. The Ala-linker (S)-enantiomers exhibited lower potency compared to the (R)-enantiomers (compare compounds of Examples 1 vs 5, 3 vs 6, and 4 vs 7). Other substitutions at the methylene Gly-linker included ethyl (compounds of Examples 8 and 9), bis-methylene to form a cyclopropyl (Example 10), dimethyl (compounds of Example 12), Ser-linker (compounds of Examples 13-16), hydroxyethyl (compounds of Examples 17 and 18), Thr-linker (compounds of Examples 19 and 20), aminomethyl (compounds of Examples 21 and 22) and Asp-linker (compounds of Examples 23 and 24), and all resulted in compounds with reduced affinity compared to the Ala-linker analogs.

With the incorporation of the optimized (R)-Ala linker, the benzoic acid ring was substituted with fluorine, chlorine and methyl groups at different positions. For example, the 2-, 3-methyl and 3,5-dimethyl analogs (compounds of Examples 42, 43 and 47) gave $IC_{50}$ in the range of 4.3-6.6 µM, the 2- and 3-chloro analogs (compounds of Examples 40, 41 and 45) gave $IC_{50}$ of 3.5-4.1 µM, and finally the 2-, 3-fluoro and 3,5-difluoro analogs (compounds of Examples 37, 38, 44 and 48) gave $IC_{50}$ of 1.8-4.6 µM. The analog that stands out from all these benzoic acid substitutions is the 3-fluorobenzoic acid of Example 37 with an $IC_{50}$ of 1.8 µM, which makes this compound the most potent in the present study. An additional modification to the Ala linker was to join the two methyl groups to become a novel Pro-linker system. Thus, different analogs were prepared (compounds of Examples 25-29, 39 and 46, 56 and 60) with a range of $IC_{50}$ of 2.4-7.4 µM. From this variation, the Pro-based salicylic acid Example 25 had an $IC_{50}$ of 2.4 µM. Going from a D-proline to a D-azetidine gave an increase in potency (compound of Example 34 had an $IC_{50}$ of 0.55 µM). In summary, compared to the Gly-based analogs BP-1-102 ($IC_{50}$ 6.8 µM), SH4-54 ($IC_{50}$ 4.4 µM), and SH5-07 ($IC_{50}$ 3.9 µM), improvement in the Stat3-inhibitory potency outside of cells is observed with the Ala- and Pro-based compounds, such as the compounds of Examples 1 ($IC_{50}$ 3.0 µM), 37-($IC_{50}$ 1.8 µM), 25 ($IC_{50}$ 2.4 µM), and 34 ($IC_{50}$ 0.55 µM), and they represent a few of the most potent small molecule Stat3 inhibitors.

Example 160

Treatment of Cancer

Subjects with glioma, breast cancer or pancreatic cancer are treated by intravenous or oral administration with a compound of the Examples described herein at a dose of between 0.08 mg/kg to 0.4 mg/kg, with additional doses administered as needed. The condition of the subjects are monitored, and the shrinkage of the tumors, or slowing of the progression of tumor growth is observed. The results indicate and confirm the surprising efficacy of the exemplary Stat3 inhibitors of the present disclosure.

Patents, patent applications, publications, scientific articles, books, web sites, and other documents and materials referenced or mentioned herein are indicative of the levels of skill of those skilled in the art to which the inventions pertain. Each such referenced document and material is hereby incorporated by reference to the same extent as if it had been incorporated by reference in its entirety individually or set forth or reprinted herein in its entirety. Additionally, all claims in this application, and all priority applications, including but not limited to original claims, are hereby incorporated in their entirety into, and form a part of, the written description of the invention. Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, and the claims referred to above, including, but not limited to, any original claims.

The inventions have been described broadly and generically herein. Each of the narrower species and subgeneric groupings falling within the generic disclosure also form part of these inventions. This includes the generic description of each invention which hereby include, including any claims thereto, a proviso or negative limitation removing, or optionally allowing the removal of, any subject matter from the genus, regardless of whether or not the excised materials, or options, were specifically recited or identified in haec verba herein, and all such variations form a part of the original written description of the inventions. In addition, where features, or aspects, of an invention are described in terms of a Markush group, the invention shall be understood thereby to be described in terms of each and every, and any, individual member or subgroup of members of the Markush group.

The inventions illustratively described and claimed herein can suitably be practiced in the absence of any element or elements, limitation or limitations, not specifically disclosed herein, or described herein as essential. Thus, for example, the terms "comprising," "including," "containing," "for example," etc., shall be read expansively and without limitation. The term "including" means "including but not limited to." The phrase "for example" is not limited to, or by, the items that follow the phrase.

In claiming their inventions, the inventors reserve the right to substitute any transitional phrase with any other transitional phrase, and the inventions shall be understood to include such substituted transitions and form part of the original written description of the inventions. Thus, for example, the term "comprising" may be replaced with either of the transitional phrases "consisting essentially of" or "consisting of."

The methods and processes illustratively described herein may be suitably practiced in differing orders of steps. They are not necessarily restricted to the orders of steps indicated herein, or in the claims.

Under no circumstances may the patent be interpreted to be limited to the specific examples, or embodiments, or methods, specifically disclosed herein. Under no circumstances may the patent be interpreted to be limited by any statement made by any Examiner, or any other official or employee of the Patent and Trademark Office, unless such statement was specifically, and without qualification or reservation, expressly adopted by Applicants in a responsive writing specifically relating to the application that led to this patent prior to its issuance.

The terms and expressions employed herein have been used as terms of description and not of limitation, and there is no intention in the use of such terms and expressions, or any portions thereof, to exclude any equivalents now know or later developed, whether or not such equivalents are set forth or shown or described herein or whether or not such equivalents are viewed as predictable, but it is recognized that various modifications are within the scope of the invention claimed, whether or not those claims issued with or without alteration or amendment for any reason. Thus, it shall be understood that, although the present invention has been specifically disclosed by preferred embodiments and optional features, modifications and variations of the inventions embodied therein or herein disclosed can be resorted to by those skilled in the art, and such modifications and variations are considered to be within the scope of the inventions disclosed and claimed herein.

Specific methods and compositions described herein are representative of preferred embodiments and are exemplary of, and not intended as limitations on, the scope of the invention. Other objects, aspects, and embodiments will occur to those skilled in the art upon consideration of this specification, and are encompassed within the spirit of the invention as defined by the scope of the claims. Where examples are given, the description shall be construed to include, but not to be limited to, only those examples. It will be readily apparent to one skilled in the art that varying substitutions and modifications may be made to the invention disclosed herein, without departing from the scope and spirit of the invention, and from the description of the inventions, including those illustratively set forth herein, it is manifest that various modifications and equivalents can be used to implement the concepts of the present invention, without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the invention and within the following claims.

While this invention has been disclosed with reference to specific embodiments, it is apparent that other embodiments and variations of this invention can be devised by those skilled in the art, without departing from the true spirit and scope of the invention. The appended claims include all such embodiments and equivalent variations.

What is claimed is:

1. A compound represented by Formula I:

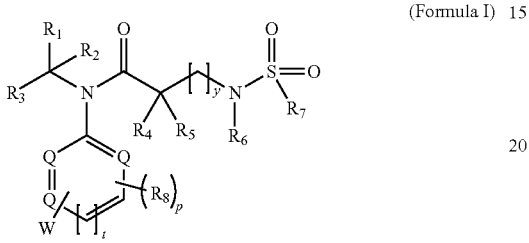

(Formula I)

wherein $R^1$ is selected from aryl or a 5 or 6-membered heteroaryl, where the heteroatoms are one or more O, N, $S(A)_2$, where S is sulfur and A is selected from oxygen or an electron pair, the aryl or the 5 or 6-membered heteroaryl are optionally substituted with halo, $CF_3$, $C_1$-$C_6$ alkyl, $C_1$-$C_6$ branched alkyl, aryl, heteroaryl, $C_3$-$C_7$ cycloalkyl, $C_3$-$C_7$ cycloalkenyl, three- to six-membered heterocycle, three- to seven-membered saturated heterocycle, fused $C_2$-$C_5$ alkylene, where one or more $CH_2$ groups can be replaced with O, $NR^9$, or $S(A)_2$ where S is sulfur and A is selected from oxygen or an electron pair, the aryl or the 5 or 6-membered heteroaryl are optionally substituted naphthalene, optionally substituted indole, benzofuran, benzothiophene; $R^2$ and $R^3$ are independently selected from H or $C_1$-$C_6$ alkyl; where $R^2$ and $R^3$ can form a $C_3$-$C_6$ cycloalkane ring, where this $C_3$-$C_6$ cycloalkane ring can be substituted with 1 or more of $C_1$-$C_6$ alkyl, hydroxyl, $NR^9R^{10}$, or $C_1$-$C_6$ alkoxy; $R^5$ is selected from H, $(CH_2)_fNR^9R^{10}$, $(CH_2)_fOR^9$, $(CH_2)_fCO_2R^9$, or $(CH_2)_fCO_2NR^9R^{10}$; $R^4$ and $R^6$ form a $C_3$-$C_6$ heterocycloalkane ring, where this $C_3$-$C_6$ heterocycloalkane ring can be substituted with 1 or more of $C_1$-$C_6$ alkyl, hydroxyl, $NR^9R^{10}$ and where one or more $CH_2$ groups can be replaced with O, $NR^9$, or $S(A)_2$ where S is sulfur and A is selected from oxygen or an electron pair; or $R^4$ and $R^6$ form an optionally substituted pyrrole ring, wherein one or more CH groups of said pyrrole ring can be replaced with O, N, or $S(A)_2$, where S is sulfur and A is selected from oxygen or an electron pair; $R^7$ is selected from $CF_3$, aryl or heteroaryl group where the aryl or heteroaryl group is substituted with 1-5 substituents selected from $C_1$-$C_6$ alkyl, halo, hydroxyl, CN, or $CF_3$; $R^8$ is substitution selected from one or more of H, $C_1$-$C_6$ alkyl, $C_1$-$C_6$ alkoxy, hydroxyl, halogen, $OC(O)CH_3$, $NR^9R^{10}$, CN, $CF_3$, $CO_2R^9$, $CO_2NR^9R^{10}$, $(CH_2)_fNR^9R^{10}$, $(CH_2)_fOR^9$, or $(CH_2)_fCO_2R^9$; $R^9$ is selected from H or $C_1$-$C_6$ alkyl;

$R^{10}$ is selected from H, or $C_1$-$C_6$ alkyl; W is selected from $CO_2H$, tetrazole, benzyl, $C(O)NHOR^{10}$ or $CF_2OH$; Q is C, CH, N, O, or S; where Q and $R^8$ can form a heterocyclic ring; p is selected from 0 or 1, y is selected from 0 or 1, f is selected from 0 to 4; t is selected from 0 or 1;

or a solvate, hydrate, or pharmaceutically acceptable salt thereof.

2. A compound represented by Formula II:

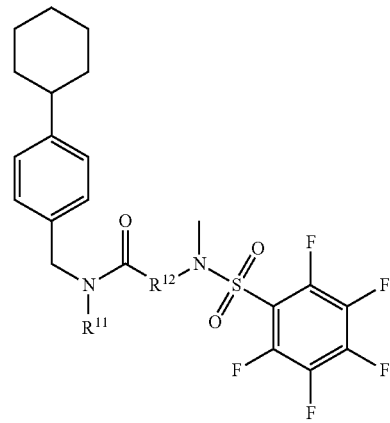

(Formula II)

wherein $R^{11}$ is selected from aryl or heteroaryl, wherein the aryl or heteroaryl can be substituted with one or more of hydroxyl, carboxylic acid, carboxylate, benzohydroxamic acid, hydroxyl-substituted alkyl;

wherein $R^{12}$ is selected from (R)—CH(CH$_3$), (S)—CHCH$_3$, (S)—CH(CH$_2$CH$_3$), (R)—CH(CH$_2$CH$_3$), bridging cylcopropyl

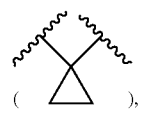

( ), (S)—CH(CH$_2$OH), (R)—CH(CH$_2$OH), (R)—CH(CH$_2$CH$_2$OH), (S)—CH(CH$_2$CH$_2$OH), (S)—CH[(R)—CH(CH$_3$)OH], (R)—CH[(S)—CH(CH$_3$)OH], (S)—CH(CH$_2$NH$_2$), (R)—CH(CH$_2$NH$_2$), (S)—CH(CH$_2$CO$_2$H), or (R)—CH(CH$_2$CO$_2$H);

or a solvate, hydrate, or pharmaceutically acceptable salt thereof.

3. A compound of claim 2, wherein the compound is represented by Formula III:

(Formula III)

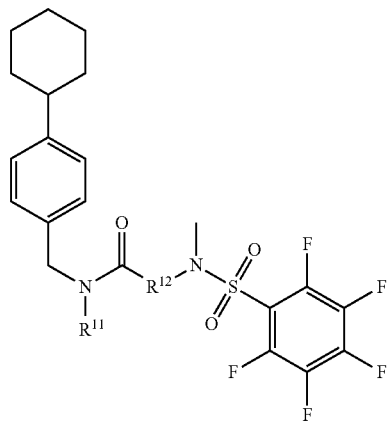

wherein R¹¹ is selected from aryl or heteroaryl,
wherein the aryl or heteroaryl can be substituted with one or more of hydroxyl, carboxylic acid, carboxylate, benzohydroxamic acid, nitroso, alkyl carboxylic acid, C1-C6 alkyl, or halo;
wherein R¹² is (R)—CH(CH₃);
or a solvate, hydrate, or pharmaceutically acceptable salt thereof.

4. A compound of claim 3 wherein R¹¹ is selected from:

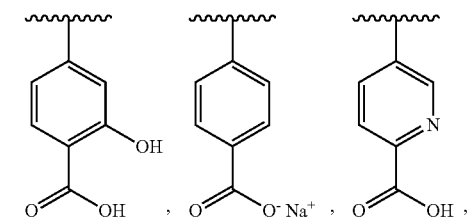

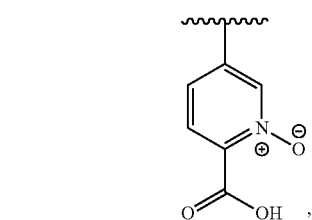

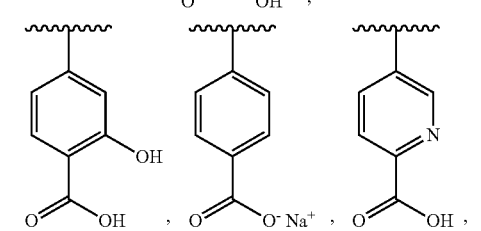

-continued

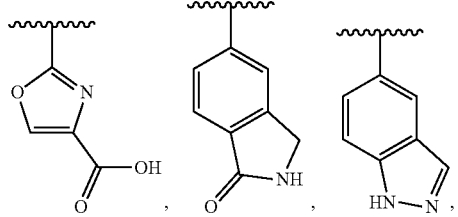

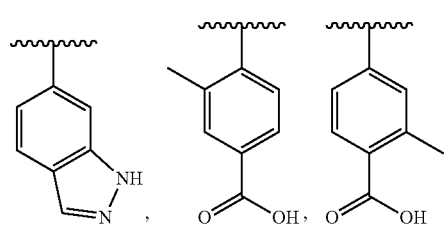

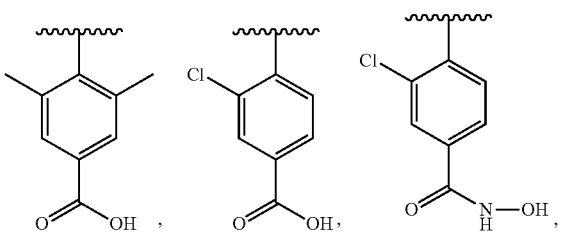

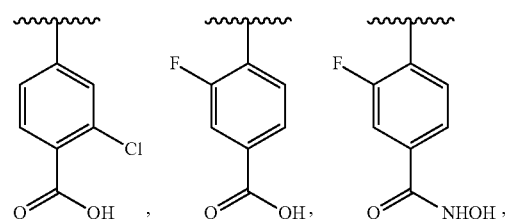

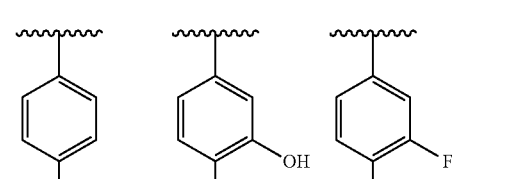

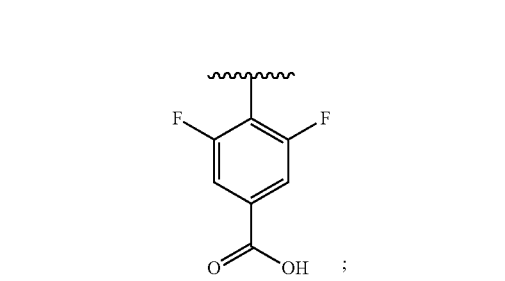

or a salt thereof.

5. A compound represented by Formula IV:

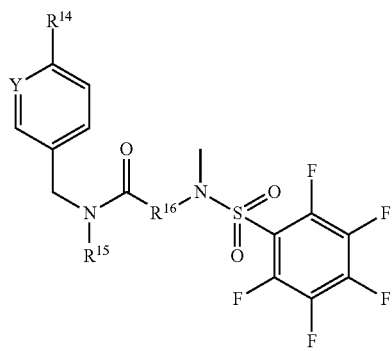
(Formula IV)

wherein $R^{14}$ is selected from a five- to seven-membered cycloalkyl or heteroxycloalkyl group, wherein the cycloalkyl group can be substituted with one or more of halo;
wherein $R^{15}$ is selected from substituted aryl, wherein the substitution is one or more of hydroxy, carboxylic acid, or benzohydroxamic acid;
wherein $R^{16}$ is (R)—CH(CH$_3$);
wherein Y is selected from CH or N;
or a solvate, hydrate, or pharmaceutically acceptable salt thereof.

6. A compound of claim 5, wherein $R^{14}$ is selected from:

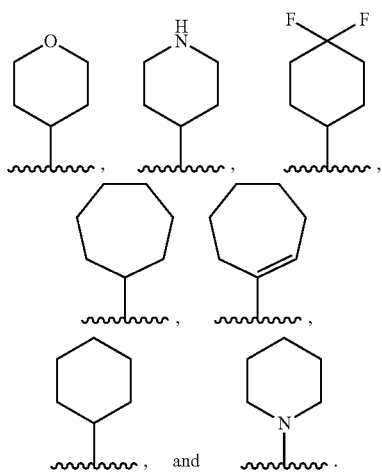

7. A compound of claim 5, wherein $R^{15}$ is selected from:

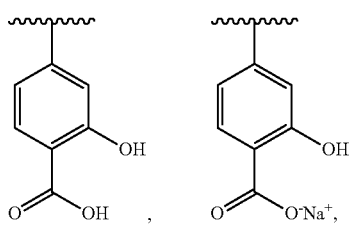

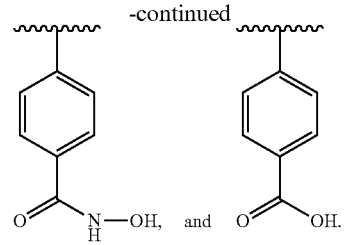

8. A compound of claim 5, wherein the compound is represented by Formula V:

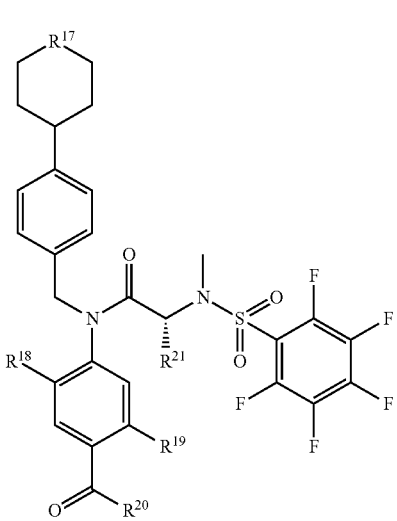
(Formula V)

wherein $R^{17}$ is selected from CH$_2$ or O;
wherein $R^{18}$ is selected from hydrogen or halo;
wherein $R^{19}$ is selected from hydrogen or hydroxyl;
wherein $R^{20}$ is selected from —OH, —NHOH, or —(O', Na$^+$);
wherein $R^{21}$ is CH$_3$;
or a solvate, hydrate, or pharmaceutically acceptable salt thereof.

9. A compound of claim 1, wherein the compound is represented by Formula VI:

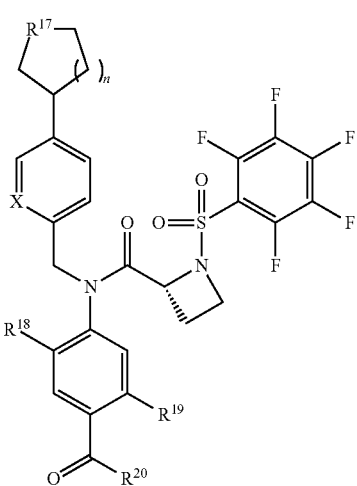
Formula VI wherein n is selected from 1 to 3
wherein X is selected from CH or N;

wherein R$^{17}$ is selected from CH$_2$ or O;
wherein R$^{18}$ is selected from hydrogen or halo;
wherein R$^{19}$ is selected from hydrogen or hydroxyl;
wherein R$^{20}$ is selected from —OH, NHOH, or —(O', Na$^+$),
or a solvate, hydrate, or pharmaceutically acceptable salt thereof.
10. A compound of claim 1, wherein the compound is selected from:
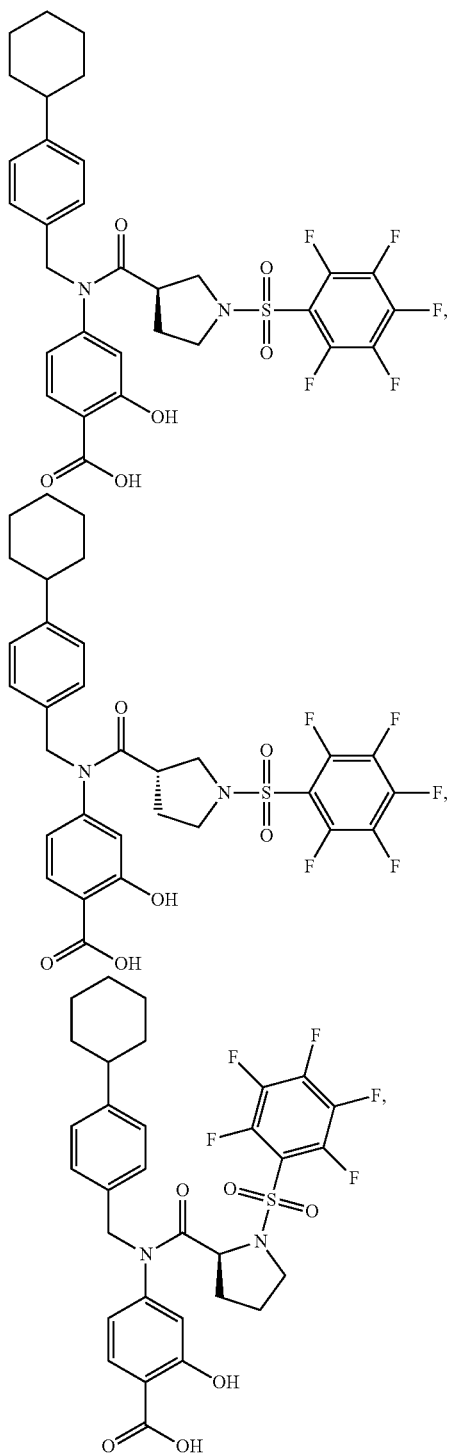
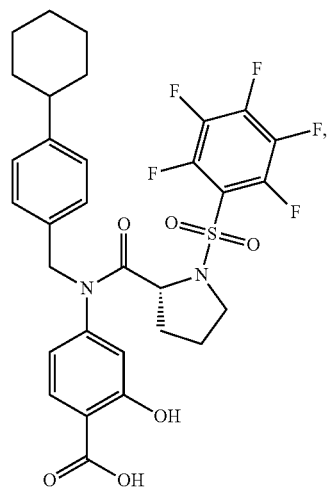
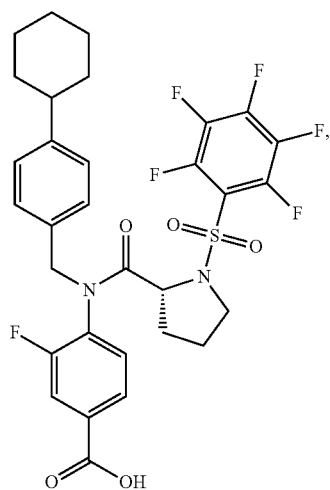
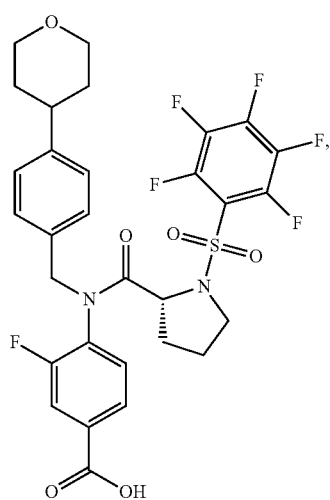

431
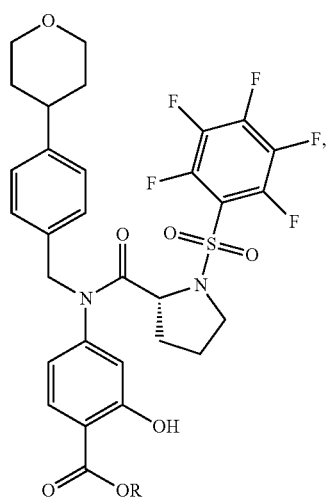
(wherein R = H)
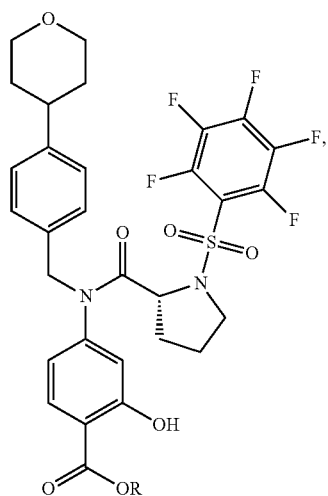
(wherein R = Na)
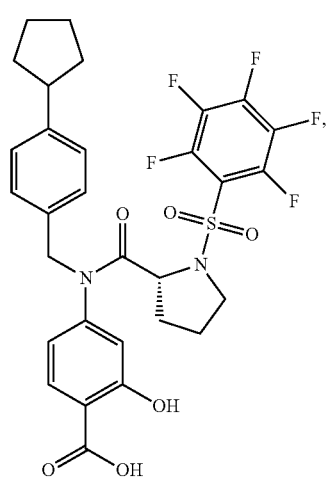
432
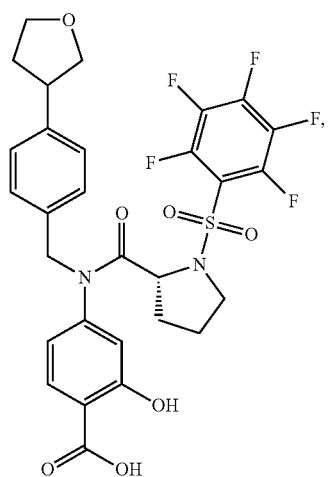
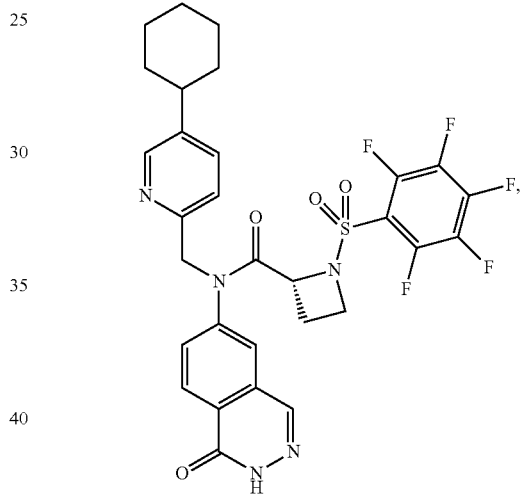
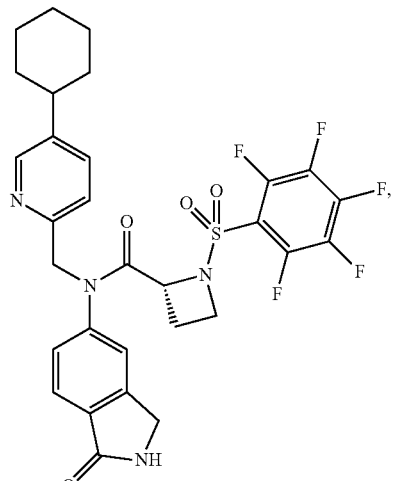

433
-continued
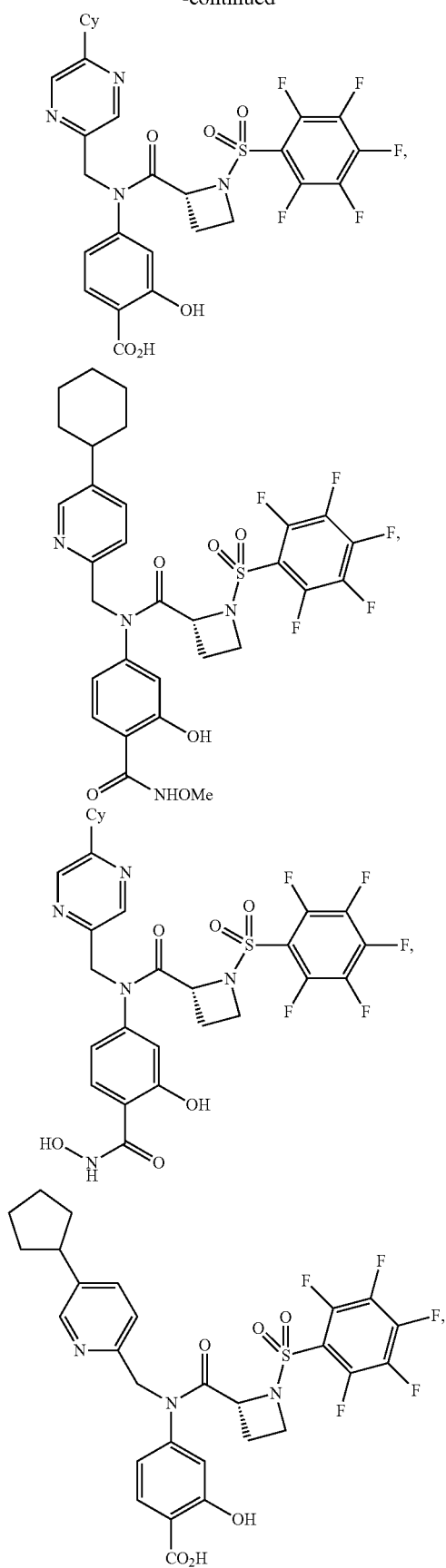
434
-continued
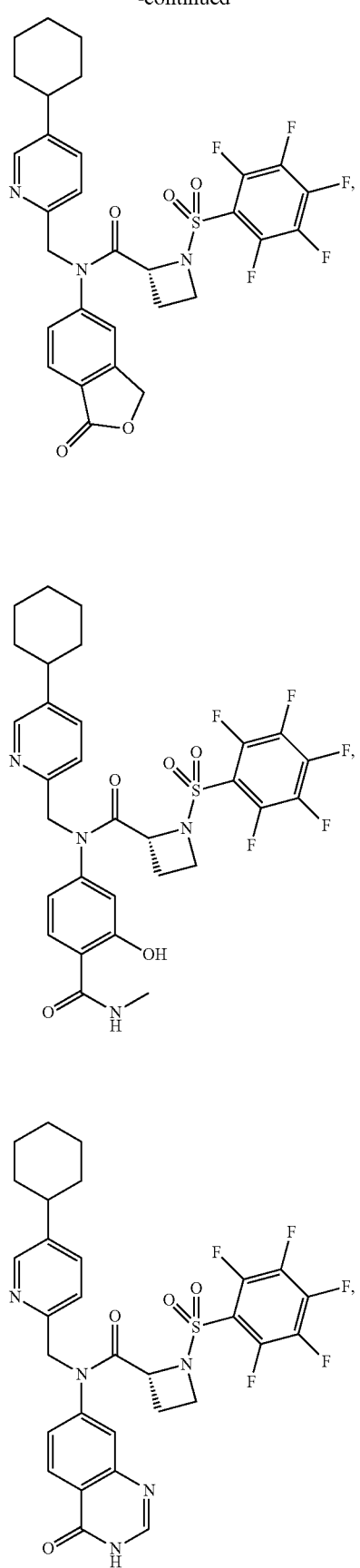

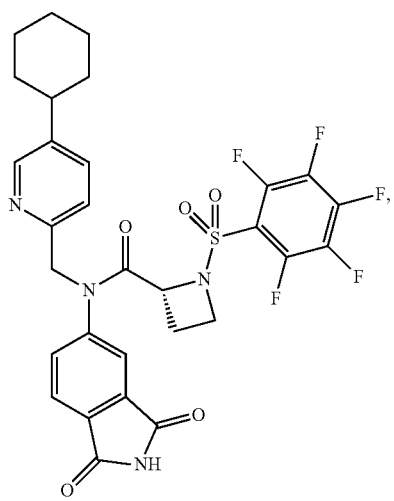
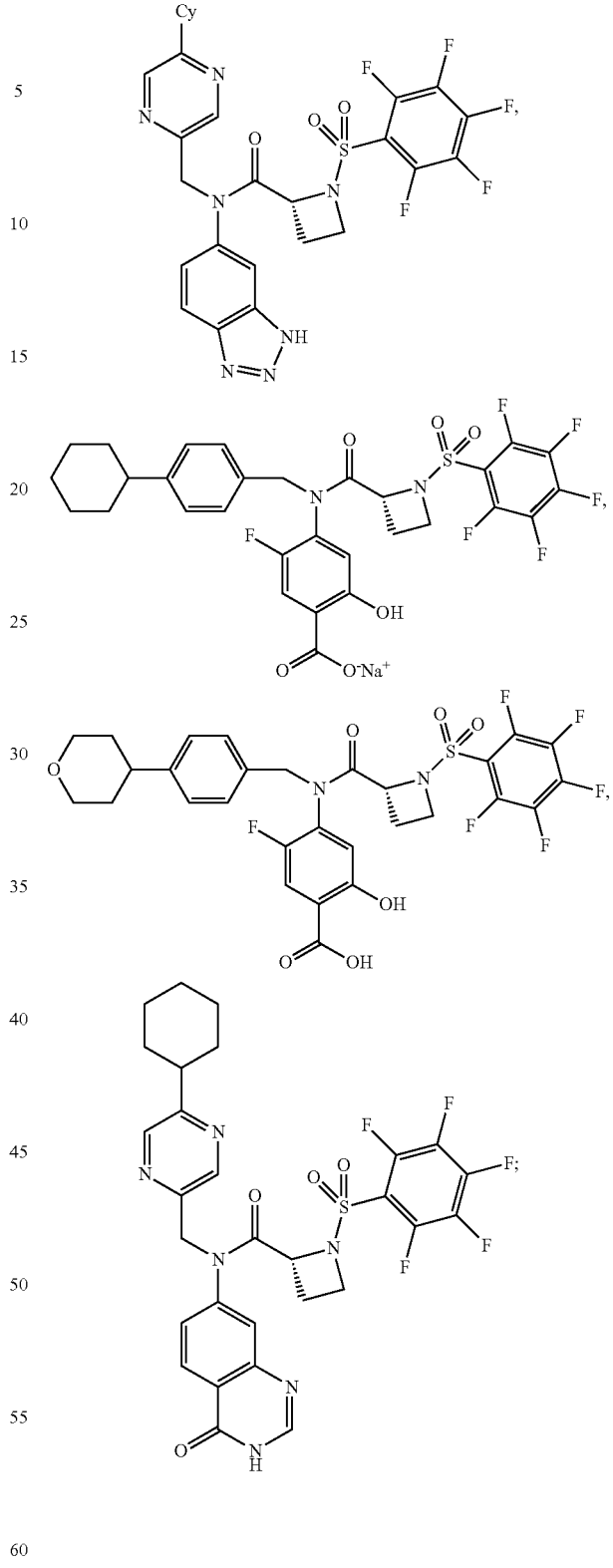
or a solvate, hydrate, or pharmaceutically acceptable salt thereof.
11. A compound of claim 1, wherein the compound is selected from:

437
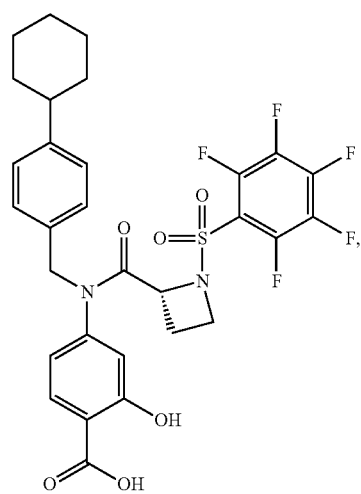
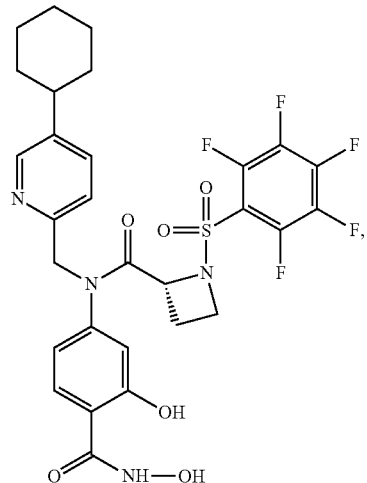
438
-continued
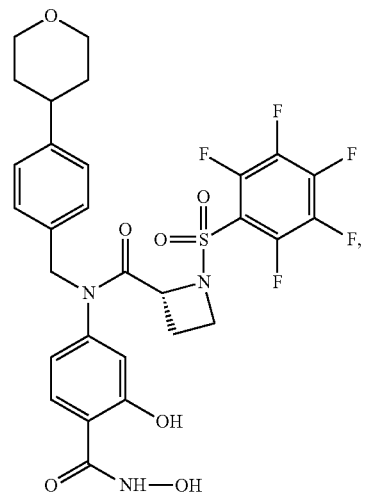
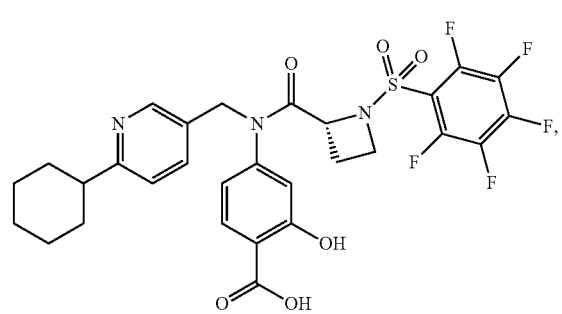
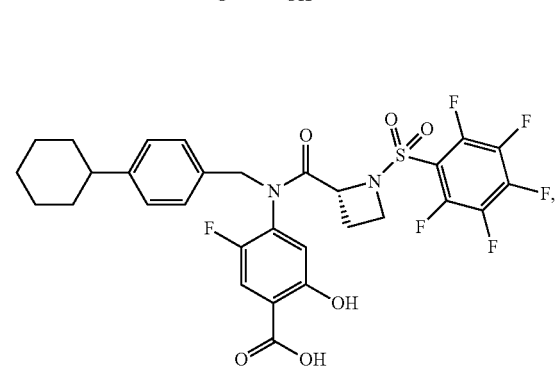

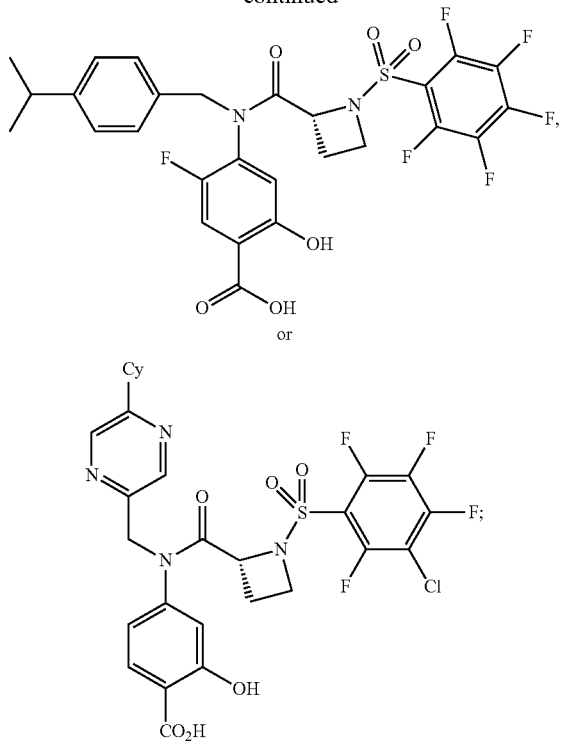

or a solvate, hydrate, or pharmaceutically acceptable salt thereof.

12. A compound represented by Formula VII:

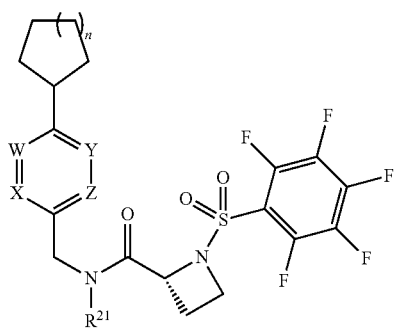

Formula VII wherein W, X, Y, and Z each independently can include or exclude CH or N, wherein $R^{21}$ is selected from optionally substituted aryl, optionally substituted heteroaryl, or an optionally substituted aryl fused with a heterocyclic ring, wherein the substituted aryl or substituted heteroaryl or the substituted aryl fused with a heterocyclic ring can be substituted with one or more of hydroxyl, carboxylic acid, carboxylate, hydroxamic acid, amide, alkyl amide, dialkylamide, alkoxyamino, alkyl carboxylic acid, C1-C6 alkyl, or halo, wherein n is selected from 1 to 3;

or a solvate, hydrate, or pharmaceutically acceptable salt thereof.

13. The compound of claim 12, wherein $R^{21}$ is selected from any of the following moieties:

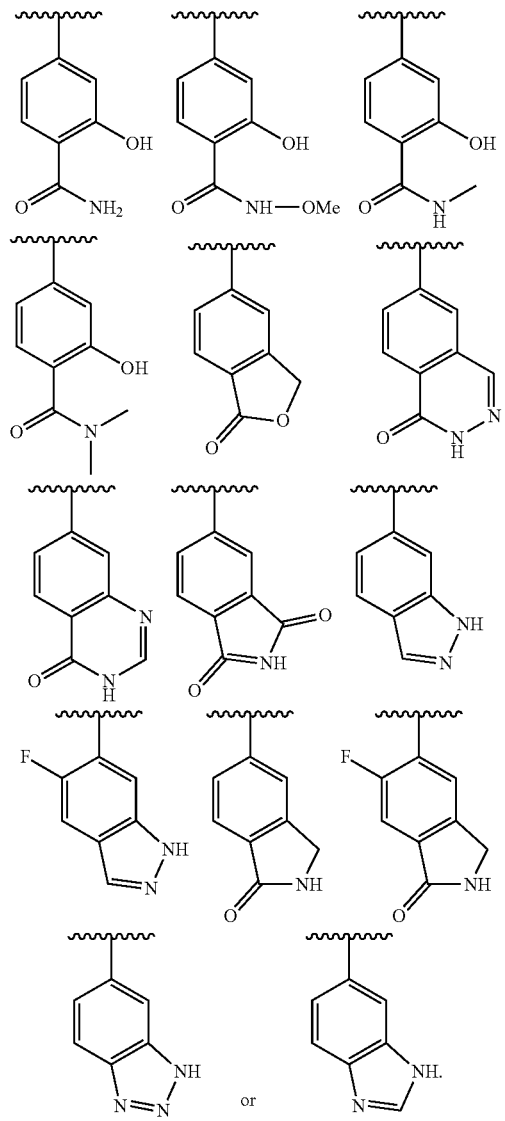

14. A compound represented by Formula VIII:

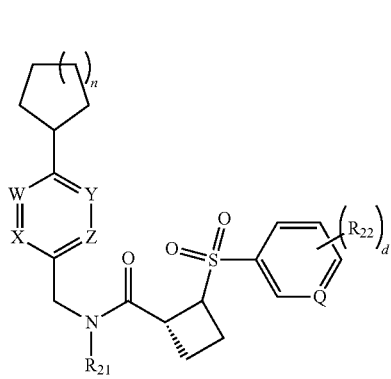

Formula VIII wherein W, X, Y, Z, and Q each independently can include or exclude CH or N, wherein d is selected from 0, 1, 2, 3, or 4, wherein $R^{21}$ is selected from optionally substituted aryl, optionally substituted heteroaryl, or an optionally substituted aryl fused with a heterocyclic ring, and wherein $R^{22}$ is halogen.

15. The compound of claim 14, wherein $R^{21}$ is selected from any of the following moieties:

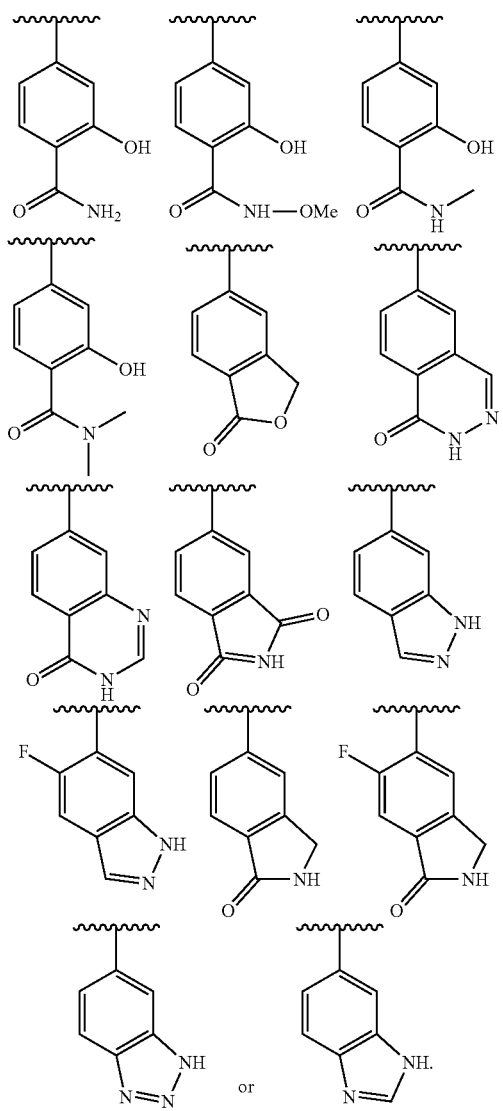

16. The compound of claim 14, wherein halogen is fluorine.

17. A pharmaceutical composition comprising a therapeutically effective amount of a compound, salt, crystal or polymorph in any one of claims 1-16, and a pharmaceutically acceptable excipient.

18. A composition comprising a therapeutically effective amount of a compound of any one of claims 1-16 and a pharmaceutically acceptable carrier.

19. A method of therapeutic treatment cancer, comprising administering to a subject in need thereof, a therapeutically effective dose of a composition of claim 17.

20. The method of claim 19, wherein the therapeutically effective dose of the composition ranges from about 0.05 mg/kg to about 5 g/kg.

21. The method of claim 19, wherein the therapeutically effective dose of the composition is given in one or more doses of about 0.05 mg/kg to about 5 g/kg.

22. The method of claim 19, wherein the therapeutically effective dose of the composition is from about 0.08 mg/kg to about 0.5 mg/kg, from about 0.08 to about 0.24 mg/kg, or from about 0.24 to about 0.5 mg/kg, or from about 0.08 to 0.5 mg/kg.

23. The method of claim 19, wherein the one or more therapeutically effective doses of the composition are administered orally.

24. The method of claim 19, wherein the one or more therapeutically effective doses of the composition are administered subcutaneously, intravenously, or intramuscularly.

25. The method of claim 19, wherein the cancer is a solid tumor.

26. The method of claim 25, wherein the solid tumor comprises glioma, breast cancer or pancreatic cancer.

27. The method of claim 19, wherein the cancer is selected from the group consisting of: lung, breast, prostate, pancreatic, ovarian, bladder, head and neck, thyroid, brain, skin and kidney.

28. The method of claim 19, wherein the cancer is selected from the group consisting of: brain tumors, gliomas, breast, and malignant melanoma.

29. The method of claim 19, wherein each therapeutically effective dose of the composition is between about 0.08 mg/kg and less than about 0.5 mg/kg, and said dose is administered by a delivery route selected from the group consisting of oral, intradermal, intramuscular, intraperitoneal, intravenous, topical, subcutaneous, and epidural routes.

* * * * *